US 8,150,128 B2

(12) United States Patent
Konofagou et al.

(10) Patent No.: US 8,150,128 B2
(45) Date of Patent: Apr. 3, 2012

(54) SYSTEMS AND METHOD FOR COMPOSITE ELASTOGRAPHY AND WAVE IMAGING

(75) Inventors: Elisa E. Konofagou, New York, NY (US); Simon Fung-Kee-Fung, Buffalo, NY (US); Shougang Wang, New York, NY (US); Wei-Ning Lee, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 851 days.

(21) Appl. No.: 11/899,004

(22) Filed: Aug. 30, 2007

(65) Prior Publication Data

US 2008/0285819 A1    Nov. 20, 2008

Related U.S. Application Data

(60) Provisional application No. 60/841,926, filed on Aug. 30, 2006.

(51) Int. Cl.
*G06K 9/00* (2006.01)
*A61B 8/00* (2006.01)

(52) U.S. Cl. ........................ 382/131; 600/737

(58) Field of Classification Search .................. 382/128, 382/129, 130, 131, 132, 133, 134; 600/407, 600/410, 443, 437, 447, 450; 378/4, 21–27, 378/901; 128/916, 920, 922, 915, 900; 601/2; 433/86, 119

See application file for complete search history.

(56) References Cited

U.S. PATENT DOCUMENTS 3,598,111 A    8/1971    Kahn
(Continued)

FOREIGN PATENT DOCUMENTS

WO    WO2008/027520    3/2008
(Continued)

OTHER PUBLICATIONS

Avolio, A. P., S. G. Chen, R. P. Wang, C. L. Zhang, M. F. Li and M. F. O'Rourke. Effects of aging on changing arterial compliance and left ventricular load in a northern Chinese urban community. Circulation (1983) 68(1): 50-8.

(Continued)

*Primary Examiner* — Abolfazl Tabatabai
(74) *Attorney, Agent, or Firm* — Baker Botts L.L.P.

(57) ABSTRACT

Systems and methods for composite elastography and wave imaging are presented. In exemplary embodiments of the present invention an imaging modality field of view, such as, for example, that of ultrasound, can be divided into N sectors, each having 1/Nth of a full field of view. In exemplary embodiments of the present invention a temporal series of 2D or 3D ultrasound images for each of the N sectors can be acquired over a duration of one or more periods of a periodic signal. Substantially simultaneously, such a periodic signal can also be acquired, wherein each of said series of 2D ultrasound images for each sector can be triggered or gated using said periodic signal. For example, for ultrasound imaging of the heart, an ECG signal can function as such a periodic signal. The data from the various N sectors can be synchronized in time using the ECG signals, and the ultrasound signals from each of the N sectors combined to generate a series of composite ultrasound images at the frame rate of the individual sectors. In exemplary embodiments of the present invention such a composite image can be further processed to estimate displacement between consecutive frames, remove noise, accumulate displacement with time for an entire cardiac cycle, and derive strain in the cardiac muscle, vessel or any other organ or tissue under motion. In exemplary embodiments of the present invention the derived strain data can be overlaid onto all or part of the composite ultrasound images, and one or more of such overlaid images can be displayed to a user.

34 Claims, 229 Drawing Sheets
(84 of 229 Drawing Sheet(s) Filed in Color)

U.S. PATENT DOCUMENTS

| | | | |
|---|---|---|---|
| 4,463,608 A | | 8/1984 | Takeuchi et al. |
| 4,777,599 A | | 10/1988 | Dorogi et al. |
| 4,882,679 A | | 11/1989 | Tuy et al. |
| 5,038,787 A | | 8/1991 | Antich et al. |
| 5,107,837 A | | 4/1992 | Ophir et al. |
| 5,178,147 A | | 1/1993 | Ophir et al. |
| 5,309,914 A | | 5/1994 | Iinuma |
| 5,433,708 A | | 7/1995 | Nichols et al. |
| 5,435,310 A | | 7/1995 | Sheehan et al. |
| 5,457,754 A | | 10/1995 | Han et al. |
| 5,601,084 A | | 2/1997 | Sheehan et al. |
| 5,606,971 A | | 3/1997 | Sarvazyan |
| 5,662,113 A | | 9/1997 | Liu |
| 5,752,515 A | | 5/1998 | Jolesz et al. |
| 5,810,731 A | | 9/1998 | Sarvazyan et al. |
| 5,840,028 A | | 11/1998 | Chubachi et al. |
| 6,026,173 A | | 2/2000 | Svenson et al. |
| 6,102,865 A | * | 8/2000 | Hossack et al. ............... 600/459 |
| 6,106,465 A | | 8/2000 | Napolitano et al. |
| 6,246,895 B1 | * | 6/2001 | Plewes .......................... 600/410 |
| 6,309,355 B1 | | 10/2001 | Cain et al. |
| 6,413,216 B1 | * | 7/2002 | Cain et al. ..................... 600/439 |
| 6,425,867 B1 | | 7/2002 | Vaezy et al. |
| 6,488,629 B1 | * | 12/2002 | Sætre et al. ................... 600/443 |
| 6,491,636 B2 | | 12/2002 | Chenal et al. |
| 6,508,768 B1 | | 1/2003 | Hall et al. |
| 6,529,770 B1 | | 3/2003 | Grimblatov |
| 6,671,541 B2 | * | 12/2003 | Bishop et al. ................. 600/436 |
| 6,683,454 B2 | * | 1/2004 | Rehwald et al. .............. 324/307 |
| 6,689,060 B2 | | 2/2004 | Phelps et al. |
| 6,701,341 B1 | * | 3/2004 | Wu et al. ....................... 709/200 |
| 6,770,033 B1 | | 8/2004 | Fink et al. |
| 6,875,176 B2 | | 4/2005 | Mourad et al. |
| 7,055,378 B2 | | 6/2006 | Su et al. |
| 7,257,244 B2 | | 8/2007 | Miga |
| 7,331,926 B2 | * | 2/2008 | Varghese et al. .............. 600/443 |
| 7,344,509 B2 | * | 3/2008 | Hynynen et al. .................. 601/3 |
| 7,421,101 B2 | | 9/2008 | Georgescu et al. |
| 7,429,249 B1 | * | 9/2008 | Winder et al. ..................... 601/2 |
| 7,449,306 B2 | | 11/2008 | Elson et al. |
| 7,601,122 B2 | | 10/2009 | Zagzebski et al. |
| 2002/0038086 A1 | | 3/2002 | Hynynen et al. |
| 2002/0065461 A1 | | 5/2002 | Cosman |
| 2002/0095081 A1 | | 7/2002 | Vilsmeier |
| 2002/0151792 A1 | | 10/2002 | Conston et al. |
| 2002/0193784 A1 | | 12/2002 | McHale et al. |
| 2003/0097068 A1 | | 5/2003 | Hossack et al. |
| 2003/0171672 A1 | | 9/2003 | Varghese et al. |
| 2003/0220556 A1 | | 11/2003 | Porat et al. |
| 2004/0049134 A1 | | 3/2004 | Tosaya et al. |
| 2004/0054357 A1 | | 3/2004 | O'Donnell |
| 2004/0059224 A1 | | 3/2004 | Varghese et al. |
| 2004/0097805 A1 | | 5/2004 | Verard et al. |
| 2004/0210135 A1 | | 10/2004 | Hynynen |
| 2004/0236219 A1 | | 11/2004 | Liu et al. |
| 2004/0249580 A1 | | 12/2004 | Pourcelot et al. |
| 2004/0258760 A1 | | 12/2004 | Wheatley et al. |
| 2005/0004466 A1 | | 1/2005 | Hynynen et al. |
| 2005/0059876 A1 | | 3/2005 | Krishnan et al. |
| 2005/0080336 A1 | | 4/2005 | Byrd et al. |
| 2005/0201942 A1 | | 9/2005 | Dugstad et al. |
| 2005/0259864 A1 | | 11/2005 | Dickinson et al. |
| 2005/0267695 A1 | | 12/2005 | German |
| 2005/0277835 A1 | * | 12/2005 | Angelsen et al. ............. 600/437 |
| 2006/0058671 A1 | | 3/2006 | Vitek et al. |
| 2006/0058673 A1 | | 3/2006 | Aase et al. |
| 2006/0074315 A1 | | 4/2006 | Liang et al. |
| 2006/0078501 A1 | | 4/2006 | Goertz et al. |
| 2006/0173320 A1 | | 8/2006 | Radulescu |
| 2006/0241529 A1 | | 10/2006 | Hynynen et al. |
| 2007/0049824 A1 | | 3/2007 | Konofagou et al. |
| 2007/0055179 A1 | | 3/2007 | Deem et al. |
| 2007/0219447 A1 | | 9/2007 | Kanai et al. |
| 2007/0239001 A1 | | 10/2007 | Mehi et al. |
| 2007/0276245 A1 | | 11/2007 | Konofagou |
| 2008/0269668 A1 | | 10/2008 | Keenan et al. |
| 2008/0285819 A1 | | 11/2008 | Konofagou et al. |
| 2008/0319375 A1 | | 12/2008 | Hardy |
| 2009/0005711 A1 | | 1/2009 | Konofagou et al. |
| 2009/0270790 A1 | | 10/2009 | Raghavan |
| 2011/0208038 A1 | | 8/2011 | Konofagou et al. |

FOREIGN PATENT DOCUMENTS

| | | |
|---|---|---|
| WO | WO2008/062342 | 5/2008 |
| WO | WO2008/131302 | 10/2008 |
| WO | WO2008/157422 | 12/2008 |
| WO | WO2010/044385 | 4/2010 |
| WO | WO2010/063951 | 6/2010 |
| WO | WO2011/035312 | 3/2011 |

OTHER PUBLICATIONS

Brekke, S.; Tegnander, E.; Torp, H. G.; Eik-Nes, S. H.; "Tissue Doppler gated (TDOG) dynamic three-dimensional ultrasound imaging of the fetal heart," Ultrasound Obstet Gynecol 2004 vol. 24(2); pp. 192-198.

Bercoff, J., Tanter, M., and Fink, M. (2004). Supersonic shear imaging: A new technique for soft tissue elasticity mapping. *IEEE Transactions on Ultrasonics Ferroelectrics and Frequency Control* 51, 396-409.

Bonnefous, O. and P. Pesque. Time domain formulation of pulse-Doppler ultrasound and blood velocity estimation by cross correlation. Ultrason Imaging (1986) 8(2): 73-85.

Brooks, D. H., and MacLeod, R. S. (1997). Electrical imaging of the heart. *IEEE Signal Processing Magazine* 14, 24-42.

Chen, Q. et al. "Estimation of Displacement Vectors and Strain Tensors in Elastography Using Angular Insonifications." *IEEE Transactions on Medical Imaging*, vol. 23, No. 12, pp. 1479-1489 (Dec. 1, 2004).

Choi JJ, Wang S, Tung Y-S, Baseri B, Morrison B 3rd, Konofagou EE. Delivery of pharmacologically-relevant sized molecules through the ultrasound-induced blood-brain barrier opening in vivo. Neuroscience, Chicago, IL, USA, Oct. 17-21, 2009.

Choi JJ, Wang S, Brown TR, Small SA, Duff KE and Konofagou EE, Noninvasive and Transient Blood-Brain Barrier Opening in the Hippocampus of Alzheimer's Double Transgenic Mice Using Pulsed Focused Ultrasound, Ultrasonic Imaging, 189-200, 2008.

Choi, J.J. et al., Optimization of Blood-Brain Barrier Opening in Mice using Focused Ultrasound. 2006 IEEE Ultrasounics Symposium [online], Jun. 2007.

Cutnell, J. and W. Kenneth (1998). Physics, Fourth Edition. New York. Table of Contents.

Declerck, J., T. S. Denney, C. Ozturk, W. O'Dell and E. R. McVeigh. Left ventricular motion reconstruction from planar tagged MR images: a comparison. Phys Med Biol (2000) 45(6): 1611-1632.

Edwards, C. H., Rankin, J. S., Mchale, P. A., Ling, D., and Anderson, R. W. (1981). Effects of Ischemia on Left-Ventricular Regional Function in the Conscious Dog. *American Journal of Physiology* 240, H413-H420.

Feshitan, J.A. et al., Microbubble size isolation by differential centrifugation, Journal of Colloid and Interface Science 329 (2009) 316-324.

Fung, Y. C. (1993). Biomechanics—Mechanical Properties of Living Tissues. New York, Table of Contents.

Greenwald, S. E. Pulse pressure and arterial elasticity. Qjm-an International Journal of Medicine (2002) 95(2): 107-112.

Gupta, K. B., Ratcliffe, M. B., Fallert, M. A., Edmunds, L. H., and Bogen, D. K. (1994) Changes in Passive Mechanical Stiffness of Myocardial Tissue with Aneurysm Formation. *Circulation* 89, 2315-2326.

Kanai, H. Propagation of spontaneously actuated pulsive vibration in human heart wall and in vivo viscoelasticity estimation. IEEE T Ultrason Ferr (2005) 52(11): 1931-1942.

Heimdal, A., A. Stoylen, H. Torp and T. Skjaerpe. Real-time strain rate imaging of the left ventricle by ultrasound. J Am Soc Echocardiog (1998) 11(11): 1013-1019.

Henderson, A., Parmley, W. W., and Sonnenbl, E. (1971). Series Elasticity of Heart Muscle During Hypoxia. *Cardiovascular Research* 5, 10-14.

International Search Report for PCT/US07/019149 dated Feb. 29, 2008.

International Preliminary Report on Patentability for PCT/US07/019149 dated Mar. 3, 2009, including the Written Opinion of the International Searching Authority dated Feb. 29, 2008.
International Search Report for PCT/US06/061809 dated Oct. 4, 2007.
International Preliminary Report on Patentability for PCT/US06/061809 dated Jun. 11, 2008, including the Written Opinion of the International Searching Authority dated Oct. 4, 2007.
International Search Report for PCT/US06/018454 dated Aug. 9, 2007.
International Preliminary Report on Patentability for PCT/US06/018454 dated Nov. 14, 2007, including the Written Opinion of the International Searching Authority dated Aug. 9, 2007.
International Search Report for PCT/US05/037669 dated Jun. 13, 2006.
International Preliminary Report on Patentability for PCT/US05/037669 dated Apr. 17, 2007, including the Written Opinion of the International Searching Authority dated Jun. 13, 2006.
International Search Report for PCT/US05/037670 dated Nov. 22, 2006.
International Preliminary Report on Patentability for PCT/US05/037670 dated Apr. 17, 2007, including the Written Opinion of the International Searching Authority dated Nov. 22, 2006.
International Search Report and Written Opinion of the International Searching Authority for PCT/US09/052563 dated Oct. 8, 2009.
Kanai, H. and Y. Koiwa. Myocardial rapid velocity distribution. Ultrasound Med Biol (2001) 27(4): 481-498
Kanai, H., A. Umezawa and Y. Koiwa (2000). Transcutaneous measurement of frequency dispersion in the regional pulse wave velocity. IEEE Ultrasonics symposium.
Kanai, H., H. Satoh, K. Hirose and N. Chubachi. A New Method for Measuring Small Local Vibrations in the Heart Using Ultrasound. IEEE T Bio-Med Eng (1993) 40(12): 1233-1242.
Konofagou E.E. and Ophir, J., (1998) A New Elastographic Method for Estimation and Imaging of Lateral Strains, Corrected Axial Strains and Poison's Ratios in Tissues, *Ultrasound in Medicine and Biology* 24(8), 1183-1199.
Konofagou E.E., Kallel F. and Ophir J., (1998) Three-dimensional Motion estimation in Elastography, IEEE Proceedings of the Symposium of Ultrasonics, Ferroelectrics and Frequency Control in Sendai, Japan, 1745-1748.
Konofagou E.E., D'Hooge J.D., Ophir, J Myocardial Elastography—Feasibility Study In Vivo. *Ultrasound Med & Biol.*, vol. 28, No. 4, pp. 475-482 (2002).
Konofagou E E et al. "Elastographic Imaging of the Strain Distribution at the Anterior Cruciate Ligament and ACL-Bone Insertions" *27th Annual International Conference of the Engineering In Medicine and Biology Society*, pp. 972-975 (Shanghai, China Sep. 1-4, 2005).
Luo J, Fujikura K., Homma S, Konofagou EE (Aug. 2007). Myocardial elastography at both high temporal and spatial resolution for the detection of infarcts. *Ultrasound in Medicine & Biology* 33(8): 1206-23.
McDannold, N. et al., Blood-Brain Barrier Disruption Induced by Focused Ultrasound and Circulating Preformed Microbubbles Appears to be Characterized by the Mechnical Index Ultrasound Med Biol. Jan. 2008, v. 34(5), pp. 834-840.
McLaughlin, J., M. McNeill, B. Braun and P. D. McCormack. Piezoelectric sensor determination of arterial pulse wave velocity. Physiol Meas (2003) 24(3): 693-702.
McNally, D. et al. "Computer Vision Elastography: Speckle Adaptive Motion Estimation for Elastography Using Ultrasound Sequences." *IEEE Transactions on Medical Imaging*, vol. 24, No, 6, pp. 755-766 (2005).
Nichols, W. and M. F. O'Rourke (1998). Vascular impedance.In McDonald's: blood flow in arteries: theoretical, experimental and clinical principles. E. Arnold. London. Table of Contents.
Qin, S. and Ferrara, K.W., The Natural Frequency of Nonliner Oscillation of Ultrasound Contrast Agents in Microvessels, Ultrasound in Med. & Biol., vol. 33, No. 7, pp. 1140-1148, 2007.
Qin, S. and Ferrara, K.W., Acoustic response of compliable microvessels containing ultrasound contrast agents, Phys. Med. Biol. 51 (2006) 5065-5088.

Rogers, W. J., Y. L. Hu, D. Coast, D. A. Vido, C. M. Kramer, R. E. Pyeritz and N. Reichek Age-associated changes in regional aortic pulse wave velocity. J Am Coll Cardiol (2001) 38(4): 1123-9.
Roth, B. J. (2000). Influence of a perfusing bath on the foot of the cardiac action potential. *Circulation Research* 86, E19-E22.
Sandrin, L., S. Catheline, M. Tanter, X. Hennequin and M. Fink. Time-resolved pulsed elastography with ultrafast ultrasonic imaging. Ultrason Imaging (1999) 21(4):259-72.
Sarvazyan, A. P., O. V. Rudenko, S. D. Swanson, J. B. Fowlkes and S. Y. Emelianov. Shear wave elasticity imaging: A new ultrasonic technology of medical diagnostics. Ultrasound Med Biol (1998) 24(9): 1419-1435.
Sassaroli, E. and Hynynen, K., Forced linear oscillations of microbubbles in blood capillaries, J. Acoust. Soc. Am. 115 (6), Jun. 2004.
Sassaroli, E. and Hynynen, K., Resonance frequency of microbubbles in small blood vessels: a numerical study, Phys. Med. Biol. 50 (2005) 5293-5305.
Sassaroli, E. and Hynynen, K., Cavitation Threshold of Microbubbles in Gel Tunnels by Focused Ultrasound, Ultrasound in Med. & Biol., vol. 33, No. 10, pp. 1651-1660, 2007.
Silva, G.A. Nanotechnology approaches to crossing the blood-brain barrier and drug delivery to the CNS, BMC Neruosci. 9(Suppl 3): S4, 2008.
Sinkus, R., J. Lorenzen, D. Schrader, M. Lorenzen, M. Dargatz and D. Holz. High-resolution tensor MR elastography for breast tumour detection. Phys Med Biol (2000) 45(6): 1649-1664.
Spach, M. S., Heidlage, J. F., Dolber, P. C., and Barr, R. C. (1998). Extracellular discontinuities in cardiac muscle—Evidence for capillary effects on the action potential foot. *Circulation Research* 83, 1144-1164.
Sutherland, G. R. Color Doppler Myocardial Imaging—Potential Applications in Acquired and Congenital Heart-Disease. Acta Paediatr (1995) 84: 40-48.
Tanter, M., J. Bercoff, L. Sandrin and M. Fink. Ultrafast compound imaging for 2-D motion vector estimation: application to transient elastography. IEEE Trans Ultrason Ferroelectr Freq Control (2002) 49(10): 1363-74.
Unger, E.C. et al., Therapeutic Applications of Lipid-Coated Microbubbles. Advanced Drug. Delivery Reviews. May 2004, vol. 56(9), pp. 1291-1314.
Walker, W. F. and G. E. Trahey. A Fundamental Limit on Delay Estimation Using Partially Correlated Speckle Signals. IEEE T Ultrason Ferr (1995) 42(2): 301-308.
Wang, Y. X., M. Halks-Miller, R. Vergona, M. E. Sullivan, R. Fitch, C. Mallari, B. Martin-McNulty, V. da Cunha, A. Freay, G. M. Rubanyi and K. Kauser. Increased aortic stiffness assessed by pulse wave velocity in apolipoprotein E-deficient mice. Am J Physiol Heart Circ Physiol (2000) 278(2): H428-34.
Wang, Shougang; Lee, Wei-Ning; Luo, Jianwen; Konofagou, Elisa E.; "A composite imaging technique for high frame-rate and full-view cardiovascular ultrasound and elasticity imaging,"IEEE Transactions on Ultrasonics, Ferroelectrics, and Frequency Control 2008 vol. 55(10); pp. 2221-2233.
Wang, Shougang; Lee, Wei-Ning; Luo, Jianwen; Konofagou, Elisa E.; "A composite imaging technique for high frame-rate and full-view cardiovascular ultrasound and elasticity imaging," IEEE International Ultrasonics Symposium, New York, NY, Oct. 28-31, 2007.
Yuh, El, et. al. Delivery of Systemic Chemotherapeutic Agent to Tumors by Using Focused Ultrasound: Study in a Murine Model. Radiology, 234(2): 431-437, 2005.
Zerhouni, E. A., D. M. Parish, W. J. Rogers, A. Yang and E. P. Shapiro. Human heart: tagging with MR imaging—a method for noninvasive assessment of myocardial motion. Radiology (1988) 169(1): 59-63.
Zheng, Y.P. et al. "High Resolution ultrasound elastomicroscopy imaging of soft tissues: system development and feasibility: Ultrasound elastomicroscopy," *Physics in Medicine and Biology*, vol. 49, No. 17, pp. 3925-3938 (Sep. 7, 2004).
U.S. Appl. No. 11/697,579; Nov. 17, 2009, Non-Final Rejection.
U.S. Appl. No. 11/697,579; Oct. 15, 2009, Response to Final Rejection.
U.S. Appl. No. 11/697,579; Jul. 15, 2009, Response to Final Rejection.

U.S. Appl. No. 11/697,579; Apr. 15, 2009, Final Rejection.
U.S. Appl. No. 11/697,579; Jan. 16, 2009, Response to Non-Final Rejection.
U.S. Appl. No. 11/697,579; Jul. 18, 2008, Non-Final Rejection.
U.S. Appl. No. 11/433,510; Nov. 12, 2009, Final Rejection.
U.S. Appl. No. 11/433,510; Aug. 6, 2009, Response to Non-Final Rejection.
U.S. Appl. No. 11/433,510; Mar. 17, 2009, Non-Final Rejection.
U.S. Appl. No. 11/697,579, filed Apr. 6, 2007.
U.S. Appl. No. 11/433,510, filed May 12, 2006.
U.S. Appl. No. 12/096,254, filed Nov. 26, 2008.
U.S. Appl. No. 11/697,573, filed Apr. 6, 2007.
Choi JJ, Feshitan JA, Baseri B, Wang S, Tung Y-S, Borden MA, Konofagou EE. Brain region and microbubble-size dependence of the focused ultrasound-induced blood-brain barrier opening in mice in vivo. IEEE International Ultrasonics Symposium, Rome, ITA, Sep. 20-23, 2009.
Huang et al. Watershed Segmentation for Breast Tumor in 2-D Sonography, May 2004, Ultrasound in Medicine and Biology, pp. 625-632.
Chang et al. 3-D US Frame Positioning Using Speckle Decorrelation and Image Registration, Jun. 2003, Ultrasound in Medicine and Biology, pp. 801-812.
U.S. Appl. No. 11/433,510; Apr. 28, 2010, Office Action.
U.S. Appl. No. 11/697,573; Jun. 23, 2010, Office Action.
U.S. Appl. No. 11/697,579; May 17, 2010, Response.
U.S. Appl. No. 11/697,597 Aug. 6, 2010 Office Action.
U.S. Appl. No. 13/045070, filed Mar. 10, 2011.
U.S. Appl. No. 13/044,224, filed Mar. 9, 2011.
U.S. Appl. No. 11/697,573, Dated Aug. 18, 2011 Amendment and Request for Continued Examination (RCE).
U.S. Appl. No. 11/697,573, Dated Mar. 18, 2011 Final Office Action.
U.S. Appl. No. 11/6975,573, Dated Dec. 22, 2010 Response to Non-Final Office Action.
U.S. Appl. No. 11/697,579, Dated Apr. 29, 2011 Final Office Action.
U.S. Appl. No. 11/433,510, Dated May 23, 2011 Response to Non-Final Office Action.
U.S. Appl. No. 11/433,510, Dated Jan. 21, 2011 Non-Final Office Action
U.S. Appl. No. 11/433,510, Dated Oct. 28, 2010 Response to Final Office Action.
U.S. Appl. No. 12/077,612, Dated May 26, 2011 Final Office Action.
U.S. Appl. No. 12/077,612, Dated Mar. 23, 2011 Response to Non-Final Office Action.
U.S. Appl. No. 12/077,612, Dated Nov. 16, 2010 Non-Final Office Action.
International Search Report and Written Opinion for PCT/US09/056513, dated Oct. 30, 2009.
International Search Report and Written Opinion for PCT/US10/049681, dated Dec. 7, 2010.
International Search Report and Written Opinion for PCT/US10/061742, dated Mar. 1, 2011.
International Search Report for PCT/US06/36460 (Sep. 25, 2007); International Preliminary Report (Mar. 26, 2008) Written Opinion (Sep. 25, 2007).
International Search Report and Written Opinion for PCT/US09/056565, dated Nov. 2, 2009.
Epo Search Report & Opinion and Office Action for EP0684017.2 dated Dec. 7, 2009 & Mar. 8, 2010.
G Mychaskiw, A E Badr, R Tibbs, B R Clower, and J H Zhang, "Optison (FS069) disrupts the blood-brain barrier in rats," Anesthesia & Analgesia, vol. 91, pp. 798-803, 2000.
K Hynynen, n. McDannold, n. Vykhodtseva, and F a Jolesz, "Noninvasive Mr Imaging--guided Focal Opening of the Blood-Brain Barrier in Rabbits," Radiology, vol. 220, pp. 640-641, Aug. 21, 2001.
J J Choi, M Pernot, S A Small, and E E Konofagou, "Noninvasive, transcranial and localized opening of the blood-brain barrier using focused ultrasound in mice,", Ultrasound in Medicine & Biology, vol. 33(1), pp. 95-104, 2007.

N McDannold, N Vykhodtseva, and K Hynynen, "Use of ultrasound pulses combined.with definity for targeted blood-brain barrier disruption: A feasibility study," Ultrasound in medicine & biology, vol. 33(4), pp. 584-590, 2007.
W M Pardridge, "The blood-brain barrier: bottleneck in brain drug development," NeuroRx, vol. 2, pp. 3-14, 2005.
W M Pardridge, "Drug targeting to the brain," Pharmaceutical research, vol. 24(9), pp. 1733-1744, Sep. 2007.
J J Choi, M Pernot, S A Small, and E E Konofagou, "Feasibility of transcranial, localized drug-delivery in the brain of Alzheimers-model mice using focused ultrasound," Ultrasonics Symposium, 2005 IEEE, 1Sep. 8-21, 2005, pp. 988-991.
M Kinoshita, N McDannold, F A Jolesz, and K Hynynen, "Noninvasive localized delivery of Herceptin to the mouse brain by MRI-guided focused ultrasound-induced blood-brain.barrier disruption," Proceedings of the National Academy of Sciences, vol. 103(31), p. 11719-11723, Aug. 1, 2006.
M Kinoshita, N McDannold, F A Jolesz, and K Hynynen, "Targeted delivery of.antibodies through the blood—brain barrier by MRI-guided focused ultrasound,", Biochemical and Biophysical Research Communications, vol. 340, pp. 1085-1090, 2006.
S B Raymond et al., "Ultrasound Enhanced Delivery of Molecular Imaging and Therapeutic Agents in Alzheimers Disease Mouse Models," PLoS One, vol. 3(5): e2175, 2008.
G J Siegel and N B Chauhan, "Neurotrophic factors in Alzheimers and Parkinsons disease.brain," Brain Research Reviews, vol. 33, pp. 199-227, 2000.
Tuszynski et al., "A phase 1 clinical trial of nerve growth factor gene therapy for Alzheimer disease," Nature medicine, vol. 11(5), pp. 551-555, 2005.
NK Patel and SS Gill, "GDNF delivery for Parkinsons disease," ACTA Neurochirurgica-Supplementum Then Supplement-Wien-, vol. 97(2), pp. 135-154, 2007.
M H Tuszynski, "Nerve growth factor gene therapy in Alzheimer disease," Alzheimer Disease & Associated Disorders, vol. 21(2), p. 179-189, 2007.
J A Korecka, J Verhaagen, and E M Hol, "Cell-replacement and gene-therapy strategies for Parkinsons and Alzheimers disease," Regen. Med., vol. 2(4), pp. 425-446, 2007.
D Schenk et al., "Immunization with amyloid-beta attenuates Alzheimer-disease-like pathology in the PDAPP mouse," Nature, vol. 400, pp. 173-177, Jul. 8, 1999.
B K Fiske, M A Frasier, and T B Sherer, "Special focus section: Gene therapy for Parkinsons disease," Experimental Neurology, vol. 209, pp. 28-29, 2008.
FJ Fry, "Transkull transmission of an intense focused ultrasonic beam," Ultrasound in medicine & biology, vol. 3, p. 179-184, 1977.
FJ Fry et al., "A focused ultrasound system for tissue vol. ablation in deep seated brain sites," IEEE 1986 Ultrasonics Symposium, pp. 1001-1004, 1986.
M Tanter, J L Thomas, and M Fink, "Focusing and steering through absorbing and aberrating layers: Application to ultrasonic propagation through the skull," The Journal of the Acoustical Society of America, vol. 103, p. 2403-2410, 1998.
K Hynynen and F A Jolesz, "Demonstration of potential noninvasive ultrasound brain therapy through an intact skull," Ultrasound in medicine & biology, vol. 24(2), pp. 275-283, 1998.
G T Clement, J Sun, T Giesecke, and K Hynynen, "A hemisphere array for non-invasive ultrasound brain therapy and surgery," Phys Med Biol, vol. 45, pp. 3707-3719, Dec. 2000.
J Jagannathan et al., "High-Intensity Focused Ultrasound Surgery of the Brain: Part 1-A Historical Perspective With Modern Applications," Neurosurgery, vol. 64(2), pp. 201-211, 2009.
N McDannold, N Vykhodtseva, and K Hynynen, "Targeted disruption of the blood-brain barrier with focused ultrasound: association with cavitation activity," Physics in Medicine and Biology, vol. 51, pp. 793-808, 2006.
M Lu, M Wan, F Xu, X Wang, and X Chang, "Design and experiment of 256-element ultrasound phased array for noninvasive focused ultrasound surgery," Ultrasonics, vol. 44, pp. e325-e330, 2006.

K Hynynen and J Sun, "Trans-skull ultrasound therapy: the feasibility of usingimage- derived skull thickness information to correct the phasedistortion," IEEE Transactions on Ultrasonics, Ferroelectrics and Frequency Control, vol. 46(3), pp. 752-755, May 1999.

J F Aubry, M Tanter, M Pernot, J L Thomas, and M Fink, "Experimental demonstration of noninvasive transskull adaptive focusing based on prior computed tomography scans," The Journal of the Acoustical Society of America, vol. 113, p. 84, 2003.

F Marquet et al., "Non-invasive transcranial ultrasound therapy based on a 3D CT scan: protocol validation and in vitro results," Phys. Med. Biol, vol. 54, pp. 2597-2613, 2009.

S Behrens, M Daffertshofer, D Spiegel, and M Hennerici, "Low-frequency, low-intensity ultrasound accelerates thrombolysis through the skull," Ultrasound in medicine & biology, vol. 25(2), pp. 269-273, 1999.

E C Everbach and C W Francis, "Cavitational mechanisms in ultrasound-accelerated thrombolysis at 1 MHz," Ultrasound in medicine & biology, vol. 26(7), pp. 1153-1160, 2000.

S Datta et al., "Correlation of cavitation with ultrasound enhancement of thrombolysis," Ultrasound in medicine & biology, vol. 32(8), pp. 1257-1267, 2006.

M Daffertshofer et al., "Transcranial low-frequency ultrasound-mediated thrombolysis in brain ischemia: increased risk of hemorrhage with combined ultrasound and tissue plasminogen activator: results of a phase II clinical trial," Stroke, vol. 36, p. 1441-1446, Jun. 9, 2005.

T Azuma et al., "Bubble generation by standing wave in water surrounded by cranium with transcranial ultrasonic beam," Japanese Journal of Applied Physics, vol. 44, pp. 4625-4630, 2005.

L A Crum, "Bjerknes forces on bubbles in a stationary sound field," The Journal of the Acoustical Society of America, vol. 57, p. 1363, 1975.

P Brundin and C W Olanow, Restorative Therapies in Parkinsons Disease.: Springer Verlag, 2006.

E Giacobini, "Alzheimer disease, from molecular biology to therapy. ," Advances in experimental medicine and biology, vol. 429, p. 235-245, 1997.

J J Choi, S Wang, Y S Tung, B Morrison, and E E Konofagou, "Molecules of Various Pharmacologically-Relevant Sizes Can Cross the Ultrasound-induced Blood-brain Barrier Opening in vivo," Ultrasound in Medicine & Biology, 36(1):58-67, 2010.

Y S Tung et al., "Identifying the inertial cavitation threshold in a vessel phantom using focused ultrasound and microbubbles.," The Journal of the Acoustical Society of America, vol. 124, p. 2486, 2008.

JJ Choi, M Pernot, TR Brown, SA Small, and EE Konofagou, "Spatio-temporal analysis of molecular delivery through the blood-brain barrier," Physics in Medicine and Biology, vol. 52, pp. 5509-5530, 2007.

M R DeLong, "Primate models of movement disorders of basal ganglia origin," Trends Neurosci, vol. 13, pp. 281-285, 1990.

G L Wenk, "A primate model of Alzheimers disease," Behavioural brain research, vol. 57, pp. 117-122, 1993.

Anthony Ws Chan, "Transgenic nonhuman primates for neurodegenerative diseases," Reproductive Biology and Endocrinology, vol. 2, p. 39, 2004.

I H Philippens, "Non-human primate models for Parkinsons disease," Drug Discovery Today: Disease Models, vol. 5(2), pp. 105-111, 2008.

J J Kaufman, G Luo, and R S Siffert, "Ultrasound simulation in bone," IEEE Transactions on Ultrasonics Ferroelectrics and Frequency Control, vol. 55(6), pp. 1205-1218, Jun. 2008.

PJ White, GT Clement, and K Hynynen, "Longitudinal and shear mode ultrasound propagation in human skull bone," Ultrasound in medicine & biology, vol. 32(7), pp. 1085-1096, 2006.

X Yin and K Hynynen, "A numerical study of transcranial focused ultrasound beam propagation at low frequency," Physics in Medicine and Biology, vol. 50, pp. 1821-1836, 2005.

CW Connor, "Simulation methods and tissue property models for non-invasive transcranial focused ultrasound surgery," Ph.D. Thesis 2005.

CW Connor, G T Clement, and K Hynynen, "A unified model for the speed of sound in cranial bone based on genetic algorithm optimization," Physics in Medicine and Biology, vol. 47, pp. 3925-3944, 2002.

K S Kunz, and R J Luebbers, "The finite difference time domain method for electromagnetics. 1993 CRC Press," Boca Raton, USA, Table of Contents.

F Duck, "Physical properties of tissue: a comprehensive reference book. 1990 Academic Press," London, UK.

F W Kremkau, R W Barnes, and C P McGraw, "Ultrasonic attenuation and propagation speed in normal human brain," The Journal of the Acoustical Society of America, vol. 70(1), pp. 29-38, 1981.

S Pichardo and K Hynynen, "Multi frequency characterization of speed of sound for longitudinal transmission on freshly exised human skulls," in 9th International Society on Therapeutic Ultrasound, 2009, p. 136.

M Styner et al., "Automatic brain segmentation in rhesus monkeys," Medical imaging, 2007.

J C Mazziotta, A W Toga, A Evans, P Fox, and J Lancaster, "A probabilistic atlas of the human brain: theory and rationale for its development the international consortium for brain mapping (ICBM)," Neuroimage, vol. 2, pp. 89-101, 1995.

JA Jensen and NB Svendsen, "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.

S C Tang and G T Clement, " Standing-Wave Suppression for Transcranial Ultrasound by Random Modulation," IEEE transactions on Biomedical Engineering, vol. 57, issue 1, 2010, p. 203-205.

FG Mitri, JF Greenleaf, and M Fatemi, "Chirp imaging vibroacoustography for removing the ultrasound standing wave artifact," IEEE transactions on medical imaging, vol. 24(10), pp. 1249-1255, Oct. 2005.

T N Erpelding, K W Hollman, and M O'Donnell, "Bubble-based acoustic radiation force using chirp insonation to reduce standing wave effects," Ultrasound in medicine & biology, vol. 33(2), pp. 263-269, 2007.

D Melodelima et al., "Thermal Ablation by High-Intensity-Focused Ultrasound Using a Toroid Transducer Increases the Coagulated Volume. Results of Animal Experiments," Ultrasound in Medicine & Biology, vol. 35(3), pp. 425-435, 2009.

J D Lee, C H Huang, and S T Lee, "Improving stereotactic surgery using 3-D reconstruction," IEEE Engineering in Medicine and Biology Magazine, vol. 21, pp. 109-116, 2002.

Bers, D.M., "Cardiac excitation-contraction coupling", Nature, Jan. 10, 2002, vol. 415:198-205.

Ashikaga H et al. (2007) Transmural Dispersion of Myofiber Mechanics: Implications for Electrical Heterogeneity in Vivo. Journal of the American College of Cardiology 49:909-916.

Cordeiro JM, Greene L, Heilmann C, Antzelevitch D, Antzelevitch C (2004) Transmural heterogeneity of calcium activity and mechanical function in the canine left ventricle. Am J Physiol Heart Circ Physiol 286:H1471-1479.

Zhang X et al. (2005) Noninvasive three-dimensional electrocardiographic imaging of ventricular activation sequence. Am J Physiol Heart Circ Physiol 289:H2724-2732.

Ramanathan C, Ghanem RN, Jia P, Ryu K, Rudy Y (2004) Noninvasive electrocardiographic imaging for cardiac electrophysiology and arrhythmia. Nat Med 10(4):422-428.

Berger T et al. (2006) Single-Beat Noninvasive Imaging of Cardiac Electrophysiology of Ventricular Pre-Excitation. Journal of the American College of Cardiology 48(10):2045-2052.

Schilling RJ, Peters NS, Davies DW (1998) Simultaneous endocardial mapping in the human left ventricle using a noncontact catheter: comparison of contact and reconstructed electrograms during sinus rhythm. Circulation 98:887-98.

Tavarozzi I et al. (2002) Magnetocardiography: current status and perspectives. Part II: Clinical applications. Ital Heart J 3:151-165.

Greenstein JL, Hinch R, Winslow R (2006) Mechanisms of Excitation-Contraction Coupling in an Integrative Model of the Cardiac Ventricular Myocyte. Biophysical Journal 90:77-91.

Rice JJ, Wang F, Bers DM, de Tombe PP, "Approximate model of cooperative activation and crossbridge cycling in cardiac muscle using ordinary differential equations" Biophys. J 95:2368-2390, Sep. 2008.

Campbell SG, Flaim SN, Leem CH, McCulloch AD, "Mechanisms of transmurally varying myocyte electromechanics in an integrated computational model", Phl. Trans. R. Soc. A., 366:3361-3380, Jul. 1, 2008.

Gurev V, Constantino J, Rice JJ, Trayanova N., "Distribution of Electromechanical Delay in the Heart: Insights from a Three-Dimensional Electromechanical Model", Biophysical Journal 99:745-754, Aug. 2010.

Badke FR, Boinay P, Covell JW (1980) Effects of ventricular pacing on regional left ventricular performance in the dog. Am J Physiol Heart Circ Physiol 238:H858-867.

Wyman BT, Hunter WC, Prinzen FW, McVeigh ER (1999) Mapping propagation of mechanical activation in the paced heart with MRI tagging. Am J Physiol Heart Circ Physiol 276:H881-891.

Prinzen FW et al. (1992) The time sequence of electrical and mechanical activation during spontaneous beating and ectopic stimulation. Eur Heart J 13:535-543.

Provost J, Lee W, Fujikura K, Konafagou E (2010) Electromechanical Wave Imaging of Normal and Ischemic Hearts in Vivo. IEEE Trans. Med. Imaging 29(3):625-635.

Shehata M, Cheng S, Osman N, Bluemke D, Lima J (2009) Myocardial tissue tagging with cardiovascular magnetic resonance. Journal of Cardiovascular Magnetic Resonance 11:55.

Zwanenburg JJM et al. (2004) Timing of cardiac contraction in humans mapped by high-temporal-resolution MRI tagging: early onset and late peak of shortening in lateral wall. Am J Physiol Heart Circ Physiol 286:H1872-1880.

Walker W, Trahey G (1994) A fundamental limit on the performance of correlation based phase correction and flow estimation techniques. Ultrasonics, Ferroelectrics and Frequency Control, IEEE Transactions on 41(5):644-654, Sep. 1994.

Pernot et al., "Electromechanical Imaging of the Myocardium at Normal and Pathological States", Ultrasonics Symposium, 2005 IEEE, pp. 1091-1094, 2005.

Pernot M, Fujikura K, Fung-Kee-Fung SD, Konofagou EE (2007) ECG-gated, Mechanical and Electromechanical Wave Imaging of Cardiovascular Tissues in Vivo Ultrasound in Medicine & Biology 33(7):1075-1085.

Provost J, Gurev V, Trayanova N, Konofagou EE (2008) in 2008 IEEE International Ultrasonics Symposium (Beijing, China).

Durrer D et al. (1970) Total Excitation of the Isolated Human Heart. Circulation 41:899912.

Sengupta Pp, Tondato F, Khandheria Bk, Belohlavek M, Jahangir A (2008) Electromechanical activation sequence in normal heart. Heart Fail Clin 4:303-14.

Scher Am, Young AC (1956) the pathway of ventricular depolarization in the dog. Circ Res 4:461-469.

Faris Op et al. (2003) Novel Technique for Cardiac Electromechanical Mapping with Magnetic Resonance Imaging Tagging and an Epicardial Electrode Sock. Ann Biomed Eng. 31:430-440.

Gurev V, Provost J, Konofagou EE, Trayanova N (2009) in silico characterization of ventricular activation pattern by electromechanical wave imaging. Supplement to Heart Rhythm 6:S357.

Ramanathan C, Jia P, Ghanem R, Ryu K, Rudy Y., "Activation and repolarization of the normal human heart under complete physiological conditions", Proceedings of the National Academy of Sciences 103(16):6309 -6314, Apr. 18, 2006.

Ghosh S, Rhee EK, Avari JN, Woodard PK, Rudy Y (2008) Cardiac Memory in Patients With Wolff-Parkinson-White Syndrome: Noninvasive Imaging of Activation and Repolarization Before and After Catheter Ablation. Circulation 118:907-915.

Lee W et al., "Theoretical Quality Assessment of Myocardial Elastography with in Vivo Validation", Ultrasonics, Ferroelectrics and Frequency Control, IEEE Transactions on 54(1):2233-2245, Nov. 11, 2007.

Kimber S et al. (1996) A Comparison of Unipolar and Bipolar Electrodes During Cardiac Mapping Studies. Pacing Clin Electra 19:1196-1204.

Kallel F, Ophir J (1997) "A least-squares strain estimator for elastography", Ultrason. Imaging 19:195-208.

Luo J, Konofagou EE., "High-frame rate, full-view myocardial elastography with automated contour tracking in murine left ventricles in vivo", IEEE Transactions on Ultrasonics, Fenoelectrics and Frequency Control, 55(1):240-248, Jan. 2008.

Lai Wm, Rubin D, Kxempl E (1993) Introduction to Continuum Mechanics (Pergamon.Pr). 3rd Ed., Contents.

P. A. Stewart and U. I. Tuor, "Blood-eye barriers in the rat: Correlation of ultrastructure.with function," J. Comp. Neurol., vol. 340, No. 4, pp. 566-576, 1994.

N. J. Abbott, L. Ronnback, and E. Hansson, "Astrocyte-endothelial interactions at the.blood-brain barrier," Nat. Rev. Neurosci., vol. 7, No. 1, pp. 41-53, 2006.

N. Sheikov, N. McDannold, S. Sharma, and K. Hynynen, "Effect of focused ultrasound.applied with an ultrasound contrast agent on the tight junctional integrity of the brain microvascular endothelium," Ultrasound Med. Biol., vol. 34, No. 7, pp. 1093-1104, 2008.

K.Hynynen, N. McDannold, N. Vykhodtseva, S.Raymond, R.Weissleder, F. A. Jolesz, and N. Sheikov, "Focal disruption of the blood-brain barrier due to 260-kHz ultrasound.bursts: A method for molecular imaging and targeted drug delivery," J. Neurosurg., vol. 105, No. 3, pp. 445-454, 2006.

N. Sheikov, N. McDannold, F. Jolesz, Y. Z. Zhang, K. Tam, and K. Hynynen, "Brain arterioles show more active vesicular transport of blood-borne tracer molecules than.capillaries and venules after focused ultrasound-evoked opening of the blood-brain.barrier," Ultrasound Med. Biol., vol. 32, No. 9, pp. 1399-1409, 2006.

N. Sheikov, N. McDannold, N. Vykhodtseva, F. Jolesz, and K. Hynynen, "Cellular.mechanisms of the blood-brain barrier opening induced by ultrasound in presence of.microbubbles," Ultrasound Med. Biol., vol. 30, No. 7, pp. 979-989, 2004.

McDannold, N. Vykhodtseva, S. Raymond, F. A. Jolesz, and K. Hynynen, "MRI-guided targeted blood-brain barrier disruption with focused ultrasound: Histological findings in rabbits," Ultrasound Med. Biol., vol. 31, No. 11, pp. 1527-1537, 2005.

L. H. Treat, N. McDannold, N. Vykhodtseva, Y. Zhang, K. Tam, and K. Hynynen, "Targeted delivery of doxorubicin to the rat brain at therapeutic levels using MRI-guided focused ultrasound," Int. J. Cancer, vol. 121, No. 4, pp. 901-907, 2007.

S. Wang, J. J. Choi, Y.-S. Tung, B. Morrison III, and E. E. Konofagou, "Qualitative and quantitative analysis of the molecular delivery through the ultrasound-enhanced blood-brain barrier opening in the murine brain," presented at the IEEE Symp. Ultrason. Ferroelectr. Freq. Control, Beijing, China, 2008.

V. Zlokovic, "The blood-brain barrier in health and chronic neurodegenerative disorders," Neuron, vol. 57, No. 2, pp. 178-201, 2008.

C. F. Caskey, D. E. Kruse, P. A. Dayton, T. K. Kitano, and K. W. Ferrara, "Microbubble oscillation in tubes with diameters of 12, 25, and 195 microns," Appl. Phys. Lett., vol. 88, No. 3, pp. 033902-1—033902-3, 2006.

C. F. Caskey, S.M. Stieger, S. Qin, P. A. Dayton, andK.W. Ferrara, "Direct observations of ultrasound microbubble contrast agent interaction with the microvessel wall," J. Acoust. Soc. Amer., vol. 122, No. 2, pp. 1191-1200, 2007.

S. M. Stieger, C. F. Caskey, R. H. Adamson, S. Qin, F. R. Curry, E. R. Wisner, and K. W. Ferrara, "Enhancement of vascular permeability with low-frequency contrast-enhanced ultrasound in the chorioallantoic membrane model," Radiology, vol. 243, No. 1, pp. 112-121, 2007.

H. Zheng, P. A. Dayton, C. Caskey, S. Zhao, S. Qin, and K. W. Ferrara, "Ultrasound-driven microbubble oscillation and translation within small phantom vessels," Ultrasound Med. Biol., vol. 33, No. 12, pp. 1978-1987, 2007.

M. Cavaglia, S. M. Dombrowski, J. Drazba, A. Vasanji, P. M. Bokesch, and D. Janigro, "Regional variation in brain capillary density and vascular response to ischemia," Brain Res., vol. 910, No. 1-2, pp. 81-93, 2001.

B. Klein, W. Kuschinsky, H. Schrock, and F. Vetterlein, "Interdependency of local capillary density, blood flow, andmetabolism in rat brains," Amer. J. Physiol., vol. 251, No. 6 Pt 2, pp. H1333-H1340, 1986.

S. Kvale, H. A. Jakobsen, O. A. Asbjornsen, and T. Omtveit, "Size fractionation of gas-filled microspheres by flotation," Separations Technol., vol. 6, No. 4, pp. 219-226, 1996.

B. Baseri, J. J. Choi, Y. S. Tung, and E. E. Konofagou, "Multi-Modality Safety assessment of blood-brain barrier opening using focused ultrasound and definity microbubbles: A short-term study," Ultrasound Med. Biol., 6(9): 1445-1459, 2010.

E. Talu, K. Hettiarachchi, S. Zhao, R. L. Powell, A. P. Lee, M. L. Longo, and P. A. Dayton, "Tailoring the size distribution of ultrasound contrast agents: Possible method for improving sensitivity in molecular imaging," Mol. Imag., vol. 6, No. 6, pp. 384-392, 2007.

A. M. Gañán-Calvo and J. M. Gordillo, "Perfectly monodisperse microbubbling by capillary flow focusing," Phys. Rev. Lett., vol. 87, No. 27 Pt 1, pp. 274501-1—274501-4, Dec. 31, 2001.

J. H. Xu, S. W. Li, Y. J. Wang, and G. S. Luo, "Controllable gas-liquid phase flow patterns and monodisperse microbubbles in a microfluidic T-junction device," Appl. Phys. Lett., vol. 88, No. 13, pp. 133506-1—133506-3, 2006.

U. Farook, H. B. Zhang, M. J. Edirisinghe, E. Stride, and N. Saffari, "Preparation of microbubble suspensions by co-axial electrohydrodynamic atomization," Med. Eng. Phys., vol. 29, No. 7, pp. 749-754, 2007.

J. E. Chomas, P. Dayton, D. May, and K. Ferrara, "Threshold of fragmentation for ultrasonic contrast agents," J. Biomed. Opt., vol. 6, No. 2, pp. 141-150, 2001.

S. Samuel, M. A. Cooper, J. L. Bull, J. B. Fowlkes, and D. L. Miller, "An ex vivo study of the correlation between acoustic emission and microvascular damage," Ultrasound Med. Biol., vol. 35, No. 9, pp. 1574-1586, 2009.

S. Chen, R.V. Shohet, R. Bekeredjian, P. Frenkel, and P.A.Grayburn, "Optimization of ultrasound parameters for cardiac gene delivery of adenoviral or plasmid deoxyribonucleic acid by ultrasound-targeted microbubble destruction," J. Amer. Coll. Cardiol., vol. 42, No. 2, pp. 301-308, 2003.

Rockenstein, L. Crews, and E. Masliah, "Transgenic animal models of neurodegenerative diseases and their application to treatment development," Adv. Drug Del. Rev., vol. 59, No. 11, pp. 1093-1102, 2007.

P. Coyle, "Spatial features of the rat hippocampal vascular system," Exp. Neurol., vol. 58, No. 3, pp. 549-561, 1978.

P. Coyle, "Arterial patterns of the rat rhinencephalon and related structures," Exp. Neurol., vol. 49, No. 3, pp. 671-690, 1975.

P. Coyle, "Vascular patterns of the rat hippocampal formation," Exp. Neurol., vol. 52, No. 3, pp. 447-458, 1976.

E. Sykova and C. Nicholson, "Diffusion in brain extracellular space," Physiol. Rev., vol. 88, No. 4, pp. 1277-1340, 2008.

C. Baron, J. F. Aubry, M. Tanter, S. Meairs, and M. Fink, "Simulation of intracranial acoustic fields in clinical trials of sonothrombolysis," Ultrasound Med. Biol., vol. 35, No. 7, pp. 1148-1158, 2009.

T. Deffieux and E. E. Konofagou, "Transcranial focused ultrasound for blood-brain barrier opening—Numerical simulations with in vitro validation in human and monkey skulls," abstract for the AIUM Annual Convention, San Diego, CA, 2010.

Luo et al., "Pulse wave imaging of normal and aneurysmal abdominal aortas in vivo", IEEE Trans. Med. Imaging 28(4): 477-486, 2009.

Luo and Konofagou, A fast normalized cross-correlation method for motion estimation, IEEE Trans. Ultrason. Ferroelectr. Control 57(6): 1347-1357, Jun. 2010.

Maleke et al., "Single-Element focused Ultrasound Transducer Method for Harmonic Motion Imaging" Ultrason. Imagin, vol. 28, No. 3, pp. 144-158, 2006.

Maleke et al., "*In Vivo* Feasibility of Real-time Monitoring of Focused Ultrasound Surgery (FUS) Using Harmonic Motion Imaging (HMI)" IEEE Trans. Biomed. Eng., vol. 57(1), pp. 7-11, Jan. 2010.

Vappou et al., "Quantitive Viscoelastic Parameters Measured by Harmonic Motion Imaging", Phys. Med. Biol., vol. 54, pp. 3579-3595, Mar. 2009.

Ophir et al., "Elastography: A quantitative method for imaging the elasticity of biological tissues," Ultrasonic Imaging, vol. 13(2), pp. 111-134, 1991.

Konofagou et al. "Mechanism and safety at the Threshold of Blood-Brain Barrier Opening *In Vivo*," International Society on Therapeutic Ultrasound (ISTU), Aix-en-Provence, France, Sep. 24-26, 2009.

Sirsi et al. "Effect of microbubble size on fundamental mode high frequency ultrasound imaging in mice," Ultrasound in Med. & Bio., vol. 36, No. 6, pp. 935-948, 2010.

Klempner et al. "Neutrophil Plasma Membranes I. High-Yield Purification of Human Neutrophil Plasma Membrane Vesicles by Nitrogen Cavitation and Differential Centrifugation," Journal of Cell Biology, Jul. 1, 1980, vol. 86, pp. 21-28.

Luo, J et al. "Myocardial elastography at both high temporal and spatial resolution for the detection of infarcts," Ultrasound in Med. & Bio, vol. 33(8), pp. 1206-1223, Aug. 2007.

Konofagou et al., "Three-dimensional Motion estimation in Elastography," IEEE Proceedings of the Symposium of Ultrasonics, Ferroelectrics, and Frequency Control in Sendai Japan, pp. 1745-48, vol. 2, 1998.

J.A. Feshitan et al., "Microbubble size isolation by differential centrifugation," Journal of Colloid and Interface Science 329 (2009) 316-324.

Qin, S.,et al., "Acoustic response of compliable microvessels containing ultrasound.contrast agents," Phys. Med. Biol. 51 (2006) 5065-5088.

H.L. Liu, Y.Y. Wai, W.S. Chen, J.C. Chen, P.H. Hsu, X.Y. Wu, W.C. Huang, T.C. Yen, and J.J. Wang, "Hemorrhage detection during focused-ultrasound induced blood-brain-barrier opening by using suscepitbility-weighted magnetic resonance imagin," Ultrasound Med Biol, vol. 34(4), pp. 598-606, Apr. 2008.

H.L. Liu, P.H. Hsu, P.C. Chu, Y.Y. Wai, J.C. Chen, C.R. Shen, T.C. Yen, and J.J. Wang,."Magnetic resonance imaging enhanced by superparamagnetic iron oxide particles: usefulness for distinguishing between focused ultrasound-induced blood-brain barrier disruption and brain hemorrhage," J. Magn. Reson. Imaging, vol. 29(1), pp. 31-38, Jan. 2009.

Yao-Sheng Tung, Fabrice Marquet, Tobias Teichert, Vincent Ferrera, Elisa E. Konofagou, "Feasibility of noninvasive cavitation-guided blood-brain barrier opening using focused ultrasound and microbubbles in nonhuman primates", Applied Physics Letters 98, No. 16, 2001, 163704.

Yao-Sheng Tung, James J. Choi, Babak Baseri, Elisa E. Konofagou, "Identifying the.inertial cavitation threshold and skull effects in a vessel phantom using focused ultrasound and microbubbles", Ultrasound in Medicine & Biology, 36(5): 840-852, 2010.

Azzdine Y. Ammi, Robin O. Cleveland, Jonathan Mamou, Member, Grace I. Wang, S.Lori Bridal, Member, William D. O'Brien, Jr., " Ultrasonic contrast agent shell rupture.detected by inertial cavitation and rebound signals", IEEE Transactions, 53(1): 126-136, Jan. 2006.

Emmanuel Gaud, Peter J. A. Frinking, Marcel Arditi, "Acoustic characterization of single ultrasound contrast agent microbubbles", The Journal of the Acoustic Society of America, 124(6): 4091, 2008.

Abbas Sabraoui, Claude Inserra, Bruno Gilles, Jean-Christopher Bera, Jean-Louis Mestas, "Feedback loop process to control acoustic cavitation" Ultrasonics Sonochemistry 18(2): 589-594, Mar. 2011.

Yao-Sheng Tung, Fotis Vlachos, Thomas Deffieux, James Choi, "Noninvasive in vivo cavitation threshold detection during blood-brain barrier opening using focused ultrasound and the contrast agent and definity", Joint 159th Meeting of the Acoustic Society of America, Apr. 19, 2010.

Choi et al., "Focused Ultrasound-Induced Molecular Delivery Through the Blood-Brain Barrier", presented at the IEEE Symp. Ultrason. Ferroelect. Freq. Control, New York, NY, Oct. 28-31, 2007.

Konofagou et al., "noninvasive Electromechanical Wave Imaging and Conduction Velocity Estimation *In Vivo*", Ultrasonics Symposium, 2007 IEEE, pp. 969-972, 2007.

Sandberg et al., "Brief Communicatoin: Neural transplants disrupt the blood-brain barrier and allow peripherally acting drugs to exert a centrally mediated behavioral effect", Experimental Neurology, vol. 102, pp. 149-152, 1988.

U.S. Appl. No. 12/096,254, Dated Oct. 5, 2011 Non-Final Office Action.

U.S. Appl. No. 112/077,612, Dated Oct. 26, 2011 Amendment and Request for Continued Examination (RCE).

* cited by examiner

Sector Data Acquisition

Each Raw Data Sector contains a series of 2D images over a defined period of time (e.g., 1 or more cardiac cycles) for a defined portion of a FOV

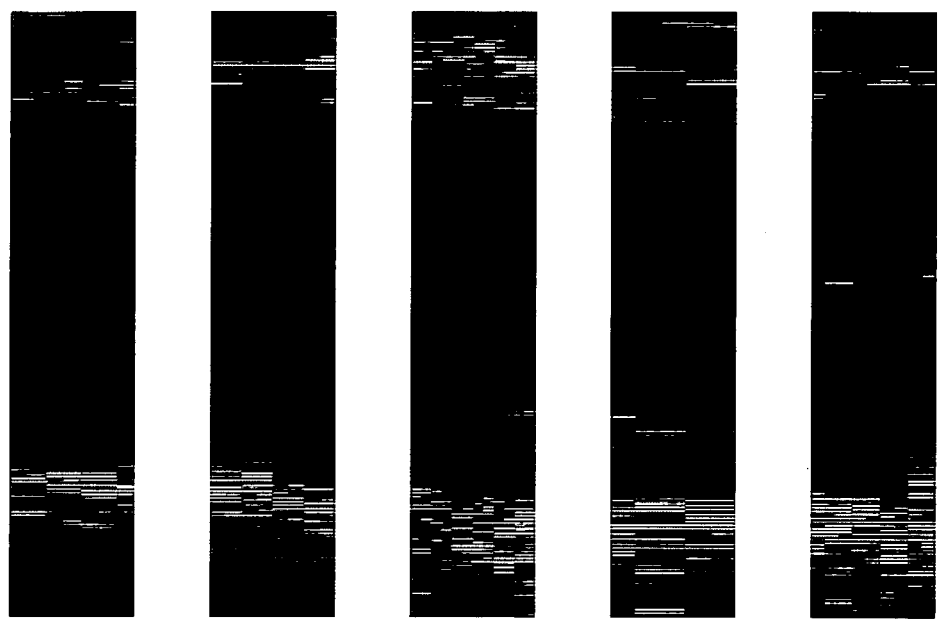
Fig. 4 – Output of 305

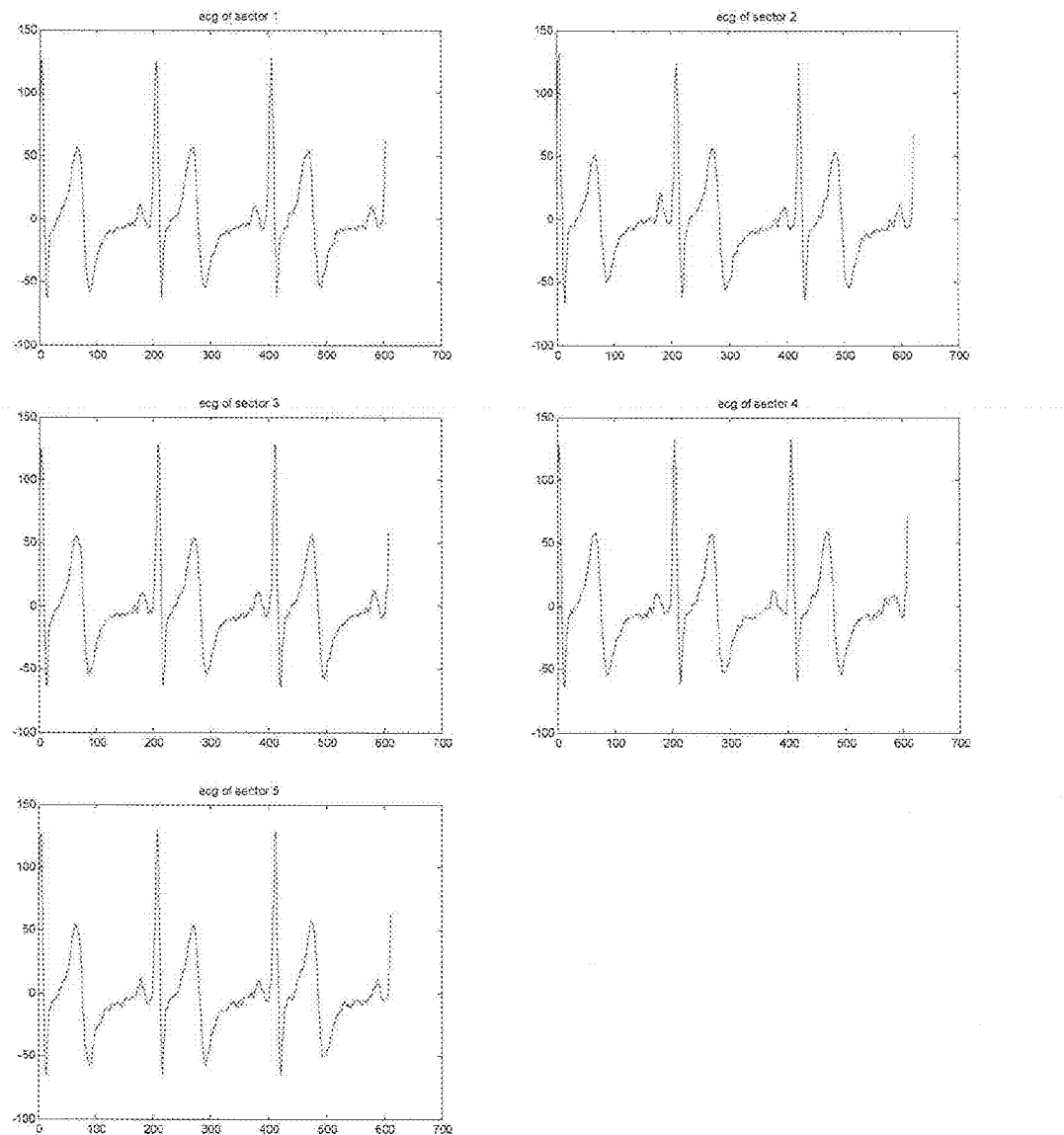
Fig. 5 – Output of 310

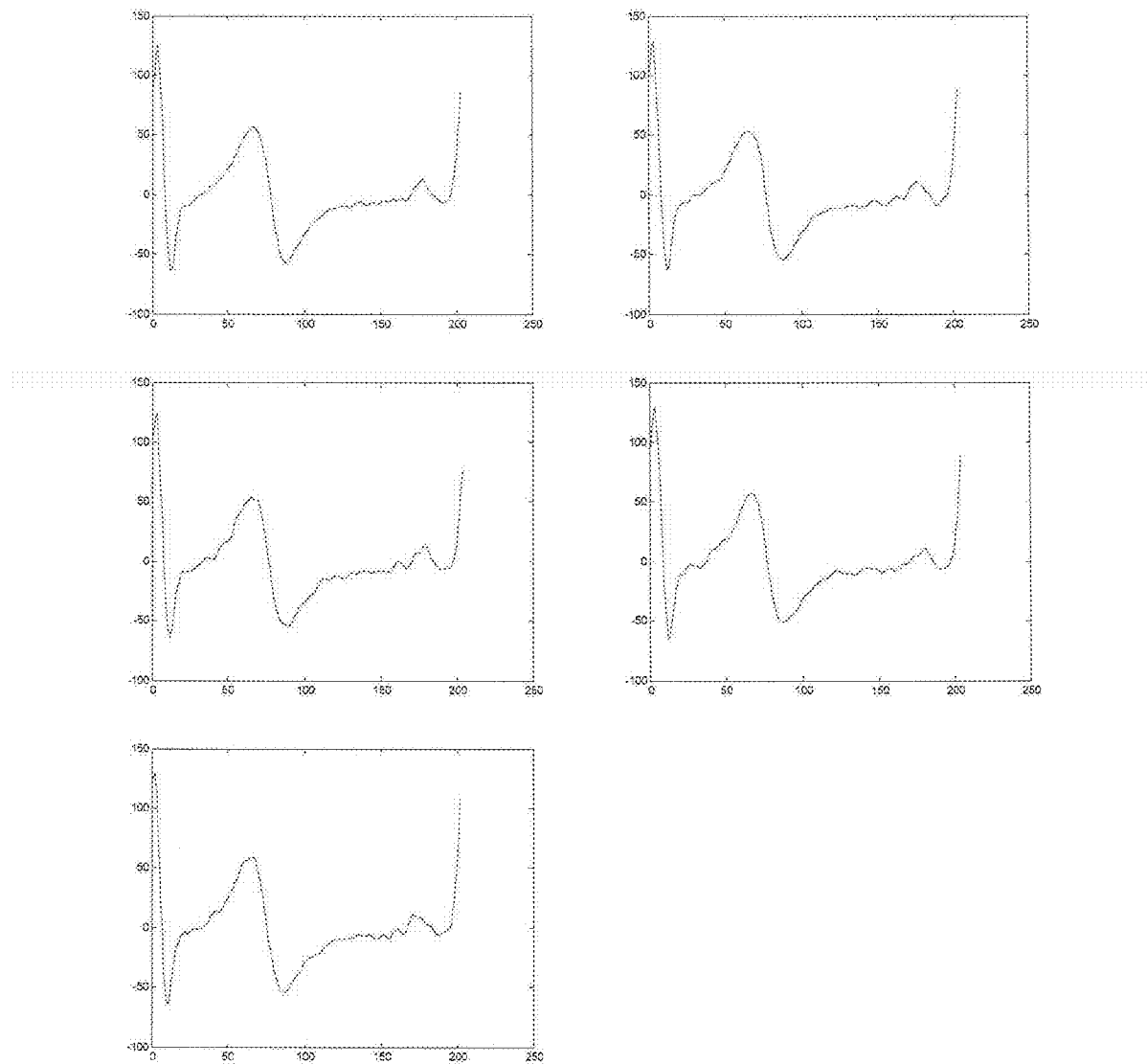
Fig. 6 – Output of 320

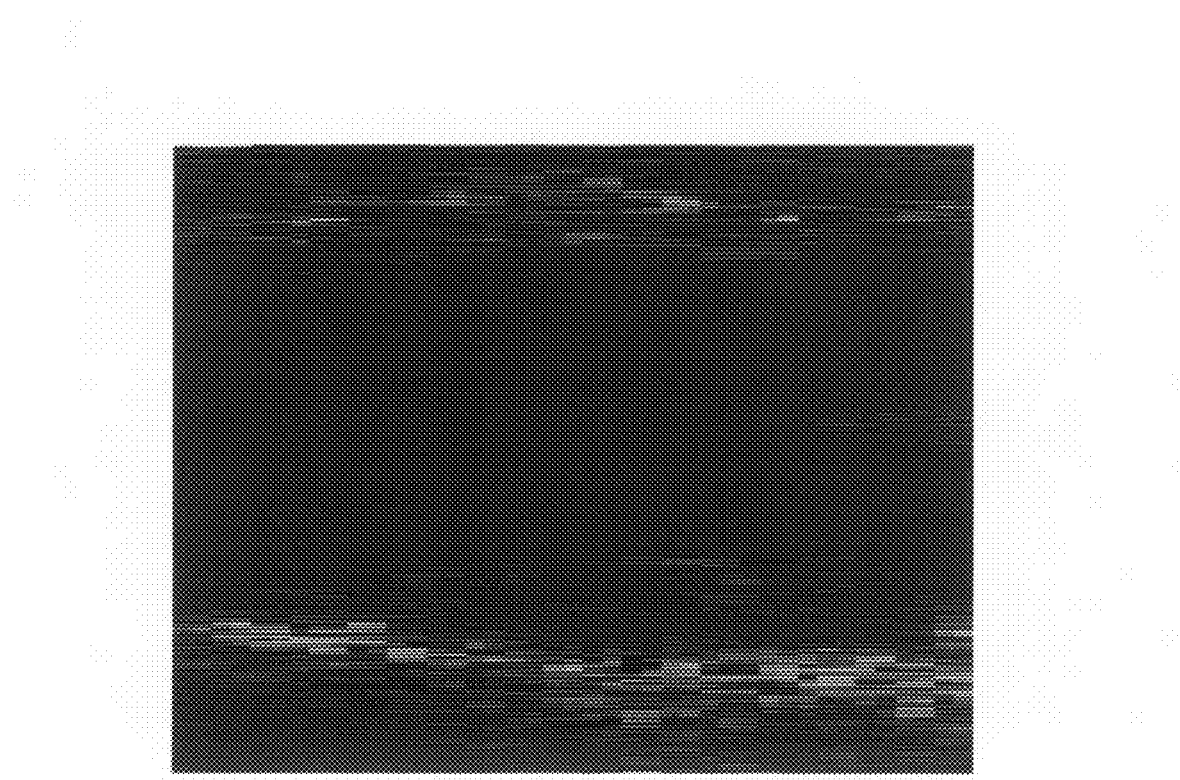
Fig. 7 – Output of 330 incremental lateral displacement
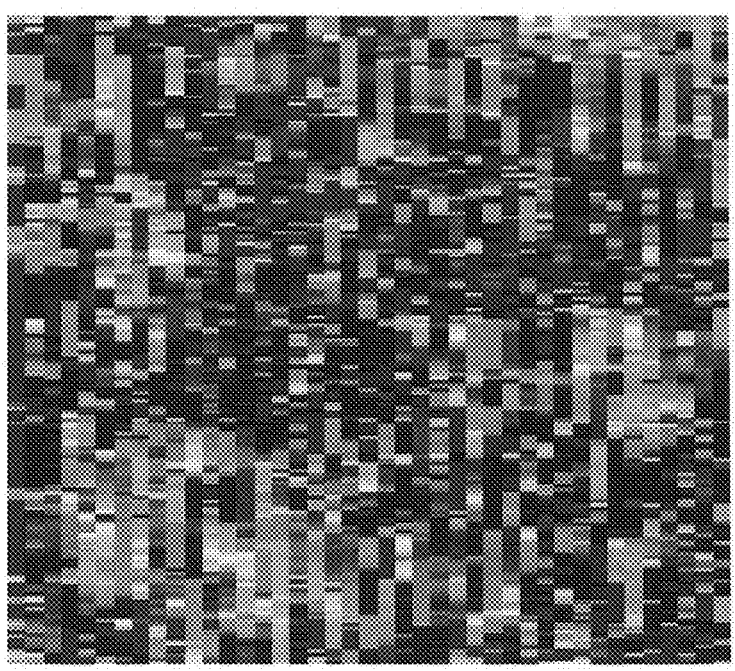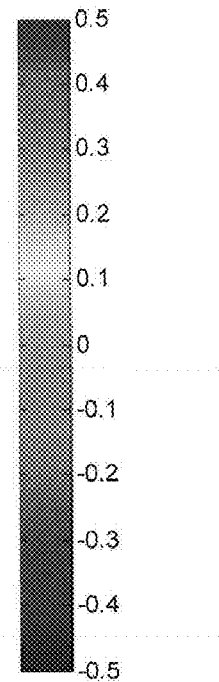
incremental axial displacement
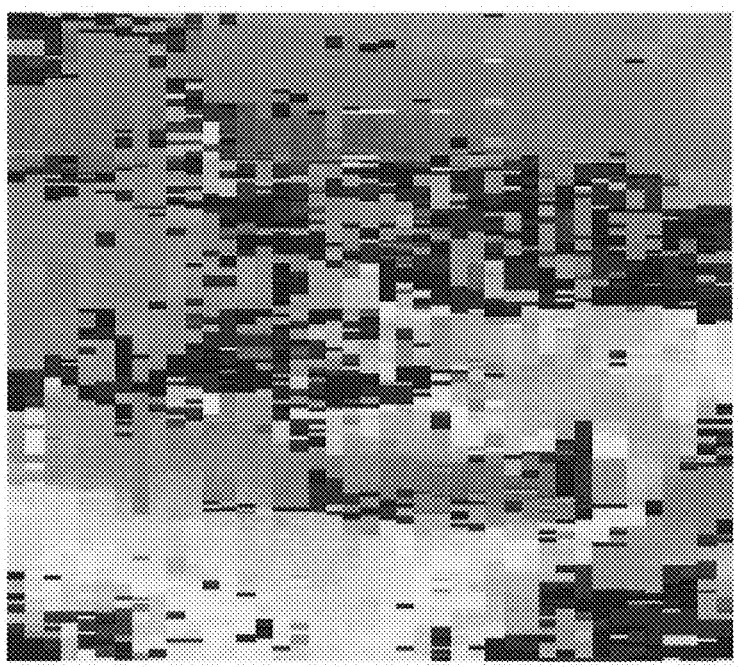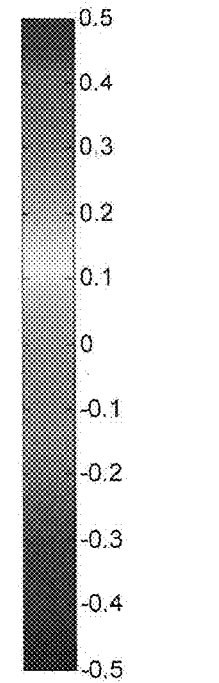
Fig. 8 – Output of 340 incremental lateral displacement
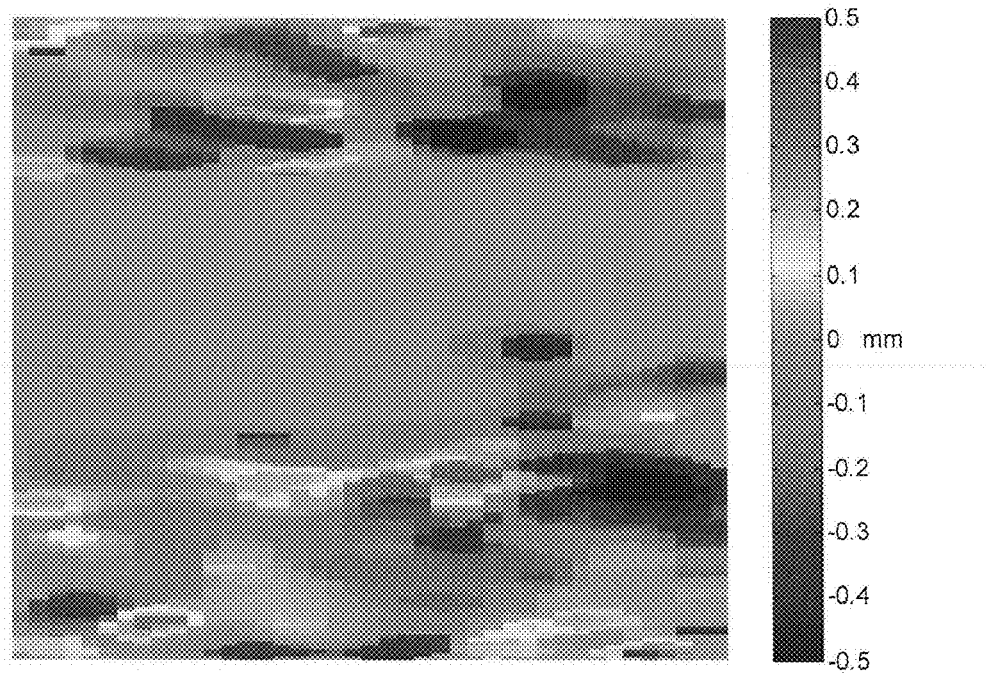
incremental axial displacement
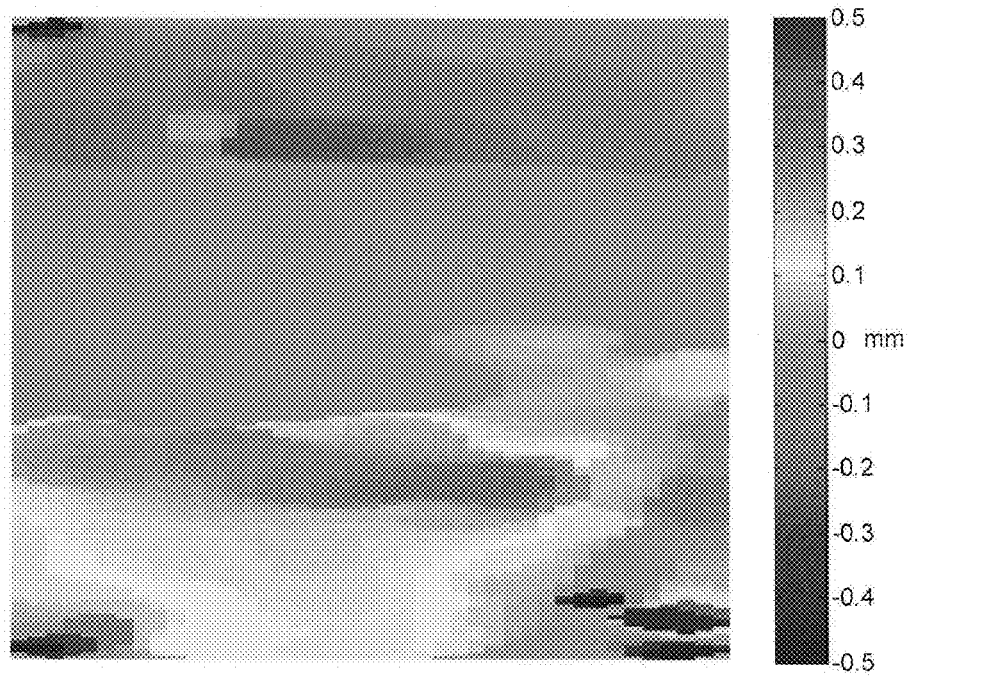
Fig. 9 – Output of 350 cumulative lateral displacement
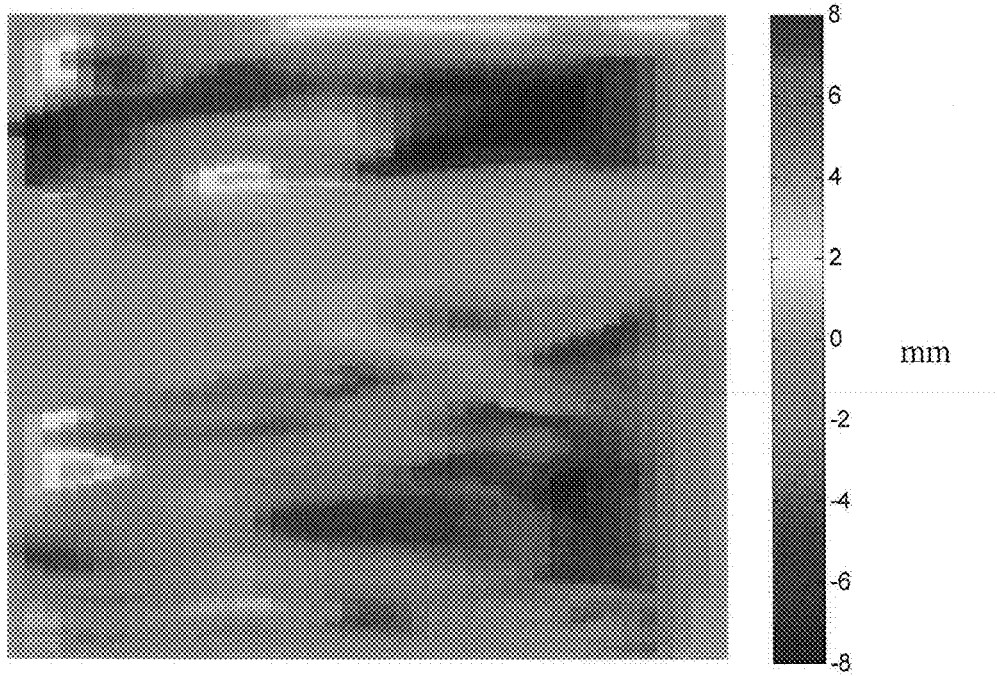
cumulative axial displacement
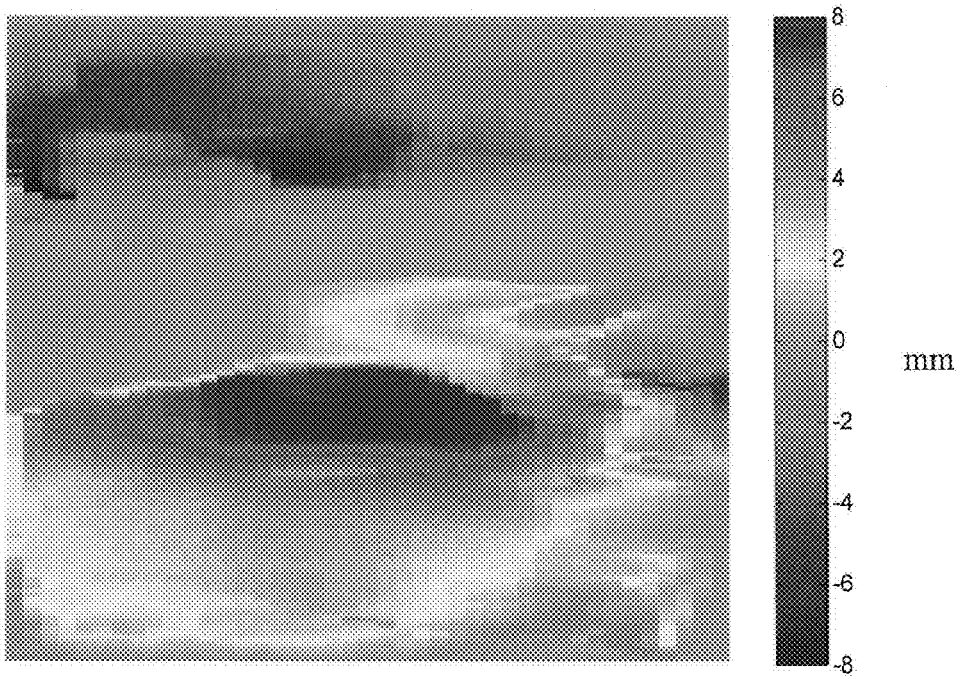
Fig. 10 – Output of 360 cumulative lateral strain
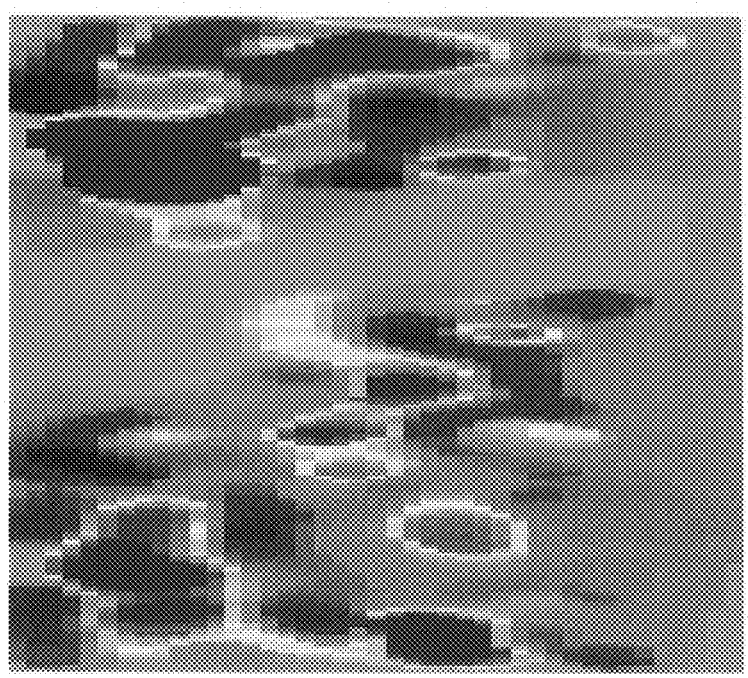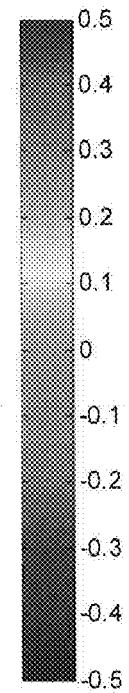
cumulative axial strain
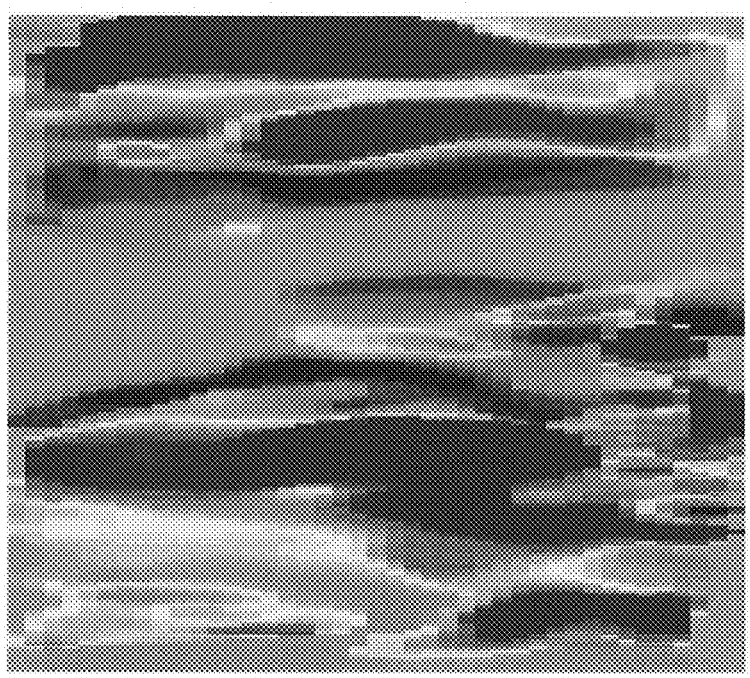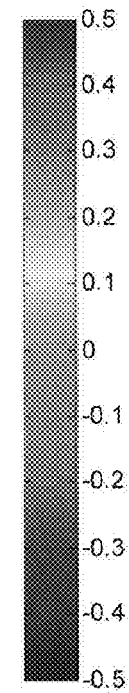
Fig. 11 – Output of 365

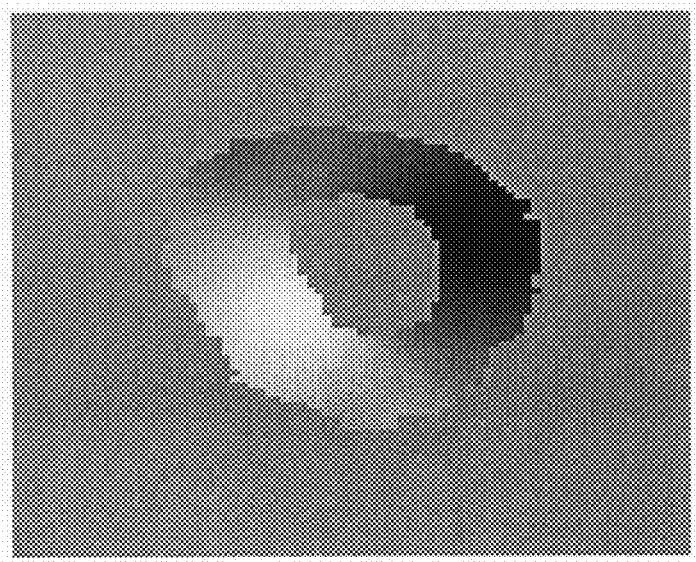
Fig. 12A(a)

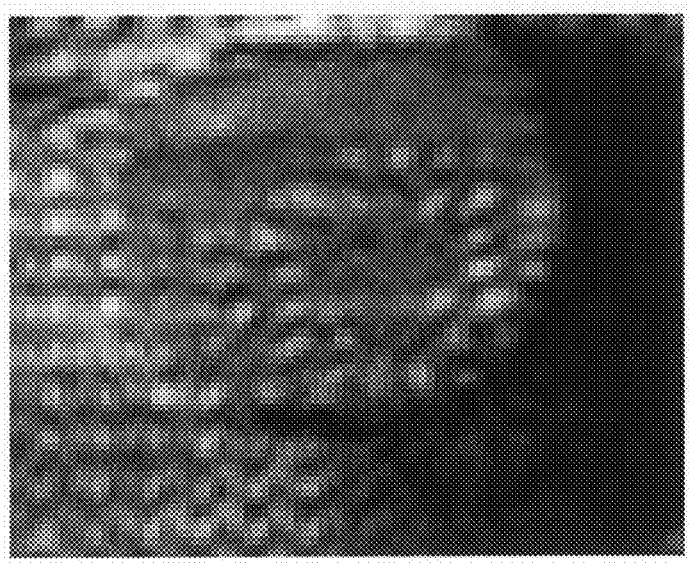
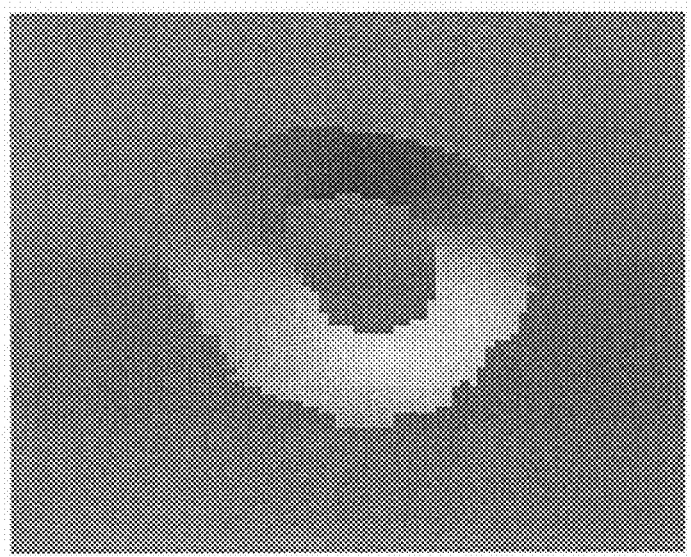
Fig. 12A(c)

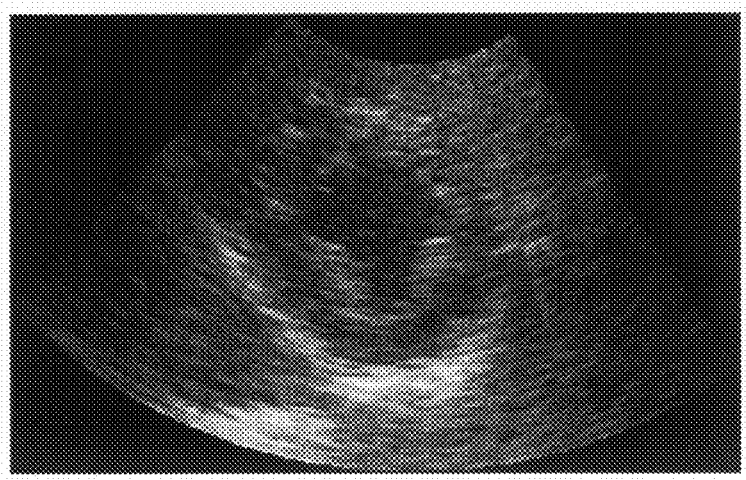
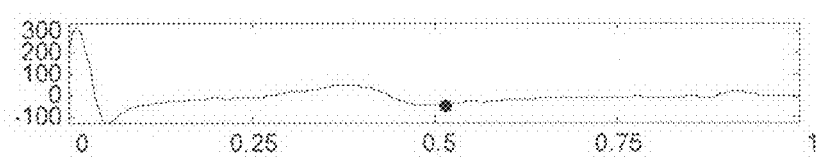
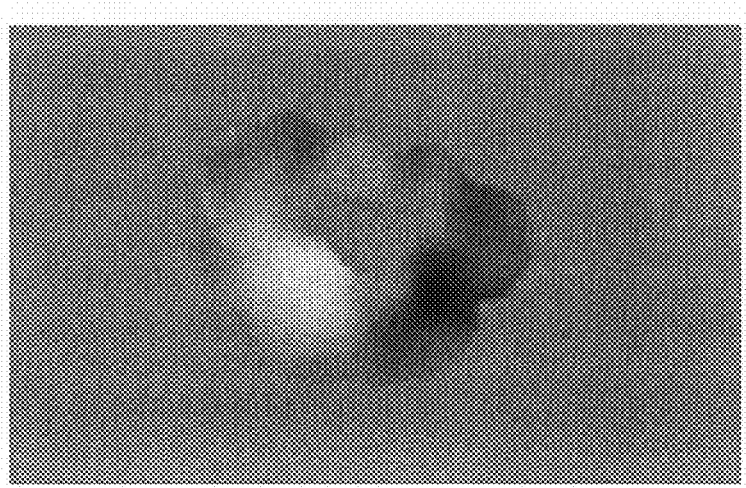
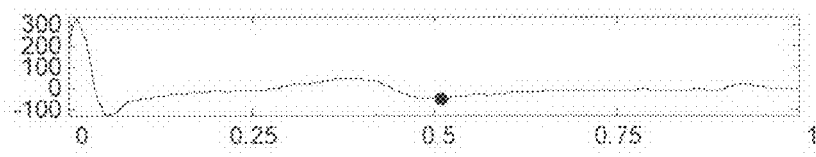
Fig. 12A(d)

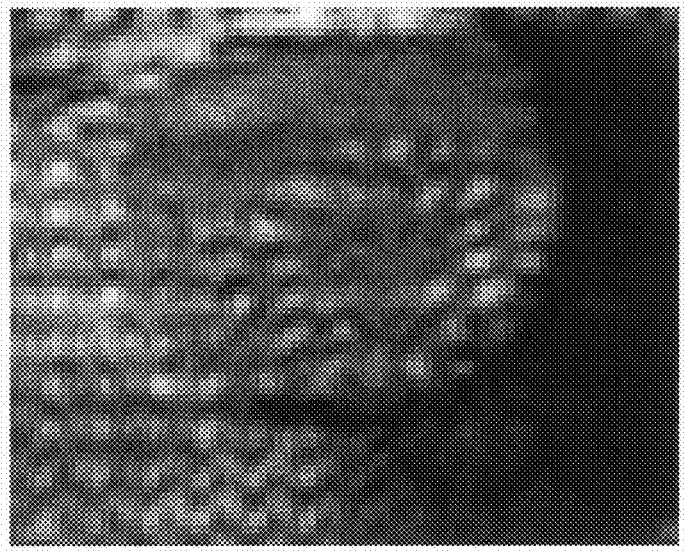
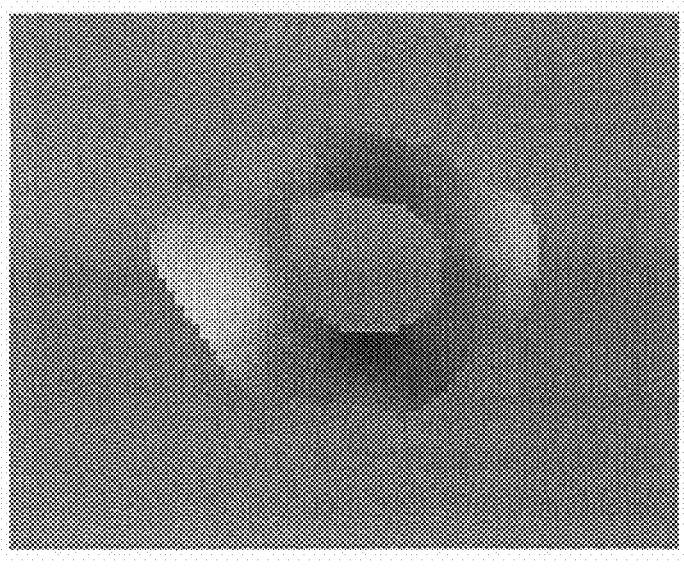
Fig. 13A(a)

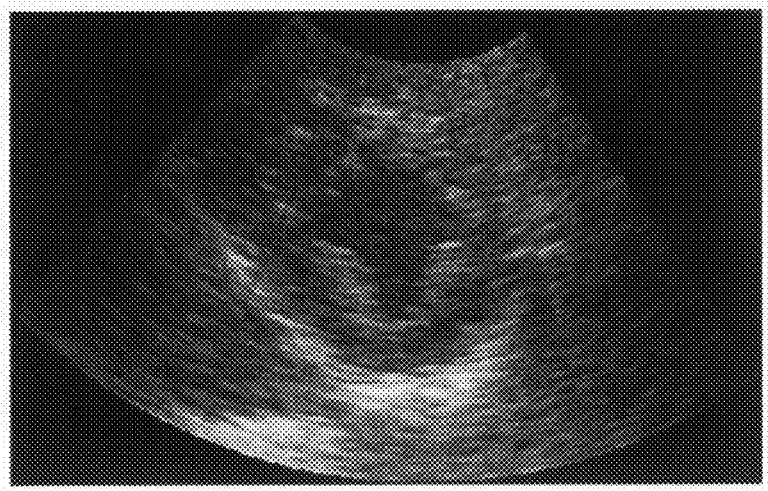
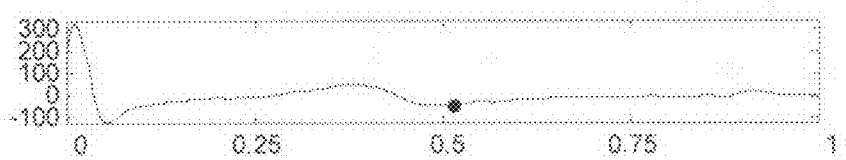
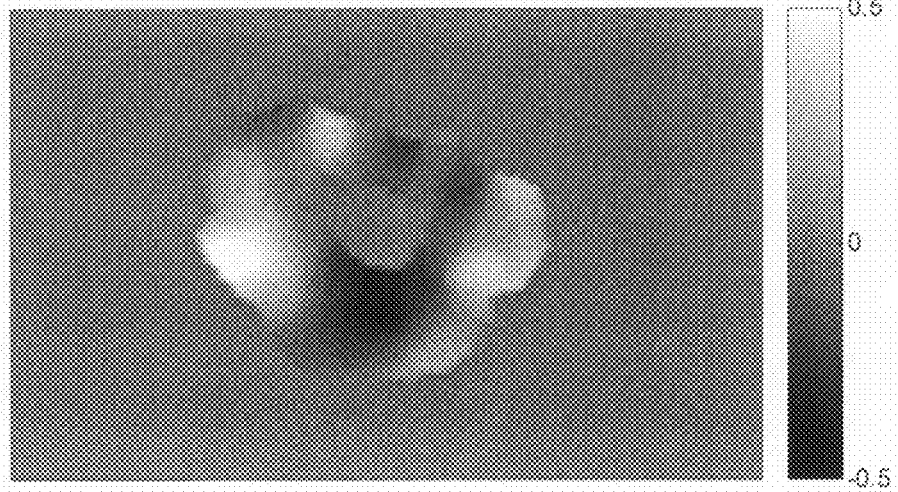
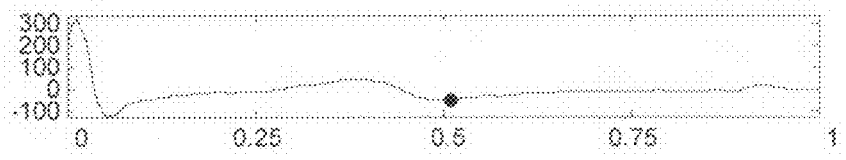
Fig. 13A (b)

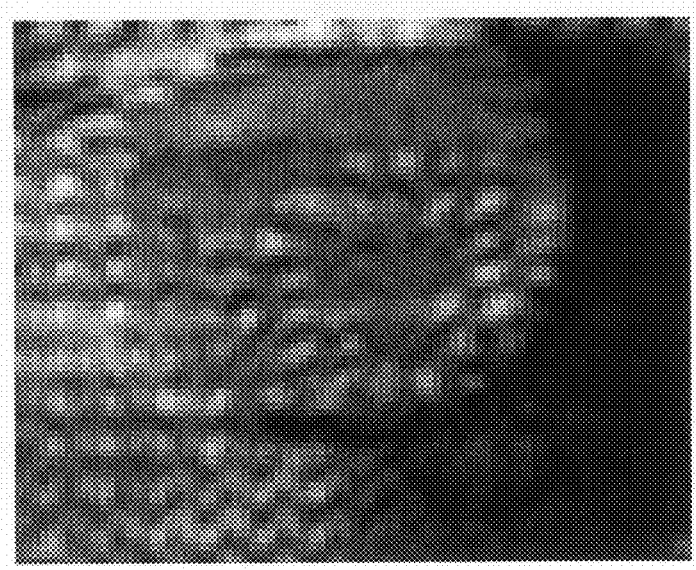
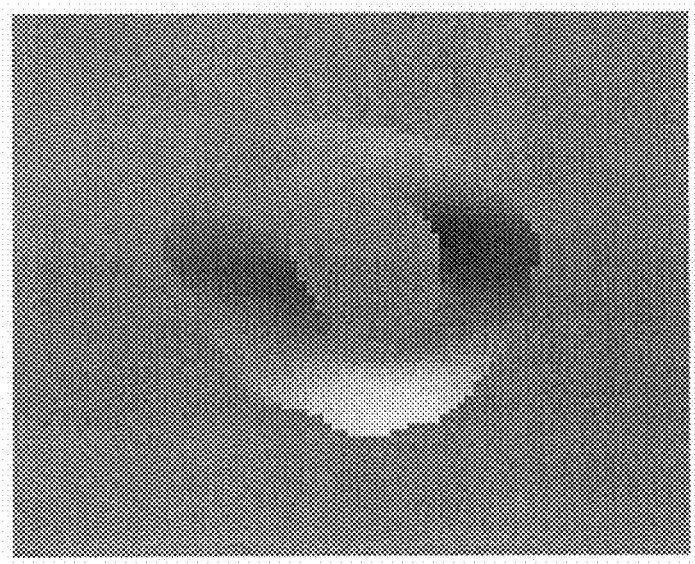
Fig. 13A(c)

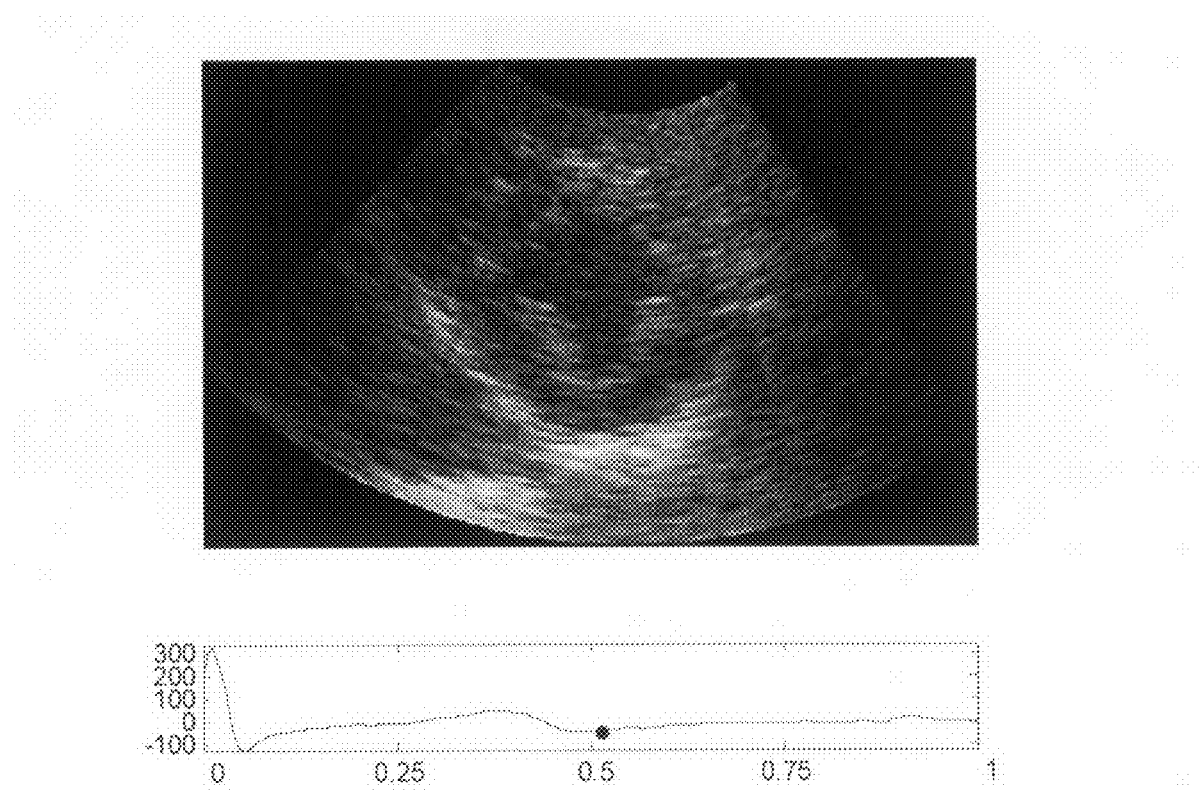
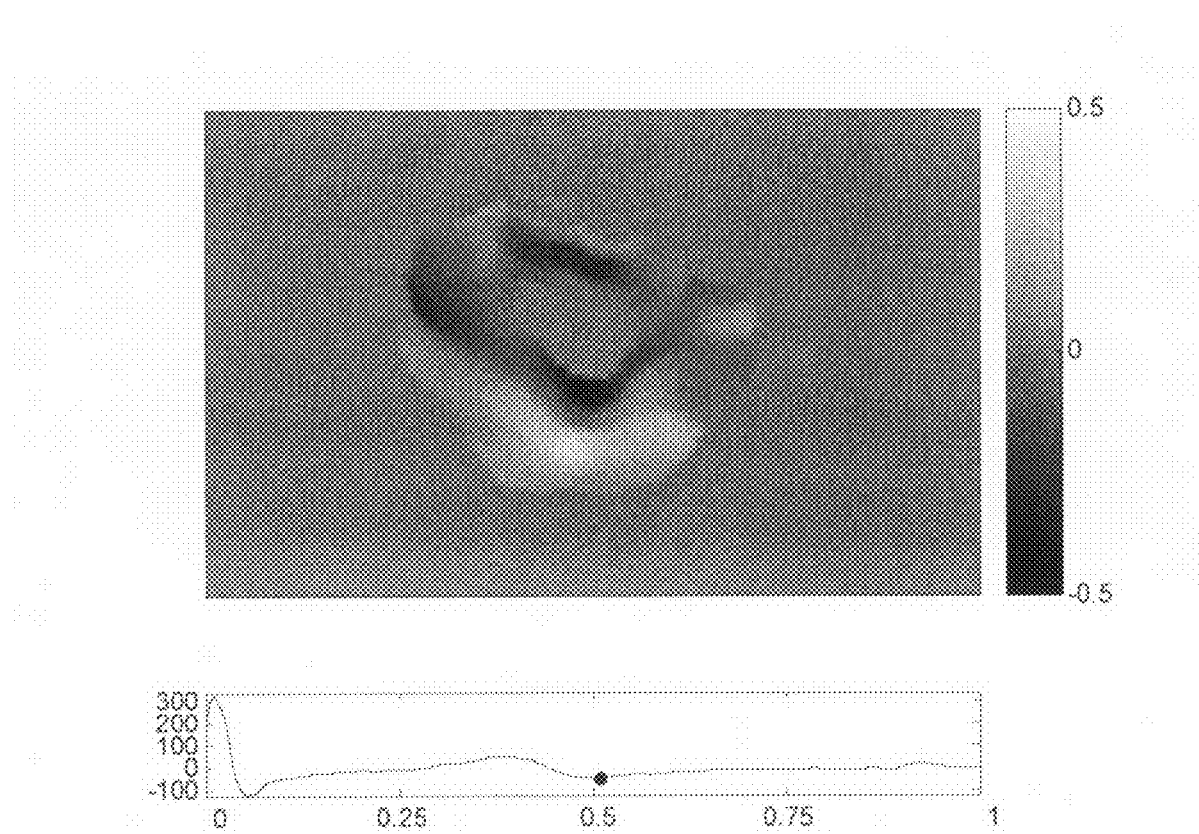
Fig. 13A(d)

B-mode image 325
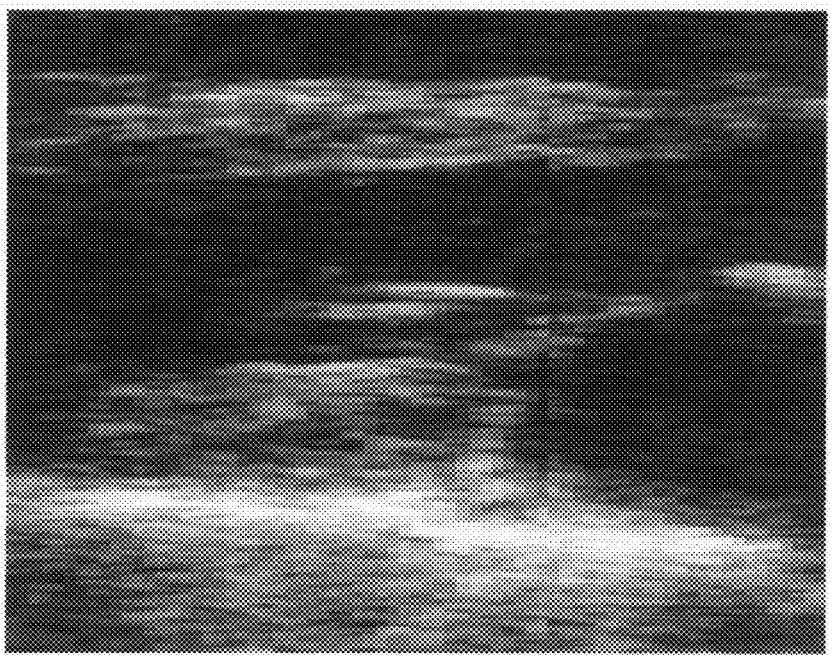
scan-converted B-mode image
Fig. 14 – Output of 325

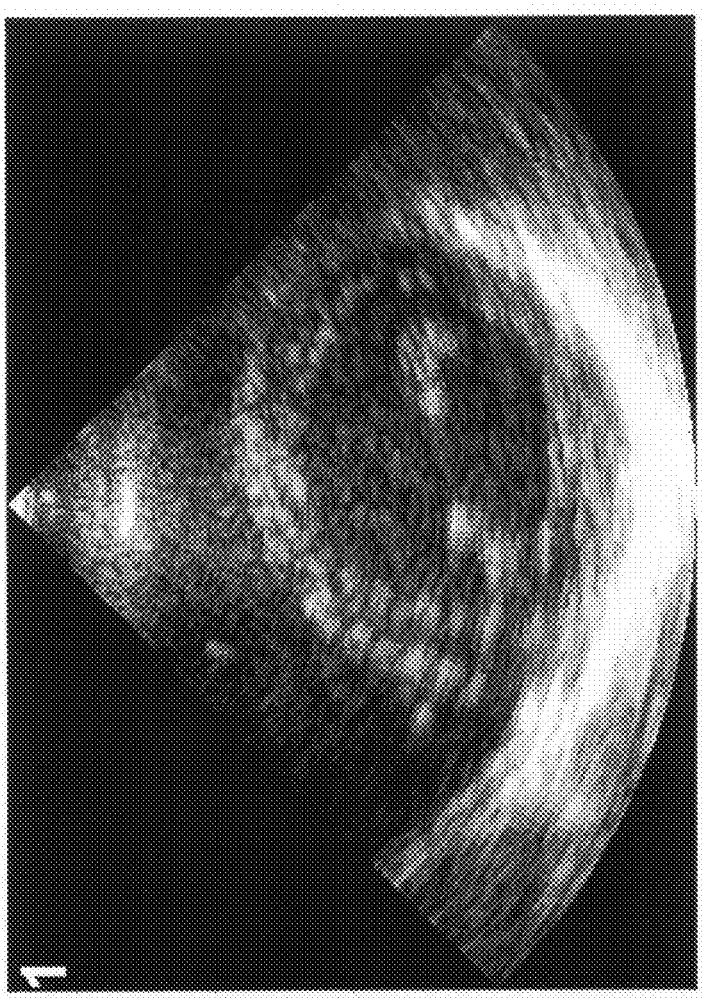
Fig. 15 – Exemplary B-Mode Image

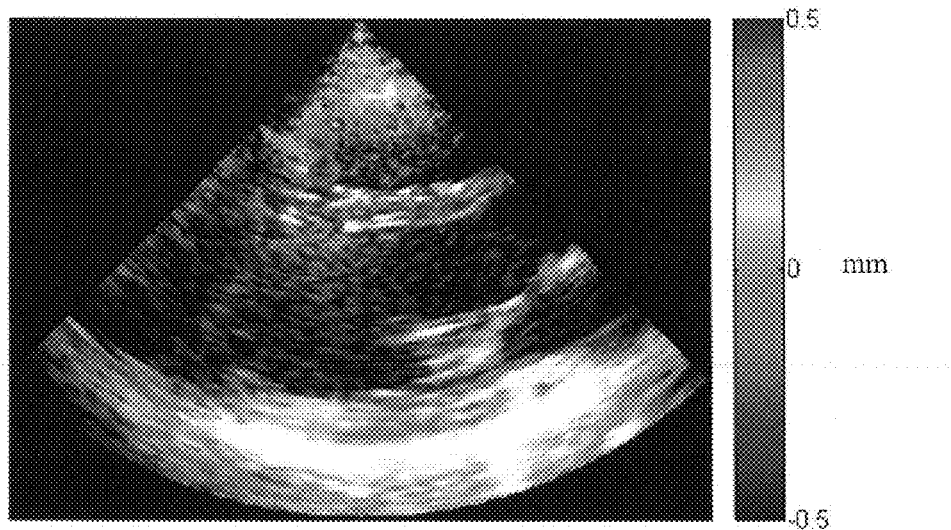
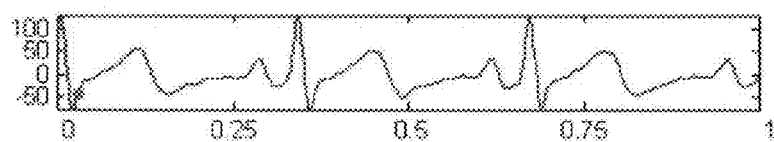
Fig. 16(a)
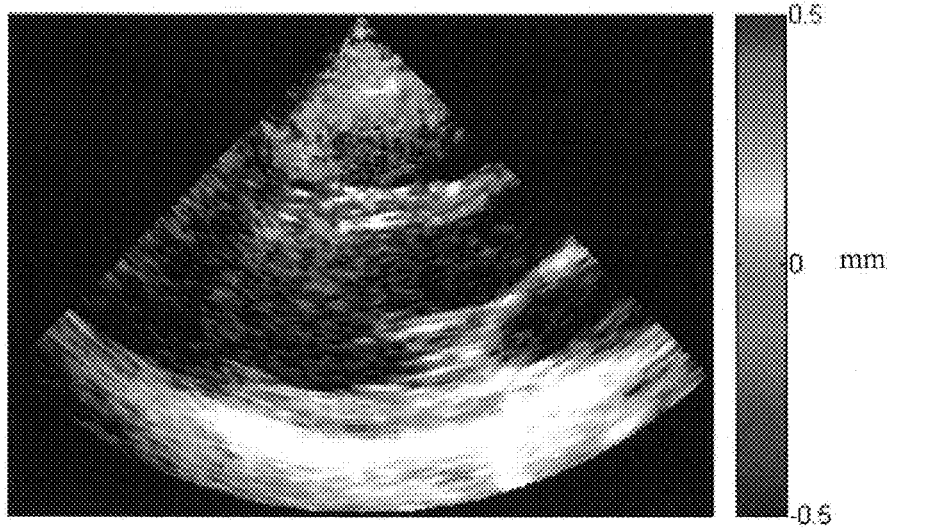
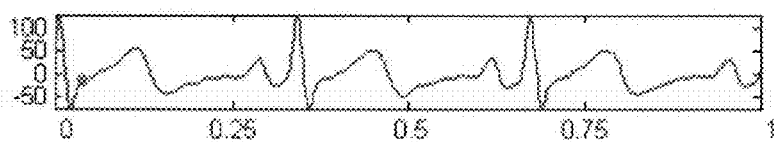
Fig. 16(b)

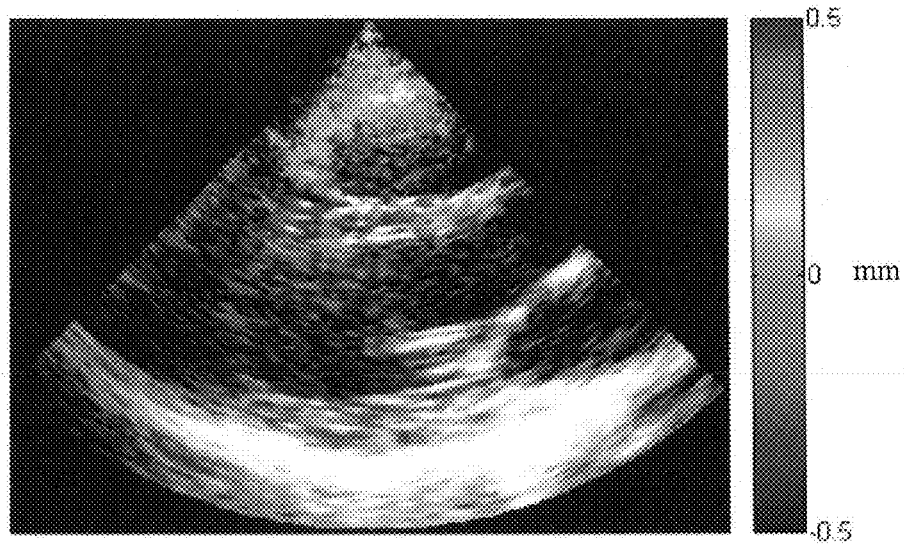
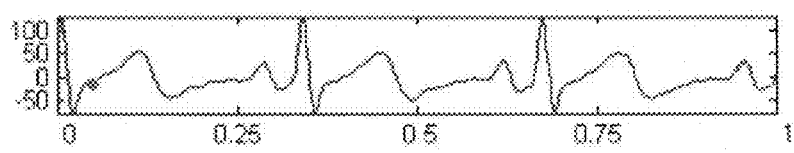
Fig. 16(c)
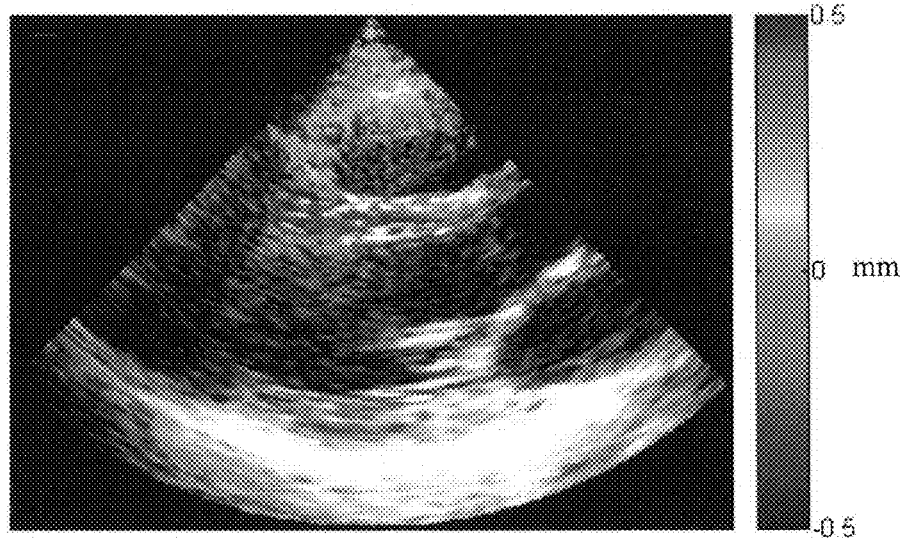
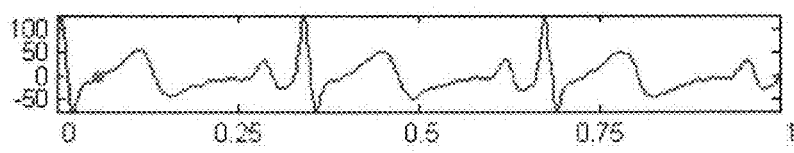
Fig. 16(d)

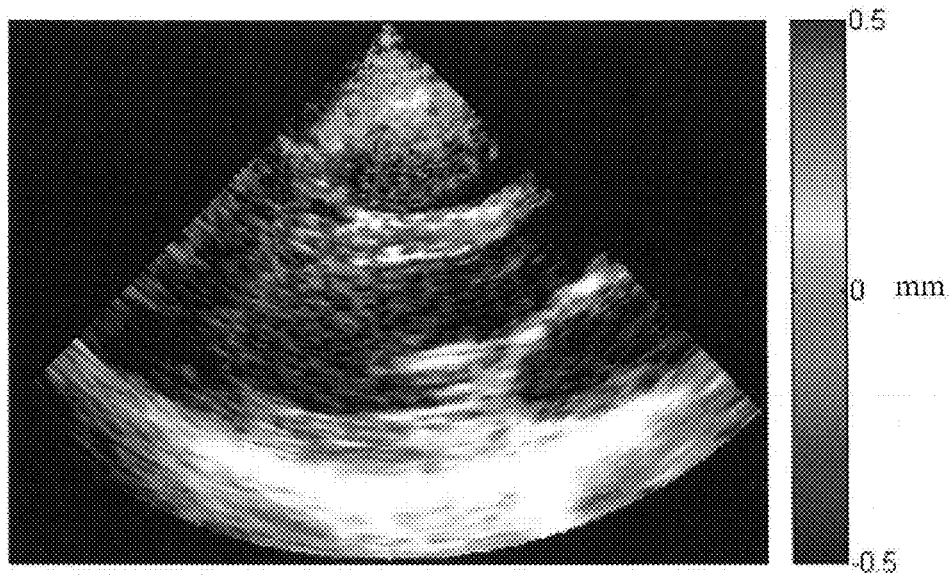
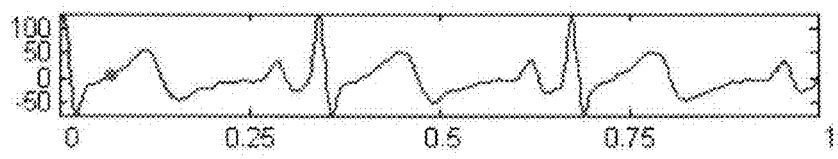
Fig. 16(e)
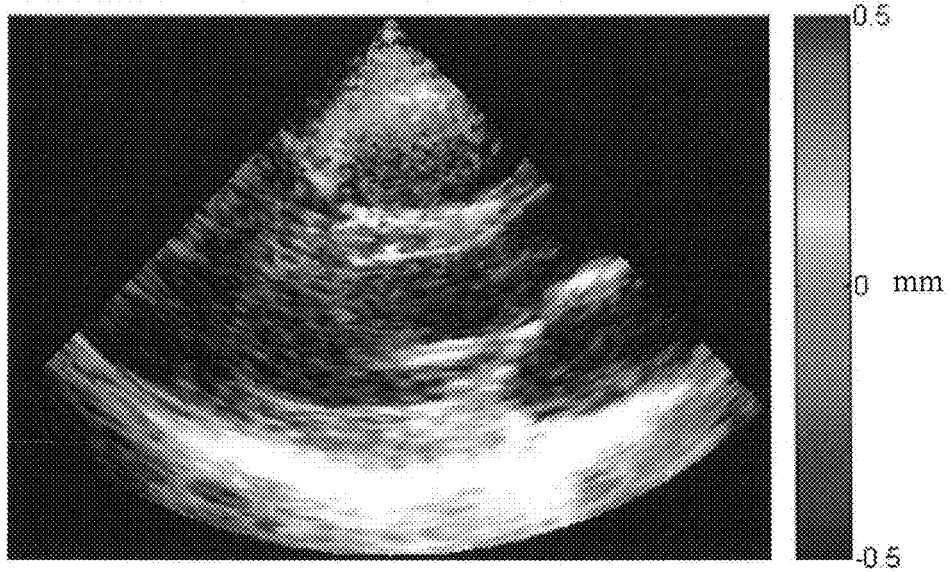
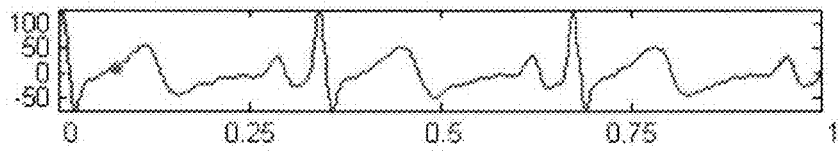
Fig. 16(f)

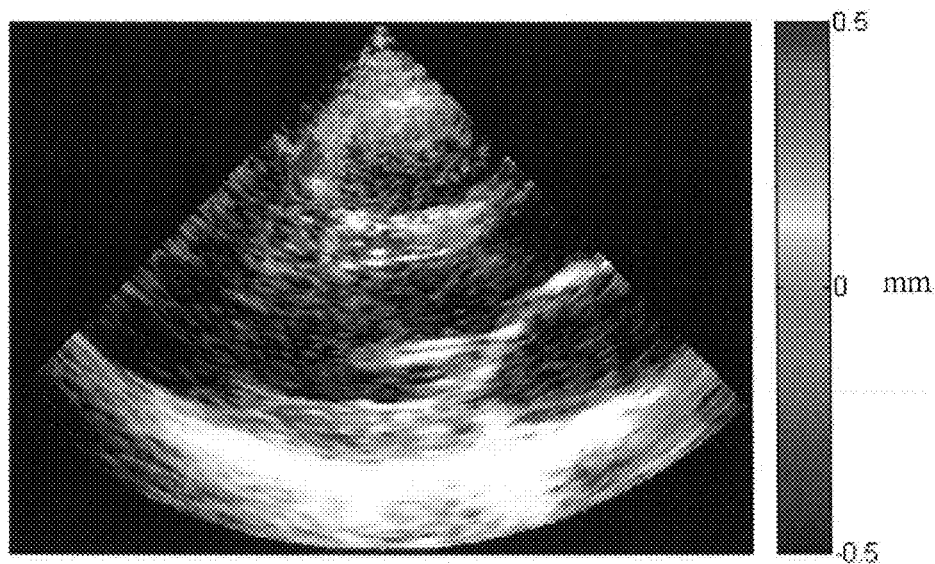
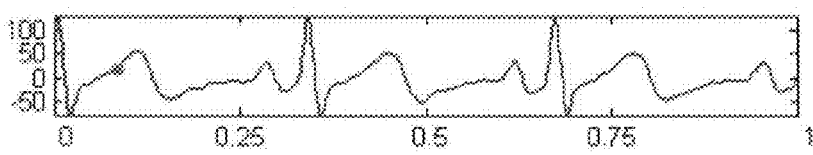
Fig. 16(g)
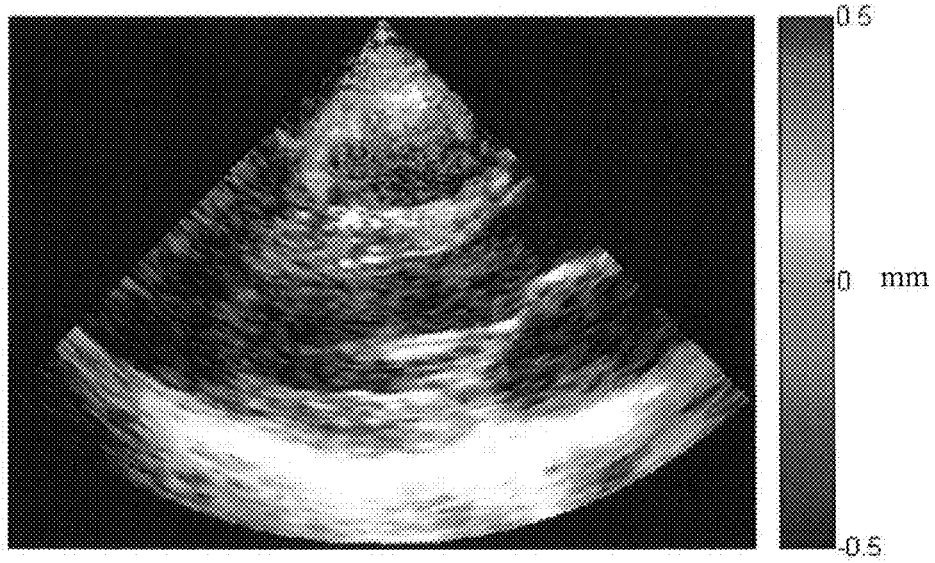
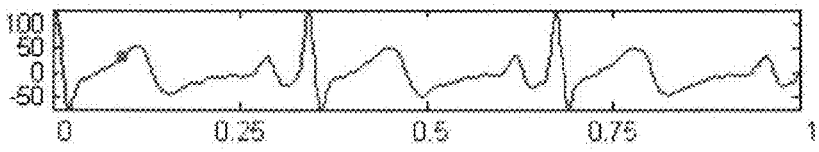
Fig. 16(h)

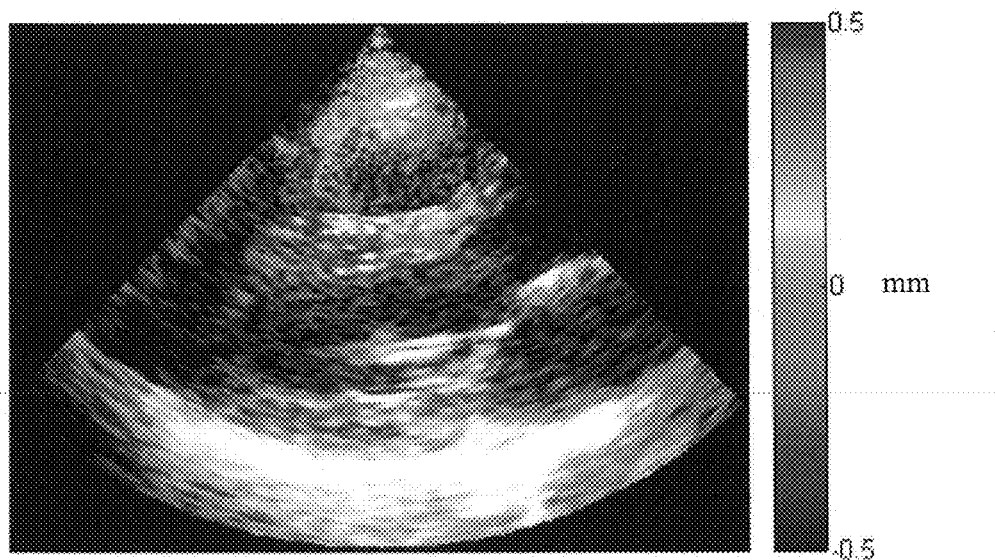
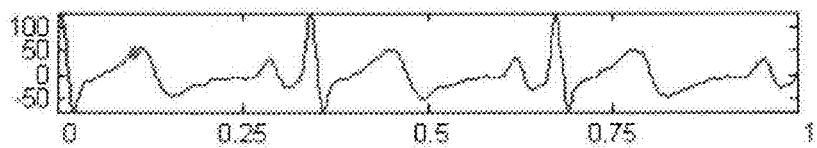
Fig. 16(i)
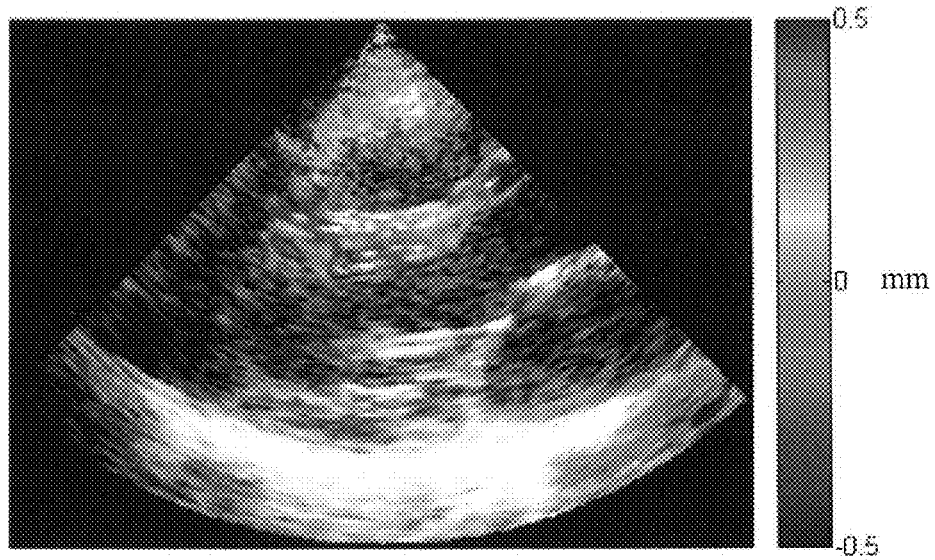
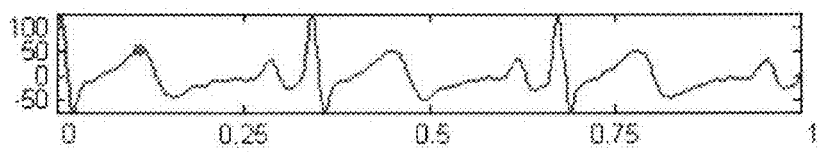
Fig. 16(j)

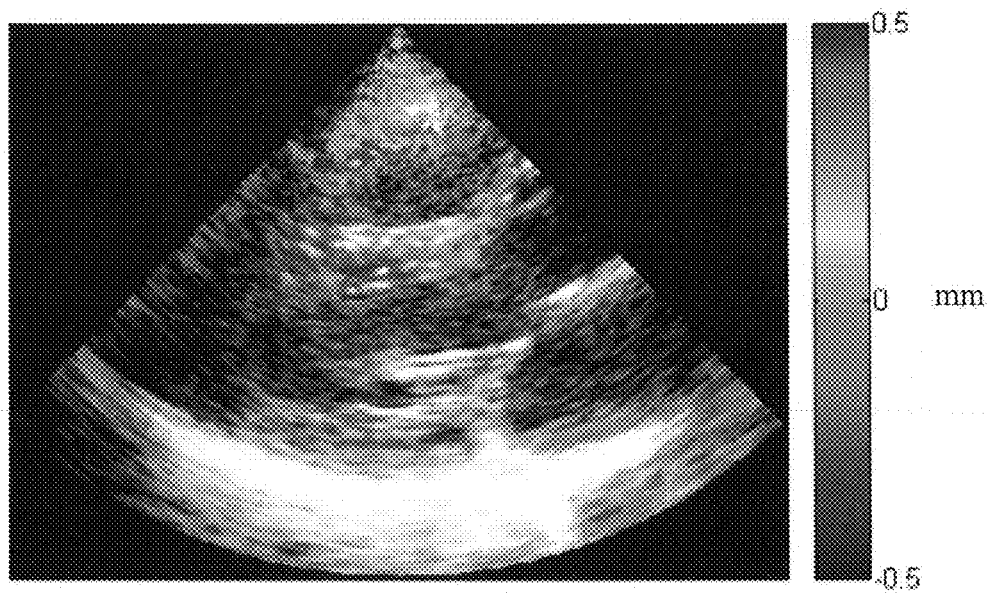
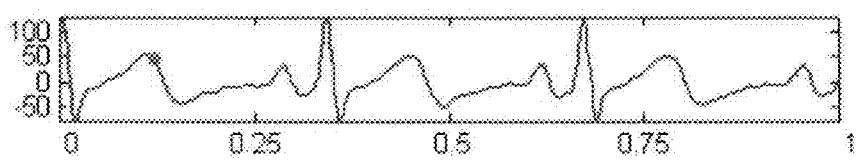
Fig. 16(k)
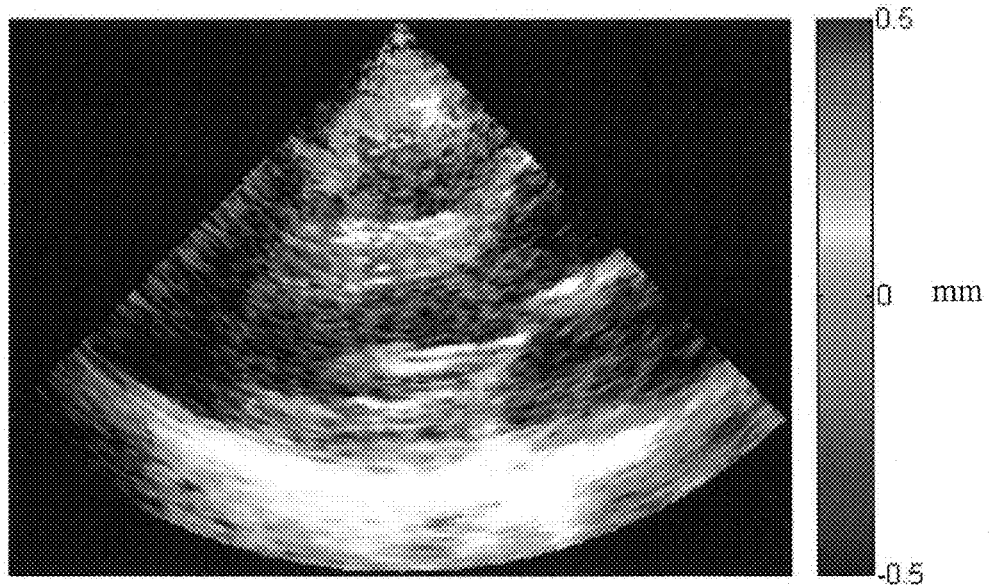
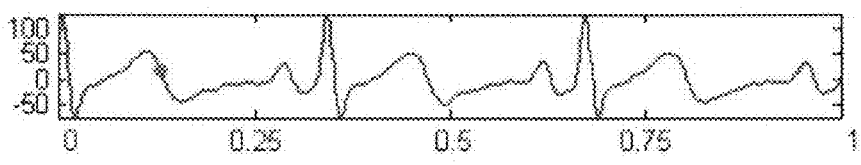
Fig. 16(l)

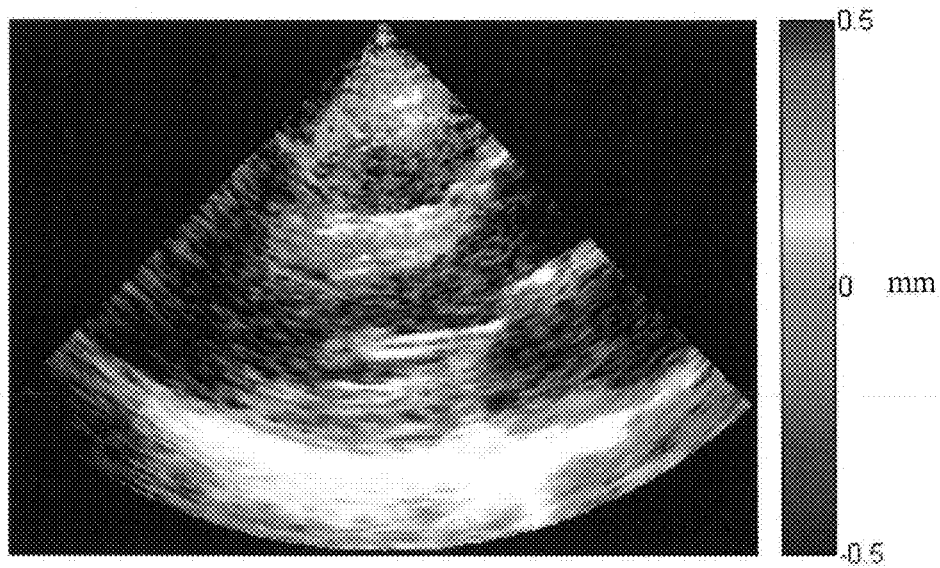
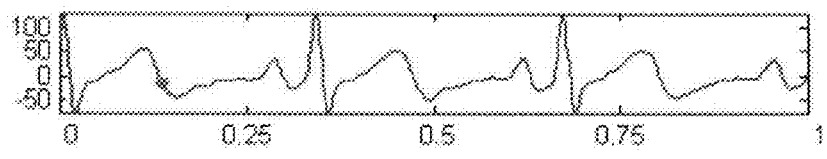
Fig. 16(m)
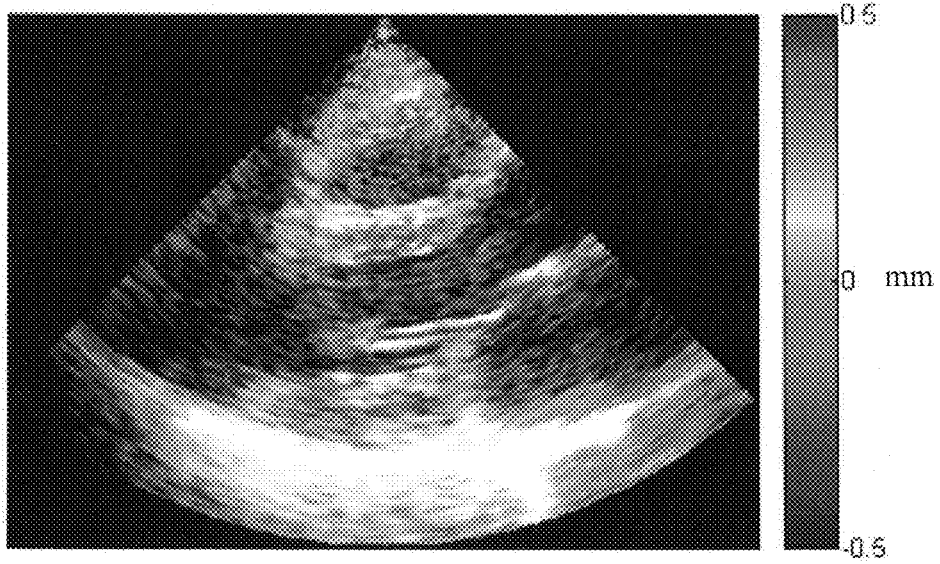
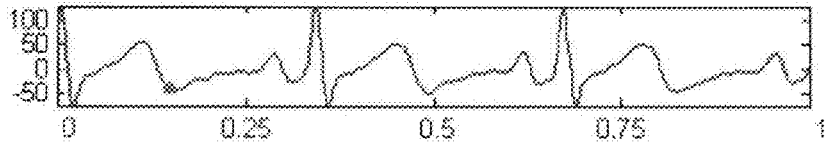
Fig. 16(n)

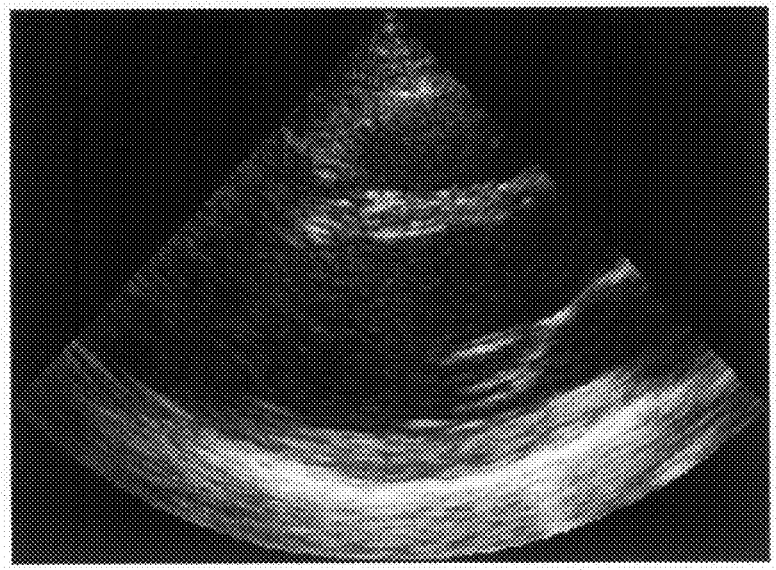
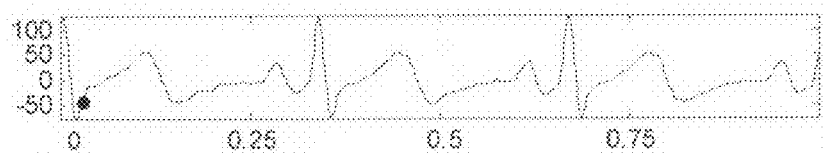
Fig. 16A(a1)
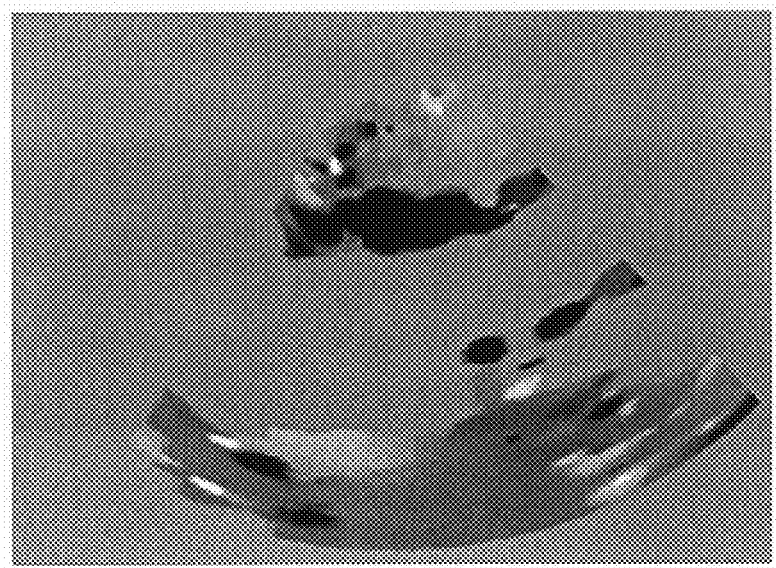
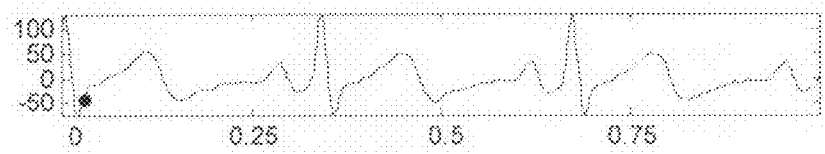
Fig. 16A(a2)

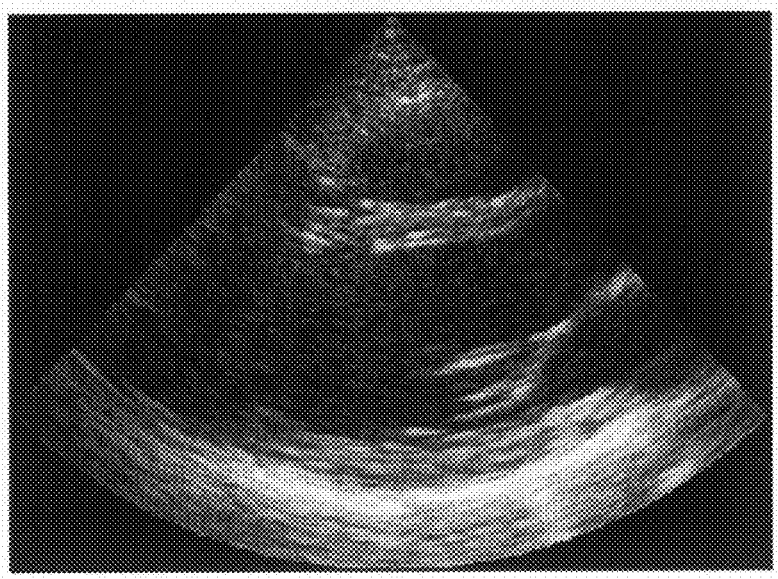
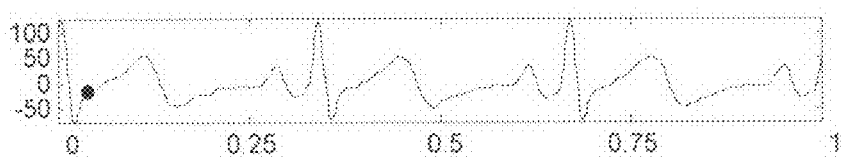
Fig. 16A(b1)
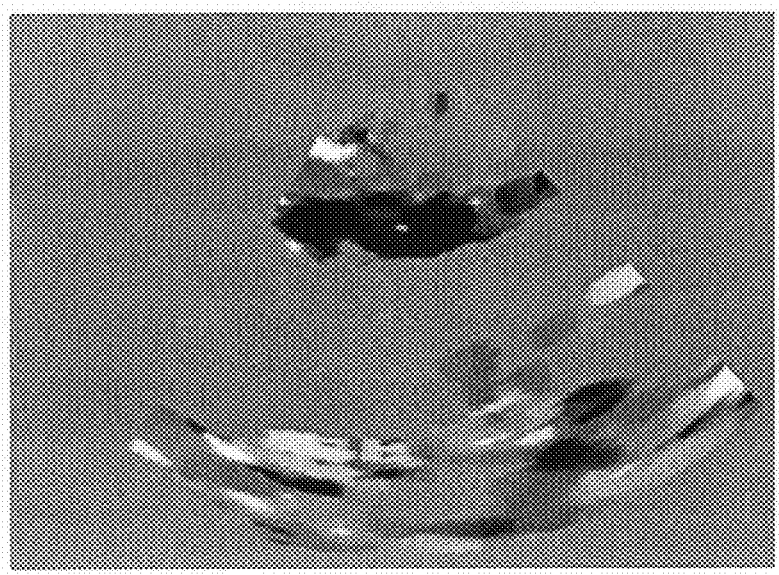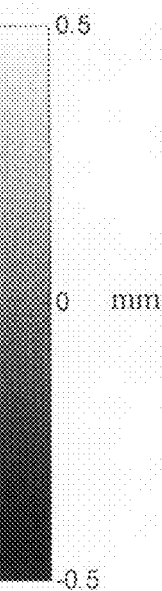
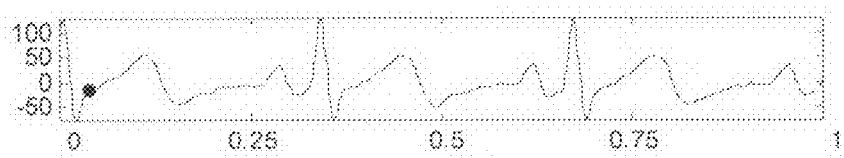
Fig. 16A(b2)

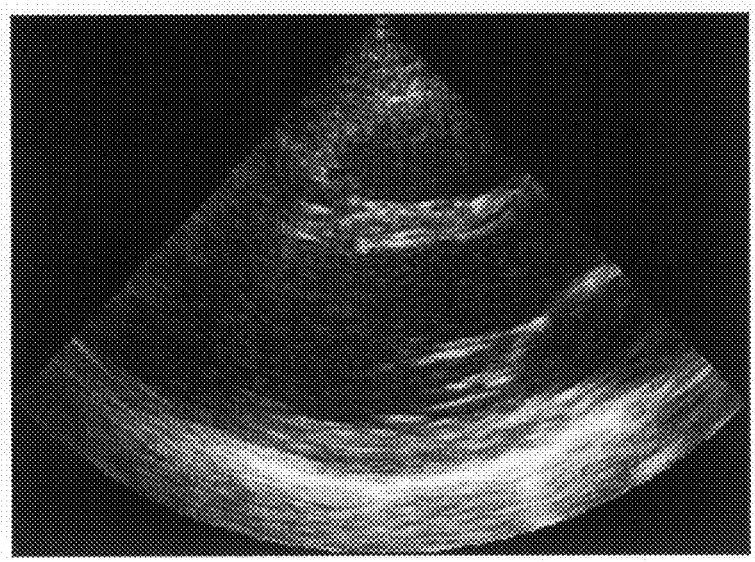
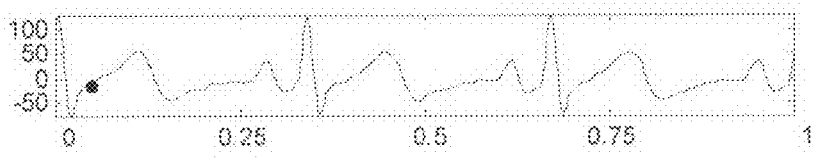
Fig. 16A(c1)
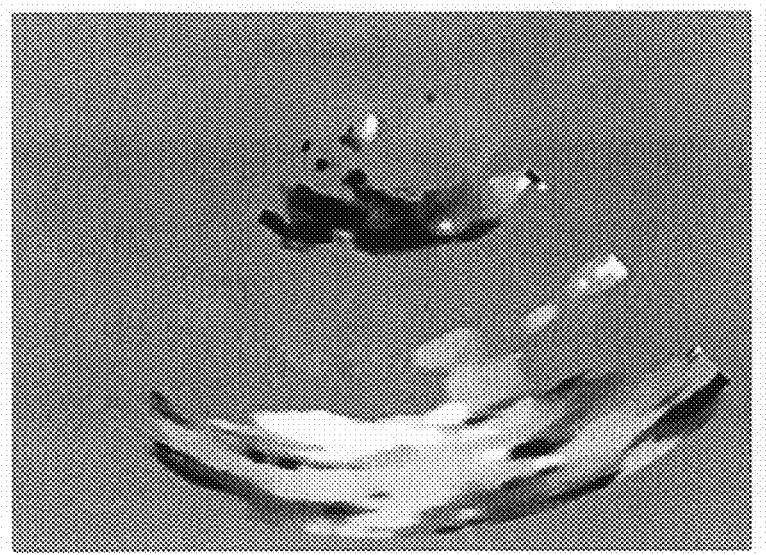
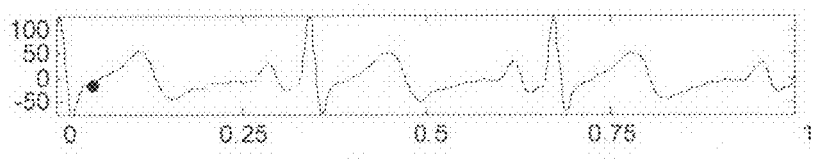
Fig. 16A(c2)

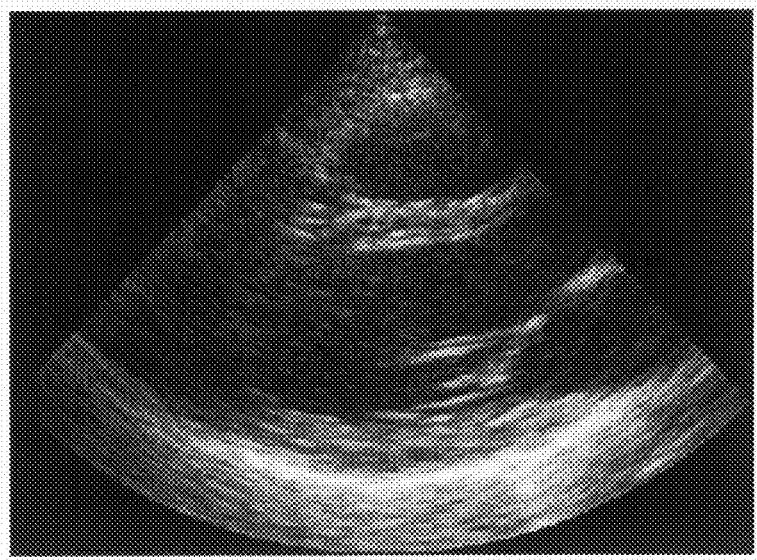
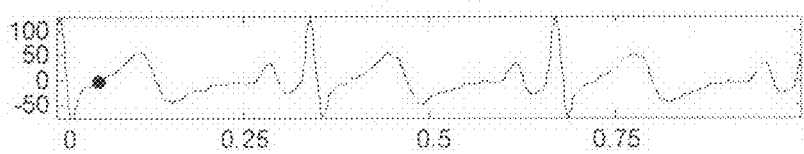
Fig. 16A(d1)
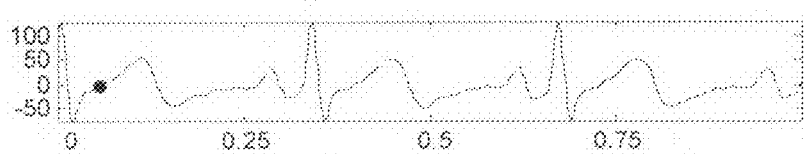
Fig. 16A(d2)

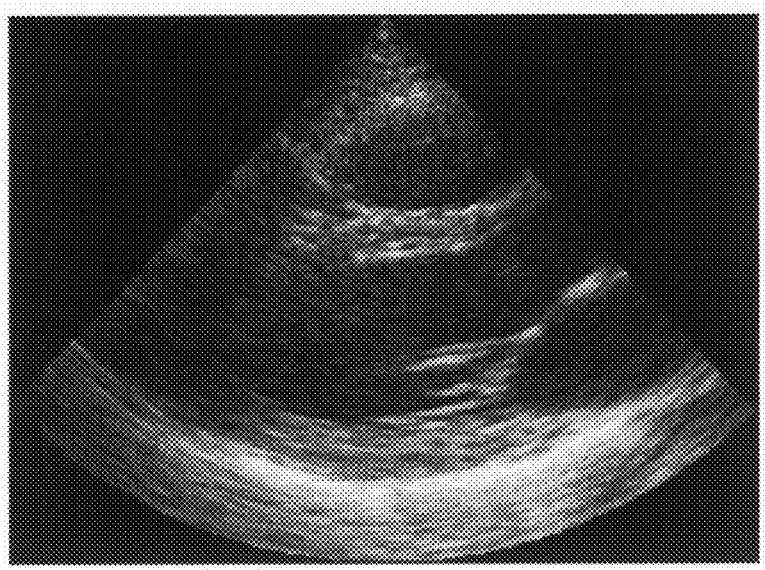
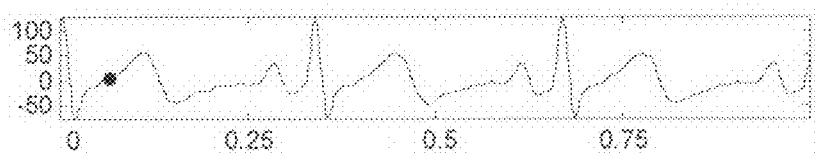
Fig. 16A(e1)
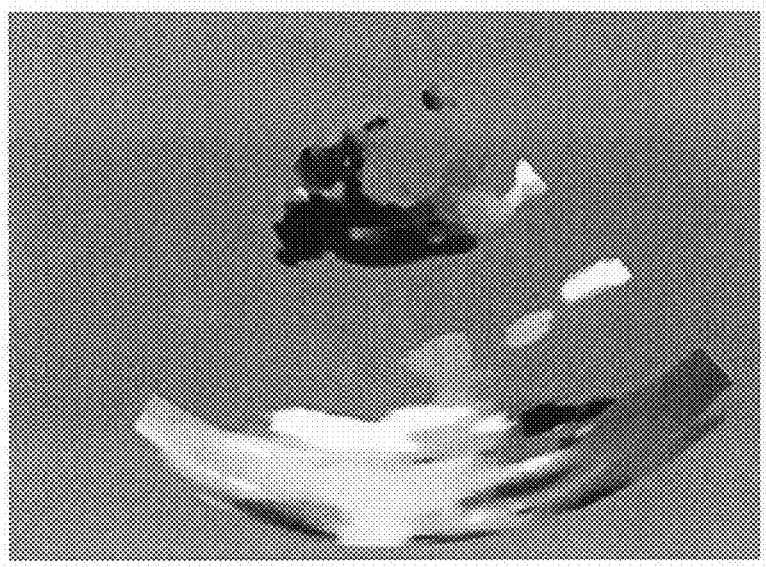
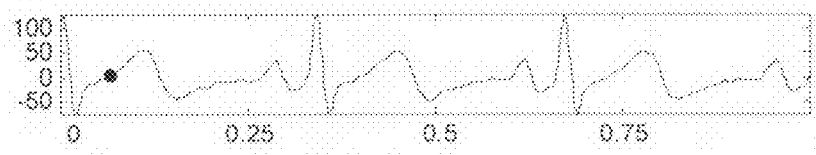
Fig. 16A(e2)

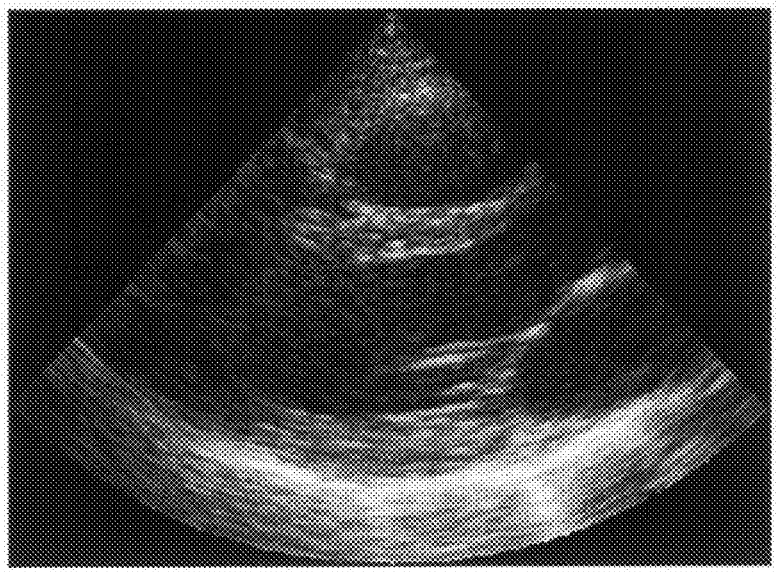
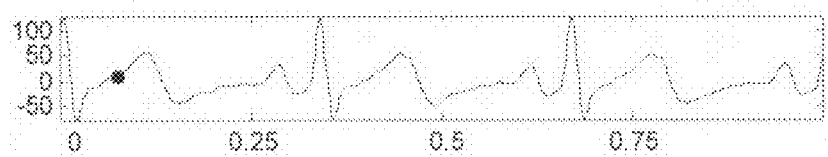
Fig. 16A(f1)
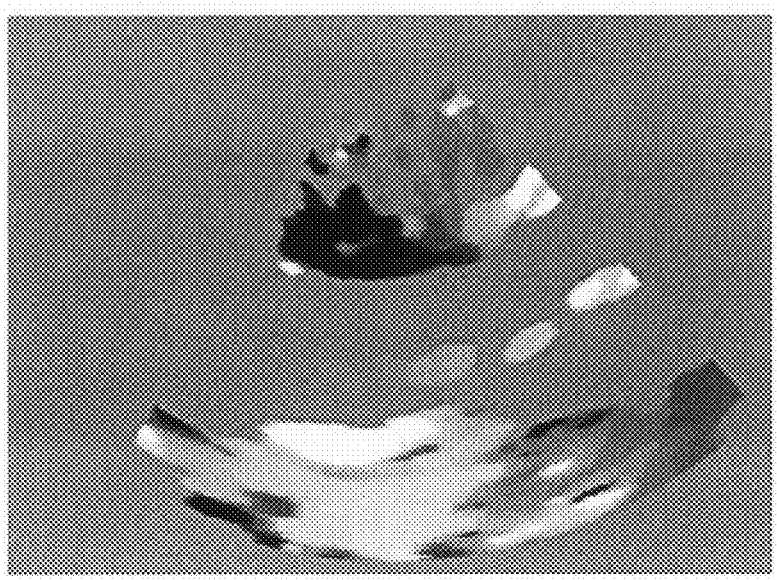
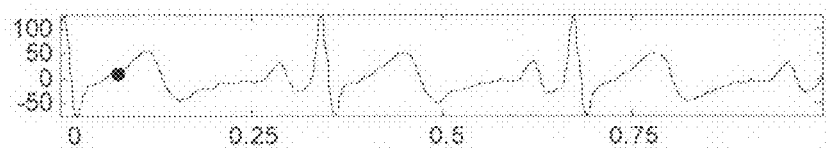
Fig. 16A(f2)

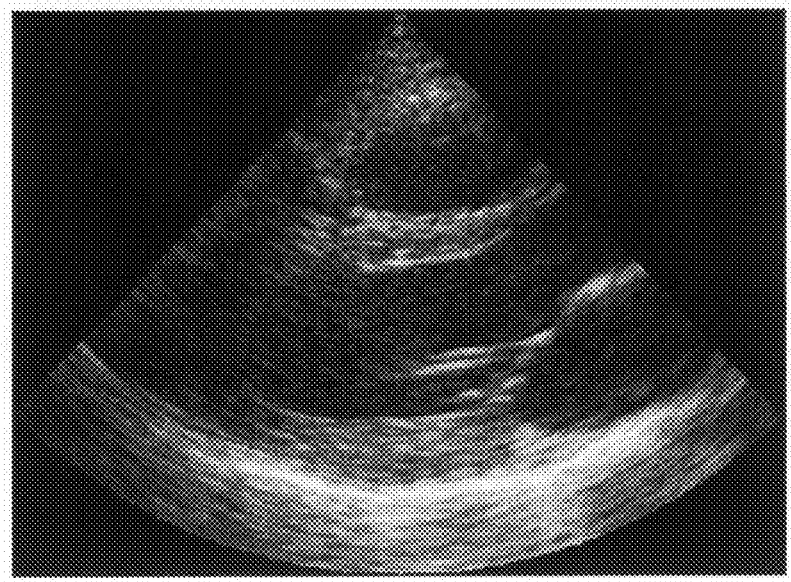
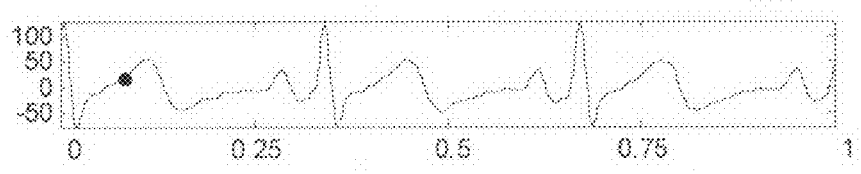
Fig. 16A(g1)
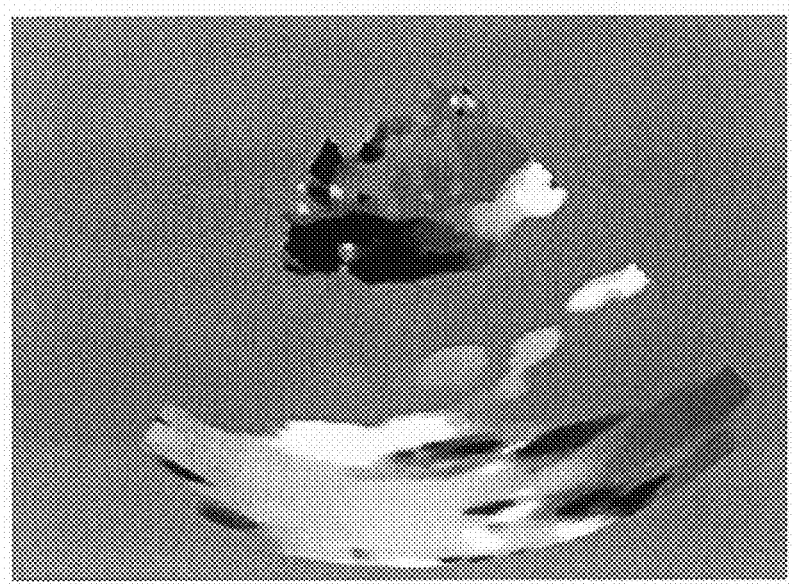
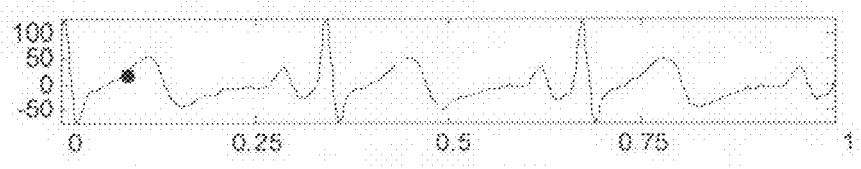
Fig. 16A(g2)

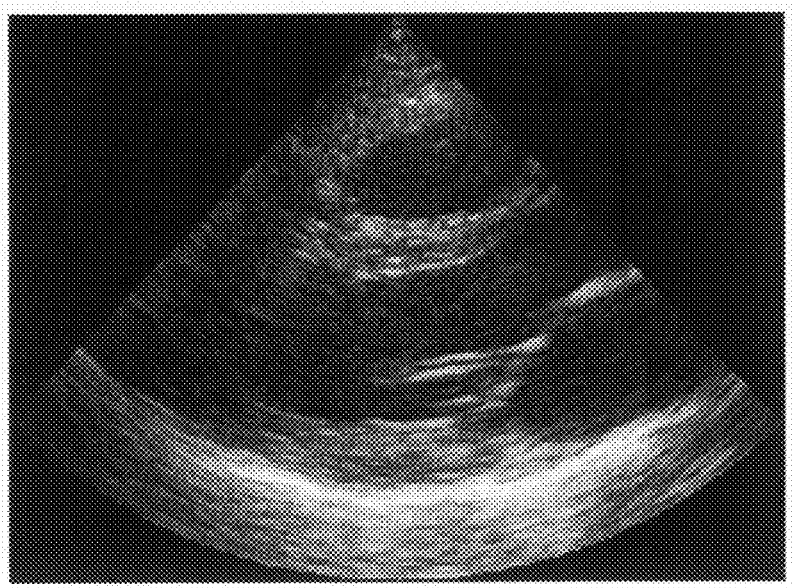
Fig. 16A(h1)
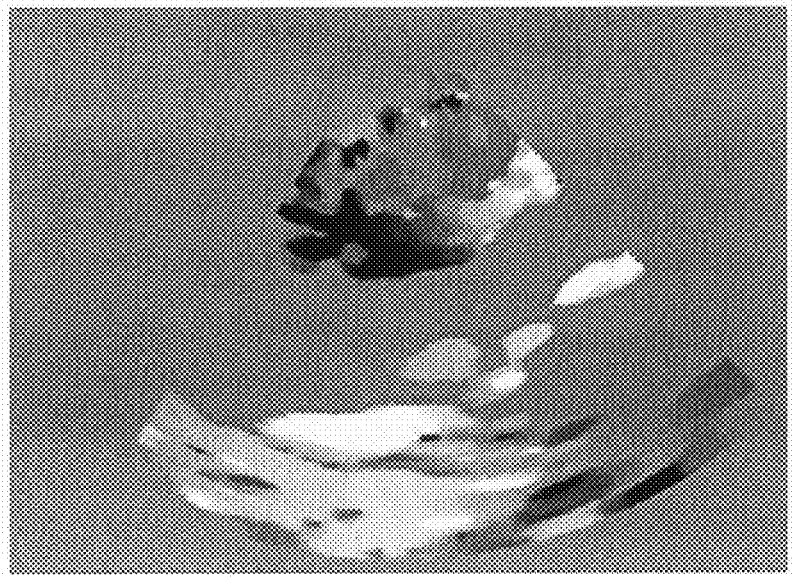
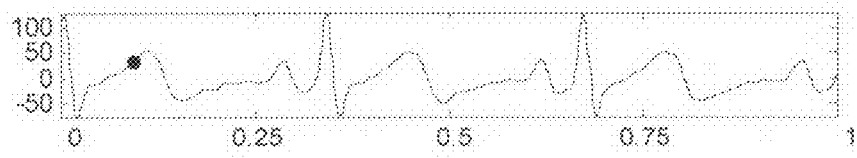
Fig. 16A(h2)

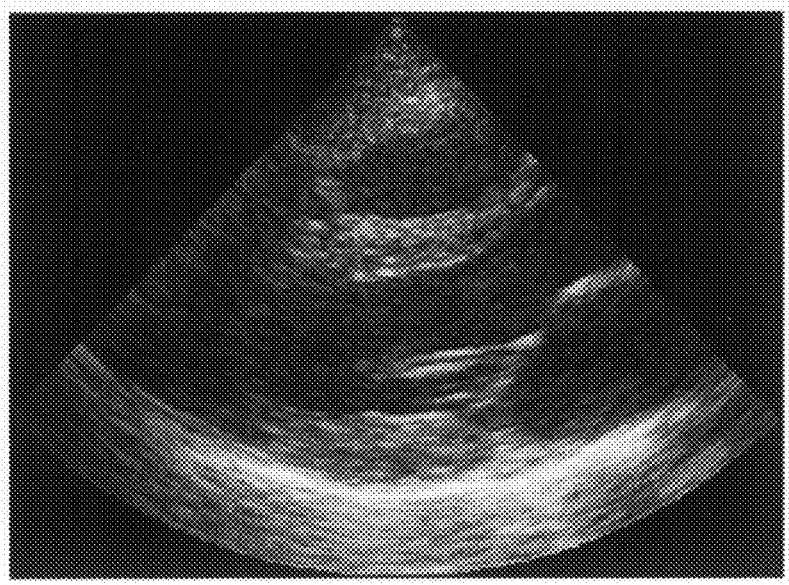
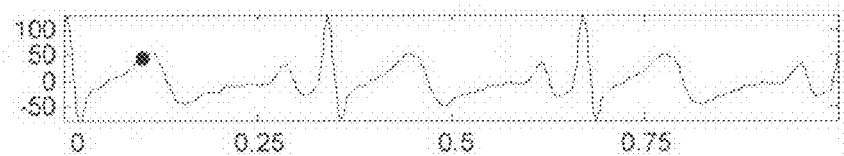
Fig. 16A(i1)
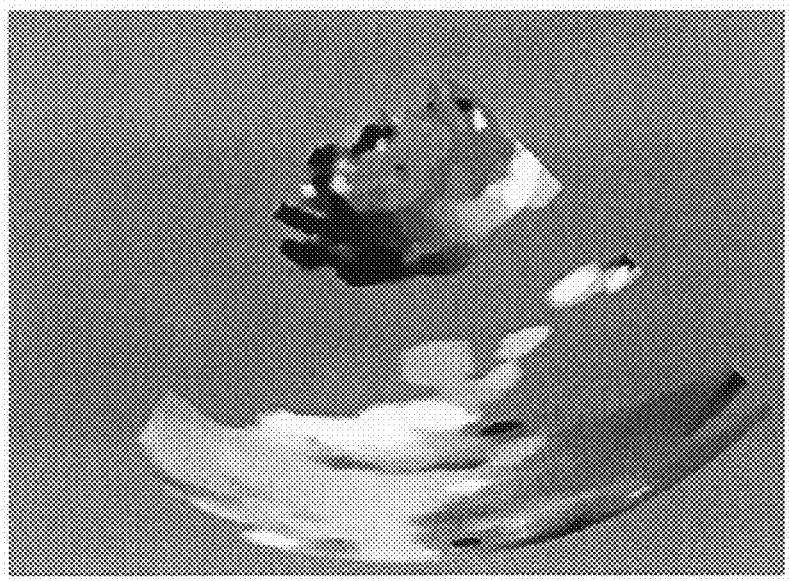
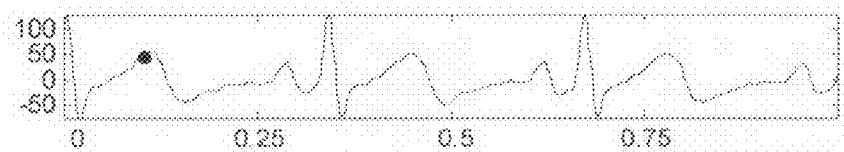
Fig. 16A(i2)

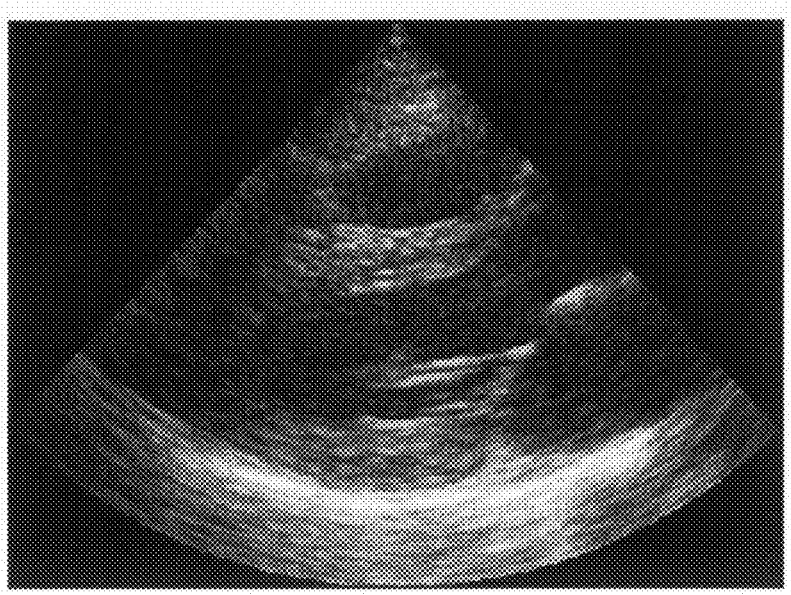
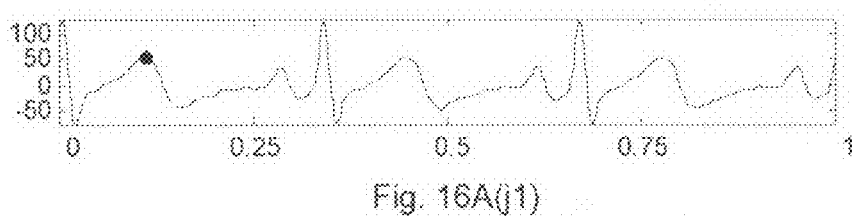
Fig. 16A(j1)
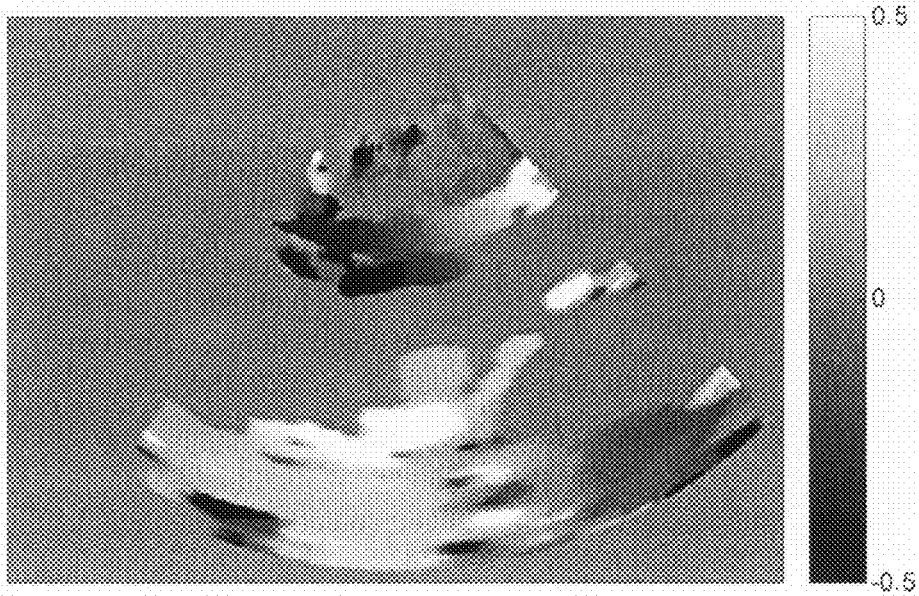
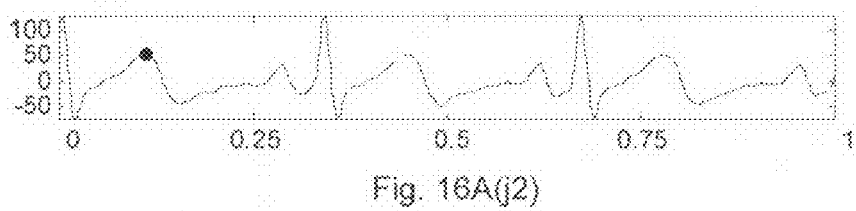
Fig. 16A(j2)

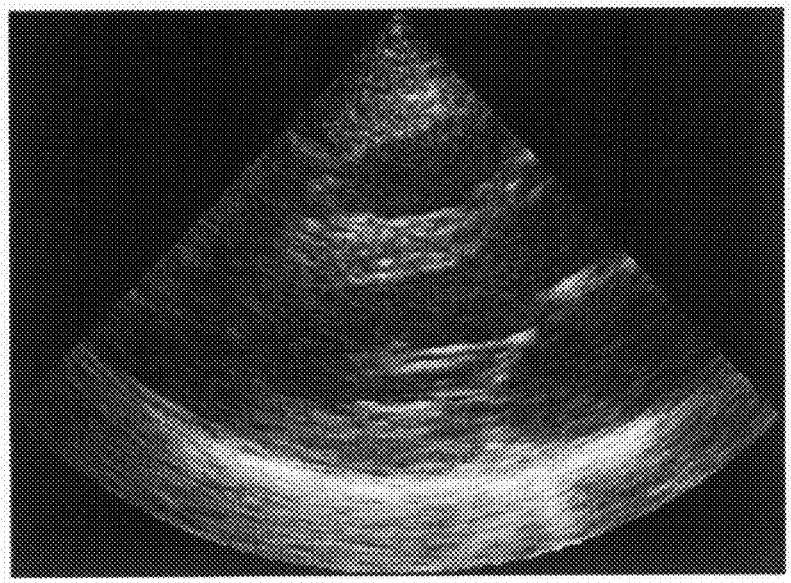
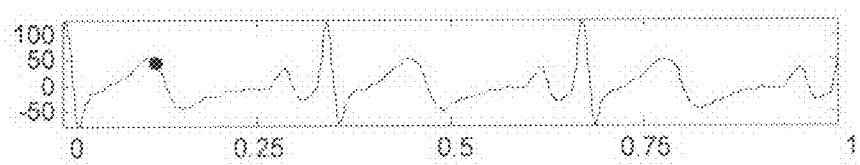
Fig. 16A(k1)
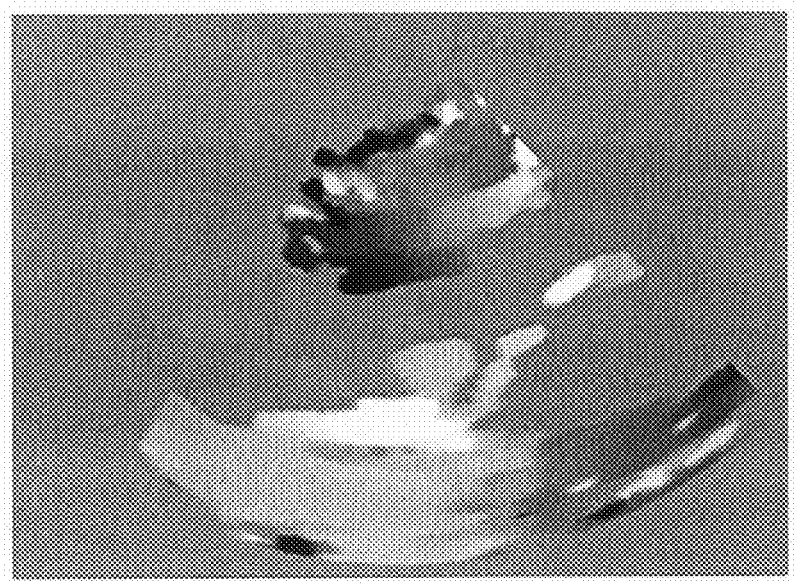
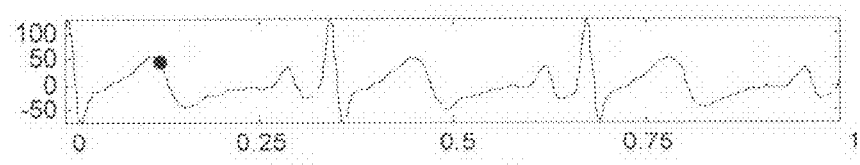
Fig. 16A(k2)

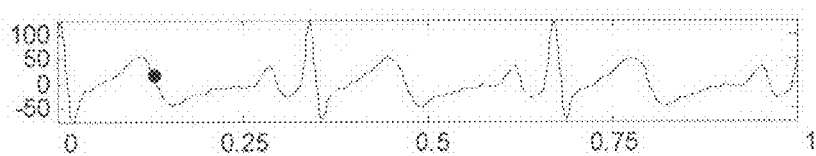
Fig. 16A(I1)
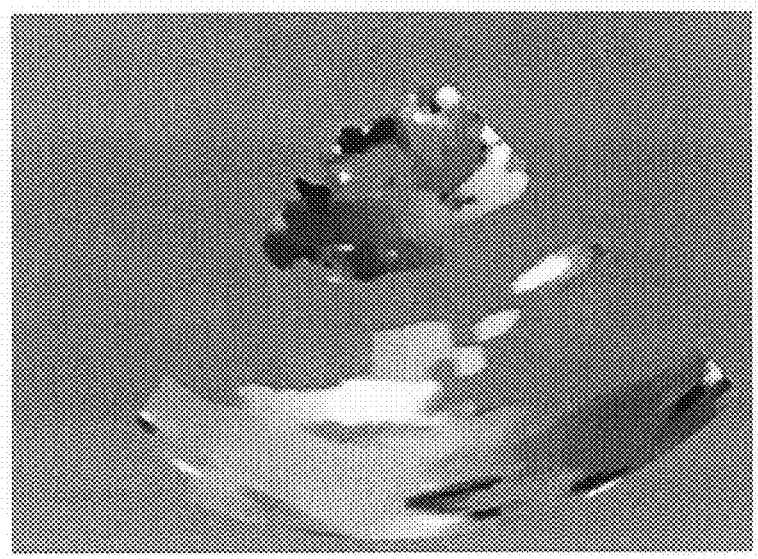
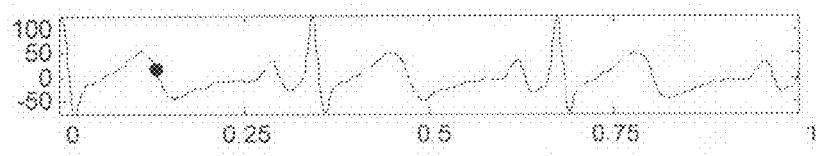
Fig. 16A(I2)

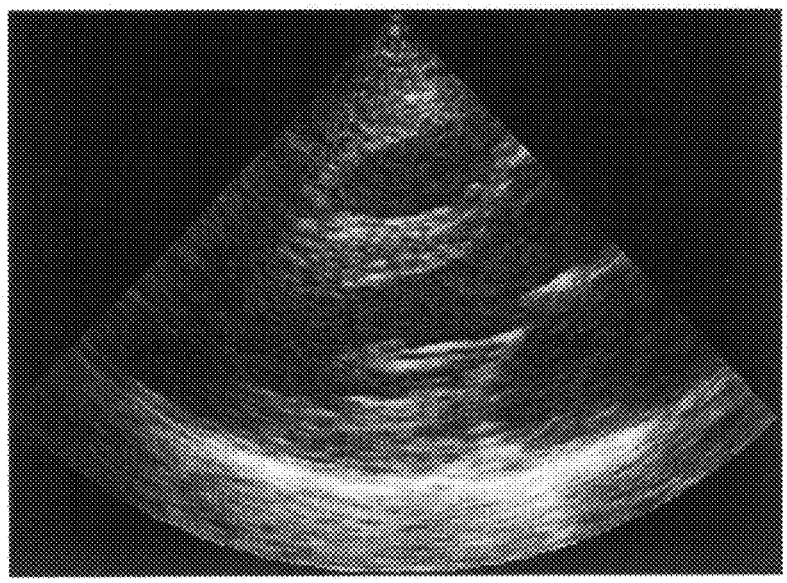
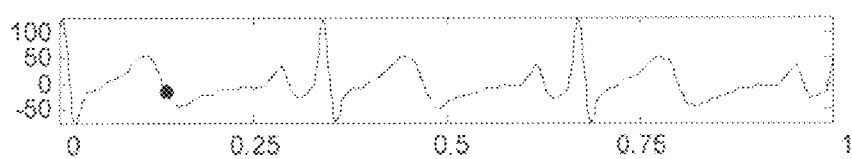
Fig. 16A(m1)
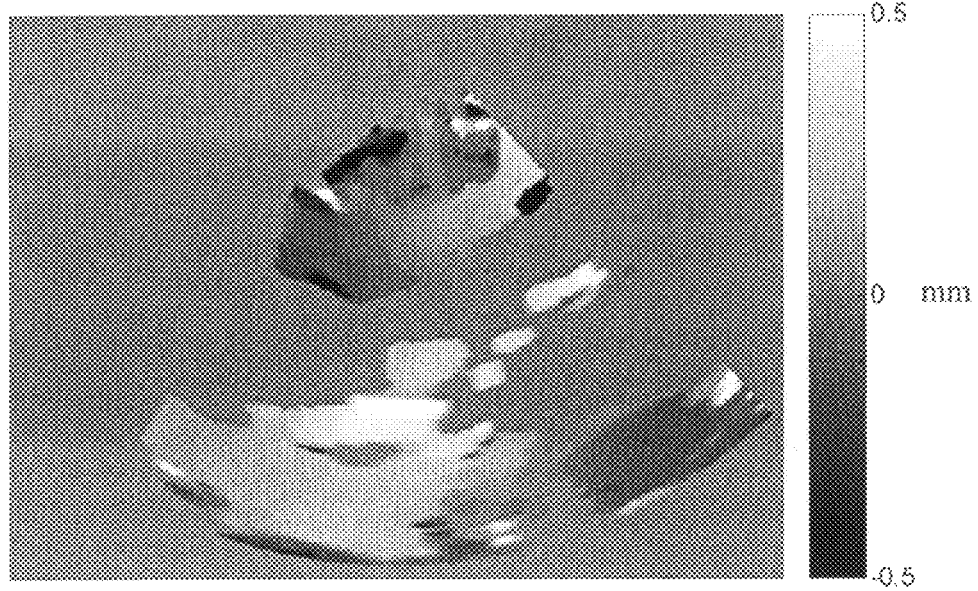
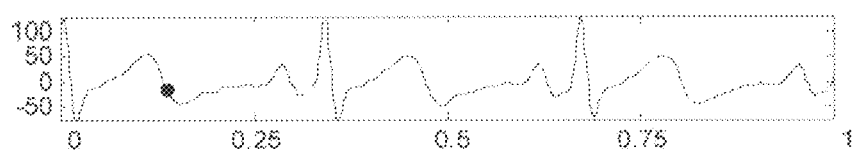
Fig. 16A(m2)

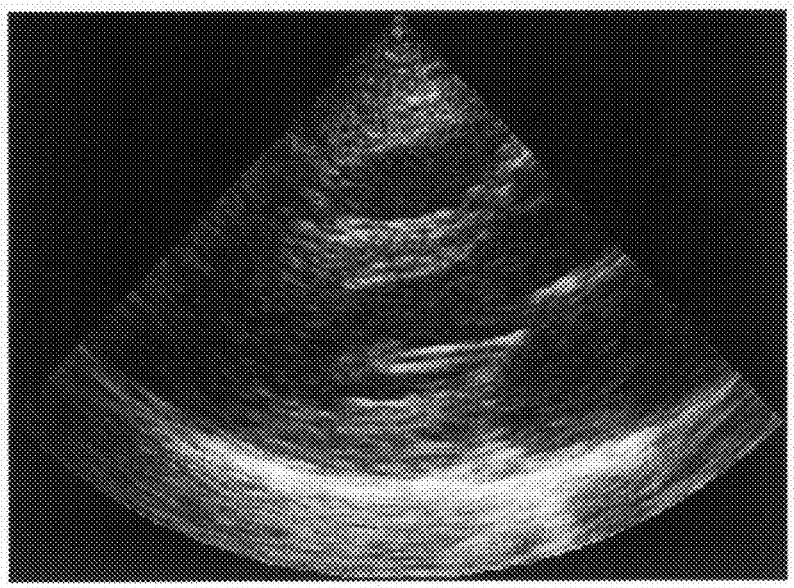
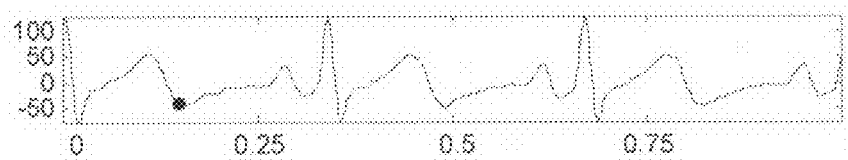
Fig. 16A(n1)
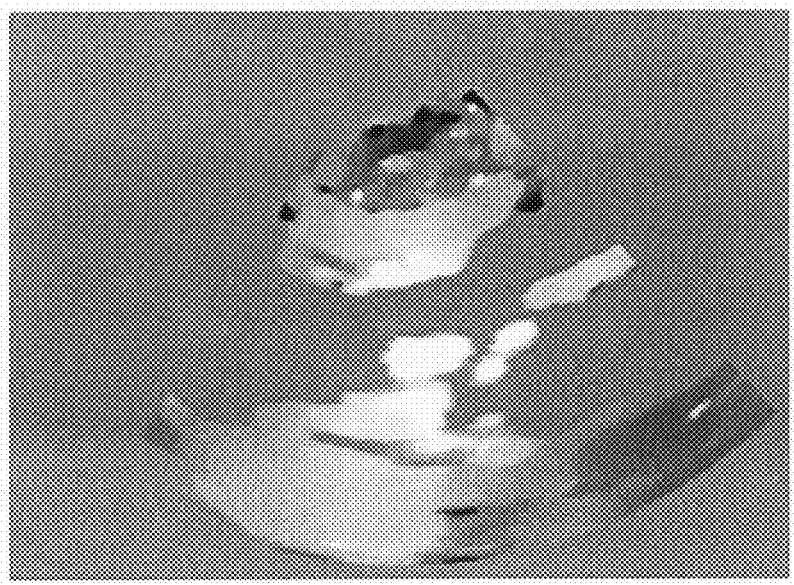
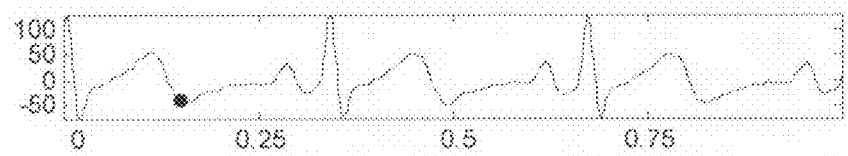
Fig. 16A(n2)

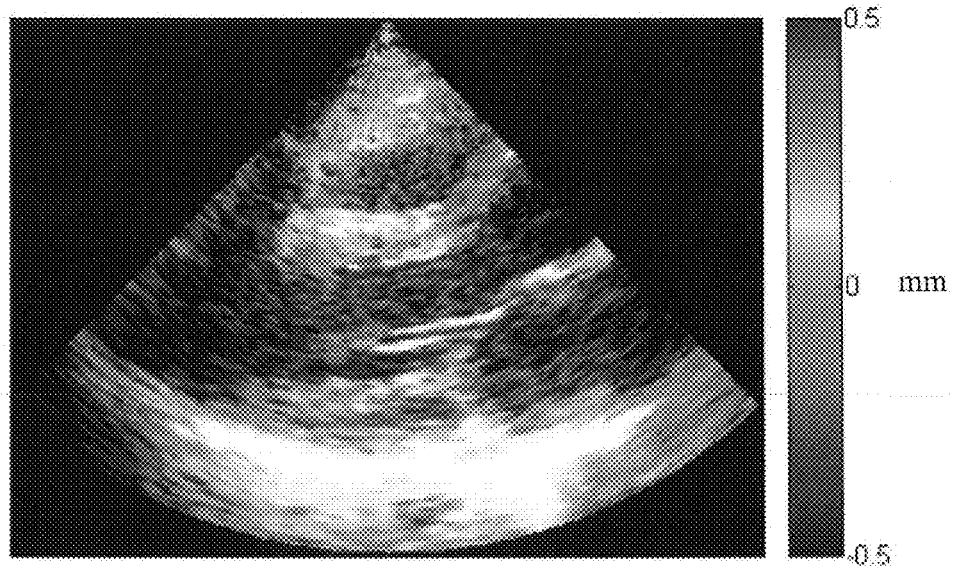
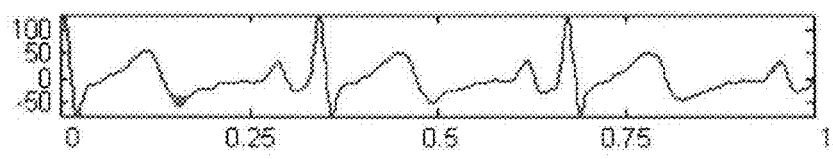
Fig. 17(a)
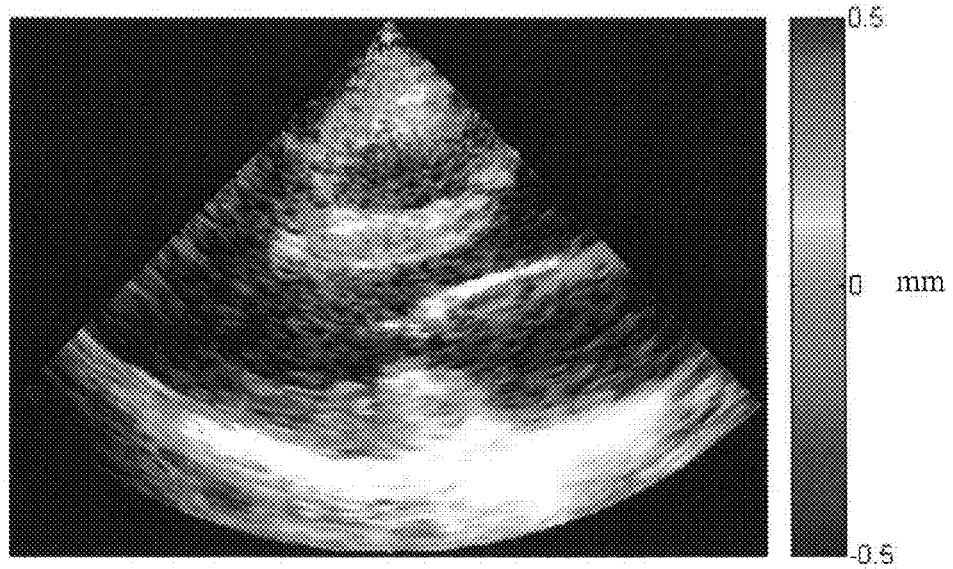
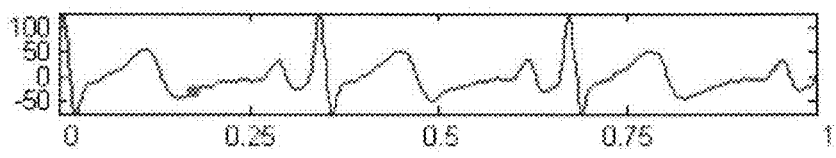
Fig. 17(b)

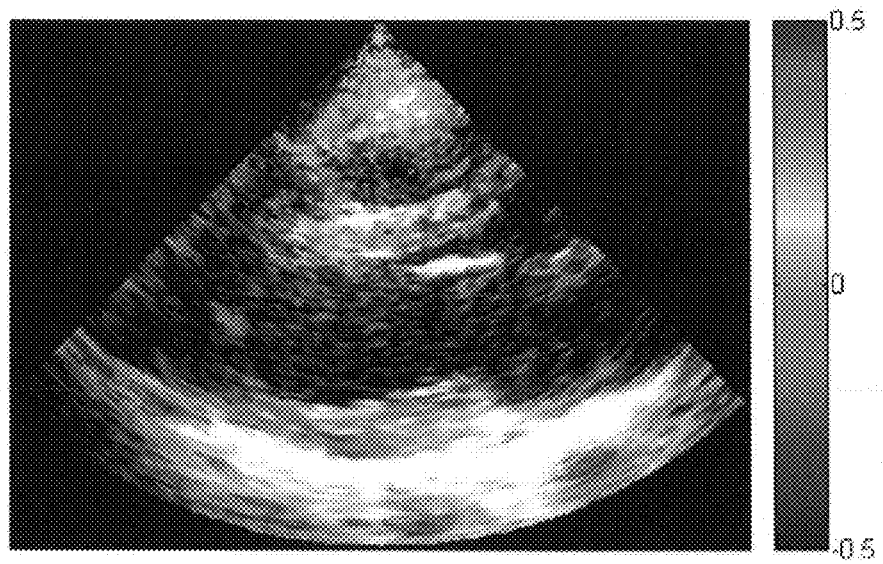
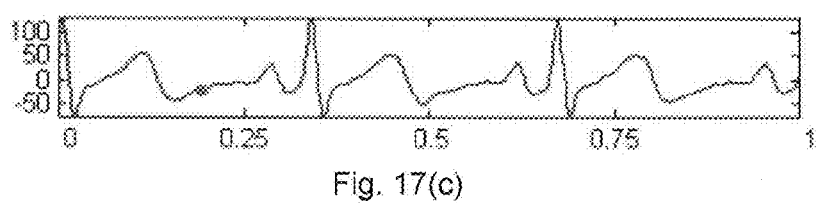
Fig. 17(c)
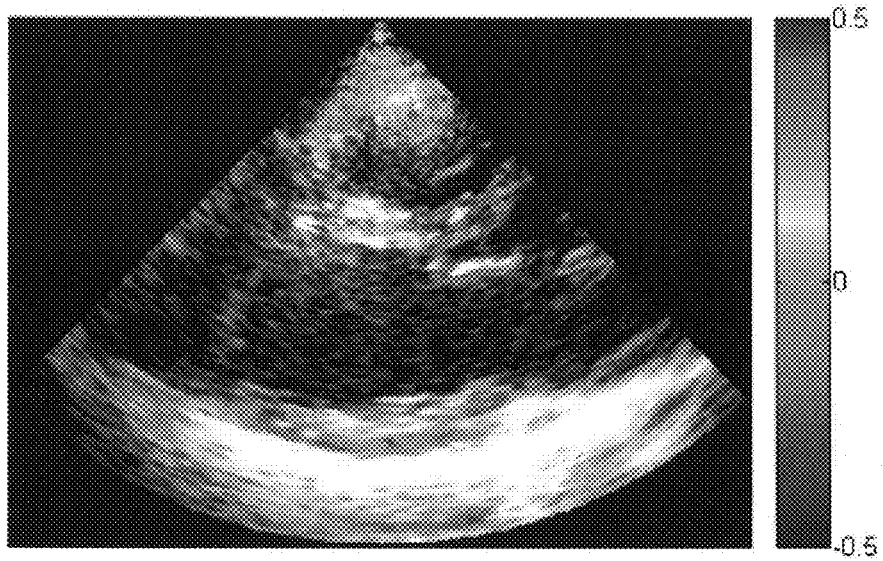
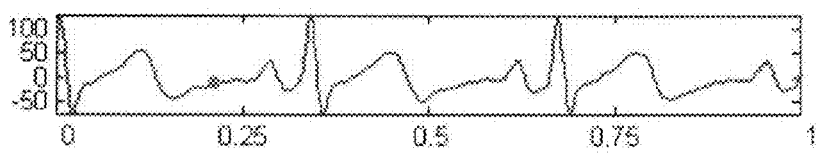
Fig. 17(d)

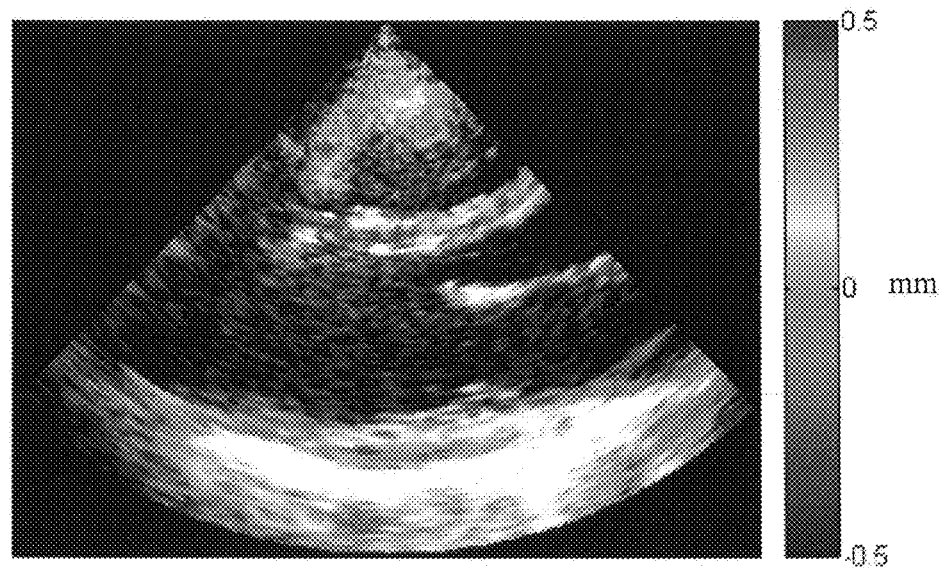
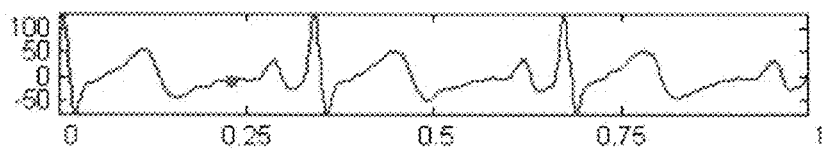
Fig. 17(e)
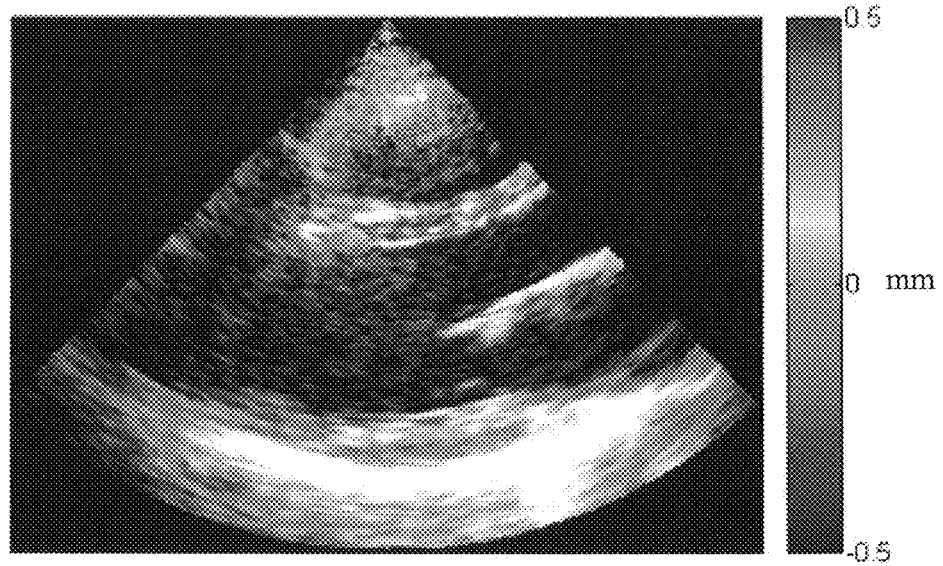
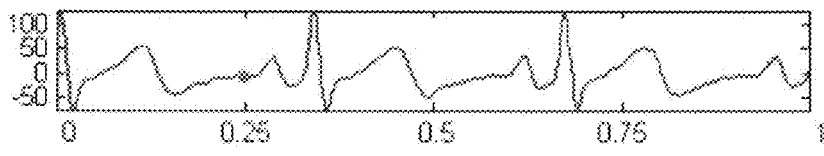
Fig. 17(f)

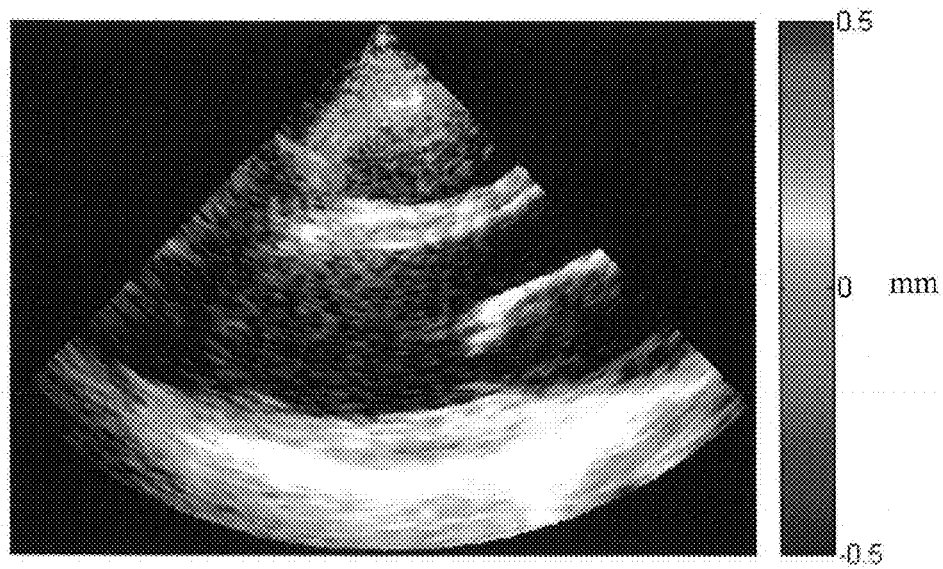
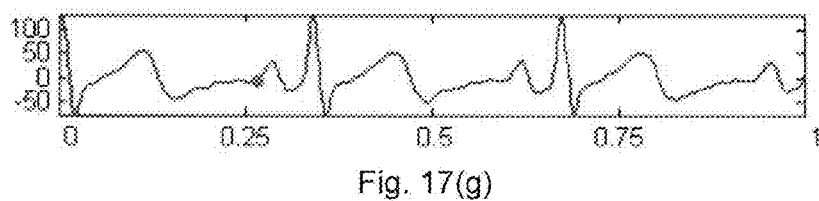
Fig. 17(g)
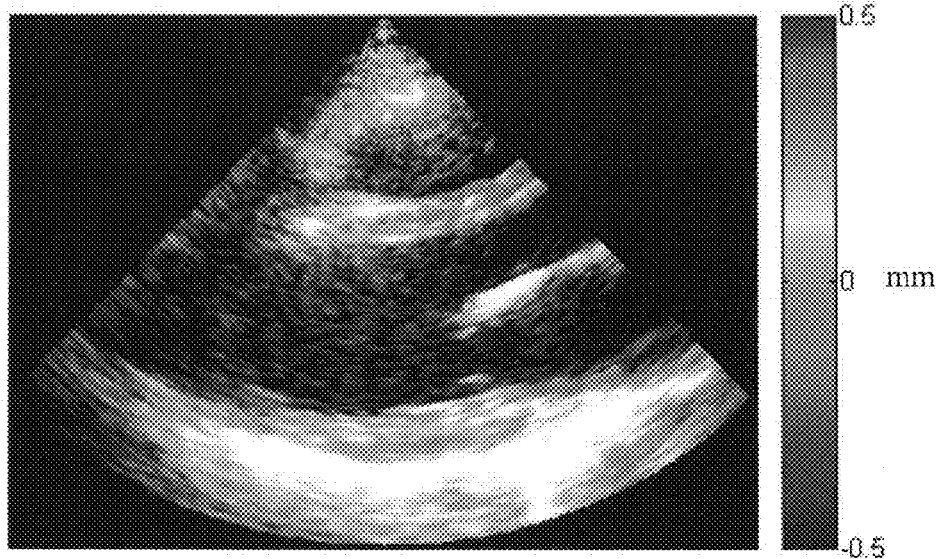
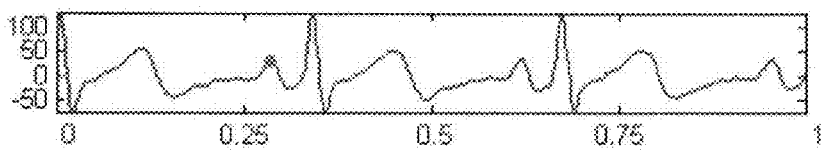
Fig. 17(h)

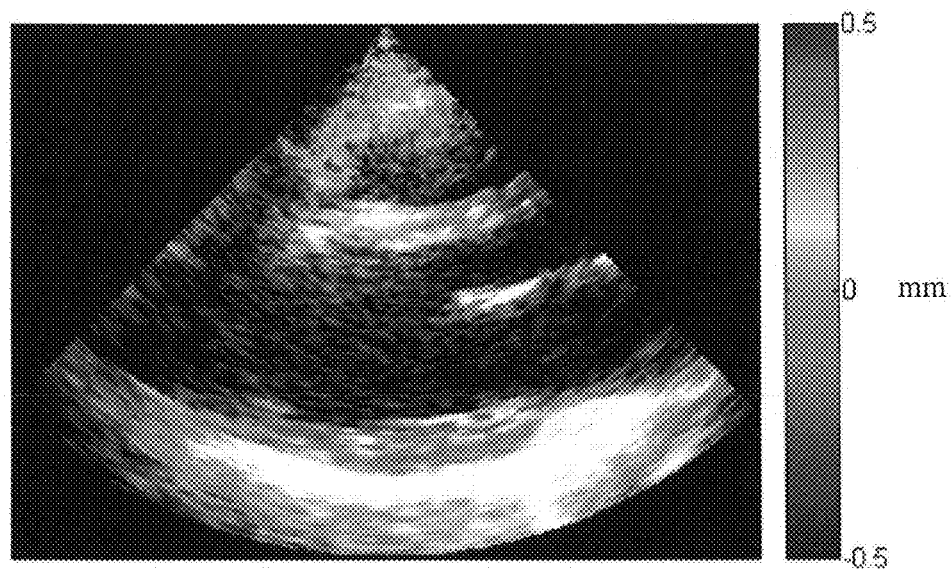
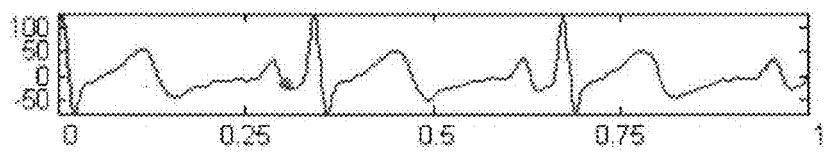
Fig. 17(i)
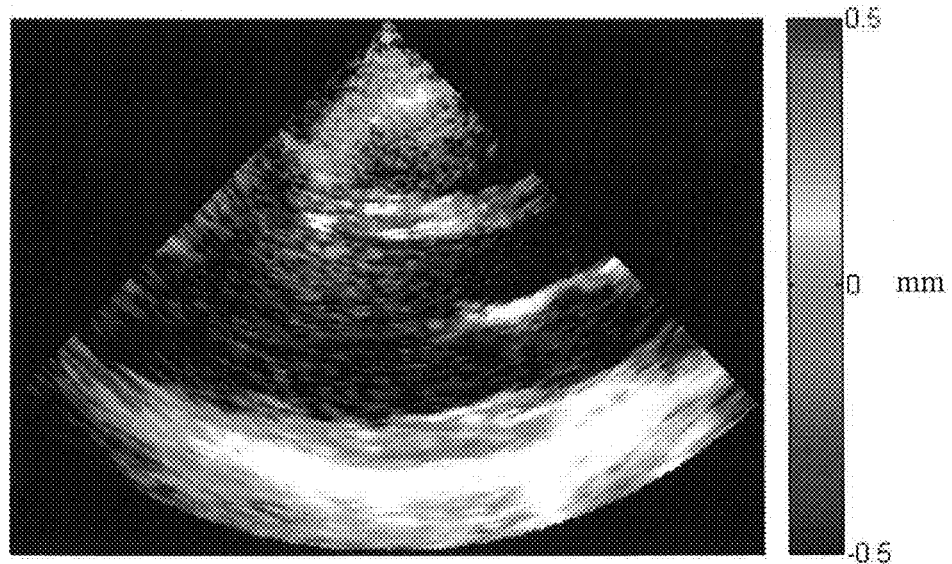
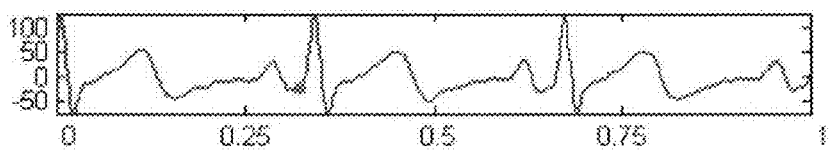
Fig. 17(j)

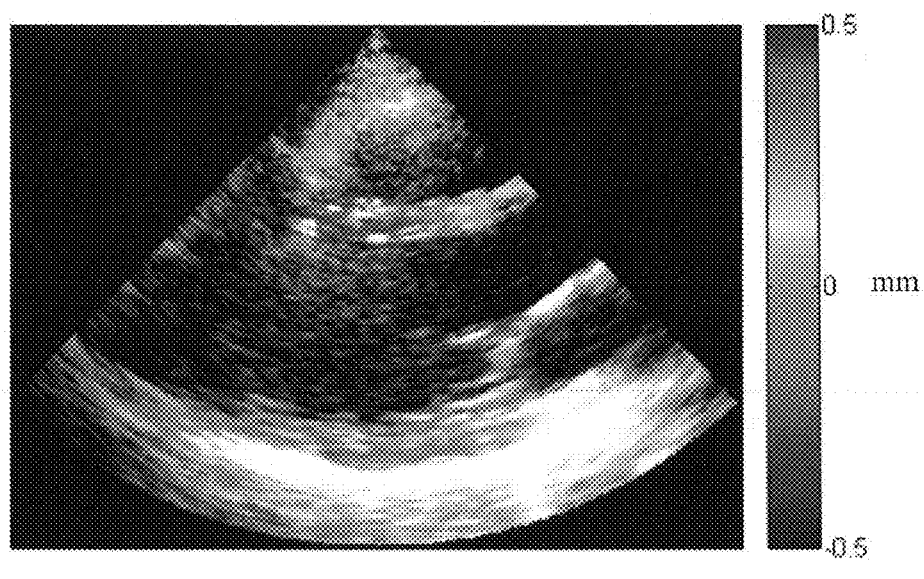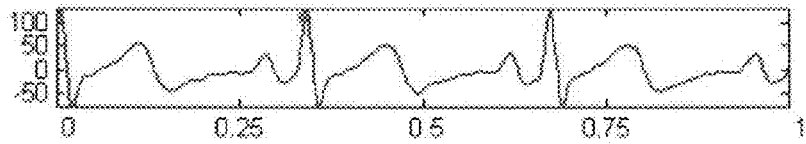
Fig. 17(k)

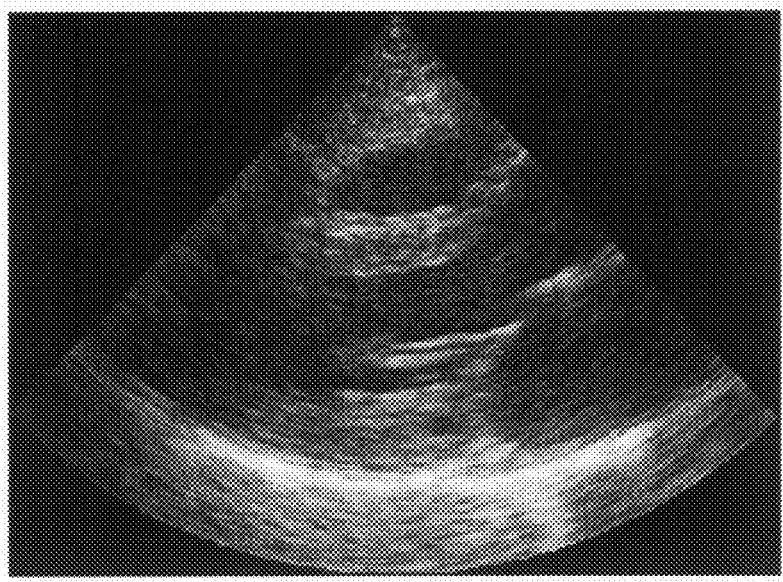
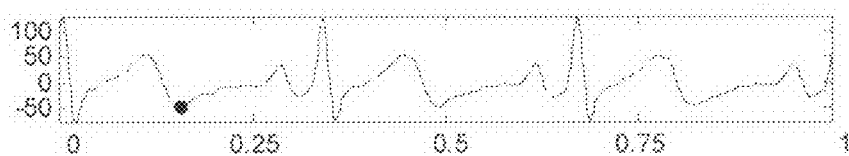
Fig. 17A(a1)
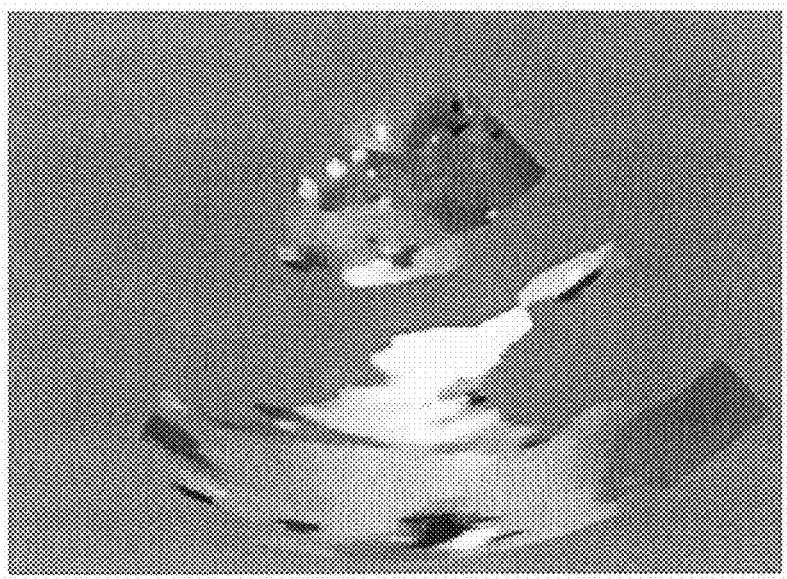
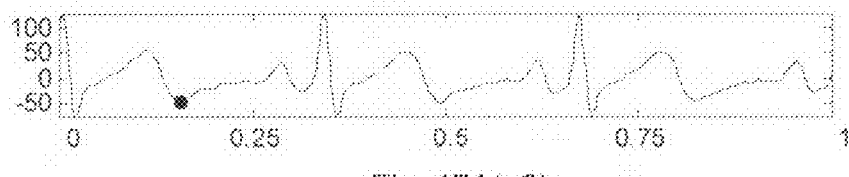
Fig. 17A(a2)

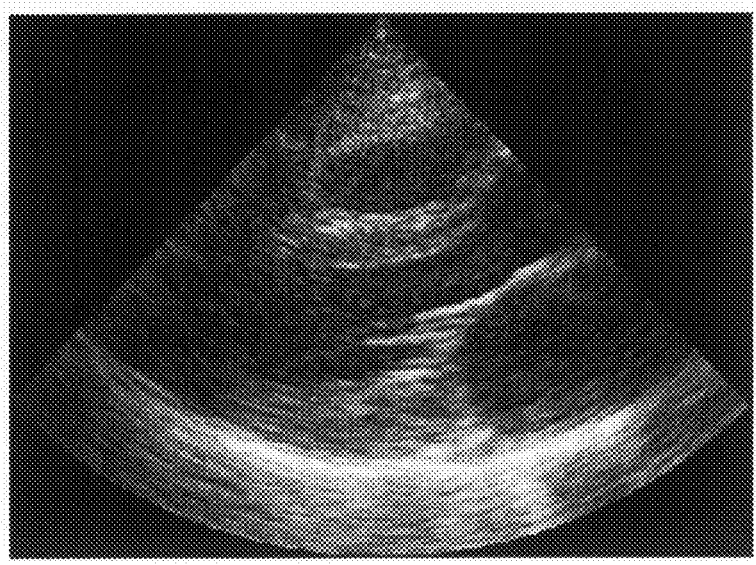
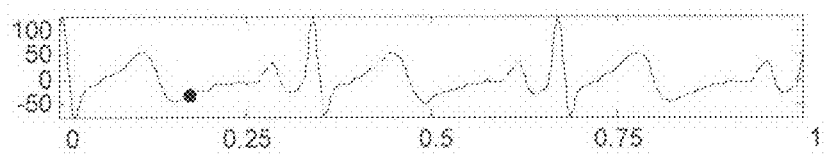
Fig. 17A(b1)
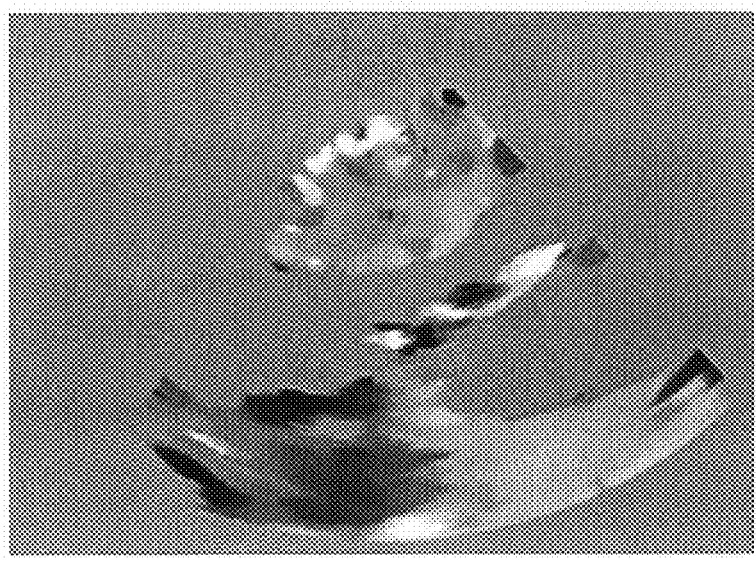
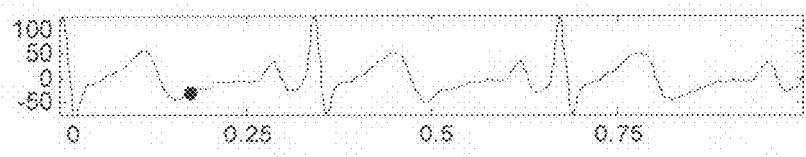
Fig. 17A(b2)

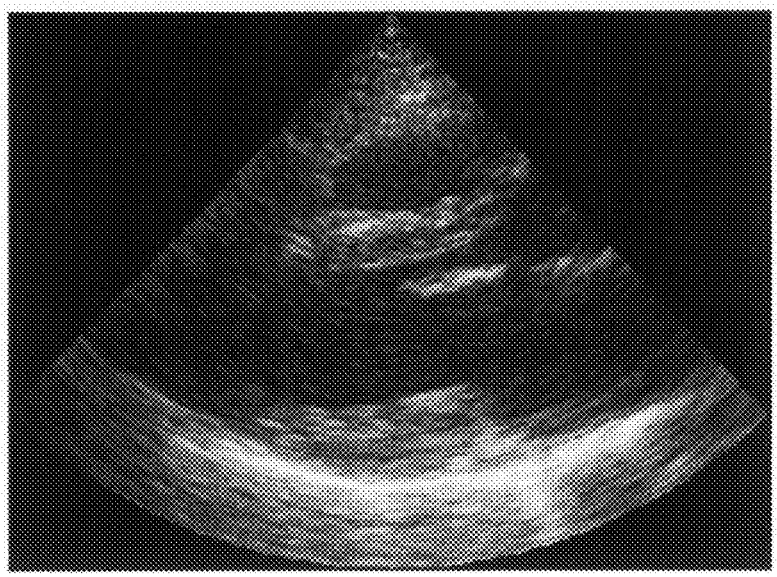
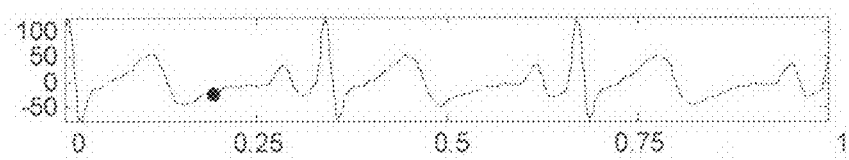
Fig. 17A(c1)
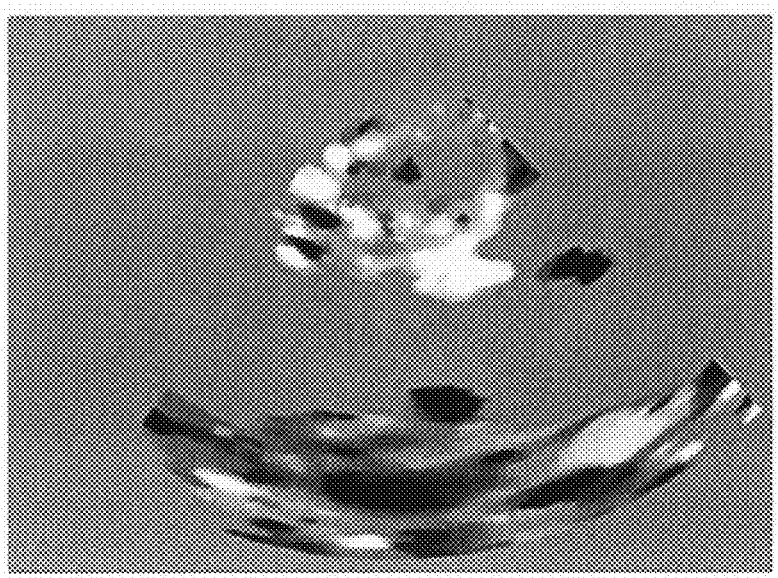
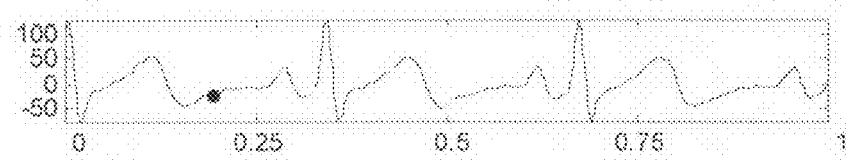
Fig. 17A(c2)

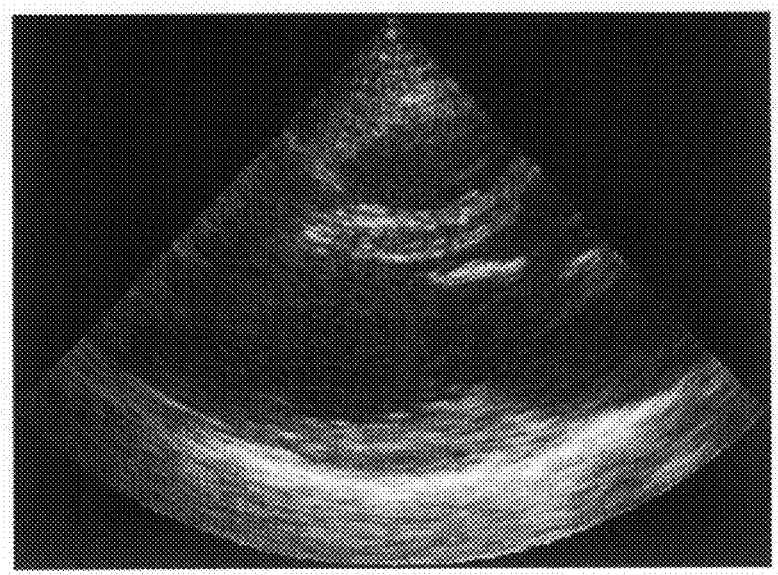
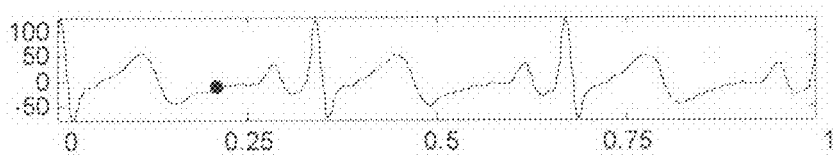
Fig. 17A(d1)
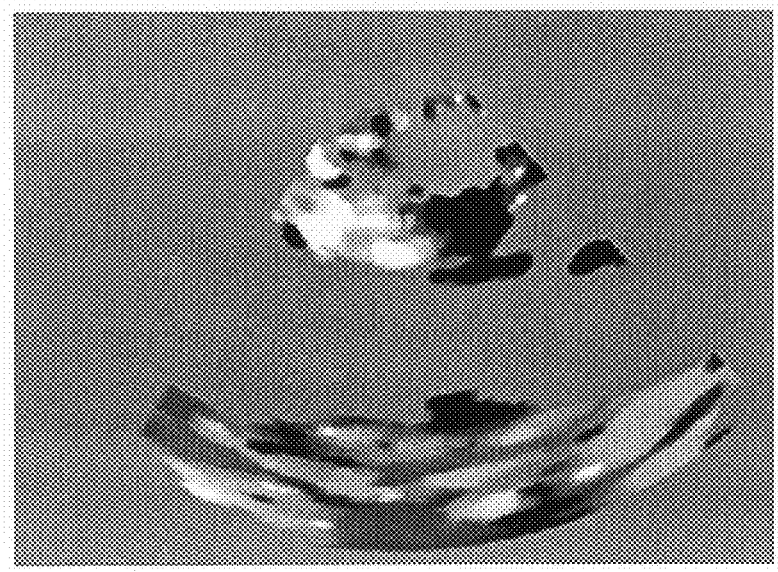
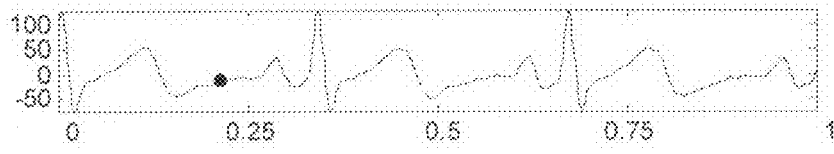
Fig. 17A(d2)

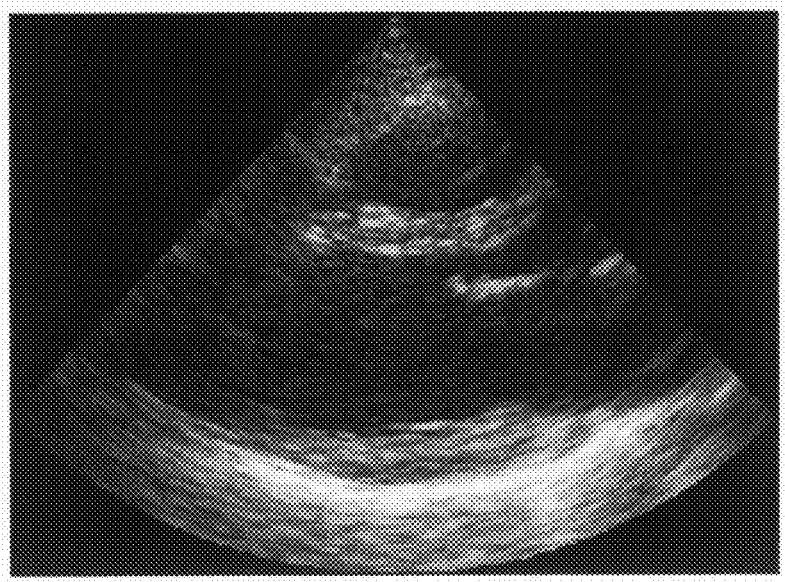
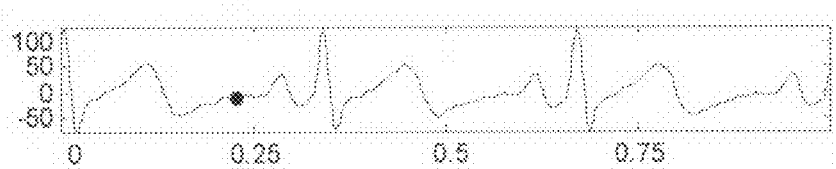
Fig. 17A(e1)
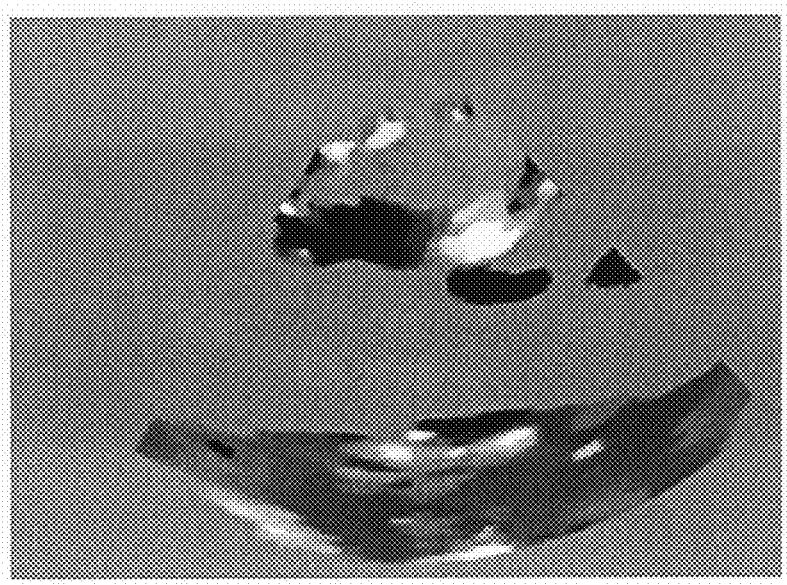
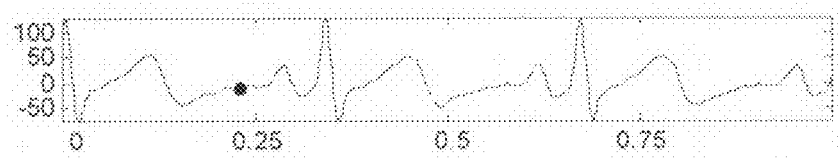
Fig. 17A(e2)

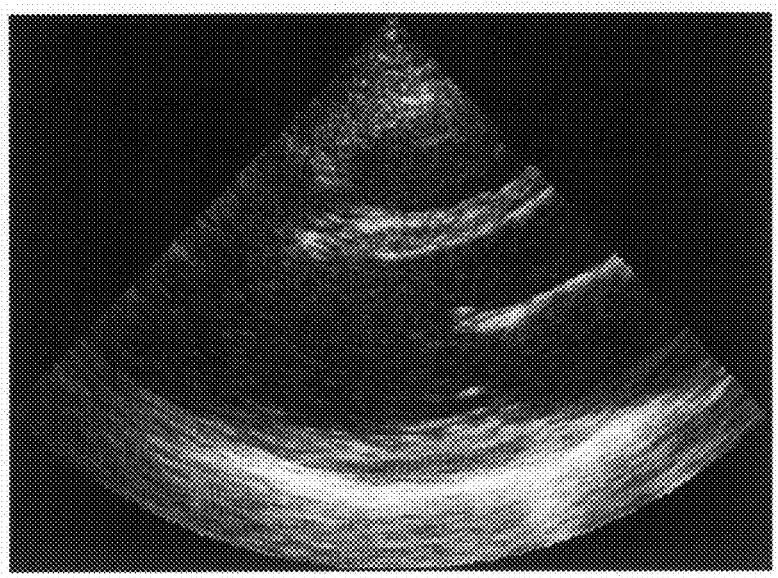
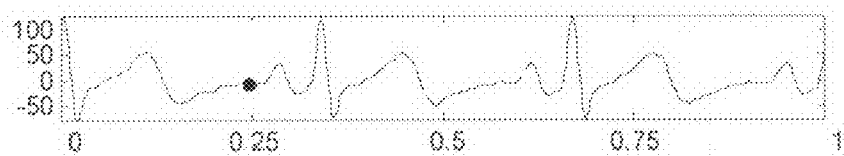
Fig. 17A(f1)
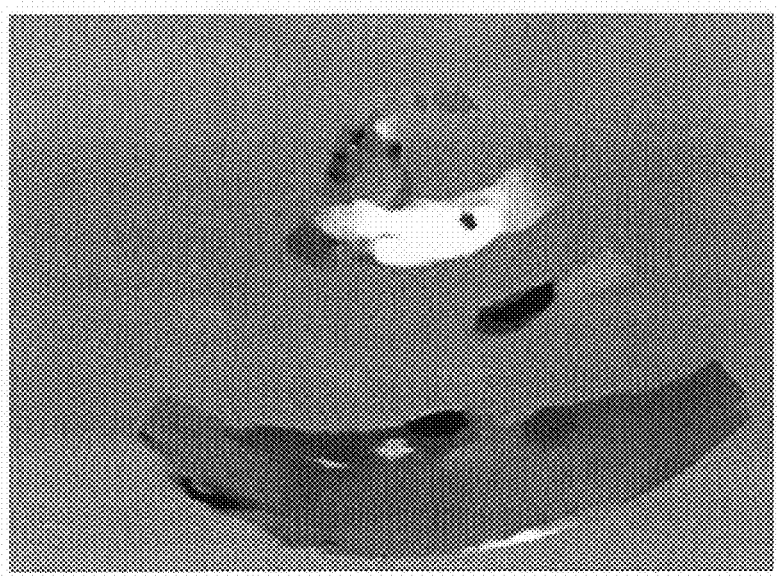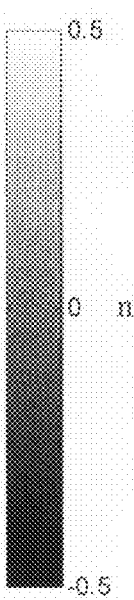
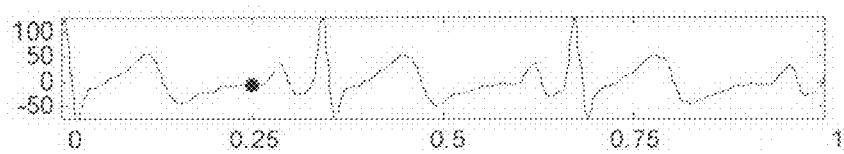
Fig. 17A(f2)

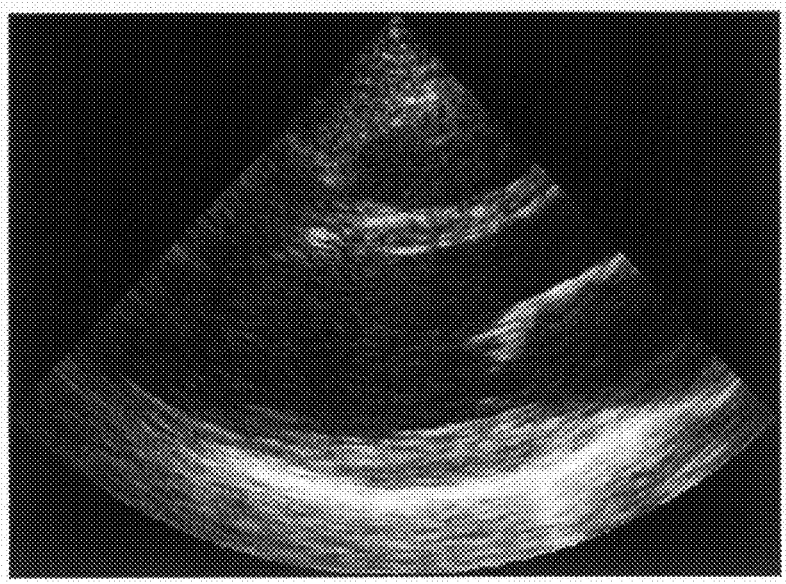
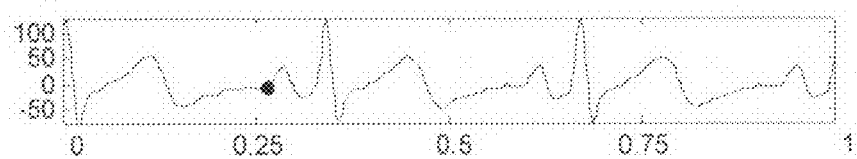
Fig. 17A(g1)
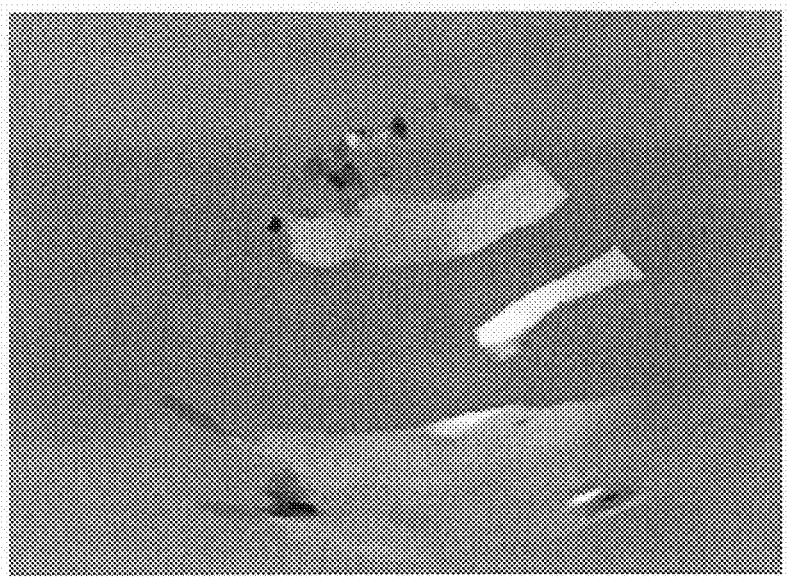
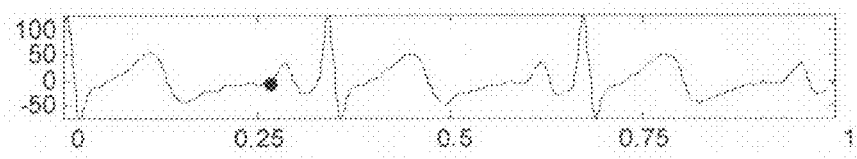
Fig. 17A(g2)

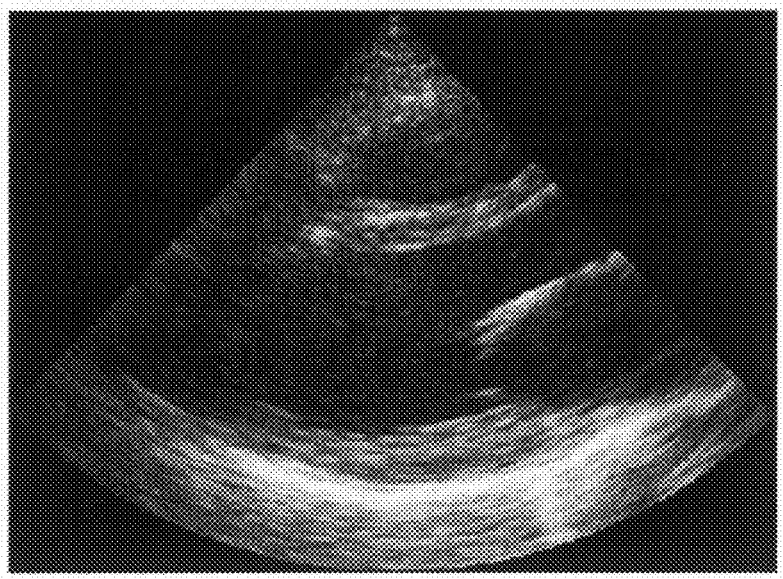
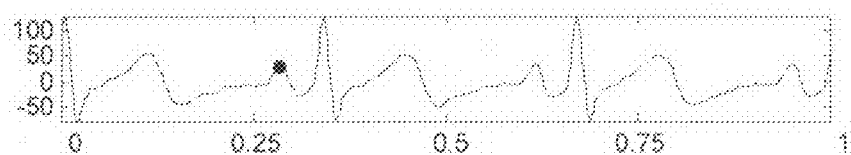
Fig. 17A(h1)
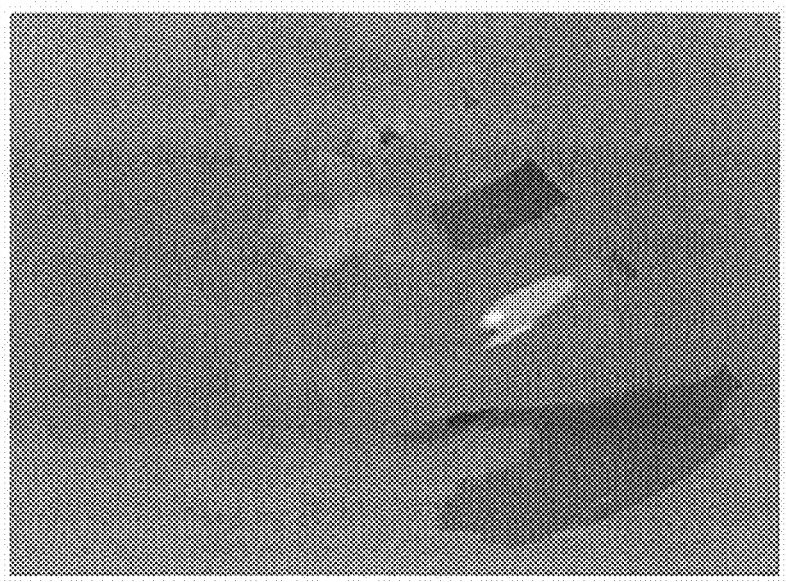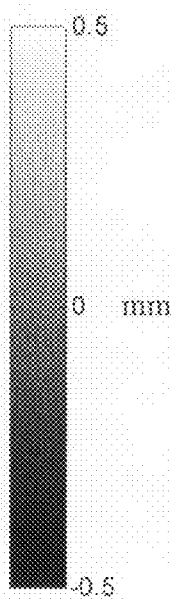
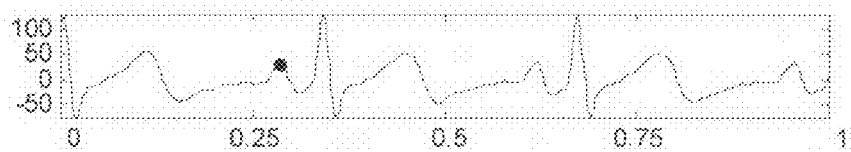
Fig. 17A(h2)

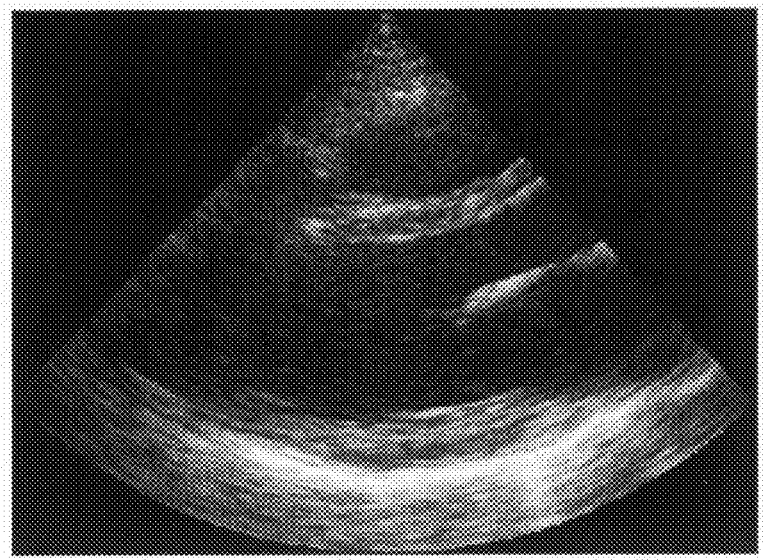
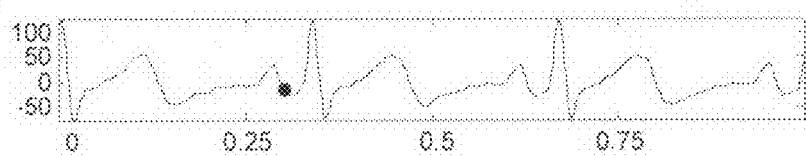
Fig. 17A(i1)
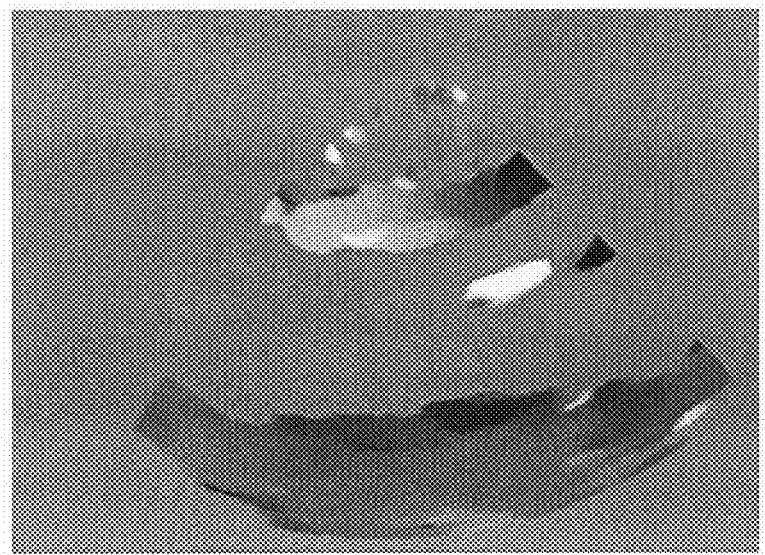
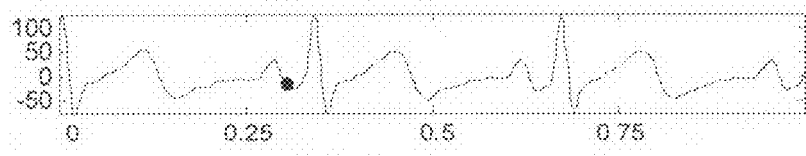
Fig. 17A(i2)

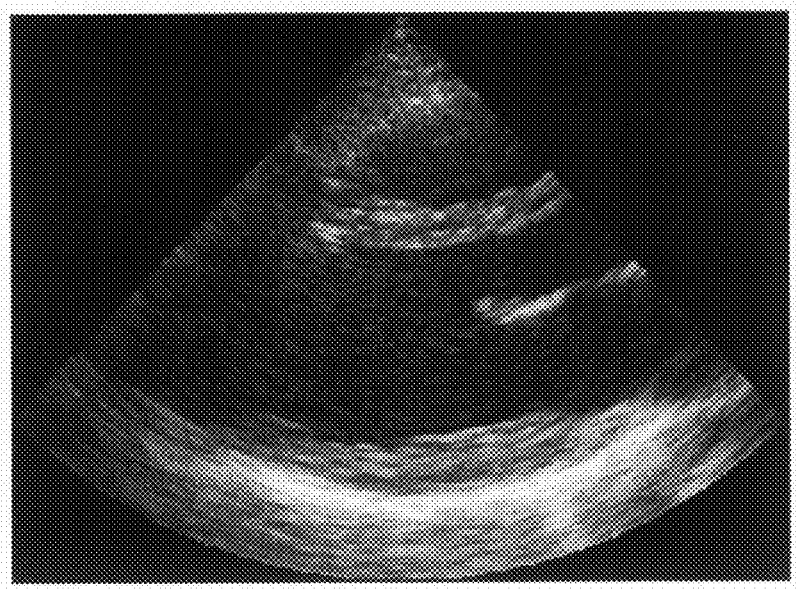
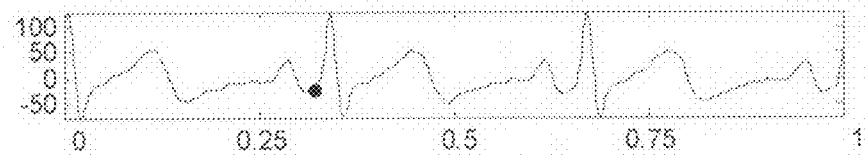
Fig. 17A(j1)
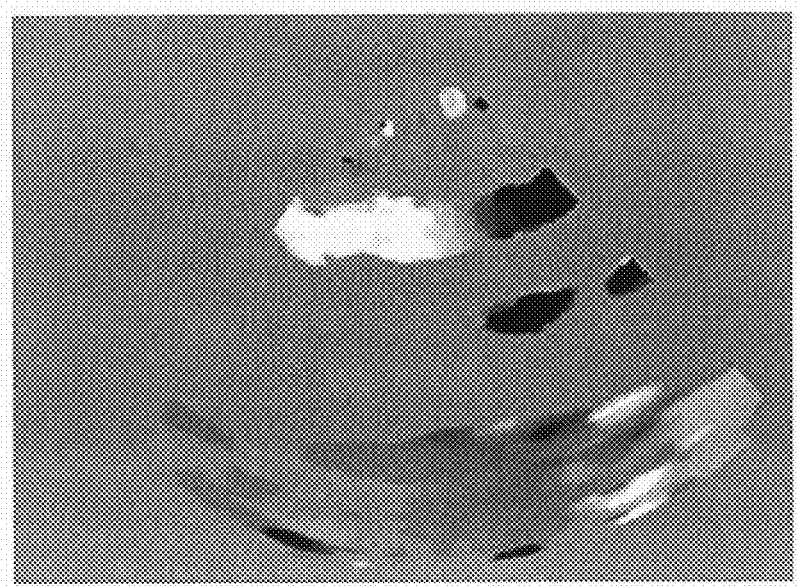
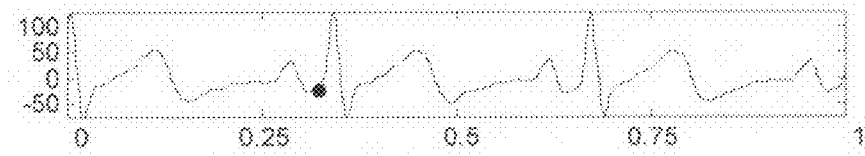
Fig. 17A(j2)

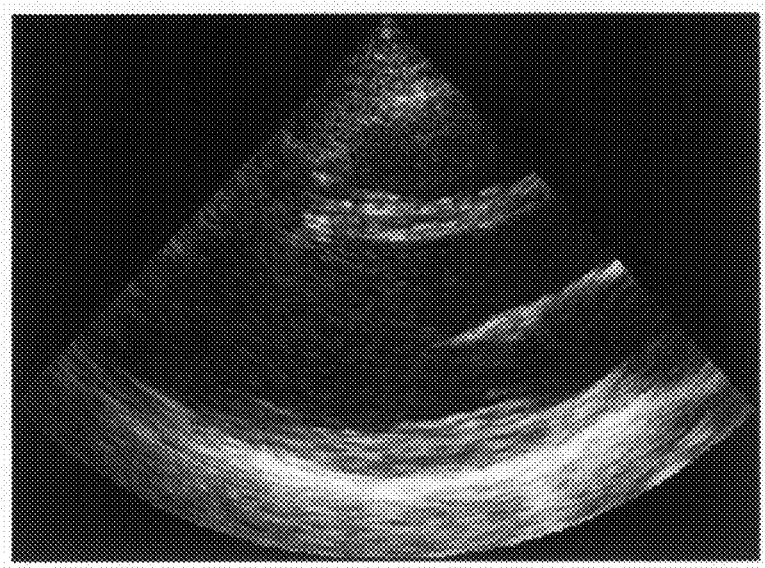
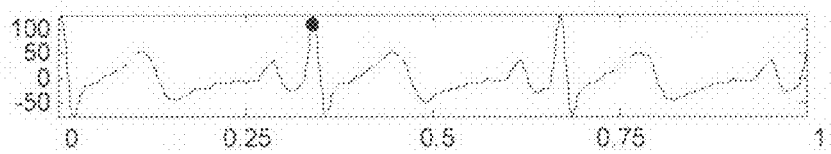
Fig. 17A(k1)
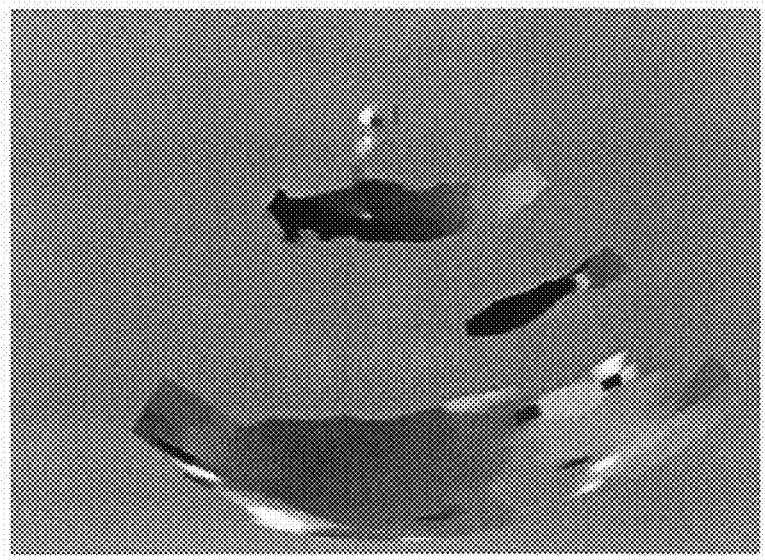
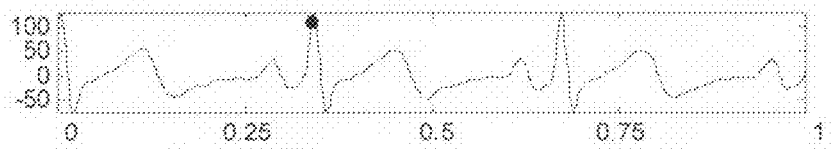
Fig. 17A(k2)

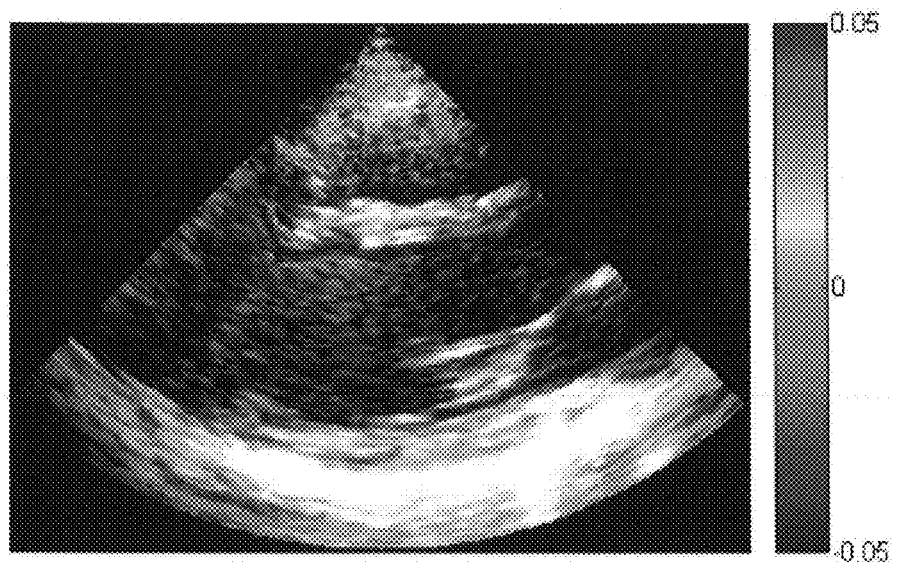
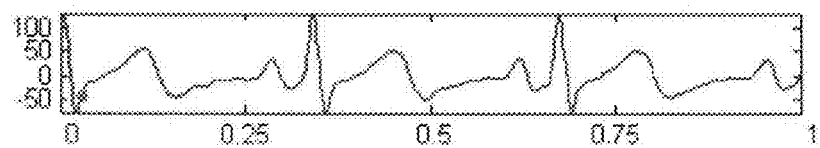
Fig. 18(a)
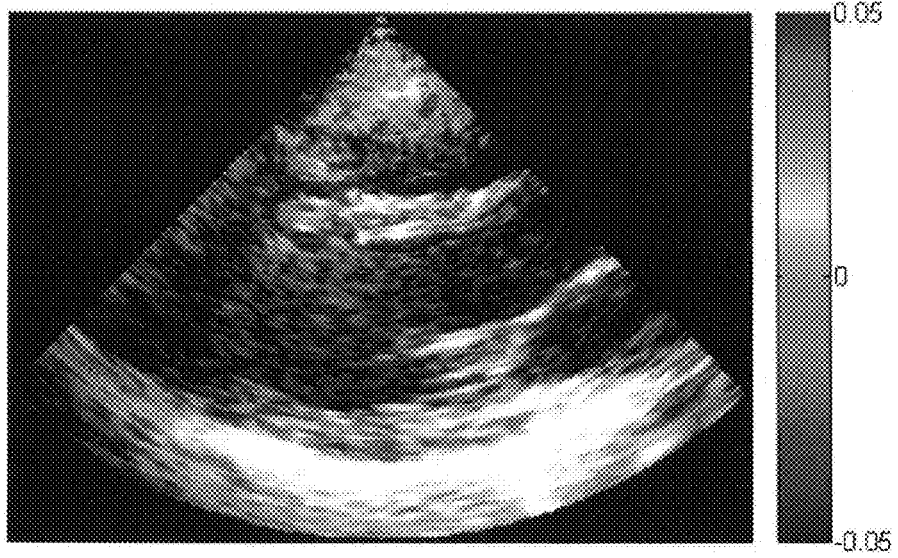
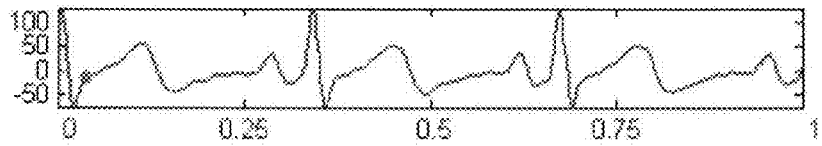
Fig. 18(b)

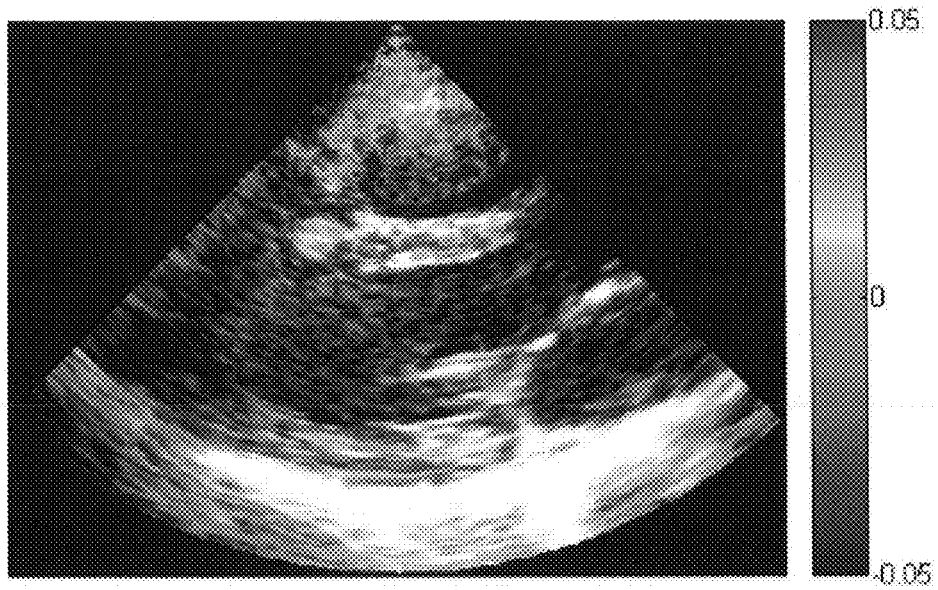
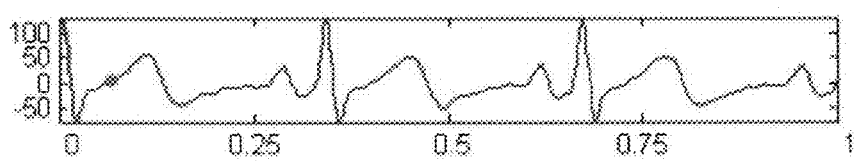
Fig. 18(e)
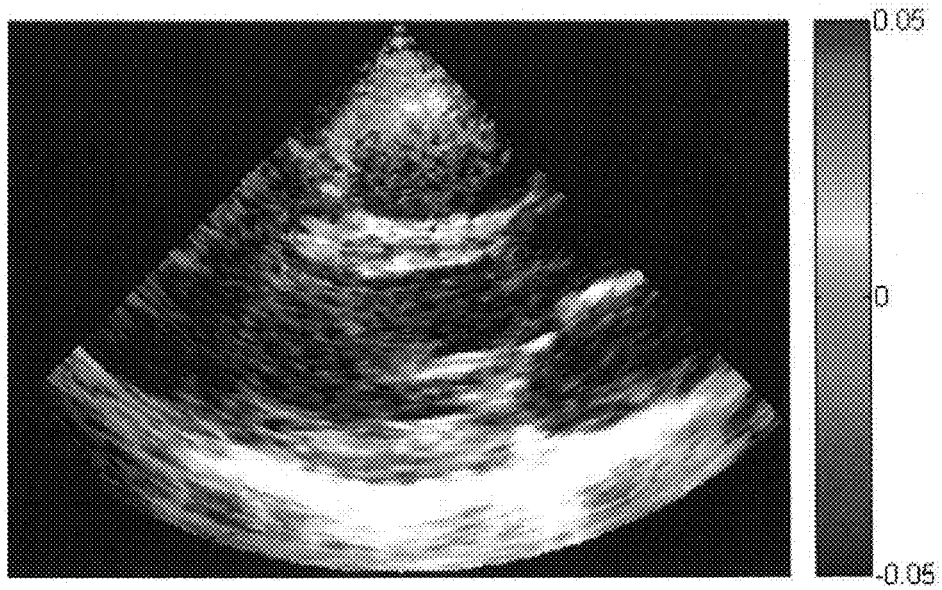
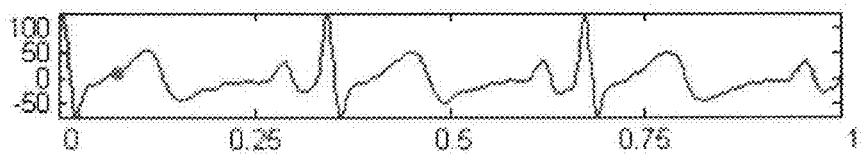
Fig. 18(f)

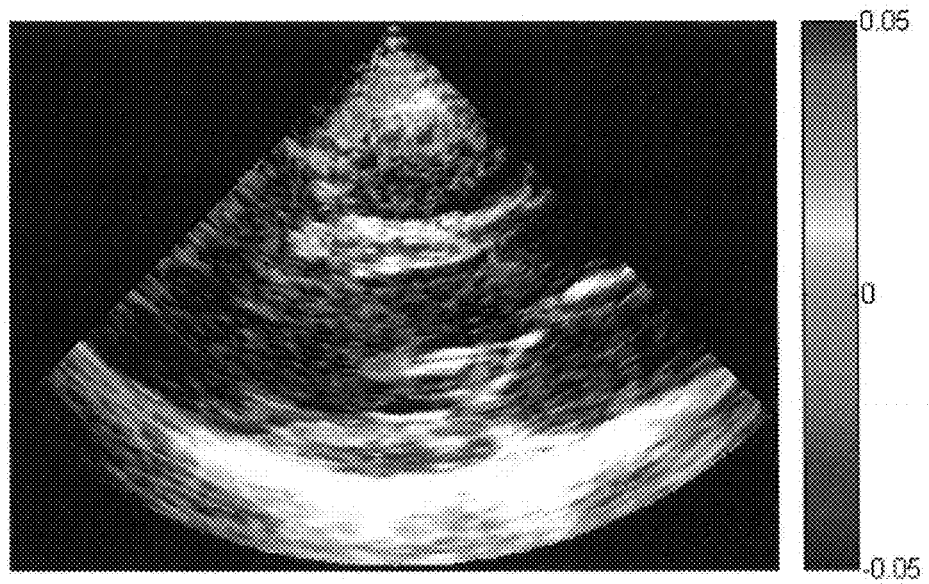
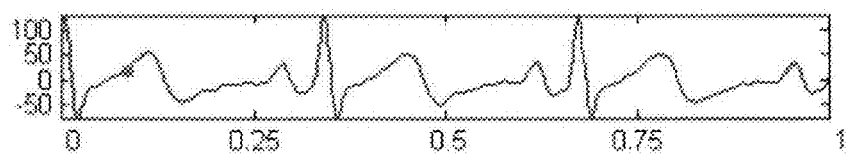
Fig. 18(g)
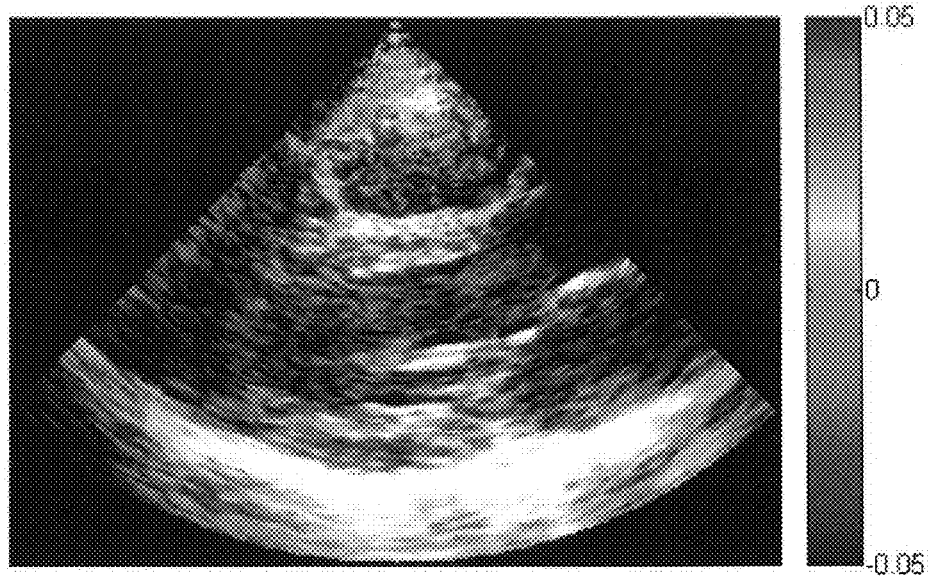
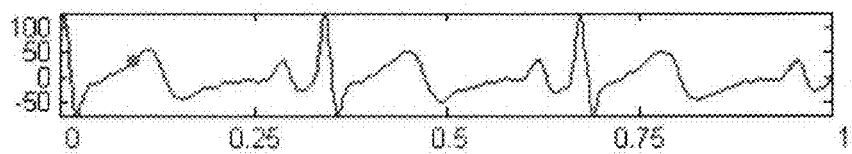
Fig. 18(h)

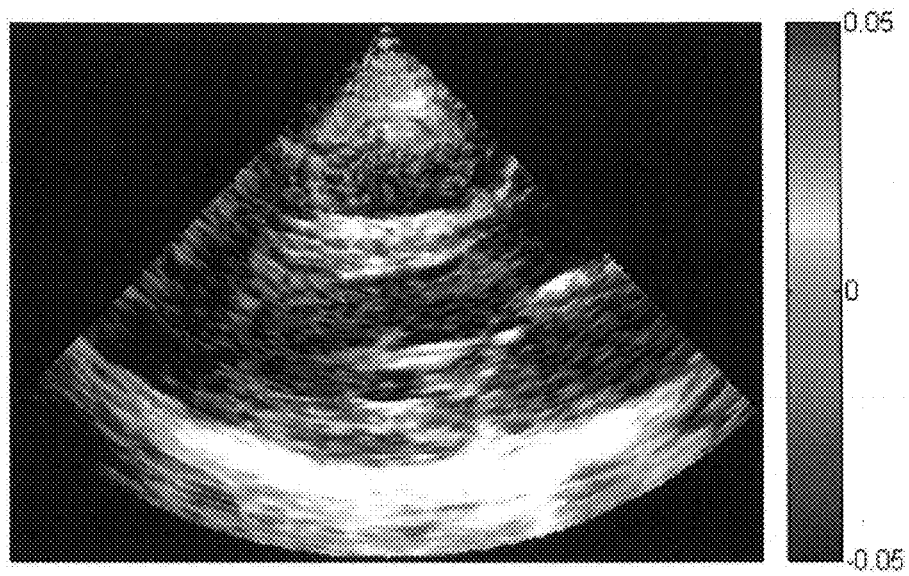
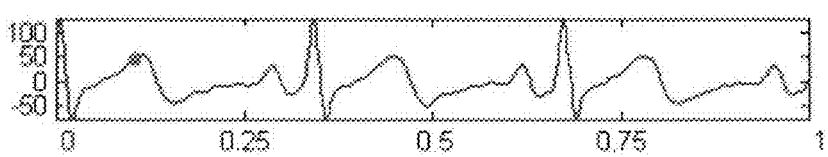
Fig. 18(i)
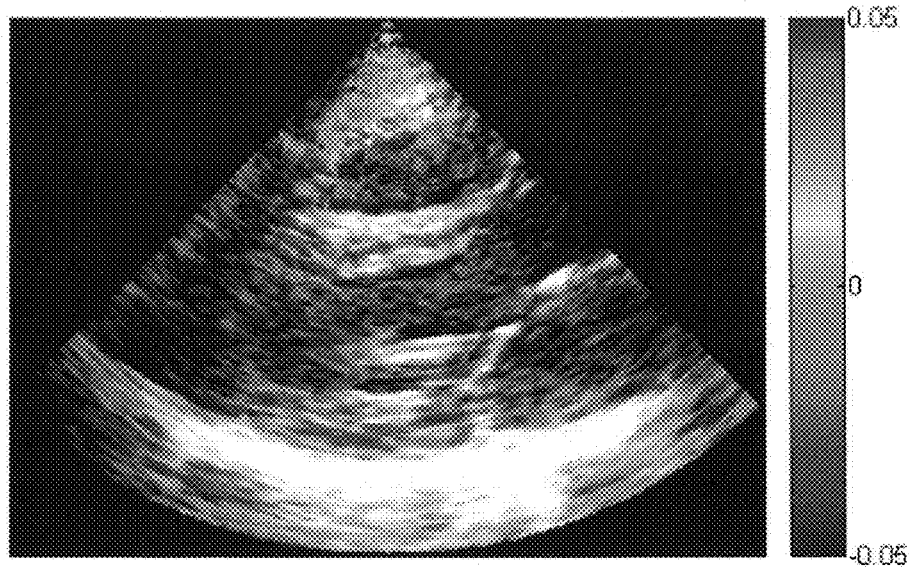
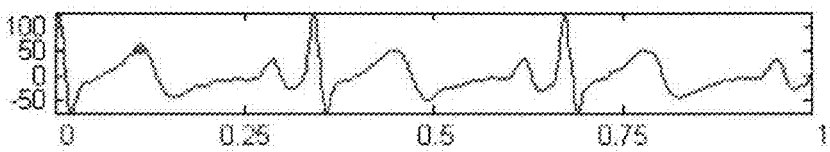
Fig. 18(j)

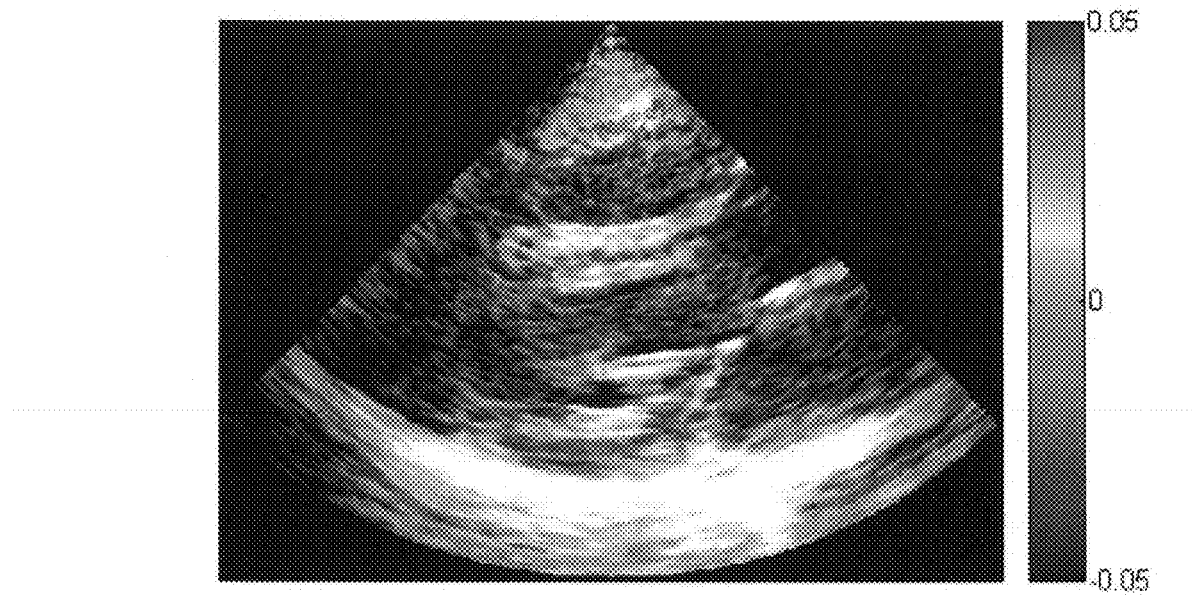
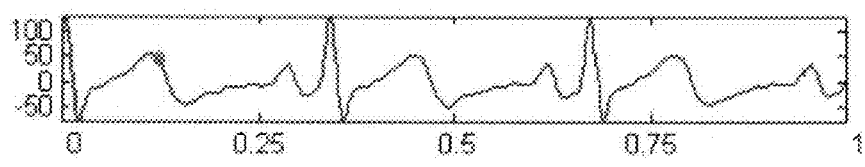
Fig. 18(k)
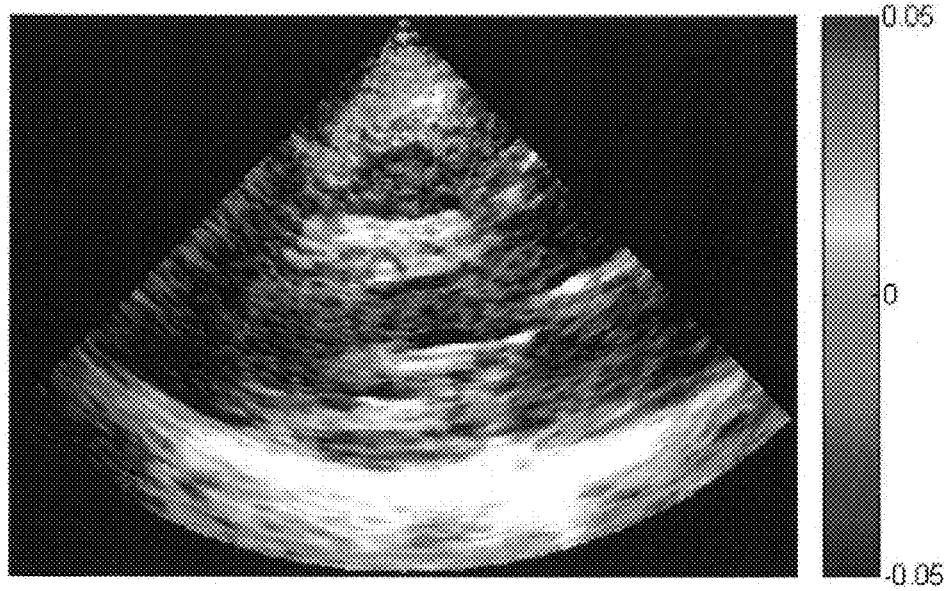
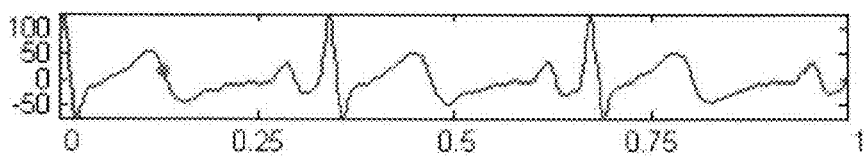
Fig. 18(l)

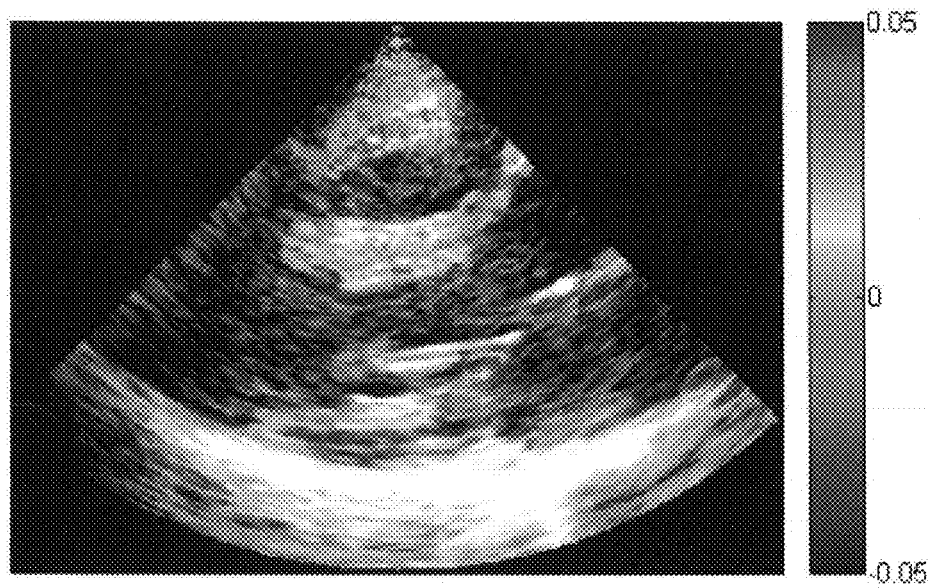
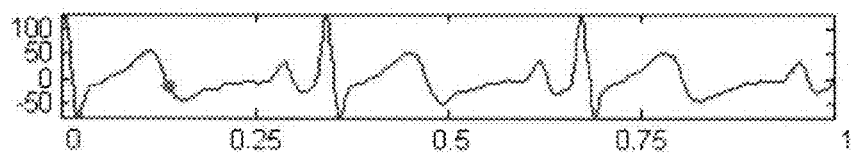
Fig. 18(m)
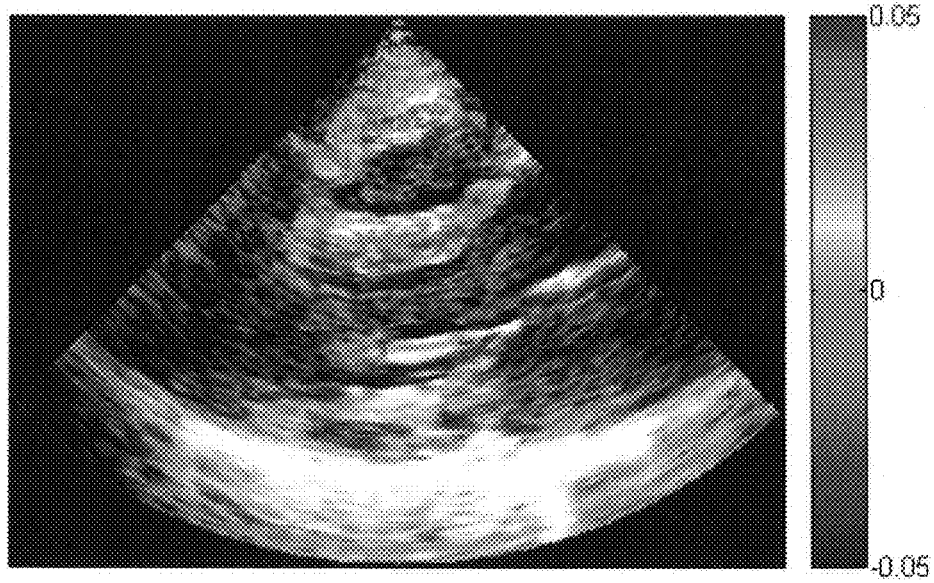
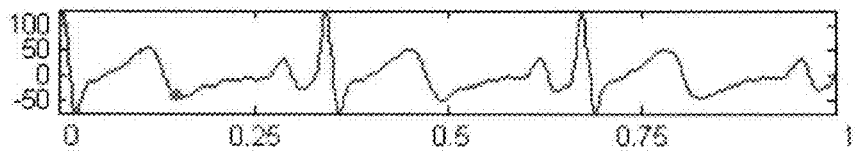
Fig. 18(n)

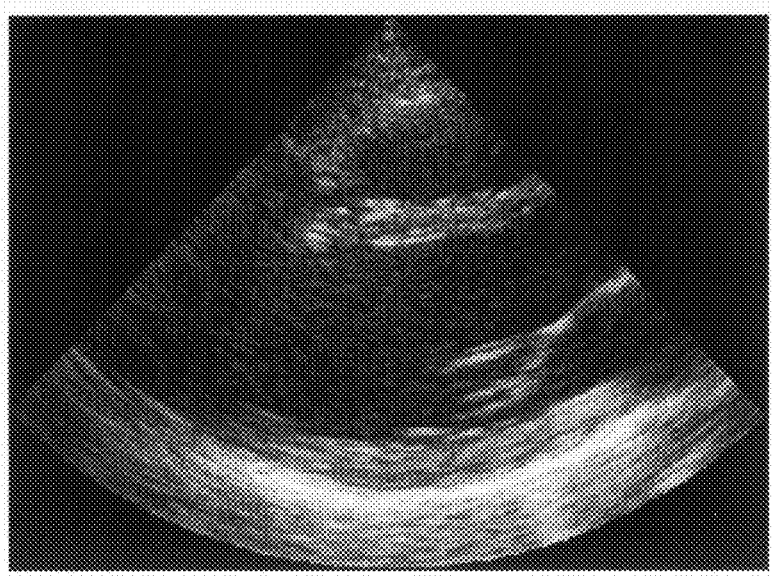
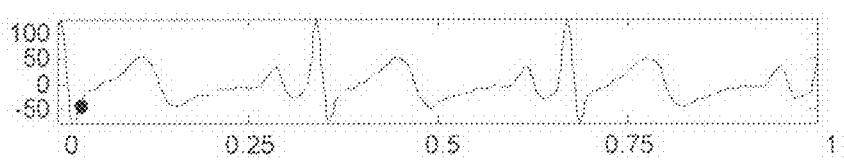
Fig. 18A(a1)
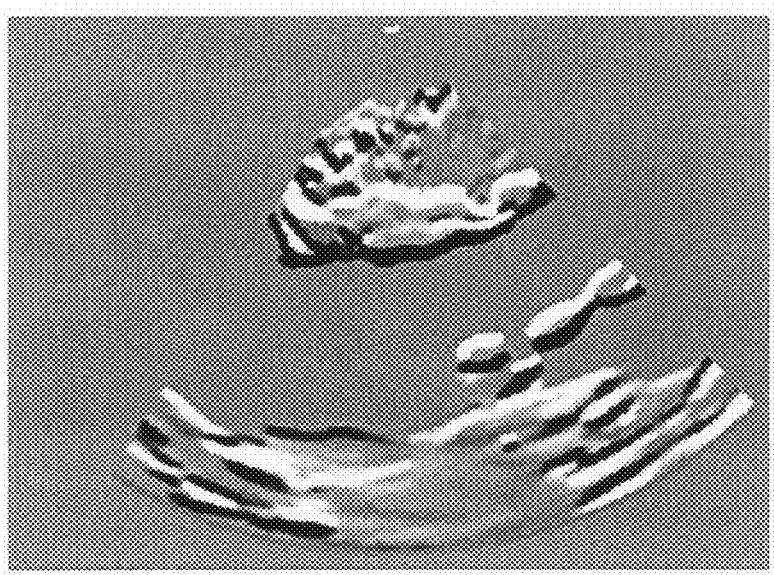
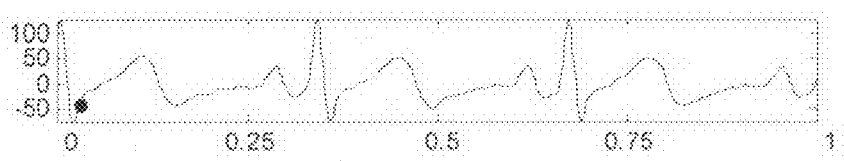
Fig. 18A(a2)

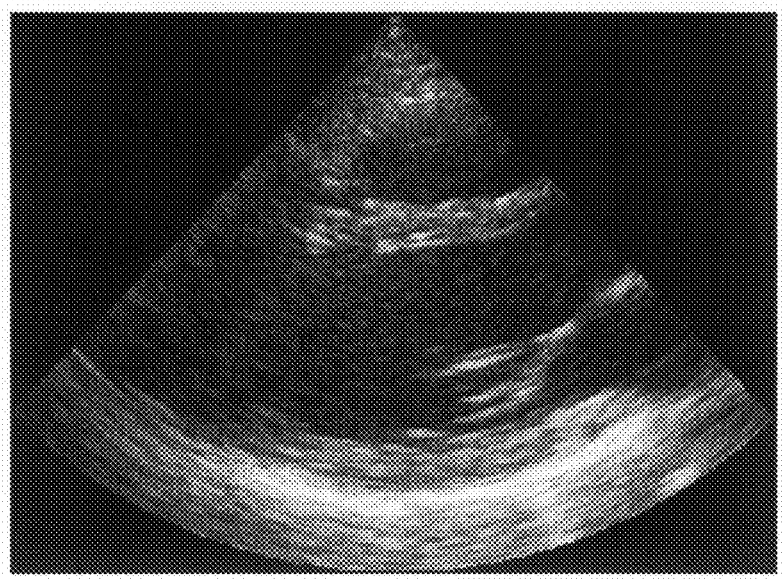
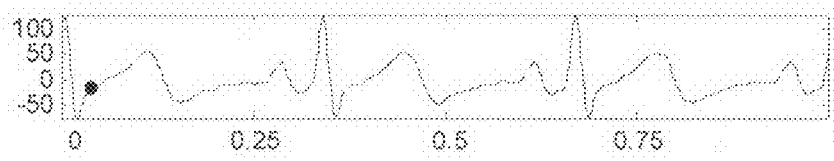
Fig. 18A(b1)
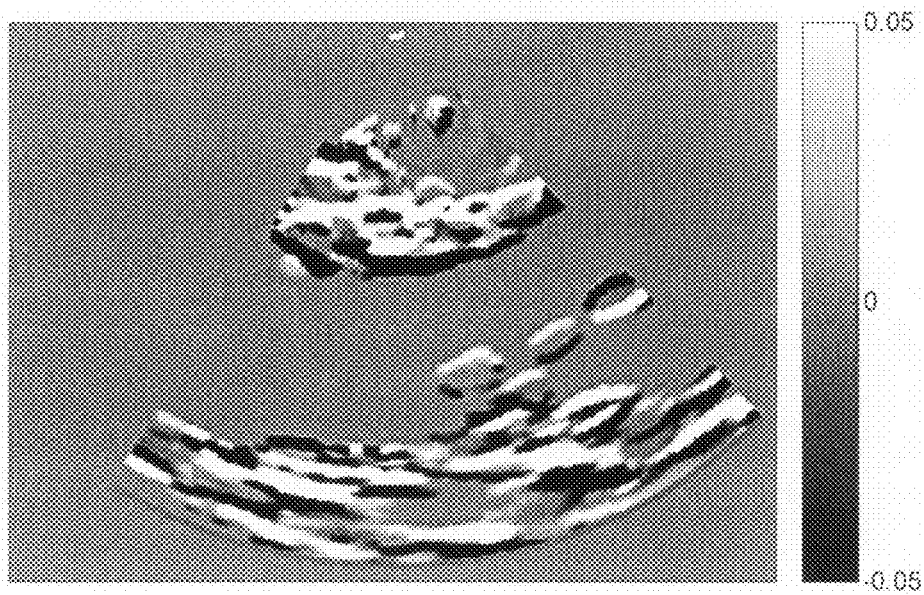
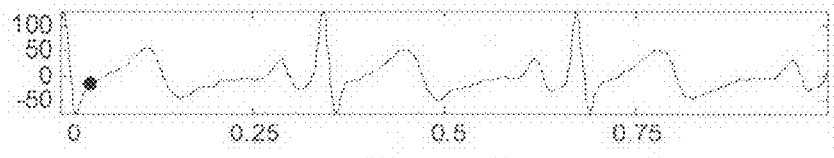
Fig. 18A(b2)

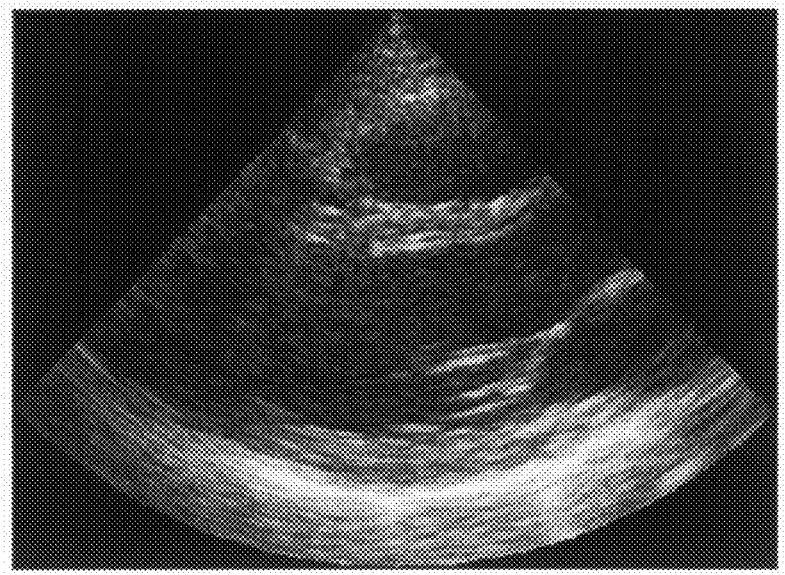
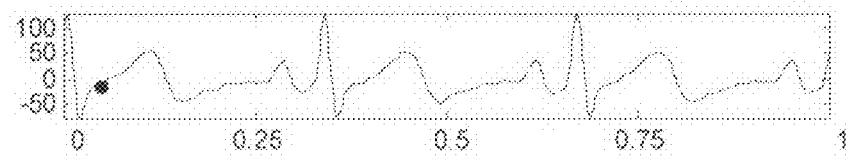
Fig. 18A(c1)
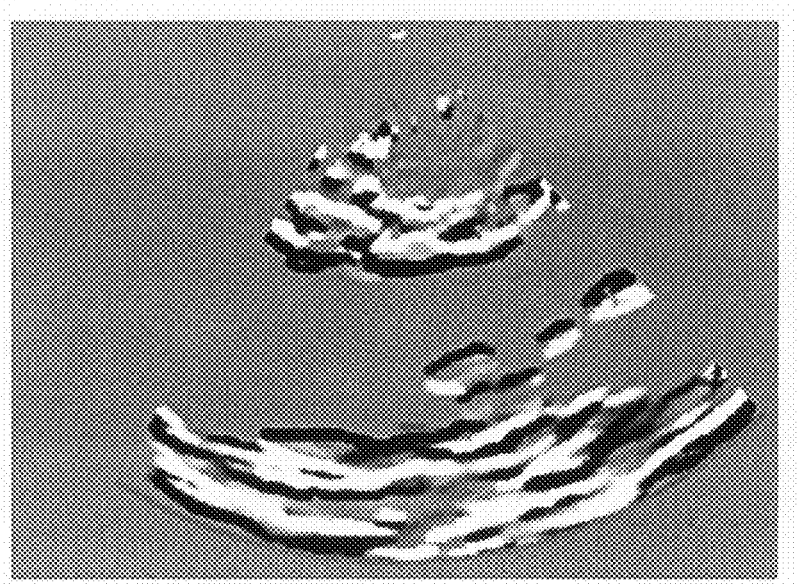
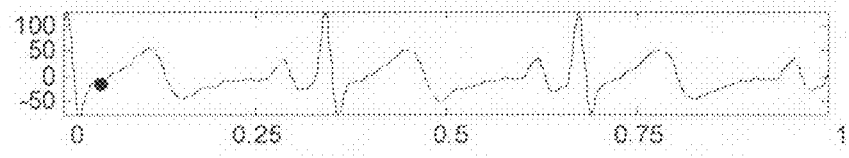
Fig. 18A(c2)

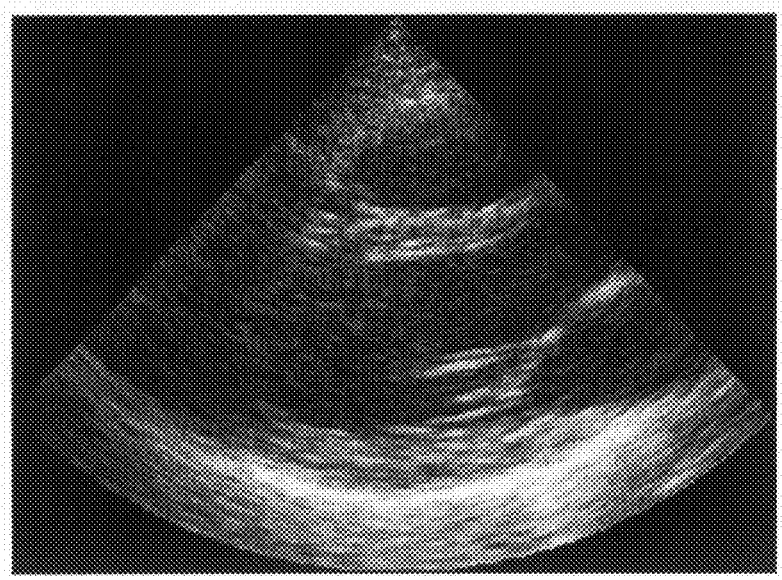
Fig. 18A(d1)
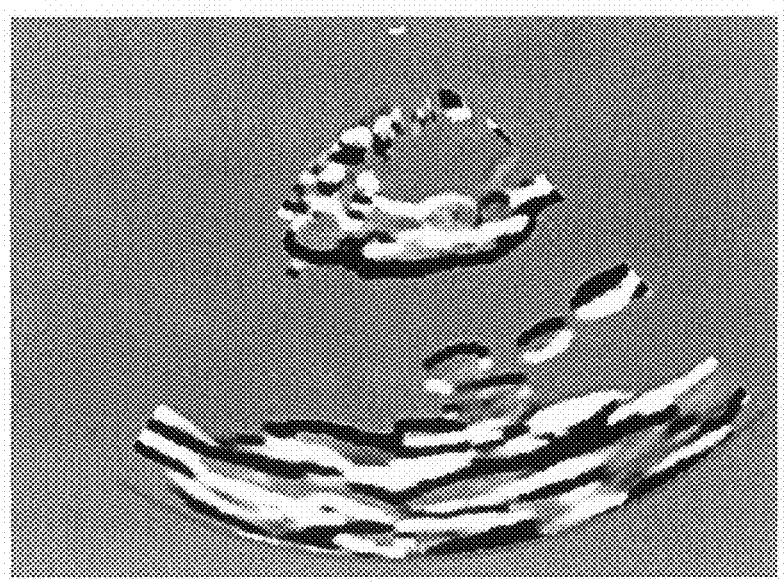
Fig. 18A(d2)

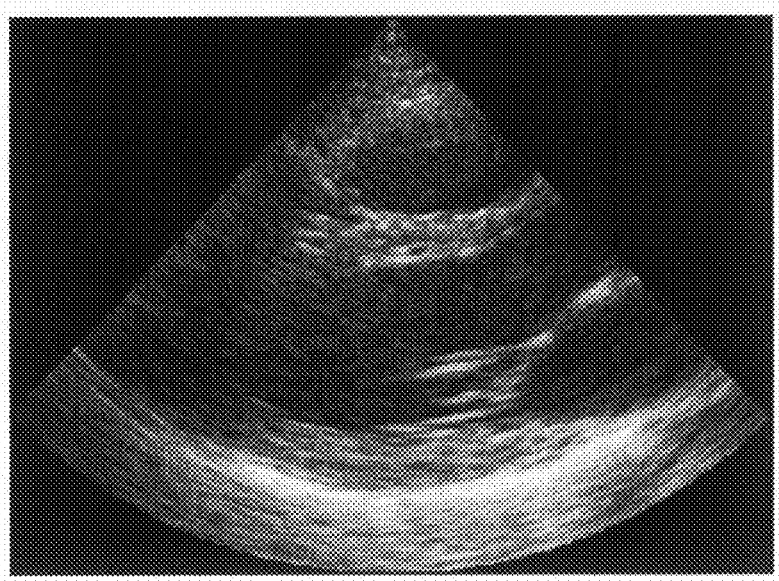
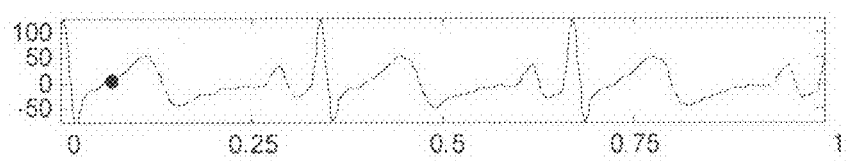
Fig. 18A(e1)
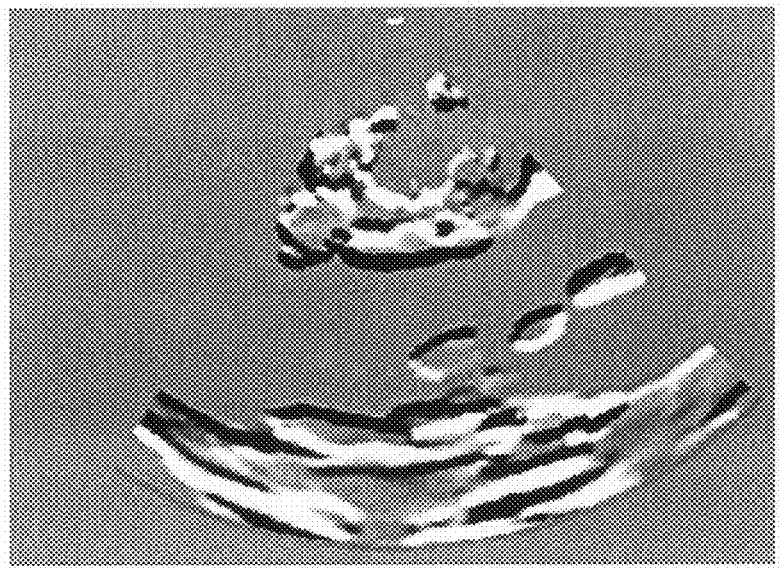
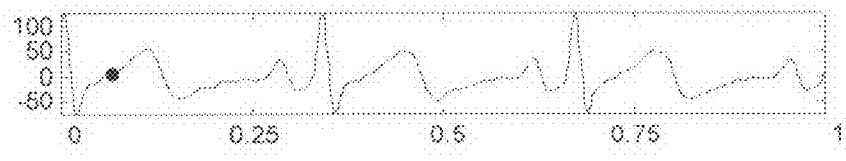
Fig. 18A(e2)

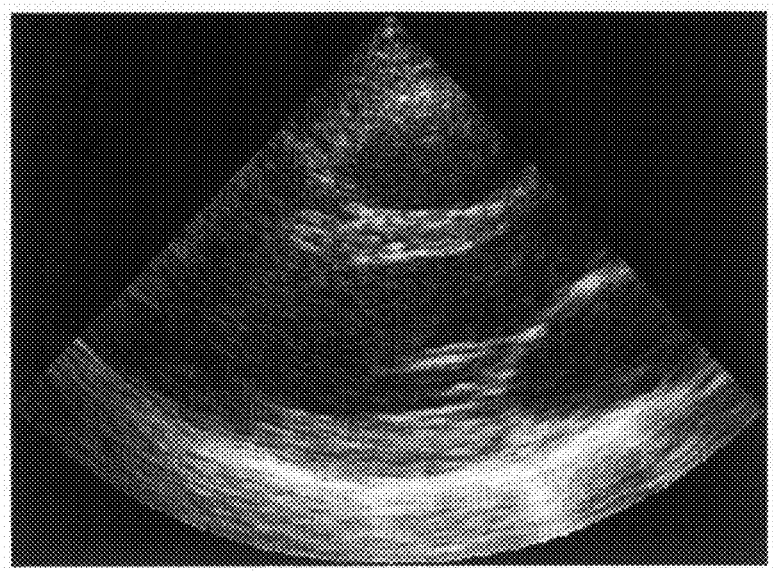
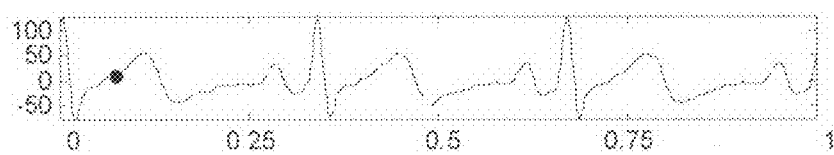
Fig. 18A(f1)
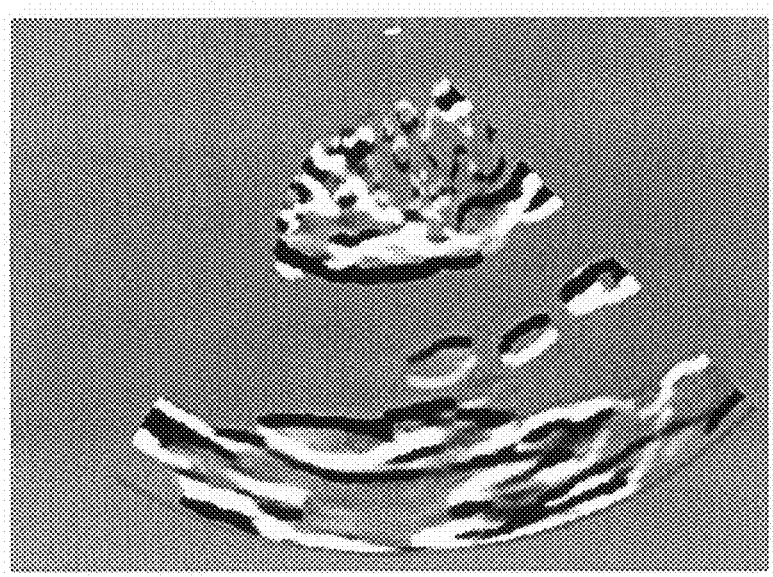
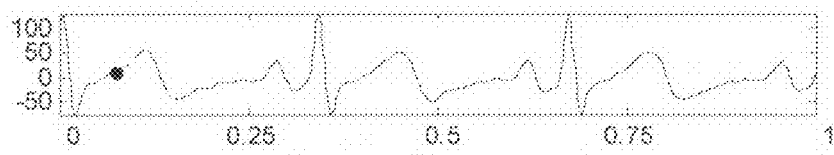
Fig. 18A(f2)

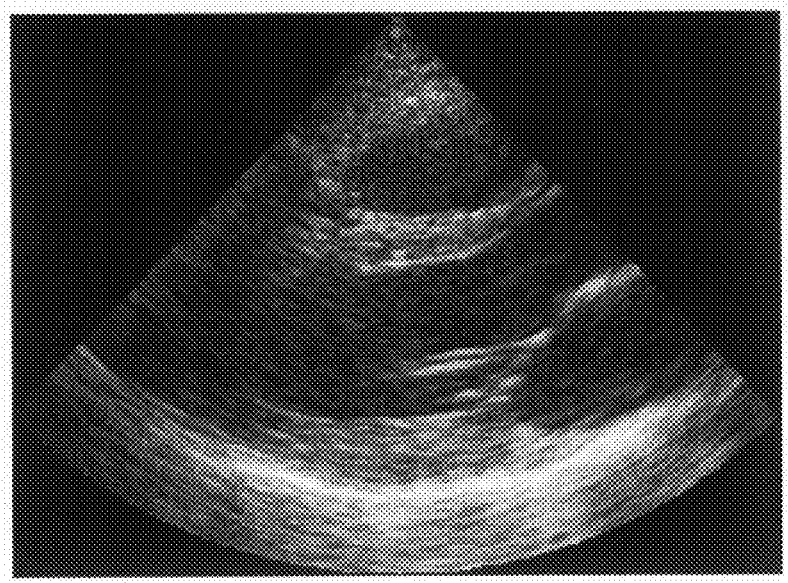
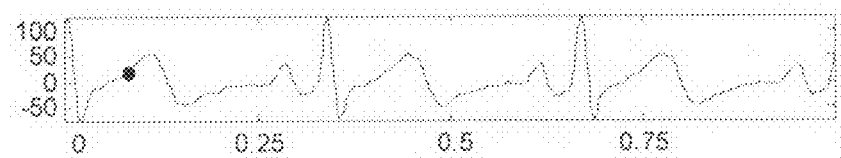
Fig. 18A(g1)
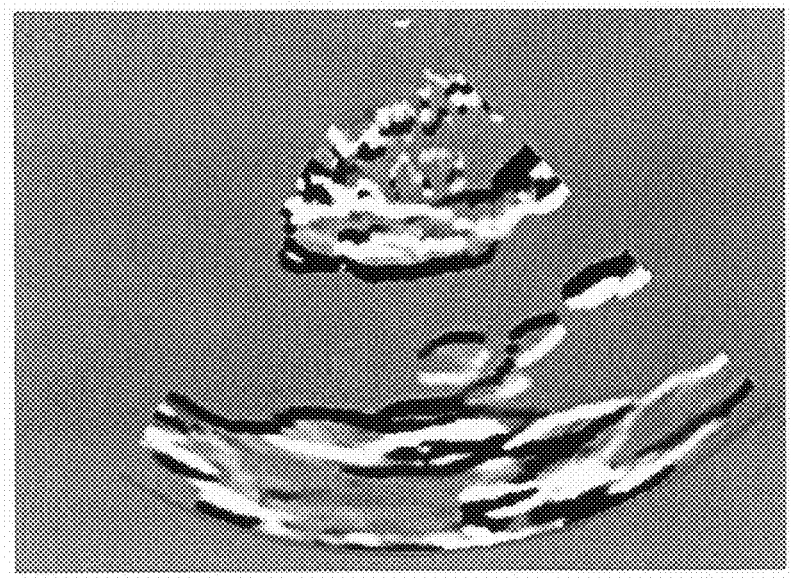
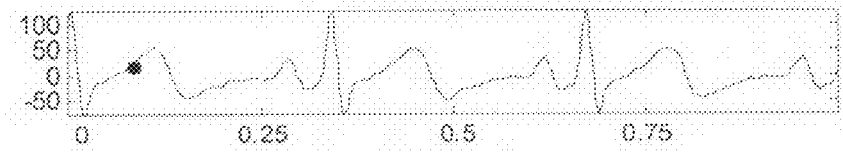
Fig. 18A(g2)

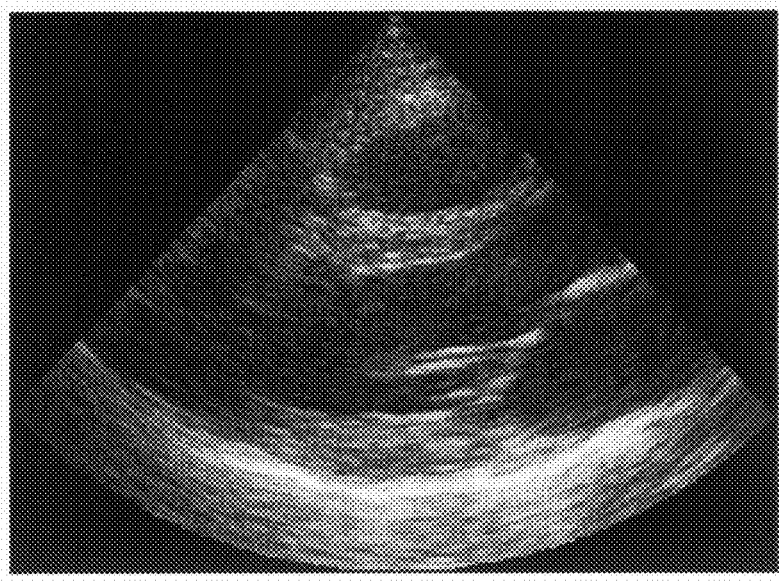
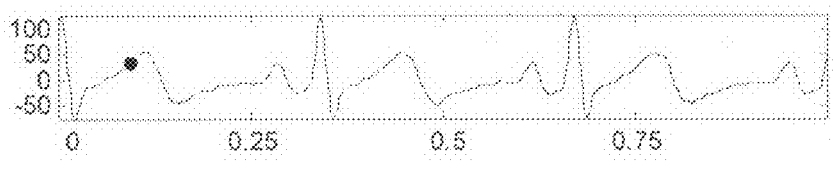
Fig. 18A(h1)
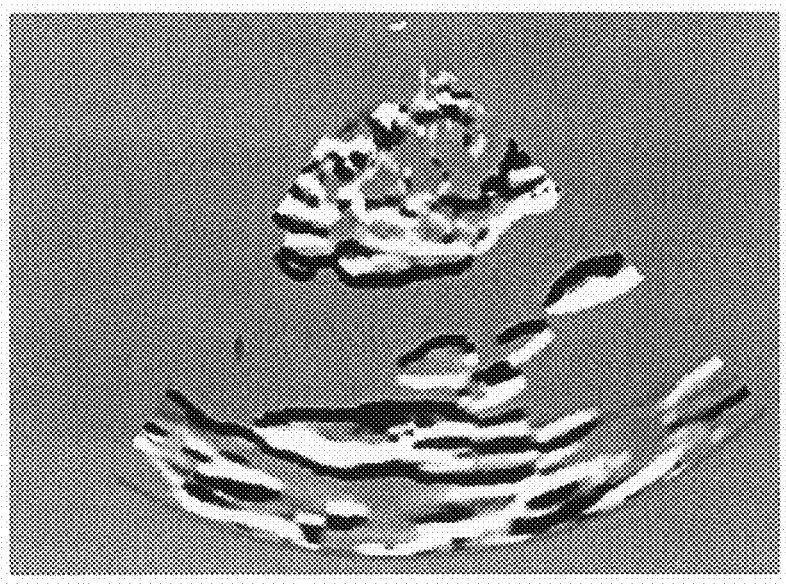
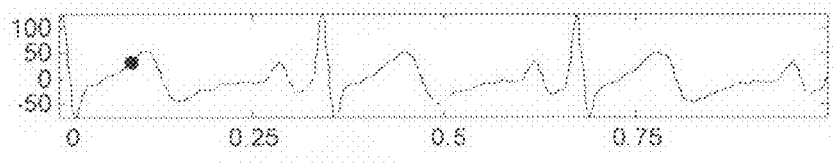
Fig. 18A(h2)

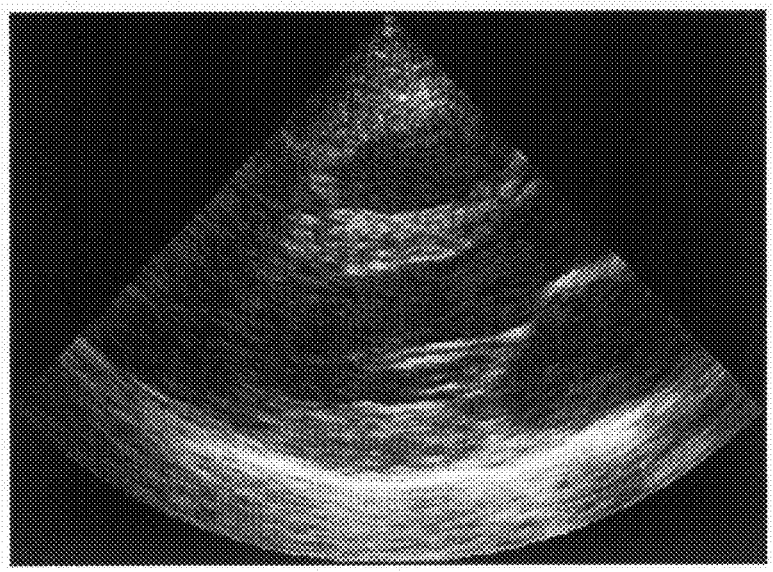
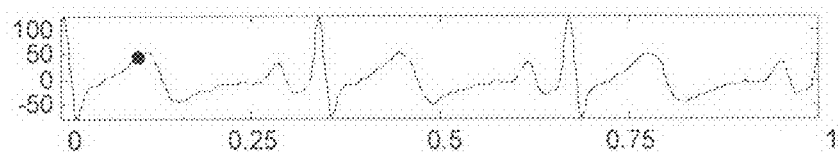
Fig. 18A(i1)
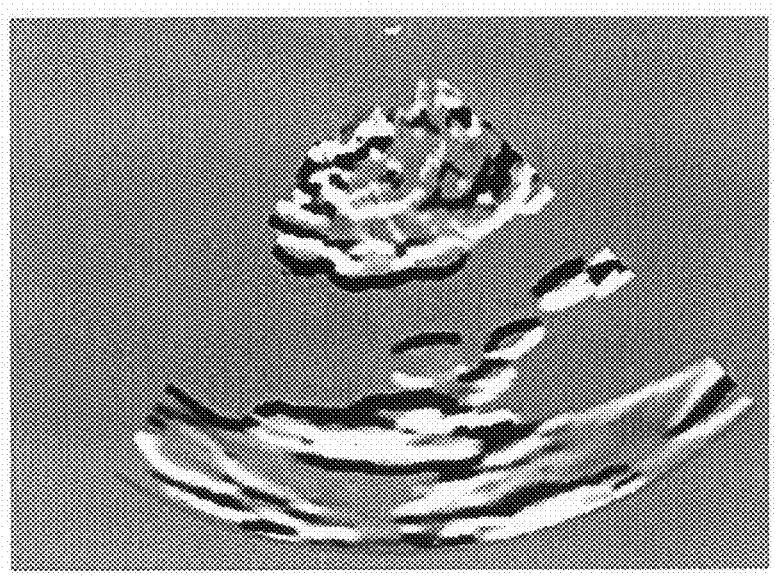
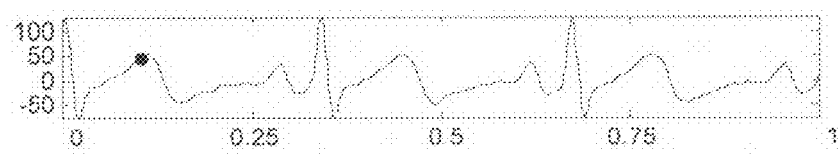
Fig. 18A(i2)

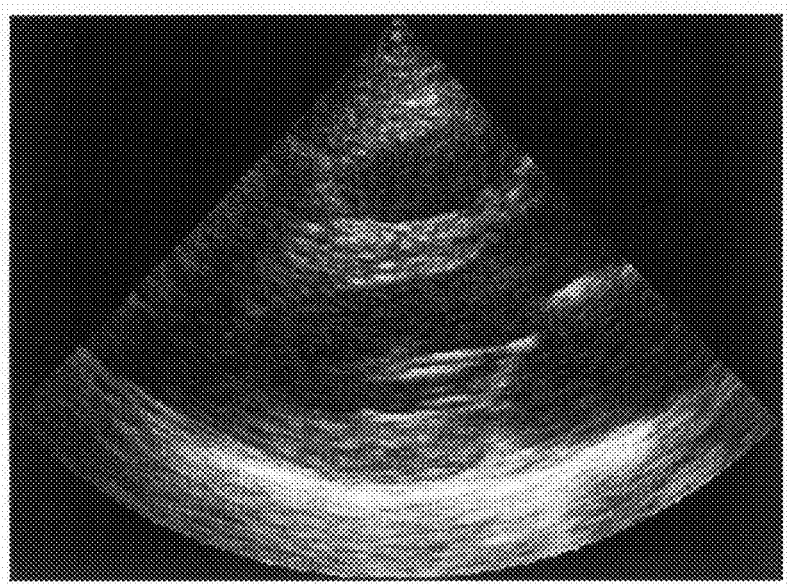
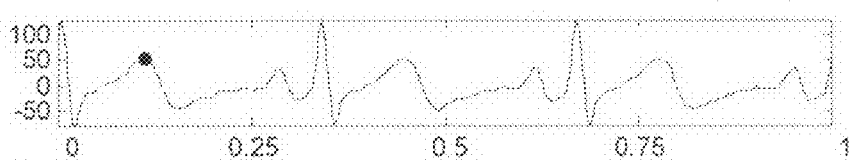
Fig. 18A(j1)
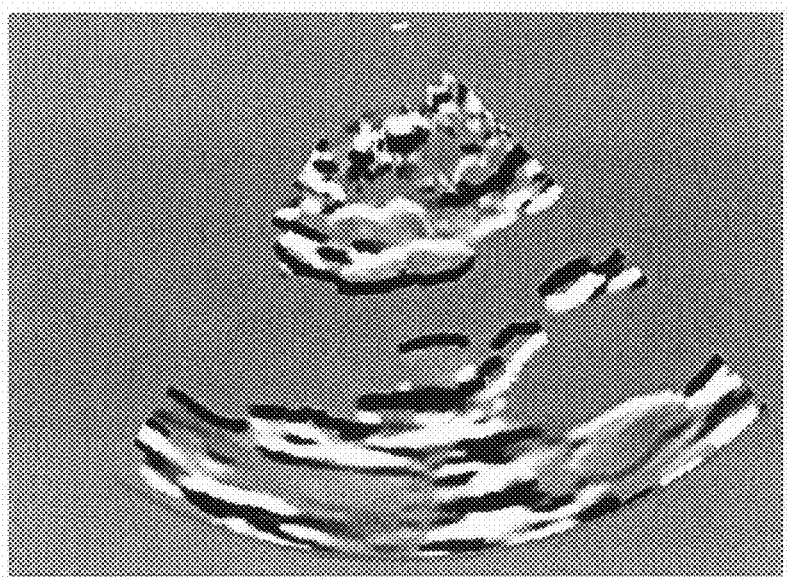
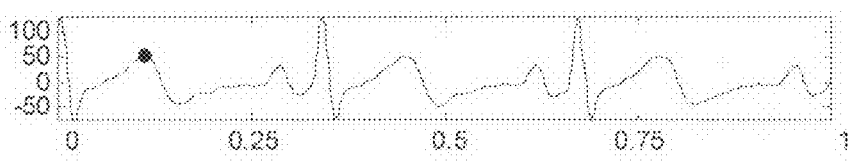
Fig. 18A(j2)

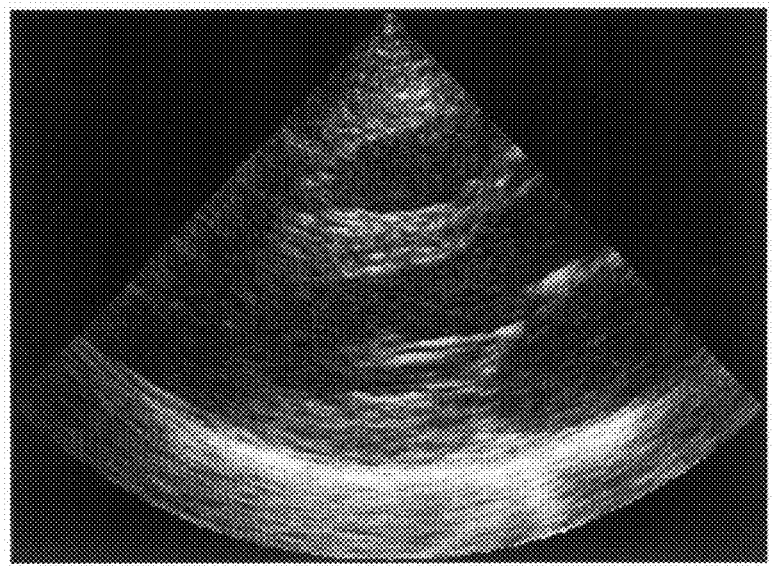
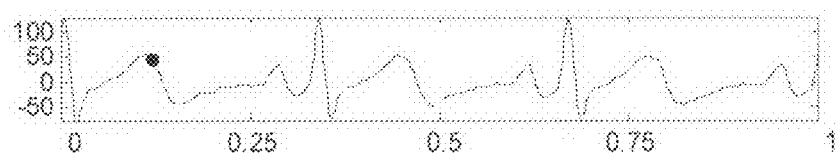
Fig. 18A(k1)
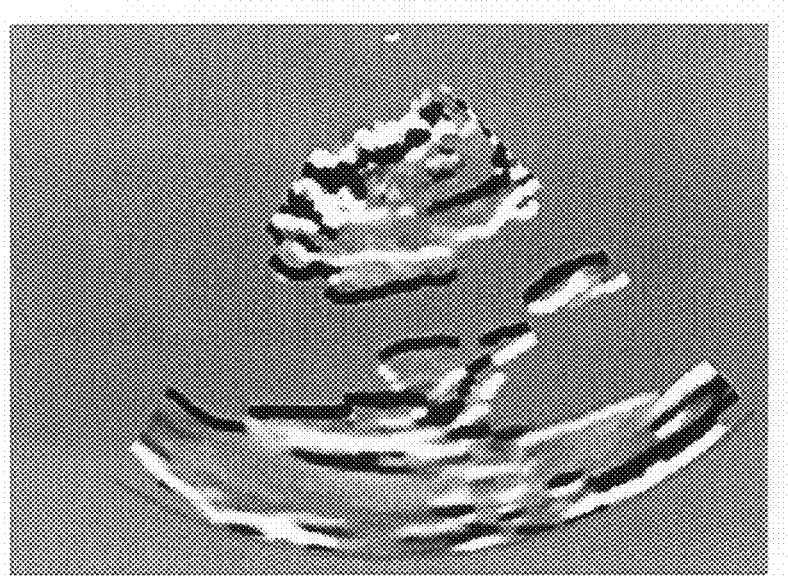
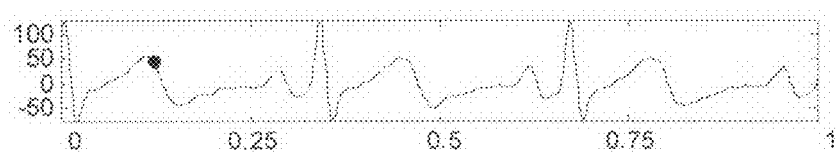
Fig. 18A(k2)

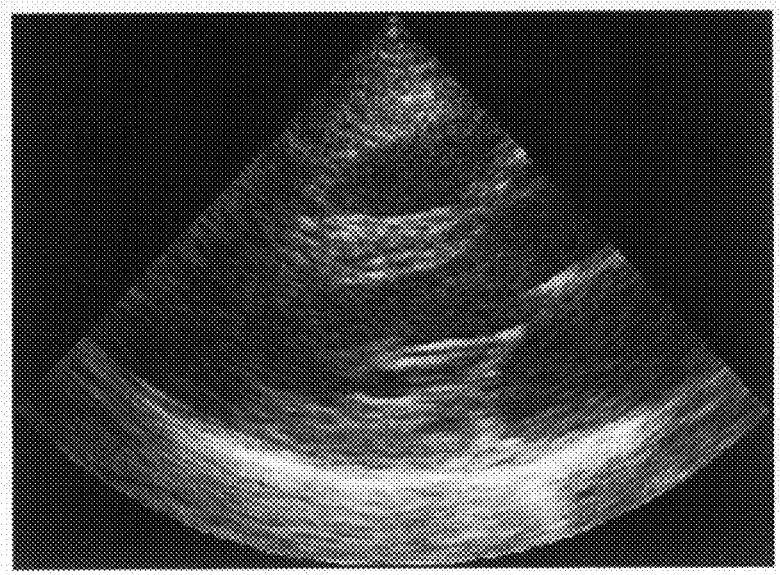
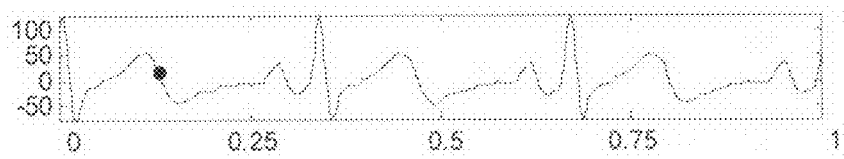
Fig. 18A(I1)
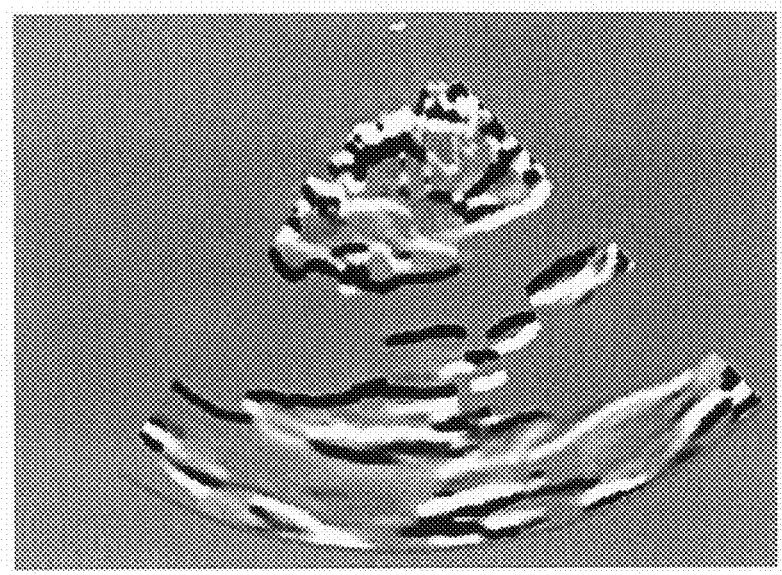
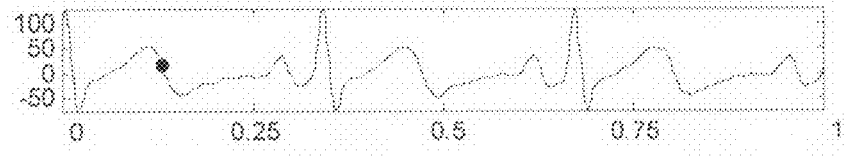
Fig. 18A(I2)

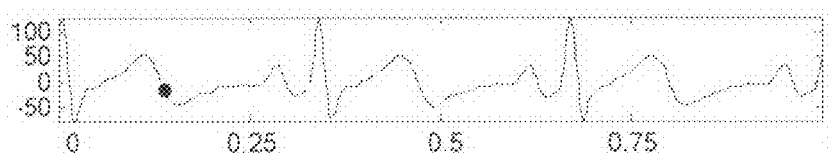
Fig. 18A(m1)
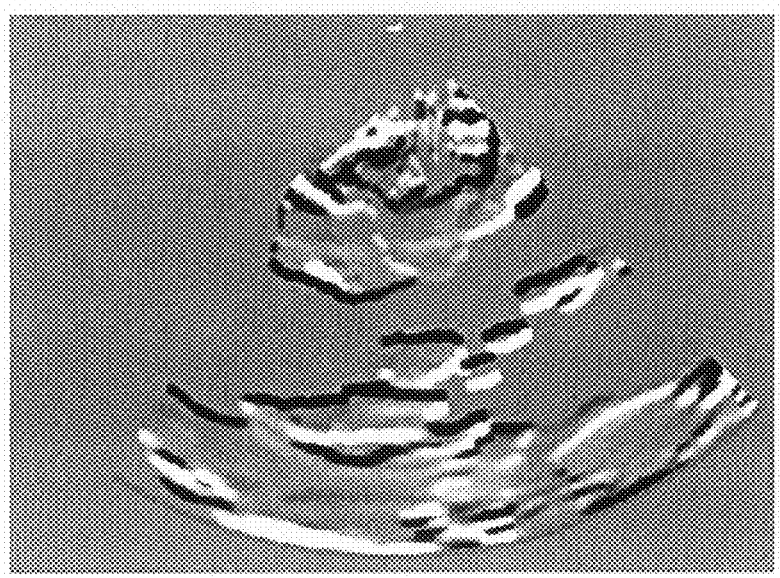
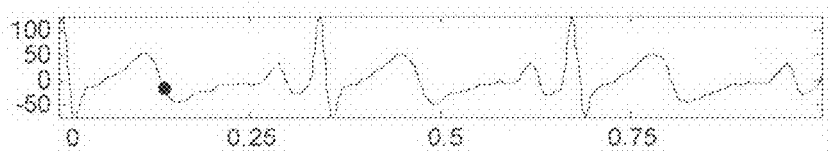
Fig. 18A(m2)

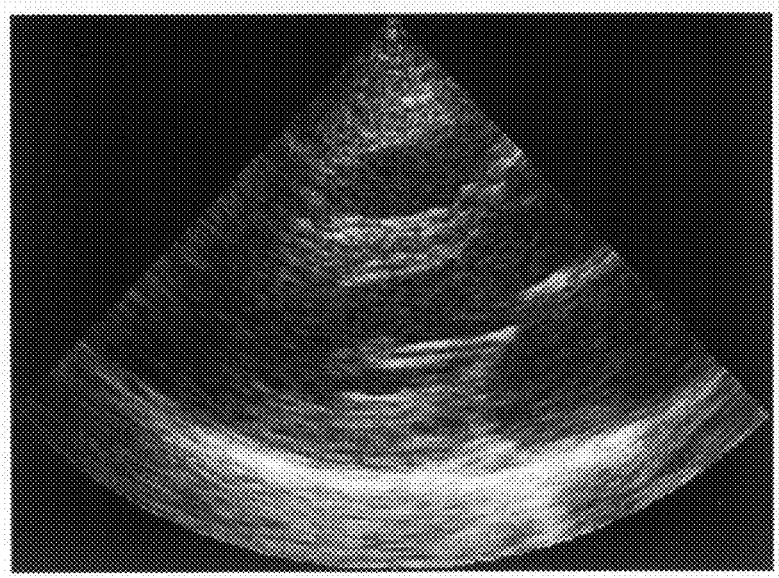
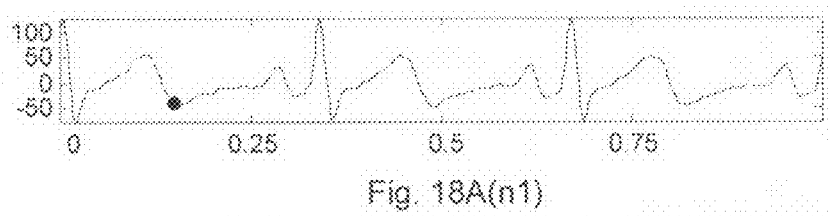
Fig. 18A(n1)
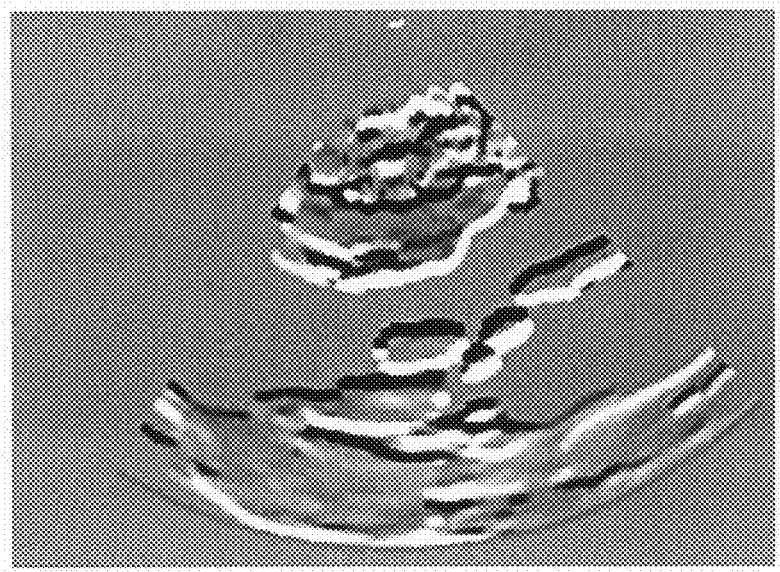
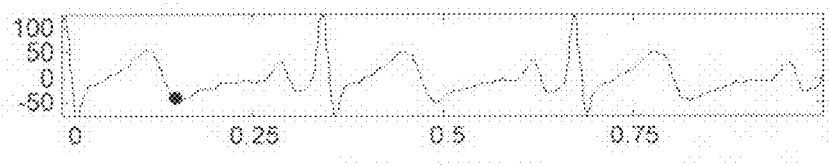
Fig. 18A(n2)

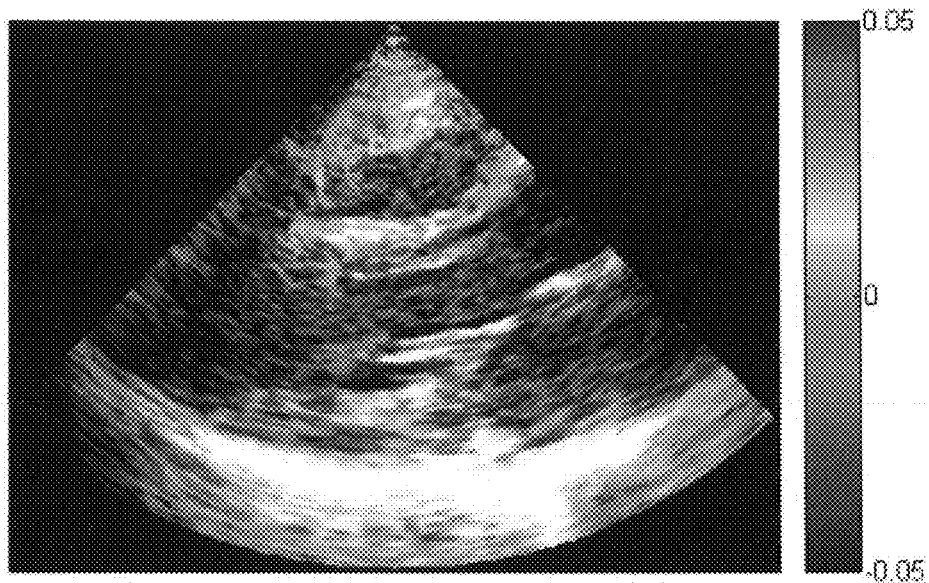
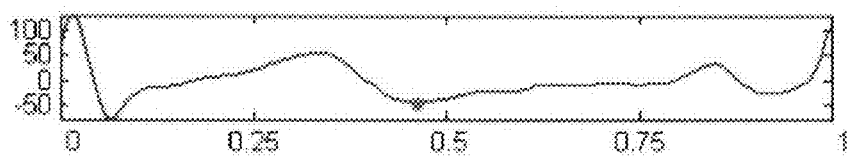
Fig. 19(a)
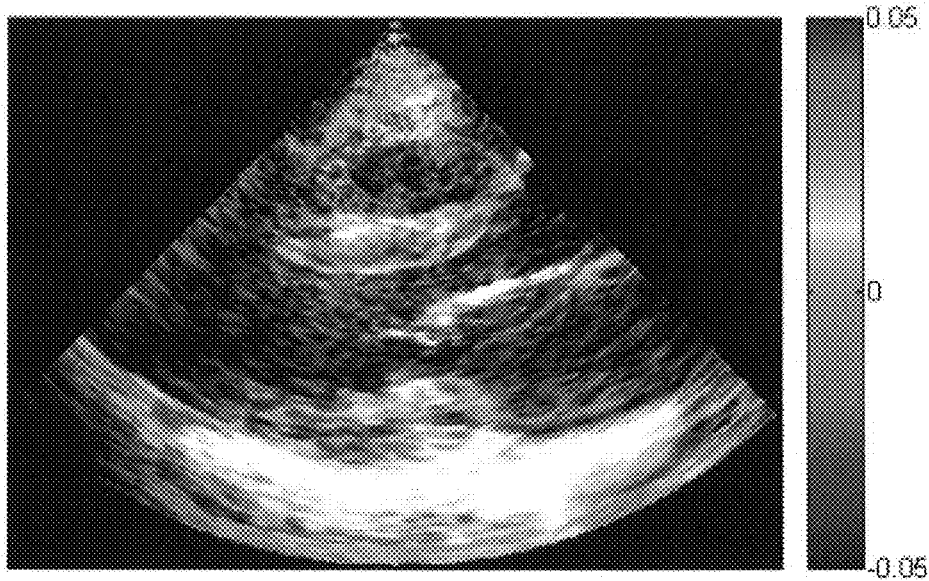
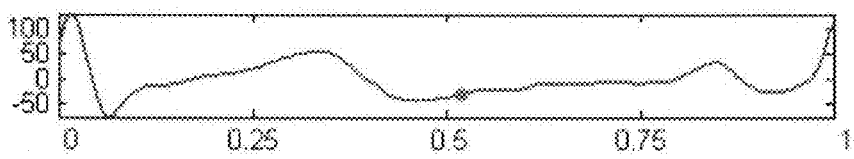
Fig. 19(b)

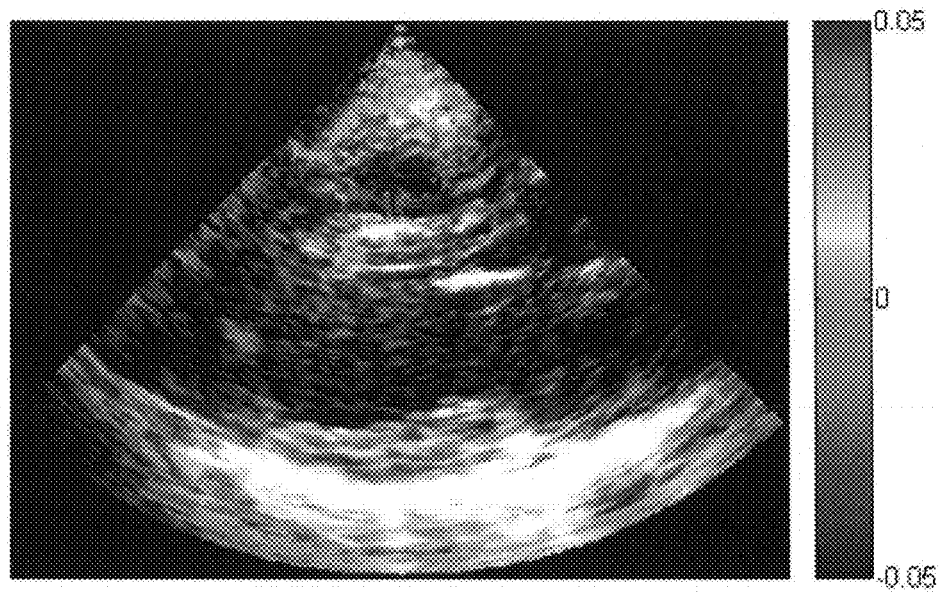
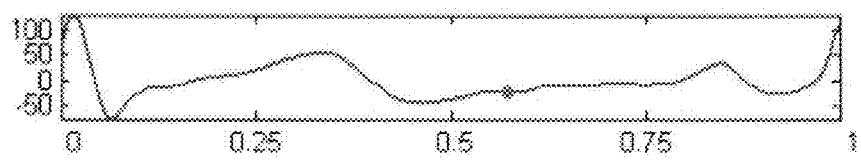
Fig. 19(c)
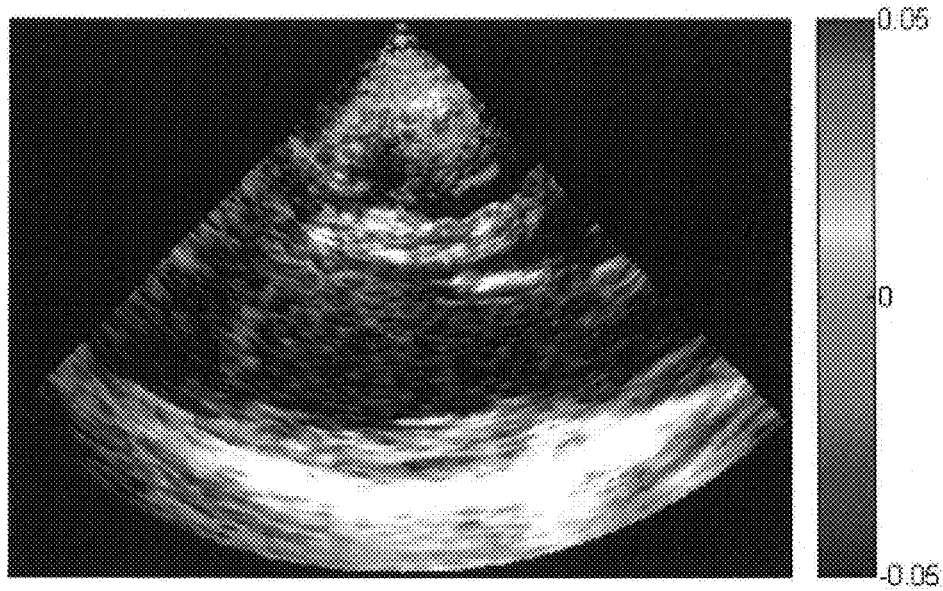
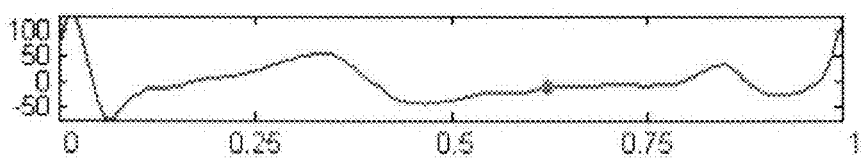
Fig. 19(d)

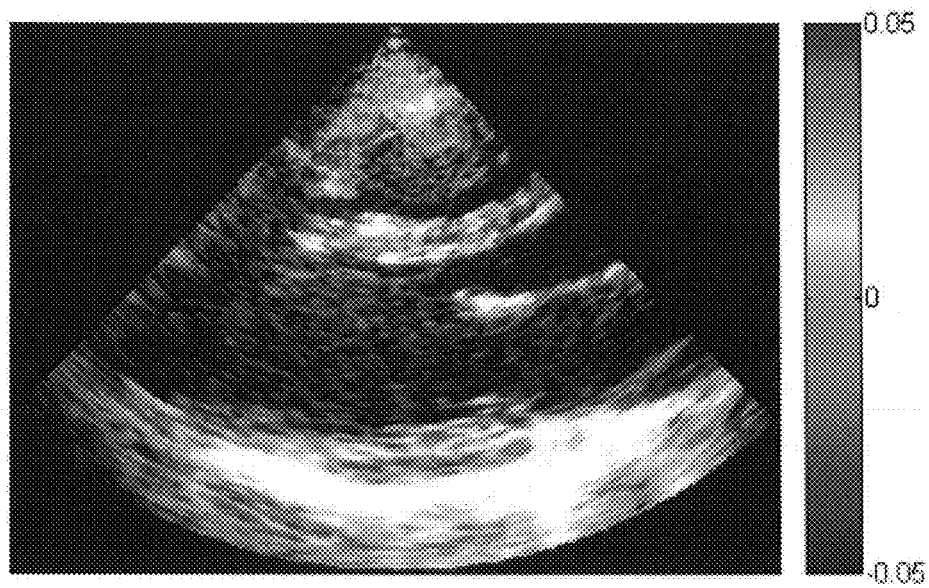
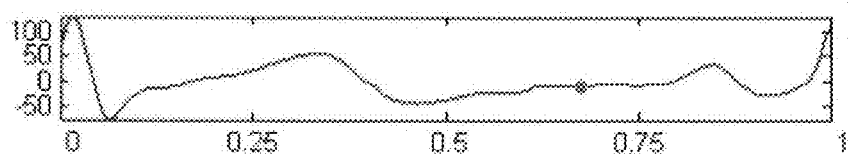
Fig. 19(e)
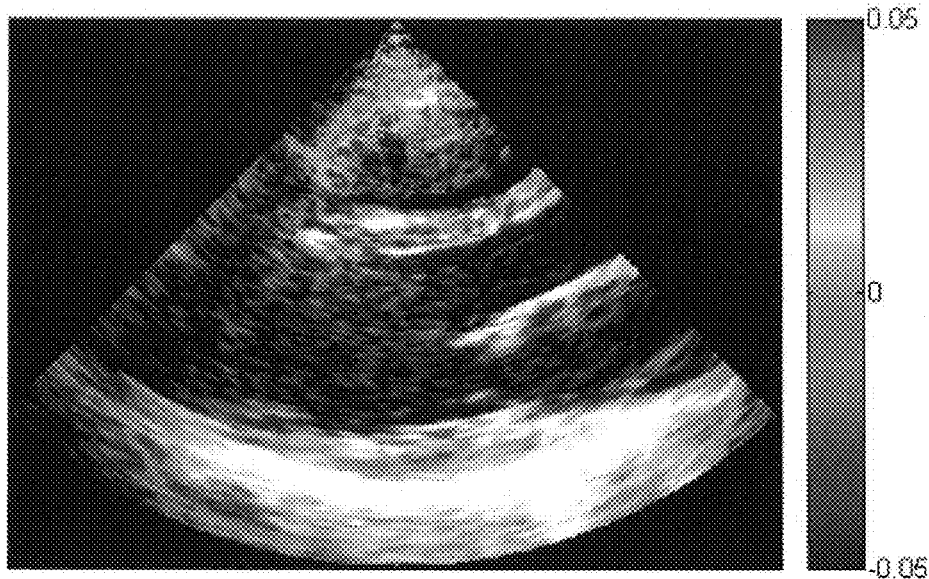
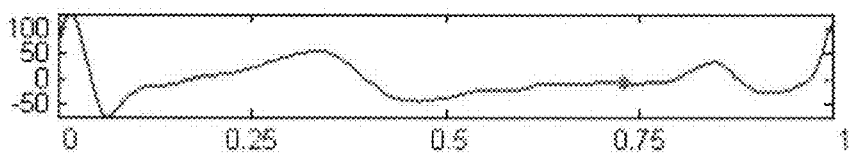
Fig. 19(f)

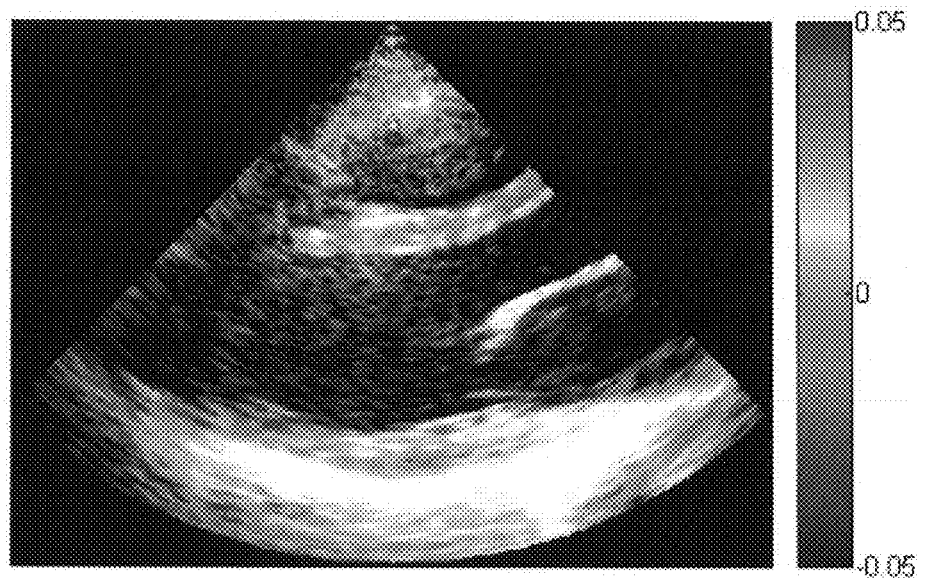
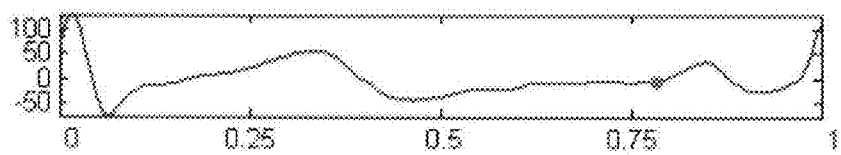
Fig. 19(g)
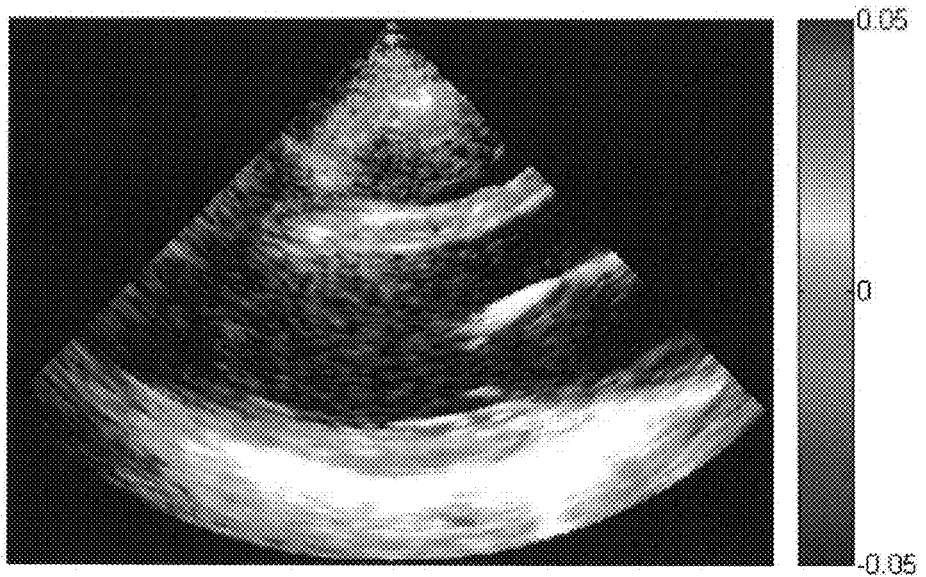
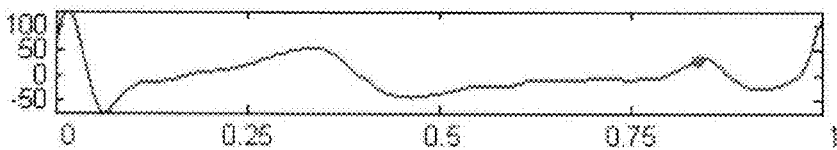
Fig. 19(h)

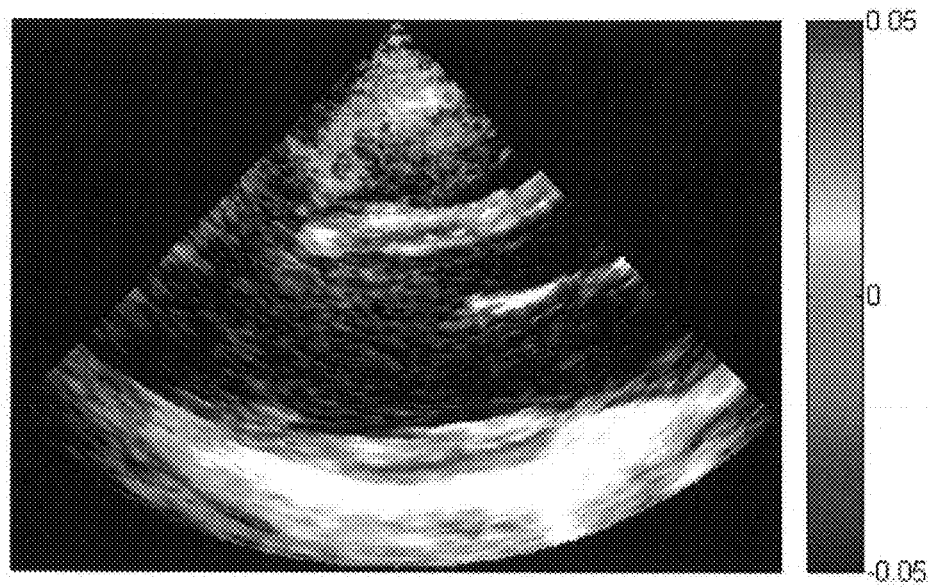
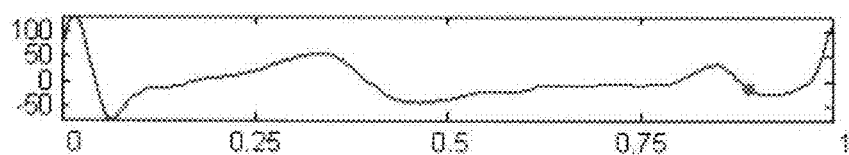
Fig. 19(i)
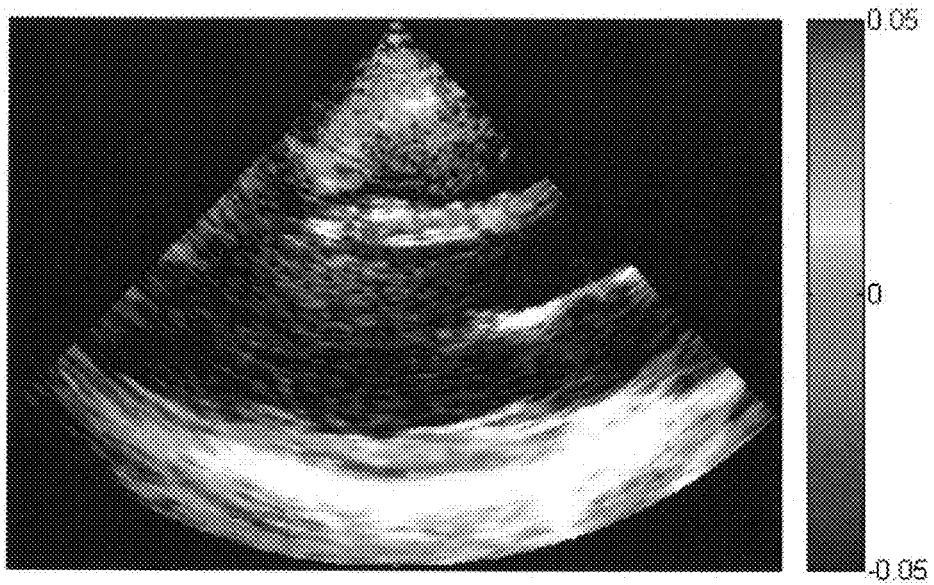
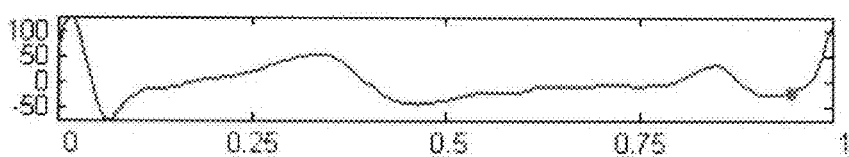
Fig. 19(j)

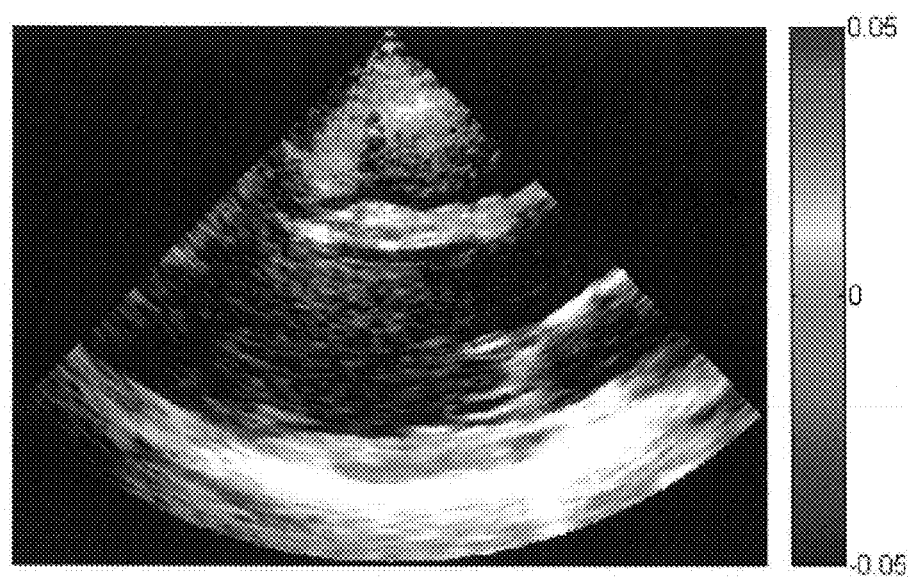
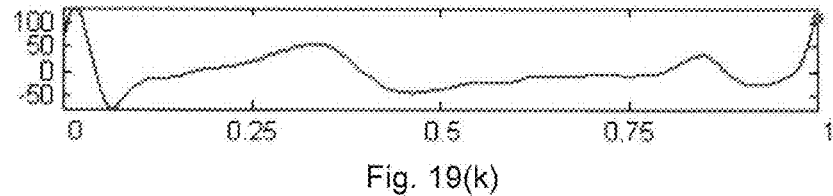
Fig. 19(k)

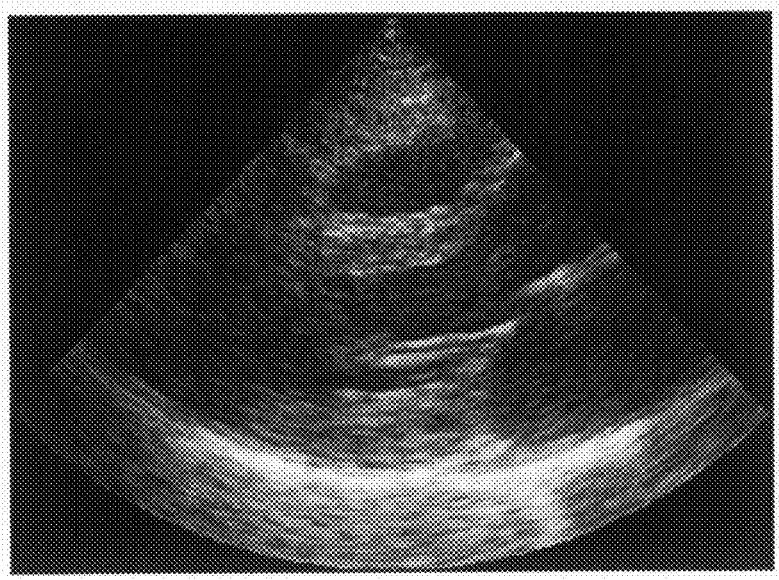
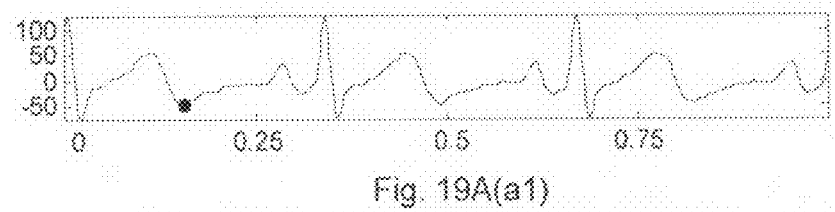
Fig. 19A(a1)
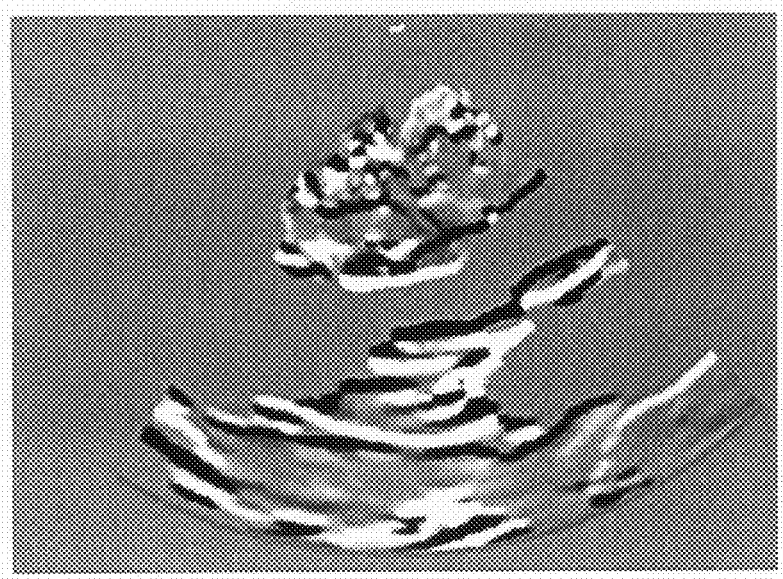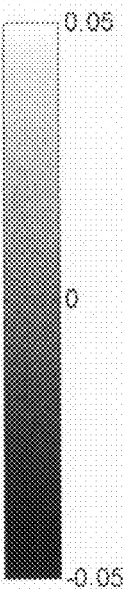
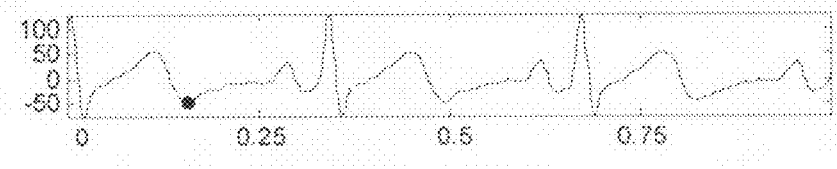
Fig. 19A(a2)

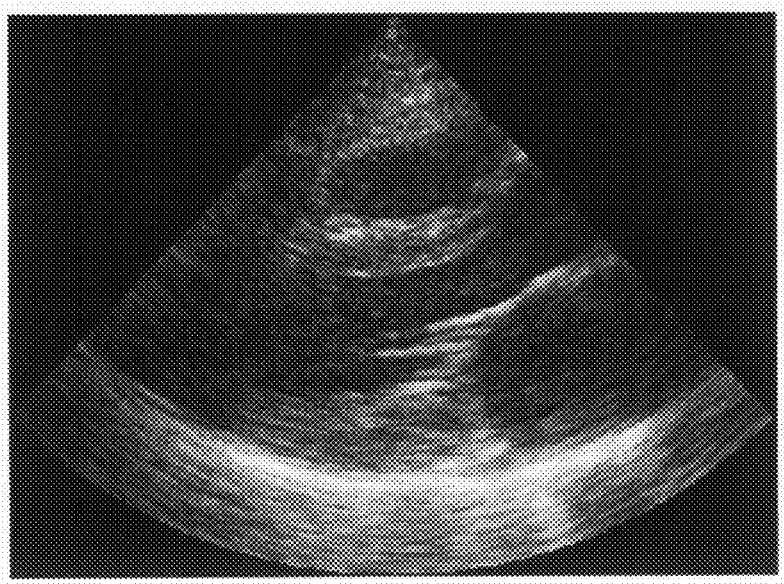
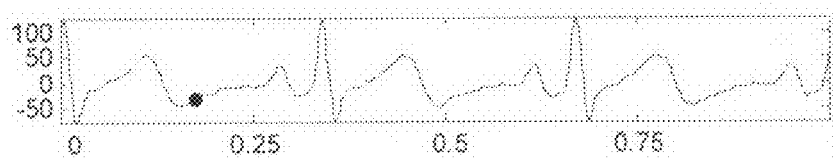
Fig. 19A(b1)
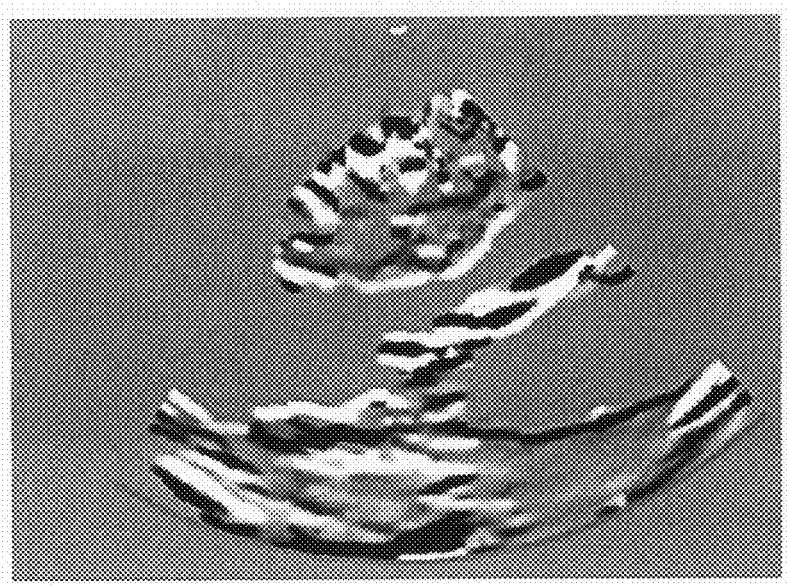
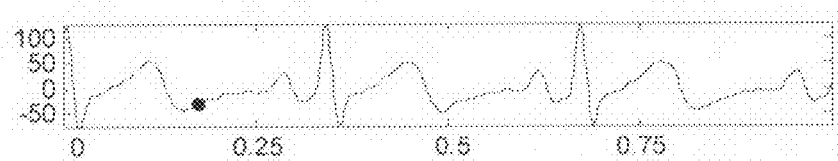
Fig. 19A(b2)

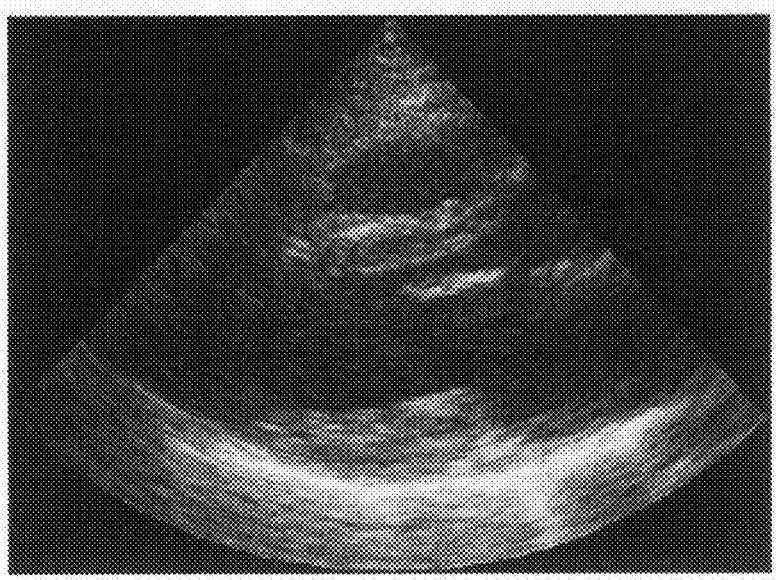
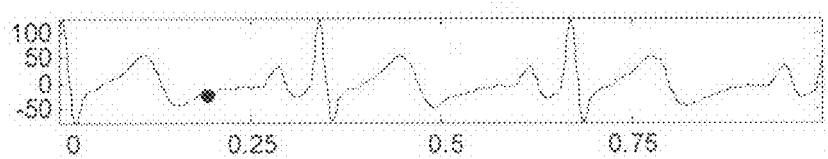
Fig. 19A(c1)
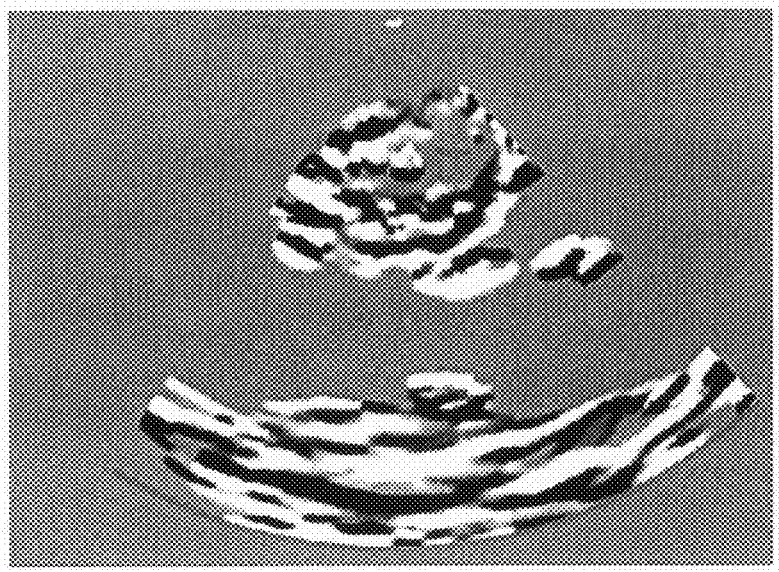
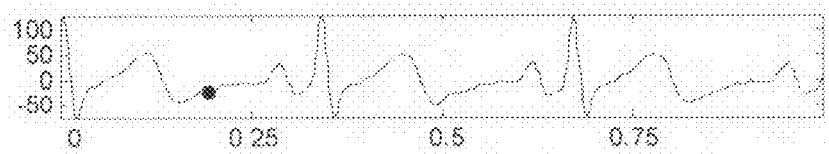
Fig. 19A(c2)

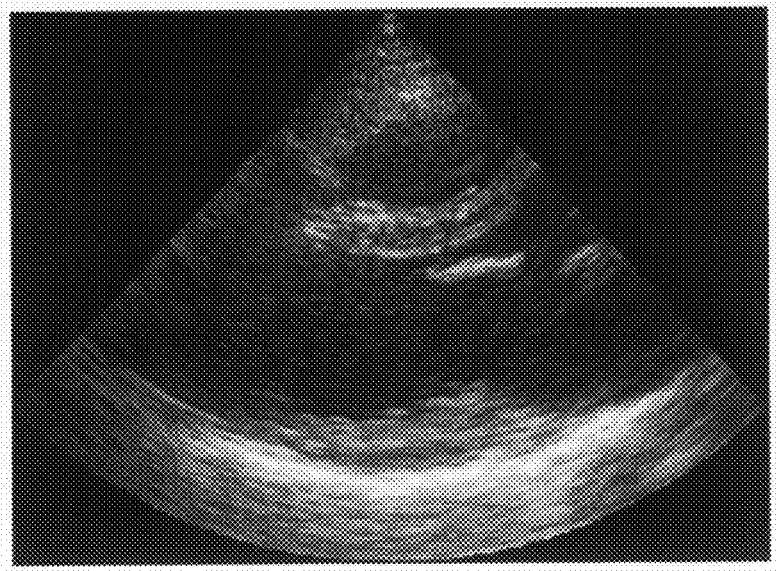
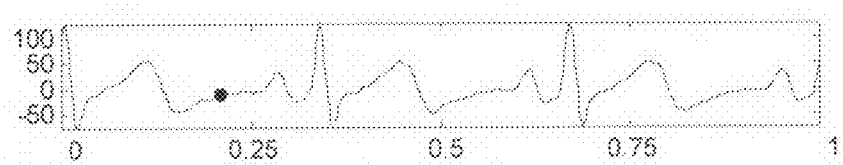
Fig. 19A(d1)
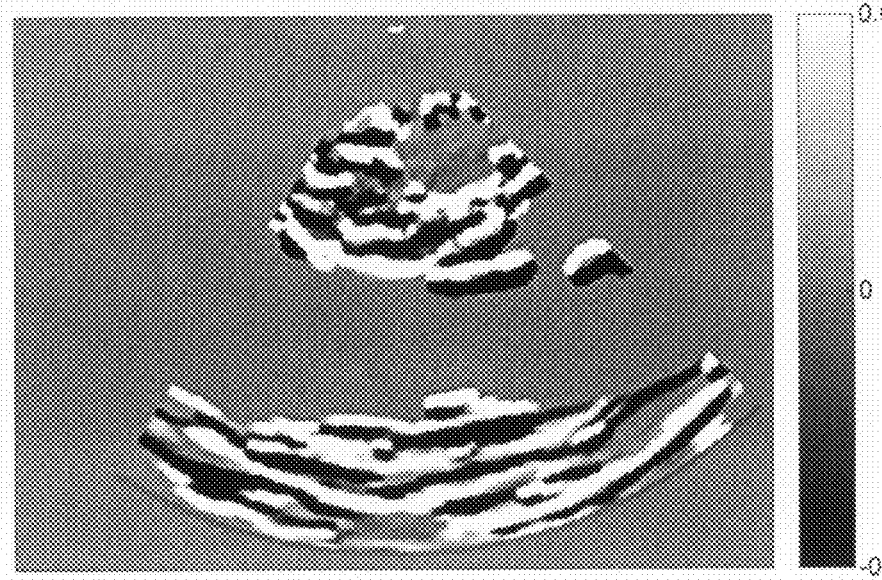
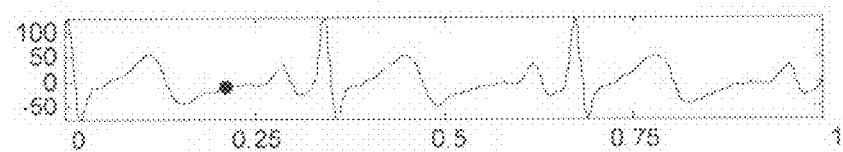
Fig. 19A(d2)

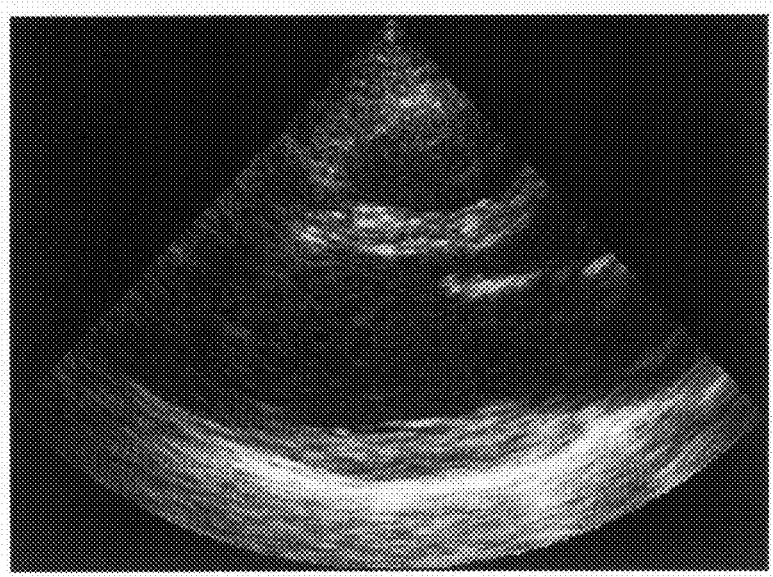
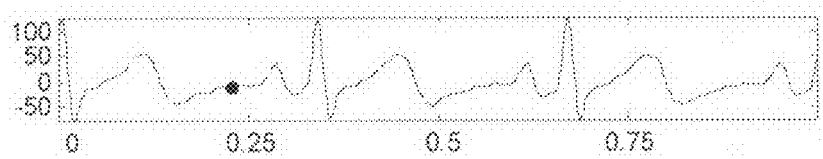
Fig. 19A(e1)
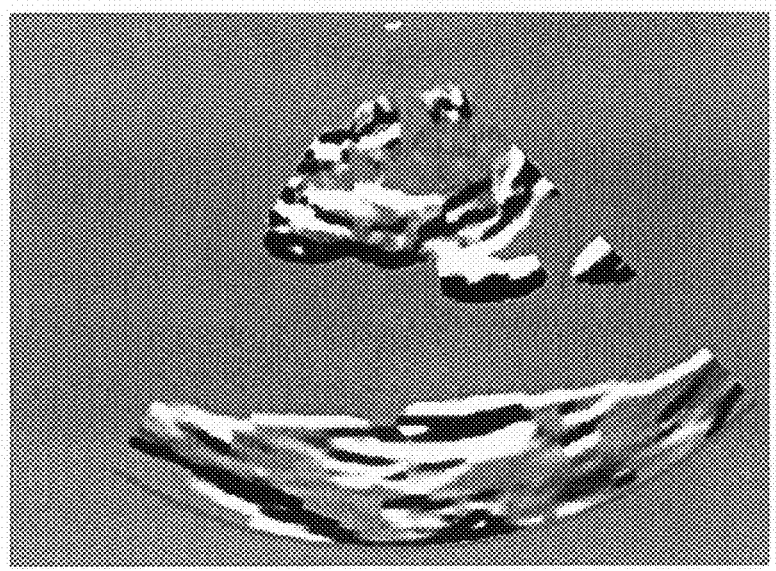
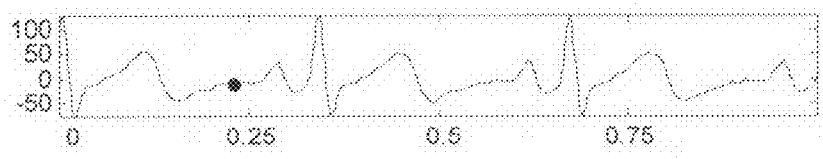
Fig. 19A(e2)

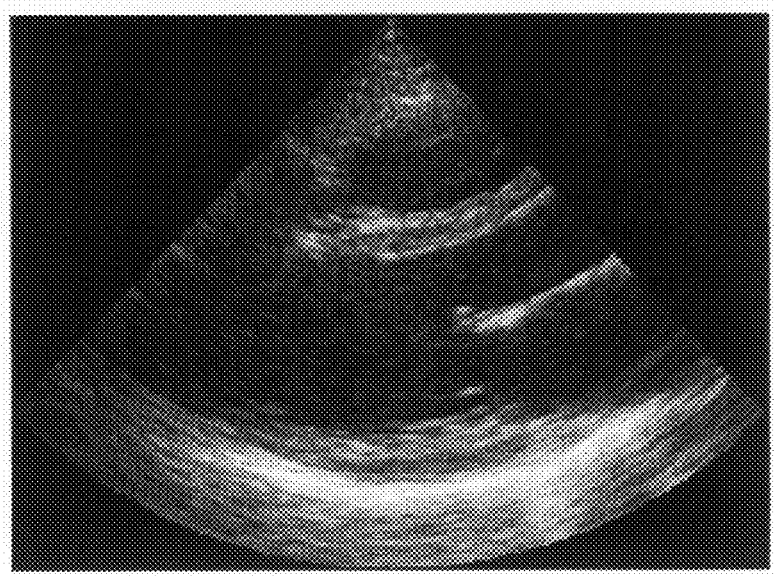
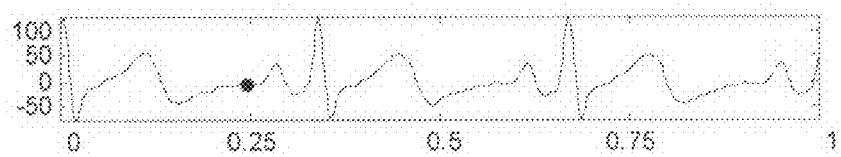
Fig. 19A(f1)
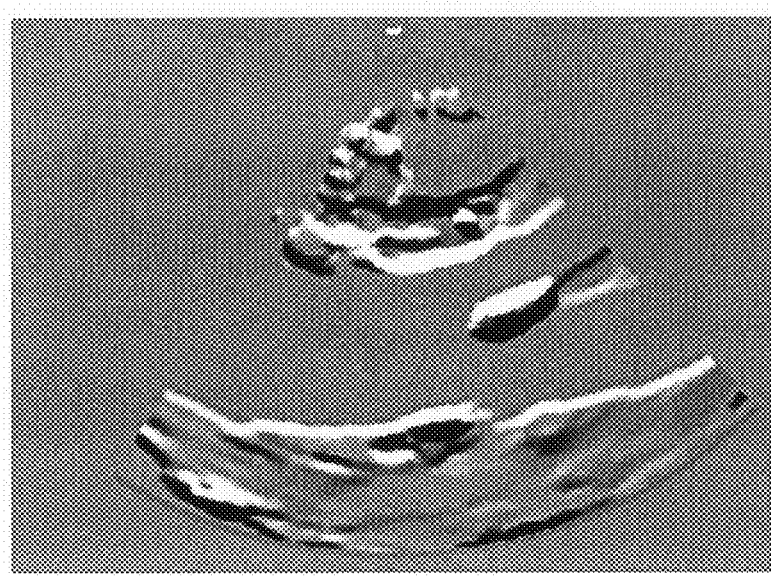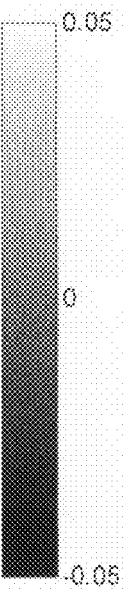
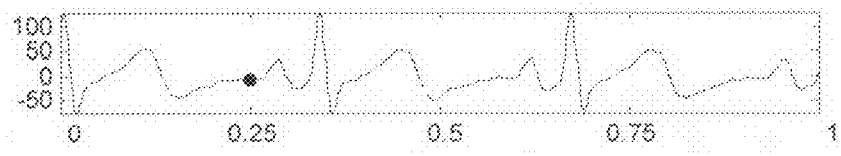
Fig. 19A(f2)

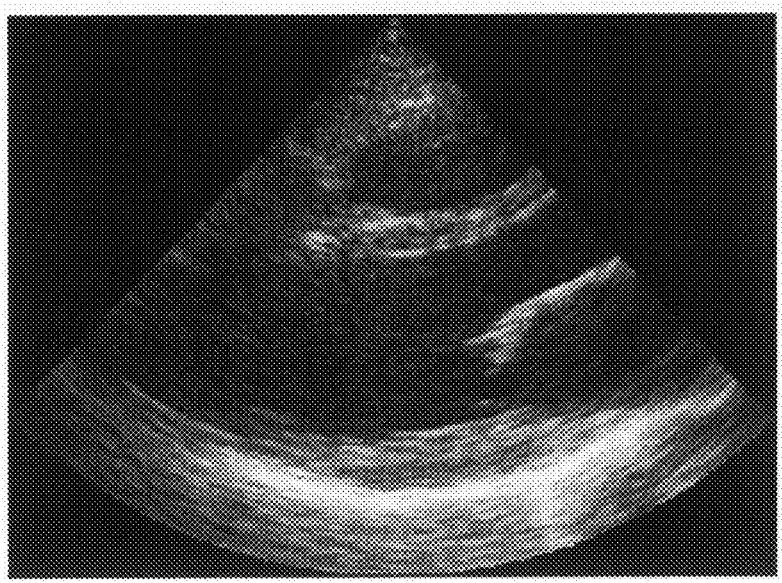
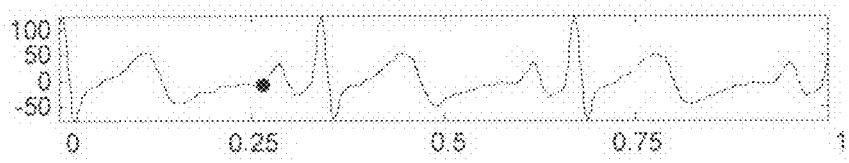
Fig. 19A(g1)
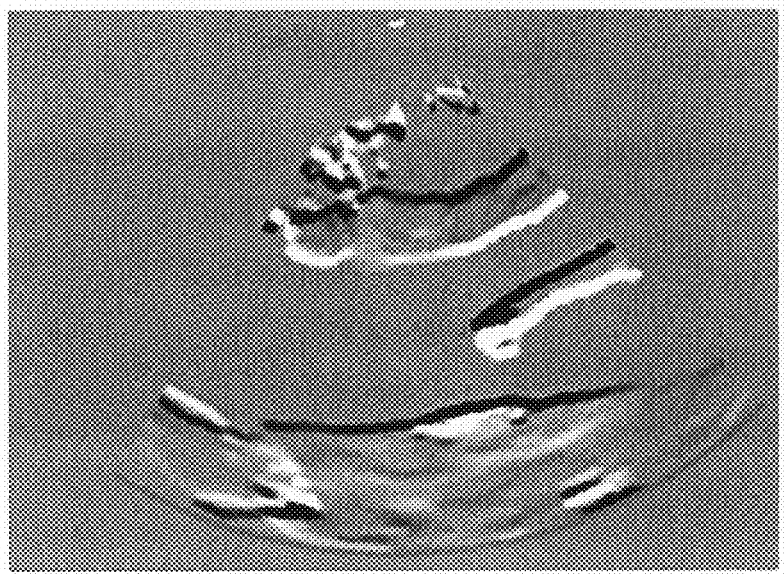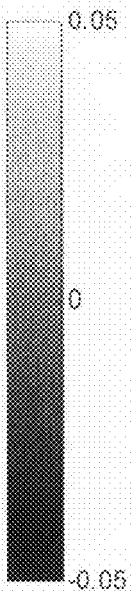
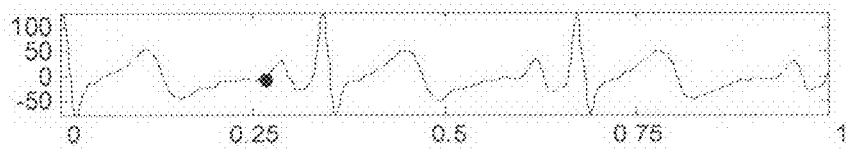
Fig. 19A(g2)

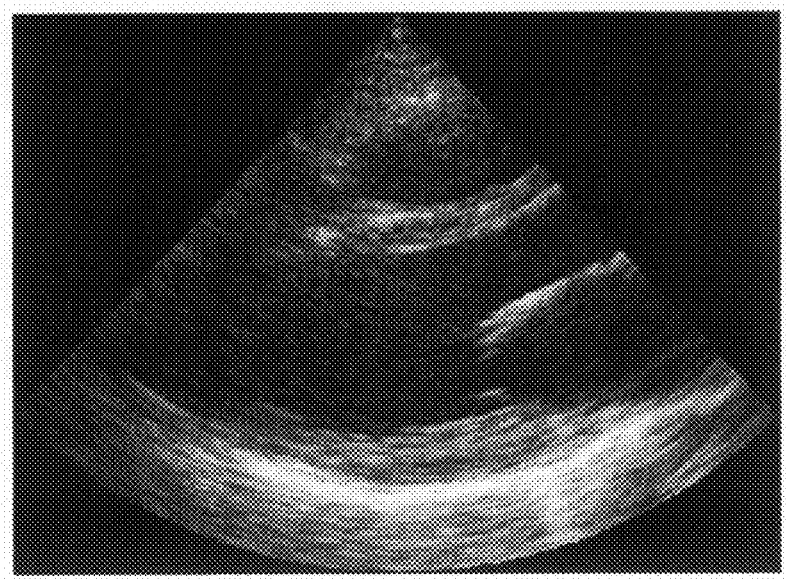
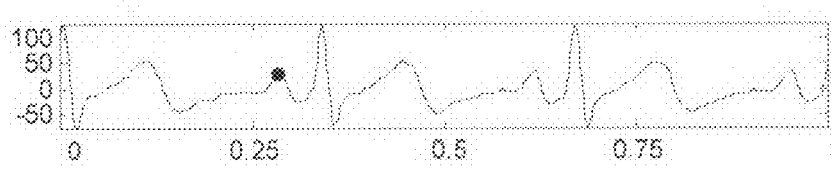
Fig. 19A(h1)
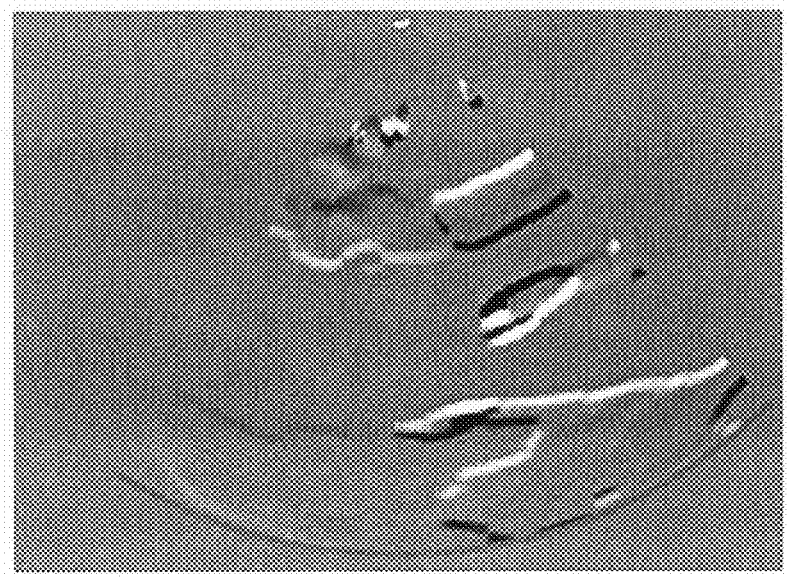
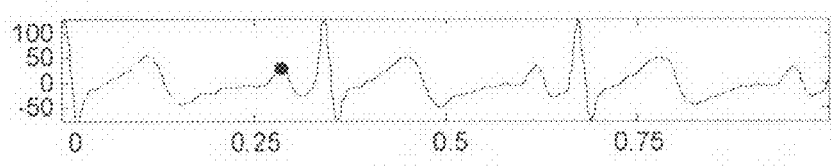
Fig. 19A(h2)

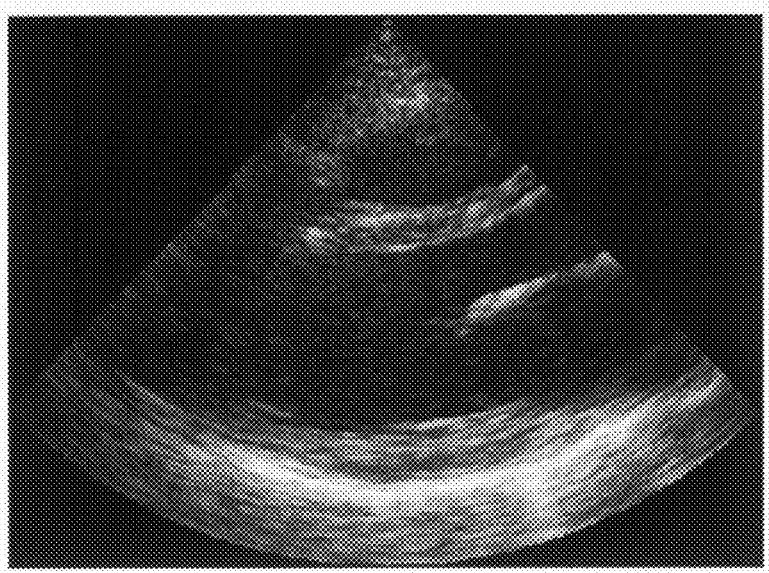
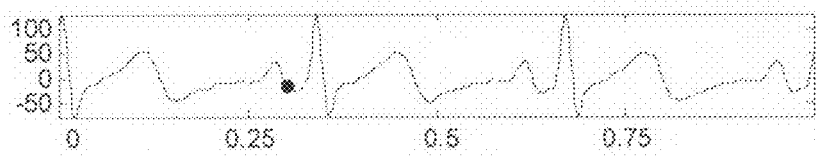
Fig. 19A(i1)
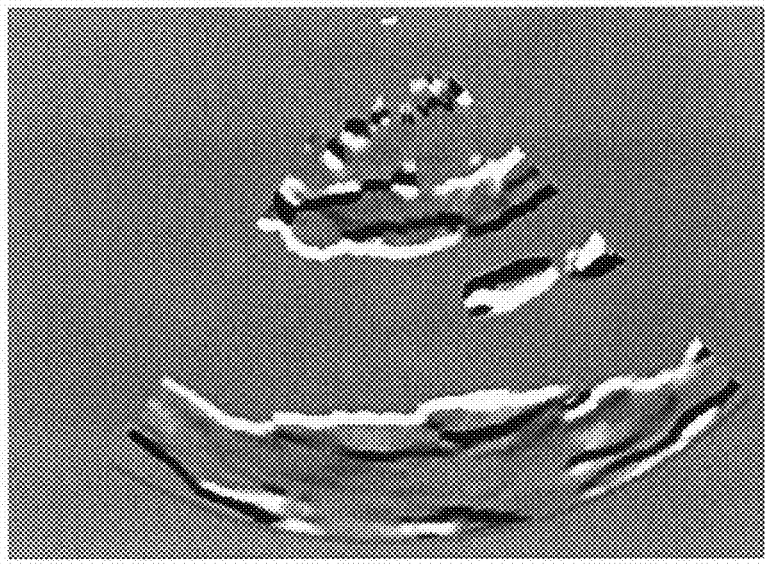
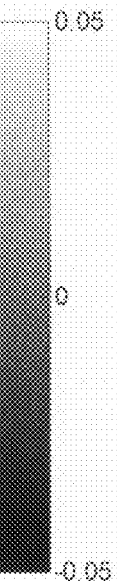
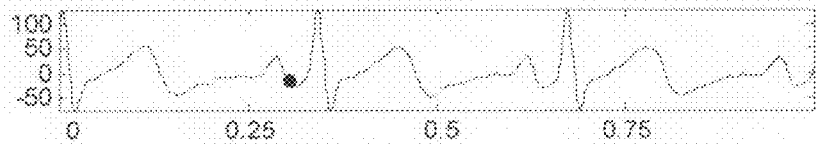
Fig. 19A(i2)

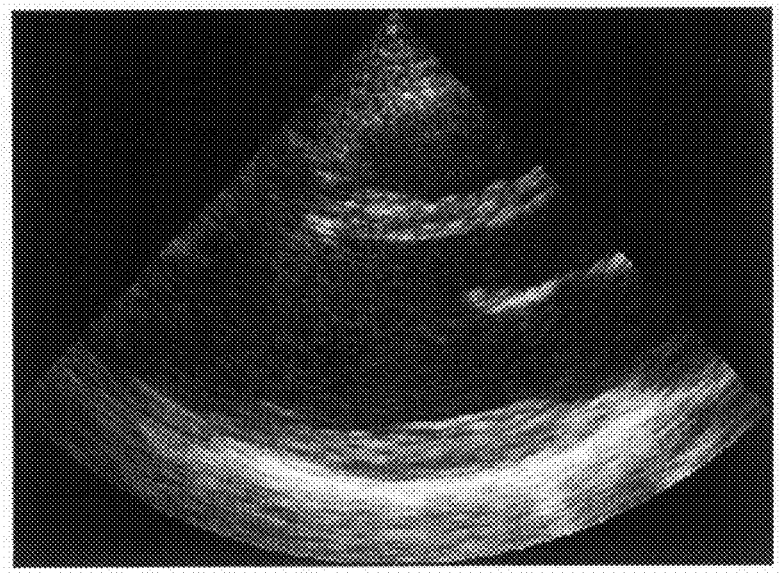
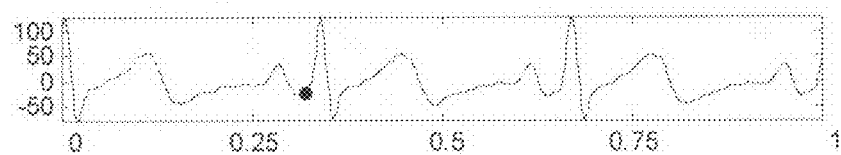
Fig. 19A(j1)
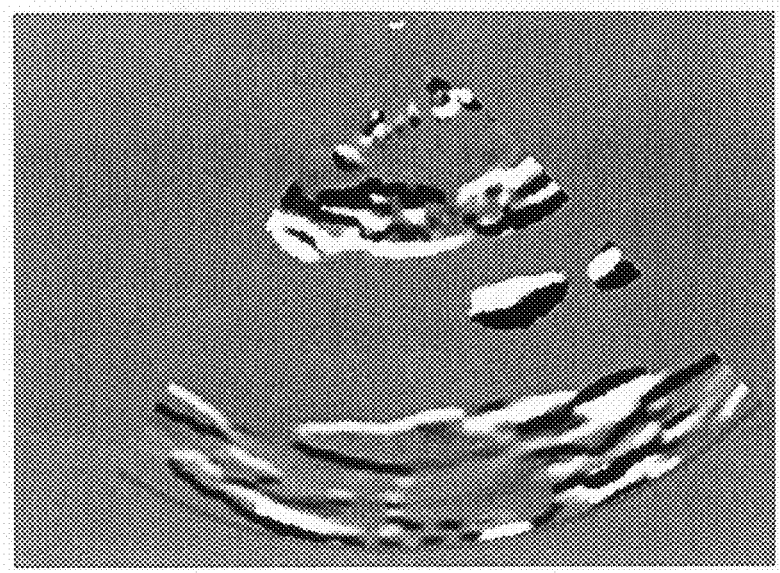
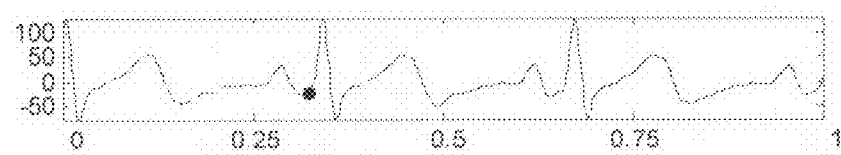
Fig. 19A(j2)

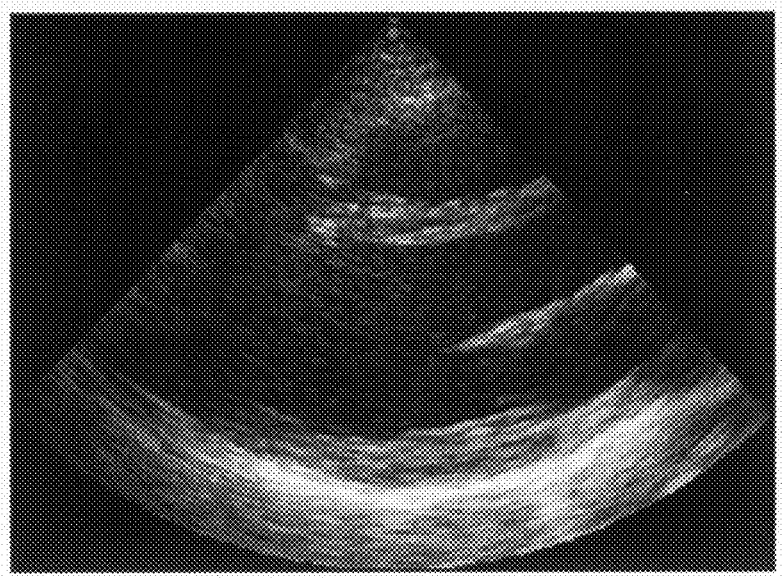
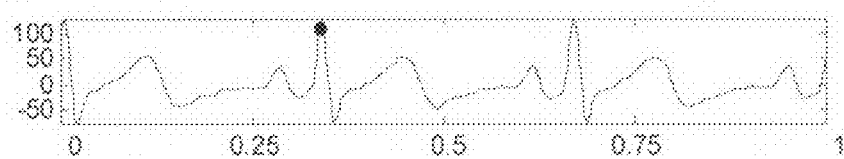
Fig. 19A(k1)
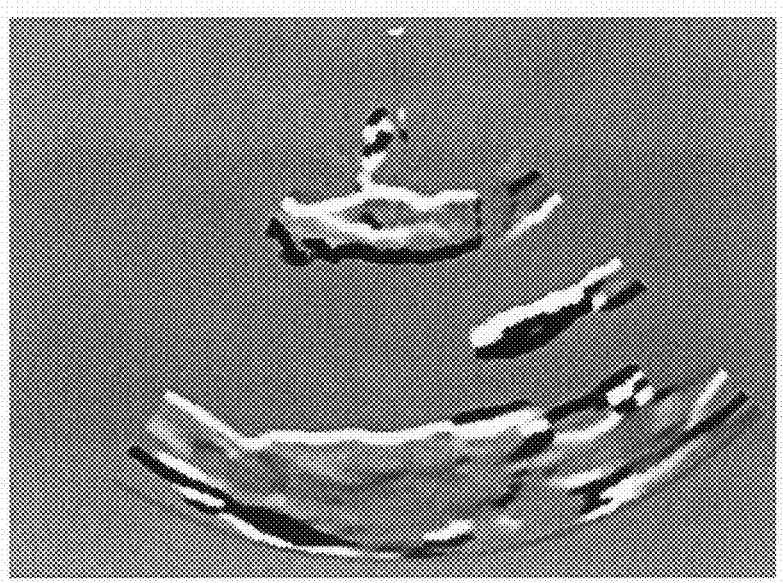
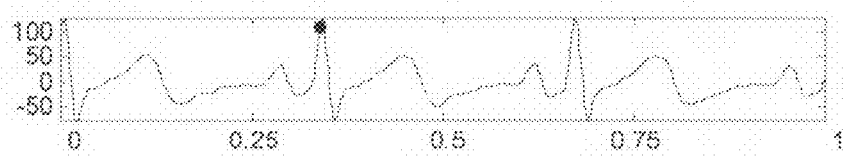
Fig. 19A(k2)

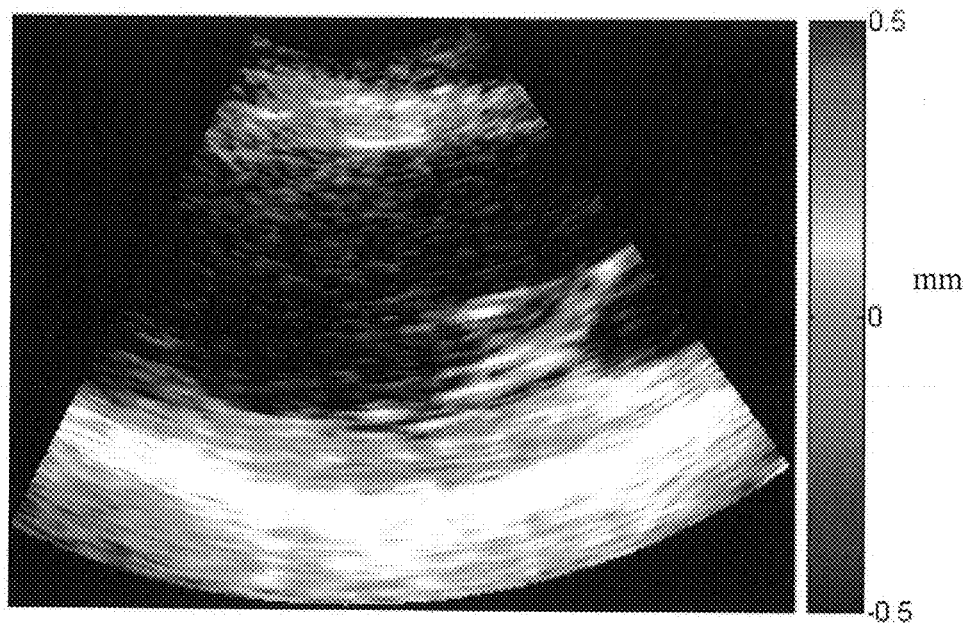
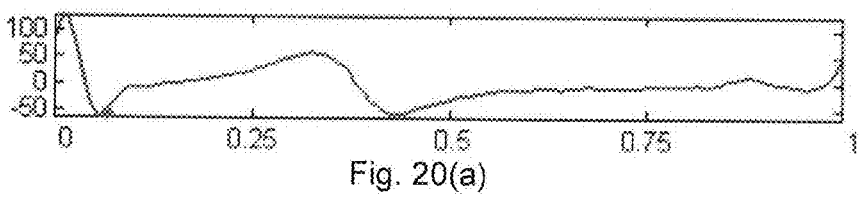
Fig. 20(a)
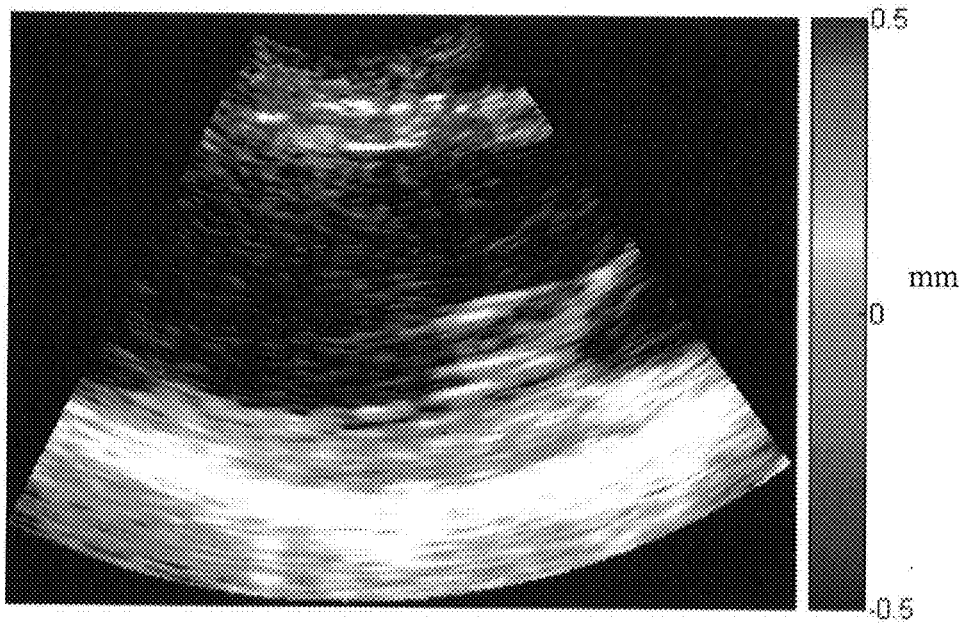
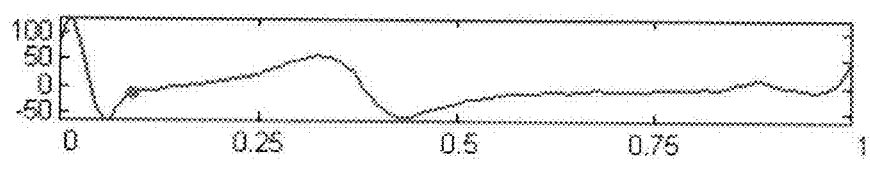
Fig. 20(b)

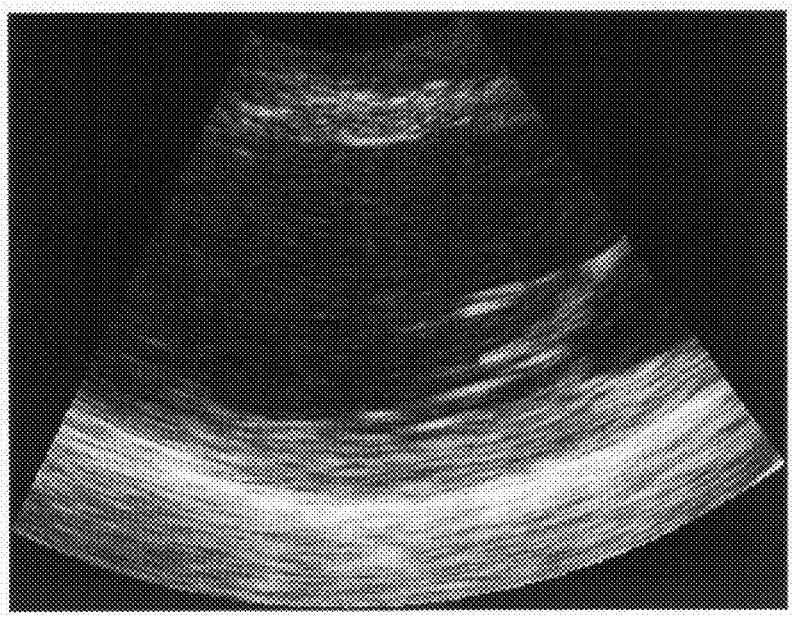
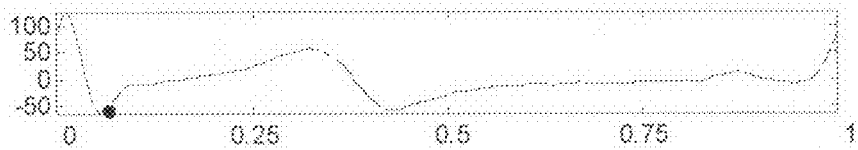
Fig. 20A(a1)
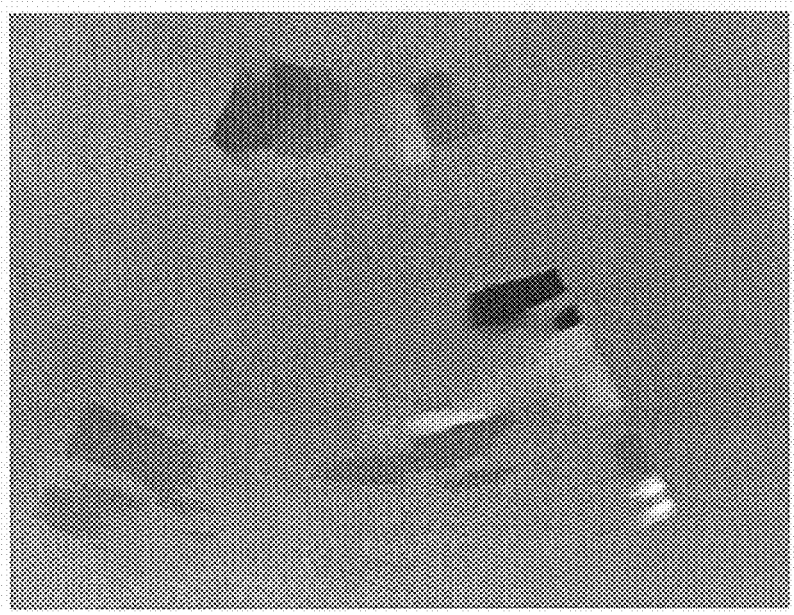
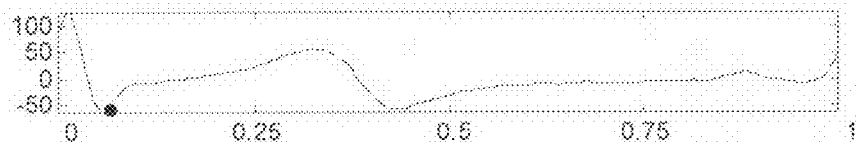
Fig. 20A(a2)

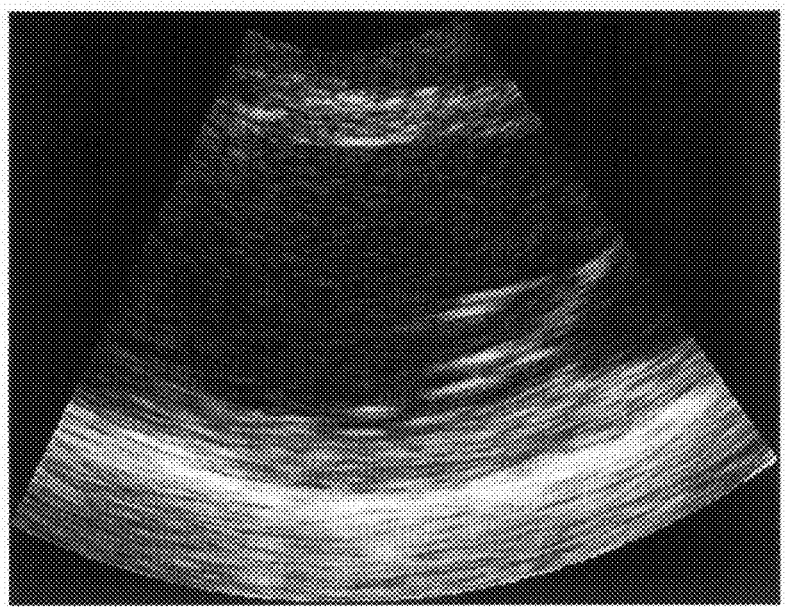
Fig. 20A(b1)
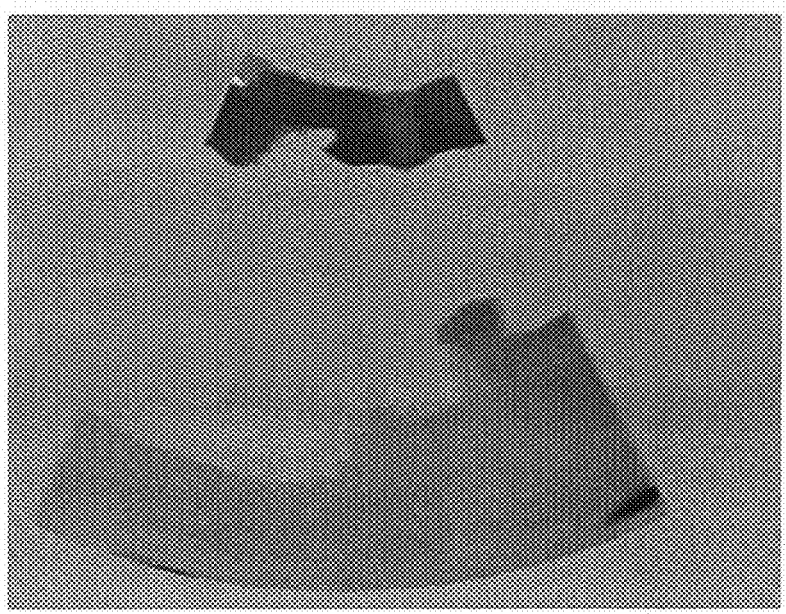
Fig. 20A(b2)

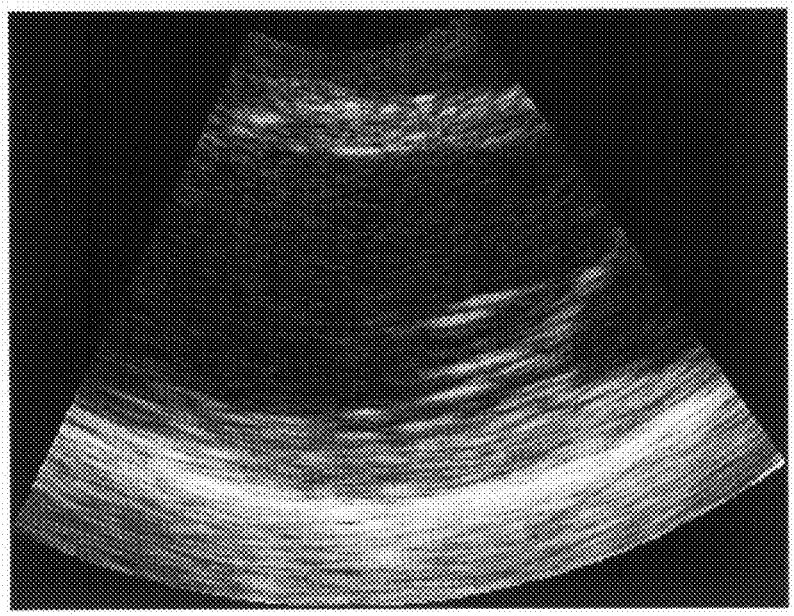
Fig. 20A(c1)
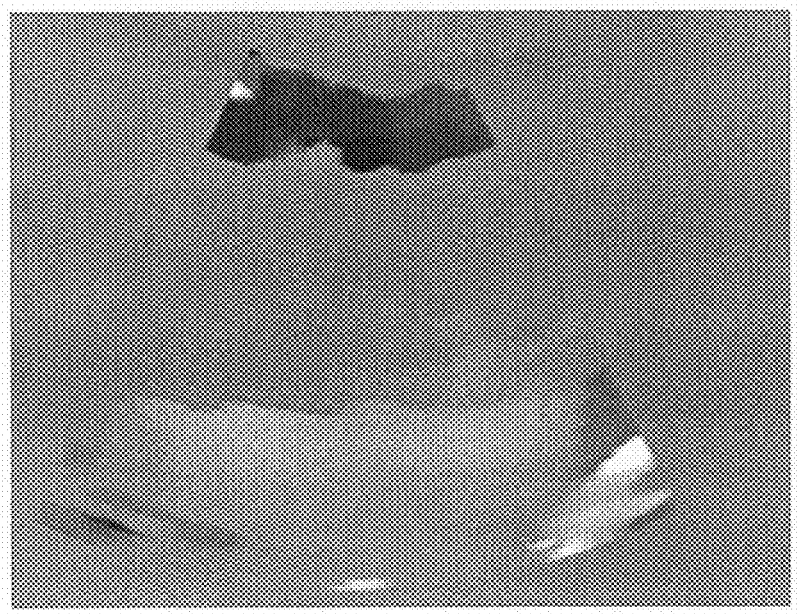
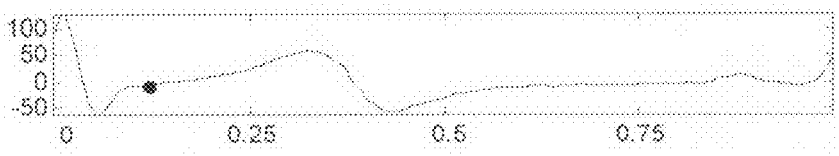
Fig. 20A(c2)

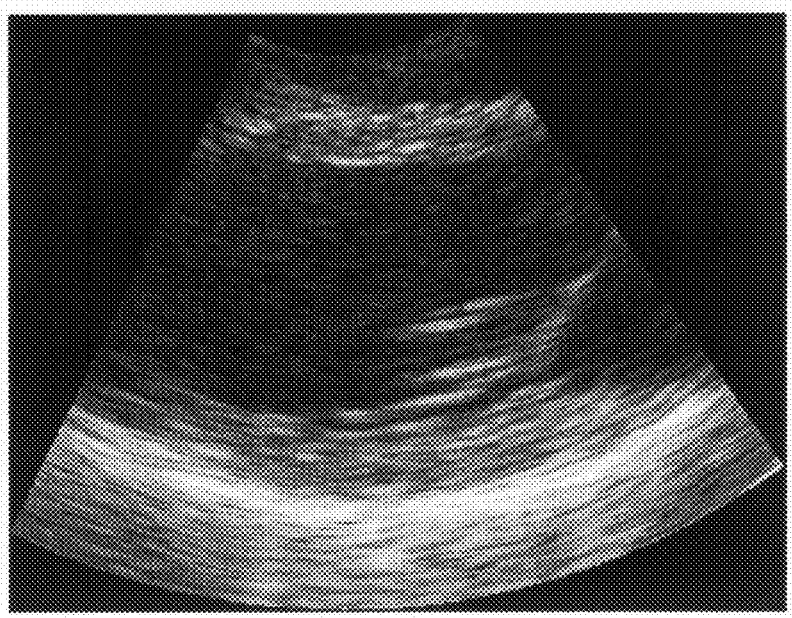
Fig. 20A(d1)
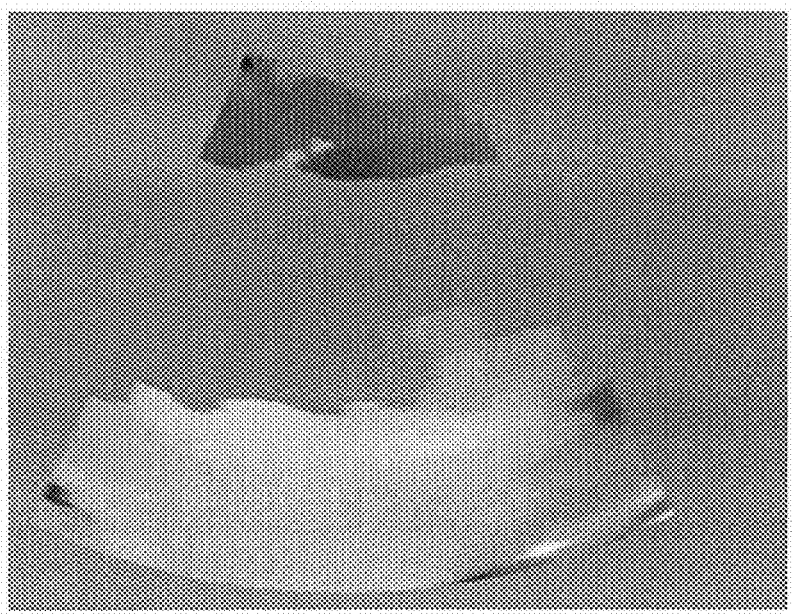
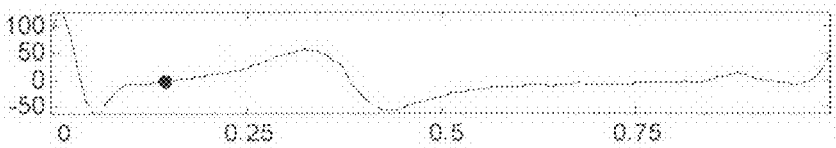
Fig. 20A(d2)

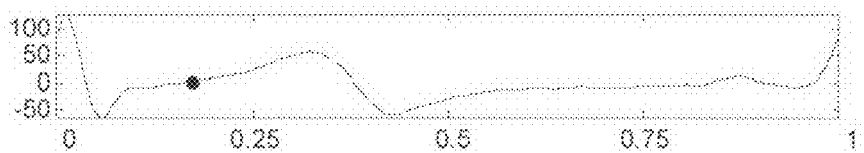
Fig. 20A(e1)
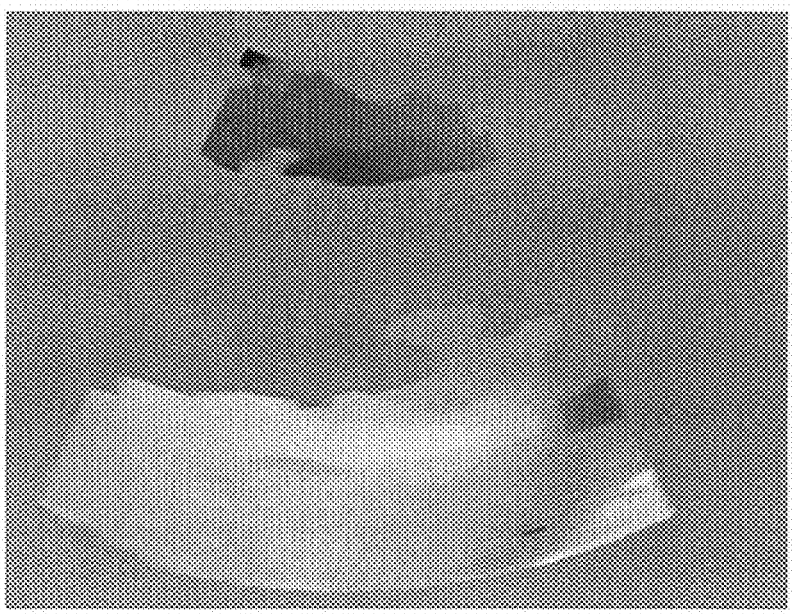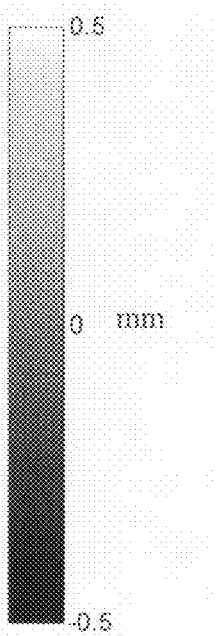
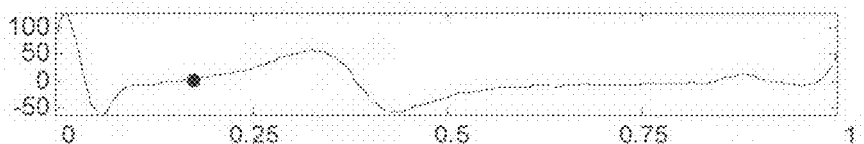
Fig. 20A(e2)

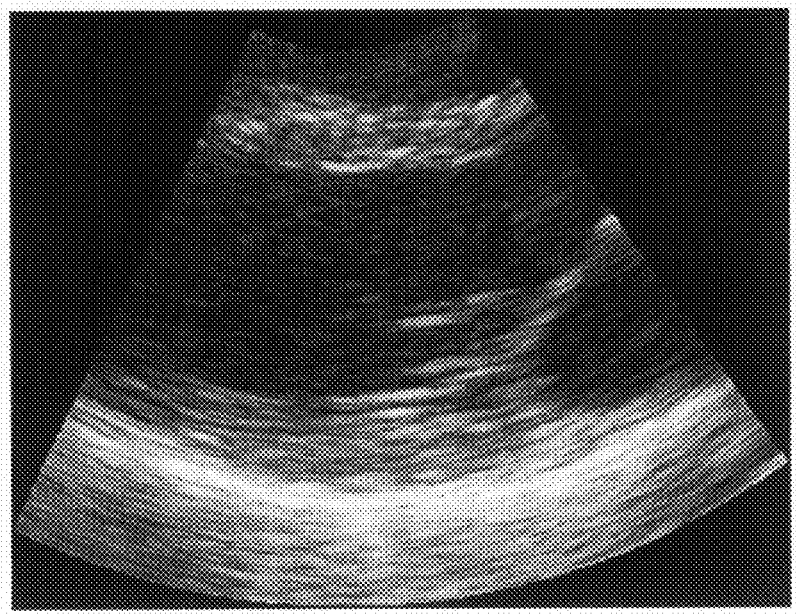
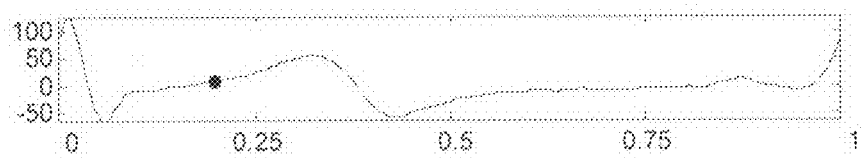
Fig. 20A(f1)
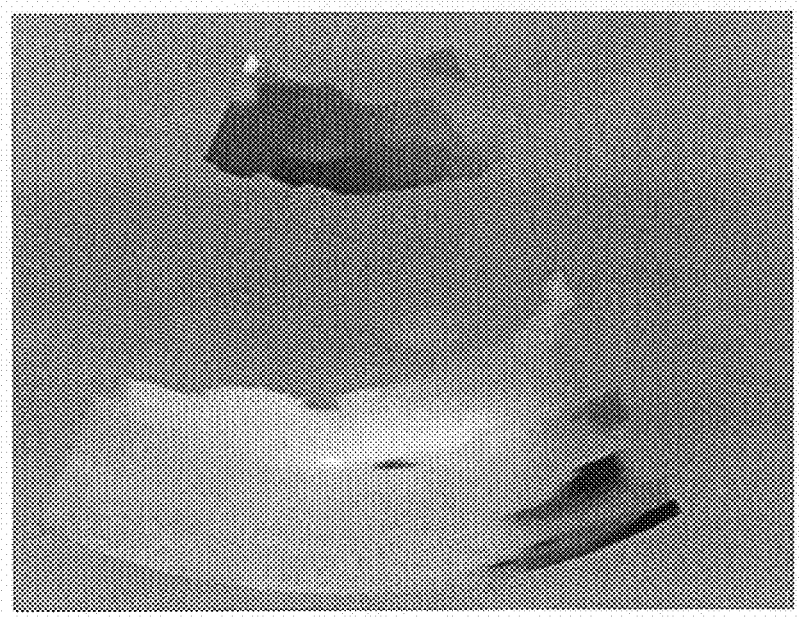
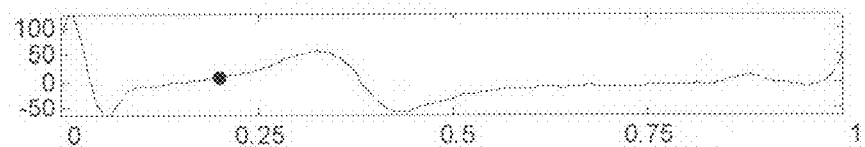
Fig. 20A(f2)

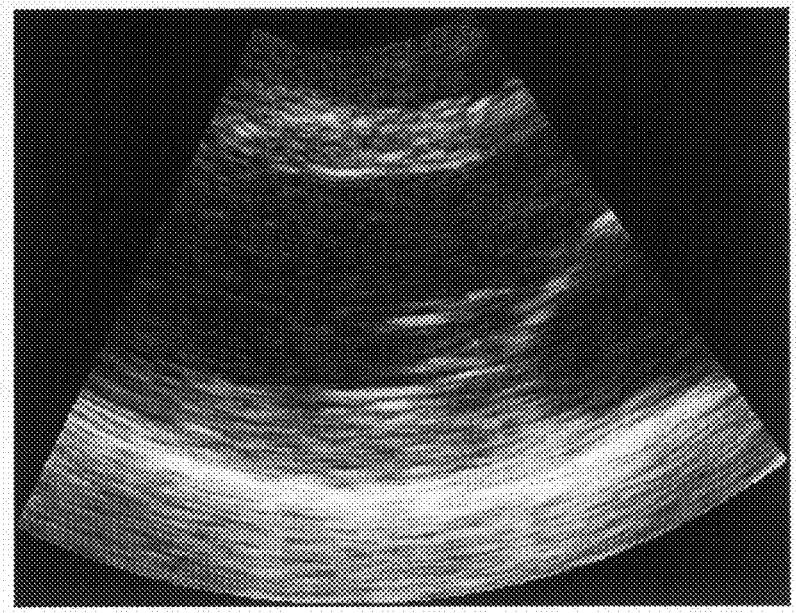
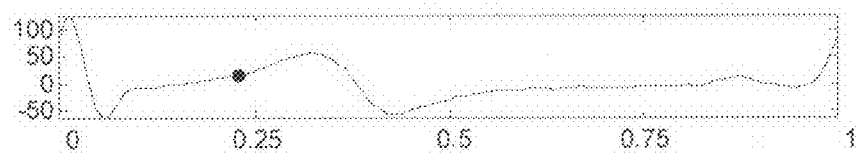
Fig. 20A(g1)
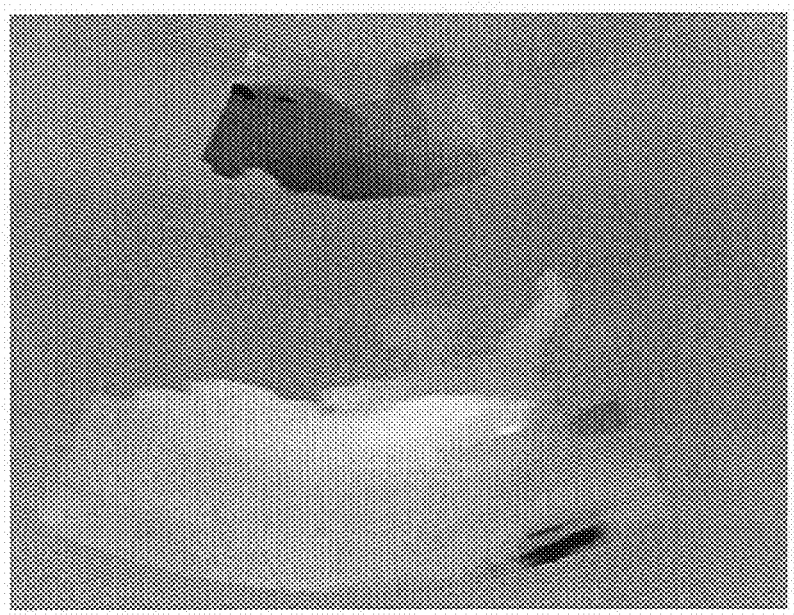
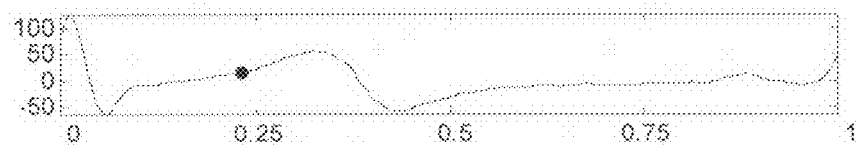
Fig. 20A(g2)

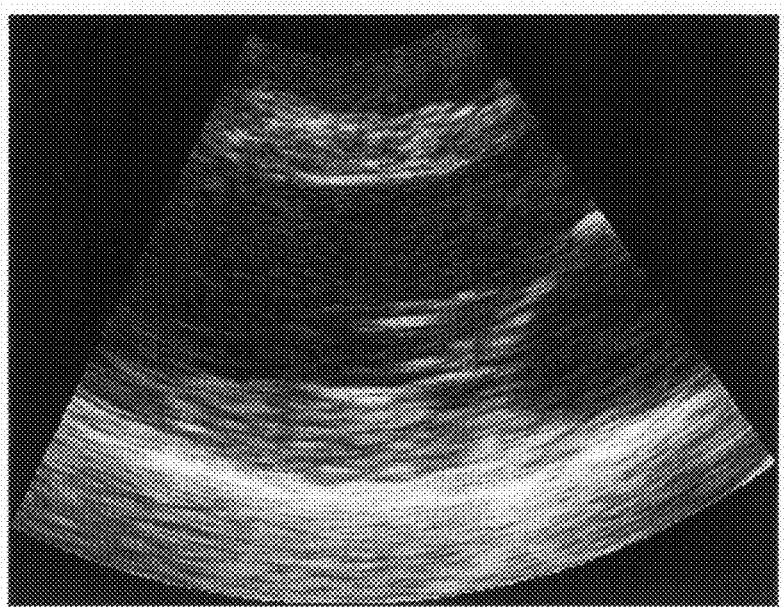
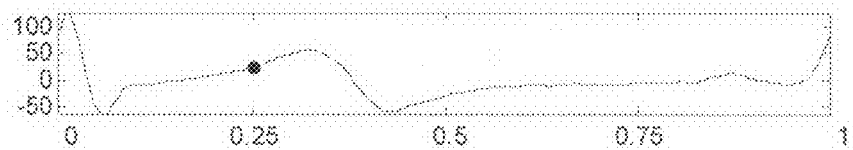
Fig. 20A(h1)
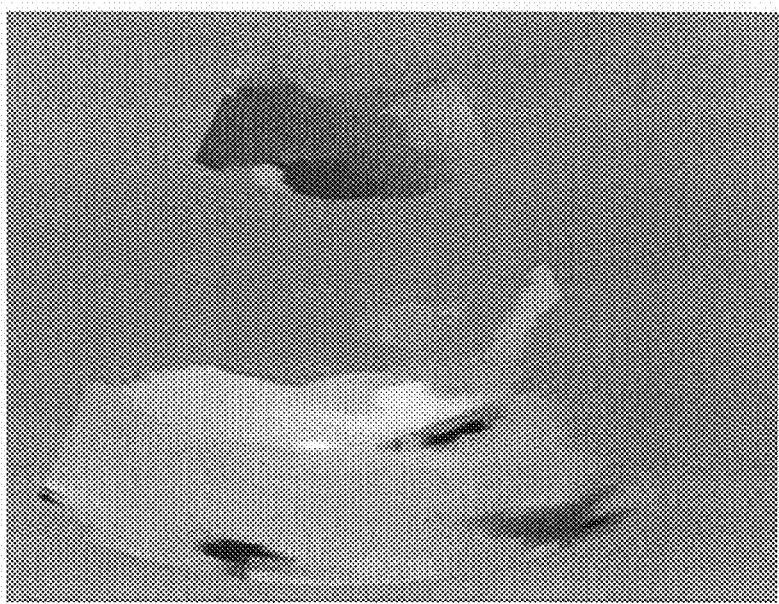
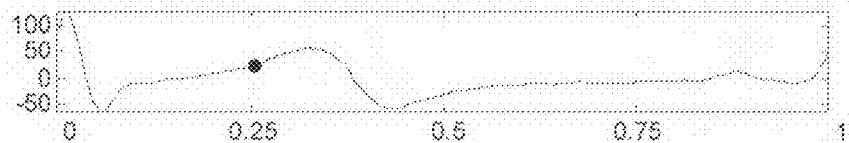
Fig. 20A(h2)

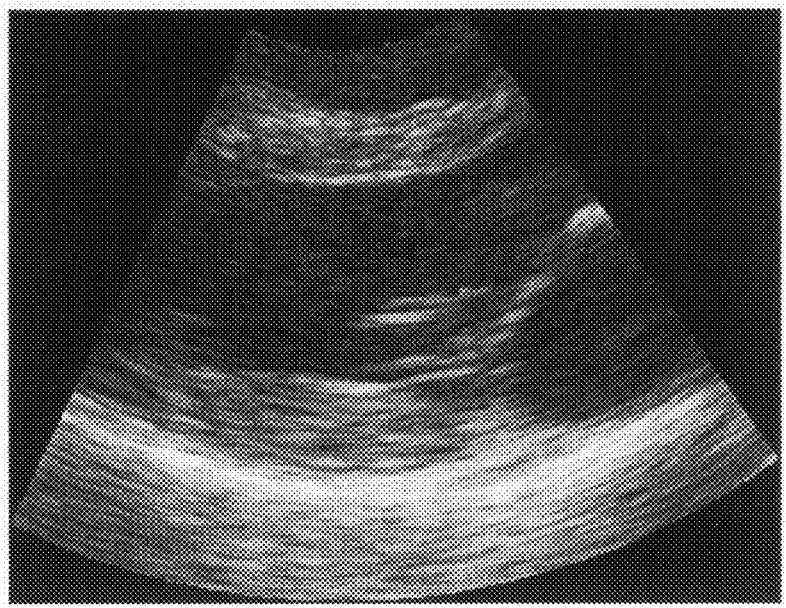
Fig. 20A(i1)
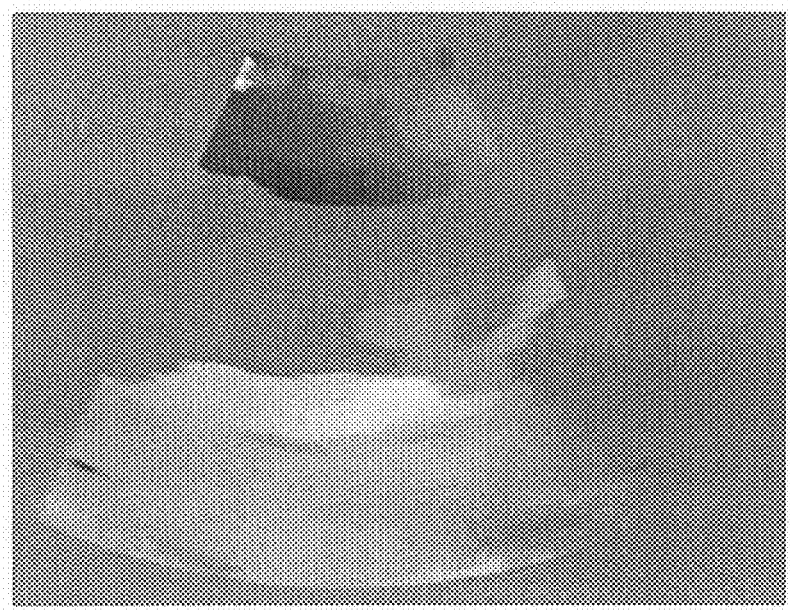
Fig. 20A(i2)

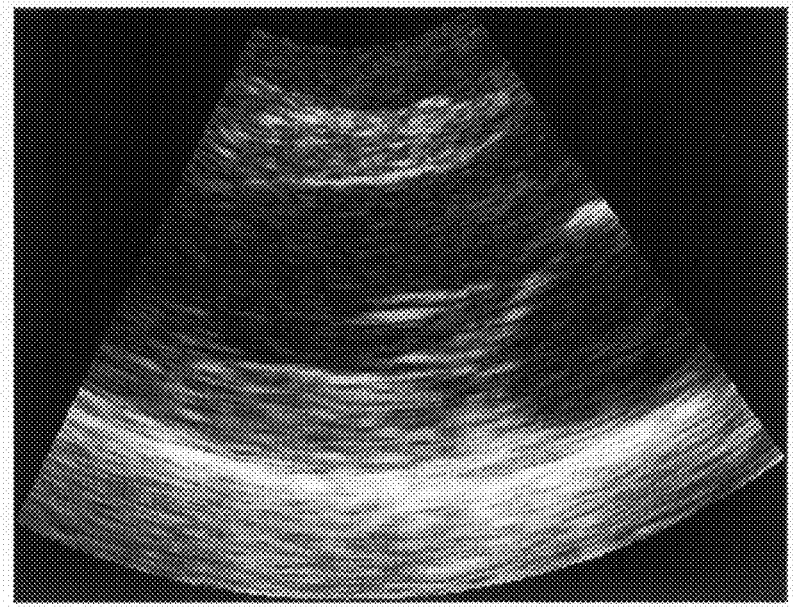
Fig. 20A(j1)
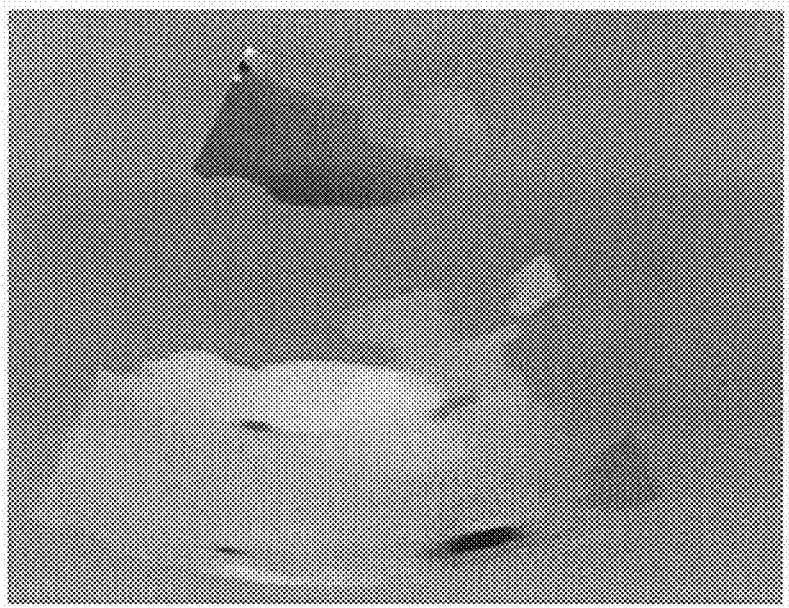
Fig. 20A(j2)

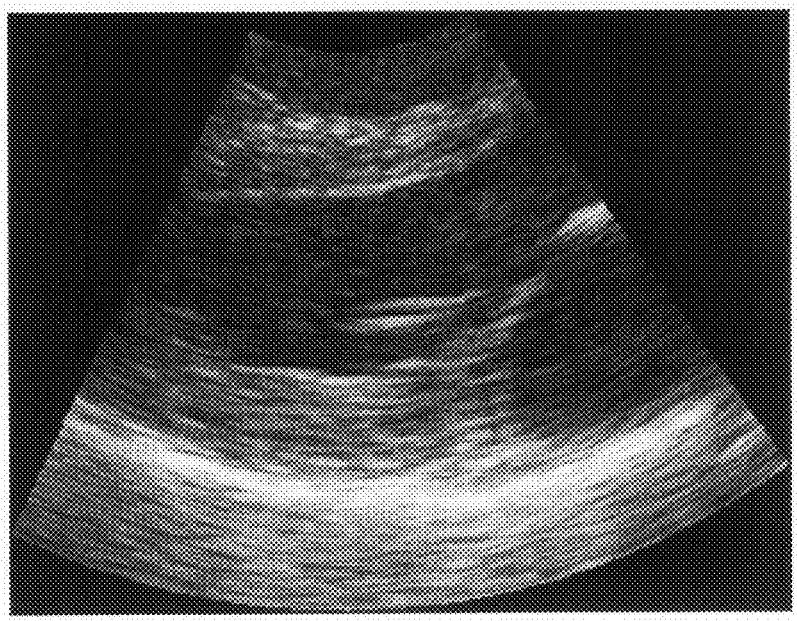
Fig. 20A(k1)
Fig. 20A(k2)

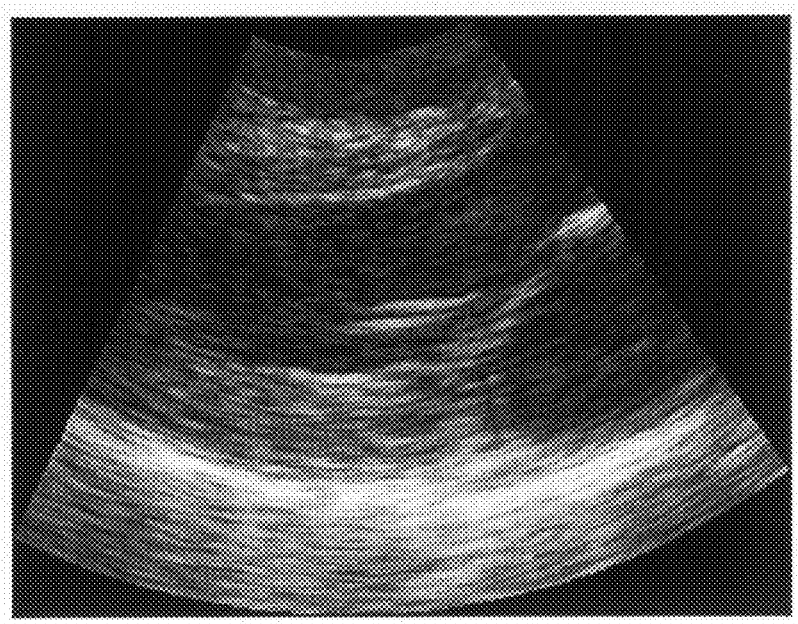
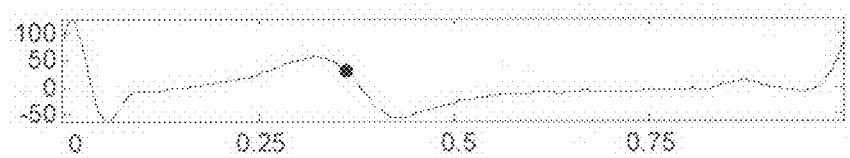
Fig. 20A(I1)
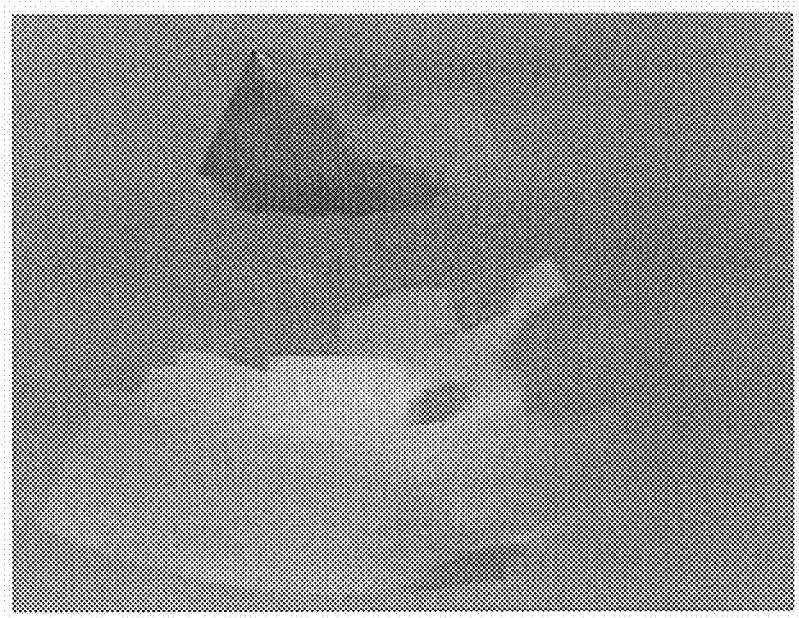
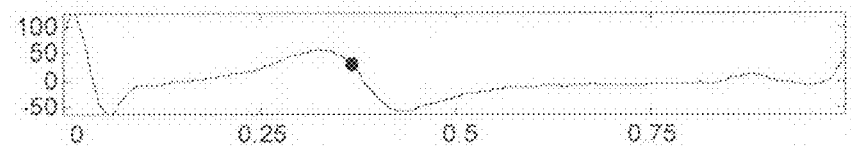
Fig. 20A(I2)

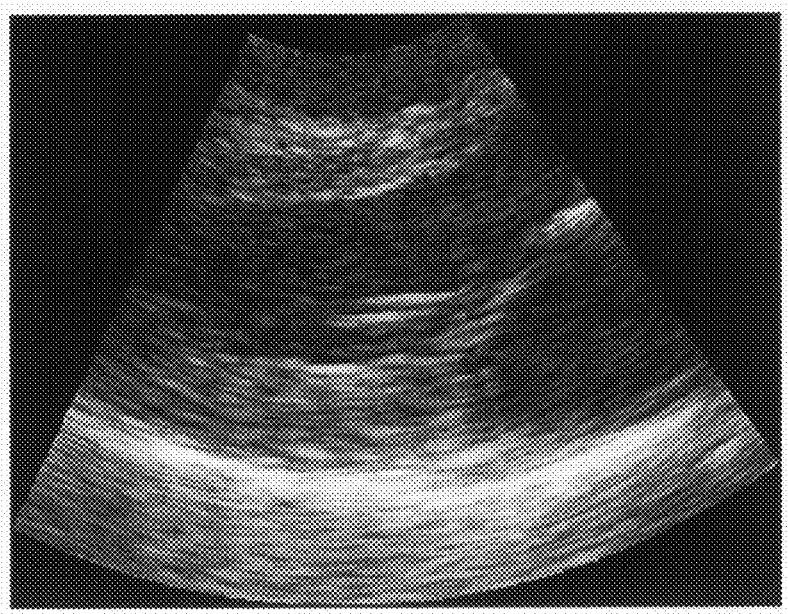
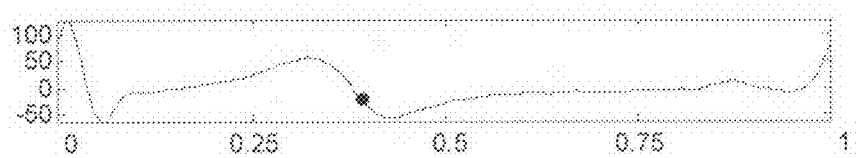
Fig. 20A(m1)
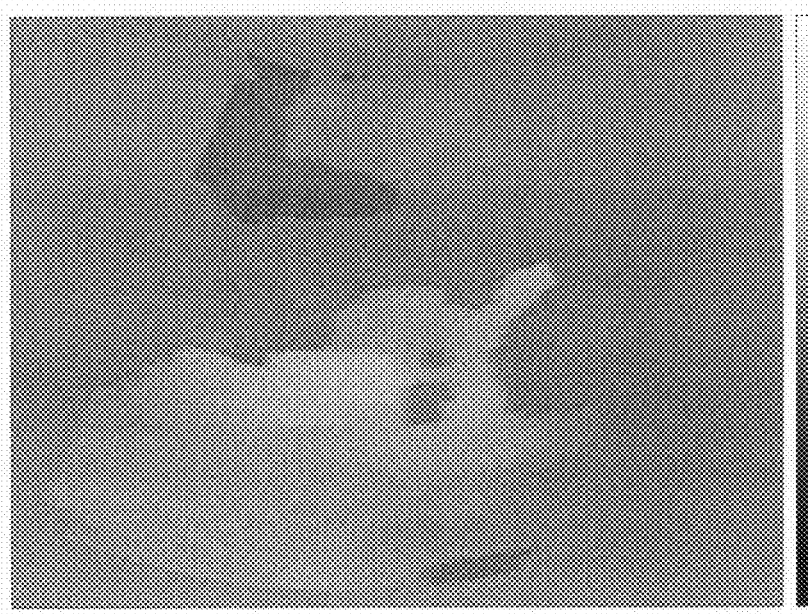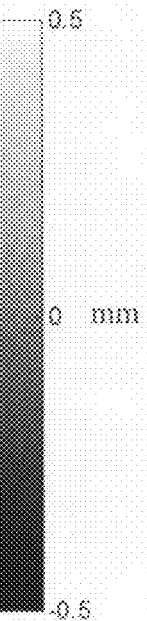
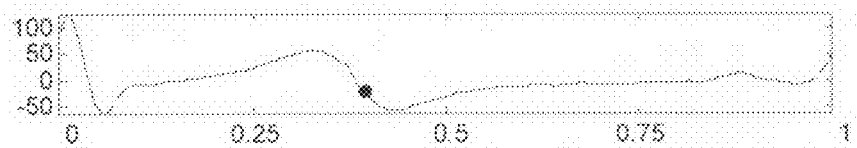
Fig. 20A(m2)

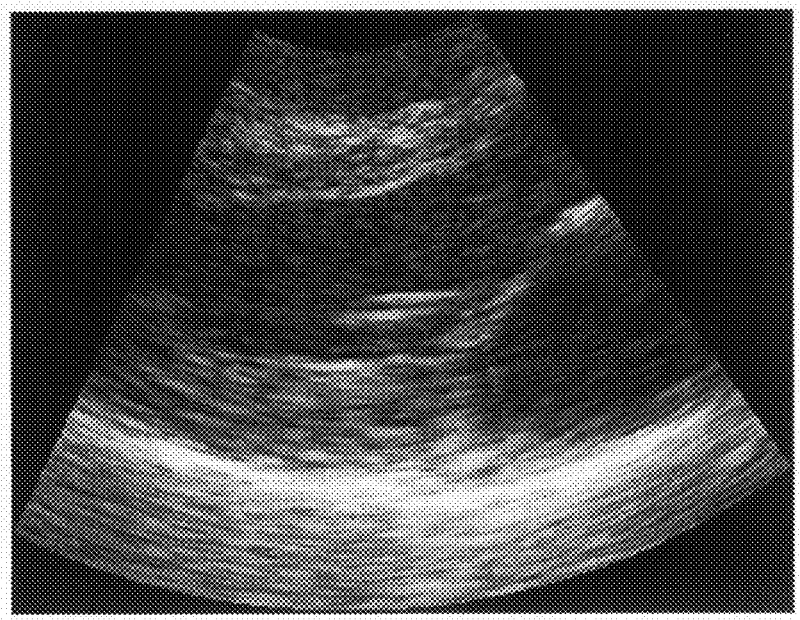
Fig. 20A(n1)
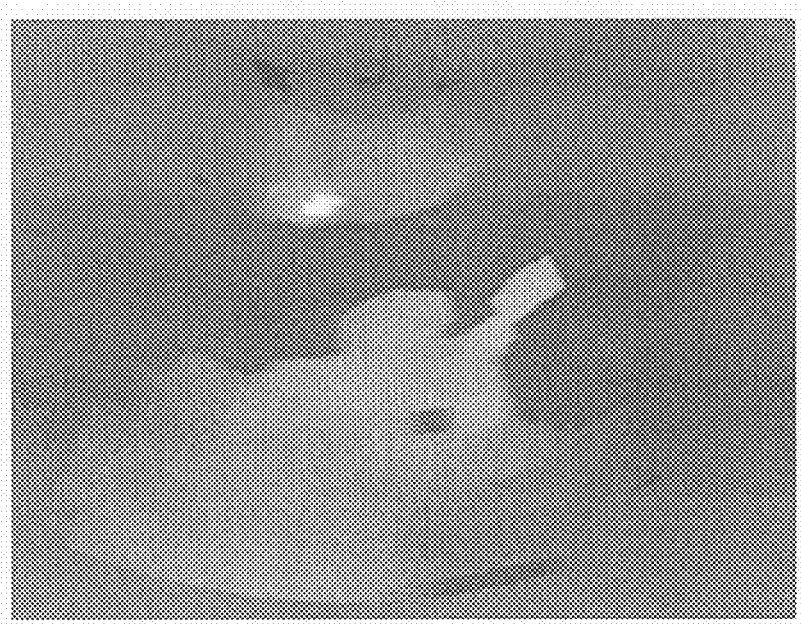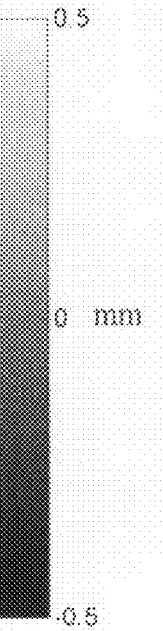
Fig. 20A(n2)

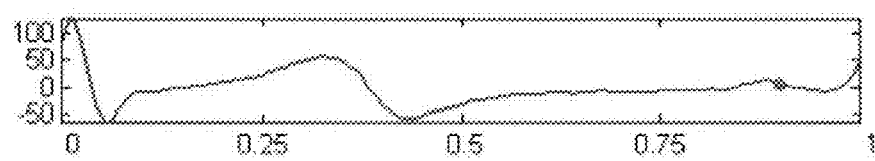
Fig. 21(m)
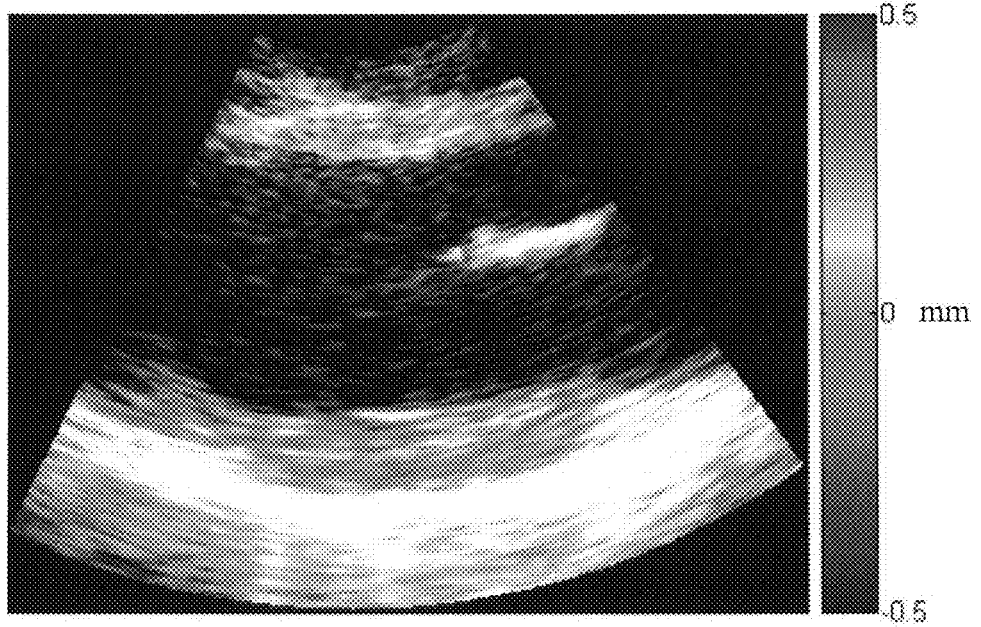
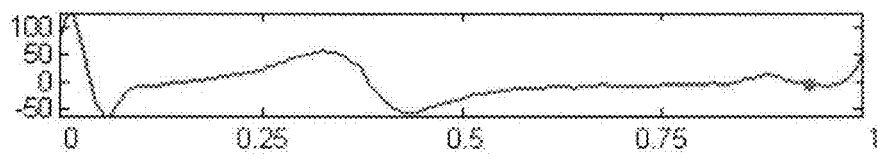
Fig. 21(n)

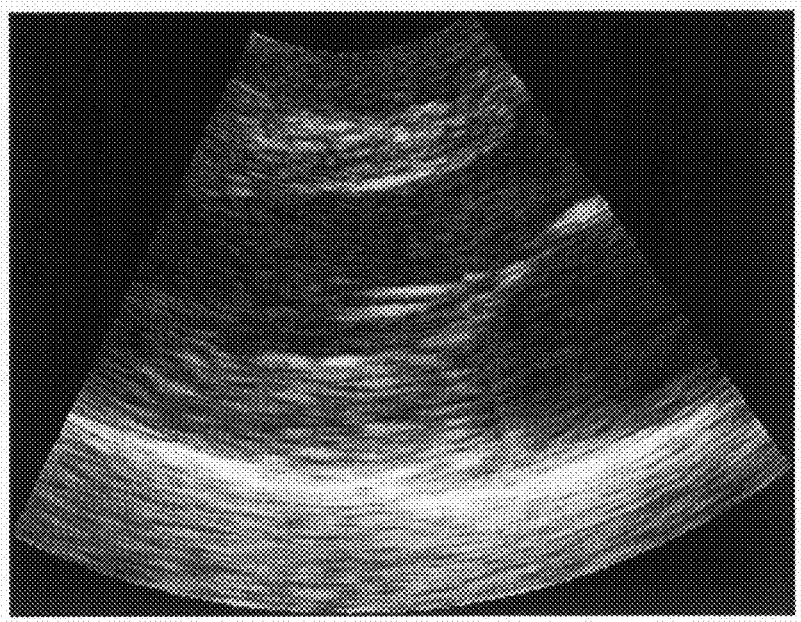
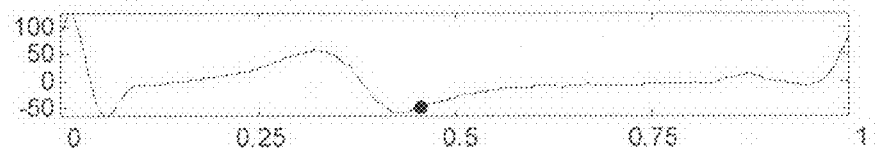
Fig. 21A(a1)
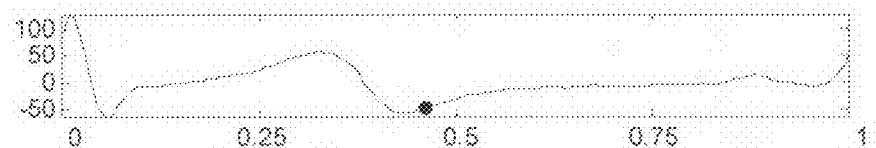
Fig. 21A(a2)

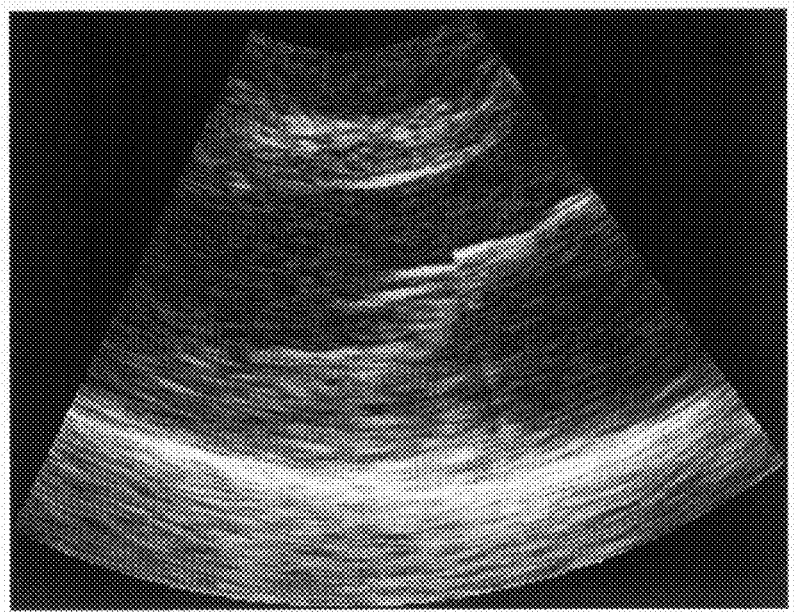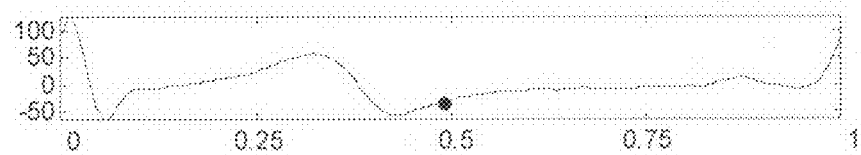
Fig. 21A(b1)
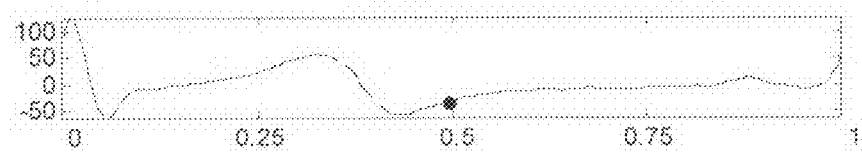
Fig. 21A(b2)

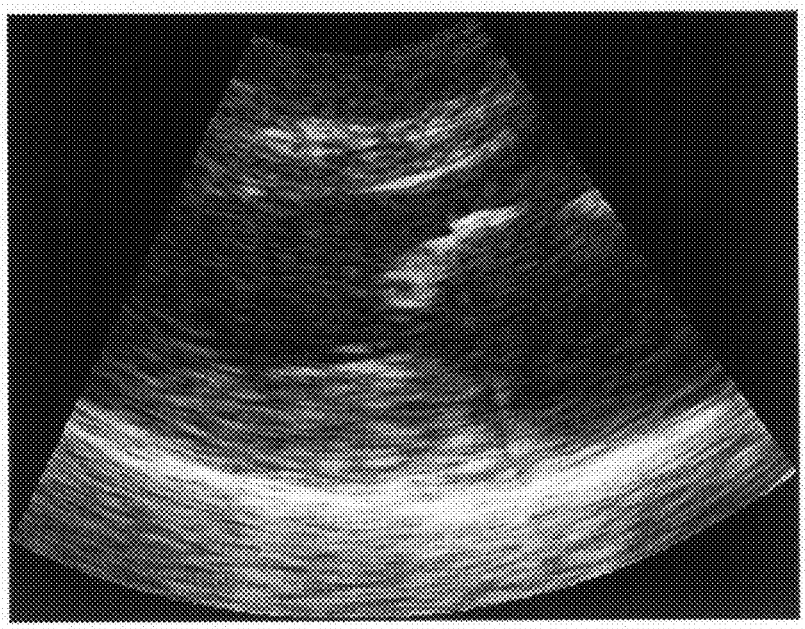
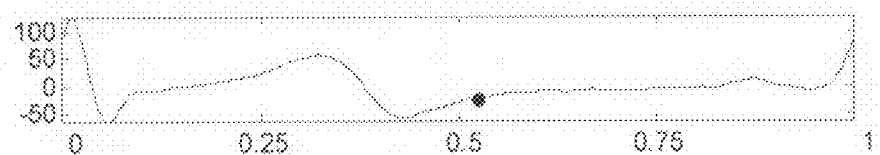
Fig. 21A(c1)
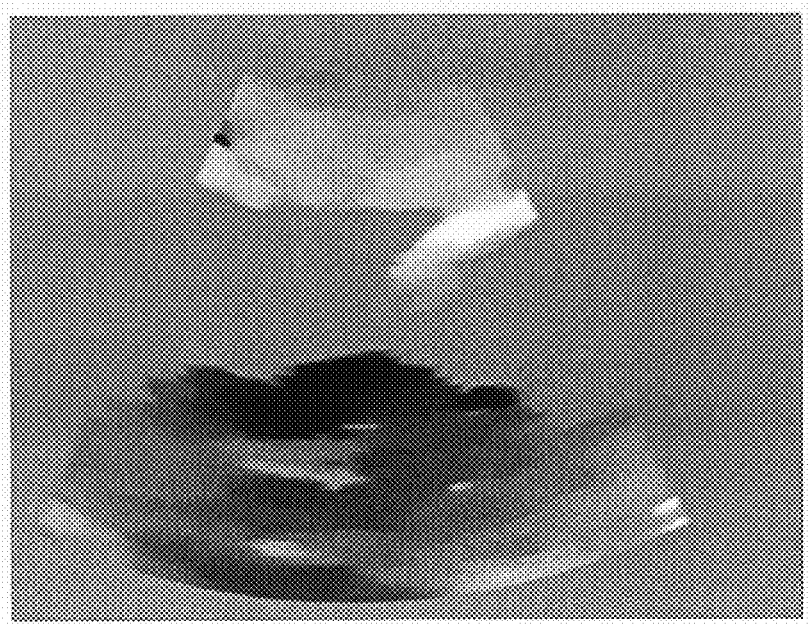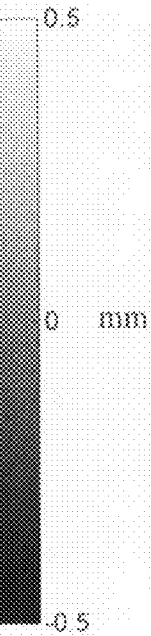
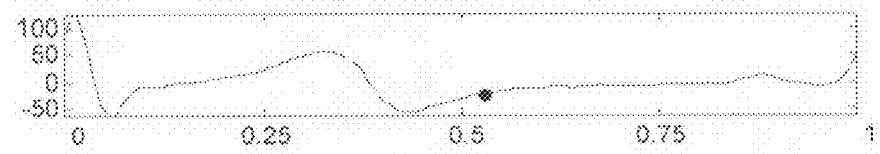
Fig. 21A(c2)

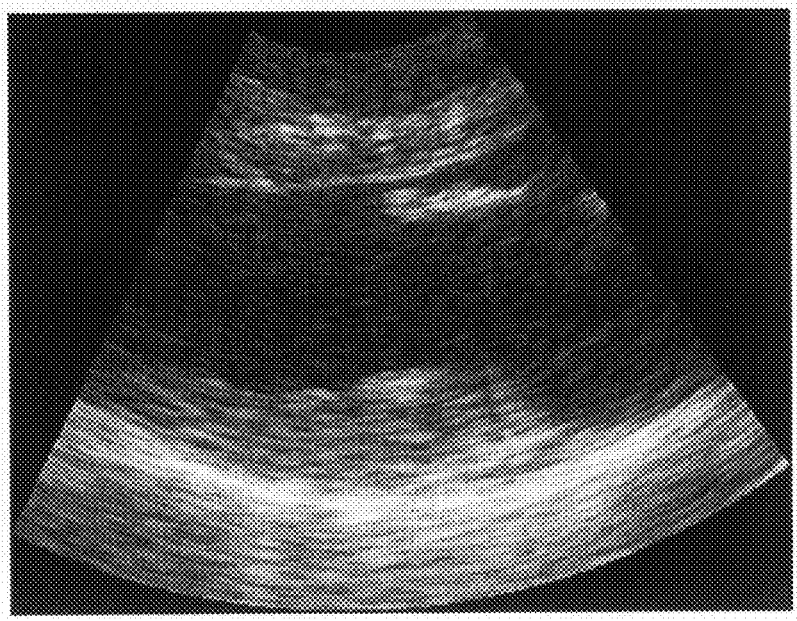
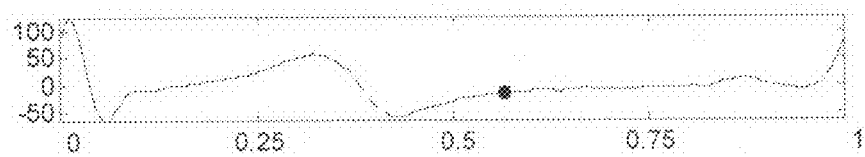
Fig. 21A(d1)
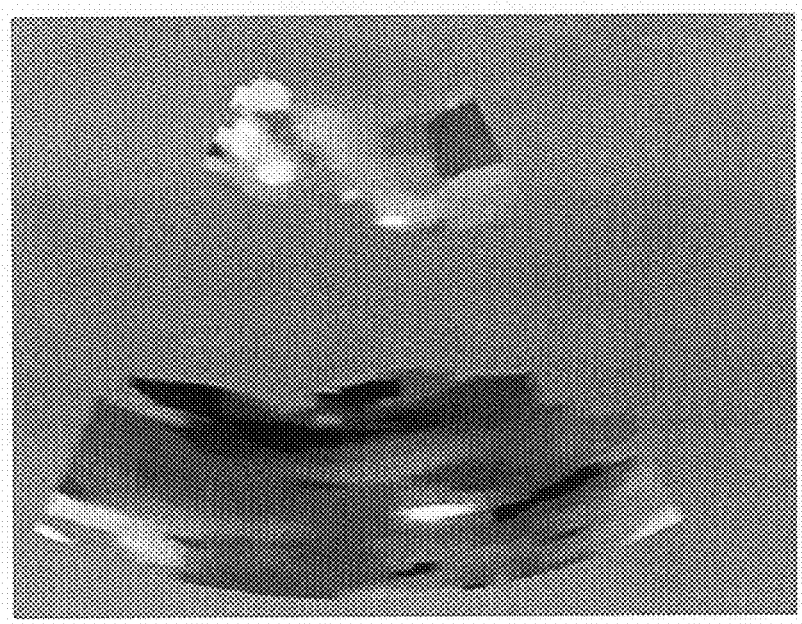
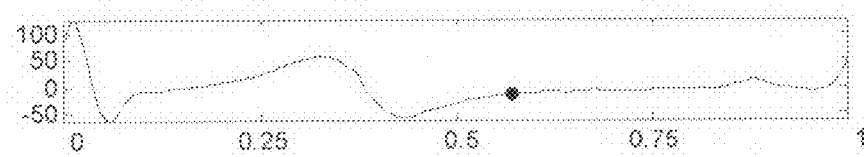
Fig. 21A(d2)

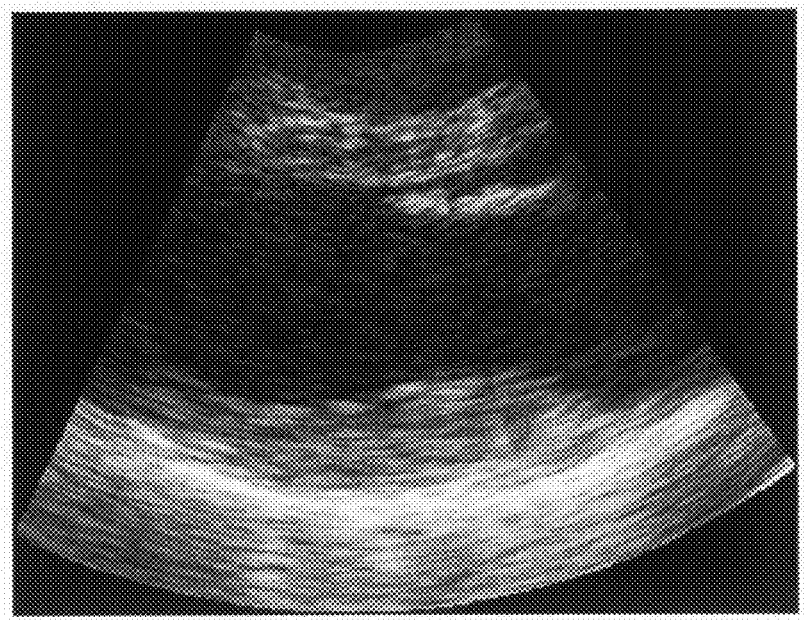
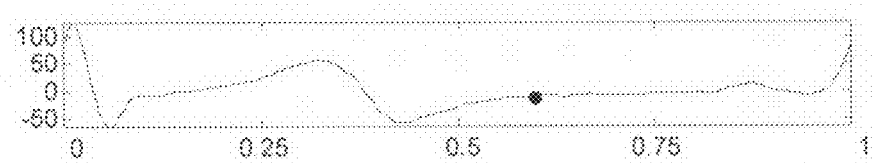
Fig. 21A(e1)
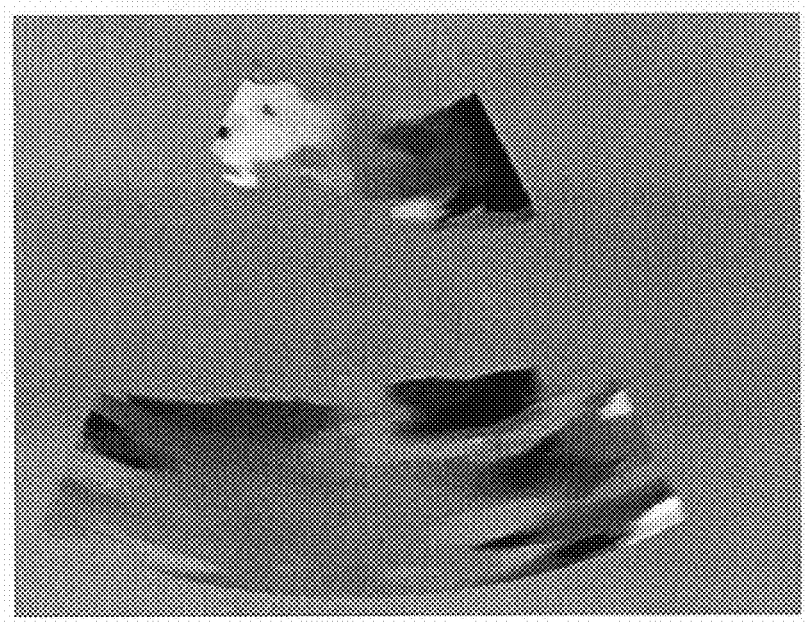
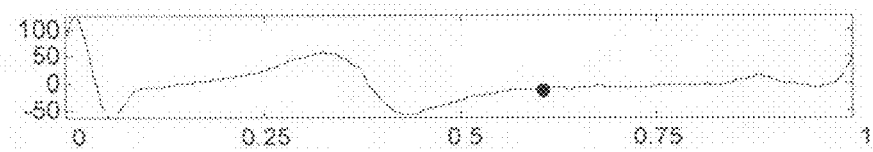
Fig. 21A(e2)

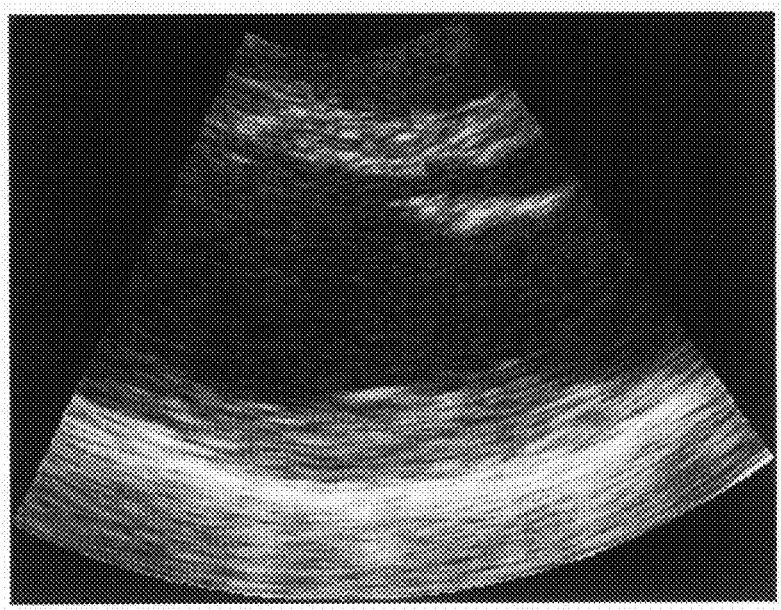
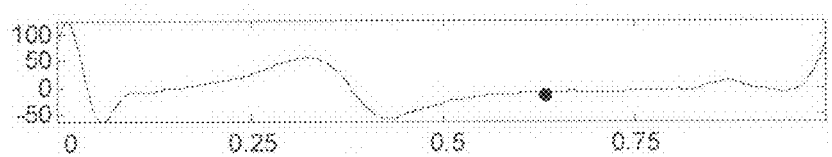
Fig. 21A(f1)
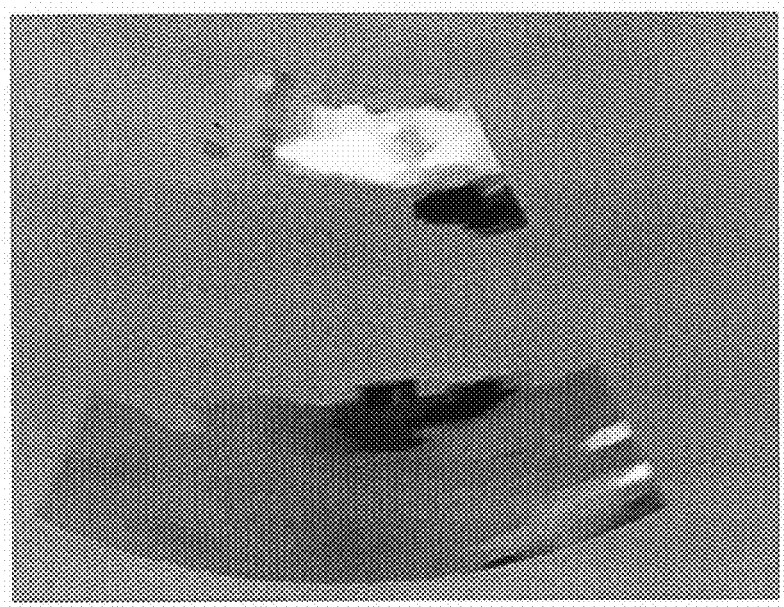
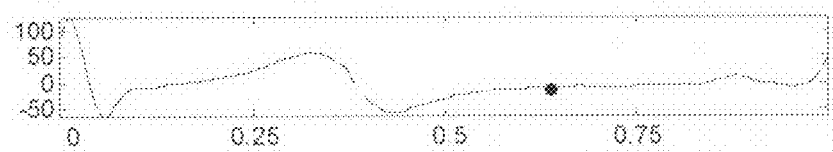
Fig. 21A(f2)

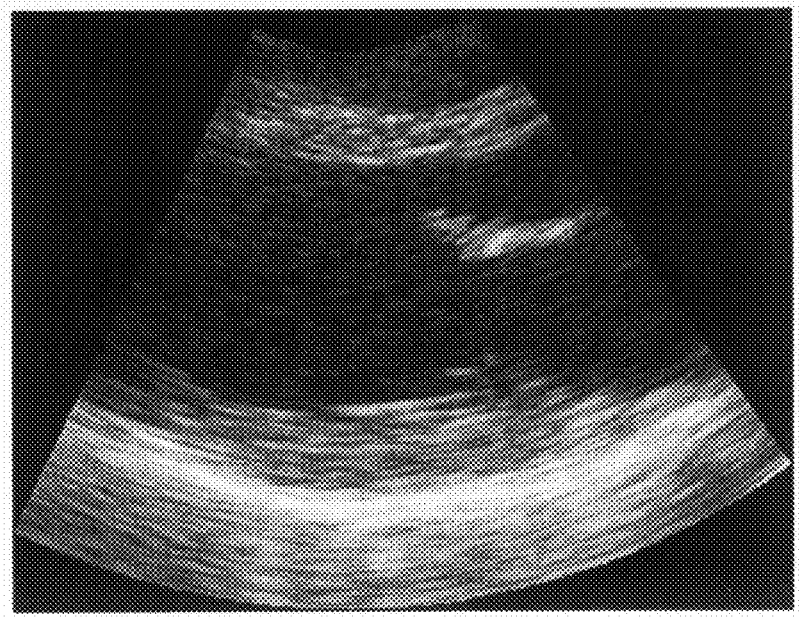
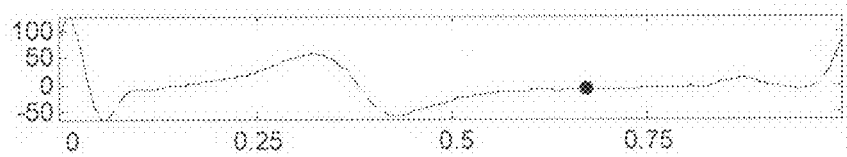
Fig. 21A(g1)
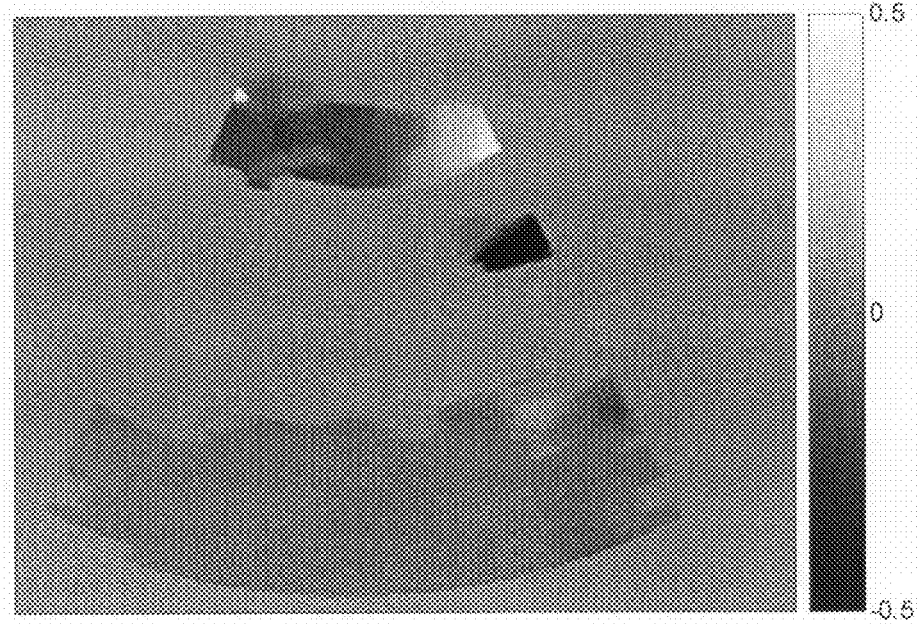
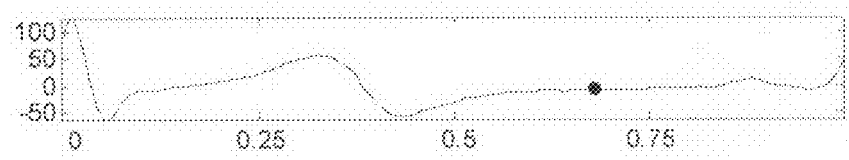
Fig. 21A(g2)

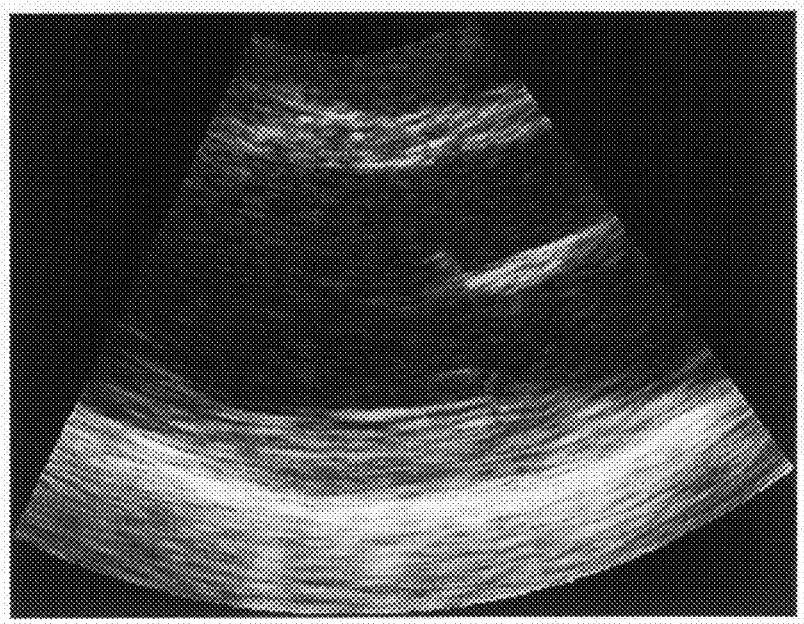
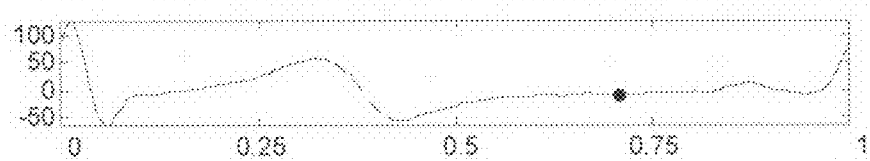
Fig. 21A(h1)
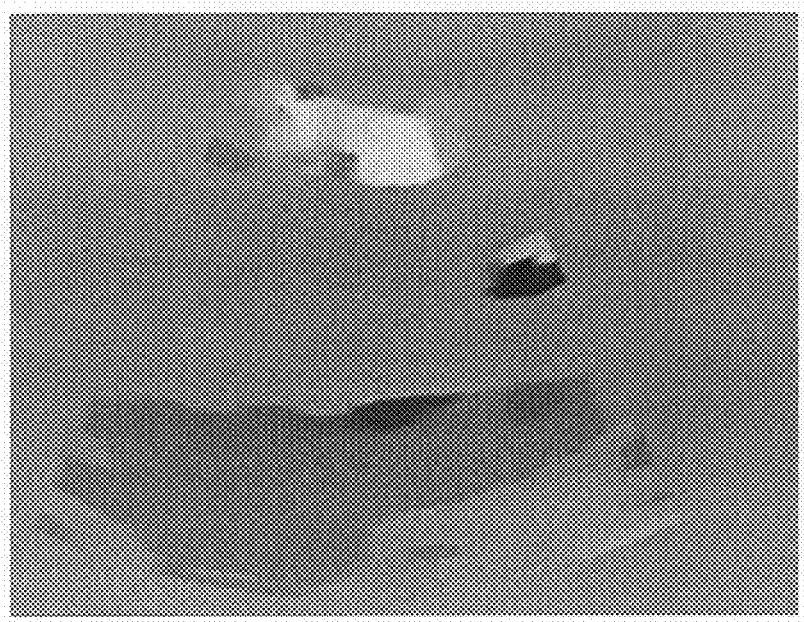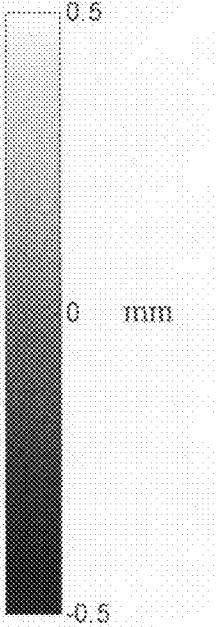
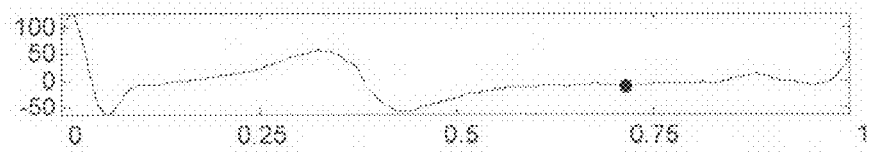
Fig. 21A(h2)

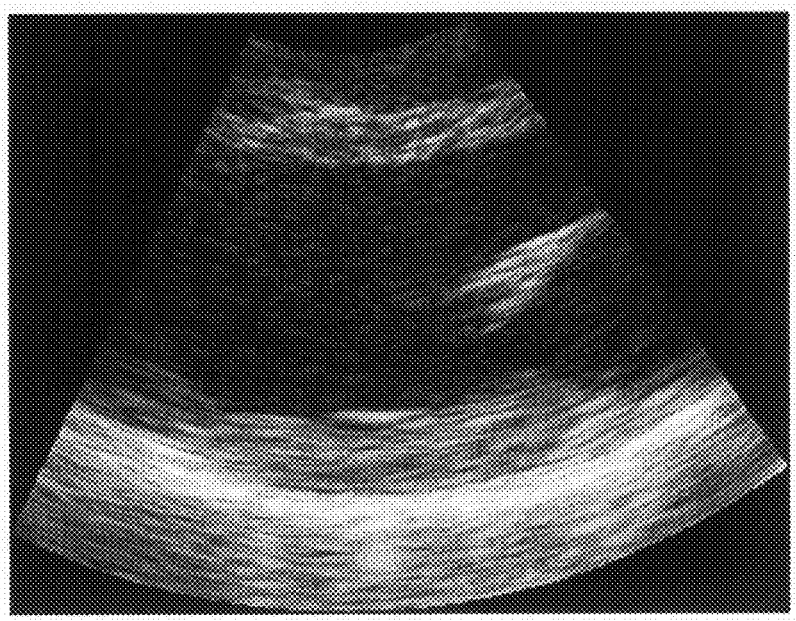
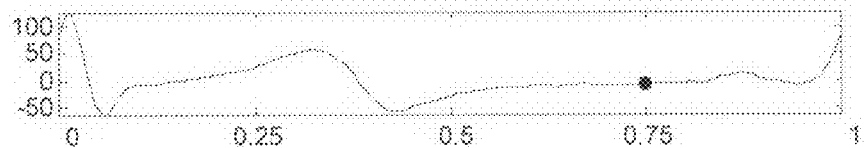
Fig. 21A(i1)
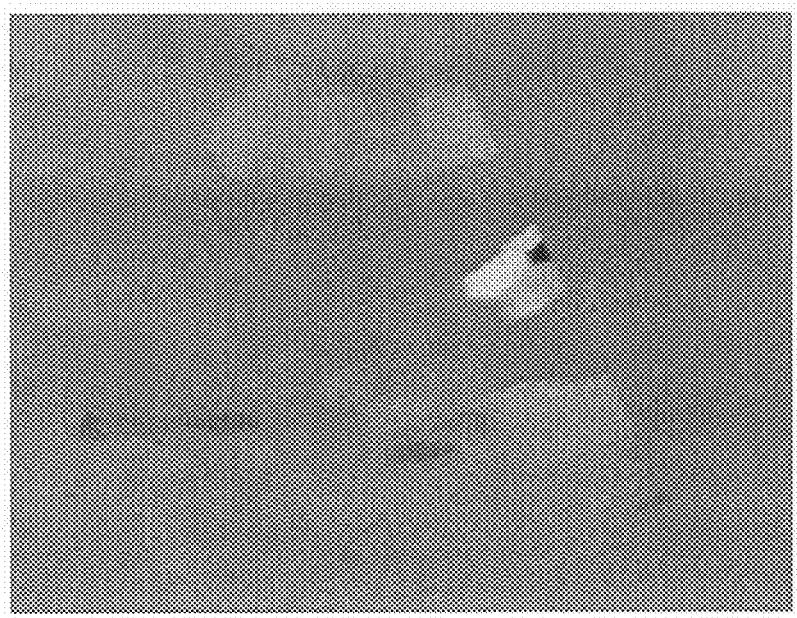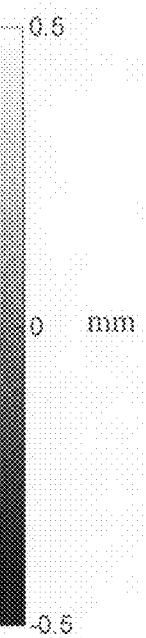
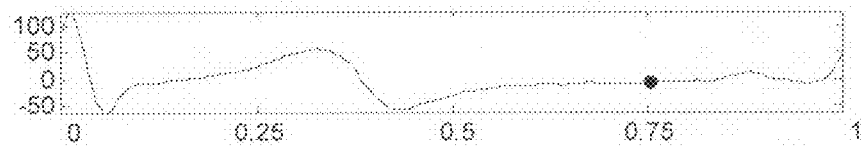
Fig. 21A(i2)

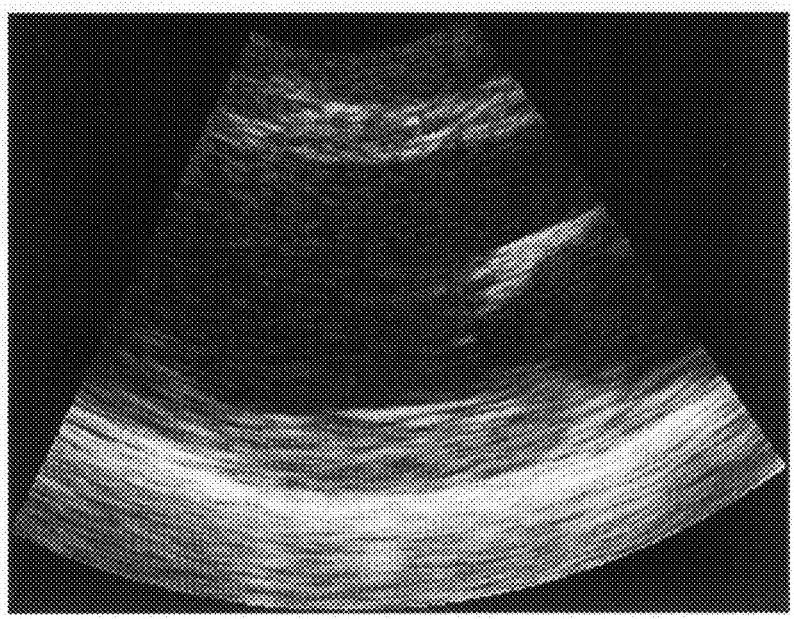
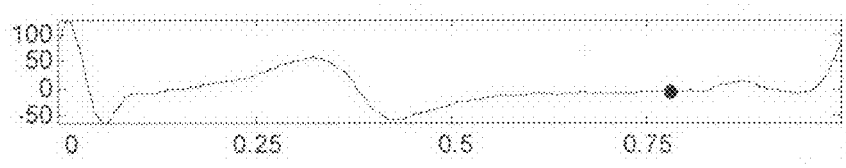
Fig. 21A(j1)
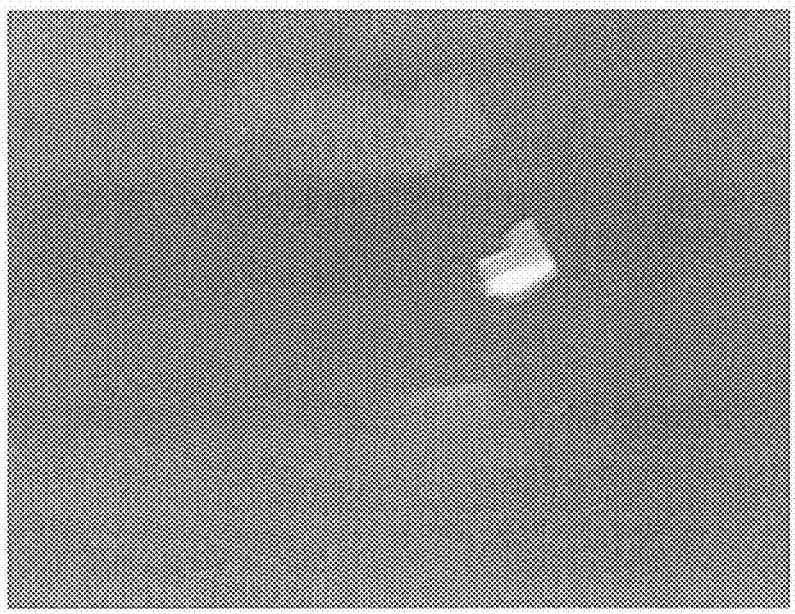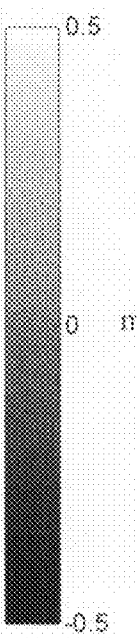
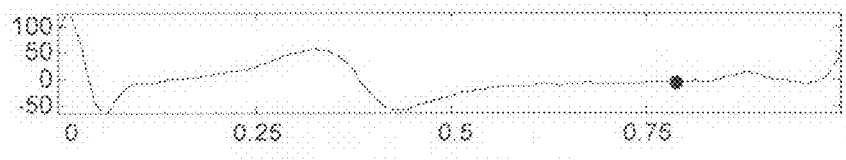
Fig. 21A(j2)

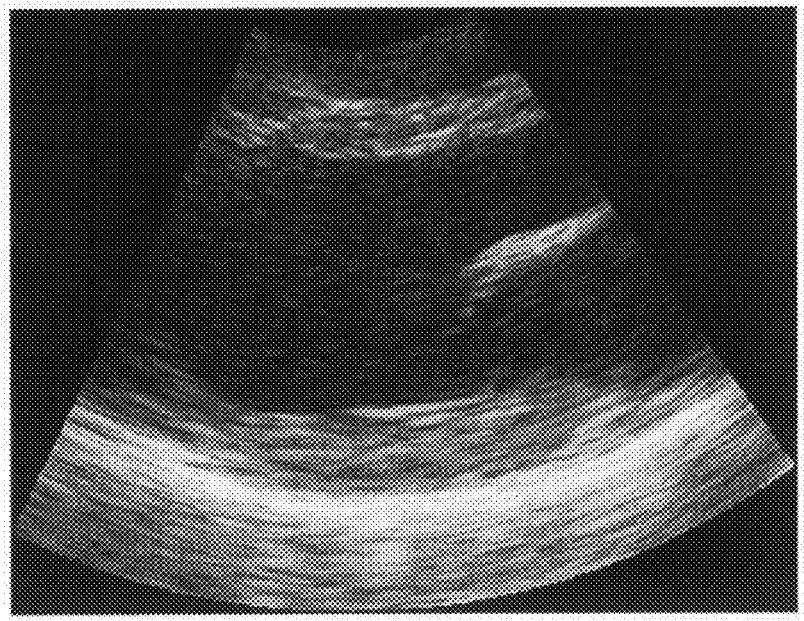
Fig. 21A(k1)
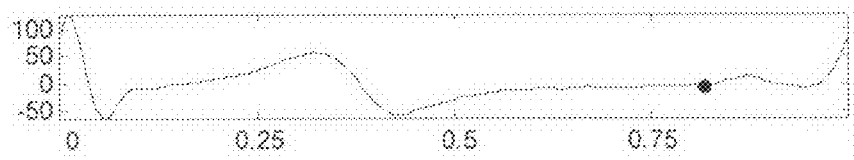
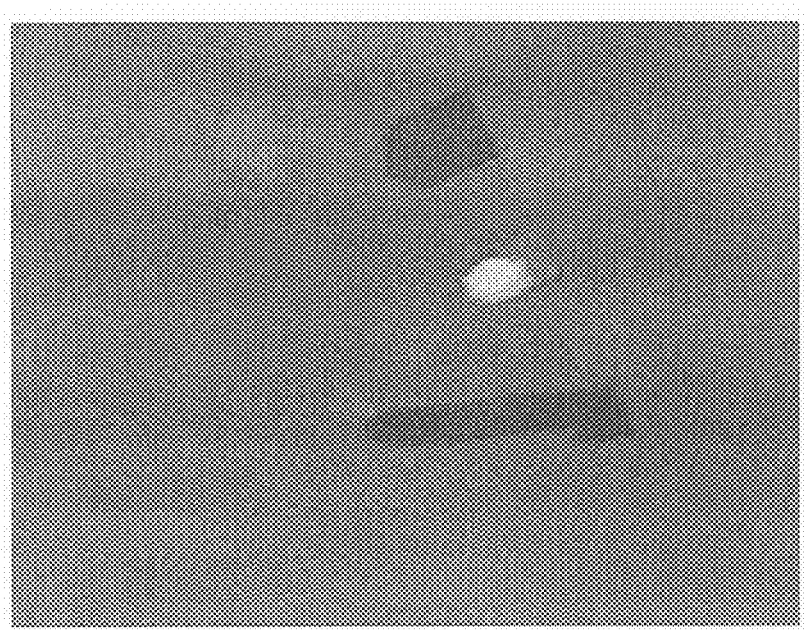
Fig. 21A(k2)

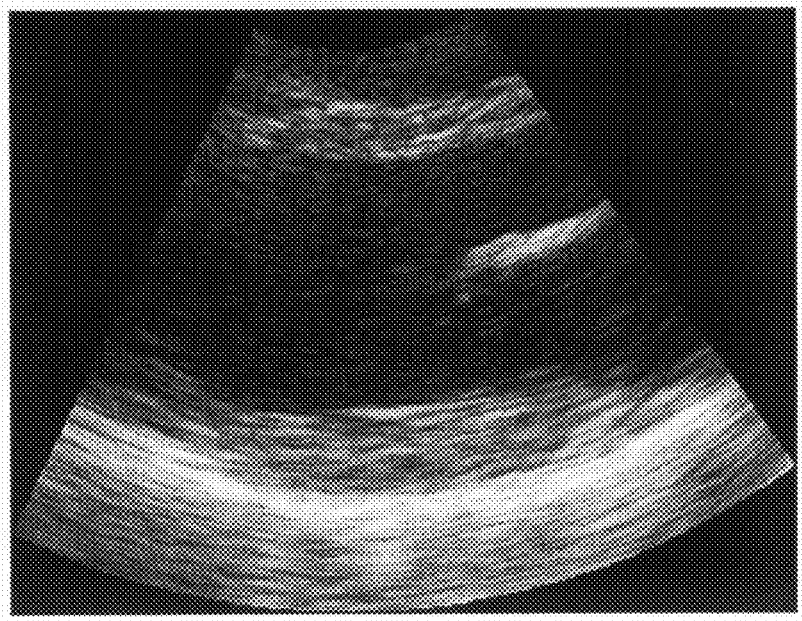
Fig. 21A(I1)
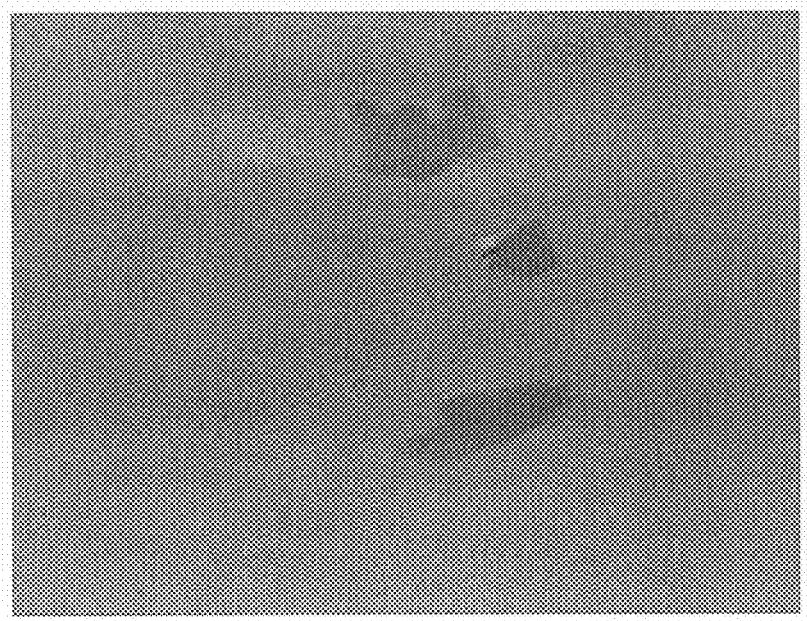
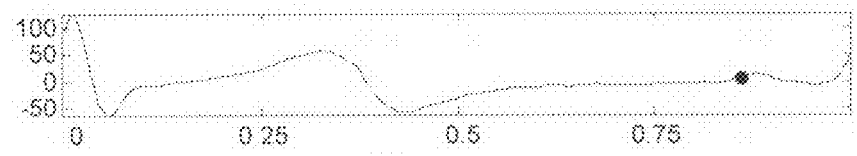
Fig. 21A(I2)

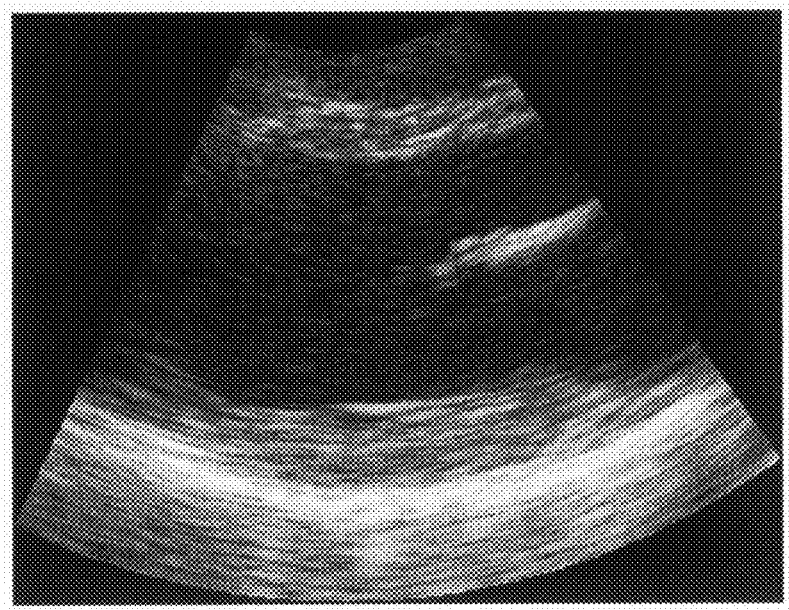
Fig. 21A(m1)
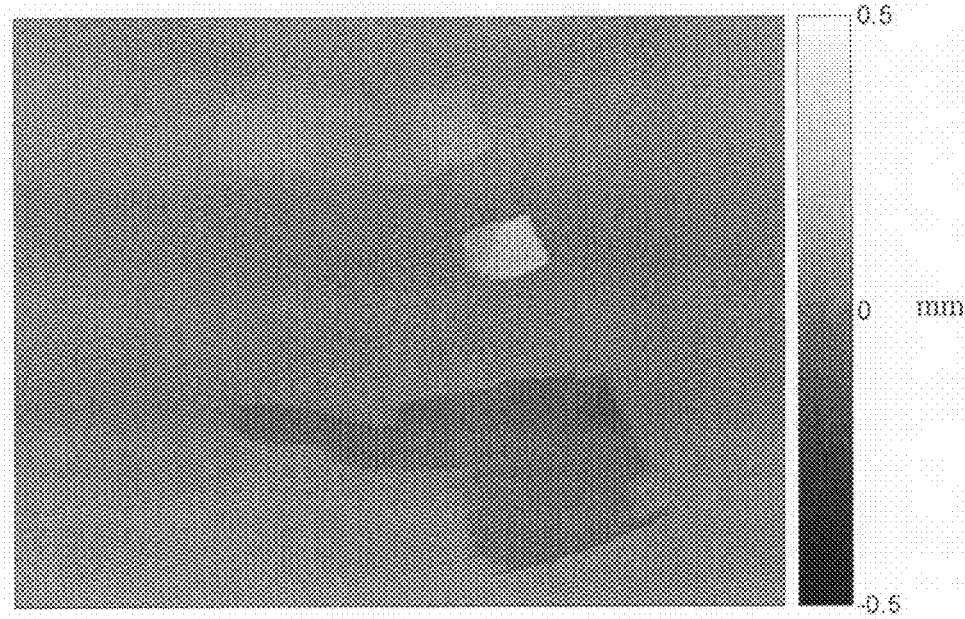
Fig. 21A(m2)

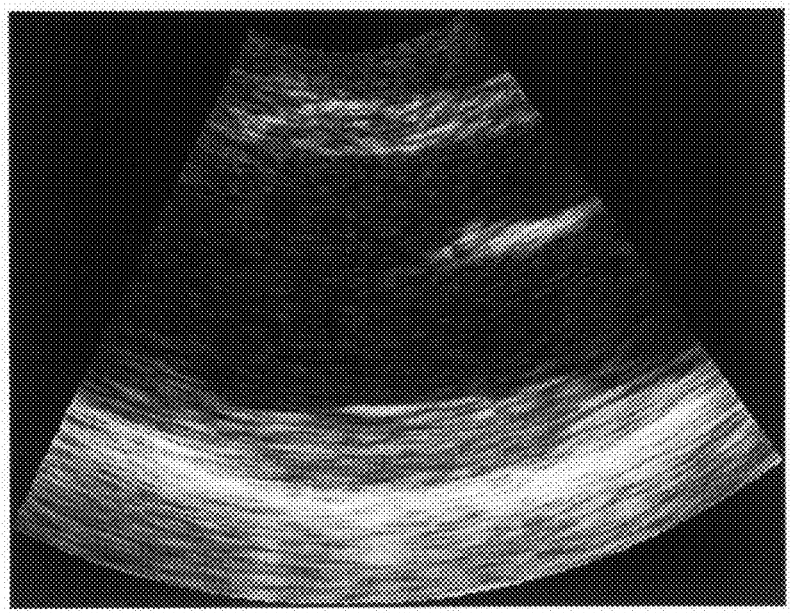
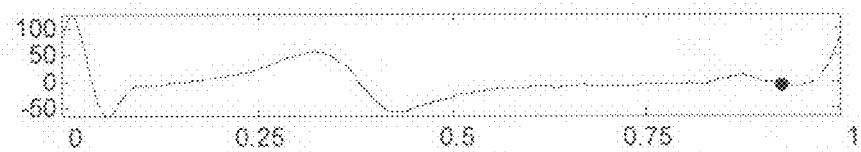
Fig. 21A(n1)
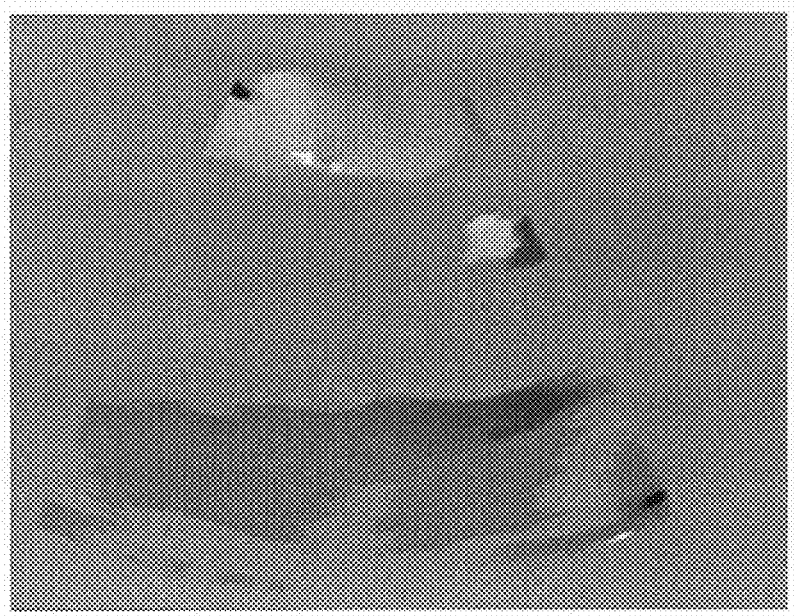
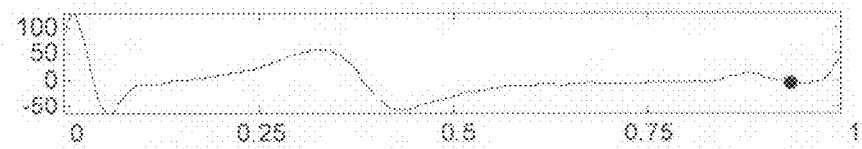
Fig. 21A(n2)

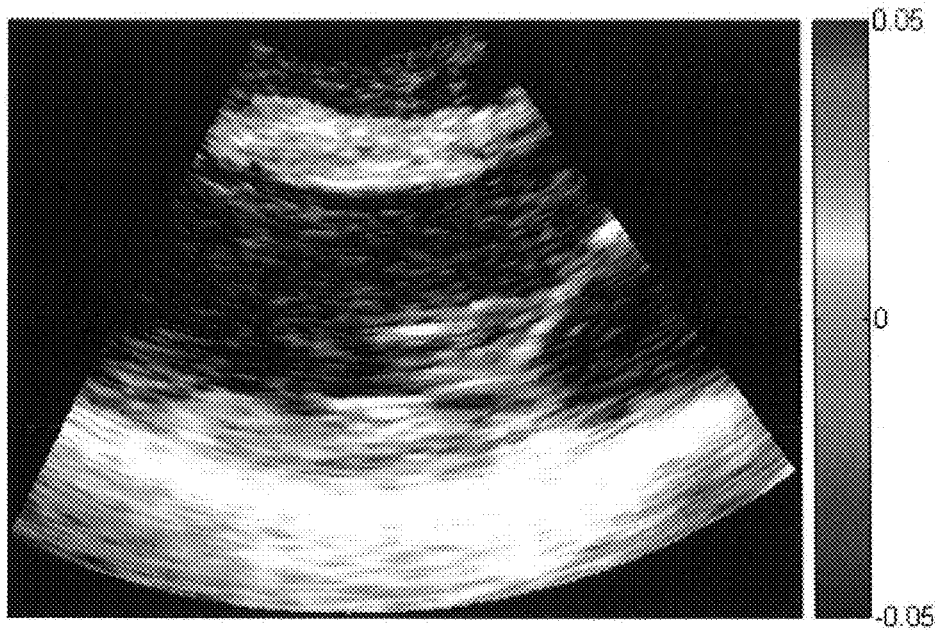
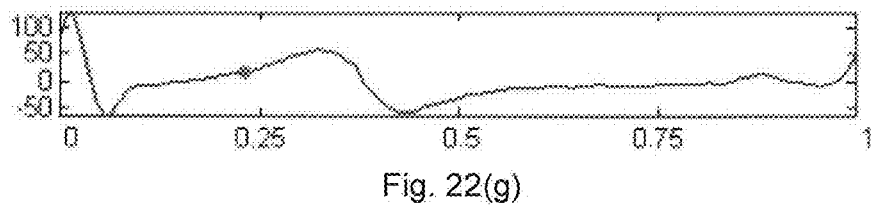
Fig. 22(g)
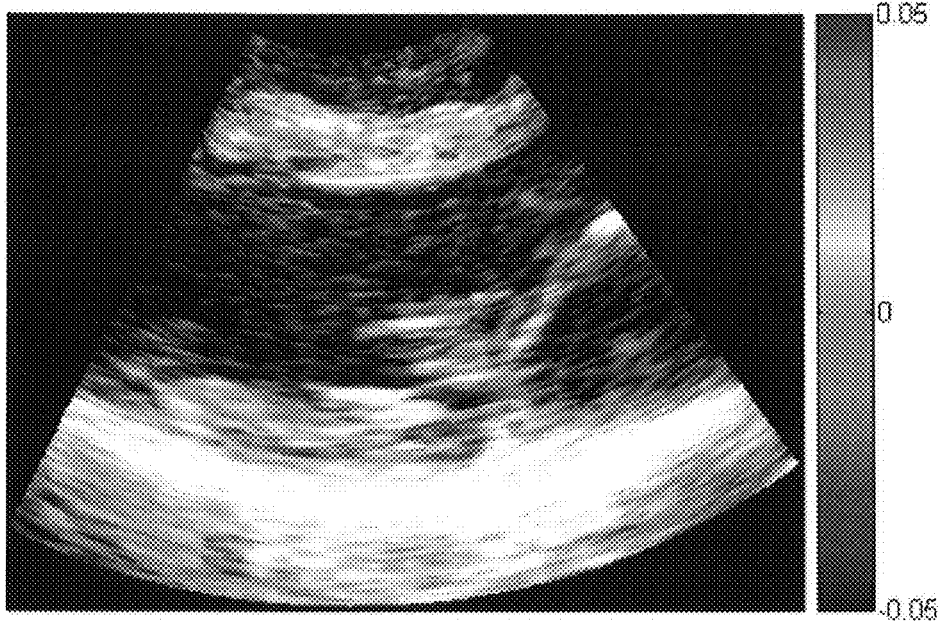
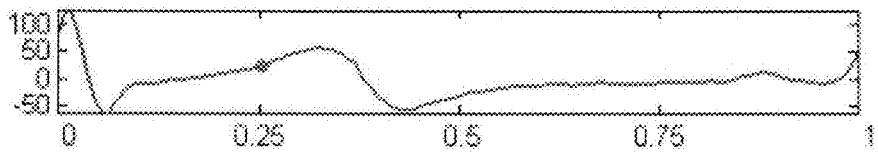
Fig. 22(h)

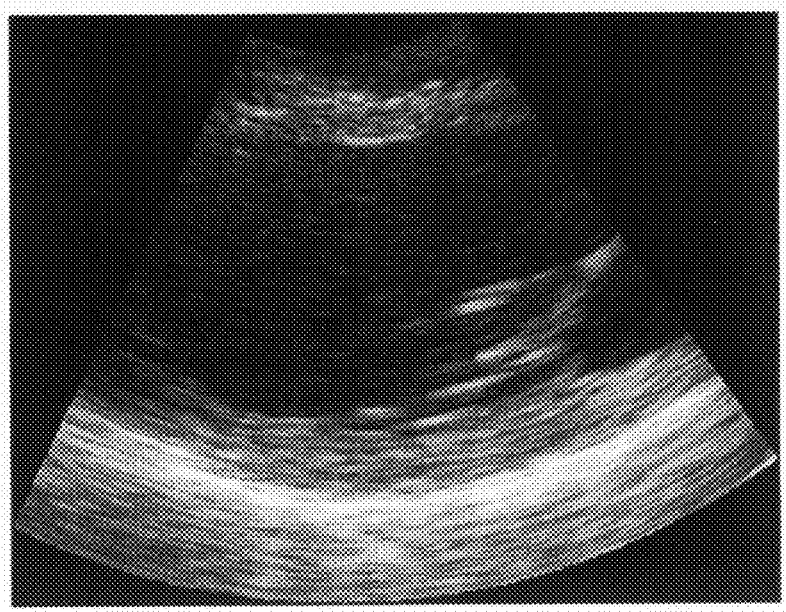
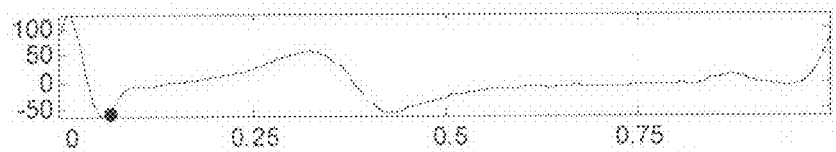
Fig. 22A(a1)
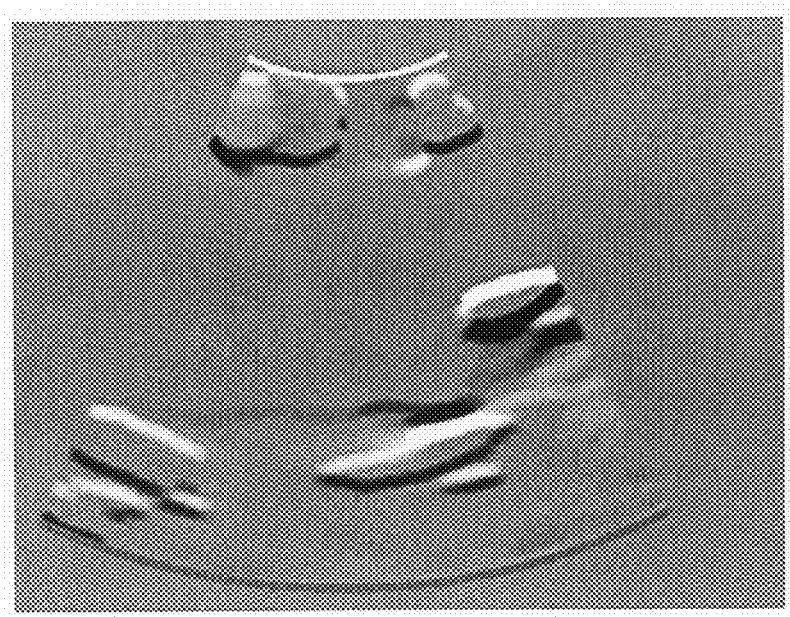
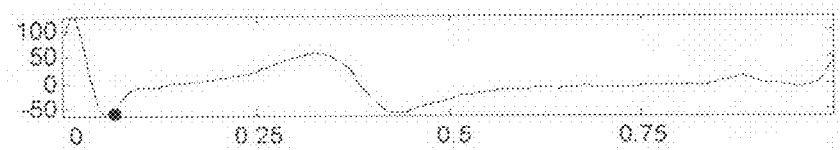
Fig. 22A(a2)

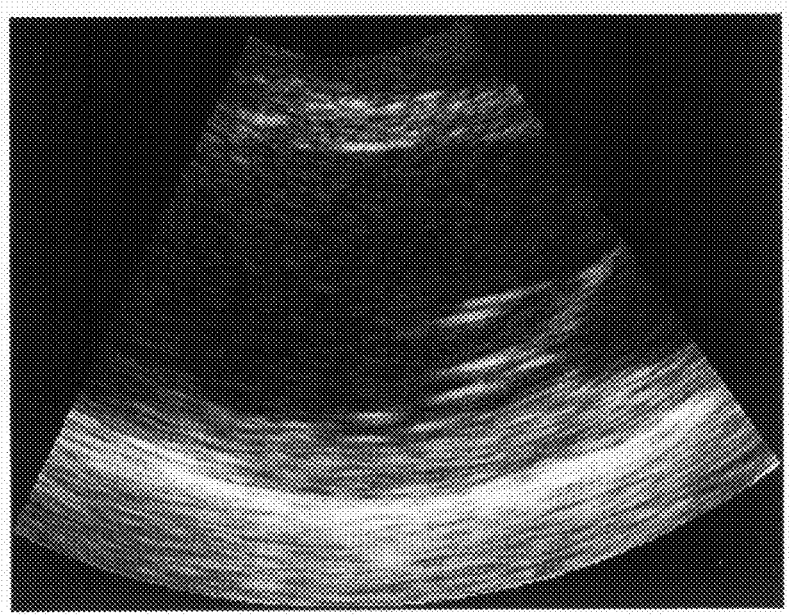
Fig. 22A(b1)
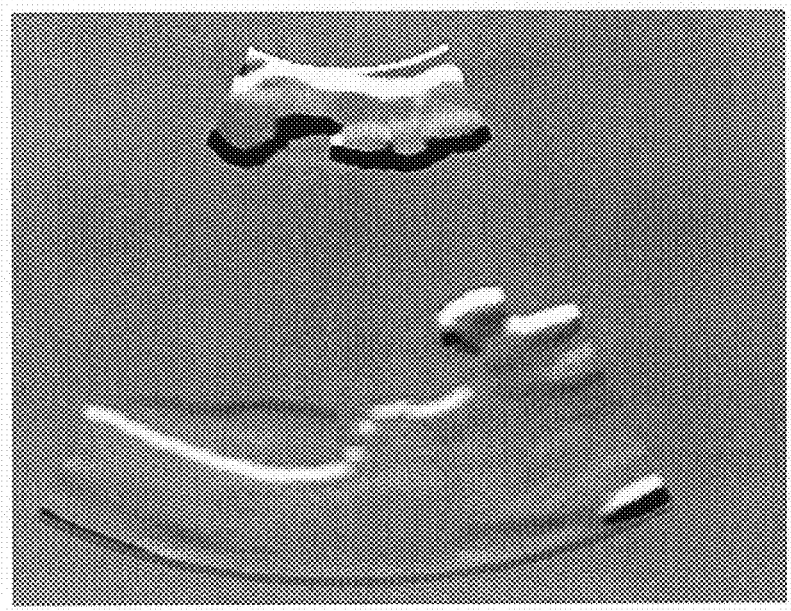
Fig. 22A(b2)

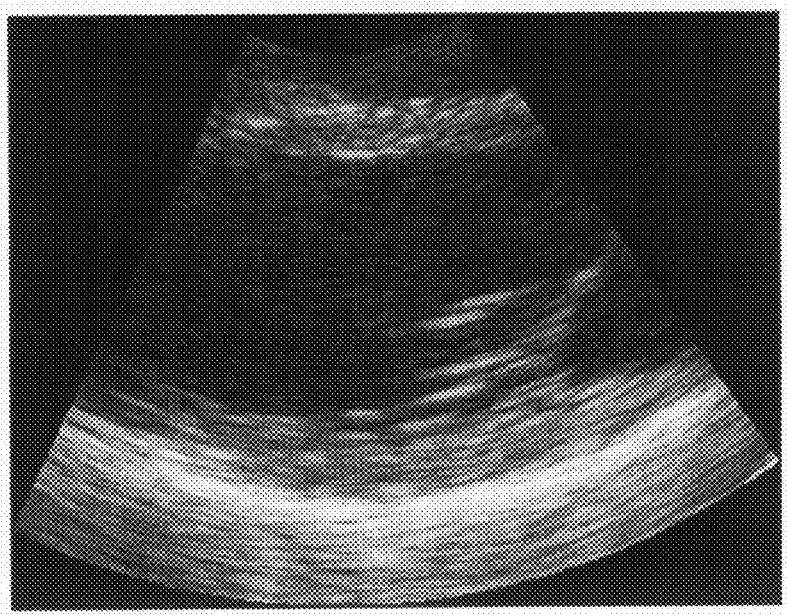
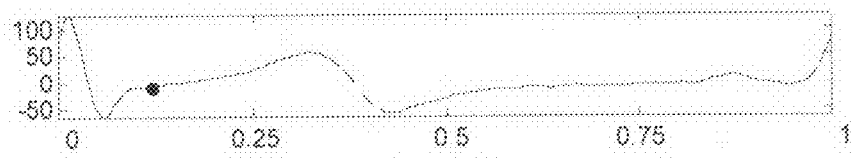
Fig. 22A(c1)
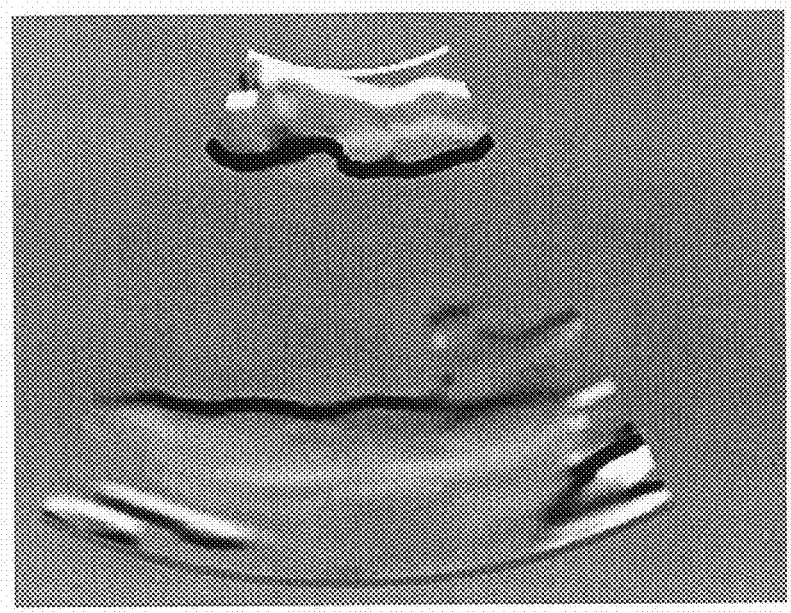
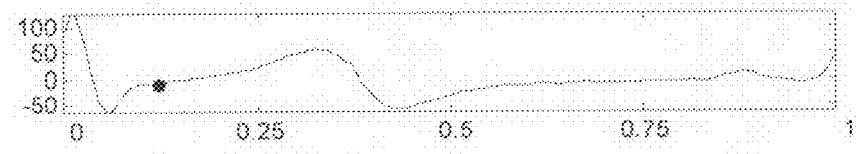
Fig. 22A(c2)

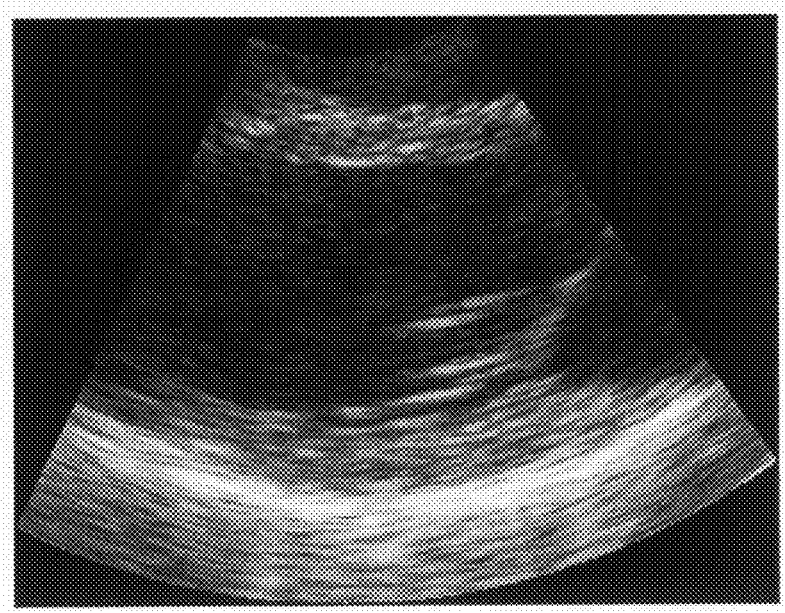
Fig. 22A(d1)
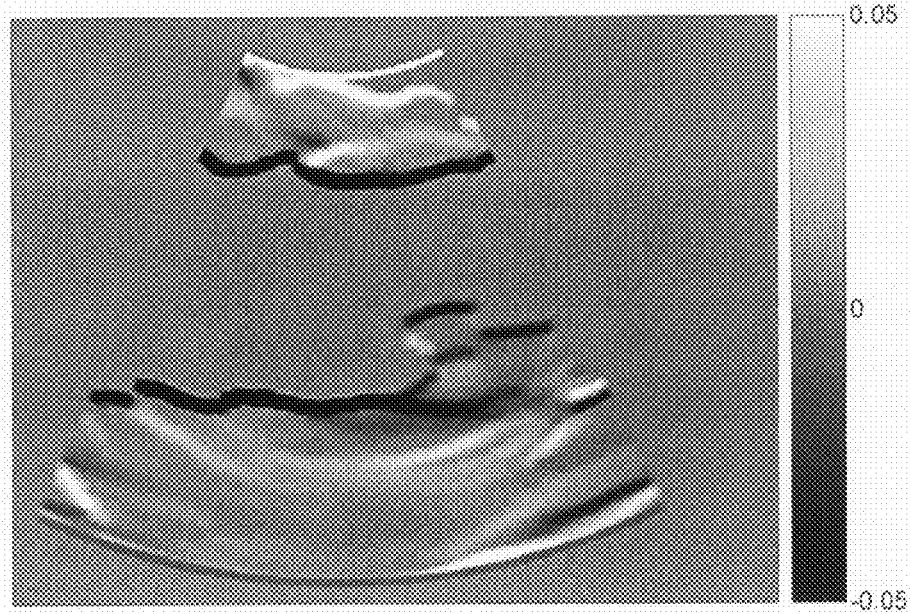
Fig. 22A(d2)

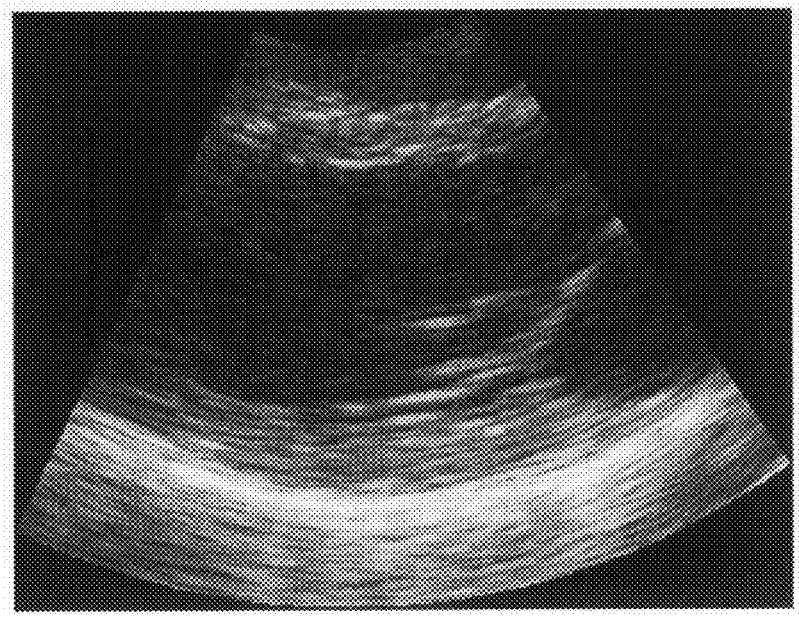
Fig. 22A(e1)
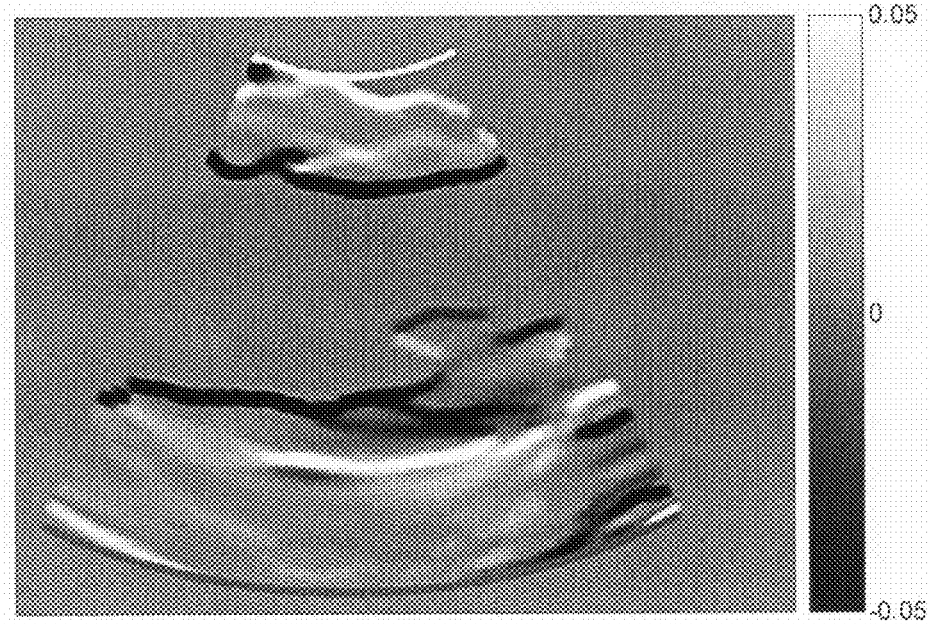
Fig. 22A(e2)

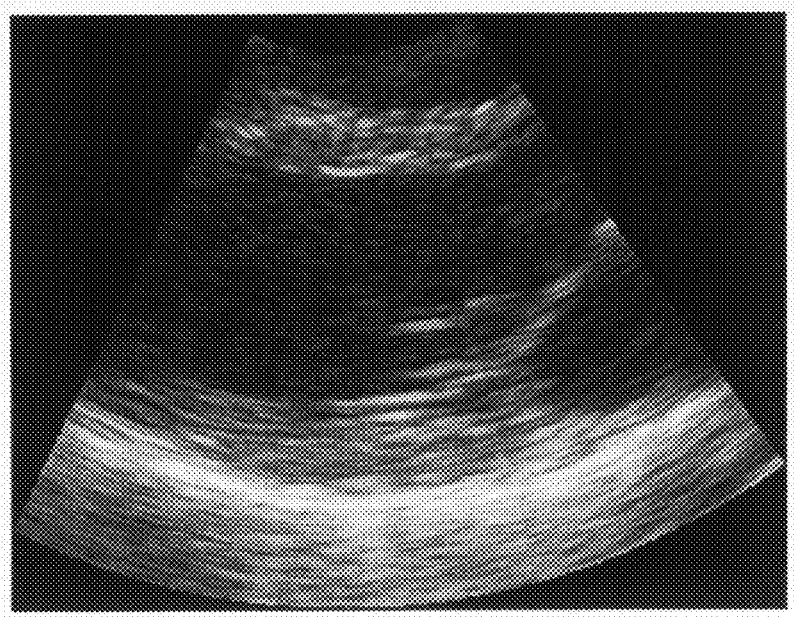
Fig. 22A(f1)
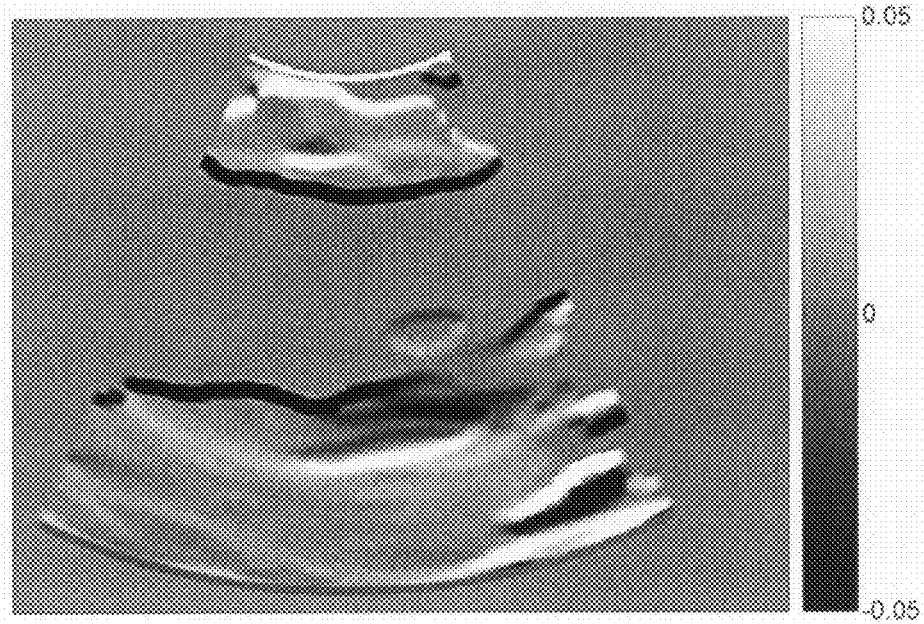
Fig. 22A(f2)

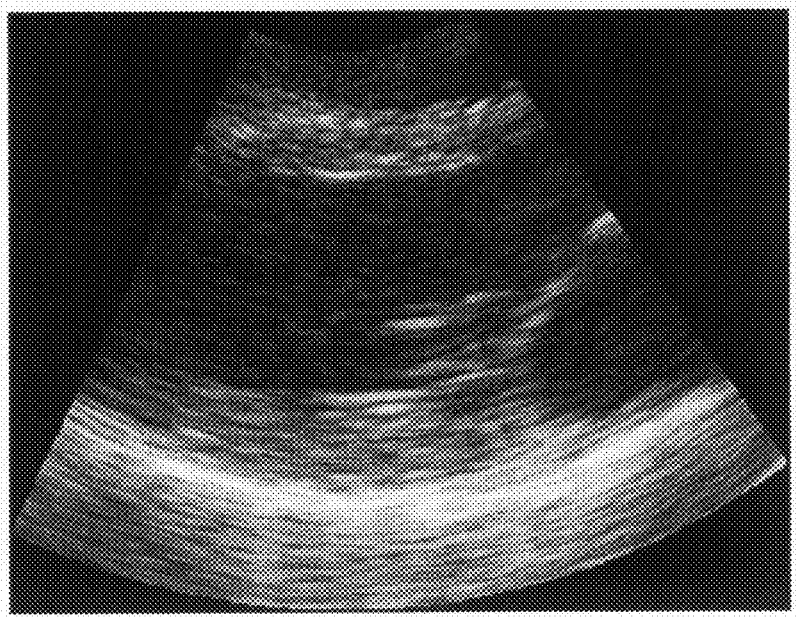
Fig. 22A(g1)
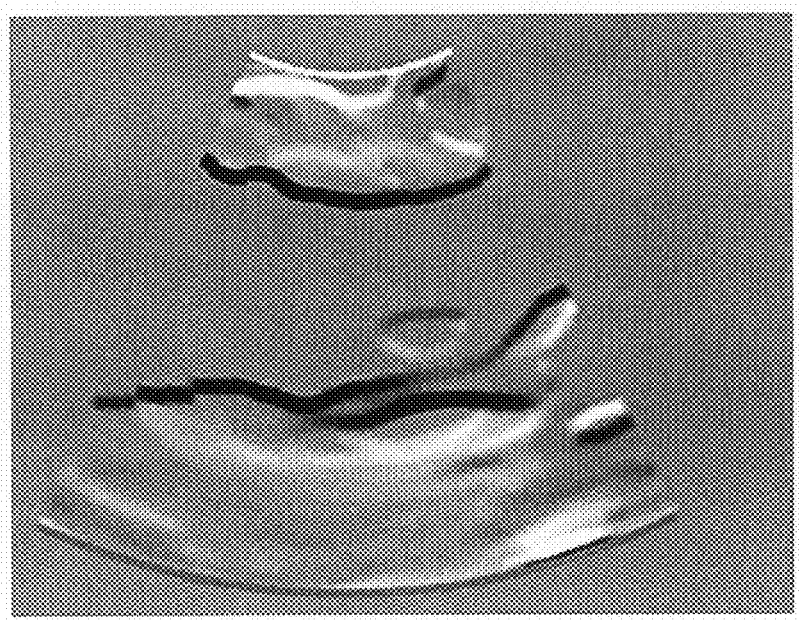
Fig. 22A(g2)

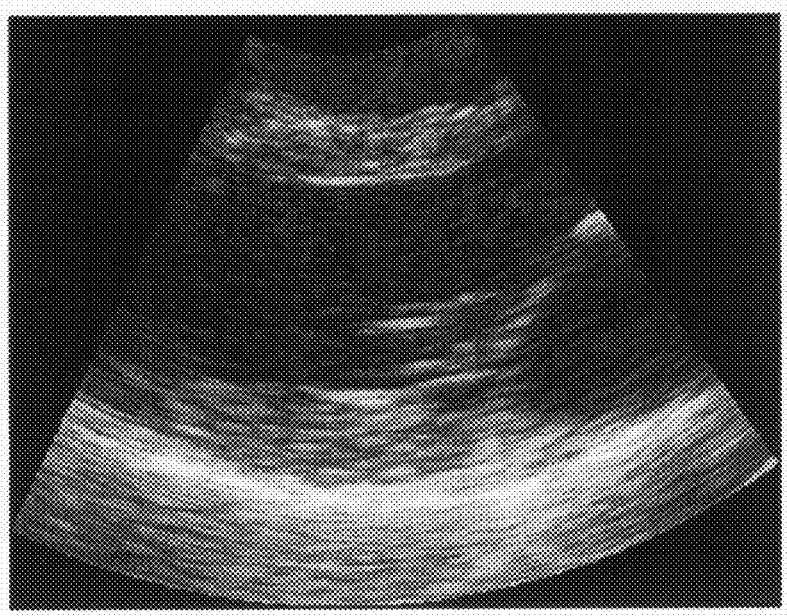
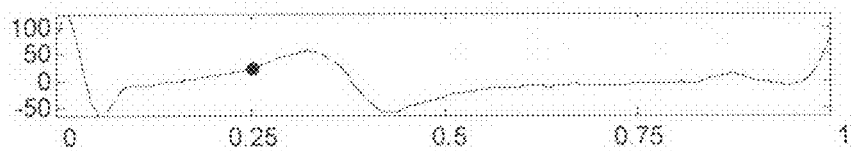
Fig. 22A(h1)
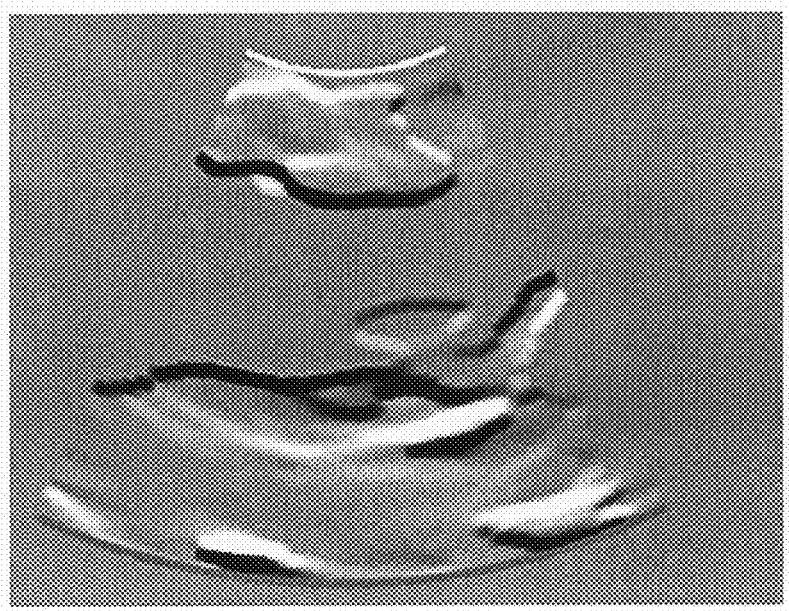
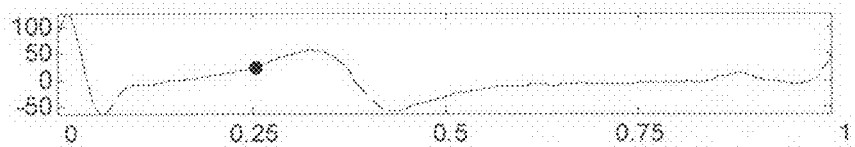
Fig. 22A(h2)

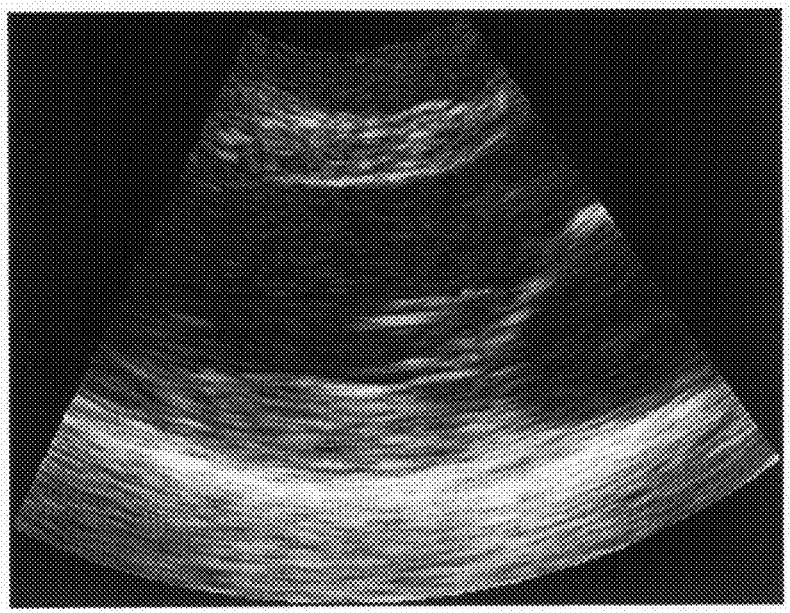
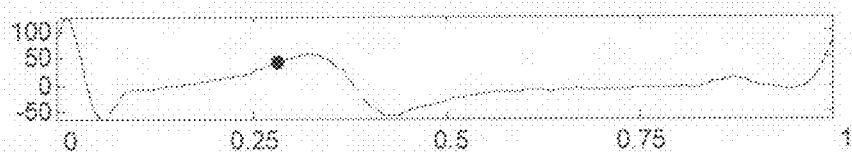
Fig. 22A(i1)
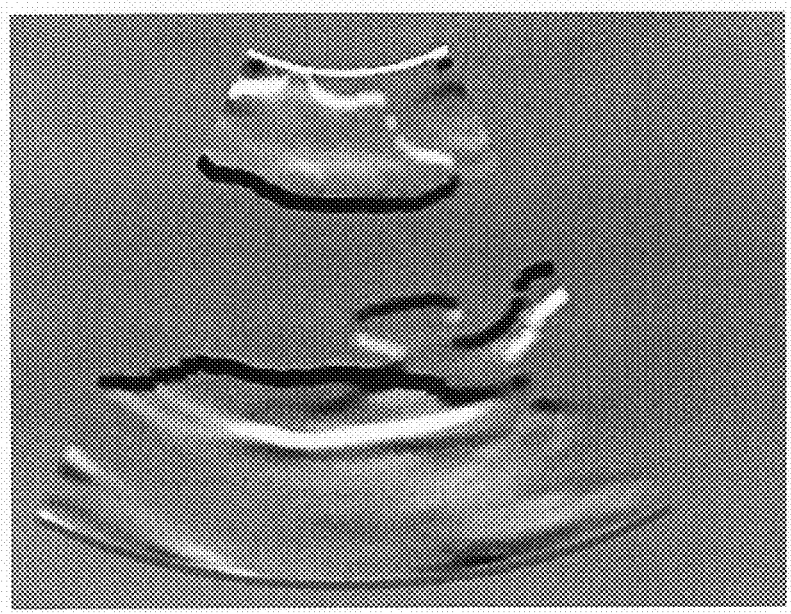
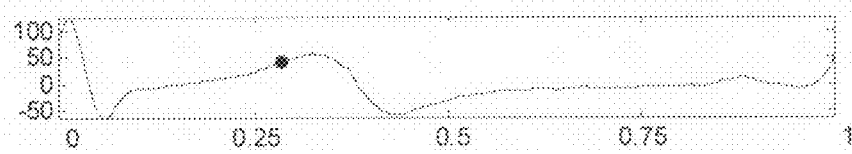
Fig. 22A(i2)

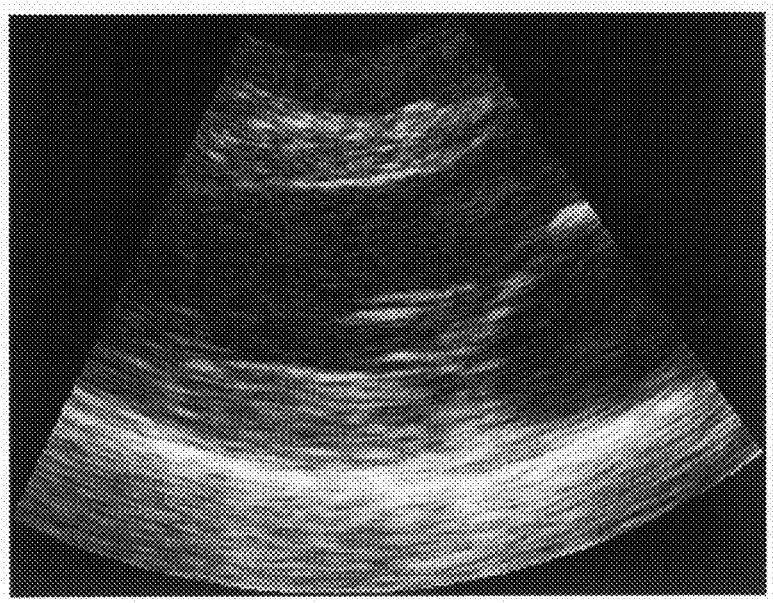
Fig. 22A(j1)
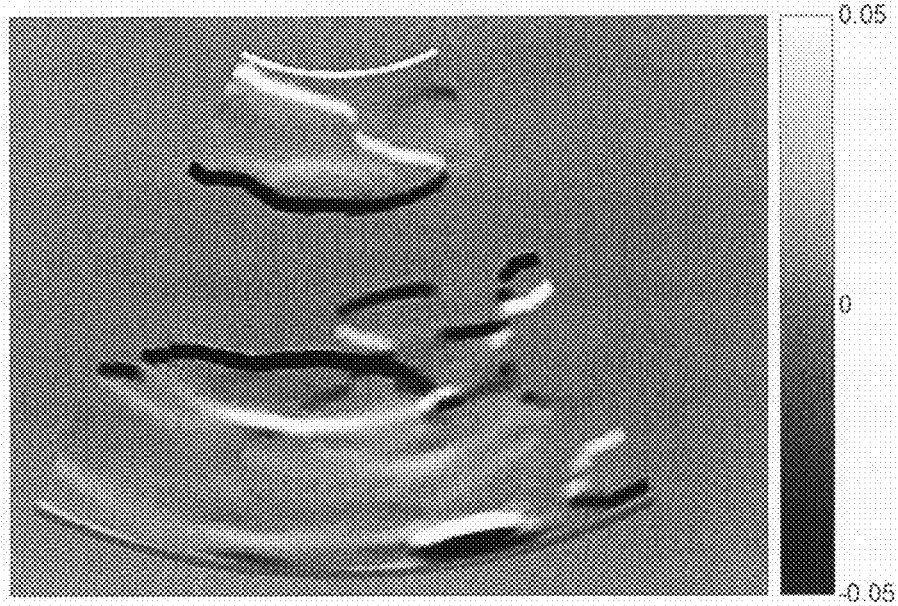
Fig. 22A(j2)

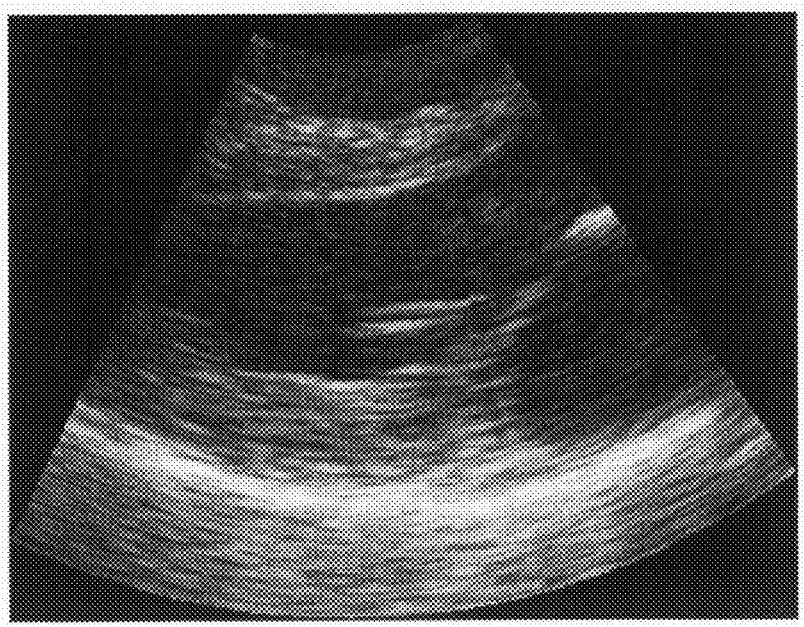
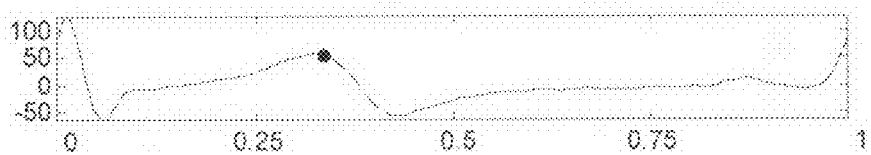
Fig. 22A(k1)
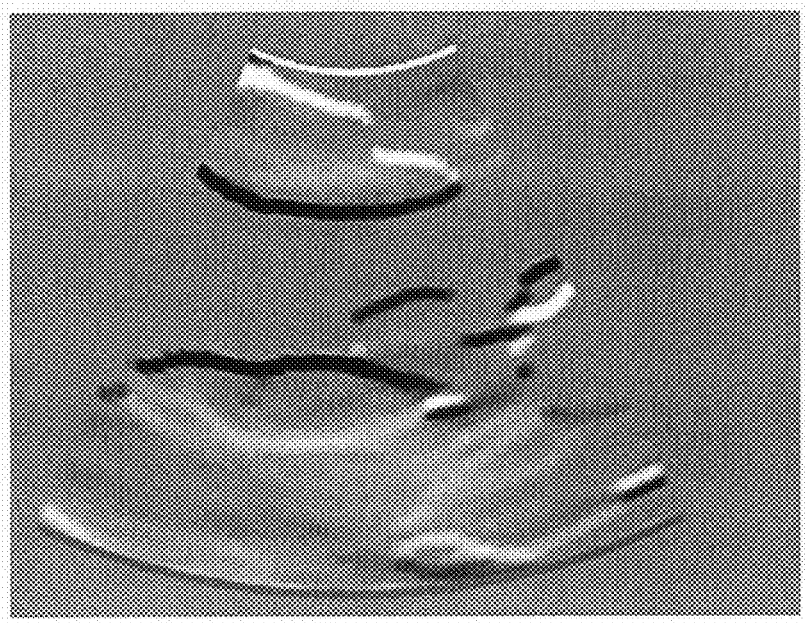
Fig. 22A(k2)

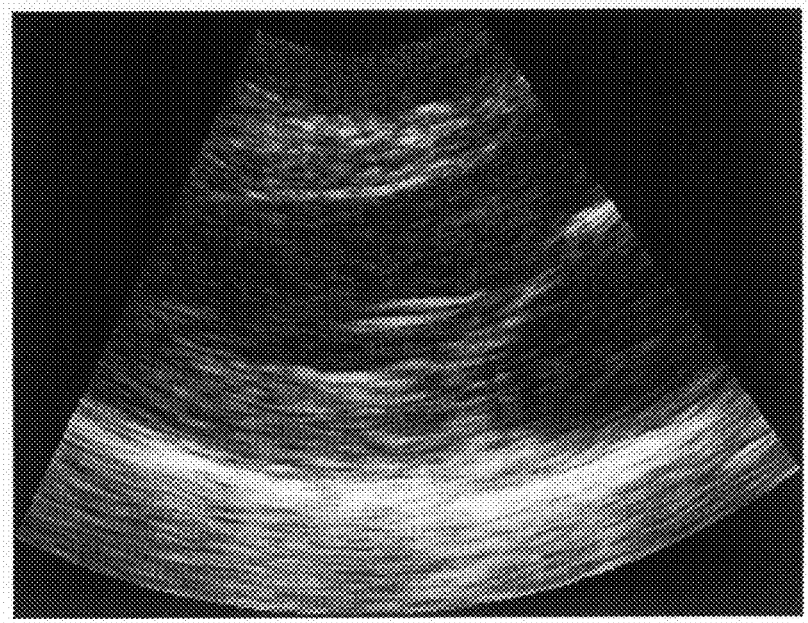
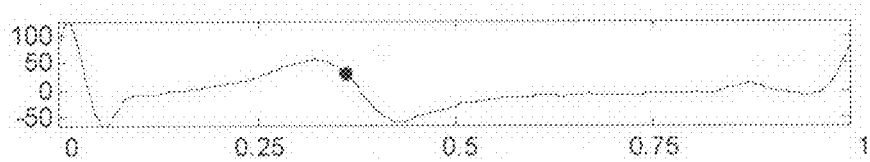
Fig. 22A(I1)
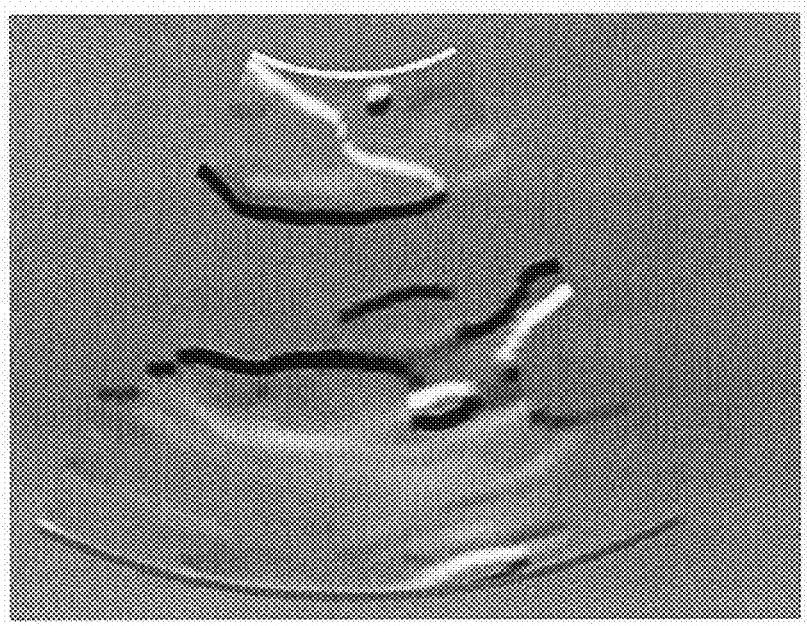
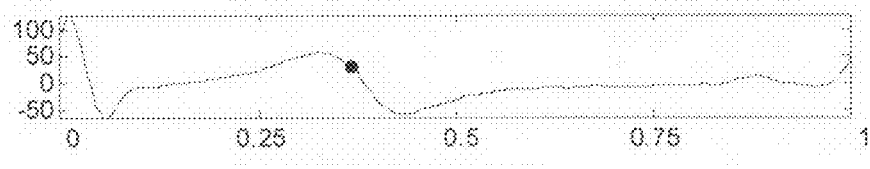
Fig. 22A(I2)

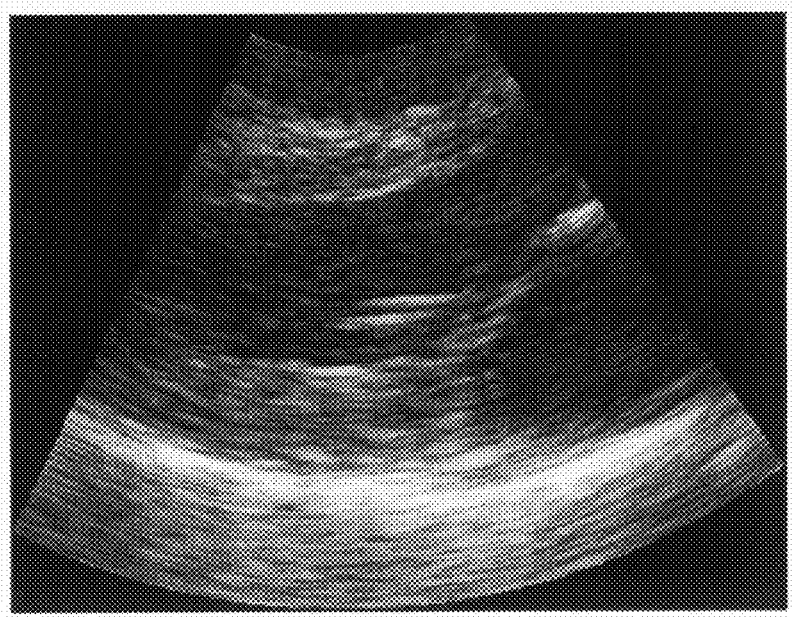
Fig. 22A(m1)
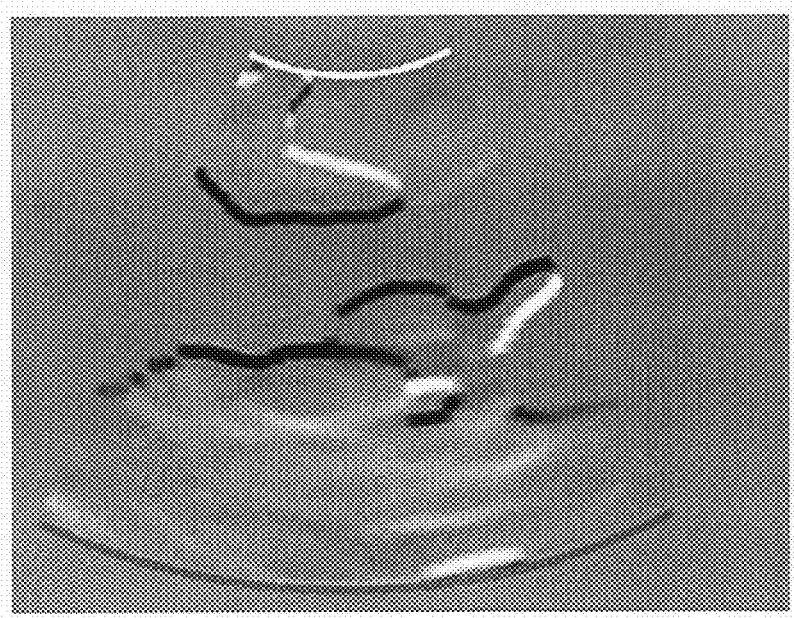
Fig. 22A(m2)

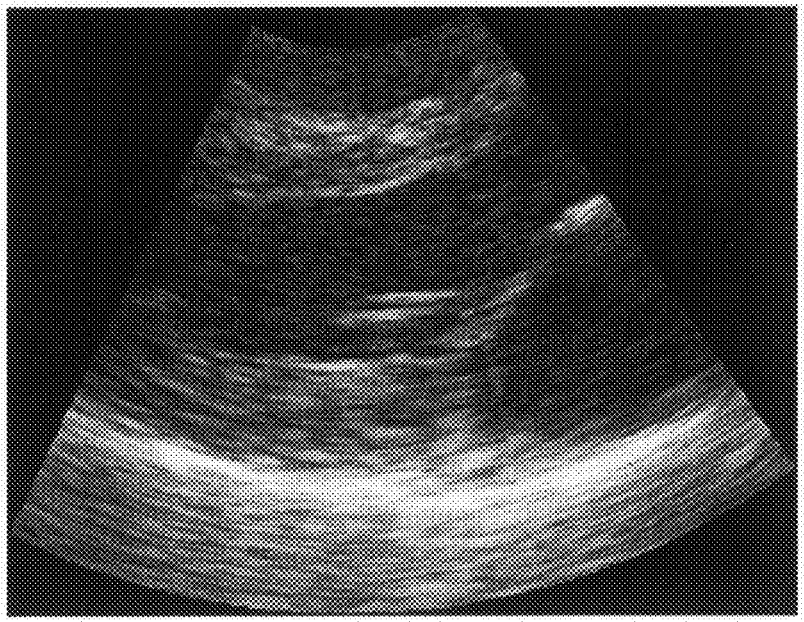
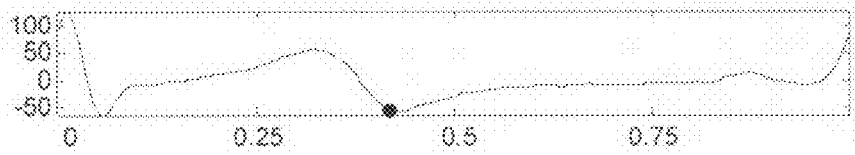
Fig. 22A(n1)
Fig. 22A(n2)

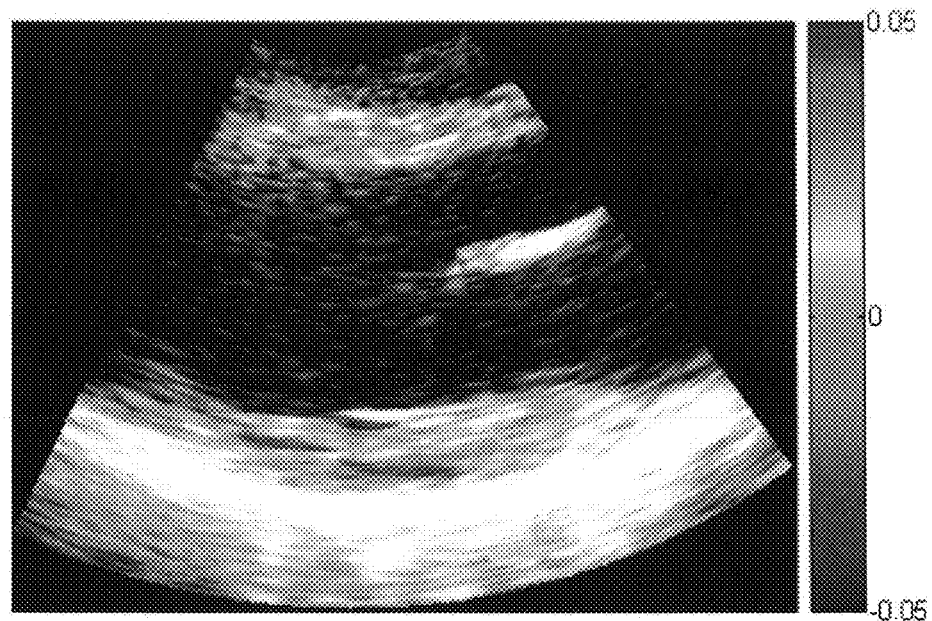
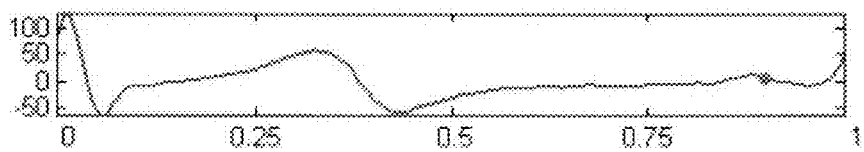
Fig. 23(m)
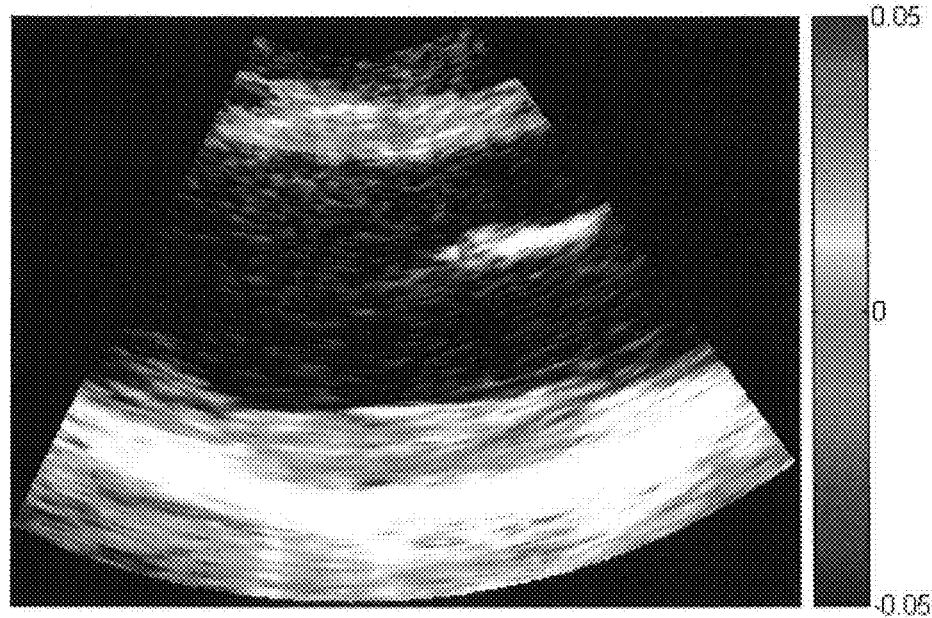
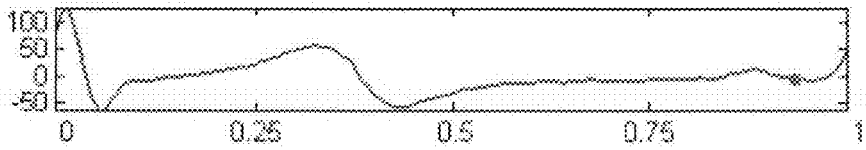
Fig. 23(n)

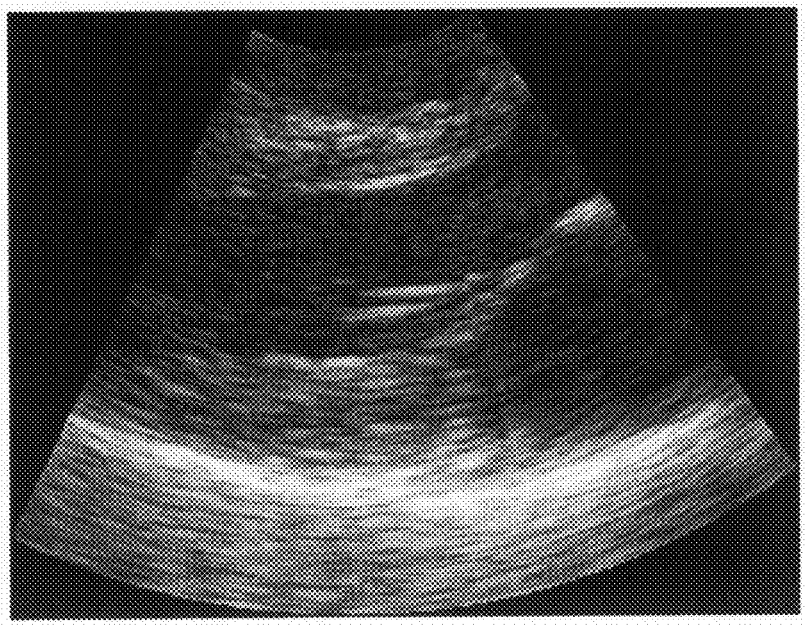
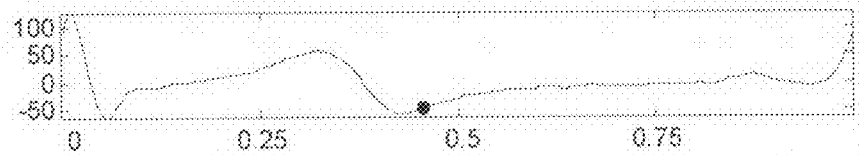
Fig. 23A(a1)
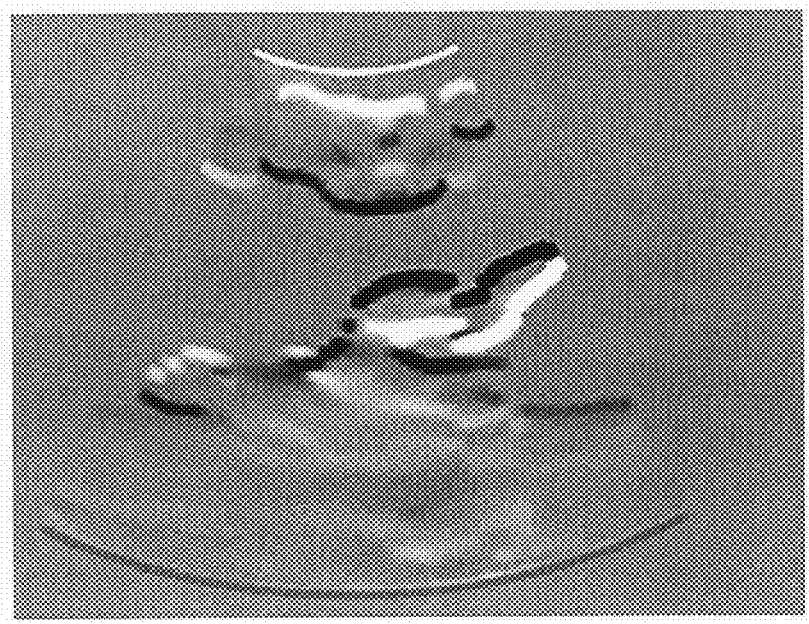
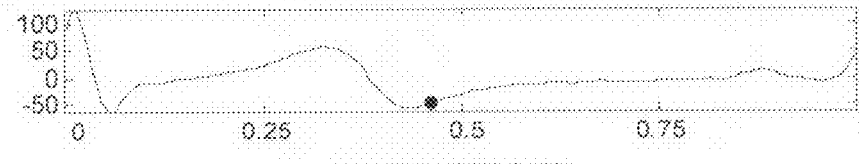
Fig. 23A(a2)

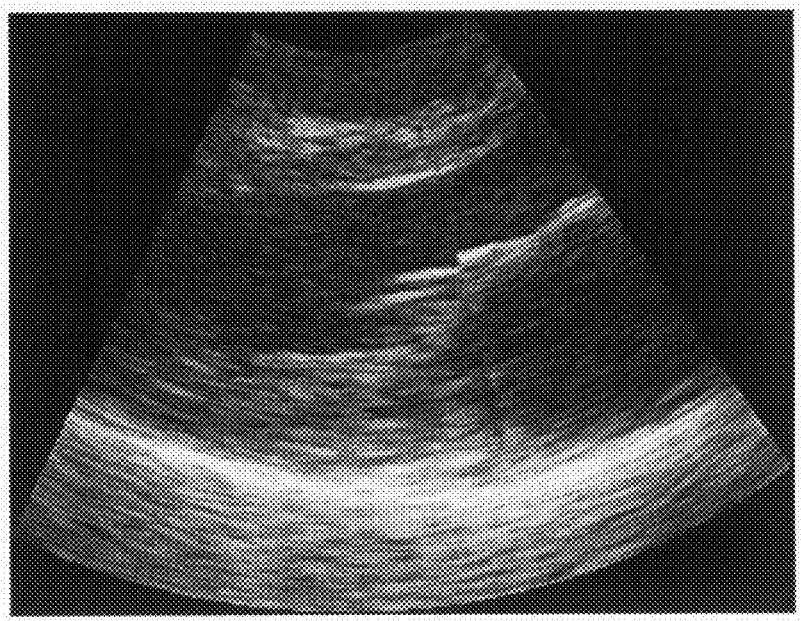
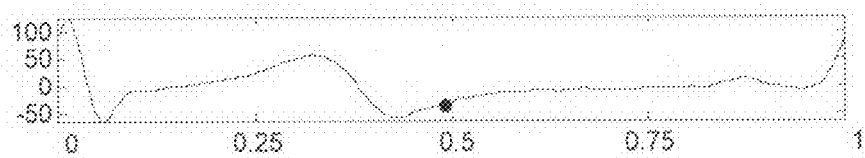
Fig. 23A(b1)
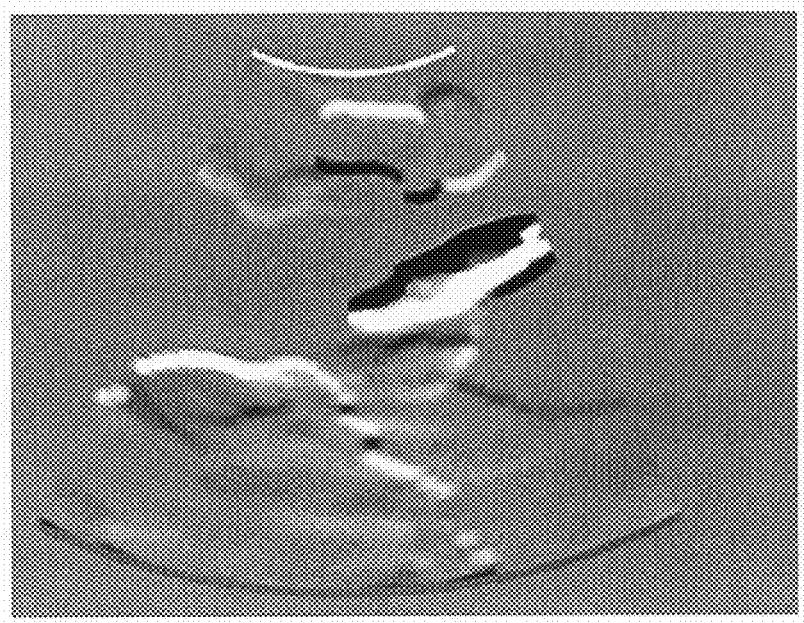
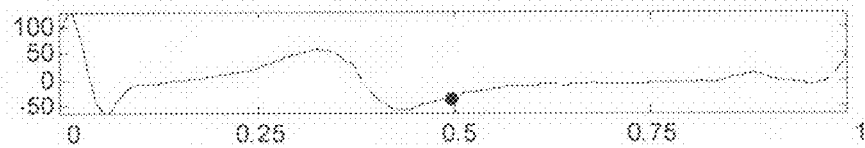
Fig. 23A(b2)

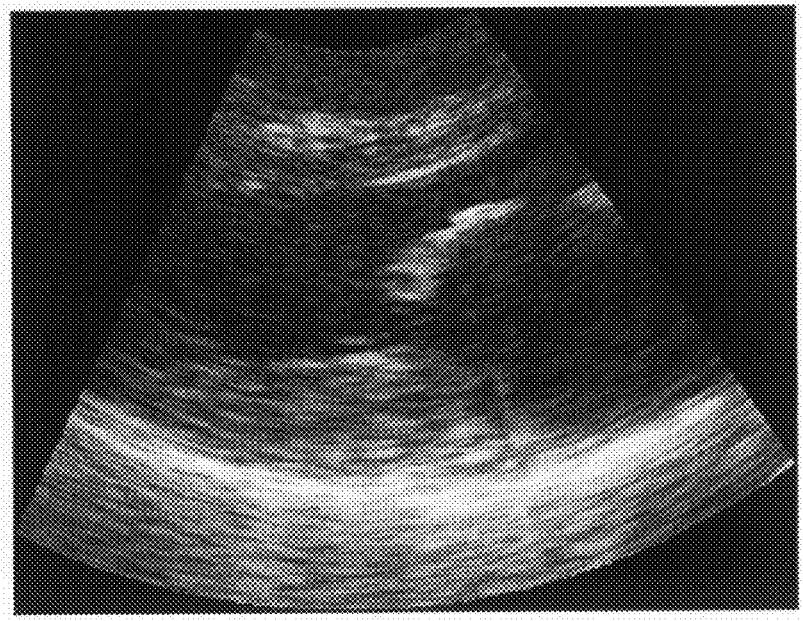
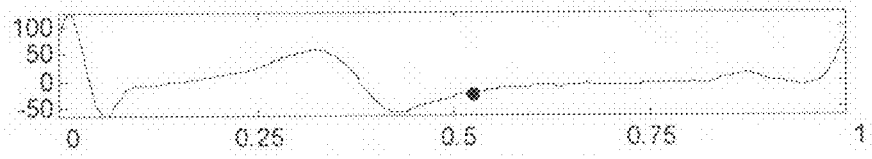
Fig. 23A(c1)
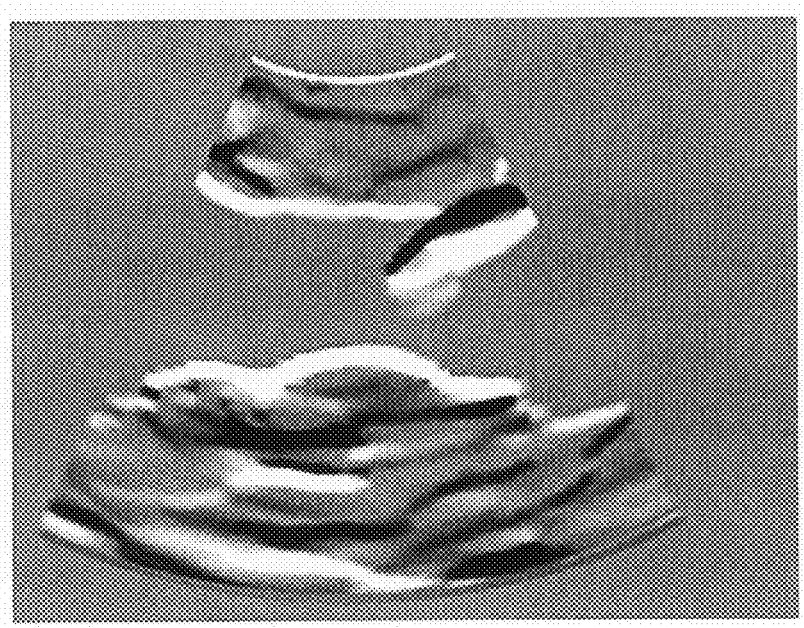
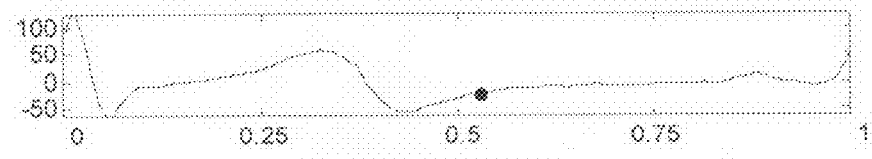
Fig. 23A(c2)

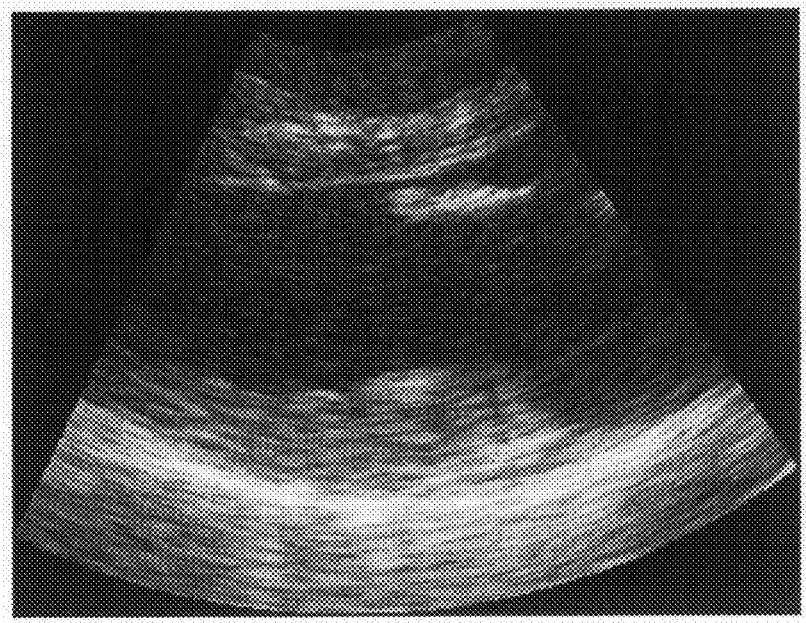
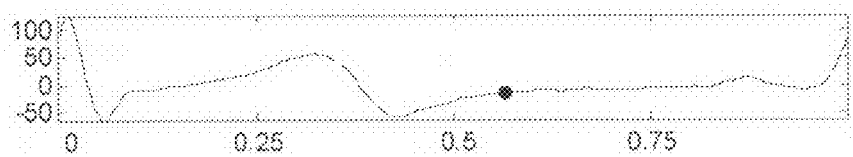
Fig. 23A(d1)
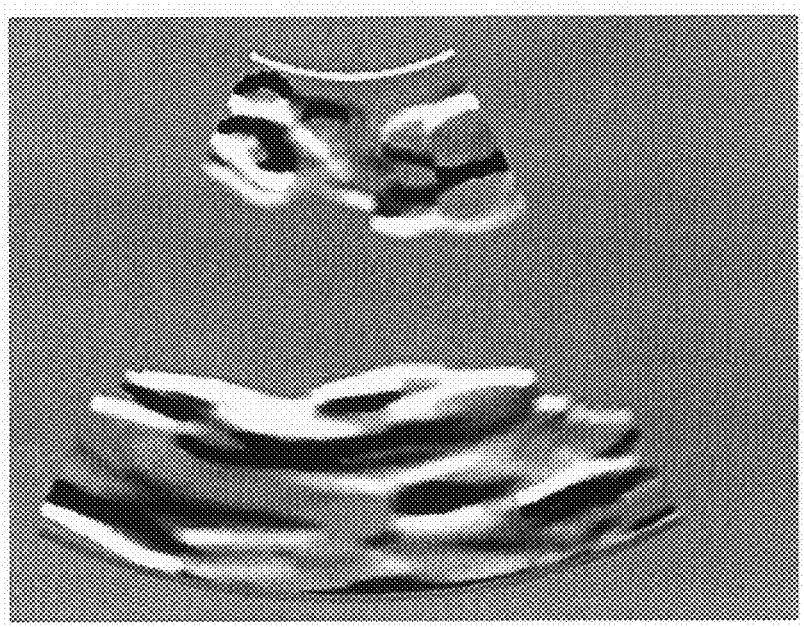
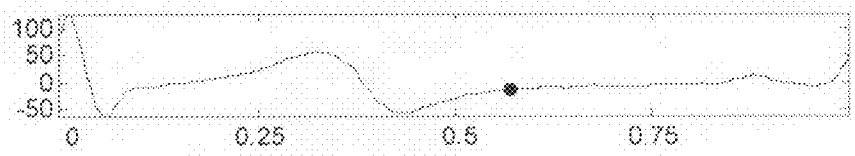
Fig. 23A(d2)

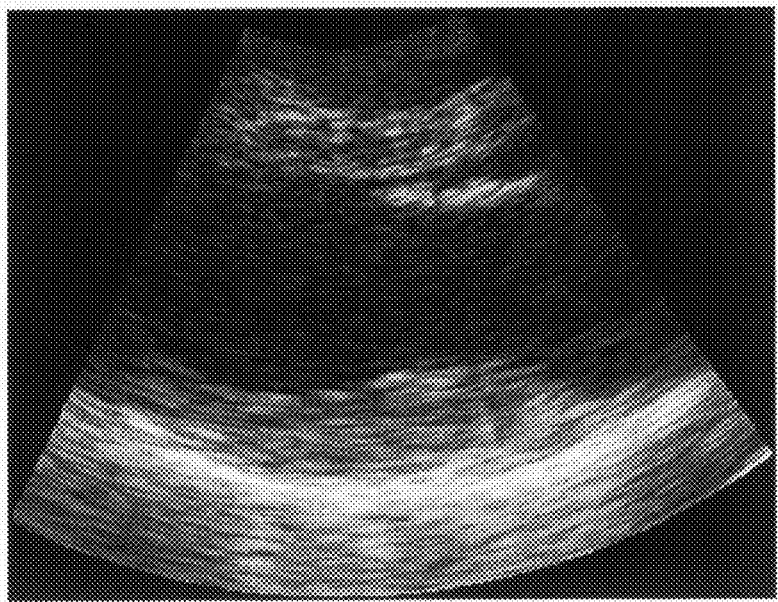
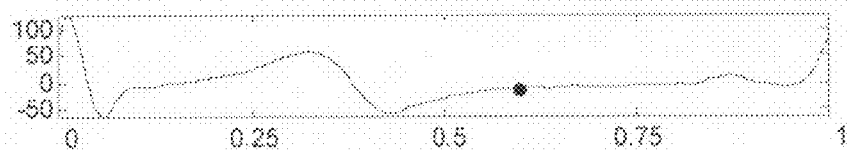
Fig. 23A(e1)
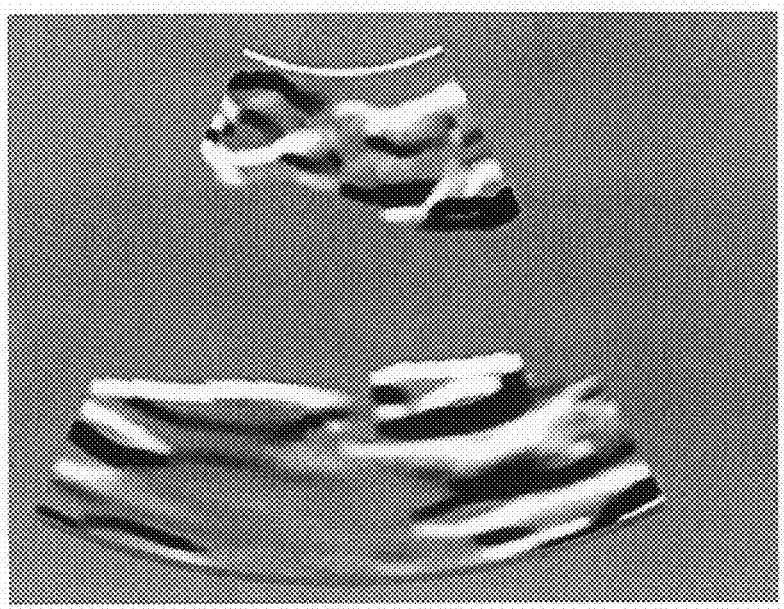
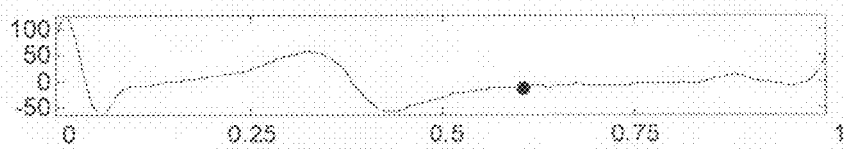
Fig. 23A(e2)

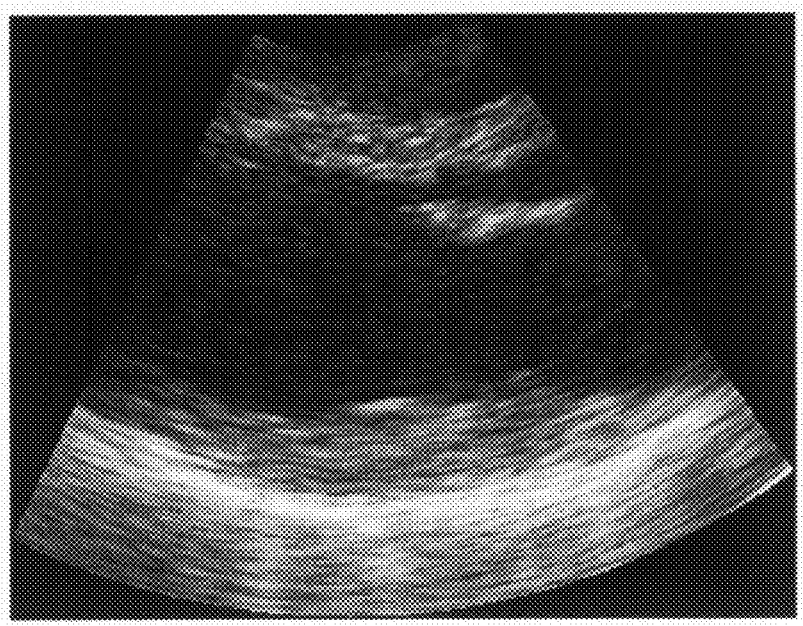
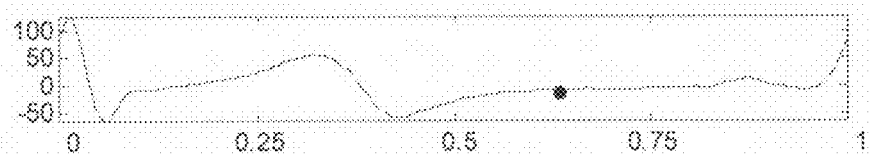
Fig. 23A(f1)
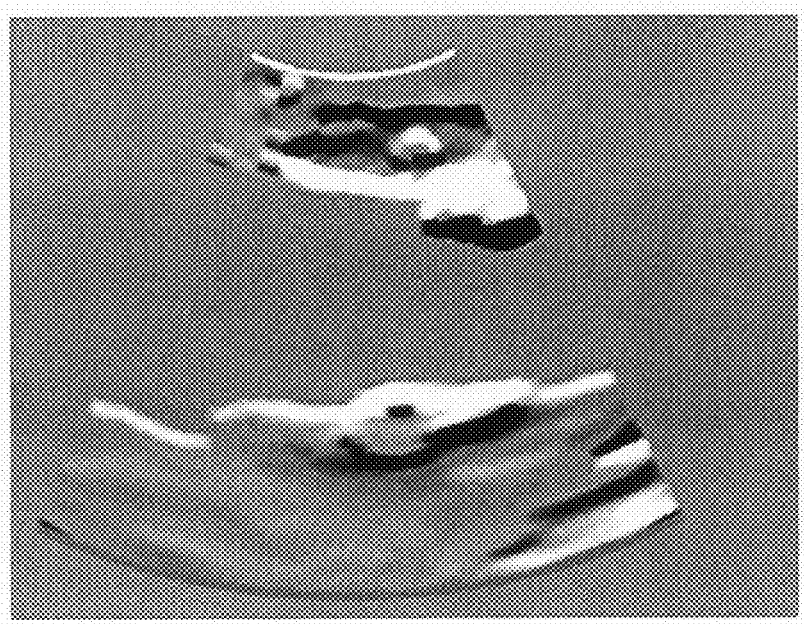
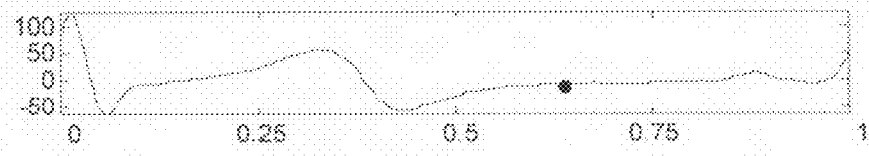
Fig. 23A(f2)

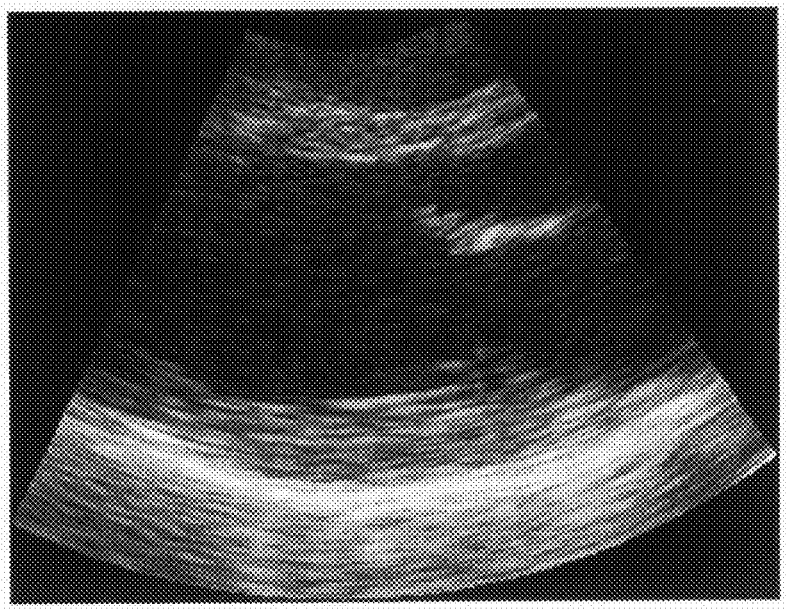
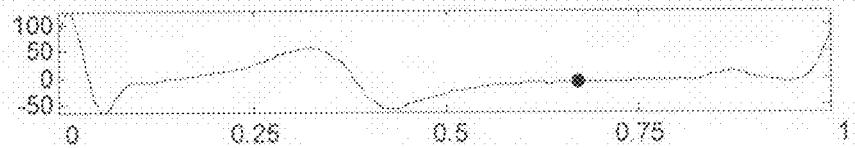
Fig. 23A(g1)
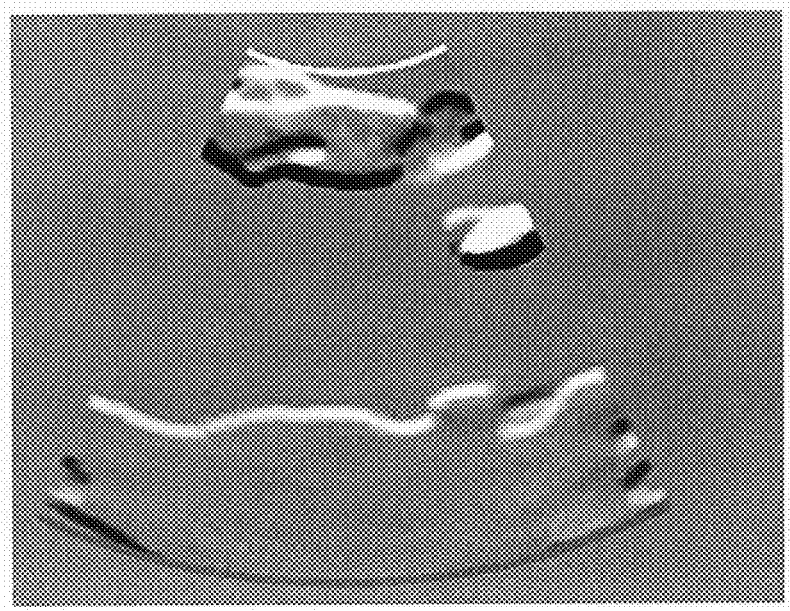
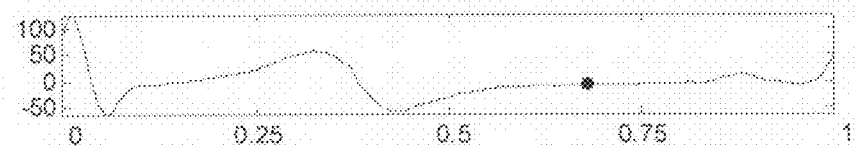
Fig. 23A(g2)

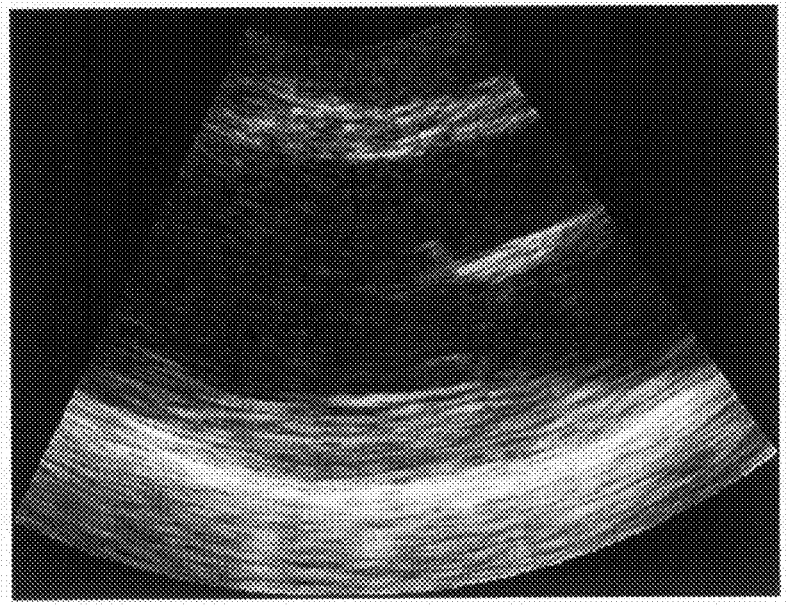
Fig. 23A(h1)
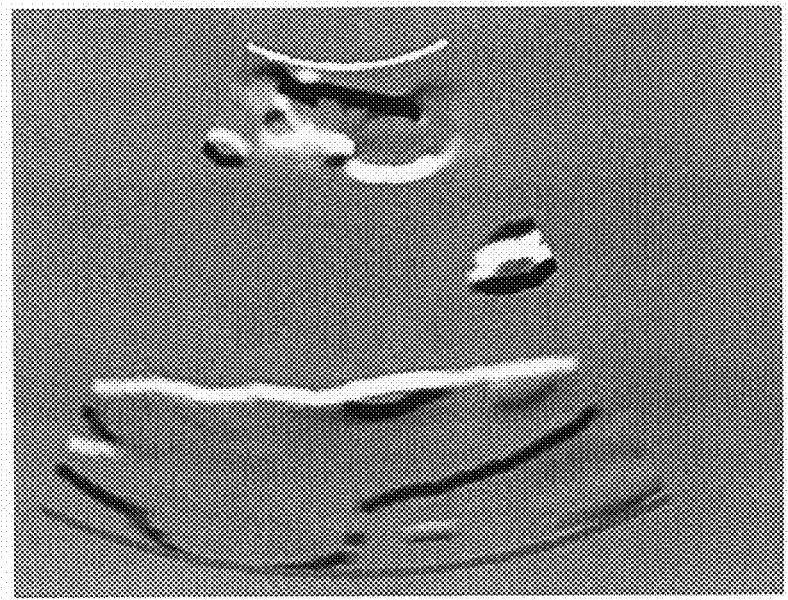
Fig. 23A(h2)

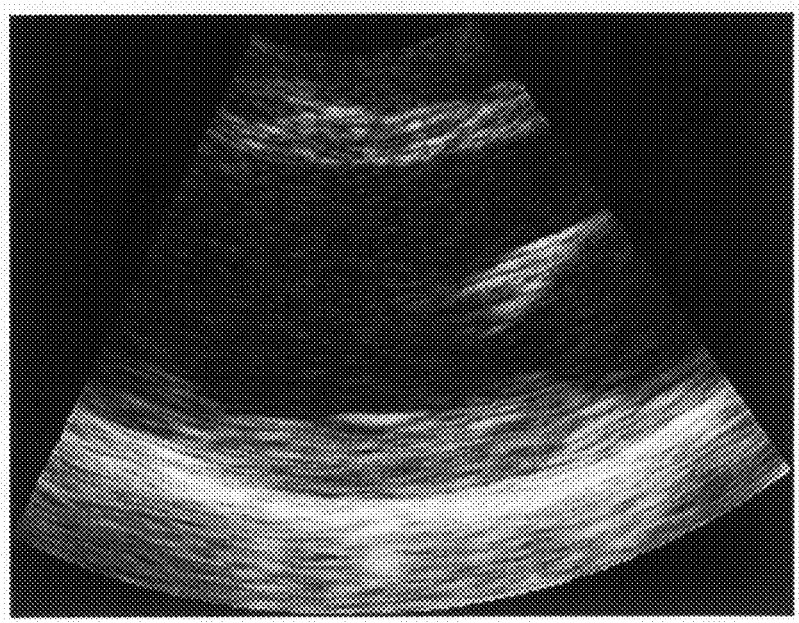
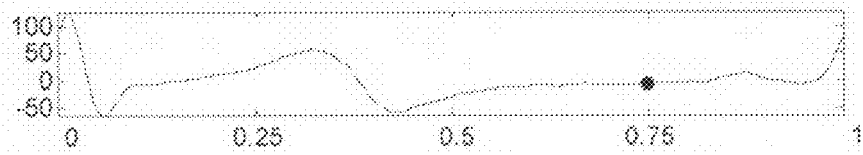
Fig. 23A(i1)
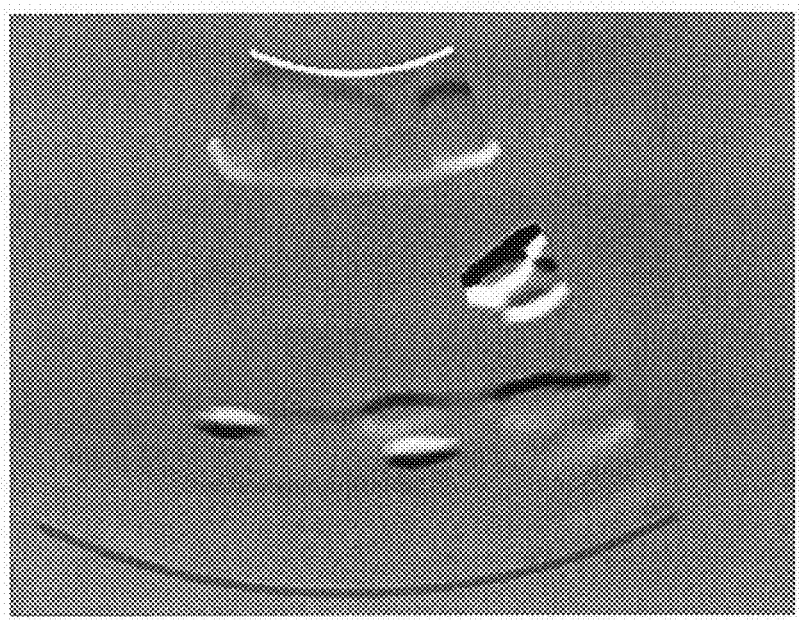
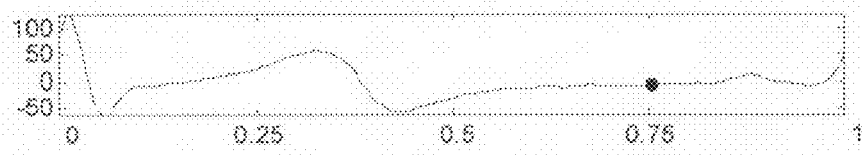
Fig. 23A(i2)

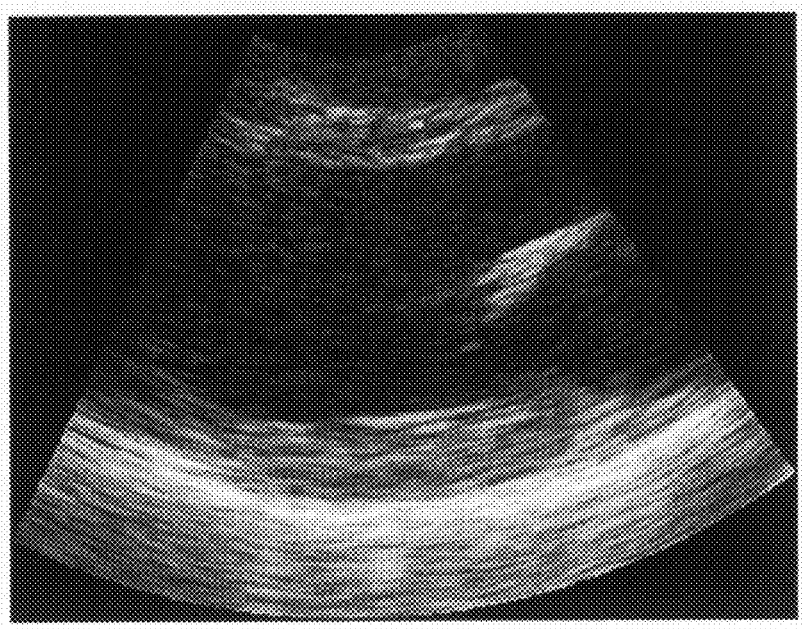
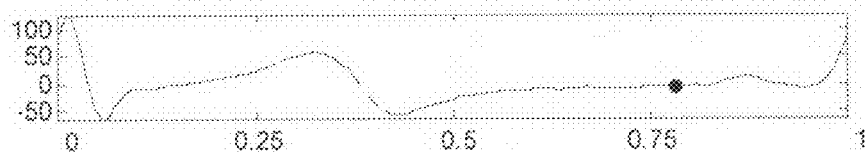
Fig. 23A(j1)
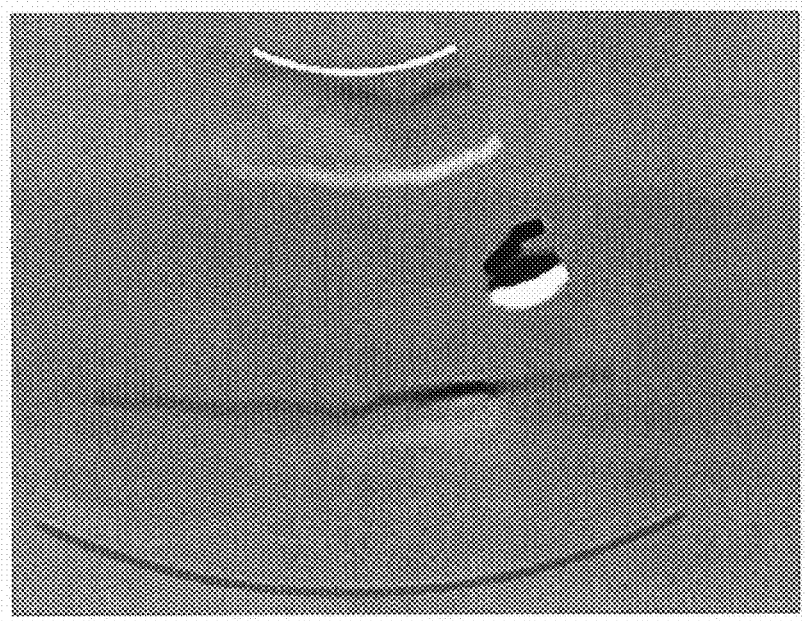
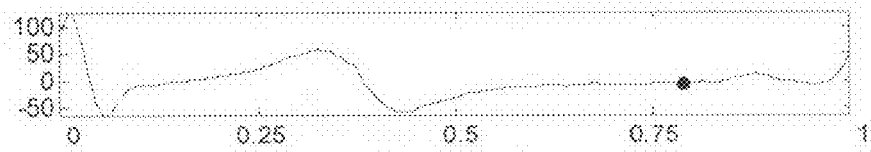
Fig. 23A(j2)

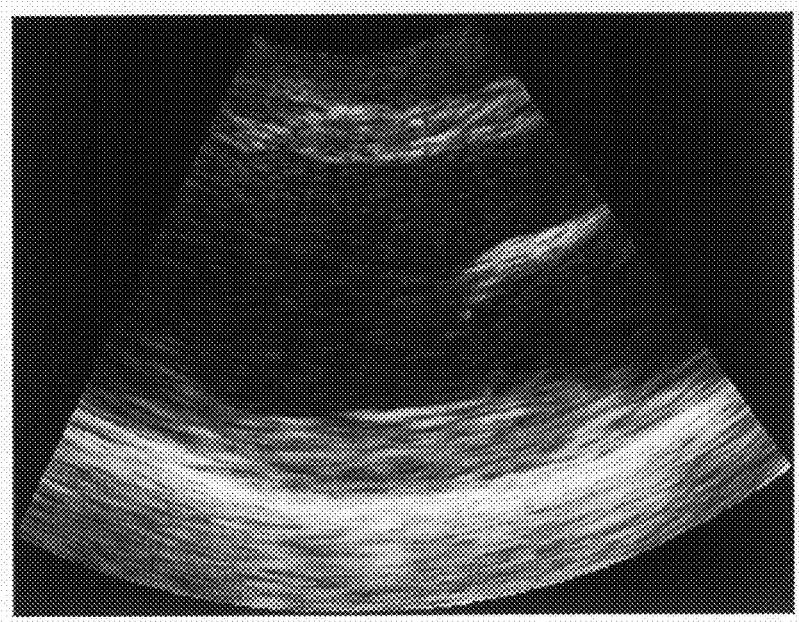
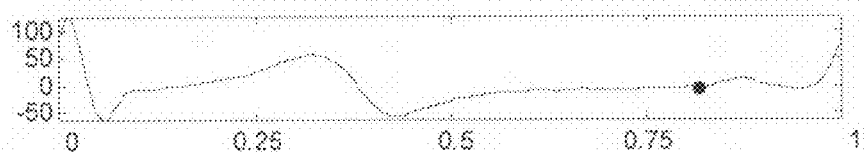
Fig. 23A(k1)
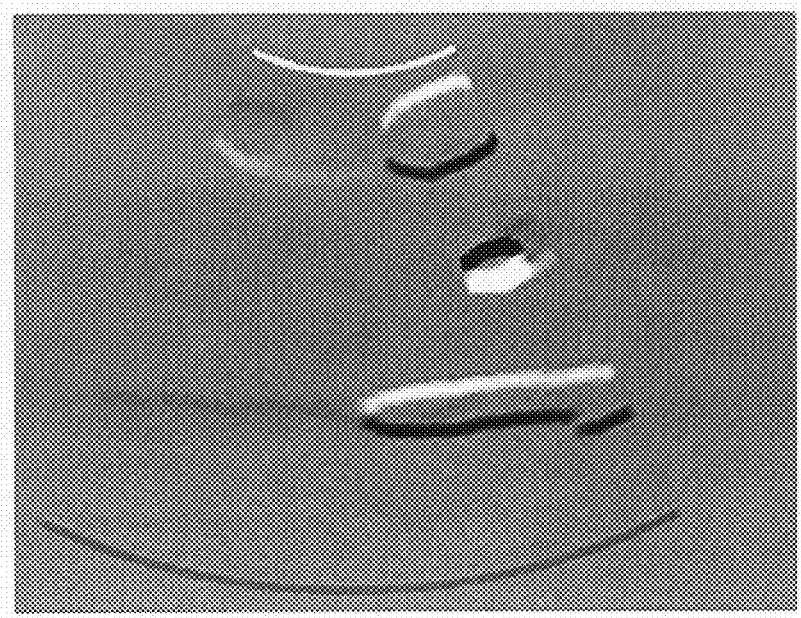
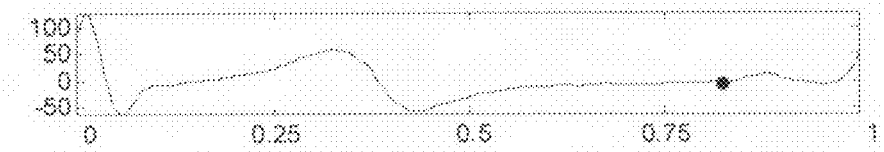
Fig. 23A(k2)

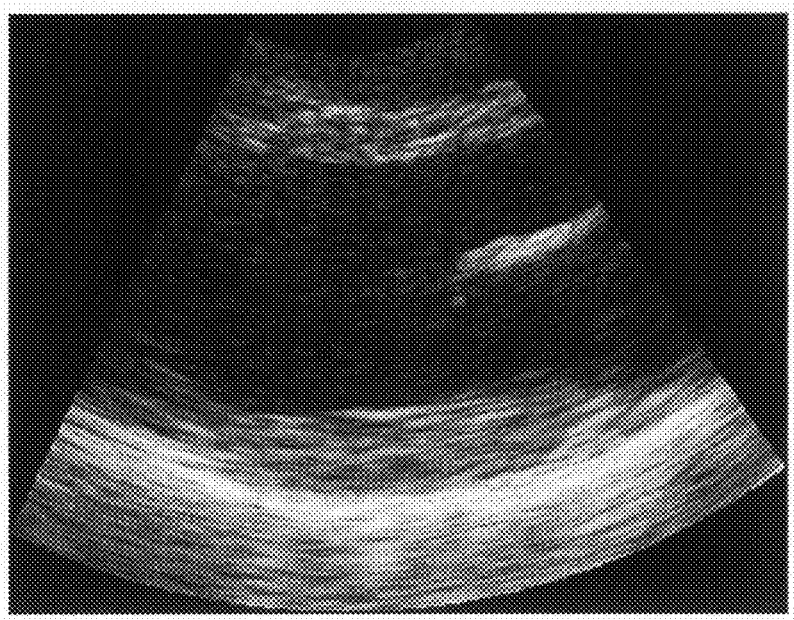
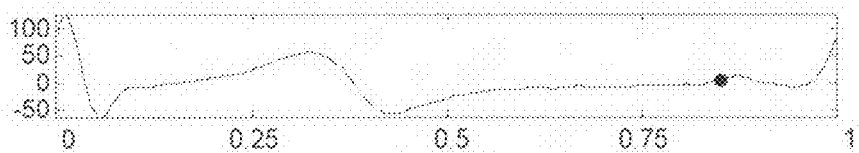
Fig. 23A(I1)
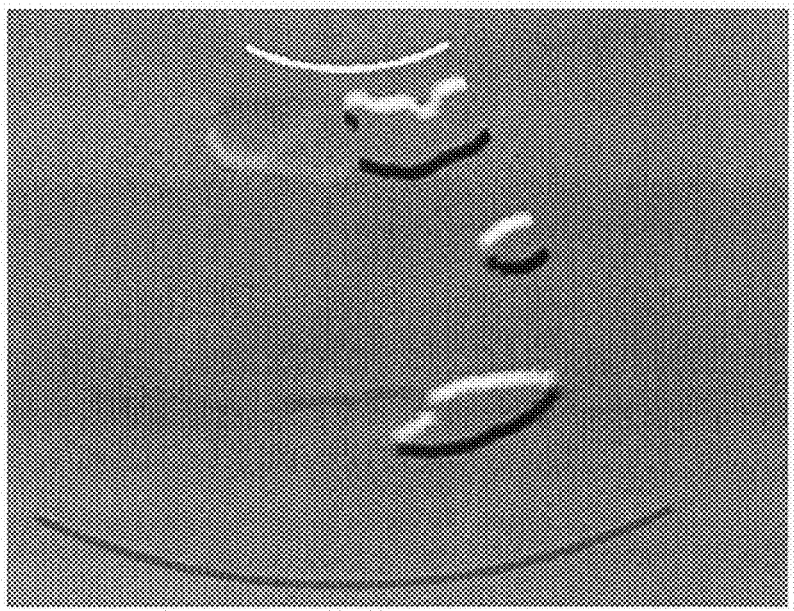
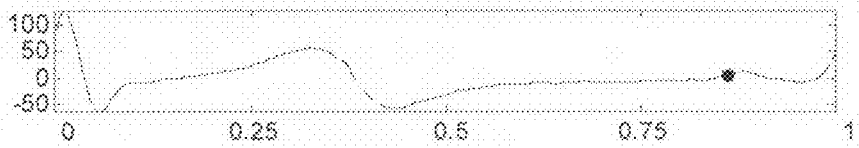
Fig. 23A(I2)

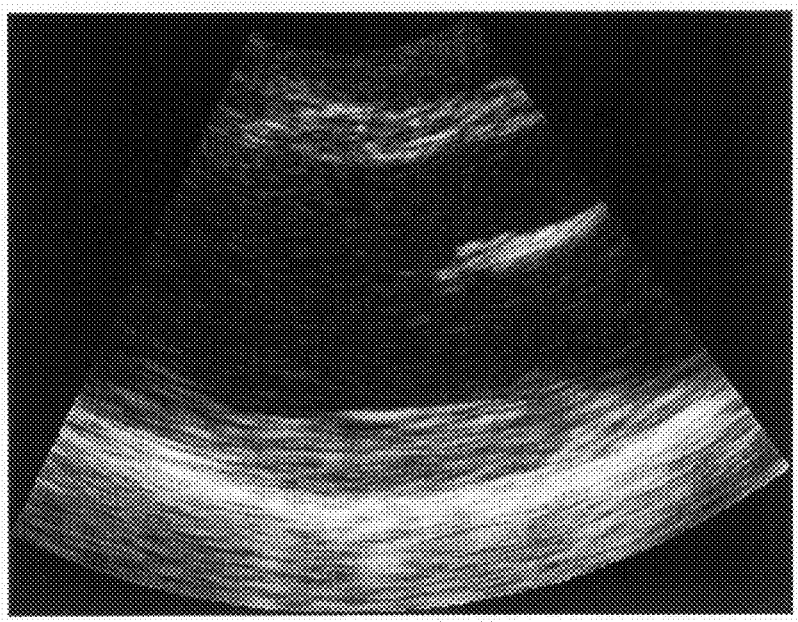
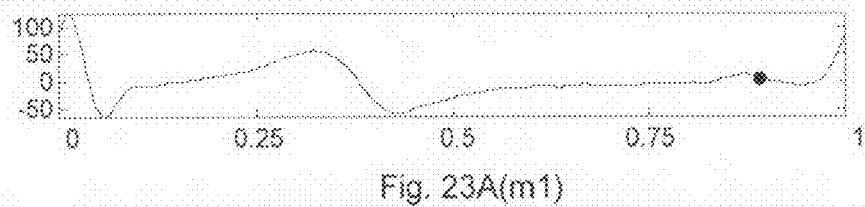
Fig. 23A(m1)
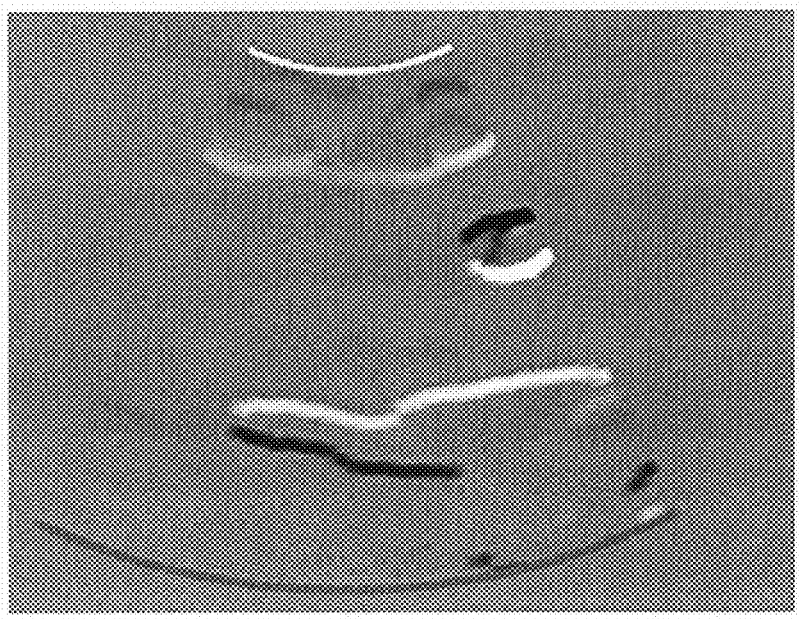
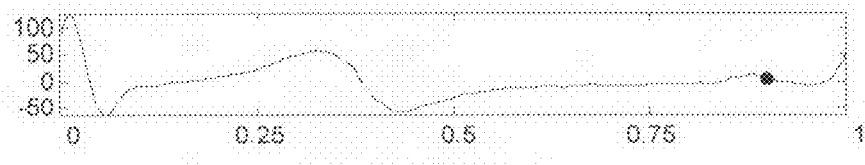
Fig. 23A(m2)

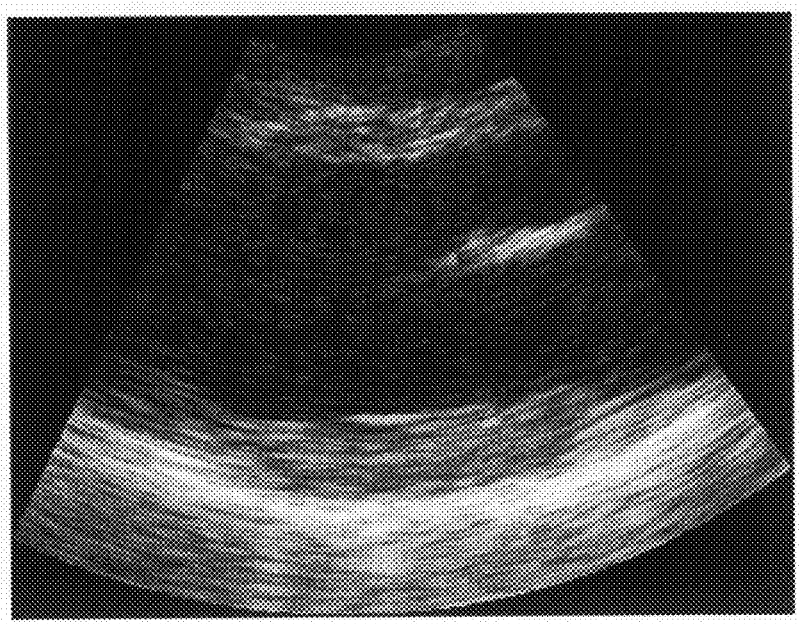
Fig. 23A(n1)
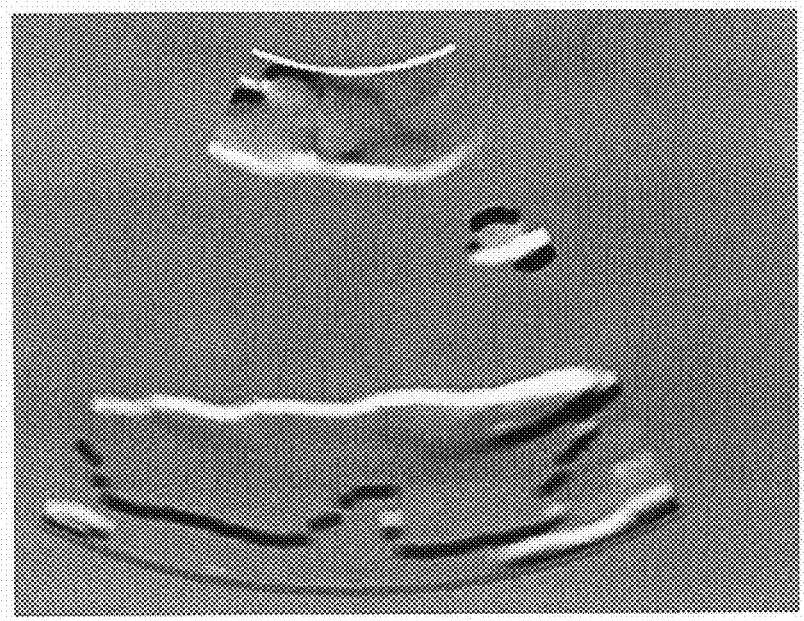
Fig. 23A(n2)

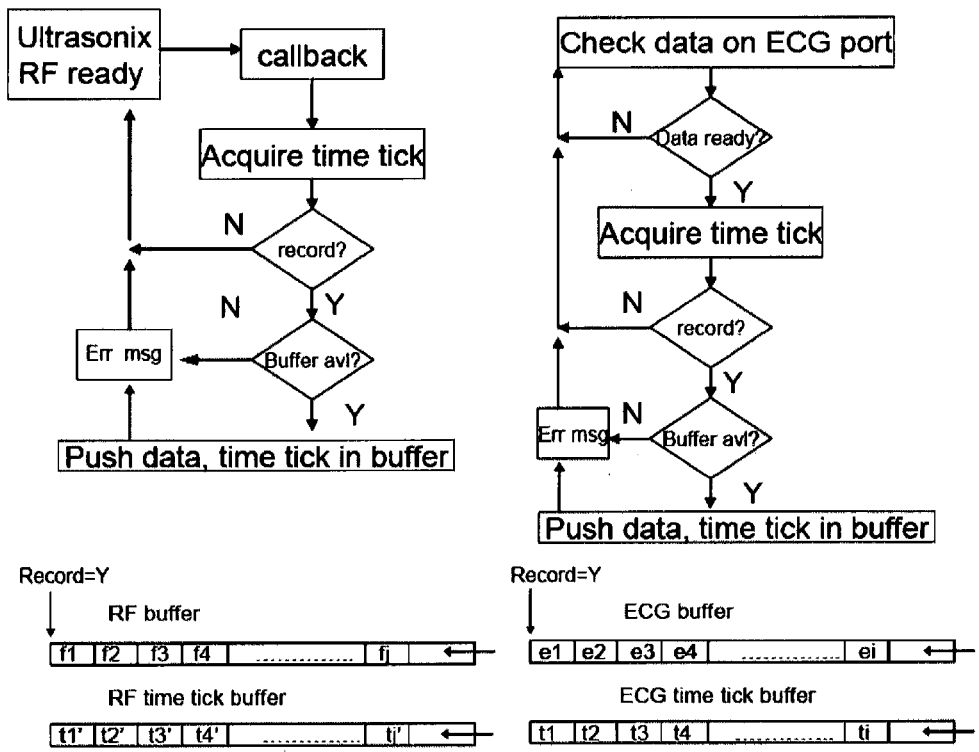
Fig. 24 – Exemplary flow charts for (1) Ultrasonix RF data acquisition; (2) ECG module data acquisition; (3) RF frame and RF frame time stamp buffer; and (4) ECG and ECG time stamp buffer;

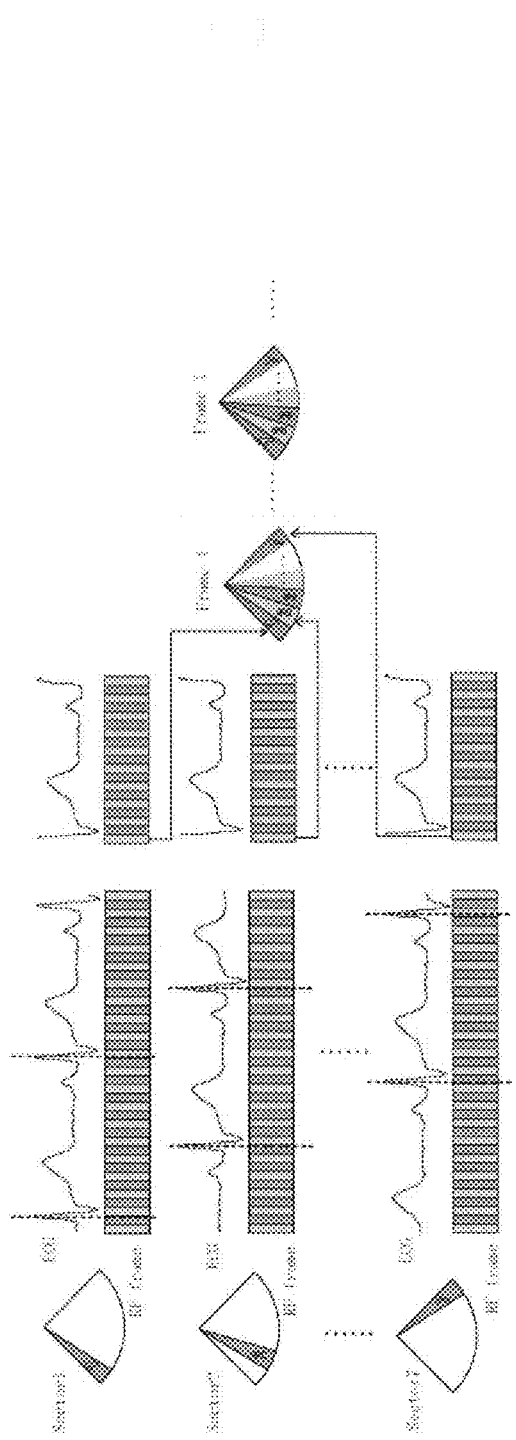

Fig. 25- Illustration of an ECG-gated multi-sector combination technique for high frame rate, full-view ultrasound imaging. A total of seven sectors at different angles are acquired in a continuous sequence during each experiment. ECG and RF frame data are cut according to the time stamp associated with each data point or frame for one cardiac cycle. Corresponding small sector frames are recombined to generate full view ultrasound images

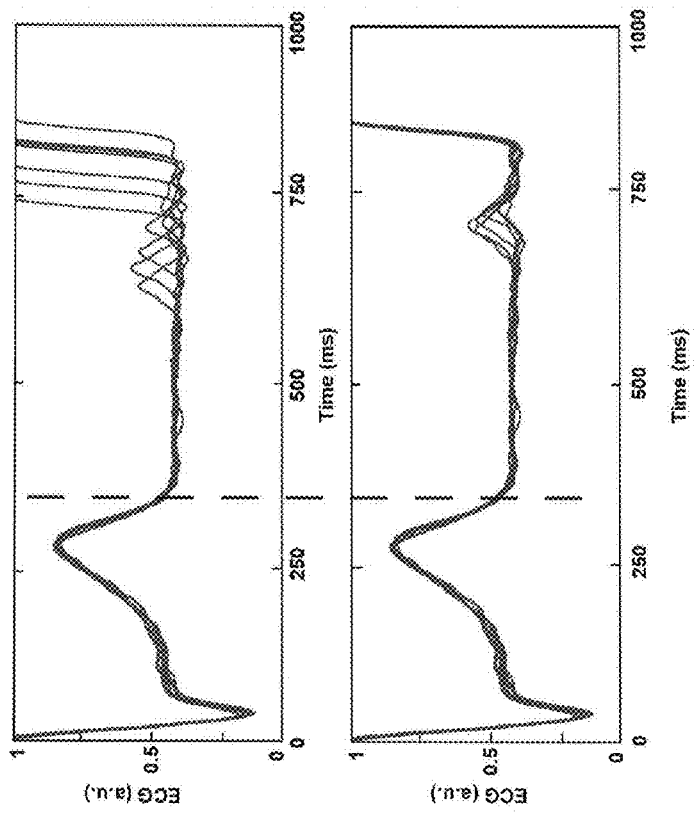

Fig. 26 - Illustration of irregular ECG interpolation. ECGs during systole, approximately $T_{es} = \sqrt{\Delta T}$ 0.343s, remain unchanged where $T_{es}$ is the duration of the systole and $\Delta T$ is the duration of the whole cardiac cycle. All seven ECGs after the slashed line are linearly interpolated to the maximum length of these signals. The corresponding RF frames associated with each ECG are also interpolated to the maximum length of these RF by linearly 2D interpolation.

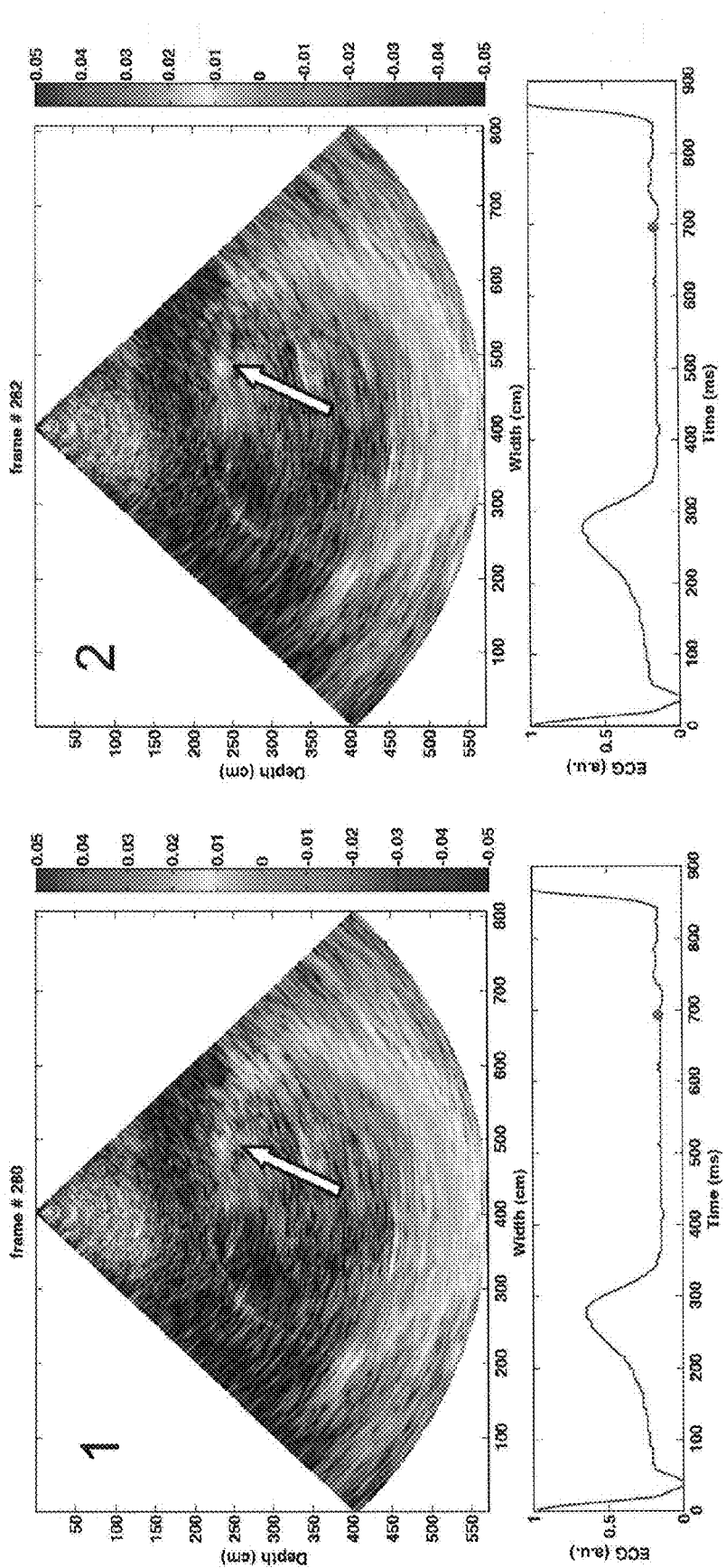
Figs. 29(a) and (b)

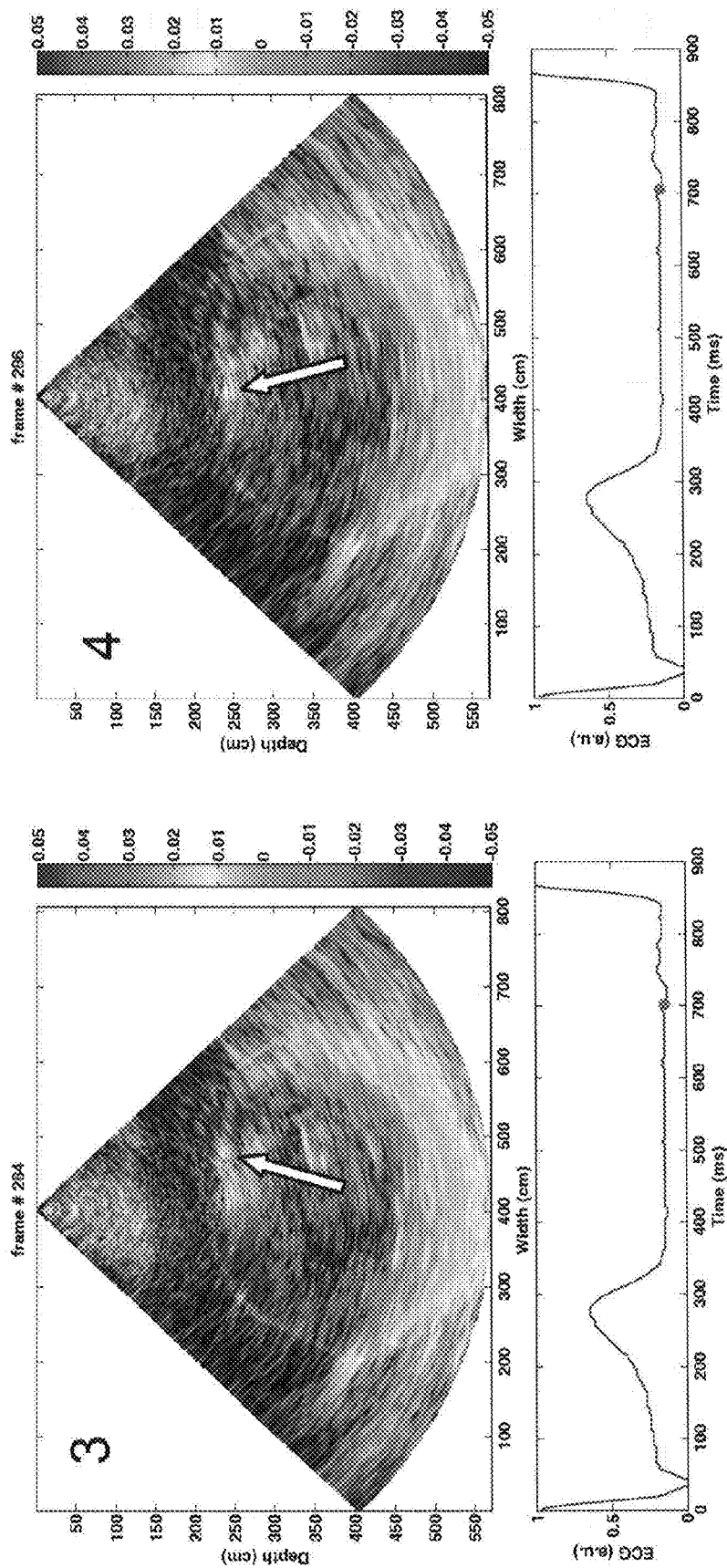
Figs. 29(c) and (d)

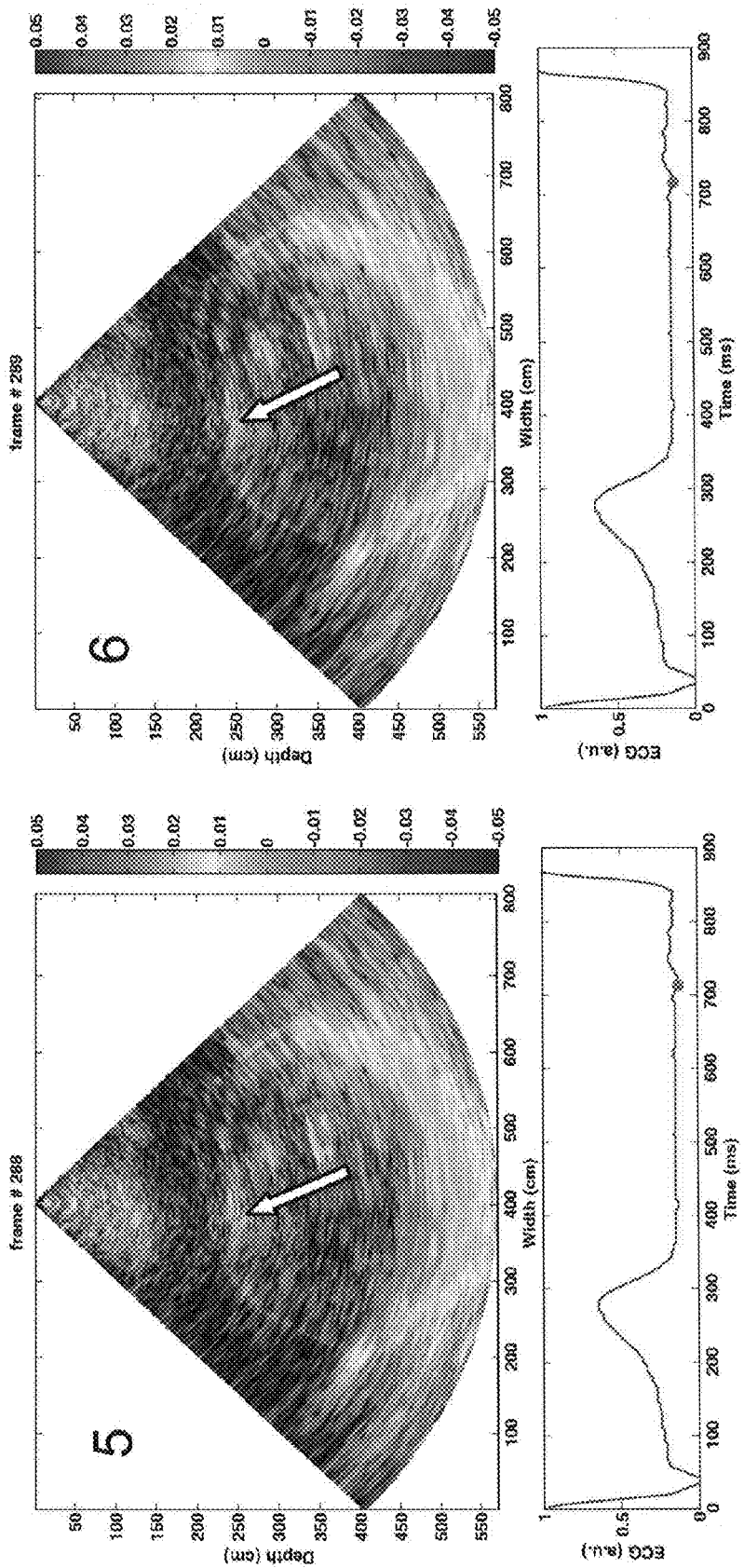
Figs. 29(e) and (f)

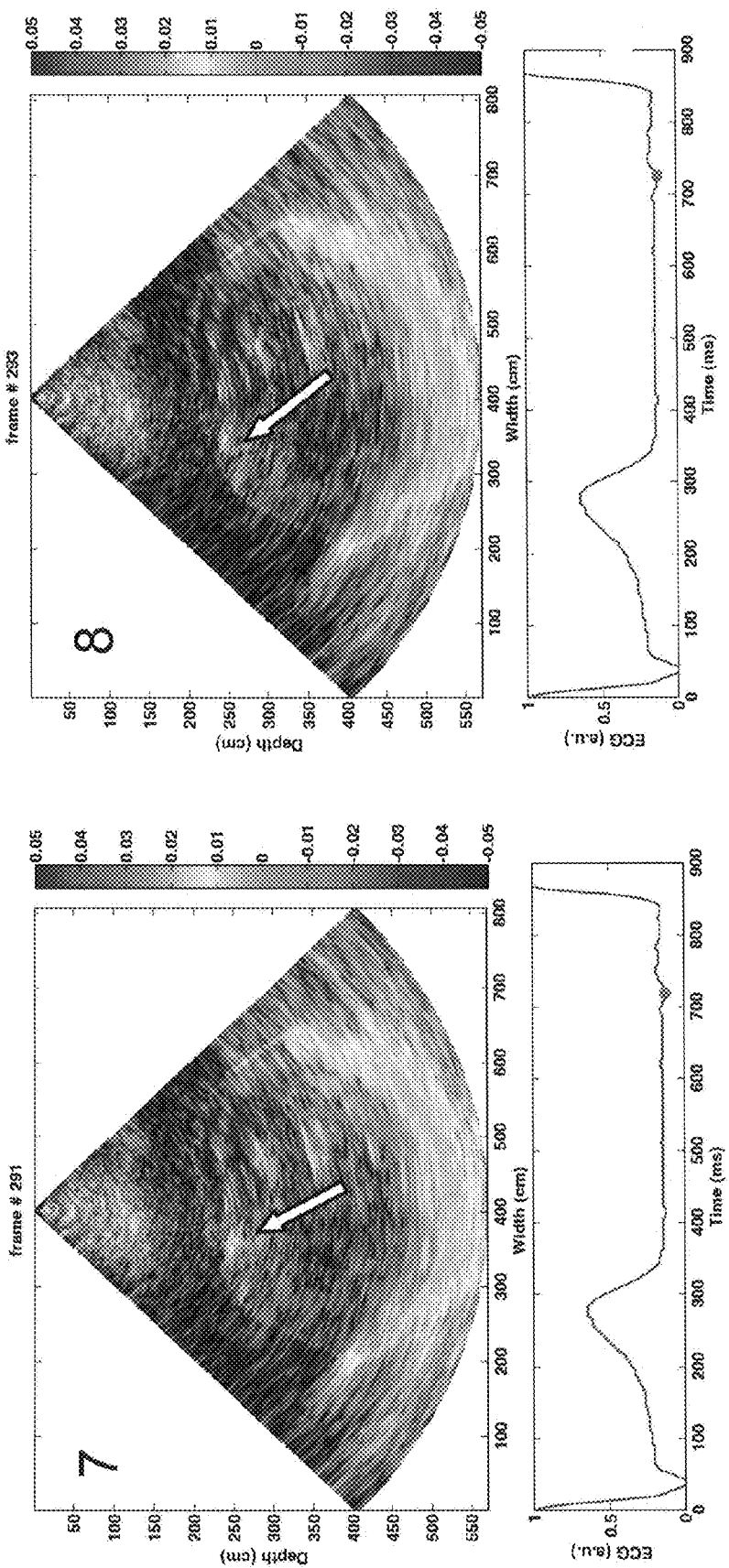
Figs. 29(g) and (h)

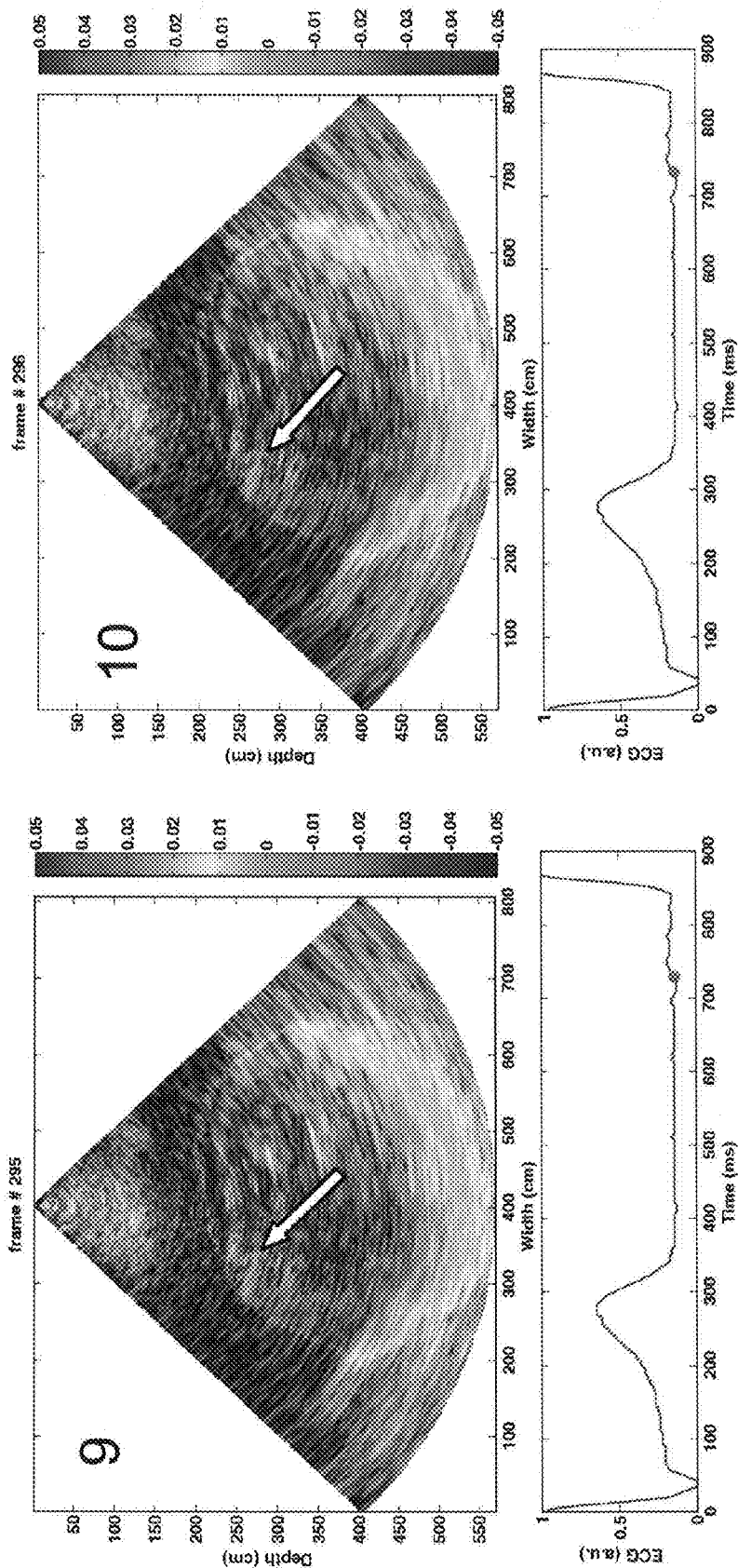
Figs. 29(i) and (j)

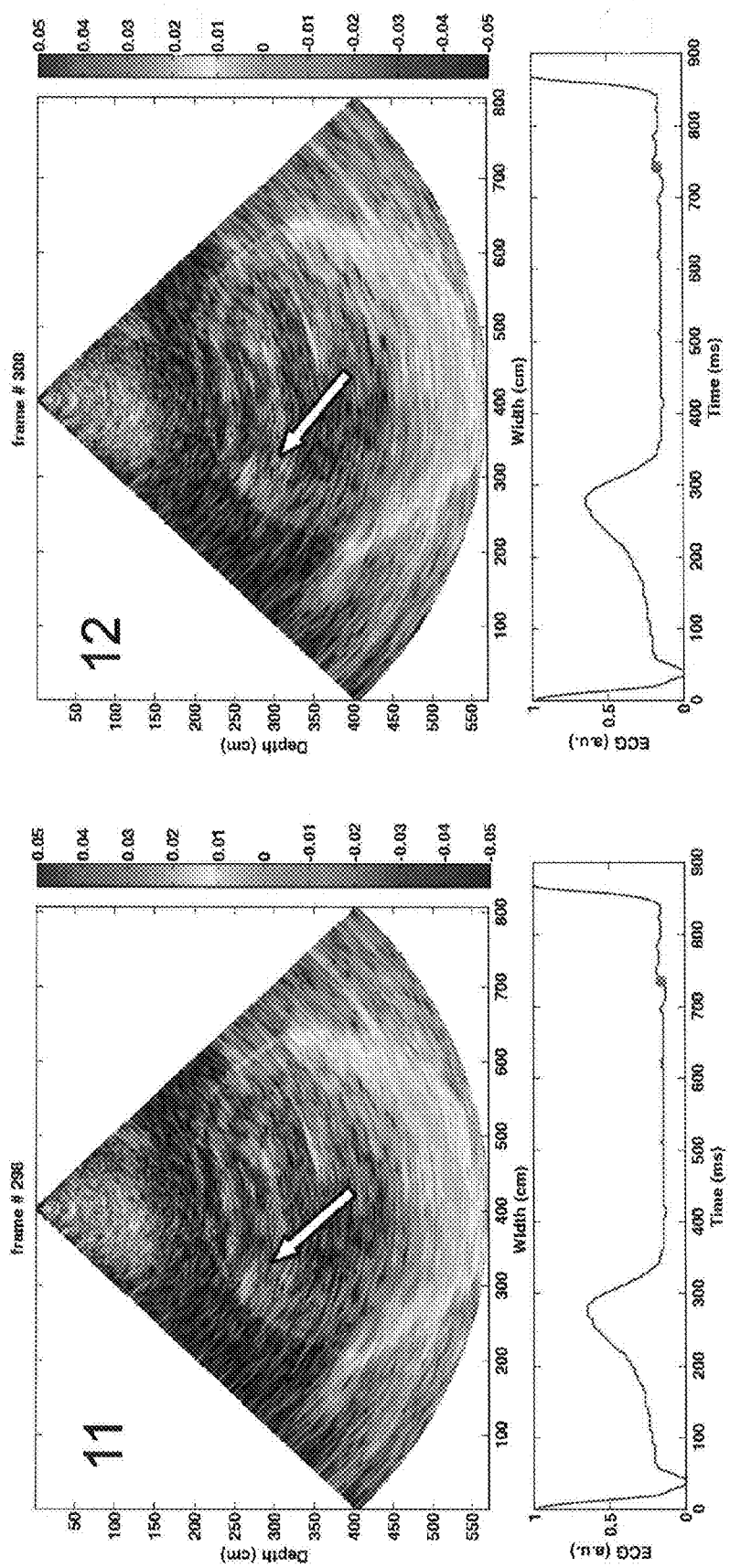
Figs. 29(k) and (l)

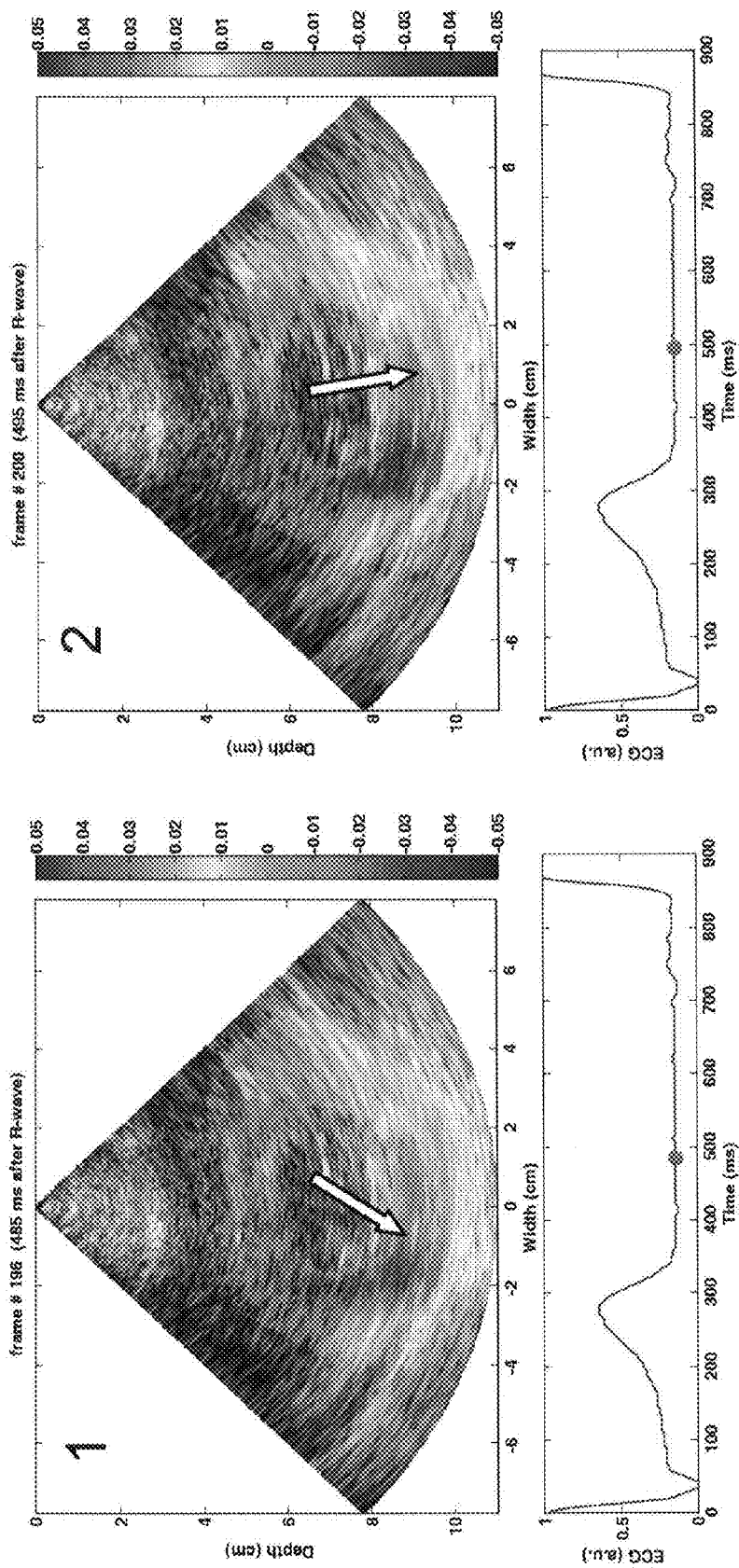
Figs. 30(a) and (b)

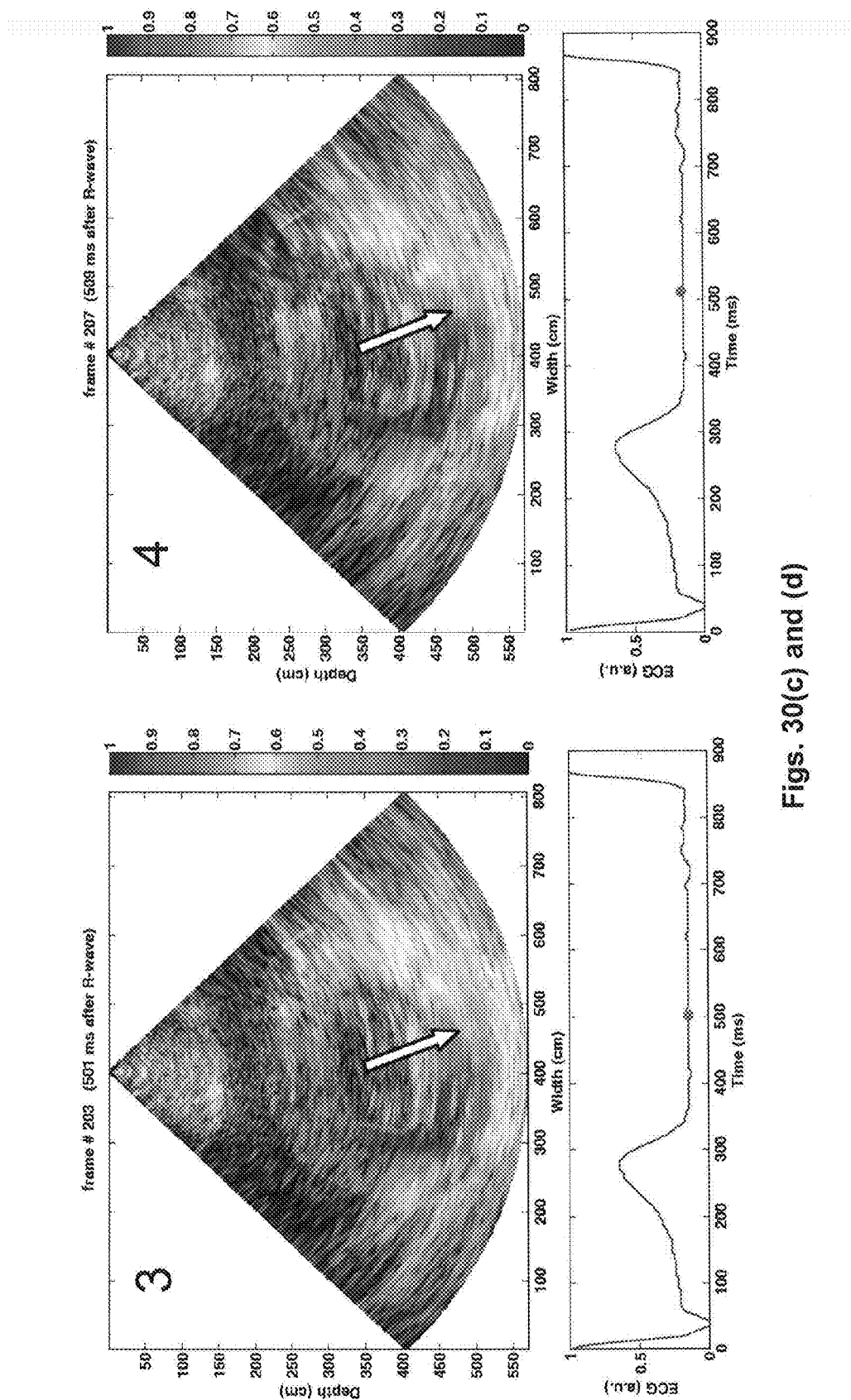
Figs. 30(c) and (d)

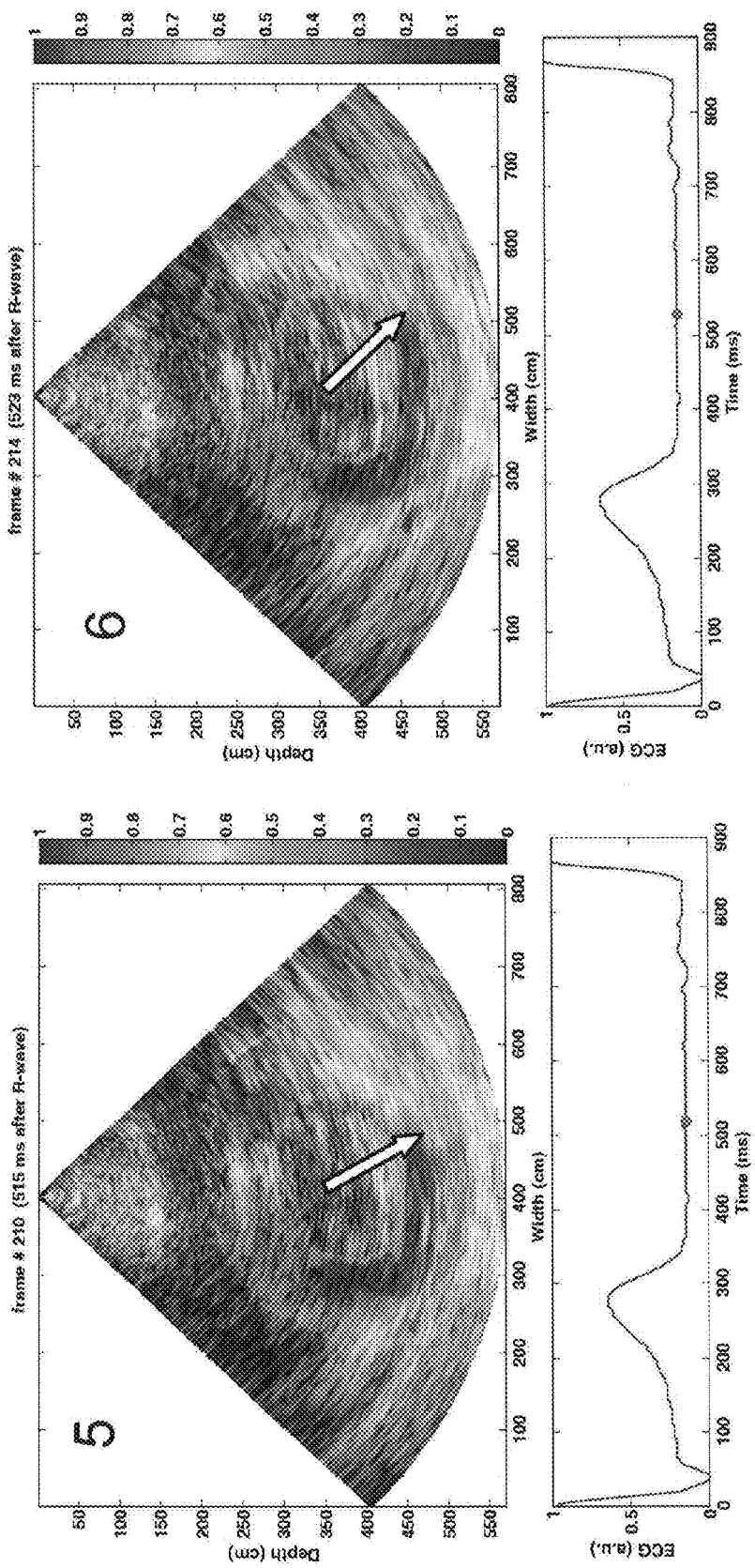
Figs. 30(e) and (f)

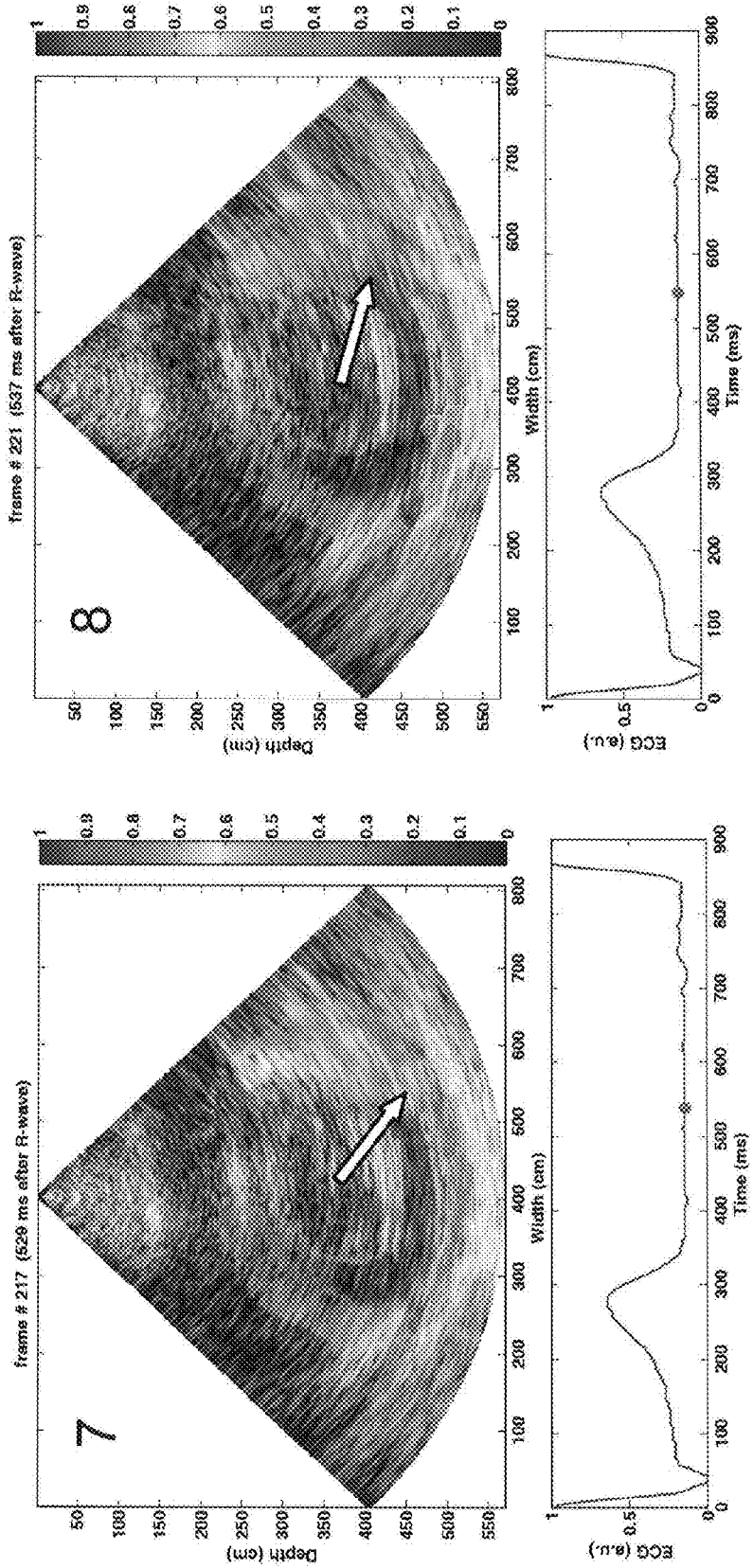
Figs. 30(g) and (h)

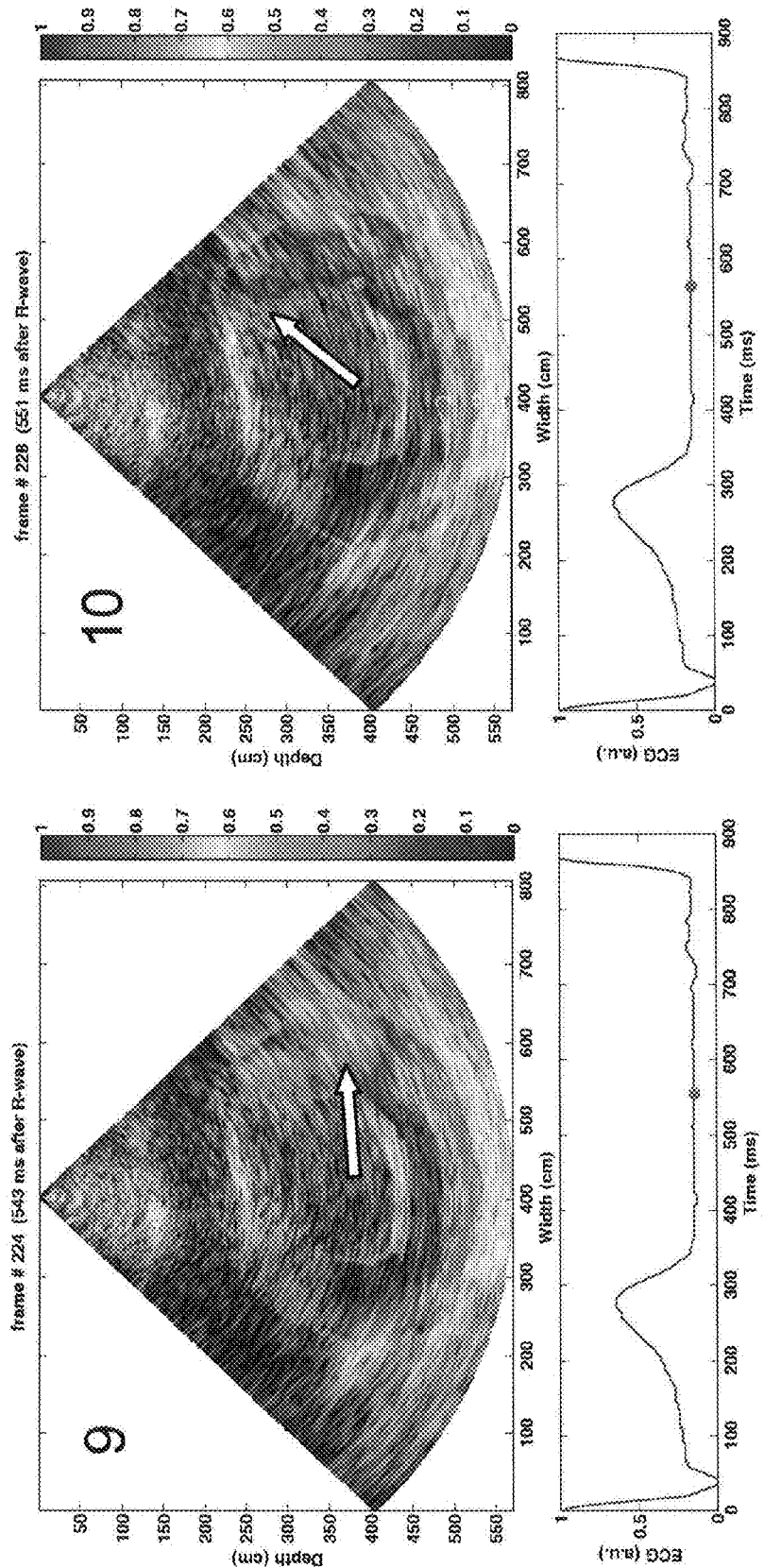
Figs. 30(i) and (j)

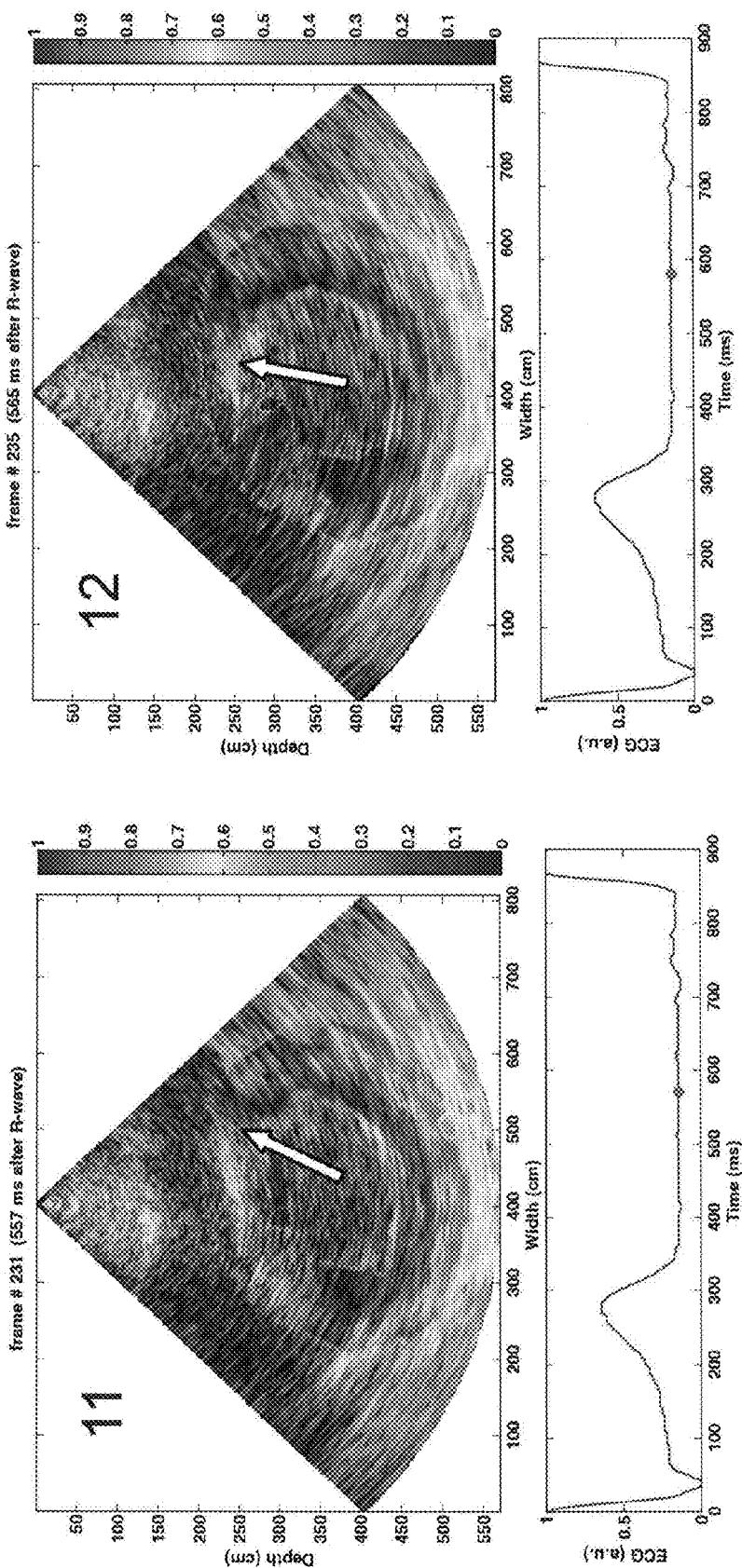
Figs. 30(k) and (l)

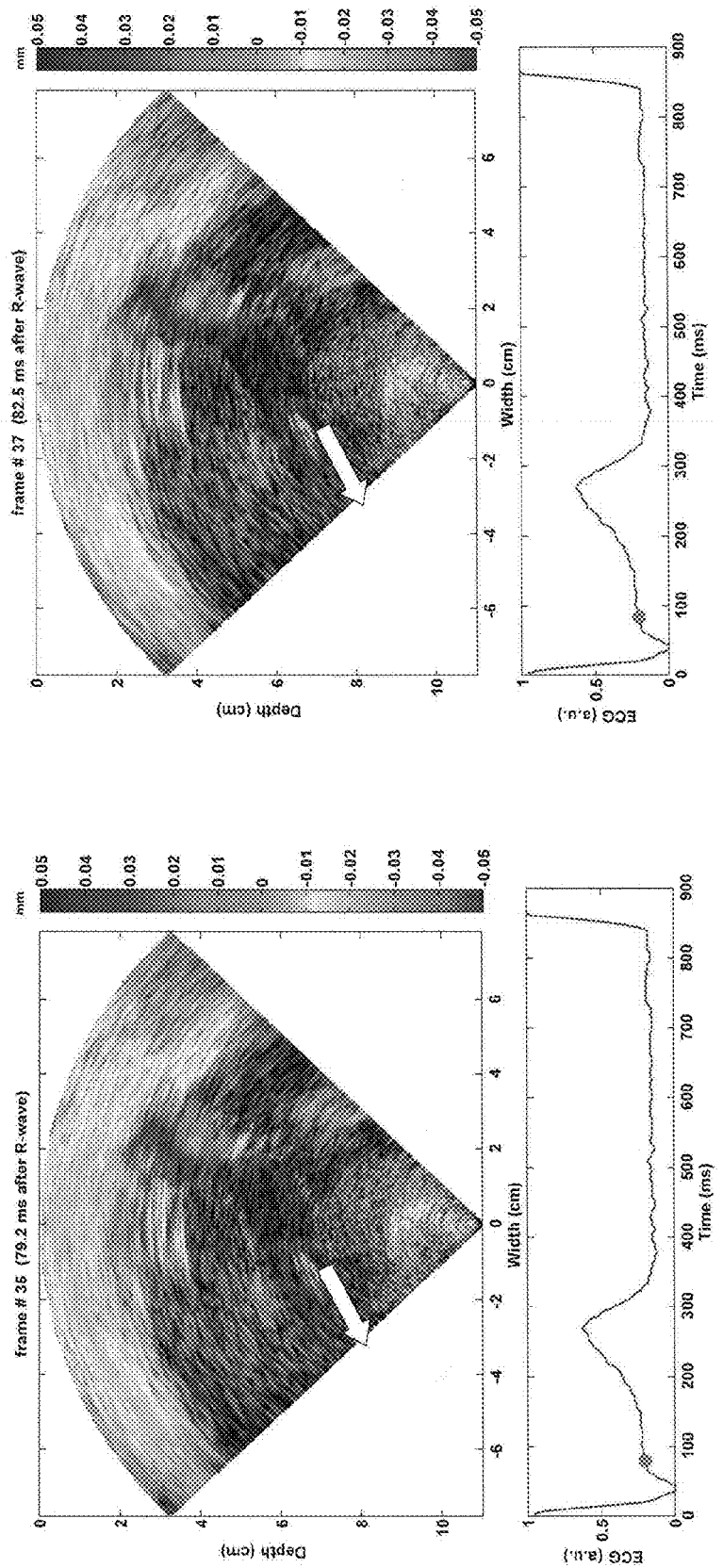
Fig. 31(a) and (b)

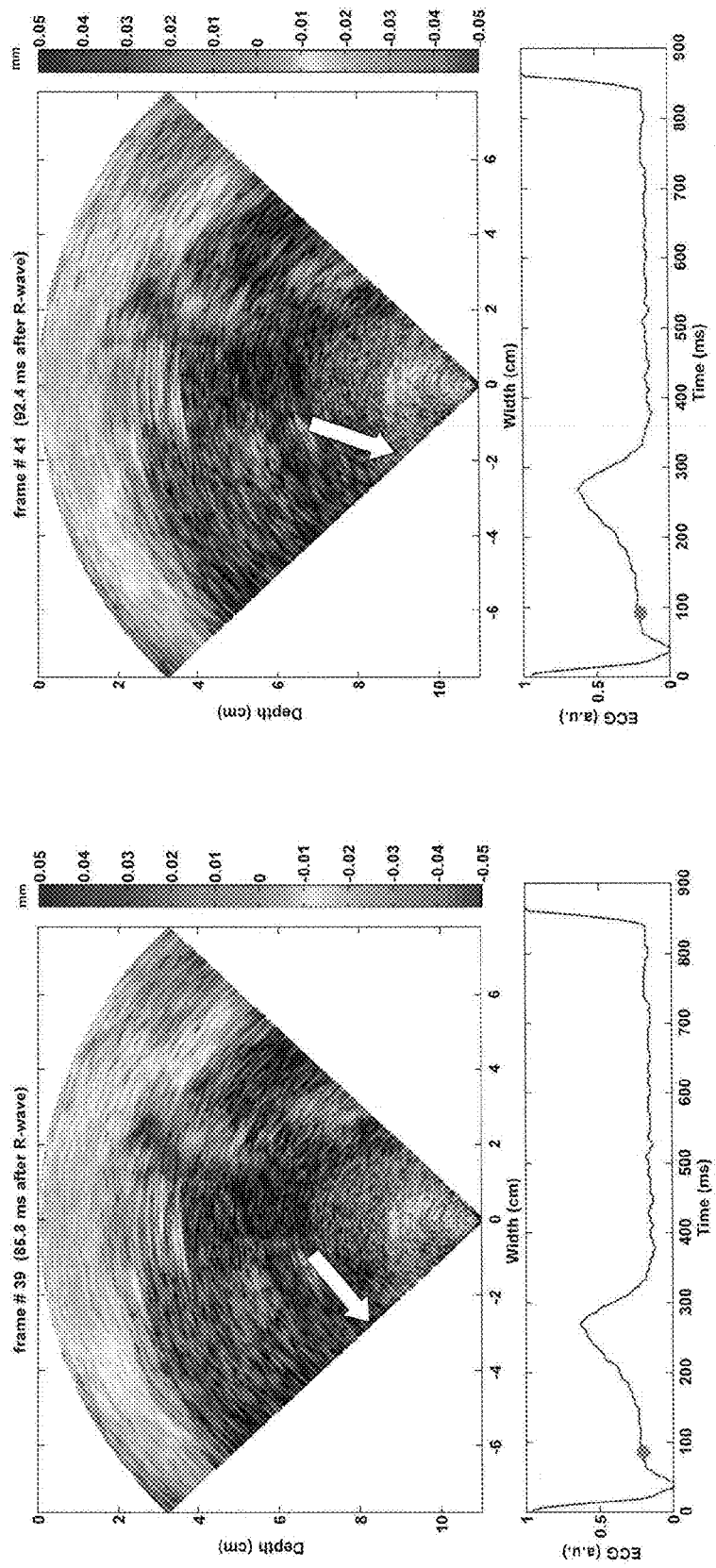
Fig. 31(c) and (d)

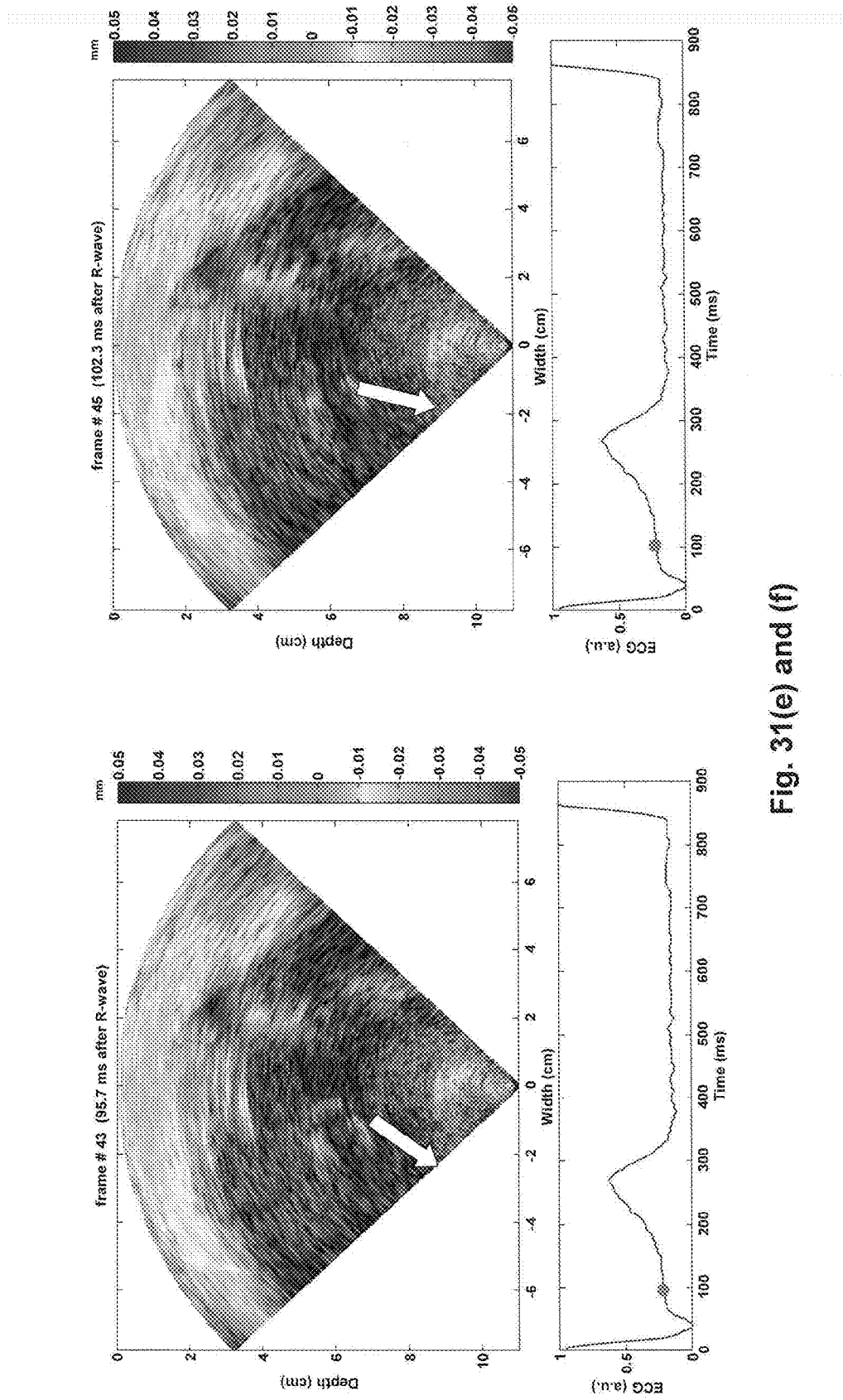
Fig. 31(e) and (f)

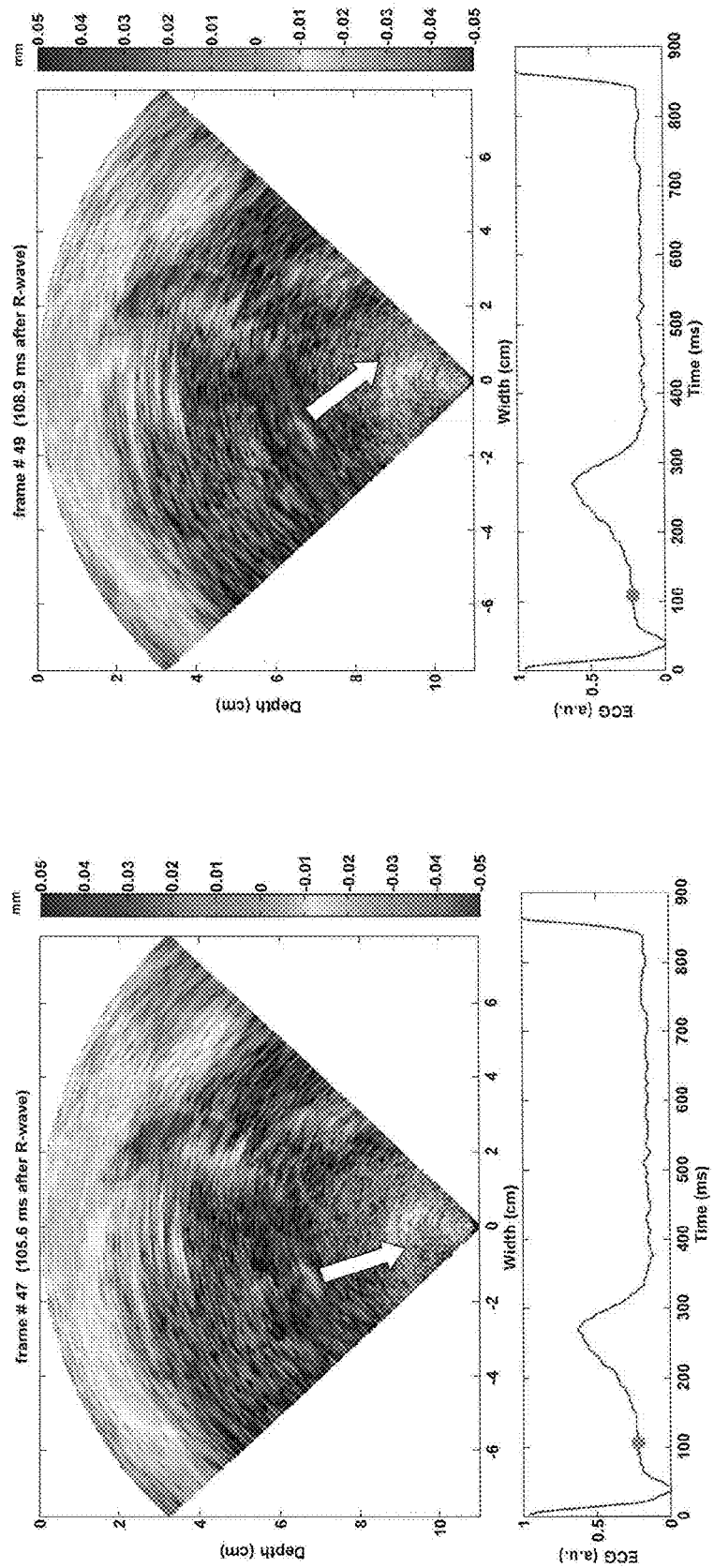
Fig. 31(g) and (h)

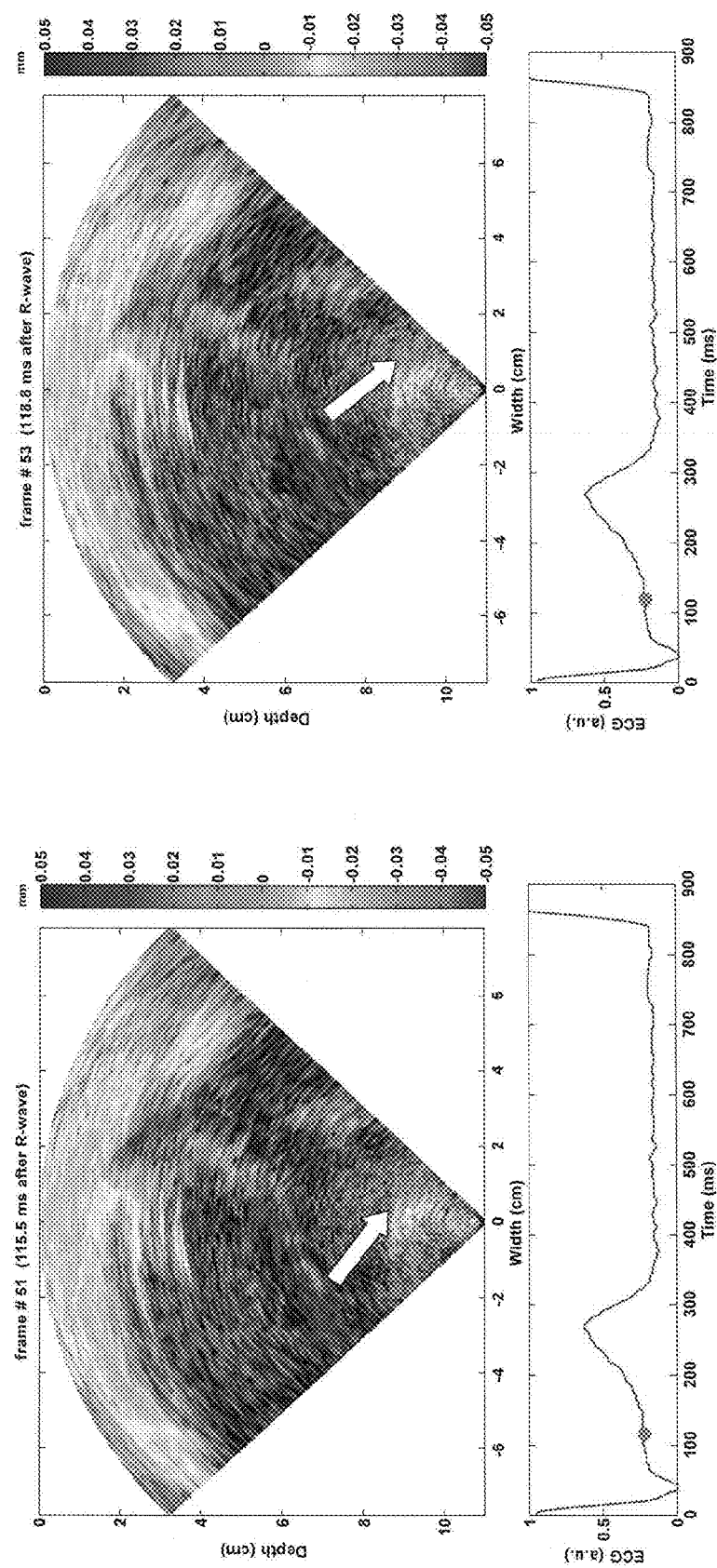
Fig. 31(i) and (j)

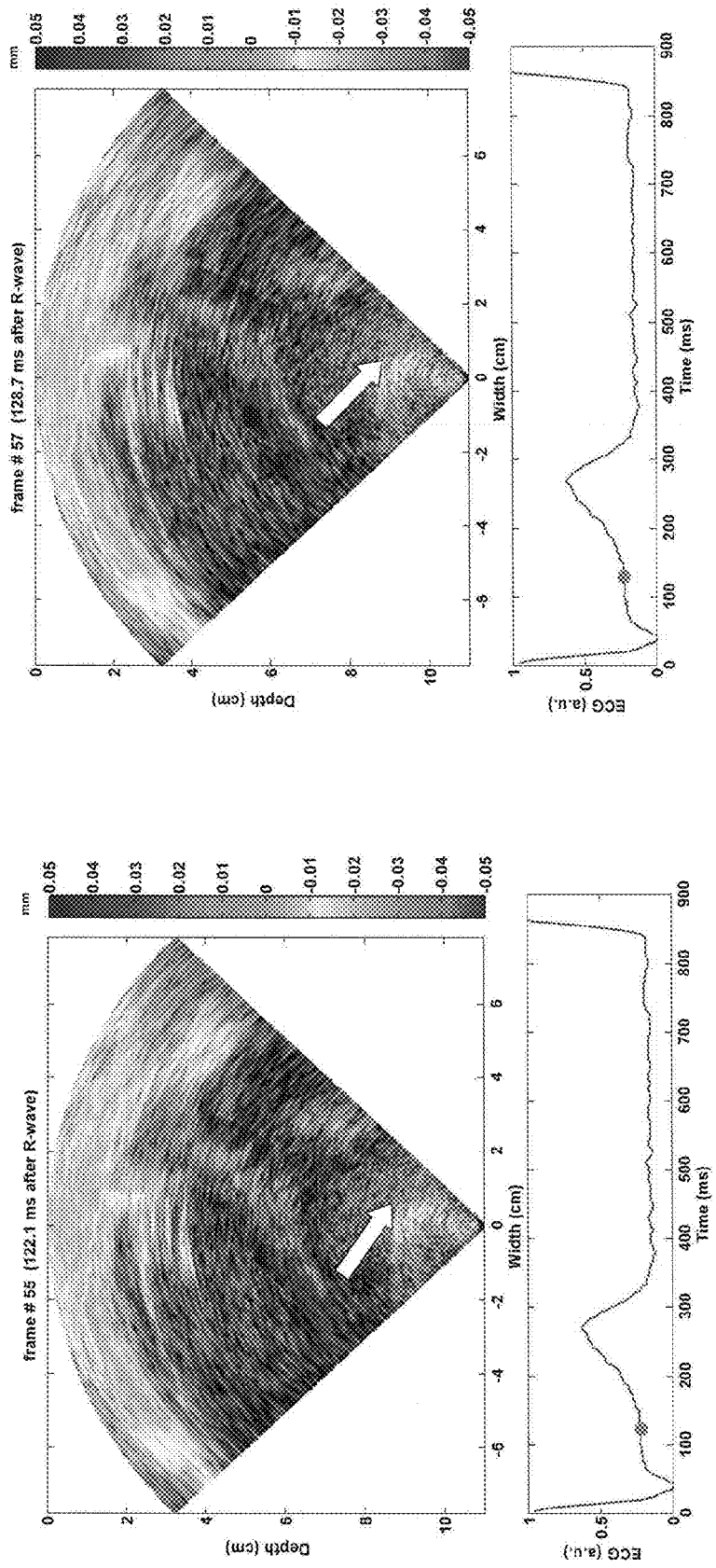
Fig. 31(k) and (l)

SYSTEMS AND METHOD FOR COMPOSITE ELASTOGRAPHY AND WAVE IMAGING

CROSS REFERENCE TO OTHER APPLICATIONS

This application claims the benefit of U.S. Provisional Patent Application No. 60/841,926 entitled "SYSTEMS AND METHODS FOR COMPOSITE MYOCARDIAL ELASTOGRAPHY", filed on Aug. 30, 2006, the disclosure of which is hereby incorporated herein by this reference.

INCORPORATION-BY-REFERENCE OF A COMPUTER PROGRAM LISTING APPENDIX

A computer program listing appendix is included pursuant to 37 C.F.R. 1.52(c) and is hereby incorporated by reference in its entirety. The computer program listing appendix was submitted via EFS on Sep. 23, 2011. The computer program listing appendix includes the following 14 files: a table of contents, submitted as the ASCII text file toc.txt, is 242 bytes; analyzeNrf.m, submitted as the ASCII text file analyzeNrf_m.txt, is 8,762 bytes; cutECG.m, submitted as the ASCII text file cutECG_m.txt, is 1,634 bytes; findSectorOverlap_m, submitted as the ASCII text file findSectorOverlap_m.txt, is 3,714 bytes; matchbestECG.m, submitted as the ASCII text file matchbestECG_m.txt, is 4,770 bytes; data2rgb.m, submitted as the ASCII text file data2rgb_m.txt, is 689 bytes; initOverlay.m, submitted as the ASCII text file initOverlay_m.txt, is 1,967 bytes; overlayData.m, submitted as the ASCII text file overlayData_m.txt, is 4,141 bytes; overlayimage.m, submitted as the ASCII text file overlayimage_m.txt, is 662 bytes; tiss2rgb.m, submitted as the ASCII text file tiss2rgb_m.txt, is 135 bytes; makeCardiacMovie.mat, submitted as the ASCII text file makeCardiacMovie_mat.txt, is 5,588 bytes; getPolTransformMap.m, submitted as the ASCII text file getPolTransformMap_m.txt, is 3,144 bytes; appPolTransform.m, submitted as the ASCII text file appPolTransform_m.txt, is 1,803 bytes; getmyparams.m, submitted as the ASCII text file getmyparams_m.txt, is 419 bytes. Each file included in the computer program listing appendix described above was created on Sep. 23, 2011. The computer program listing appendix does not include any new matter which goes beyond the disclosure of the application as filed.

GOVERNMENT SUPPORT INFORMATION

This invention was made with United States government support under Grant/Contract No. R01 EB006042-01 awarded by the National Institutes of Health. The United States government has certain rights in the invention.

TECHNICAL FIELD

The present invention relates to medical imaging, and in particular to increasing the frame rate of ultrasound imaging by dividing the field of view into sectors, obtaining a series of ultrasound images for each sector, synchronizing the images and combining them to form a composite high-frame rate image.

BACKGROUND

Ultrasound imaging can be a useful tool in cardiology, such as, for example, in the diagnosis of myocardial infarctions. Ultrasound imaging of the heart, known as echocardiography, can be used, for example, to derive strains, which are related to the contractility of the heart muscle. However, current methods of real-time raw data acquisition of a full view of the heart limit the data acquisition rate to 50 frames per second (fps). It is noted that a "full view" is actually the default size of an image plane in a given system, which can be defined by a spanned angle (i.e., arc length according to the center of an imaging probe) and a chosen depth (beam direction). Tracking rapid motion of the heart in a short period or depicting the high-speed electro-mechanical wave propagating in the heart at frame rates of 50 fps is difficult. Moreover, because strains involve motion of the heart muscle, a frame rate (effectively a sampling rate of the displacement function over time) is required to be high enough such that interframe motion is relatively small to be accurately estimated. Using conventional frame rates, strain image results tend to be both noisy and unreliable This is because the lower the frame rate, the less correlated any two consecutive frames are, which makes radio-frequency (RF)-cross-correlation based motion estimation techniques less accurate. One quantitative measure of the noise on strain images is the elastographic signal-to-noise ratio, or SNRe.

With the high frame-rate composite imaging, precise and detailed motion/strain estimates in full view can be obtained and further used to differentiate abnormal from the normal myocardium and even detect the onset and extent of the diseased muscle. From theoretical and in vivo examples, the difference between strain in a normal and an abnormal myocardium can be large in the case of acute infarction but also subtle in the case of chronic infarction, infarction scars or small infarcted regions. Visualization in the latter case is more challenging and an imaging modality that estimates the strain at high precision and thus SNRe is warranted. RF-based tracking can provide such precision to estimate subtle motion changes in the pathological myocardium. Most importantly, the ischemic region will undergo abnormal, i.e., smaller or reverse, motion due to its reduced contractility. Estimation of the resulting smaller motion and/or strain (compared to the normal case) also requires higher precision of the method used. Again, RF-based tracking (as opposed to the faster and more commonly used B-mode tracking) will yield the highest precision estimate and thus highest quality images. Due to the higher sensitivity of RF-based tracking, i.e., the higher decorrelation rate, RF tracking is best used at the highest frame rates, where consecutively acquired RF echoes are best matched because they are recorded at small incremental time intervals.

In a similar way, the same invention can be applied for visualization of all transient motion effects in tissues or vessels, such as the pulse wave traveling in the arterial tree at each heartbeat, respiratory motion, or the pulsation of internal vessels in organs, such as the liver, pancreas, kidney, thyroid or prostate.

What is thus needed in the art are systems and methods that can increase the ultrasound frame rate so as to be sufficiently high to capture cardiac motion and provide meaningful strain image results.

SUMMARY

Systems and methods for composite elastography and wave imaging are presented. In exemplary embodiments of the present invention an imaging modality field of view, such as, for example, that of ultrasound, can be divided into N sectors, each having 1/Nth of a full field of view. In exemplary embodiments of the present invention a temporal series of 2D ultrasound images for each of the N sectors can be acquired over a duration of one or more periods of a periodic signal. Substantially simultaneously, such a periodic signal can also be acquired, wherein each of said series of 2D ultrasound images for each sector can be triggered or gated using said periodic signal. For example, for ultrasound imaging of the heart, an ECG signal can function as such a periodic signal. The data from the various N sectors can be synchronized in time using the ECG signals, and the ultrasound signals from each of the N sectors combined to generate a series of composite ultrasound images at the frame rate of the individual sectors. In exemplary embodiments of the present invention such a composite image can be further processed to estimate displacements between consecutive frames, remove noise, accumulate displacements with time for an entire cardiac cycle, and derive strain in the cardiac muscle. In exemplary embodiments of the present invention the derived strain data can be overlaid onto all or part of the composite ultrasound images, and one or more of such overlaid images can be displayed to a user.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4-14 depict the intermediary outputs of various subprocesses of the exemplary process flow of FIG. 3 according to an exemplary embodiment of the present invention;

FIG. 15 depicts an exemplary B-mode image obtained according to an exemplary embodiment of the present invention;

FIGS. 16($a$)-($n$) depict incremental axial displacements during systole at 50 frames per second according to an exemplary embodiment of the present invention;

FIGS. 16A(a1),(a2)-(n1),(n2) are grayscale images corresponding to FIGS. 16($a$)-($n$) which show the displacement separately from the B-mode image;

FIGS. 17($a$)-($k$) depict incremental axial displacements during diastole at 50 frames per second according to an exemplary embodiment of the present invention;

FIGS. 17A(a1), (a2)-(k1),(k2) are grayscale images corresponding to FIGS. 17($a$)-($k$) which show the displacement separately from the B-mode image;

FIGS. 19($a$)-($k$) depict incremental strain images during diastole at 50 frames per second according to an exemplary embodiment of the present invention;

FIGS. 19A(a1),(a2)-(k1),(k2) are grayscale images corresponding to FIGS. 19($a$)-($k$) which show the strain separately from the B-mode image;

FIG. 24 depicts exemplary process flow charts for an exemplary implementation of the present invention on a programmable ultrasound machine;

FIG. 25 illustrates an exemplary multi-sector combination technique for high frame rate full view ultrasound according to an exemplary embodiment of the present invention;

FIG. 26 illustrates irregular ECG interpolation according to an exemplary embodiment of the present invention;

FIGS. 29($a$)-($l$) depict propagation of an exemplary EM wave propagating from lateral, anterior to septal walls during late diastole captured using imaging techniques according to an exemplary embodiment of the present invention;

FIGS. 30($a$)-($l$) depict propagation of an exemplary EM wave propagating from posterior to lateral wall during diastole captured using imaging techniques according to an exemplary embodiment of the present invention; FIGS. 31($a$)-($l$) depict propagation of an exemplary electromechanical wave along the posterior wall in a human left-ventricle during systole, in a long axis view of an exemplary subject.

Figure 1:
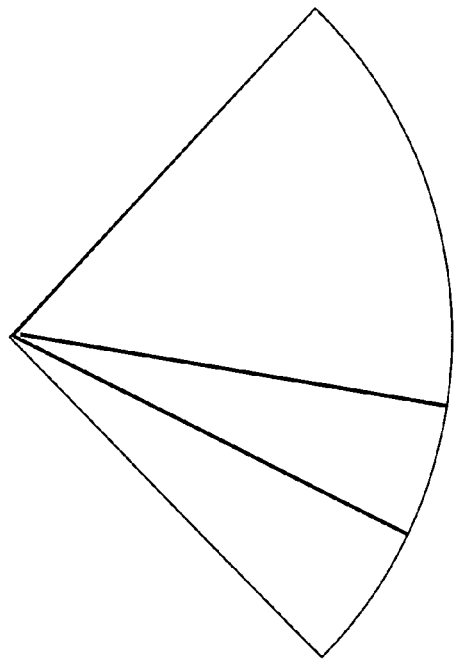
FIG. 1 illustrates exemplary sector data acquisition according to an exemplary embodiment of the present invention.

For U.S. application: it is noted that the patent or application file contains at least one drawing executed in color. Copies of this patent or patent application publication with color drawings will be provided by the U.S. Patent Office upon request and payment of the necessary fee.

It is also noted that certain figures are described as being in color. For the PCT counterpart to this application these images are provided for completeness, but are shown in grayscale to comply with PCT rules and regulations. The color scales which appear on the right of images thus refer to the color overlays onto B-mode images. All color overlays are provided separately in the grayscale images as well.

DETAILED DESCRIPTION

The present invention involves increasing the effective frame rate of an imaging modality by utilizing a periodic signal to synchronize various stored smaller portions of full scan frames and combine them in a temporally correct manner. In exemplary embodiments of the present invention the imaging modality can be, for example, ultrasound, the periodic signal can be, for example, an electrocardiogram, and the imaged anatomical area can be, for example, the heart, such imaging results being used, in particular, to analyze cardiac muscle strain.

In exemplary embodiments of the present invention, a technique known as Composite Myocardial Elastography (CME) can be performed to increase the frame rate of conventional cardiac ultrasound imaging. This technique utilizes ECG-gating to acquire several narrow views (sectors) at high frame rates (e.g., 136 fps) over several cardiac cycles. In exemplary embodiments of the present invention an ECG-gated elastocardiographic method can include, for example, combining displacements and strains obtained at smaller fields-of-view and aligning them based on a simultaneously acquired ECG signal and spatial information into a final composite image. Such a composite image can thus have a full field of view, a significantly higher frame rate, and a significantly higher $SNR_e$. The higher the frame rate, the better correlated the consecutive frames are and therefore, the higher the correlation coefficient used in estimating the displacement. This translates to a higher quality displacements and higher SNR of the elastograms, i.e., higher $SNR_e$. The $SNR_e$ is directly proportional to the correlation coefficient $\rho$ according to the Cramér-Rao Lower Bound (CRLB) is $$SNR_e = \frac{\pi \bar{\varepsilon} T \sqrt{(B^3 + 12Bf_0^2)\Delta t}}{\sqrt{12\left[\frac{1}{\rho^2}\left(1 + \frac{1}{SNR_S^2}\right) - 1\right]}},$$

where $\rho=\rho_x\rho_y\rho_z$ is the correlation coefficient (equal to the product of the correlation coefficients associated with motion in each direction), $SNR_s$ is the sonographic signal-to-noise ratio, B is the bandwidth and $f_0$ is the frequency (Varghese and Ophir 1997). The frame rate FR is equal to $c/(2(N'/N)D)$, where c is the speed of sound, N' is the number of RF signals, N is the number of sectors and D is the depth. The speed of sound in soft tissues is equal to 1540 m/s and the depth in human echocardiography is typically 10-12 cm. The highest obtainable frame rate will be achieved when the smallest number of RF signals (or, largest number of sectors) is used, i.e., N'/N=1. In that case, the frame rate would be equal to 6250 frames/s (or, 6.25 kHz). When N'/N=128 (i.e., the conventional number of RF signals used), the lowest frame rate will be achieved, i.e., 48.83 frames/s (or, 0.049 kHz). For N={6, 12, 20}, the corresponding frame rates are FR={1.04, 0.52, 0.26} kHz.

Thus, in exemplary embodiments of the present invention, a full field image can be reconstructed by combining the data from such sectors, or narrow views, into a combined image. The combined image will thus have the high frame rate of the individual sectors from which it is composed.

Strain images produced at such a higher frame rate are less-affected by noise relative to lower frame rates. This is because a higher cross-correlation coefficient can be obtained at higher frame rates. Systems and methods according to exemplary embodiments of the present invention can be utilized in various analytic, diagnostic and therapeutic applications. One exemplary application is, for example, detecting and quantifying the extent of ischemia and infarction in the myocardium at and beyond its onset due to the associated significantly alerted stiffness of the muscle.

As noted above, conventional real-time raw data acquisition of a full view of the heart limits the data acquisition rate to approximately 50 frames per second (fps). At this frame rate, tracking of rapid motion of the heart in a short period is difficult. In general, transmural (or, across the myocardial wall) infarcts can be minute (the wall maximal thickness is 1 cm and still cause problematic cardiac function that may not be evident through the use of ECG or enzymic activity (i.e., blood tests). High resolution and high sensitivity imaging will allow early detection and potentially serve as a screening technique. Additionally, strain image results produced at this rate are noisy and not reliable. Elastography involves motion imaging. Like photography, if the shutter speed is too low, the resulting picture of a moving subject will be blurry. However, if the shutter speed is high enough, the picture of a moving subject will be clear. The same principle applies in elastography that attempts to obtain motion estimates and images of the heart during contraction of the latter. Exemplary embodiments of the present invention can be used to solve such problems of conventional ultrasound systems. Next described are exemplary embodiments according to the present invention with reference to the figures.

In exemplary embodiments of the present invention, instead of having an ultrasound probe fire all of its transducer elements sequentially to complete one frame, then return to the first transducer element and repeat the process to produce a second frame, the series of sensors can be divided into a number, N, of sectors. For each of the N sectors, a number, M, of frames per second can be obtained by firing only the ultrasound emitters/detectors associated with that particular sector. Thus, for each sector, M frames of imaging data can be obtained per second. By imaging each of the N sectors sequentially, and synchronically combining the data associated with each of the N sectors together into a full field of view composite image, the equivalent of M frames per second of a full view image can be obtained, at a tradeoff of the data from the various sectors not being acquired simultaneously. For example, where each sector data acquisition takes one cardiac cycle, data from Q cardiac cycles can be combined to form a composite image. This process results in a significantly higher data rate, equal to M frames per second as opposed to M/N frames per second for conventional full view ultrasound imaging. This increased frame rate is due to the fact that only a subset of the available transducers on the ultrasound probe need to fire for each frame. The tradeoff is that each acquired frame is considerably narrower than a full view, and these narrow frames must be somehow synchronically combined into a set of full view frames.

Thus, the key to combining various narrow view images respectively corresponding to each of the N sectors into a combined full view is the ability to synchronize the various sectors in time and in space. In exemplary embodiments of the present invention such synchronization can be accomplished, for example, by gating data sector acquisition using a periodic signal, such as, for example, an electrocardiogram signal (ECG), which can also be stored and later used to temporally synchronize the various data sectors. Thus, assuming that the ECG signal is sufficiently auto-correlated across cardiac cycles, such composite images are equivalent to a full field of view image at the higher frame rate of the narrow sectors.

Sector data acquisition is illustrated in FIG. 1. In sector data acquisition each raw data sector can contain, for example, a series of 2D images over a defined period of time, such as, for example one or more cardiac cycles. As noted, each sector contains 1/N of the area of a full field of view.

Figure 2:
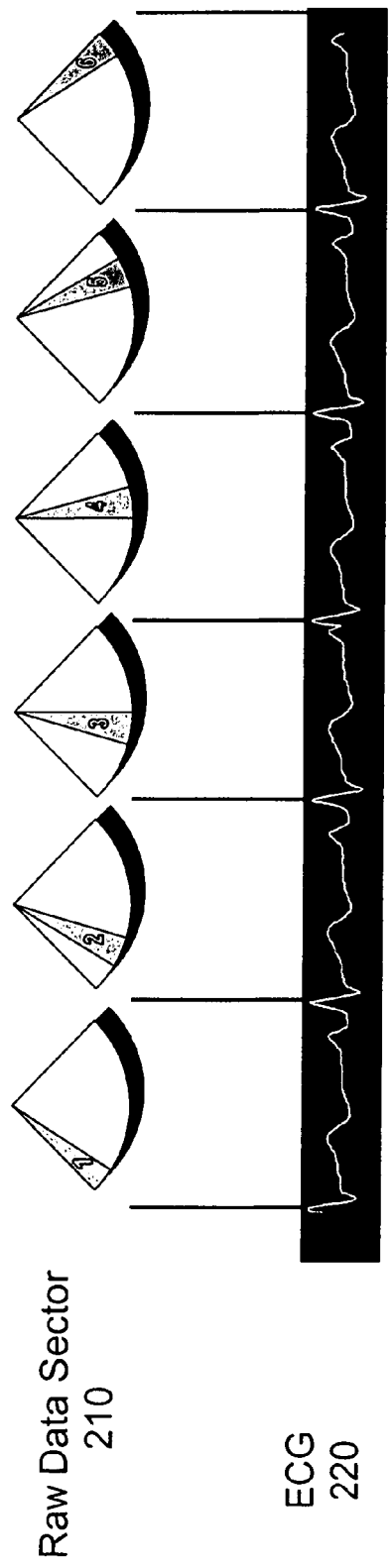
FIG. 2 illustrates exemplary ECG-gated sector data acquisition according to an exemplary embodiment of the present invention.

FIG. 2 illustrates ECG-gated data acquisition. In the exemplary embodiment of FIG. 2 the ultrasound sensors have been divided into six (6) different sectors. These constitute raw data sectors 210. Each sector can be synchronized relative to the beginning of a simultaneously acquired ECG signal 220, by, for example, identifying the QRS peak using known techniques. The ECG signal can then be used to synchronize the various data sectors in time, such as, for example, by having each sector begin at a defined time interval at or after the QRS peak.

Thus, for example, using an ultrasound probe that has 128 emitter/detector elements, sector 1 can be assigned to elements 1-21, sector 2 can assigned to elements 22-42, sector 3 can be assigned to elements 43-63, sector 4 can be assigned to elements 64-84, sector 5 can be assigned to elements 85-105 and sector six can be assigned to elements 106-126. For each sector, a series of images (frames) can be taken over one or more cardiac cycles, for example, and the data from each sector can be combined to make a set of full view ultrasound images over the same time duration.

Moreover, because while the ECG signal is highly auto-correlated in time but still may have variations from one cycle to the next, sector data from a number of different cardiac cycles can, for example, be obtained, and the best matches for each sector can be combined into a composite series of ultrasound images representing one best-fit "composite" cardiac cycle. This can be done, for example, by picking one cardiac cycle's worth of data for each sector from the multiple cardiac cycle data acquired for each sector. For example, the best matching segments of ECG based on length and shape can be used in such a calculation. As noted above, this is possible because the images for each sector can be acquired over a time span of multiple (for example, three) cardiac cycles. This "mix and match" sector combination can be done, for example, using the exemplary "matchbestECG.m" program provided in the computer program listing appendix.

Figure 3:
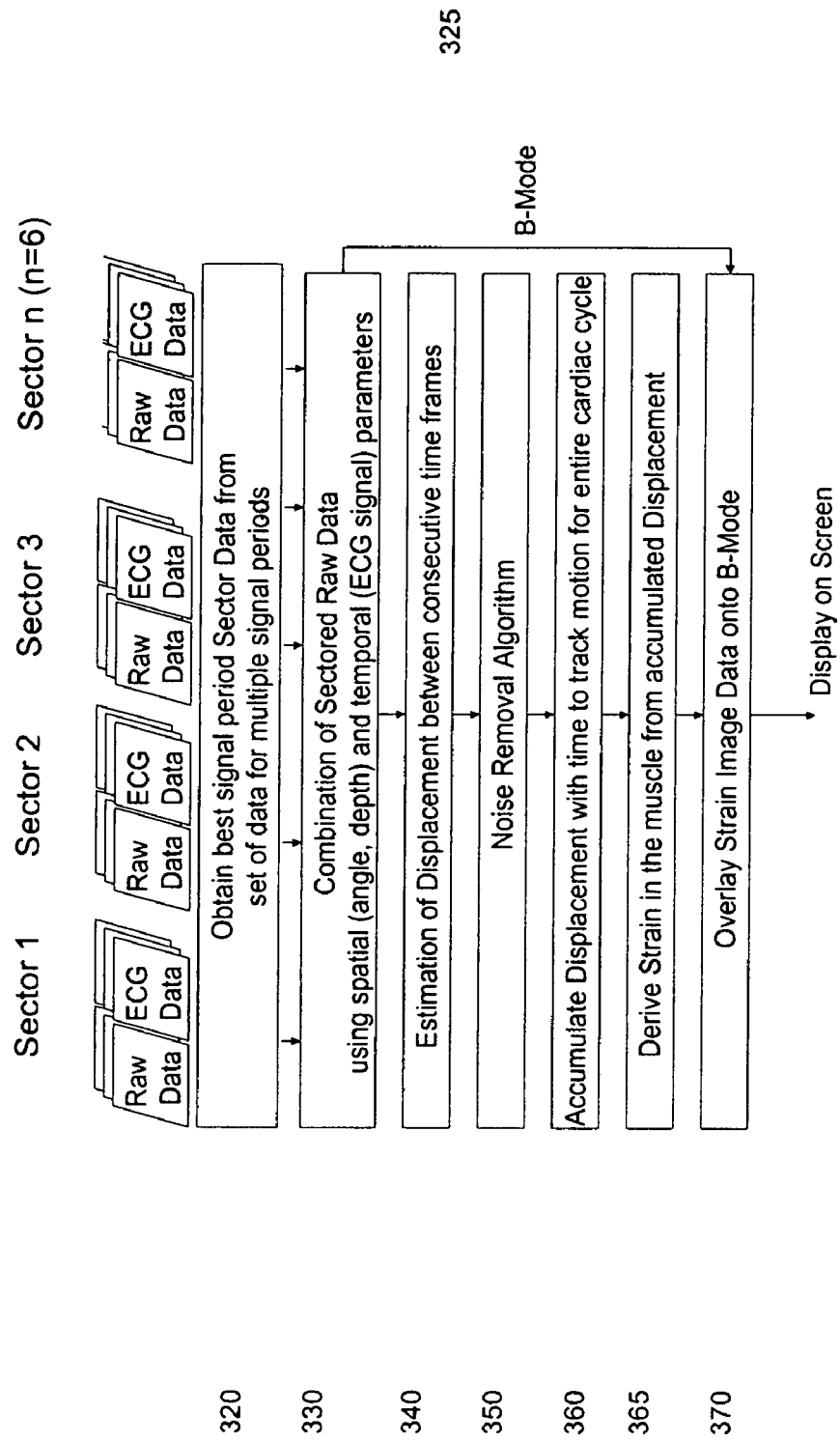
FIG. 3 depicts an exemplary overall process flow according to an exemplary embodiment of the present invention.

FIG. 3 depicts an overall process flow according to an exemplary embodiment of the present invention. Beginning at the top of FIG. 3 there can be seen sectors 1 through N (in the depicted example N=6), where for each sector raw data 305 and simultaneously acquired ECG data 310 can be collected. Using some matching criteria, such as, for example, the correlation coefficient obtained from matching, for example, the R-wave peaks of the ECG signal, as described above, at 320 the best one ECG cycle worth of data for each sector can be chosen and, at 330 the sector raw data from the various sectors can be combined using spatial (angle, depth) and temporal (ECG signal) parameters. Moreover, the sectors can have an overlap of, for example, 10-20% for registration purposes. The starting depth (i.e., beam direction), starting angle and angular increment (i.e., azimuthal direction) of each sector are recorded and used to combine multiple sectors. For example, the first sector can span from 0-11 degrees, the second 9-21, the third 19-31, etc. The spatial registration can thus be performed using the angle and depth information and temporal registration can be obtained using the ECG signal. After combination at 330, the result is a series of composite images 325 such as is shown, for example, in FIG. 15. The B-Mode image of FIG. 15 is a standard full view ultrasound image, and the series obtained in this manner has a higher temporal sampling rate than otherwise possible with full field of view imaging.

The remaining processes depicted in FIG. 3 relate to displacement identification and strain derivation therefrom. Thus, at 340, the displacements can be estimated, for example, between consecutive time frames. Here, displacements are estimated for the entire composite FOV. At 350, for example, a noise removal algorithm can be implemented, such as, for example, the CLEAN_NOISE pseudocode provided in the exemplary code provided below. Noise removal utilizes the information of correlation coefficients. Only the estimates with high correlation coefficients above 0.7 are deemed reliable. Those with lower correlation coefficients will be replaced by the average of the surrounding estimated values. At 360, for example, the displacement can be accumulated with time so as to track motion for an entire cardiac cycle, for example.

Continuing with reference to FIG. 3, at 365 strains in the cardiac muscle can, for example, be derived from the accumulated displacements generated at 360. Strains can be defined in terms of the gradient of the displacements. The cumulative 2D displacement 360 can thus, for example, be written as $u=u_x e_x + u_y e_y$, where $u_x$ and $u_y$ are lateral and axial displacements, respectively, and $e_x$ and $e_y$ are unit coordinate base vectors in lateral and axial directions, respectively. The cumulative 2D displacement gradient tensor, $\nabla u$, can be defined as:

$$\nabla u = \begin{bmatrix} \frac{\partial u_x}{\partial x} & \frac{\partial u_x}{\partial y} \\ \frac{\partial u_y}{\partial x} & \frac{\partial u_y}{\partial y} \end{bmatrix}, \quad (3)$$

and the strain tensor, E, can be defined as $$E = \frac{1}{2}(\nabla u + (\nabla u)^T + (\nabla u)^T \nabla u), \quad (4),$$

where $(\nabla u)^T$ is the transpose of $\nabla u$. The lateral and axial strains are the diagonal components of E, i.e., $E_{xx}$ and $E_{yy}$, respectively.

Given such derived strain, at 370, for example, the derived strain can be overlaid onto B-Mode image 325 generated at 330. Finally, this overlay can be displayed on the screen, as shown in FIGS. 18-19 and 22-23, and process flow ends.

Although in the above process flow description reference has only been made to a few of the exemplary Matlab™ programs provided in the computer program listing appendix, those skilled in the art will understand how each of those exemplary programs can be used to implement the various processes illustrated in FIG. 3. The following table correlates the various exemplary processes of FIG. 3 with either exemplary Matlab™ programs provided in the computer program listing appendix, along with the inputs and outputs to such programs, or with pseudocode (for steps 340, 350, 360 and 365), as provided immediately after the table. For the exemplary Matlab™ code the following variables are used:

M=number of sectors;
N=length of ECG signals for three cardiac cycles;
N1=length of ECG signals for the cardiac cycle with maximum length;
Nf=number of total frames in the beginning; and
nFrames=number of frames per sector per cardiac cycle.

| | Function name | Input | Output |
|---|---|---|---|
| Main script | analyzeNrf<br>Reconstruct several overlapping small sector RF acquisitions. | N/A | N/A |
| 305 | OPENCLP<br>(provided by EchoPAC)<br>Open the DICOM format files saved in GE Vivid 5 | filename | fid |
| | RDTISSUE<br>(provided by EchoPAC)<br>Read the b-mode data | Filename<br>infoTISS (1-by-Nf)<br>startframe (2*M-by-2)<br>stopframe (2*M-by-2) | alltiss (3D matrix) |
| | Readiq<br>(provided by EchoPAC)<br>Read the in-phase quadrature (IQ) data (i.e., raw data) | Filename<br>infoIQ (1-by-Nf)<br>startframe (2*M-by-2)<br>nFrames (2*M-by-2) | tiq (2D matrix) |
| | IQ2RF<br>(provided by EchoPAC)<br>Convert IQ data to Radial-frequency (RF) data | tiq<br>infoIQ | allrf (3D matrix) |
| 310 | readecg<br>(provided by EchoPAC)<br>Read the ECG data stored in GE Vivid 5 | Filename<br>infoTISS (1-by-Nf) | ecgTISS (1-by-N)<br>syncTISS (1-by-N) |
| 320 | matchbestECG<br>Finds the best matching segments of ECG based on length and shape | ecgTISS (1-by-M cell) | ecgbest (M-by-2)<br>{ecgTISS1, ecgTISS2, ecgTISS3, ecgTISS4, ecgTISS5} (1-by-M cell) |
| | cutECG<br>This function cuts up an ECG signal into N parts. | ECGfull (1-by-N)<br><br>syncTISS<br>syncIQ<br>ecgbest (2*M-by-2) | ECGparts (3-by-N1)<br>ECGtrigger (1-by-N1)<br>ECGpeakshift (1-by-M)<br>startframe (2*M-by-2)<br>stopframe (2*M-by-2) |
| 325 | makeCardiacMovie<br>The main script to make the movie displaying overlaid displacement image | overlayAll<br>ecgIQ1<br>syncIQ1<br>parameters<br>scanconvert (true or false) | Movie |
| | getPolTransformMap<br>Computes a polar-to-cartesian coordinate transformation map defined by prpol and prcart. | prpol (2-by-4)<br>prcart (2-by-4) | mrows (2D matrix)<br>mcols (2D matrix)<br>mmask (2D matrix) |
| | appPolTransform<br>applies a polar-to-cartesian coordinate transformation to imgpol. | Data<br>mrows (2D matrix)<br>mcols (2D matrix)<br>mmask (2D matrix)<br>flag = 1 (linear interpolation) | overlaysc (4D matrix) |
| 330 | readinfo<br>(provided by EchoPAC)<br>Read all EchoPAC file information | fid 0 | tinfo |
| | getmyparams<br>get parameters from each file | tinfo<br>paramnamesTISS or paramnamesIQ | tparams-><br>paramsIQ (M-by-6)<br>paramsTISS (M-by-6) |
| | findSectorOverlap<br>Utilizes params matrix to find overlapping regions of sectors, and returns sectorBeams, a matrix containing information about overlap and which data to utilize from each sector for the reconstructed whole sector. | paramsIQ or paramsTISS (M-by-6)<br>centerAngle<br>iSA = 3<br>iAU = 4<br>iNB = 6<br>iSD = 1<br>iDU = 2<br>iNS = 5 | sectorBMbeams (M-by-8) or sectorIQbeams (M-by-8) |
| 340 | | See pseudocode below | |
| 350 | | See pseudocode below | |
| 360 | | See pseudocode below | |
| 365 | | See pseudocode below | |
| 370 | initOverlay.m | paramsIQ (2D matrix)<br>paramsTISS (2D matrix) | oparams (structure) |
| | overlayData.m | tiss (3D matrix)<br>data (3D matrix)<br>oparams (structure)<br>TISSISRF (flag) | overlayAll (4D matrix) |

| Function name | Input | Output |
| --- | --- | --- |
| overlayimage.m | tissRGB (3D matrix) dataRGB (3D matrix) mask (3D matrix) | overlay(3D matrix) |
| tiss2rgb.m | tiss (2D matrix) paramsTISS (2D matrix) DYN (scalar) GAIN (scalar) | tissRGB (3D matrix) |
| data2rgb.m | dataResize (2D matrix) CMAP dataLIMS (1-by 2-vector) | dataRGB (3D matrix) |

Pseudocode Referred to in Above Table for 340, 350, 360 and 365 of FIG. 3:

```
340
Read raw data
Initialize window_size, overlap, interp_factor
Set sample_count to (1-overlap)*window_size
FOR 1 : shift : total_sample_points
   FOR lateral_beam_count
      2D interpolation of RF signals
      Calculate cross-correlation coefficient between signals
      Find the maximal coefficient
      Cosine interpolation around the maximal coefficient
      Store the location with the interpolated maximal coefficient
      Calculate lateral and axial displacements based the store location
   ENDFOR
ENDFOR
Generate RF signals with the removal the axial displacement and recalculate the lateral
displacement
lateral_disp= lateral displacement after axial displacement correction
axial_disp= the initial estimated axial displacement
Return lateral_disp, axial_disp, cross-correlation_coefficient
350
Function CLEAN_NOISE (displacement, cross_correlation_coefficients)
FOR each displacement
IF cross_correlation_coefficient < threshold
   The displacement value is updated with the average of the neighboring values
ENDIF
ENDFOR
360
function [cum_lateral_disp, cum_axial_disp]= CUM_DISP (lateral_disp, axial_disp)
365
function strain_tensor_2D=CALC_STRAIN (lateral_disp, axial_disp)
G11= the gradient of lateral_disp along the lateral direction
G12= the gradient of lateral_disp along the axial direction
G21= the gradient of axial_disp along the lateral direction
G22= the gradient of axial_disp along the axial direction
G(1, 1)=G11; G(1, 2)=G12; G(2, 1)=G21; G(2, 2)=G22;
strain_tensor_2D =1/2*(G + transpose (G) + transpose (G)*G)
Return strain_tesnsor_2D
```

FIGS. 4-14 depict exemplary intermediate outputs of various exemplary sub-processes of FIG. 3, generated using the exemplary Matlab™ source code provided in the computer program listing appendix. These intermediate results, and how the various modules in the exemplary source code can be used to generate them, are next described with reference to FIGS. 4-14.

It is noted that although in connection with FIG. 3, the number of sectors N was, for example, six, in the exemplary images of FIGS. 4 and 5 only five sectors were used. In general, the number of sectors depends on the individual sector size selected and on the size of the left ventricle imaged.

FIG. 4 depicts five exemplary sector outputs. The sectors were used to image the whole long axis view of the left ventricle. Each sector shows the raw data. FIG. 5 shows an exemplary 3 cardiac cycles (ECG signals) obtained while each sector was being imaged. From this data, FIG. 6 shows the best match cardiac cycle (ECG signal) from each sector. The best matched cardiac cycle can be determined according to the highest cross-correlation coefficient obtained.

FIG. 7 shows the combined raw data of the long axis view of the left ventricle, FIG. 8 shows incremental lateral and axial displacements before noise removal, and FIG. 9 shows incremental lateral and axial displacements after noise removal.

Figure 12:
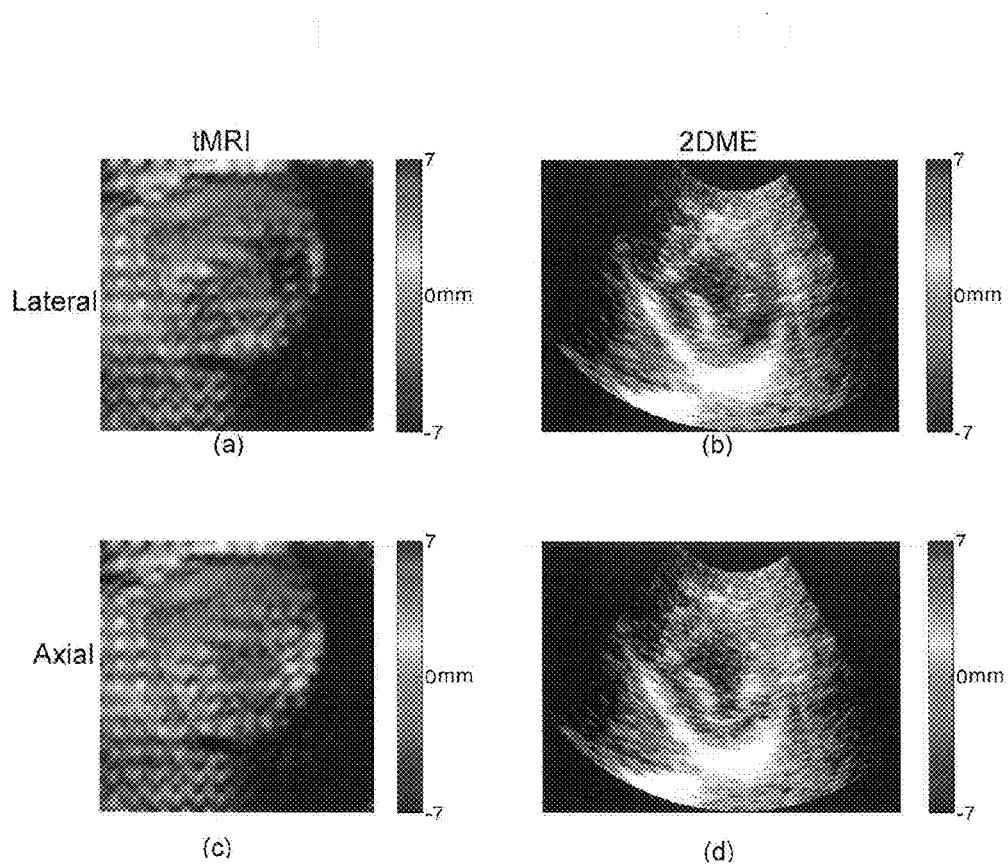
Figure 13:
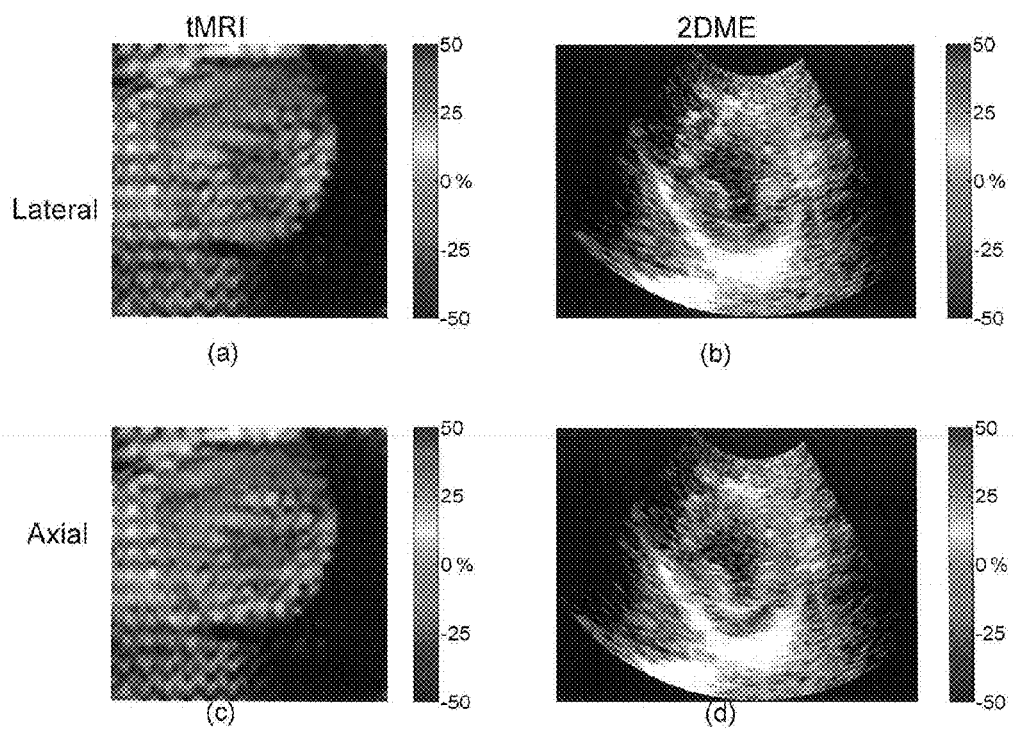

FIG. 10 shows cumulative lateral and axial displacements from end-diastole (ED) to end-systole (ES) in a long-axis view. FIG. 11 shows cumulative lateral and axial strains from ED to ES in a long-axis view. FIG. 12 depicts exemplary cumulative (a) lateral and (c) axial displacements from tagged MRI (tMRI) imaging between end-diastole (ED) and end-systole (ES), respectively; and cumulative (b) lateral and (d) axial displacements from 2D myocardial elastography (2DME) between ED and ES, respectively. All the depicted short-axis images were acquired approximately at the papillary muscle level and shown at end-systolic configuration. Similarly, FIG. 13 depicts cumulative (a) lateral and (c) axial systolic strains from tMRI between ED and ES, respectively, and cumulative (b) lateral and (d) axial systolic strains from 2DME between ED and ES, respectively. All the short-axis images were acquired approximately at the papillary muscle level and shown at end-systolic configuration. FIGS. 12 and 13 show that the estimates from myocardial elastography and tMRI are in good agreement.

Figure 12A:
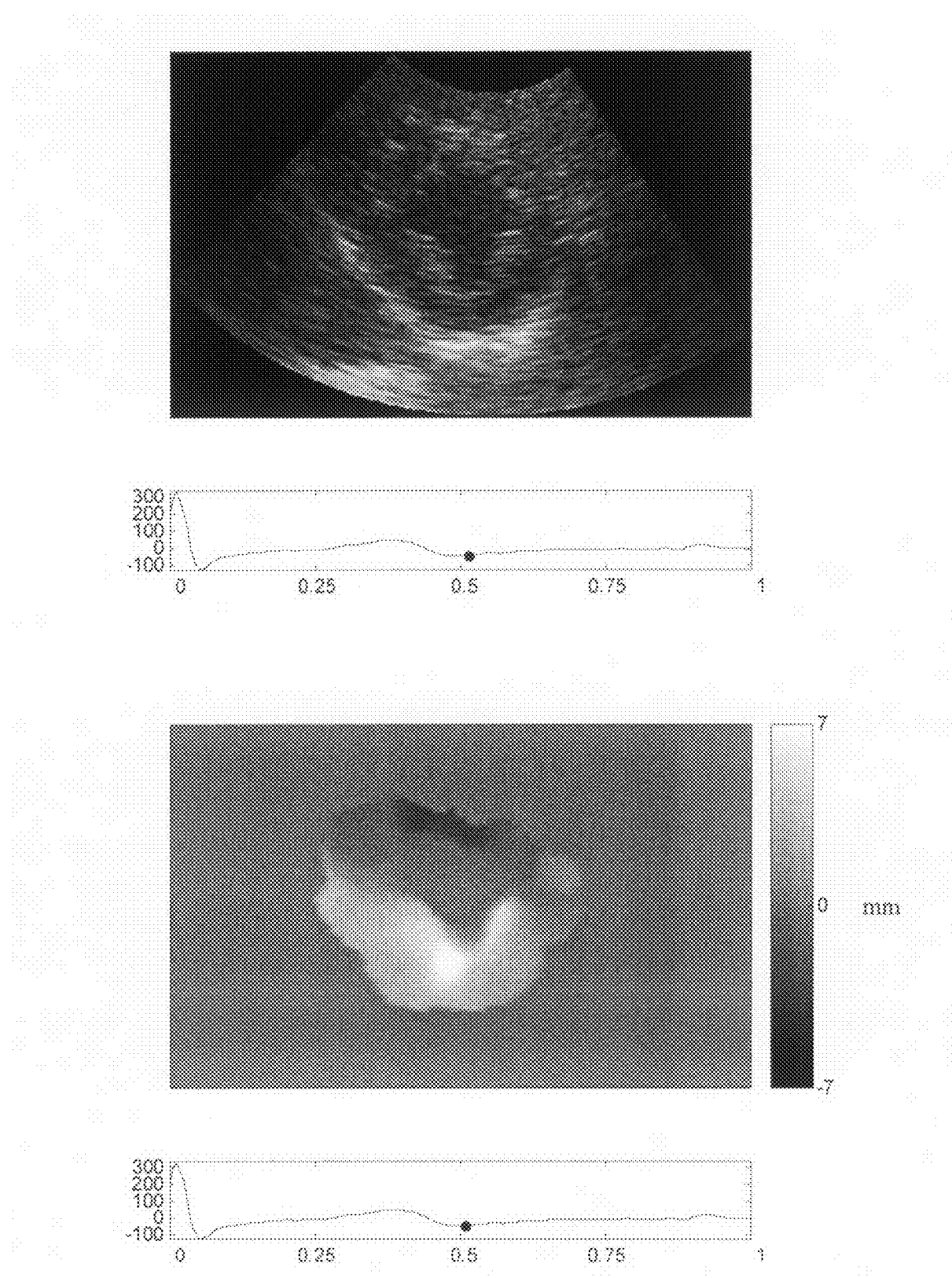
FIGS. 12A($a$)-($d$) and 13A($a$)-($d$) depict the underlying image and the overlay separately, in grayscale, and correspond to FIGS. 12($a$)-($d$) and 13($a$)-($d$), respectively.

It is noted that FIGS. 12A(a)-(d) and 13A(a)-(d) depict the underlying image and the overlay separately, in grayscale, and correspond to FIGS. 12(a)-(d) and 13(a)-(d), respectively.

Finally, FIG. 14 shows an exemplary B-mode long axis view of the left ventricle before and after scan conversion.

As noted above, FIG. 15 is an exemplary B-Mode image such as, for example, that generated at 325 in FIG. 3 from the combined sector data.

Exemplary B-Mode Images

1. Low Frame Rate Displacement Images for Systole and Diastole—FIGS. 16-17 and 16A-17A FIGS. 16(a)-(n) and 17(a)-(k) illustrate exemplary displacement results obtained during systole (contraction) and diastole (expansion), respectively, for a series of time points, wherein displacement has been color coded in each image according to the color coded bar key appearing at the right of each image. The time point within the cardiac cycle at which each image has been acquired is indicated by the solid ball below each image. FIGS. 16 and 17 are conventional full view images acquired in a conventional manner; they thus represent a frame rate of 50 frames per second. The displacement is overlaid in color on the B-mode images. FIGS. 16A and 17A are grayscale images corresponding to FIGS. 16 and 17, respectively. In the grayscale images of FIGS. 16A and 17A, the displacement has been separated from the B-mode images for ease of viewing. Thus each image in FIGS. 16 and 17 corresponds to two images in FIGS. 16A and 17A—one for the B-mode image, the other for the displacement. For example, FIG. 16(a) corresponds to FIGS. 16A(a1) and (a2); FIG. 16A(a1) presenting the B-mode image, and FIG. 16A(a2) the overlay. A similar correspondence exists between FIGS. 17-23 and FIGS. 17A-23A, respectively, described below.

Figure 18C:
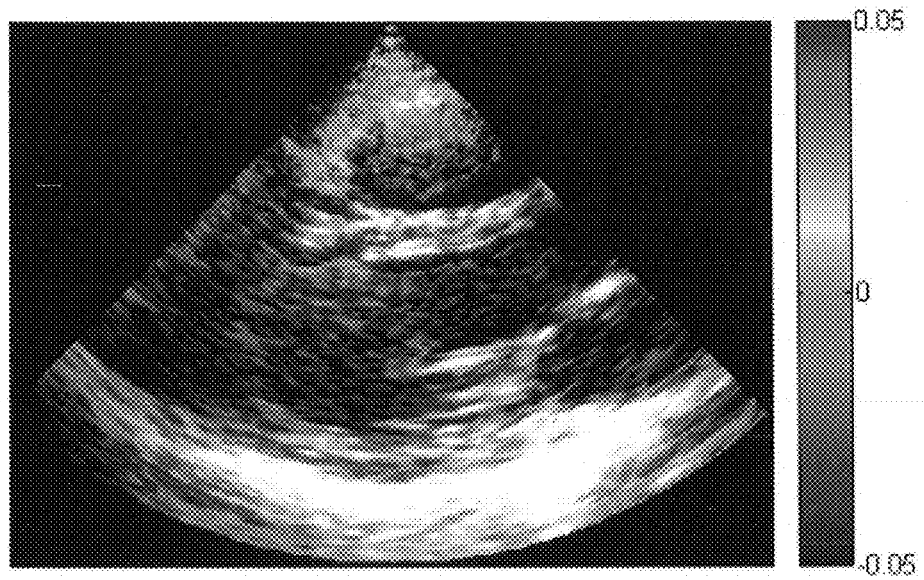
FIGS. 18($a$)-($n$) depict incremental strain images during systole at 50 frames per second according to an exemplary embodiment of the present invention.
FIGS. 18A(a1),(a2)-(n1),(n2) are grayscale images corresponding to FIGS. 18($a$)-($n$) which show the strain separately from the B-mode image.
Figure 18D:
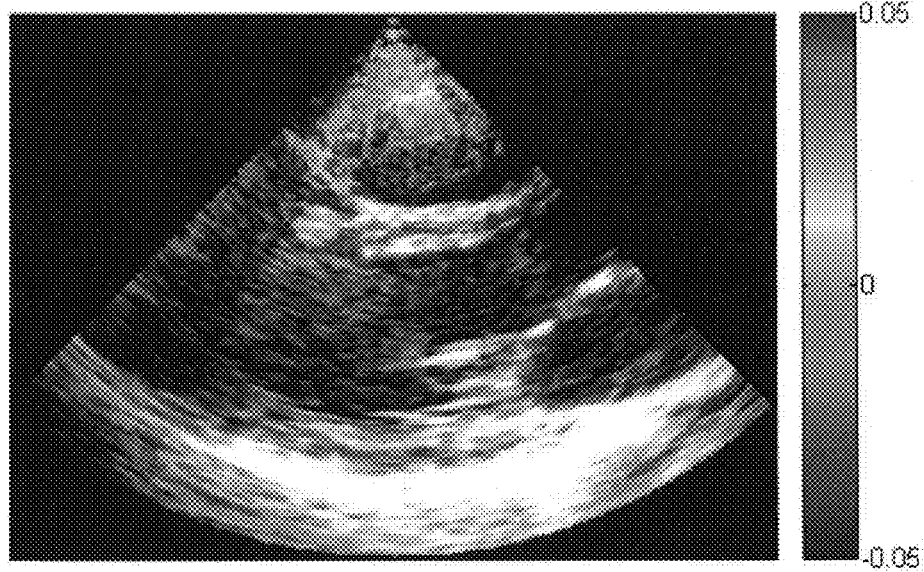

2. Low Frame Rate Strain Images for Systole and Diastole—FIGS. 18-19 and 18A-19A Similarly, FIGS. 18(a)-(n) and 19(a)-(k) show a series of strain images obtained during systole (contraction) and diastole (expansion), respectively, for a series of time points, wherein the strain has been color coded in each image according to the color coded bar key appearing at the right of each image. The time point within the cardiac cycle at which each image has been acquired is indicated by the solid ball below each image. FIGS. 18 and 19 are conventional full view images acquired in a conventional manner; they thus represent a frame rate of 50 frames per second. The strain is overlaid in color on the B-mode images. FIGS. 18A and 19A are grayscale images corresponding to FIGS. 18 and 19, respectively. In the grayscale images of FIGS. 18A and 19A, the displacement has been separated from the B-mode images for ease of viewing. Thus each image in FIGS. 18 and 19 corresponds to two images in FIGS. 18A and 19A—one for the B-mode image, the other for the displacement.

3. High Frame Rate Displacement Images for Systole and Diastole—FIGS. 20-21 and 20A-21A Similarly, FIGS. 20(a)-(n) and 21(a)-(k) show a series of composite displacement images made by combining various sectors according to an exemplary embodiment of the present invention, thus obtaining a high frame rate of, for example, 136 frames per second. The time point within the cardiac cycle at which each image has been acquired is indicated by the solid ball below each image. As above for the low frame rate images, the displacement is overlaid in color on the B-mode images.

Figure 20C:
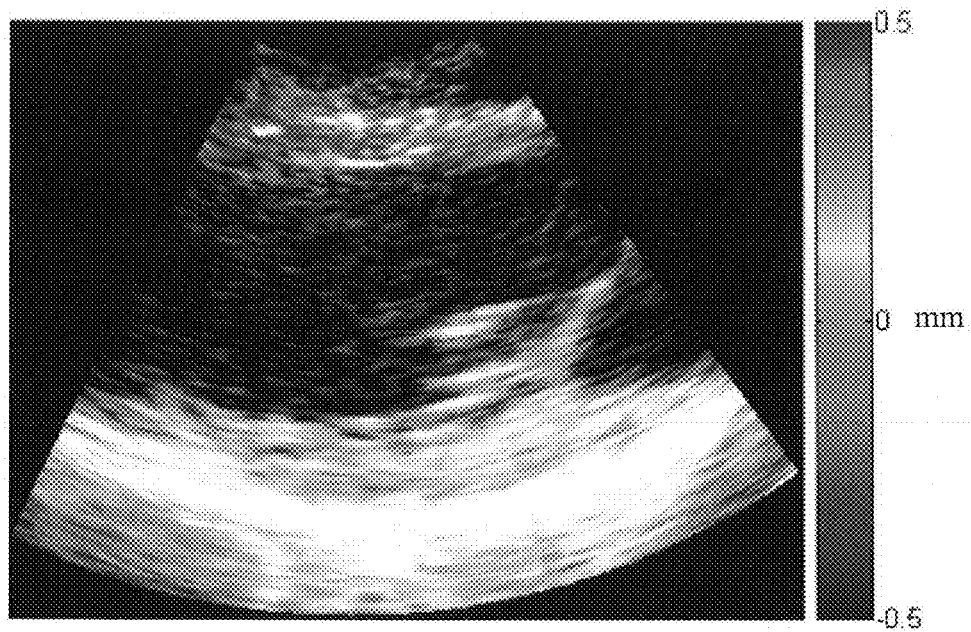
FIGS. 20($a$)-($n$) depict incremental axial displacement during systole at 136 frames per second according to an exemplary embodiment of the present invention.
FIGS. 20A(a1),(a2)-(n1),(n2) are grayscale images corresponding to FIGS. 20($a$)-($n$) which show the displacement separately from the B-mode image.
Figure 20D:
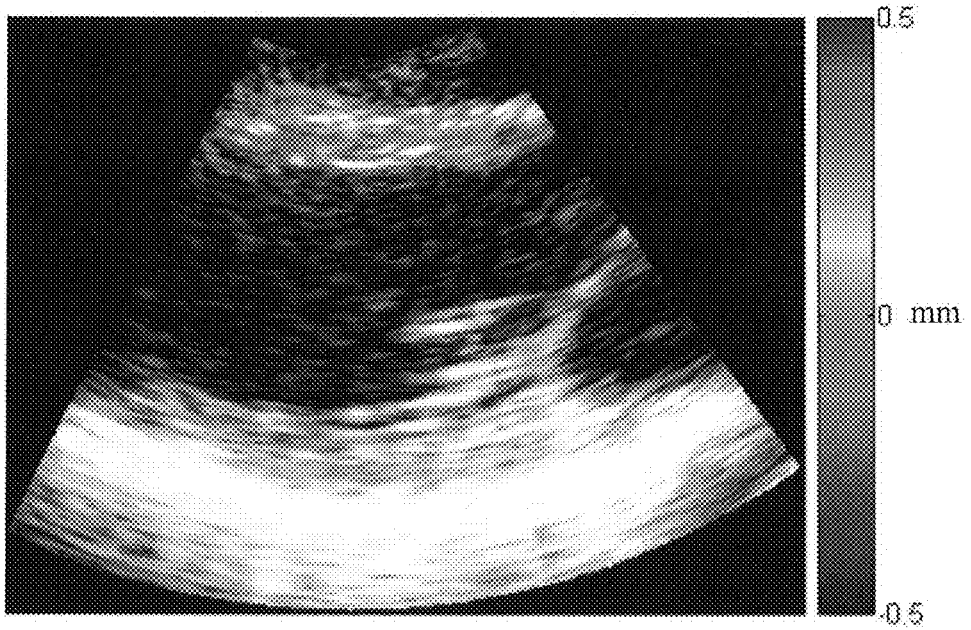
Figure 20E:
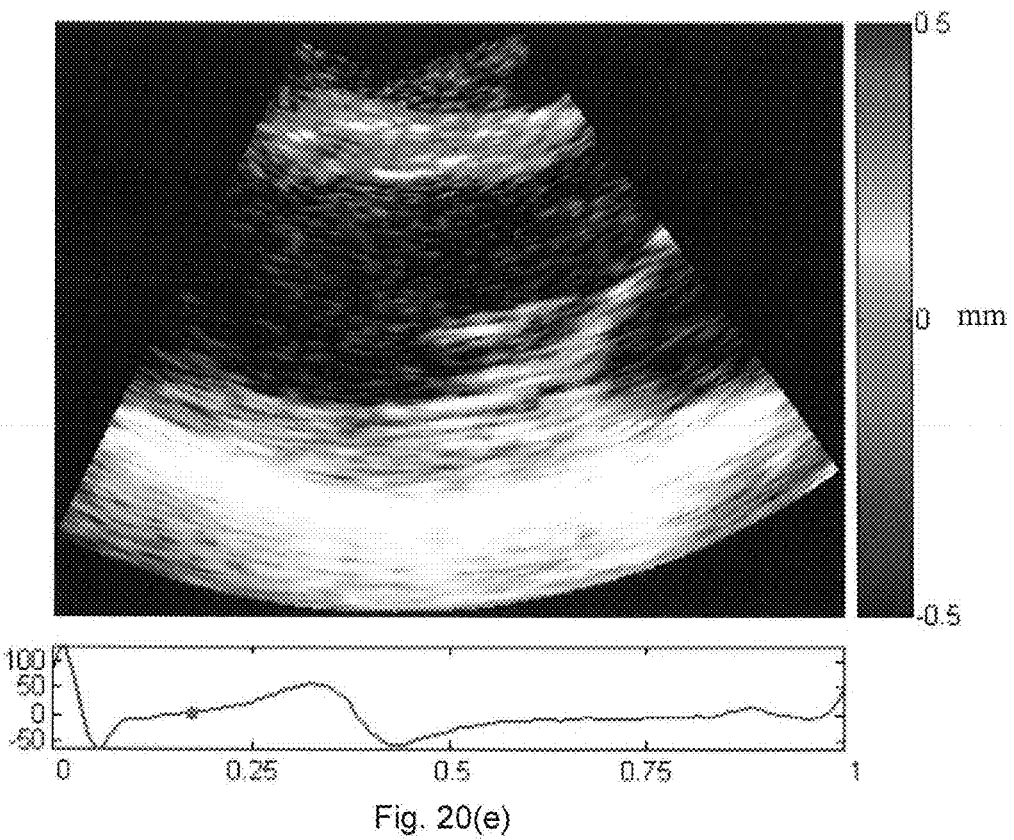
Figure 20F:
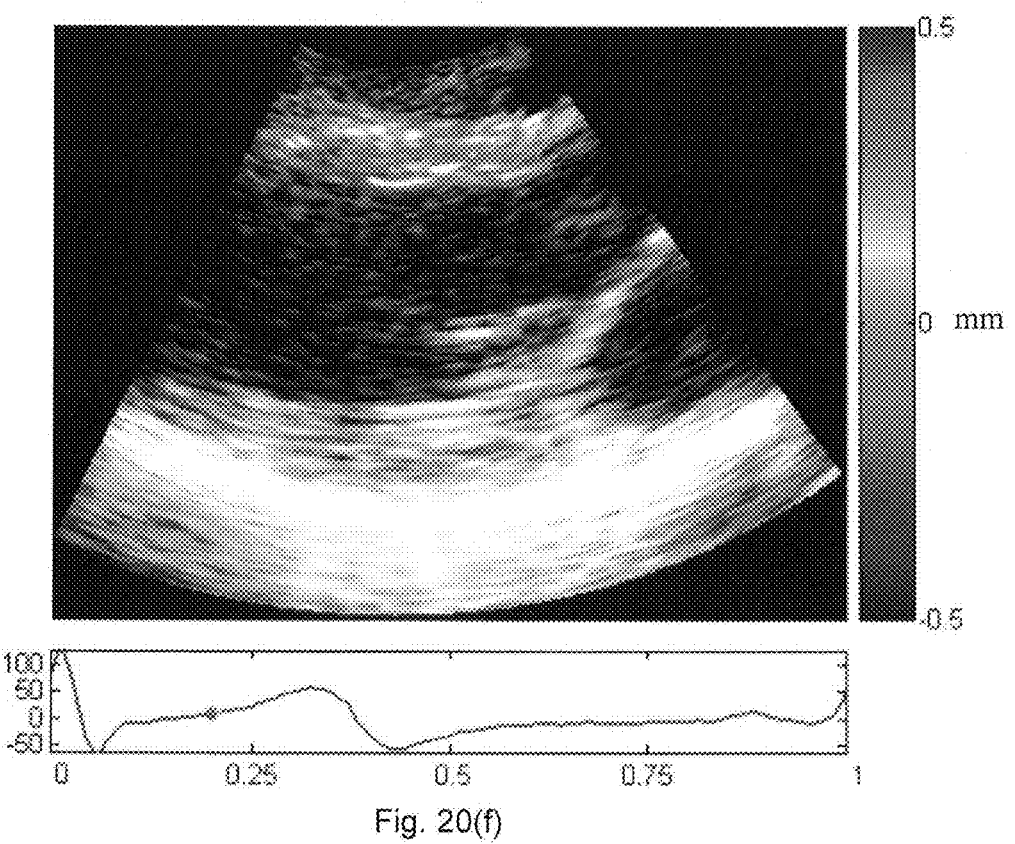
Figure 20G:
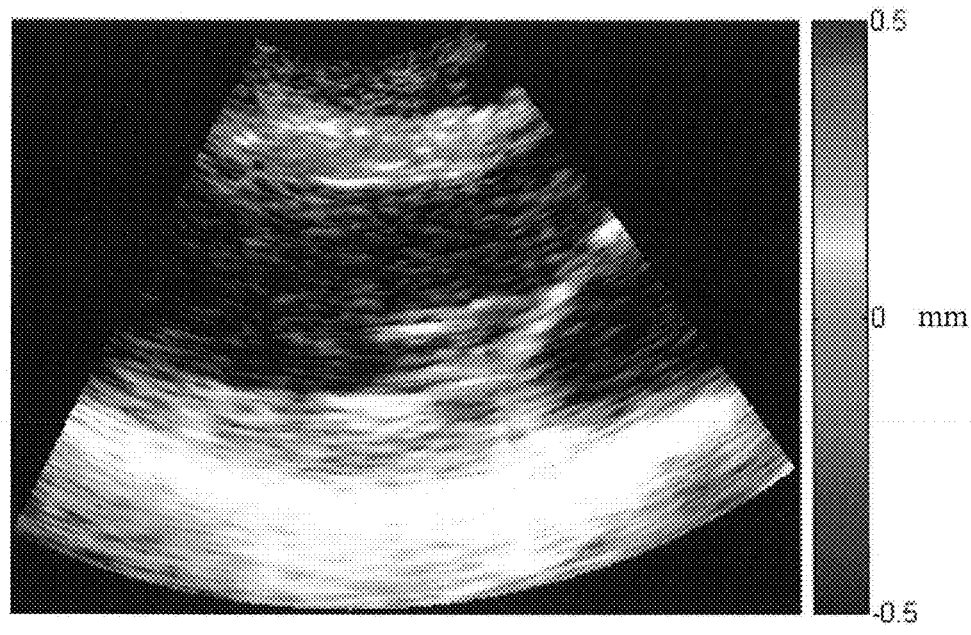
Figure 20H:
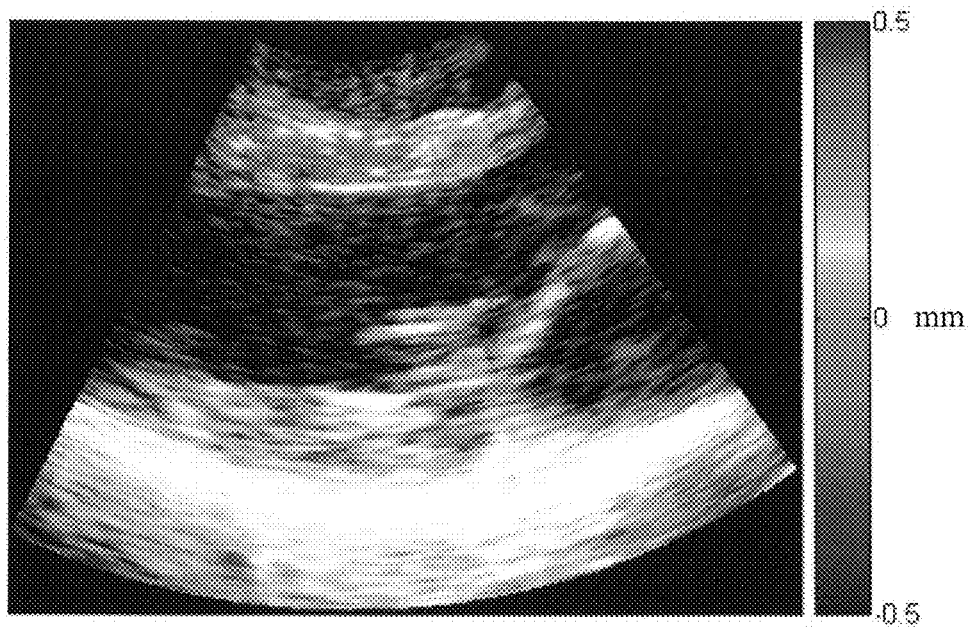
Figure 20I:
Figure 20J:
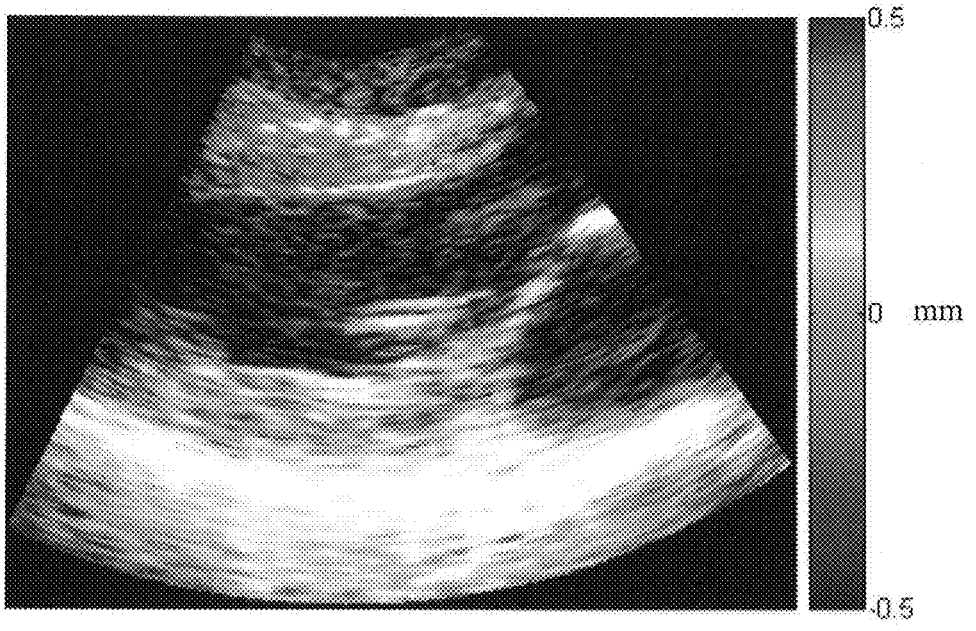
Figure 20K:
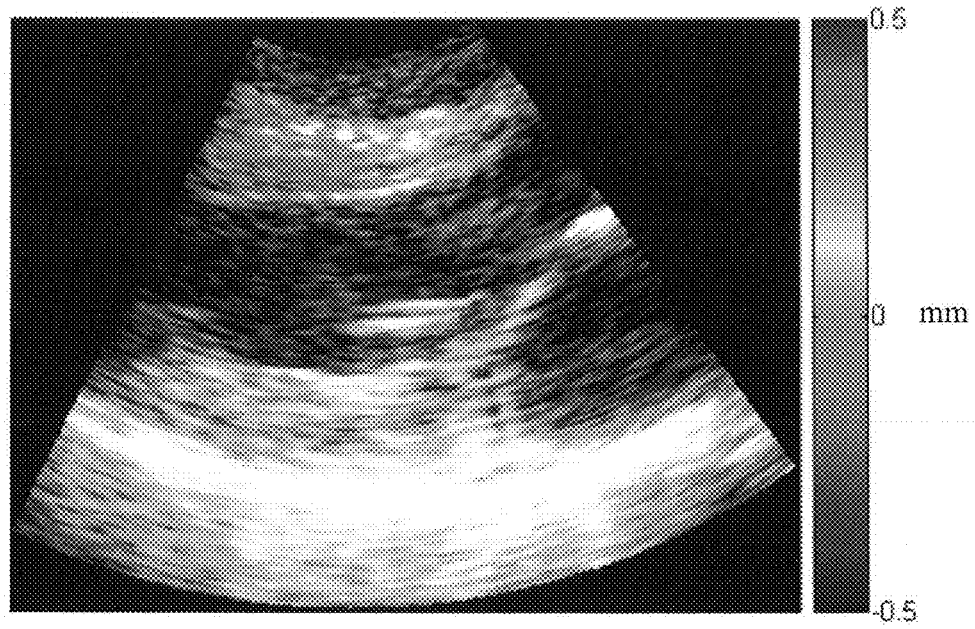
Figure 20L:
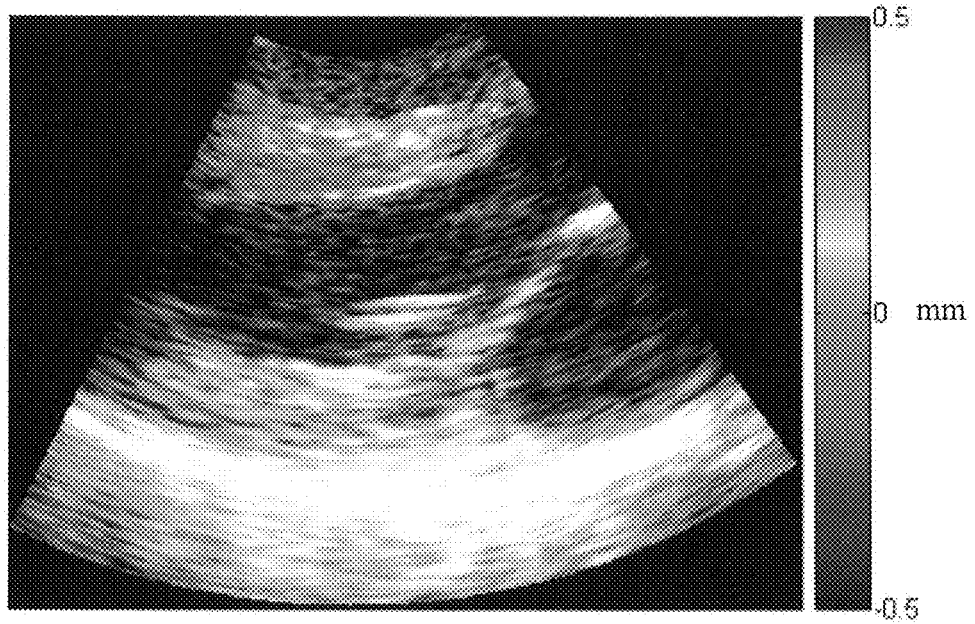
Figure 20M:
Figure 20N:
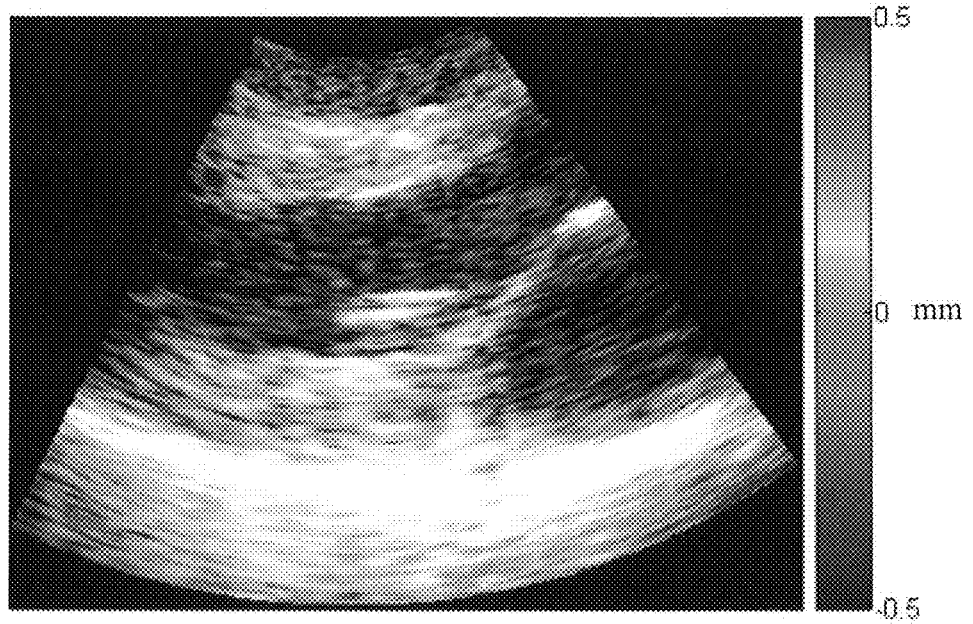
Figure 21A:
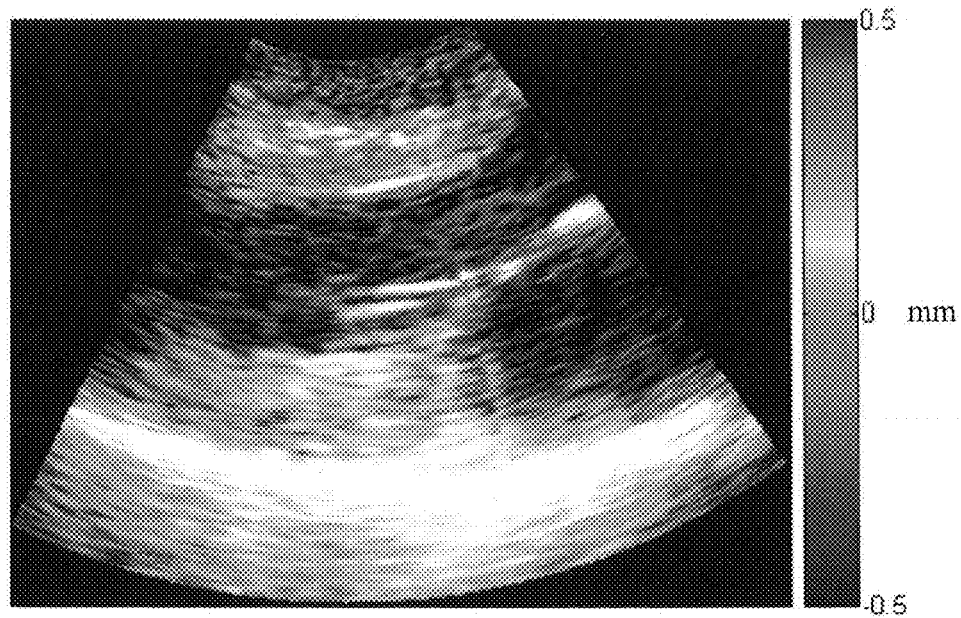
FIGS. 21A(a1),(a2)-(k1),(k2) are grayscale images corresponding to FIGS. 21($a$)-($k$) which show the displacement separately from the B-mode image.
Figure 21B:
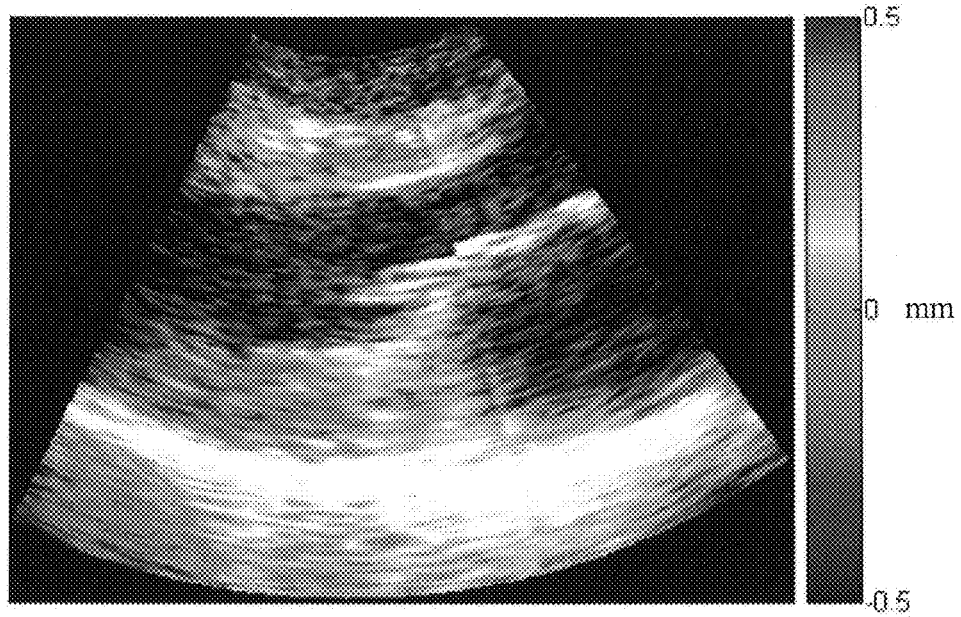
FIGS. 21($a$)-($k$) depict incremental axial displacement during diastole at 136 frames per second according to an exemplary embodiment of the present invention.
Figure 21C:
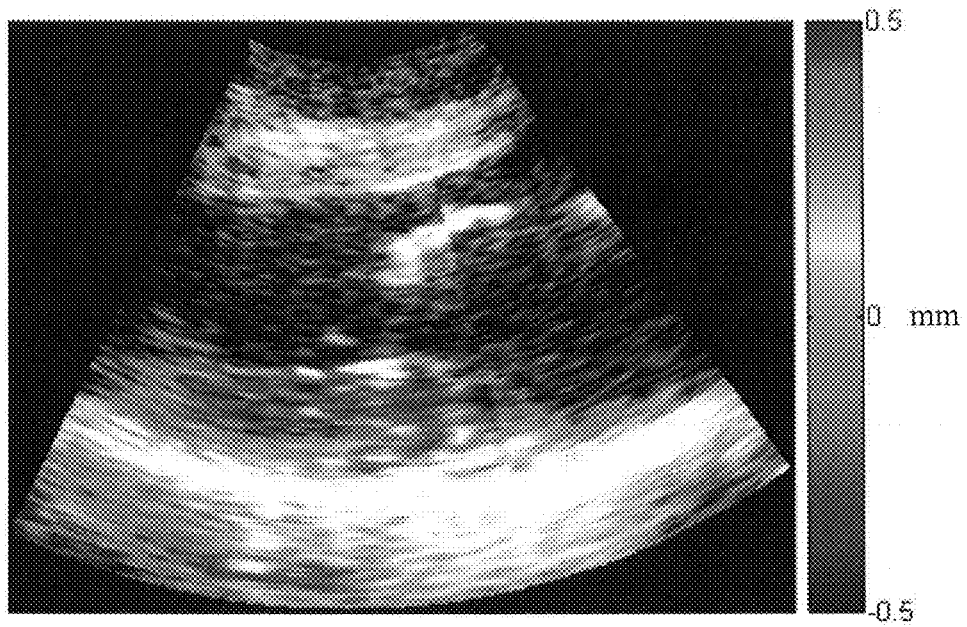
Figure 21D:
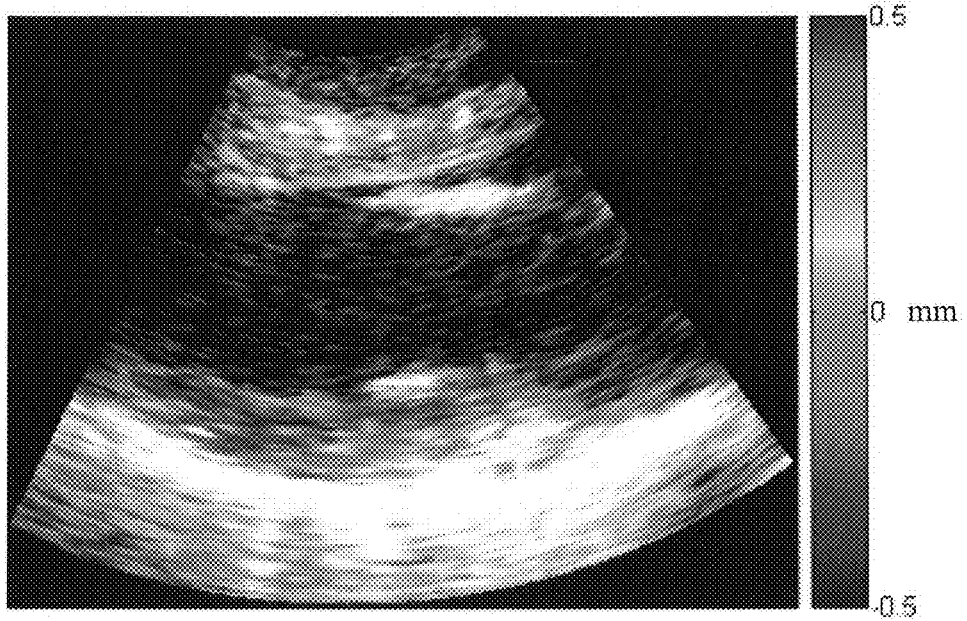
Figure 21E:
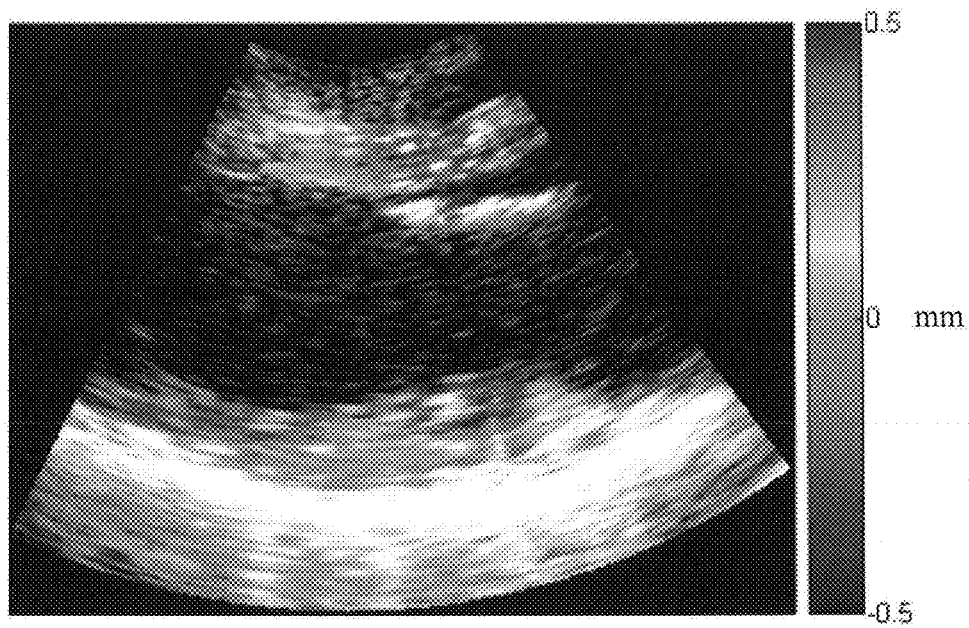
Figure 21F:
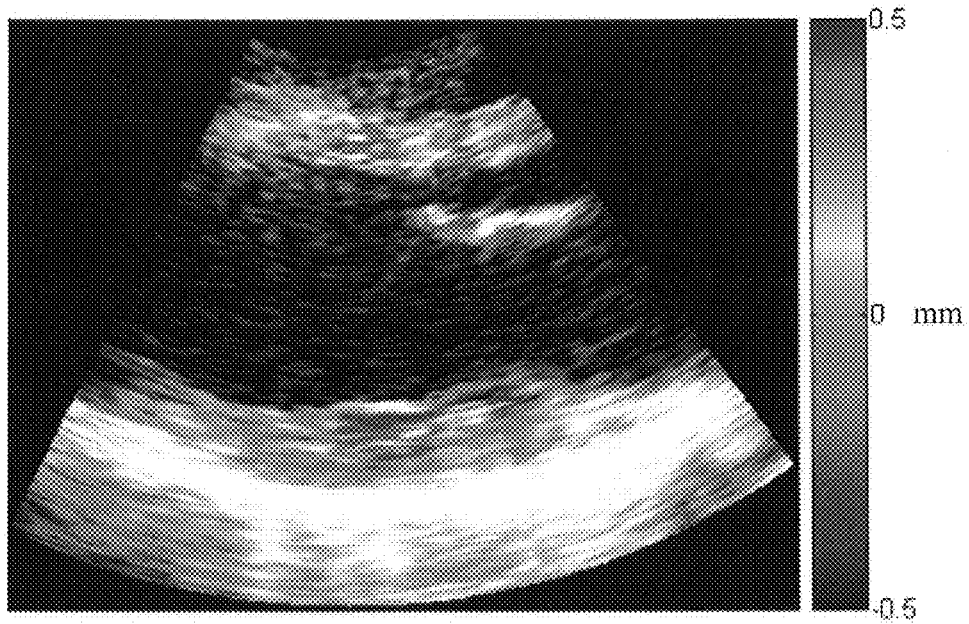
Figure 21G:
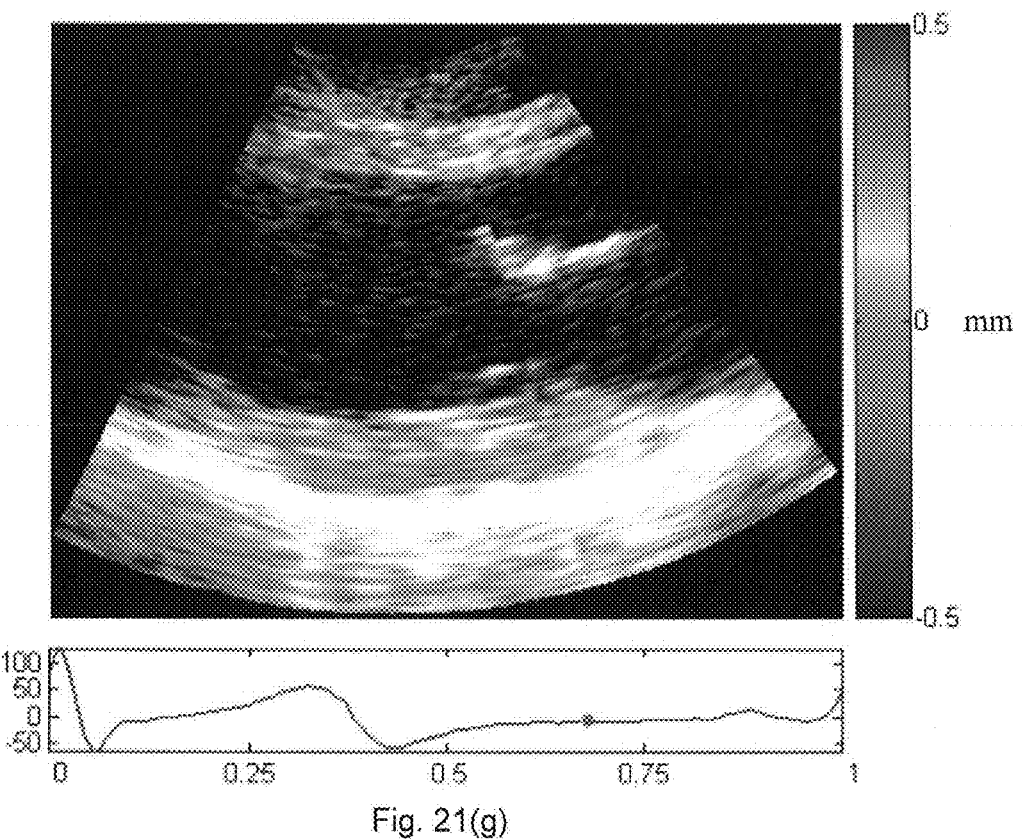
Figure 21H:
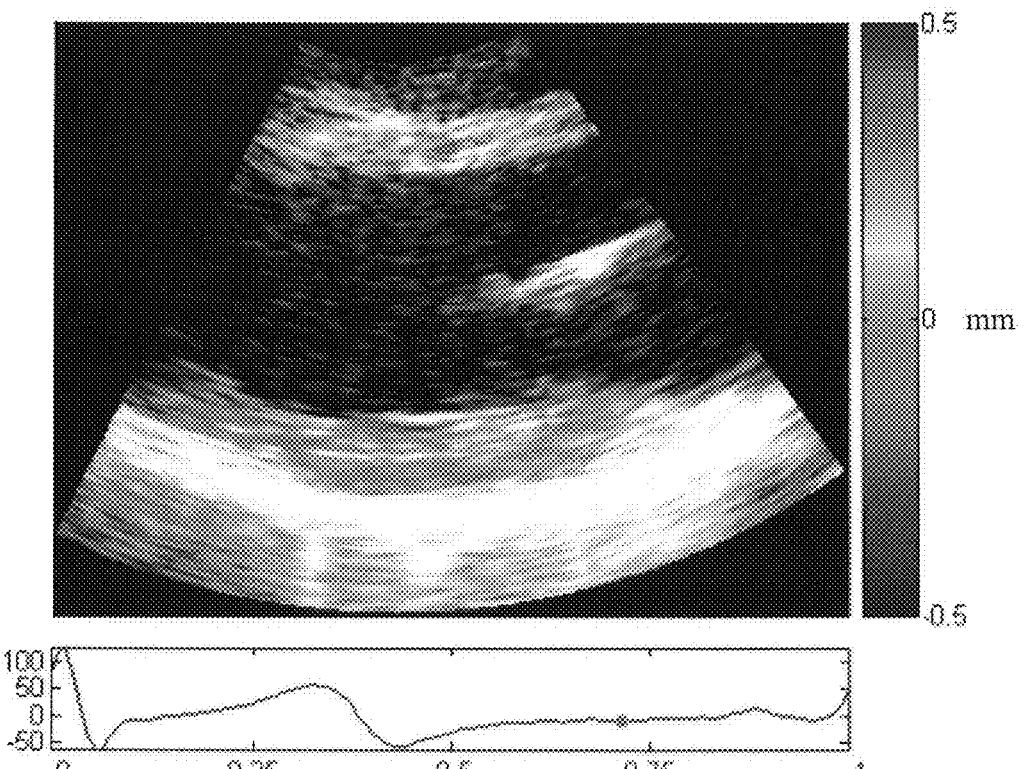
Figure 21I:
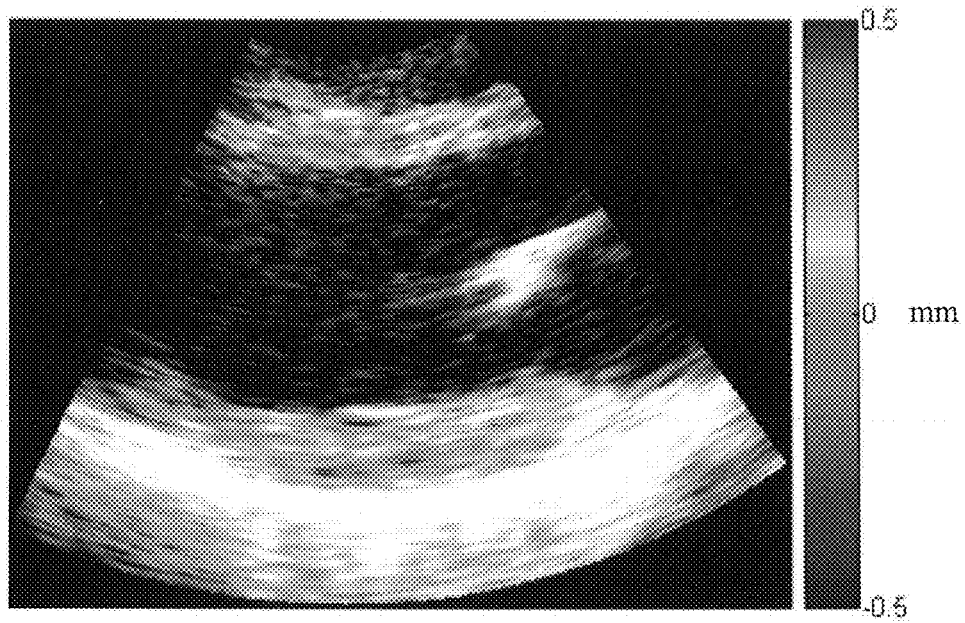
Figure 21J:
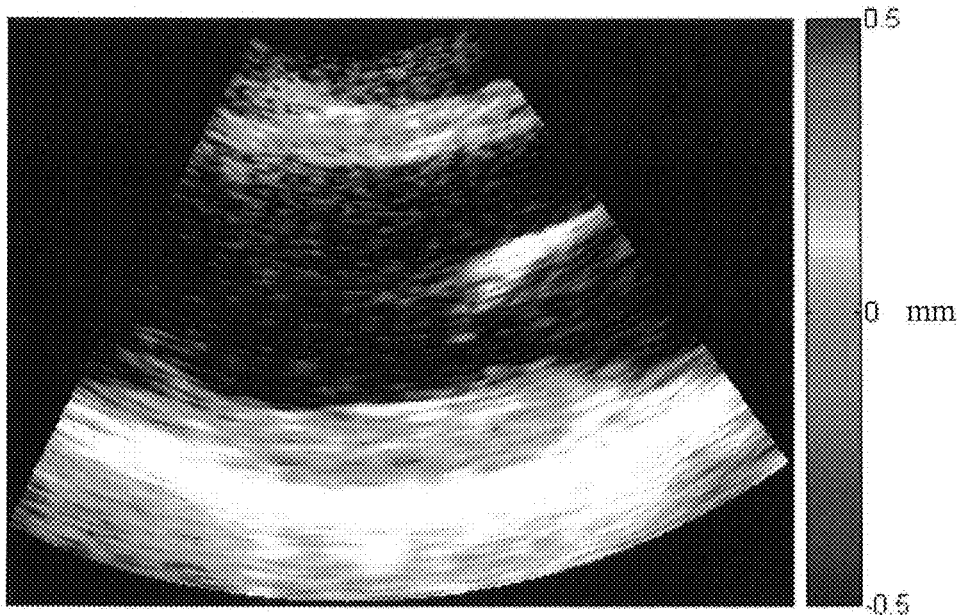
Figure 21K:
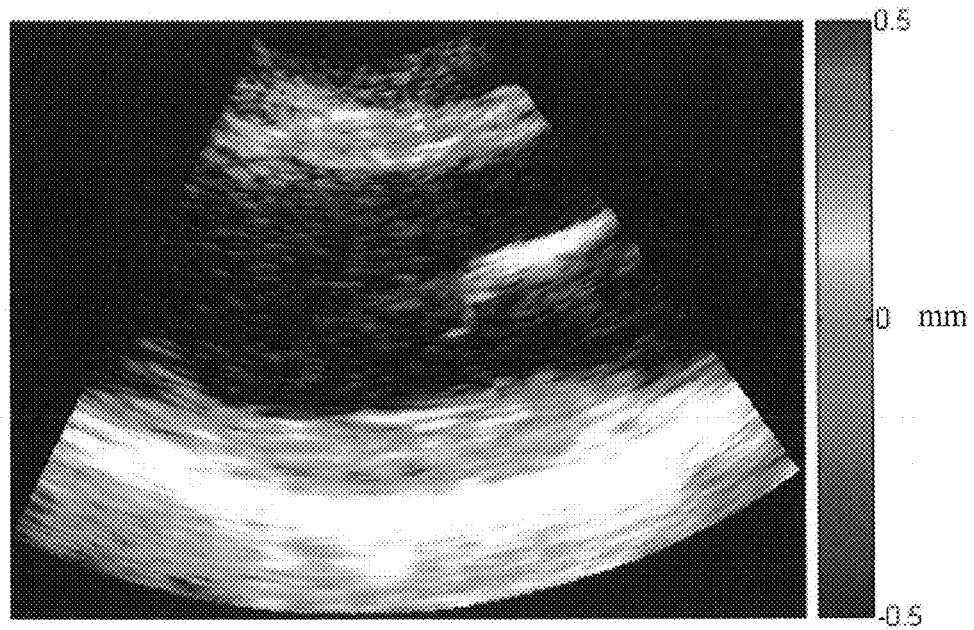
Figure 21L:
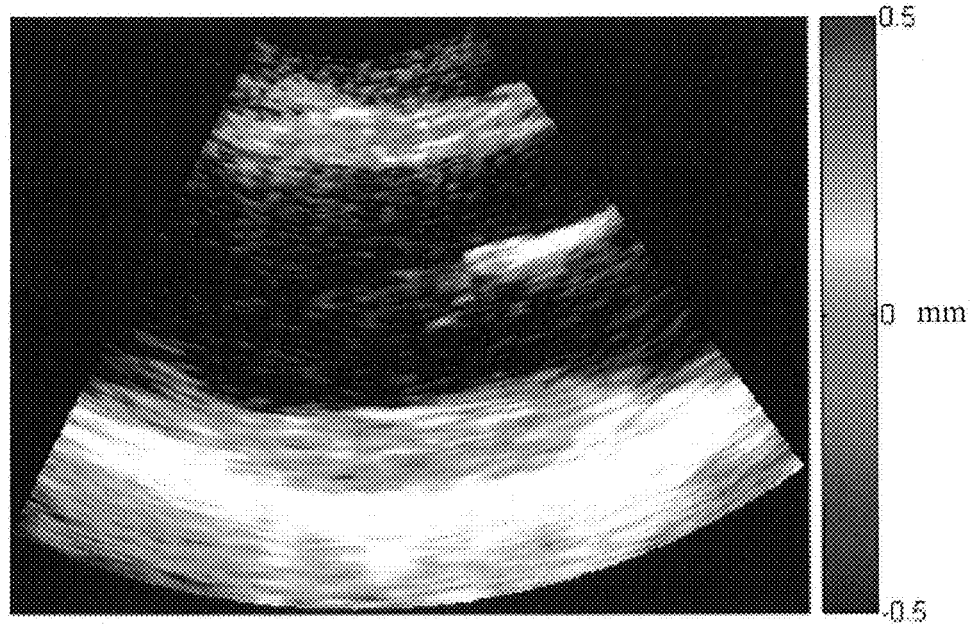

Similarly, FIGS. 20A and 21A are grayscale images corresponding to FIGS. 20 and 21, respectively. In the grayscale images of FIGS. 20A and 21A, the displacement has been separated from the B-mode images for ease of viewing. Thus each image in FIGS. 20 and 21 corresponds to two images in each of FIGS. 20A and 21A—one for the B-mode image, the other for the displacement.

4. High Frame Rate Strain Images for Systole and Diastole—FIGS. 22-23 and 22A-23A Similarly, FIGS. 22(a)-(n) and 23(a)-(n) show a series of composite strain images made by combining various sectors according to an exemplary embodiment of the present invention, thus obtaining a high frame rate of, for example, 136 frames per second. The time point within the cardiac cycle at which each image has been acquired is indicated by the solid ball below each image. As above for the low frame rate images, the strain is overlaid in color on the B-mode images.

Figure 22A:
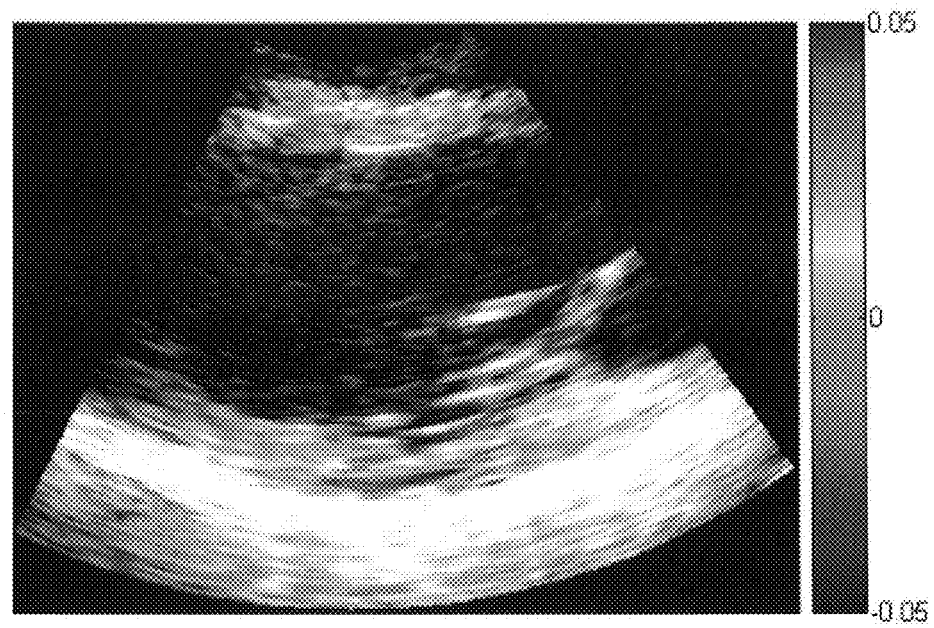
FIGS. 22A(a1),(a2)-(n1),(n2) are grayscale images corresponding to FIGS. 22($a$)-($n$) which show the strain separately from the B-mode image.
Figure 22B:
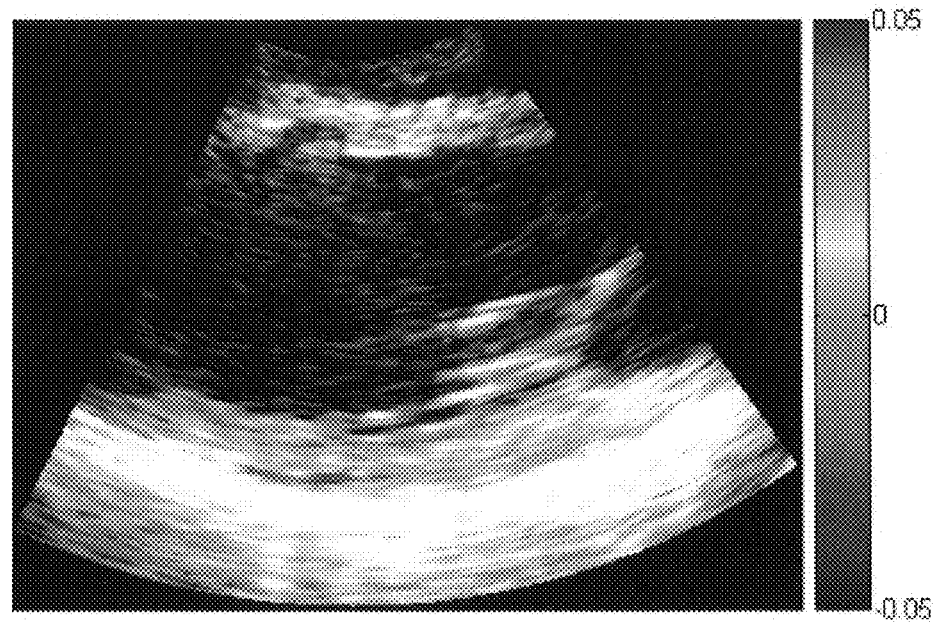
FIGS. 22($a$)-($n$) depict incremental axial strain images during systole at 136 frames per second according to an exemplary embodiment of the present invention.
Figure 22C:
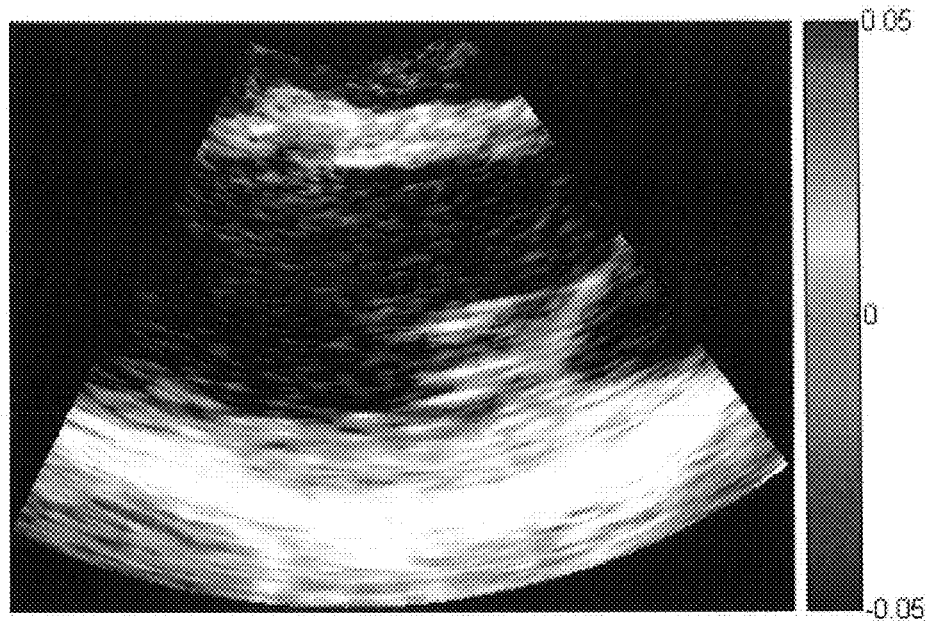
Figure 22D:
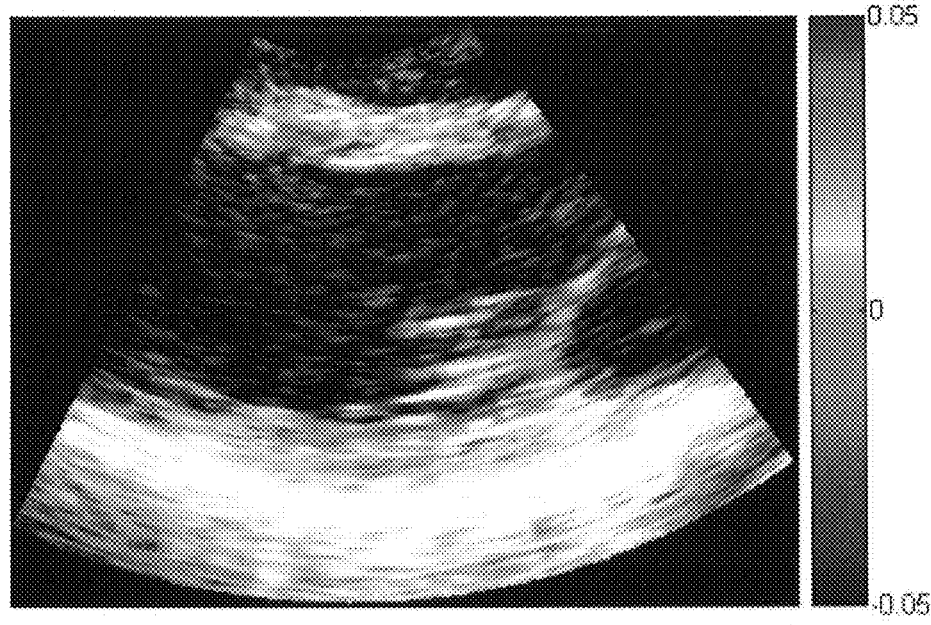
Figure 22E:
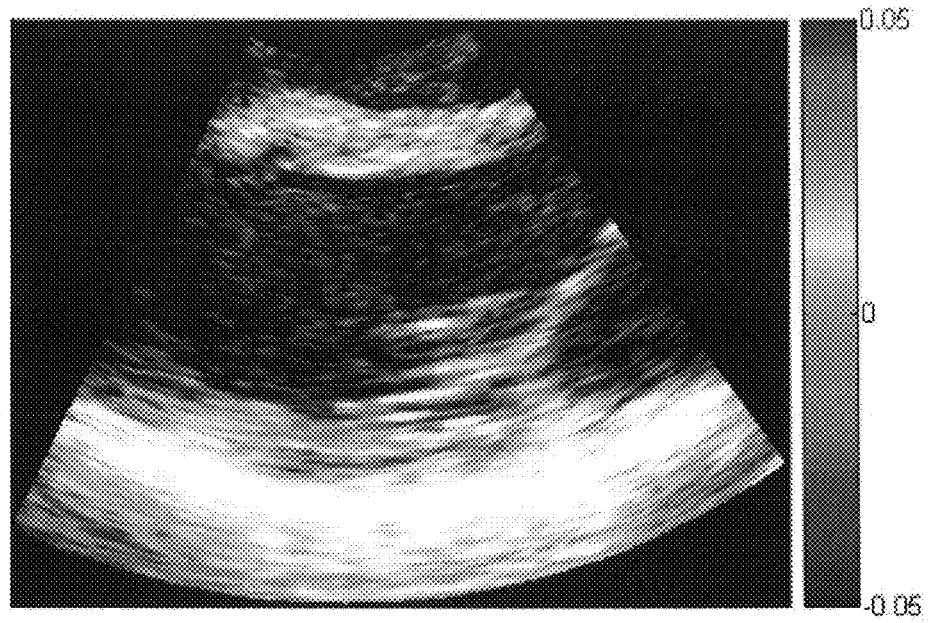
Figure 22F:
Figure 22I:
Figure 22J:
Figure 22K:
Figure 22L:
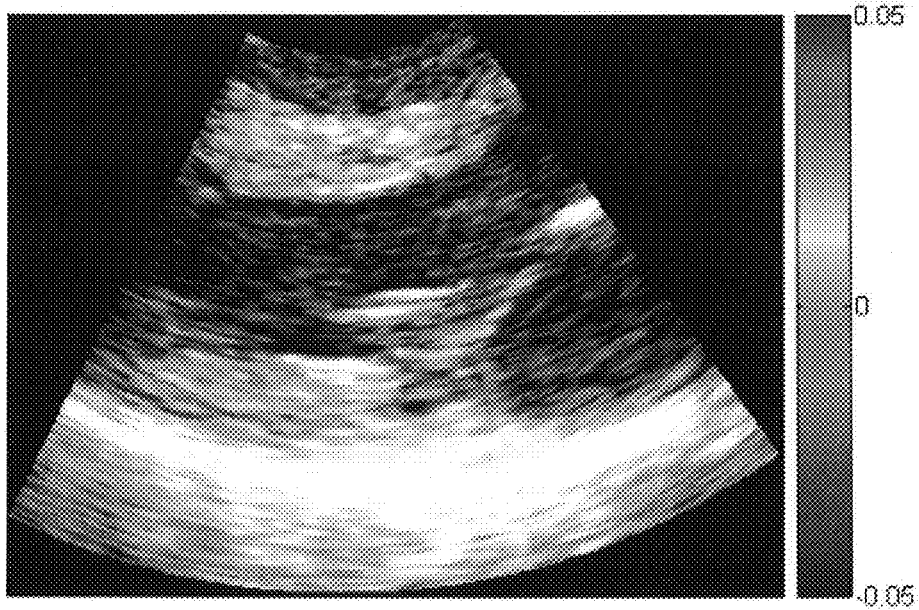
Figure 22M:
Figure 22N:
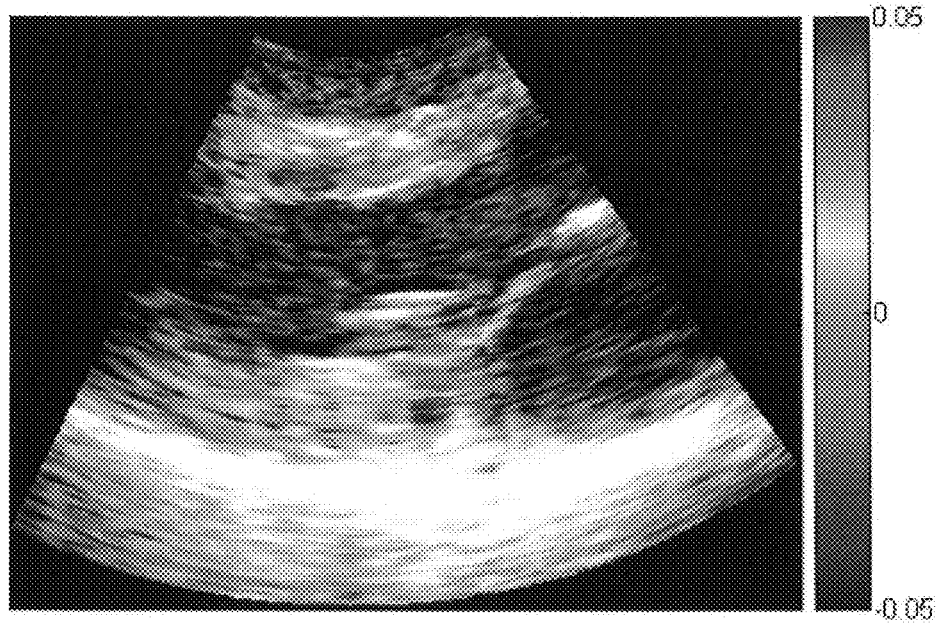
Figure 23A:
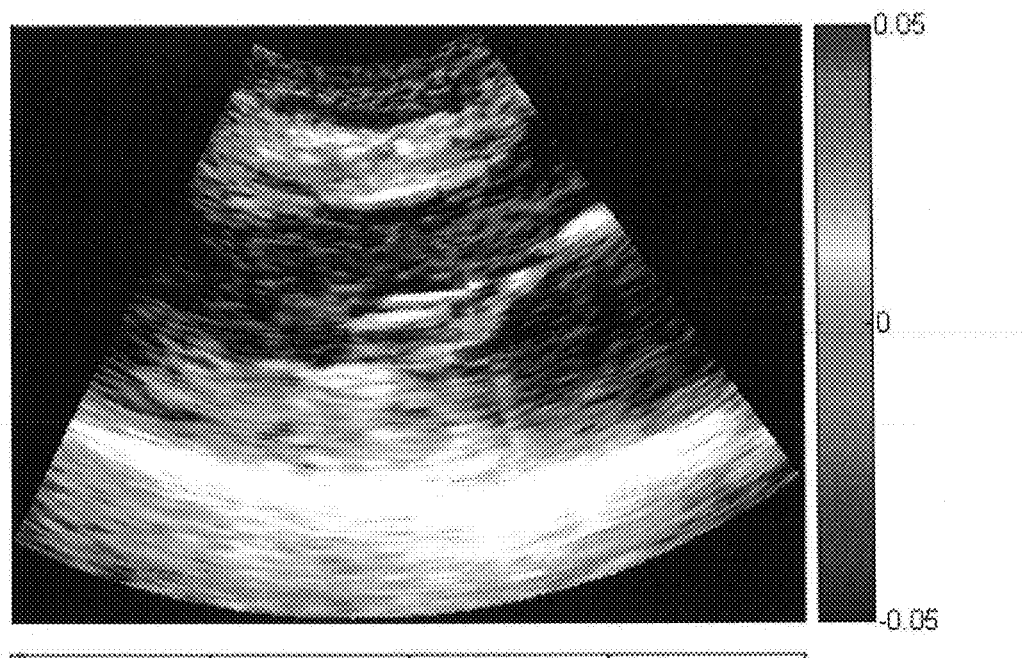
FIGS. 23A(a1),(a2)-(n1),(n2) are grayscale images corresponding to FIGS. 23($a$)-($n$) which show the strain separately from the B-mode image.
Figure 23B:
FIGS. 23($a$)-($n$) depict incremental axial strain images during diastole at 136 frames per second according to an exemplary embodiment of the present invention.
Figure 23C:
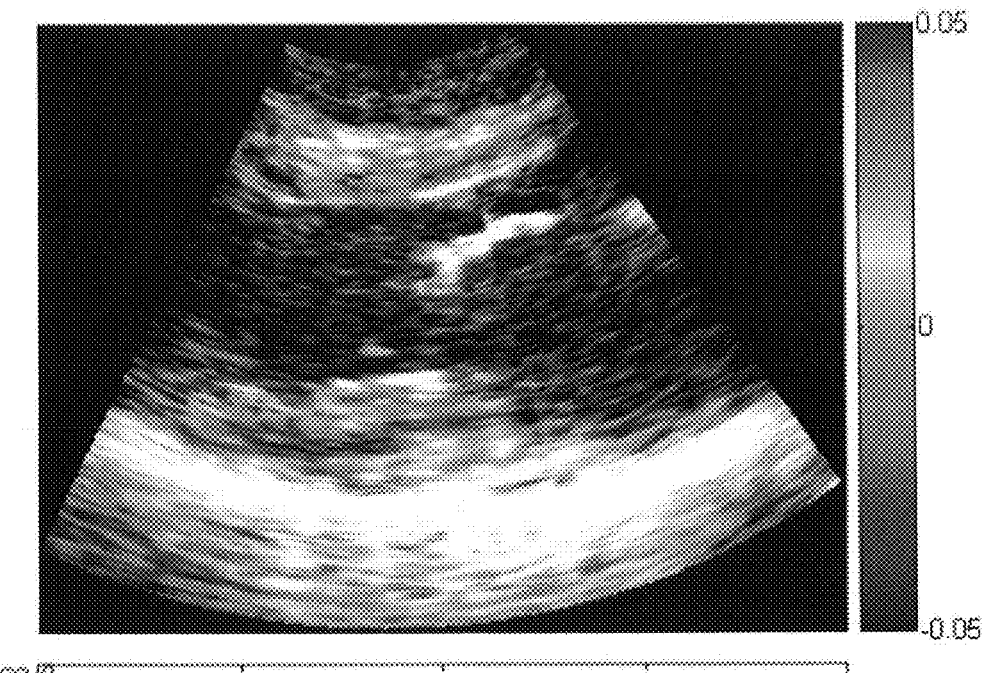
Figure 23D:
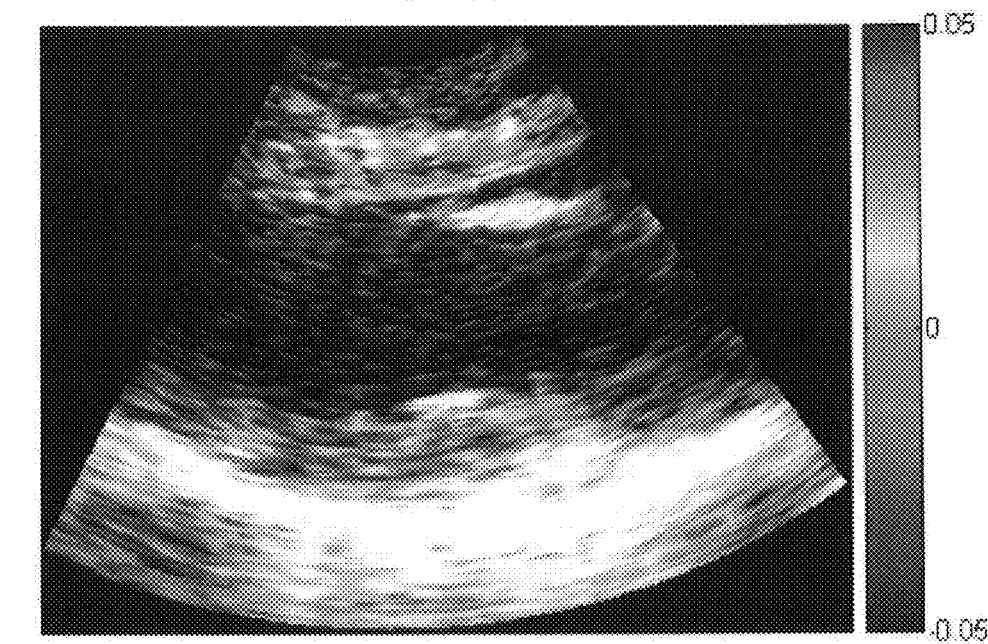
Figure 23E:
Figure 23F:
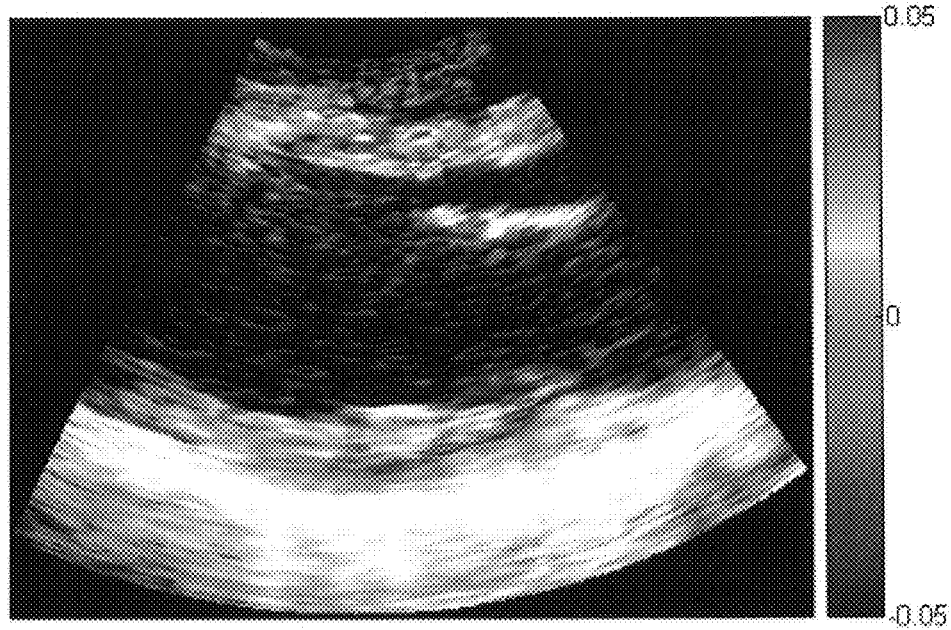
Figure 23G:
Figure 23H:
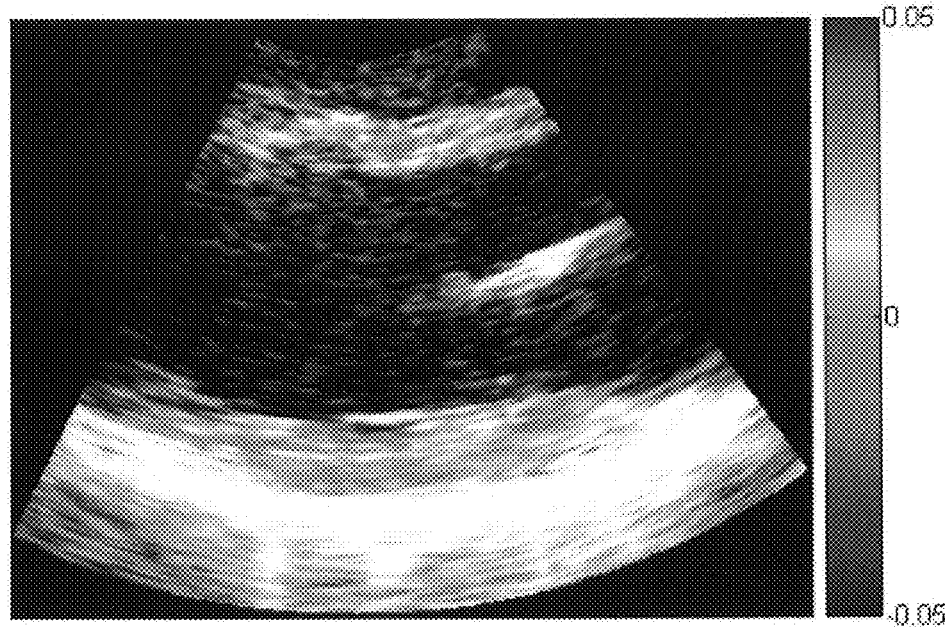
Figure 23I:
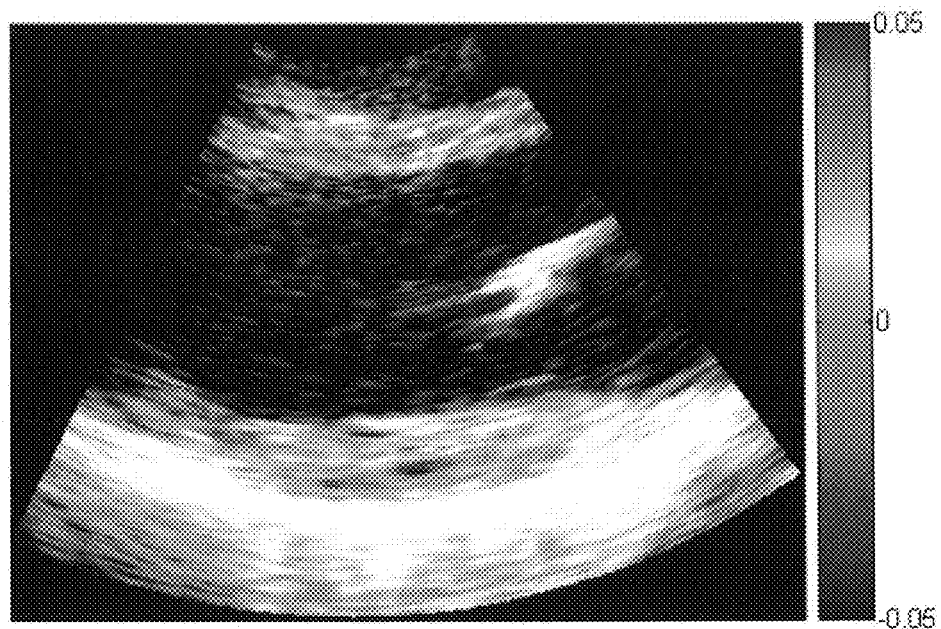
Figure 23J:
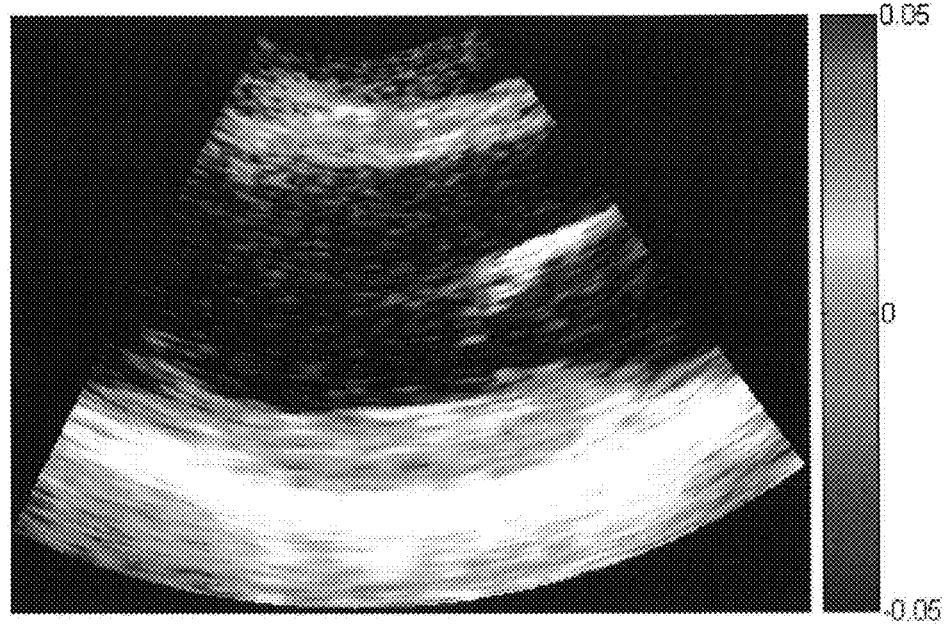
Figure 23K:
Figure 23L:
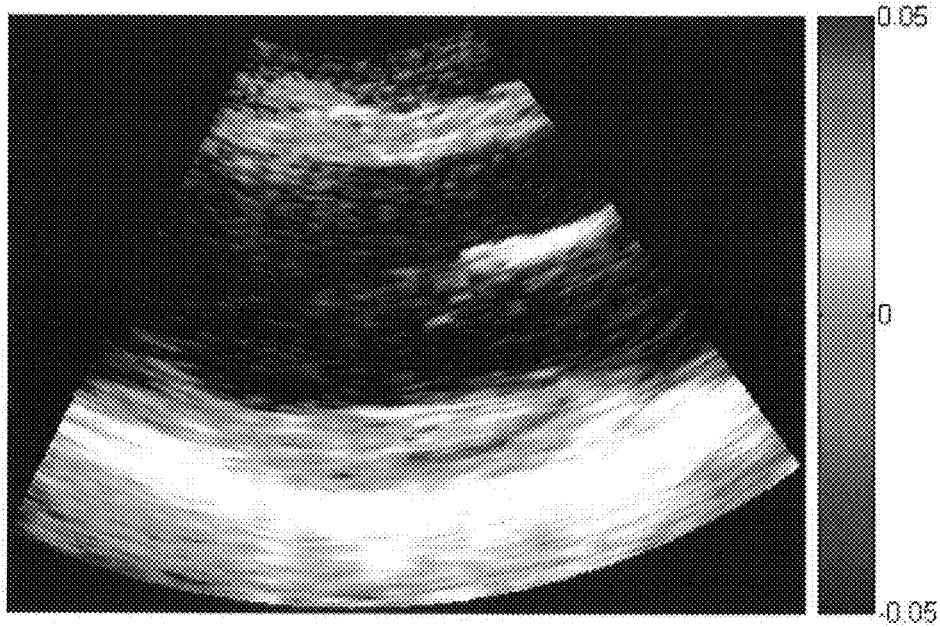

Similarly, FIGS. 22A and 23A are grayscale images corresponding to FIGS. 22 and 23, respectively. In the grayscale images of FIGS. 22A and 23A, the strain has been separated from the B-mode images for ease of viewing. Thus each image in FIGS. 22 and 23 corresponds to two images in FIGS. 22A and 23A—one for the B-mode image, the other for the strain.

Exemplary Source Code and Exemplary Systems—Conventional Ultrasound Machines

As referenced above, the computer program listing appendix includes a set of exemplary source code files implementing an exemplary embodiment of the present invention. The exemplary code is written in Matlab™, and implements various sub-processes depicted in FIG. 3, and was used to generate the exemplary images depicted in FIGS. 4-14, as described above. The code was implemented on a conventional ultrasound machine, and can be implemented or adapted to process signals obtained from most standard ultrasound machines using known techniques.

Additionally, the exemplary code provided in the computer program listing appendix can, for example, be adapted for use in a programmable ultrasound machine, such as for example, the Ultrasonix Sonix RP system. The Sonix RP system, for example, offers frame rate capabilities up to 700 fps as well as access to the beamformer, i.e., automatic sector acquisition compared with manual sector acquisition described in the previous section. This higher frame rate can, for example, ensure higher strain quality, as has been seen in a preliminary in vivo human study performed by the inventors. In addition to the higher frame rate advantages of such a platform, access to the beamformer not only allows for the selection of optimal acoustic parameters, such as, for example, frequency, aperture and beamwidth, but it can also, for example, allow for further automation of the methods of the present invention. An exemplary implementation of the present invention on such a platform was performed by the inventors, as next described.

Examplary Implementation—Programmable Ultrasound Machine

The following describes an exemplary implementation of an exemplary embodiment of the present invention. The description presents additional details, considerations and functionalities of various embodiments of the present invention.

As described above, high frame-rate ultrasound Radio-Frequency (RF) data acquisition is critical for myocardial elastography and imaging of the transient electromechanical wave propagation in cardiac and vascular tissues. To overcome the frame-rate limitations on routine ultrasound systems, the inventors developed an automated method for retrospective, multi-sector acquisition through synchronized electrocardiogram (ECG) gating on a clinical Ultrasonix RP system (Ultrasonix Medical Corp. Burnaby, Canada). A computer multithread technique was applied to acquire ECG and ultrasound RF signals simultaneously. The method achieved high spatial resolution (64-line beam density) and high temporal resolution (frame rate of 481 Hz) at a total imaging depth of 11 cm, 100% full view. A normal human heart left ventricle and a normal aorta were imaged using the same technique in vivo. Composite RF and B-scan full view frames were reconstructed by retrospectively combining all small-sector RF signals. The in-plane (lateral and axial) displacements of both long-axis and short-axis views of a healthy human left ventricle were calculated using an RF-based elastographic technique comprising 1D cross-correlation and recorrelation methods (windows size 6.9 mm, overlap 80%). A sequence of the electromechanical activation of the heart was observed through mechanical pulse waves propagating along septum (from base to apex) and posterior wall (from apex to base) during systole in human in vivo. Exemplary embodiments of this technique can, for example, expand the potential of echocardiography for quantitatively noninvasive diagnosis of cardiovascular diseases such as, for example, myocardial infarction, aneurism and early stage atherosclerosis.

Heart diseases, such as ischemia and infarction, are a growing problem world wide. It is highly useful for the early diagnosis of such cardiac disease to noninvasively detect abnormal patterns of regional myocardial deformation caused by malfunction of the electromechanical conduction. Magnetic resonance (MR) cardiac tagging has been shown capable of quantifying the mechanical properties of the myocardium at high precision. However, the relatively low spatial resolution and the low temporal resolution limited the use of tagged magnetic resonance imaging (tMRI) for the detection of the transient mechanical vibrations that are constantly generated by the heart and the arteries. Therefore, echocardiography has been the predominant imaging modality in diagnostic cardiology owning to its real time, high temporal resolution capability. Tissue doppler imaging (TDI), strain rate imaging (SRI) and elastography imaging have been introduced to image the regional motion of the myocardium noninvasively. However, their major applications remain in the global motion of the heart over a complete cardiac cycle due to the current low frame rate.

In echocardiography, a high temporal resolution, typically <5 ms, is required to observe the detailed myocardium activities, such as, for example, the fast electrical conductive sequencing pattern for early detection of cardiac diseases. The electrical excitation, which induces the contraction and relaxation of the cardiac muscle, results in a strong electromechanical wave that propagates in the myocardium at a speed up to 5 m/s. Several methods had been developed to increase the ultrasound frame rate such as coded-excitation ultrasound imaging and parallel processing techniques. Most often these methods sacrificed the field of view or ultrasound beam number to increase the frame rate. This is not favorable in clinical study and is not optimal in general. ECG triggering or gating can be used to achieve high frame rates by reconstructing RF lines at different cardiac cycle especially for large field of view and high spatial resolution. The assumption of ECG triggering or gating lies in that the heart rate does not vary significantly, and that the myocardial function is effectively identical at every cardiac cycle. As was observed (and as shown in FIG. 26), ECG signals were very similar during systole for multiple cycles but could have up to a 10% length difference during diastole. Thus, all ECGs and corresponding RF frames taken for different sectors were interpolated to the same length to get the maximum similarity for each cardiac cycle. In contrast to conventional methods that transfer ECG signals to an arbitrary waveform generator and use the ECG R-wave as a trigger to control the transmitted pulses with synchronization implemented in hardware, a computer multithread technique for data acquisition was applied that significantly lowered the system cost without losing synchronization resolution.

High frequency, high resolution small animal ultrasound systems have become commercially available, such as, for example, the Vevo 770 system (VisualSonics Inc. Toronto, Ontario, Canada). However, there is still lack of high frame rate clinical systems for human cardiovascular study. This is largely because most commercial ultrasound systems are used effectively in clinical specialty areas where B-mode images are evaluated as the "gold standard." Valuable frequency and speckle information carried by the RF echo signals is lost during conversion and compression, which occurs internally in the system. The Sonix RP system (Ultrasonix Medical Corporation, Burnaby, BC, Canada) is an open architecture system which can allow developers to easily control system parameters such as beam line density, sector size, and digitized RF signal acquisition etc. In the exemplary implementation, an Ultrasonix 500RP research platform was used to measure the ultrasound backscatter and attenuation coefficient.

Using a Sonix RP ultrasound system, an elasticity imaging method with a frame rate (480 Hz) five times higher than traditional ultrasound machine (~90 Hz) was obtained. 64 lines were kept for full sector view to reserve the high lateral resolution. The region of interest (ROI) was initially decreased to achieve the high frame rate. Then, an ECG gating technique was applied to utilize RF signals acquired during multiple cardiac cycles to retrospectively reconstruct small ROIs to a complete 100% full view cine-loop. Digitized RF and ECG signals were acquired through two computer threads running in parallel. In the exemplary implementation, local displacements were typically computed offline by applying a cross-correlation method to the pre compression ultrasonic radio frequency (RF) echo signals. Displacements were then estimated along the beam axis and displayed as an image referred to as an elastogram. The results obtained clearly showed electromechanical wave propagation in human heart during systole and a pulse wave propagating along a human aorta.

Data Acquisition

A clinical phased array transducer (Ultrasonix model # $P_4$-2/20) operating at 3.3 MHz was used for human cardiac and vascular imaging. In a phased array transducer, more than one line can be acquired at the same time rather than line-by-line data acquisition by a signal element transducer to achieve high data consistency. For further development, if sector size is decreased to only one transmission line, the method could be reduced to single element scan imaging with an even higher frame rate. A separate ECG module (MCC Gesellschaft für in Medizin und Technik mbH & Co. KG) was connected to the Sonix RP computer base running windows XP with RS232 serial interface. Two channels were recorded, from which three Einthoven and Goldberger leads were depicted. The signals were recorded digitally, processed and transmitted to the host via PC serial interface with a baud rate of 9600 baud (1 start bit, 8 data bits, 1 stop bit, no parity). The maximum sampling frequency rate for this ECG module is 300 points per second.

Since the ultrasound RF and ECG data were two separate modules, synchronized data acquisition was critical for multi-sector combination method to achieve high frame rate through ECG gating technique. An automated custom designed program was developed in C++ based on the Ulterius SDK API to control, for example, both the Sonix RP system and the ECG module for synchronized ultrasound radio frequency (RF) and electrocardiogram (ECG) signal acquisition. Digitized ECG signals were stored in a computer using multi-thread technique which was in synchronization with ultrasound RF signal.

FIG. 24 provides exemplary process flow charts from which an exemplary C++ program that was created. The flow charts illustrate functionality for RF and ECG signal acquisition: a) Ultrasonix RF data acquisition. b) ECG module data acquisition. c) ECG and ECG time stamp buffer. d) RF frame and RF frame time stamp buffer.

When imaging began, raw ultrasound RF data for each frame was stored in the system cine buffer and retrieved by a custom designed "Callback" function. The "Callback" function had the capability of recording the occurrence time of each frame by a "::QueryPerformanceCounter( )" function. This time was used as a reference for ECG gating. The ultrasound RF signals were then stored line by line and then frame by frame in the computer memory sequentially. A separate computer thread running in parallel with the "Callback" function retrieved the digitized ECG signal points with its occurrence time from the serial port buffer. The total CPU usage was 70% on an Intel Pentium 4 2.99 GHz CPU based system, with 4 Gbyte memory. All RF and ECG signals were acquired and stored in real time. Both threads started to store data in physical memory simultaneously when the start-recording flag was set to TRUE(1), and stopped when the flag was set to FALSE(0). All RF and ECG signals for the various different sectors were saved in memory first and then written to the computer hard drive after the scanning. The total memory allocation for the data acquisition program was around 700 MB.

Composite Processing Through ECG R Wave Gating

For each sector, two sets of data, an ultrasound RF signal at a frame rate of 481 Hz and an ECG signal at 300 points per second, were recorded through two threads as described above. For every sector, the R-waves of the ECG signals were obtained through automatic peak detection. The corresponding time stamps of the R-wave peaks were used to search for the RF frame with the occurrence time most closely to the R wave occurrence time by the following method:

$$\text{Min}(ABS(\text{Time\_stamp}_{RF}(i)-\text{Time\_stamp}_{ECG\_R-wave}))$$
$$i=1, 2, \ldots, N$$

$$\min(abs(\text{Time\_Stamp}_{RF}(i)-\text{Time\_Stamp}_{ECG\_R-wavre}))$$
$$i=1, 2, \ldots, N,$$

where $\text{Time\_Stamp}_{ECG\_R-wave}$ denotes the occurrence time of one of the ECG R wave peaks per sector, $\text{Time\_Stamp}_{RF}$ denotes the RF frame occurrence time, N is the total number of RF frames acquired together with ECG, and min and abs are Matlab functions used to find the minimum and absolute values of an array.

RF frames between two consecutive ECG R-waves were extracted from the original file representing one cycle of cardiac motion. Ideally the ECG cycle corresponding to each sector can be of identical duration to those of other sectors. The ith (i=1, 2, . . . ) frames of each sector can then be recombined in sequence to get the ith frame of the 100% view as is illustrated in FIG. 25. However one challenge for any ECG gated/triggered retrospective high frame rate ultrasound B mode imaging is heart rate variability. As noted, the duration of an ECG can vary by up to 10% per cycle, and the number of frames for each sector varies accordingly. As shown in FIG. 26, ECG signals during systole have very little variation. Therefore, an accurate method to solve the ECG arrhythmic is to stretch the diastolic part of the ECGs and the corresponding RF frames to the same length to achieve high similarity. One useful measure for the duration of systole is approximately $T_{es}=\sqrt{\Delta T}\cdot 0.343$ s, where $\Delta T$ is the length in seconds of the cardiac cycle. Thus the systolic part of ECG can remain unchanged and the diastolic part of the ECG was interpolated to the maximum length of all seven ECG signals. The corresponding 2D RF frames were also linearly interpolated to the maximum length of the all sector RF frame sequence for better recombination.

FIG. 25 illustrates an ECG-gated multi-sector combination technique for high frame rate, full-view ultrasound imaging. In the example of FIG. 25, a total of seven sectors at different angles were acquired in a continuous sequence during each experiment. ECG and RF frame data are shortened according to the time stamp associated with each data point or frame for one cardiac cycle. Corresponding small sector frames were, for example, recombined to generate full view ultrasound images.

FIG. 26 illustrates irregular ECG interpolation. ECGs during systole, approximately $T_{es}=\sqrt{\Delta T}\cdot 0.343$ s, remain unchanged where $T_{es}$ is the duration of the systole and $\Delta T$ is the duration of the whole cardiac cycle. All seven ECGs after the slashed line were, for example, linearly interpolated to the maximum length of these signals. The corresponding RF frames associated with each ECG were also interpolated to the maximum length of these RF by linearly 2D interpolation.

Motion Estimation

The axial displacement was estimated off-line using the normalized cross-correlation. The RF window size was equal to 6.9 mm and the window overlap was equal to 80%, deemed enough to retain good axial resolution. In the displacement estimation, the parabolic interpolation was applied to the cross-correlation function in order to further improve the precision. The displacements were then estimated using pairs of consecutive RF frames. To reduce the noise amplification effect of the gradient operator in the strain calculation, a linear Savitzky-Golay differentiation filter with a length of seven samples (140 um) was used to estimate the axial strains from the displacements. The aforementioned displacements and strains were the instantaneous or incremental displacements and strains occurring between two consecutive frames. Using the incremental displacements over one cardiac cycle, the preset points in the LV wall could be tracked automatically. Therefore, the incremental displacements and strains corresponding to the preset points could be extracted. By accumulating these incremental displacements and strains, the cumulative displacement and strains were obtained and represented the total motion and deformation from the first frame (corresponding to the first R-wave of the ECG), respectively. The displacements were color-coded and superimposed onto the grayscale B-mode images using an overlay blending mode. In the displacement images, only the estimates in the region of interest (ROI) are shown for better interpretation. An ROI was first determined through a 40- to 50-point selection performed manually in the first frame of a B-mode cine-loop (reconstructed from the RF image sequence). The selected points coincided with the myocardial boundaries (i.e., endocardium and epicardium). Using the estimated displacement field, these points could then, for example, be tracked over the entire cardiac cycle, providing the updated ROIs corresponding to different phases. The cumulative strain curve in myocardial elastography may undergo a drift, i.e., the cumulative strain does not return to zero at the end of the cardiac cycle. Thus, the drift in the cumulative displacements and strains was corrected on the assumption that the drift increases linearly with time over the duration of a cardiac cycle. Elastographic methods were implemented in MATLAB 7.1 (MathWorks, Inc., Natick, Mass., USA). The total processing time for a full cardiac cycle in the exemplary implementation was 2 to 3 hours on a PC workstation (Pentium 4 CPU 2.80 GHz, 2 GB RAM).

In Vivo Experiments

An adult healthy female heart was scanned both long axis and short axis view and the aorta with a frame rate of 481 Hz per sector through the custom automated program. The scan was performed with regular clinical ultrasound B-mode scan procedure by an experienced medical sonographer. The system parameters were set at 11 cm acquisition depth and a total of 64 lines for full 100% view. Ultrasound probe frequency was set at 3.3 MHz. Seven sectors were scanned with each sector of a 2-sec scanning time. At this time period, one or two cardiac cycles were recorded since the volunteer's heart rate ranged from 60 to 80 cycles per second. A total of 21-sec was needed for the entire experiment including scanning and data saving. Because respiratory motion can affect the heart position, breath holding was required for better composite images quality during the sector scanning. All seven sectors data was stored in memory and saved to hard drive after the scanning was completed. The patient's heart recovers to the original condition as much as possible during each cardiac cycle and the operator's hand keep still is essential to reconstruct a smooth transition from sector to sector. It is noted that although the total scanning time for a 100% 90 degree B-mode view is minimized by automatically sweeping different sectors, a patient's heart rate variability, breathing and the freehand motion of the transducer probe can pose some issues for accurate combination.

Exemplary Results

Figure 27:
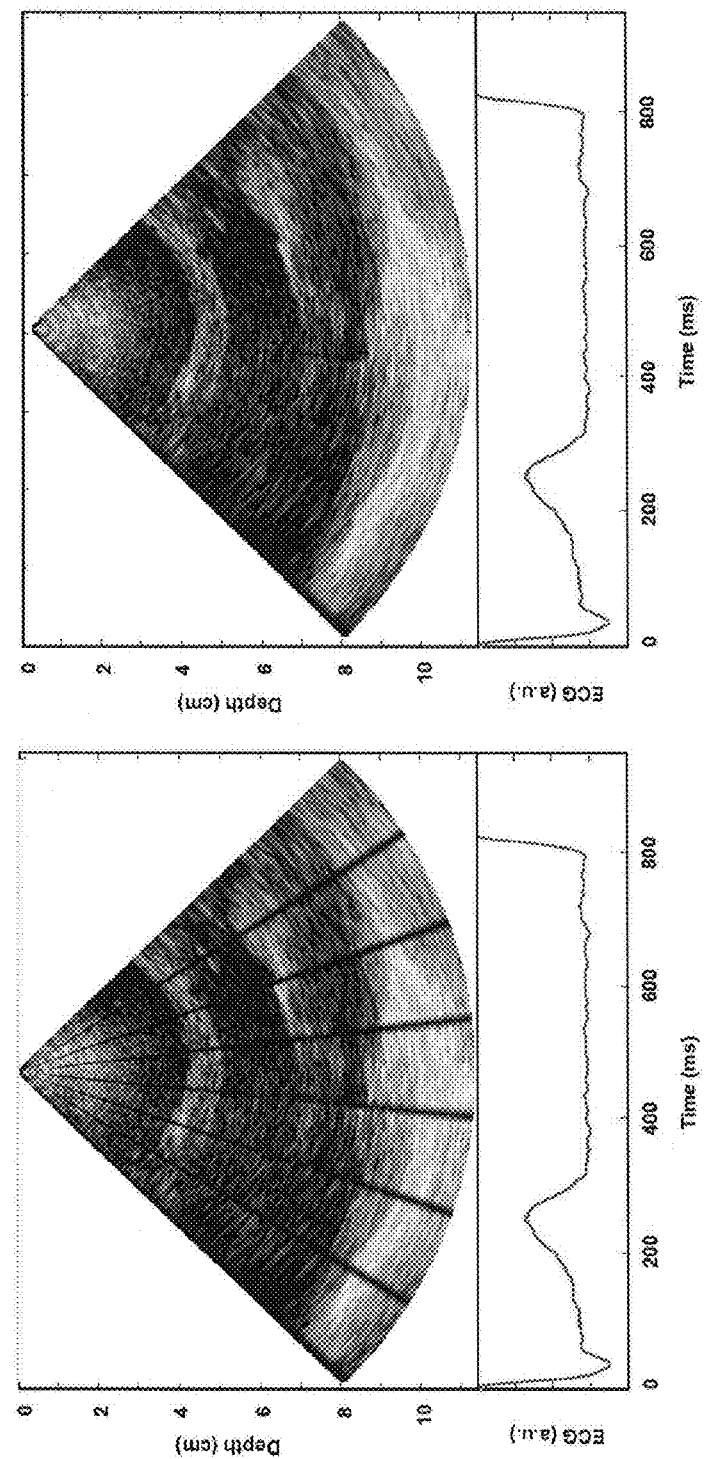
FIG. 27 depict a comparison of image quality before and after overlap processing according to an exemplary embodiment of the present invention.

FIG. 27 depict a comparison of image quality before and after overlap processing of different sectors. FIG. 27(a) (left side of FIG. 27) depicts an example of a seven-sector composite B-mode image of a subject's heart long axis view. A 20% sector was scanned with a sector angle from 36 degree to −36 degree and with a −12 degree increment on Ultrasonix RP system with custom programmed software. A total of seven sectors were acquired, each sector having 12 RF lines. Three lines were cut for each sector since overlap exists between consecutive sectors. The total line density of the full composite view was (12-3)*7=63. An equivalent B-mode image of 100% one sector view is shown on FIG. 27(b) (right side) but at lower frame rate (90 Hz). All B-mode images were reconstructed using the Hilbert transform on the corresponding RF signals through Matlab function. Both images were acquired from start-systole. The quality of the two images is nearly identical and there are no clear transitions from sector to sector which validate the correct RF data acquisition and successfully recombination from ECG gated method.

Figure 28:
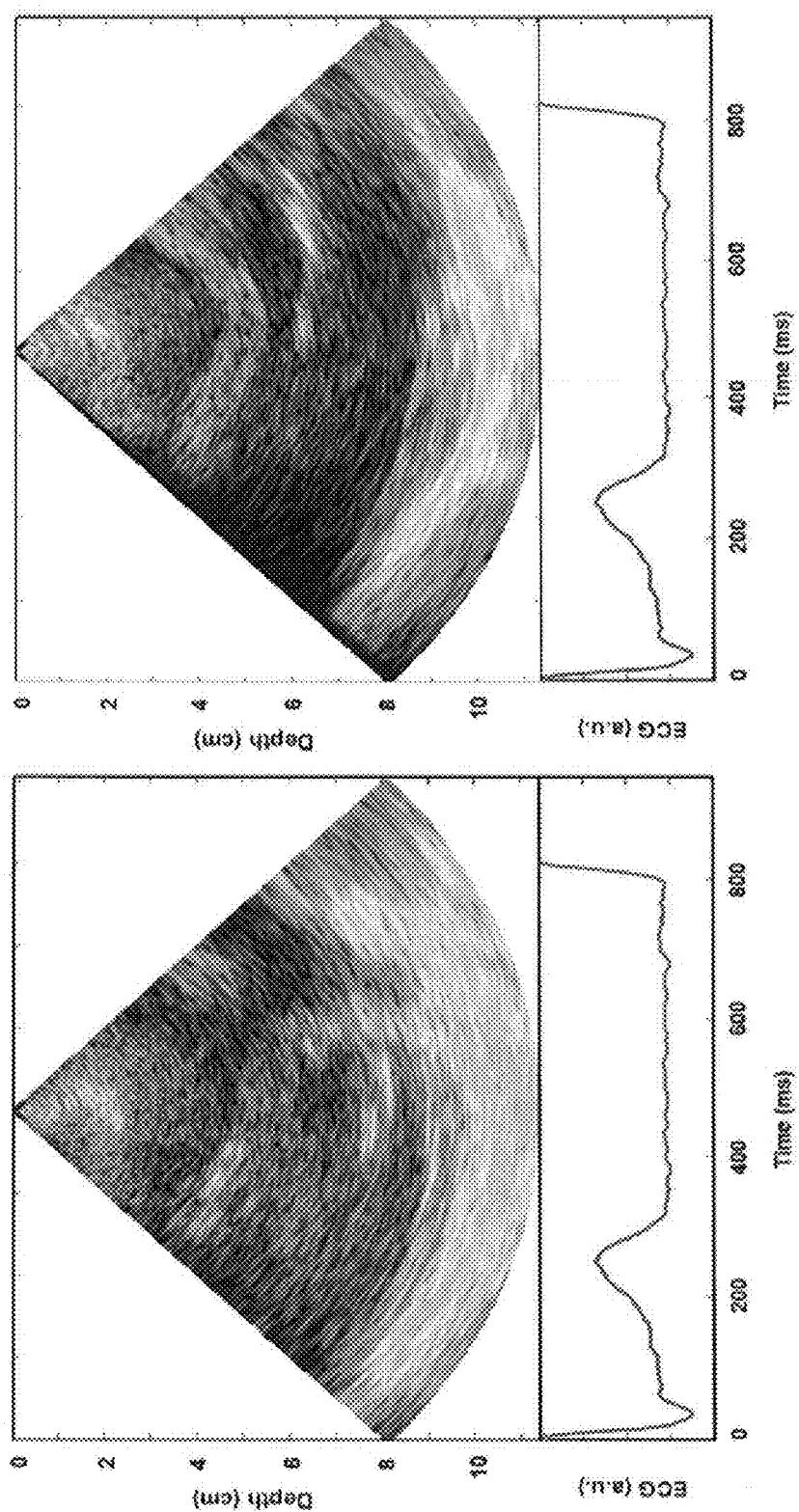
FIG. 28 depict a comparison of 7 sector B-mode composite images of an exemplary heart's long axis view according to an exemplary embodiment of the present invention with 100% B-mode images without comparison.
Figure 29A:
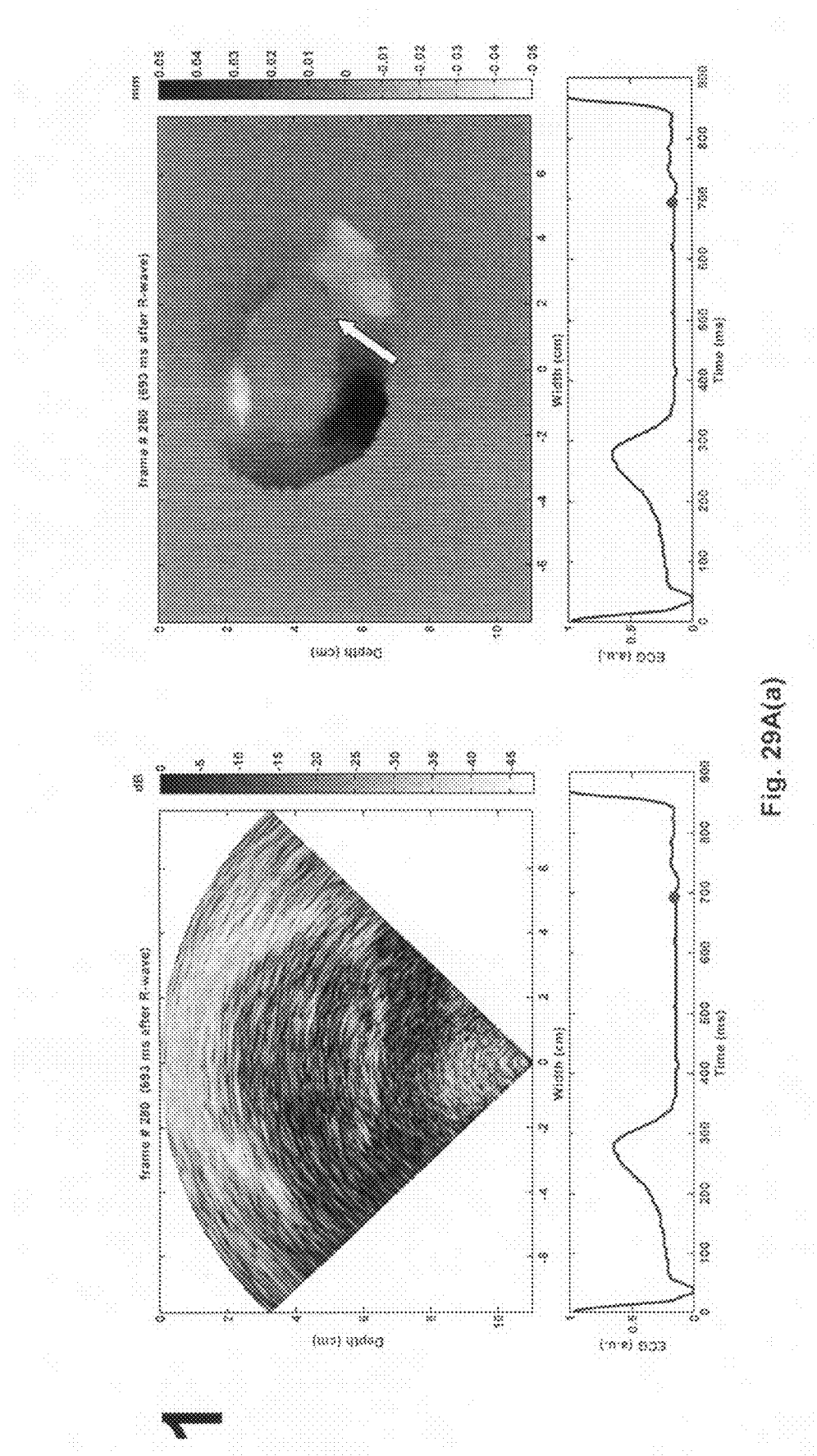
FIGS. 29A(a1),(a2)-(l1),(l2) are grayscale images corresponding to FIGS. 29($a$)-($l$) which show the displacement separately from the B-mode image.
Figure 29A:
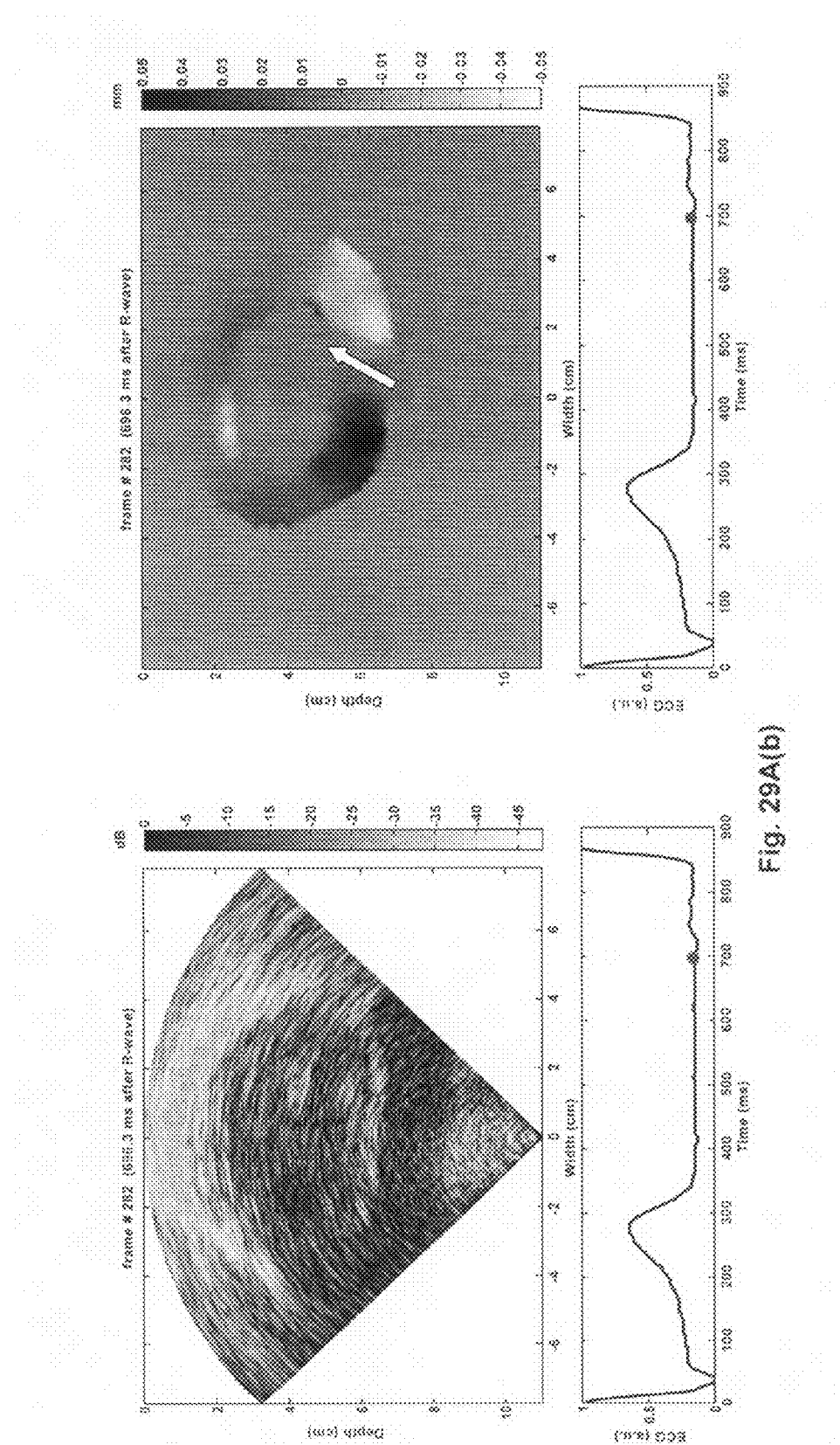
Figure 29A:
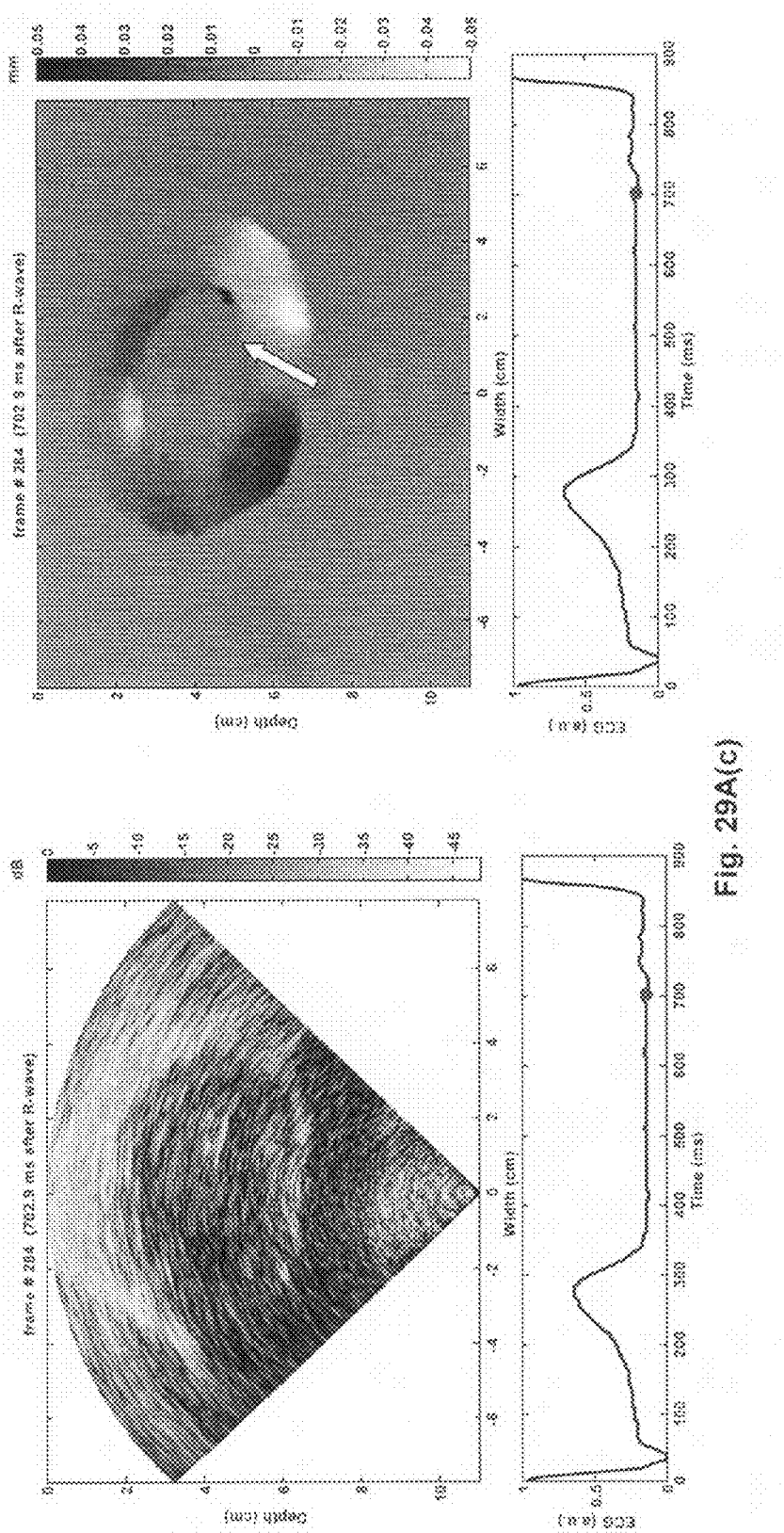
Figure 29A:
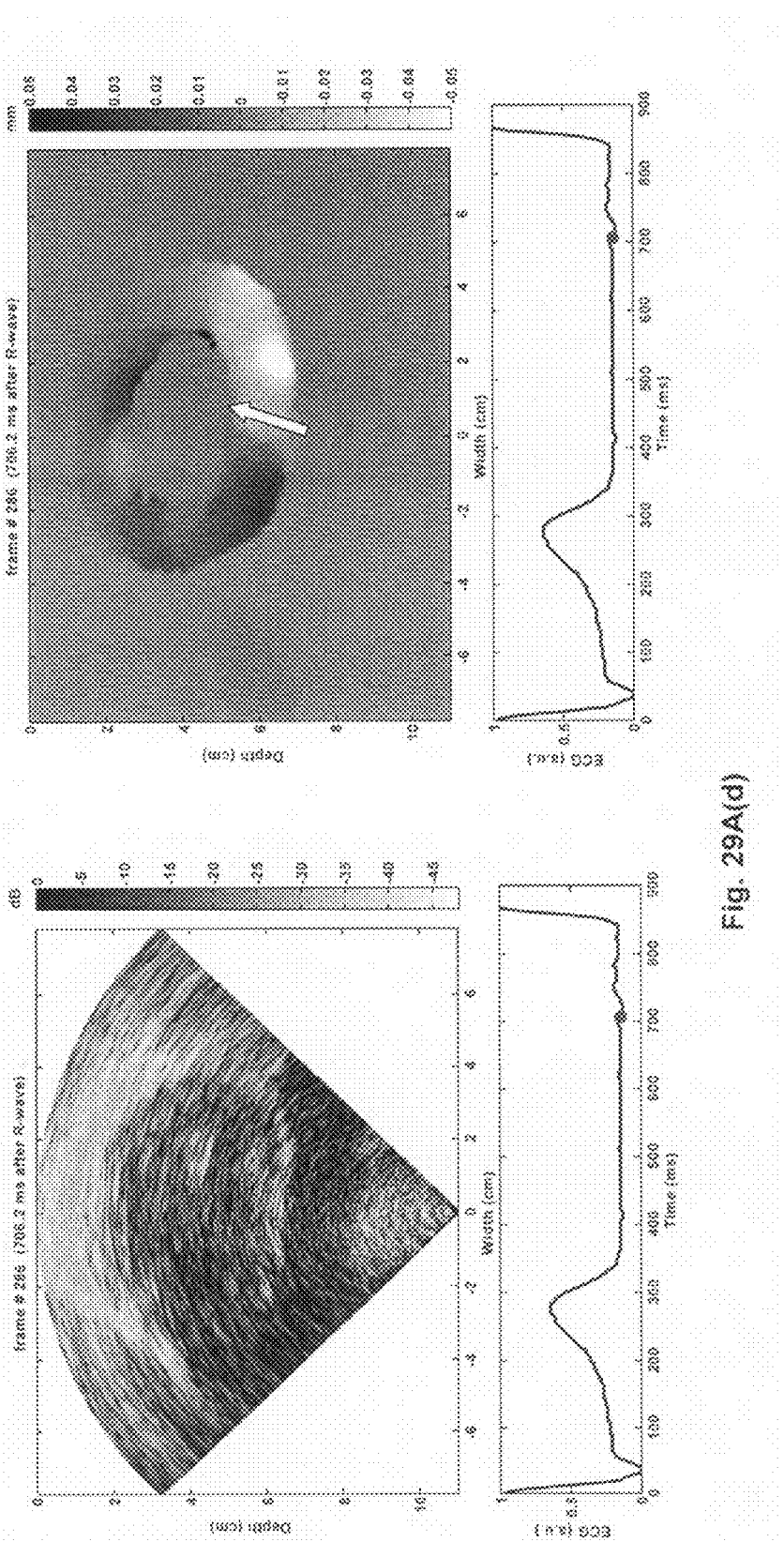
Figure 29A:
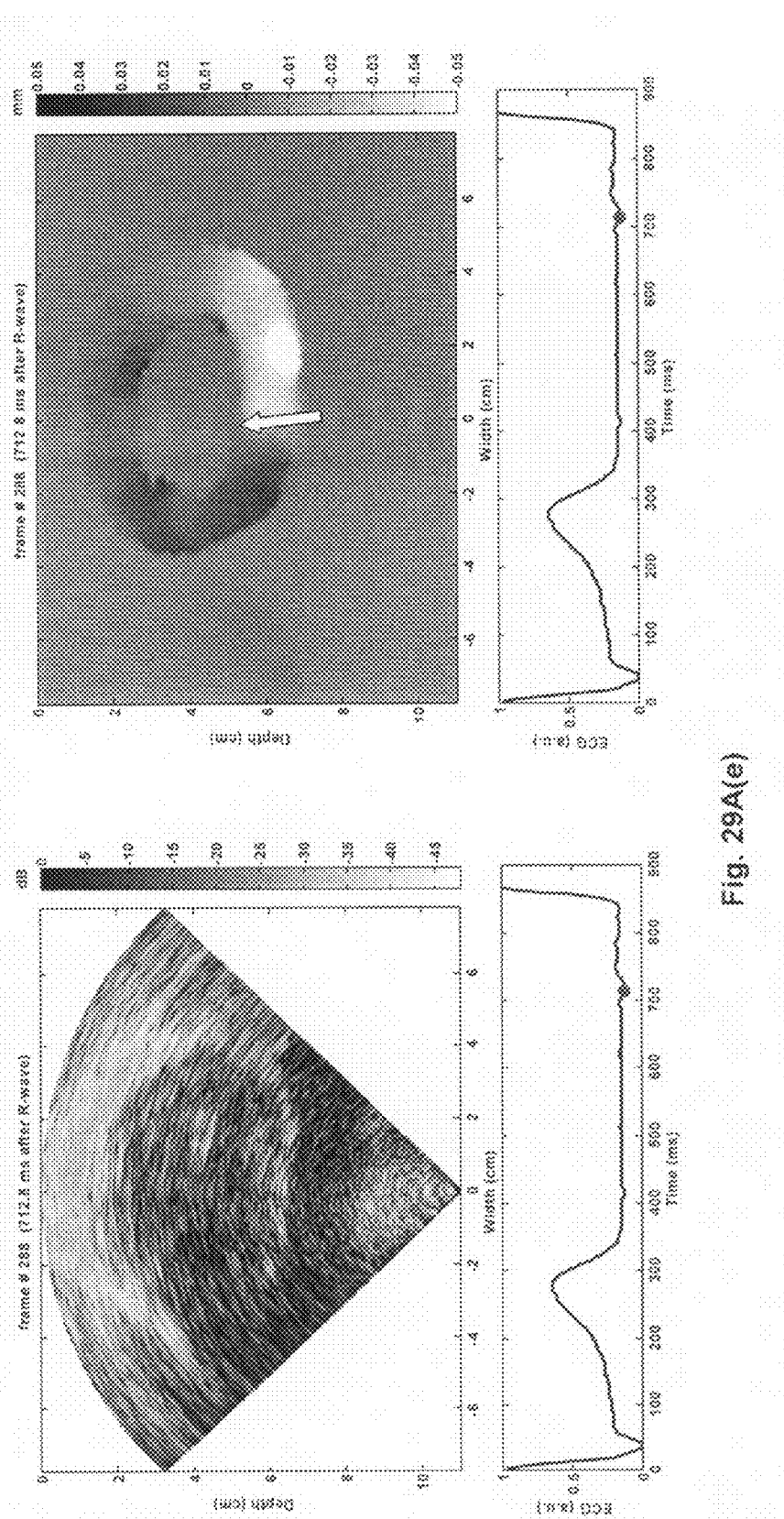
Figure 29A:
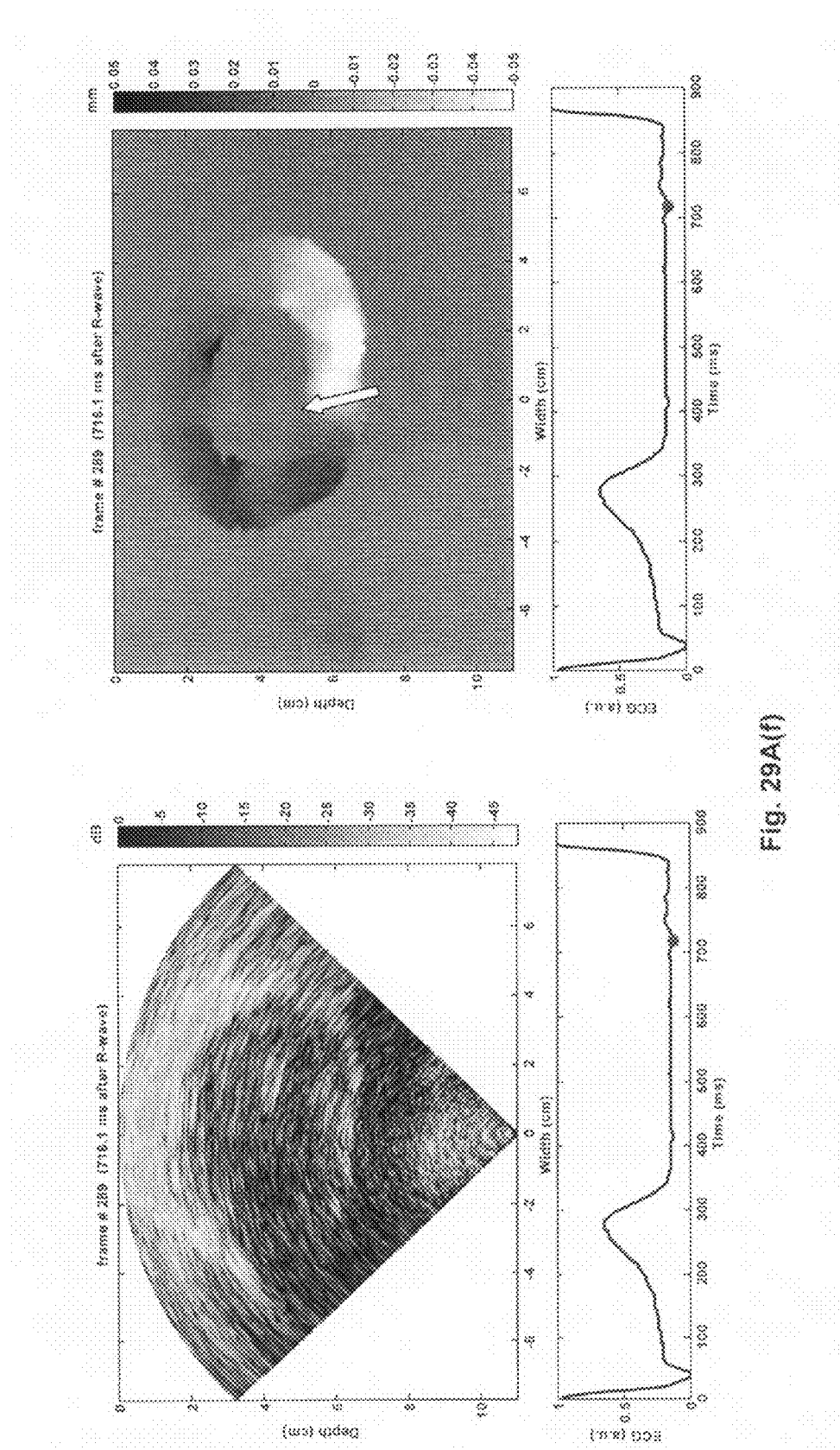
Figure 29A:
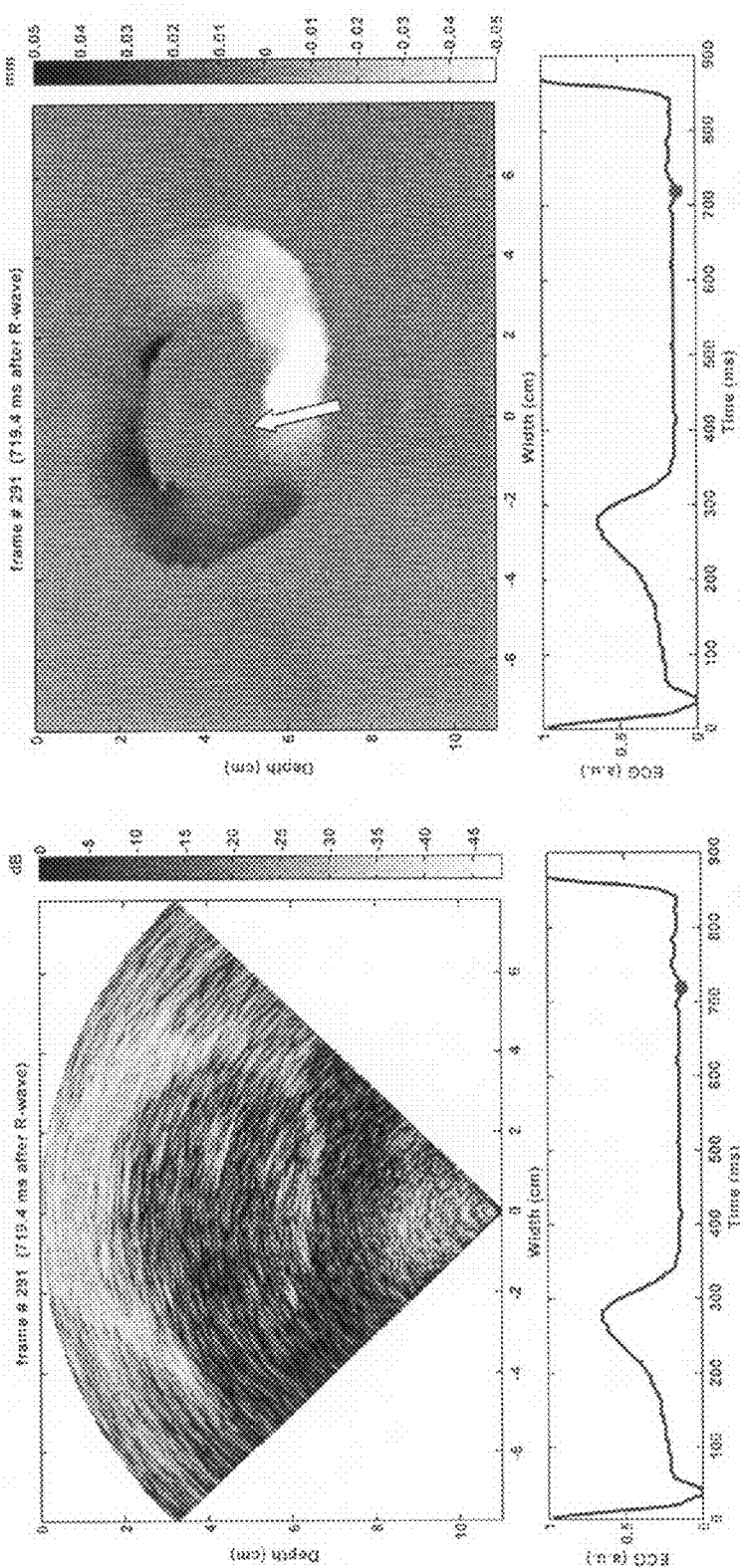
Figure 29A:
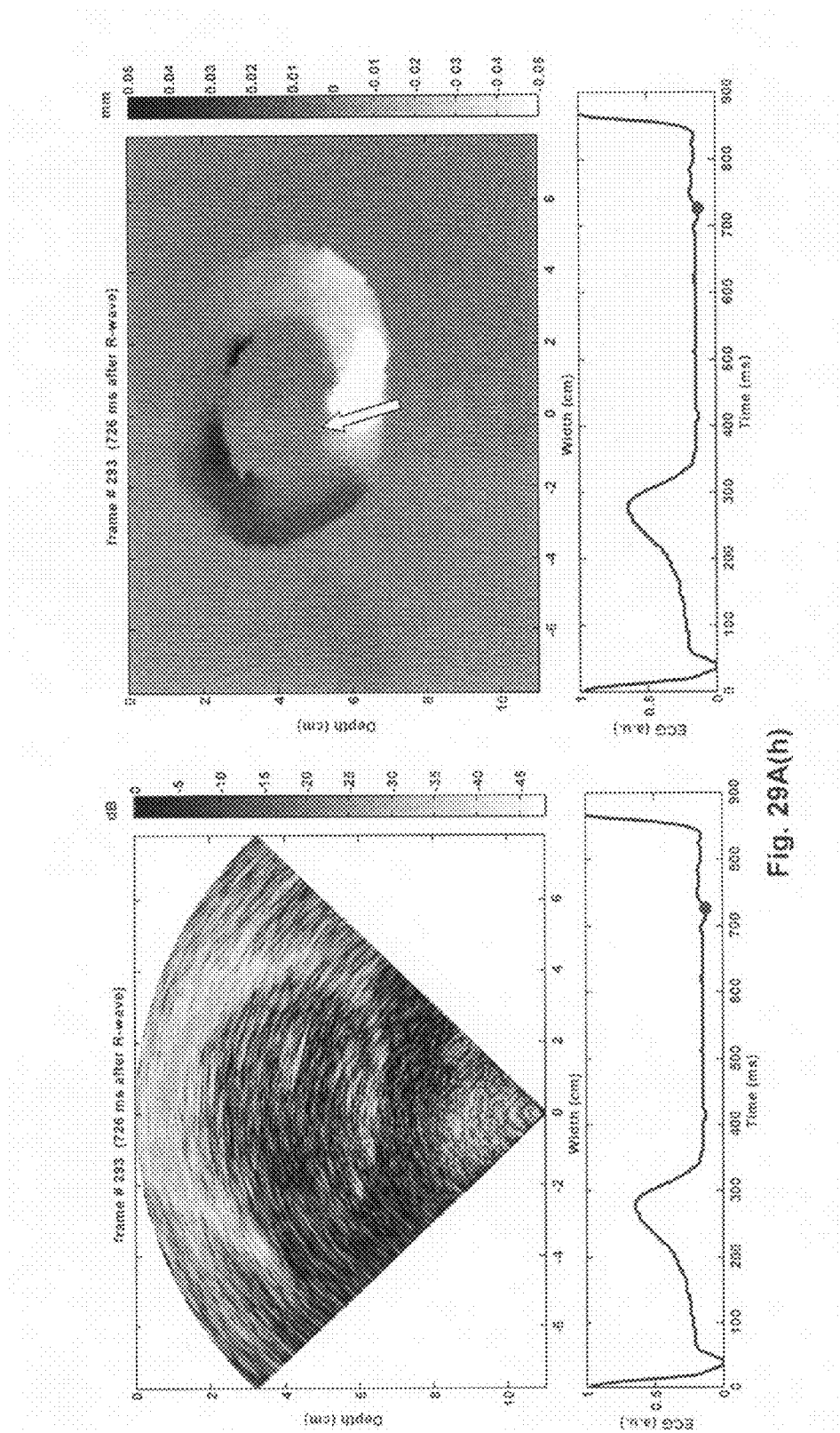
Figure 29A:
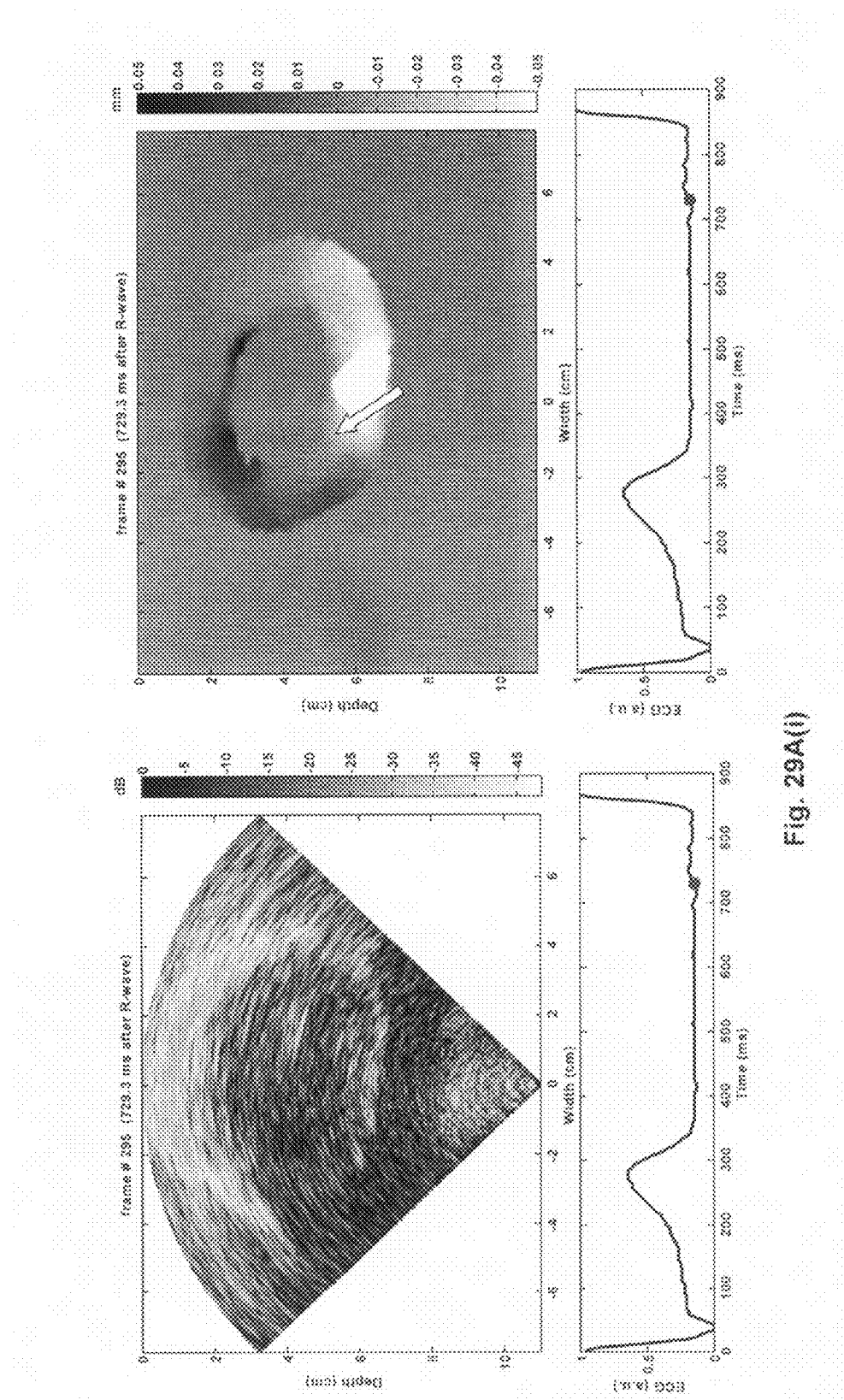
Figure 29A:
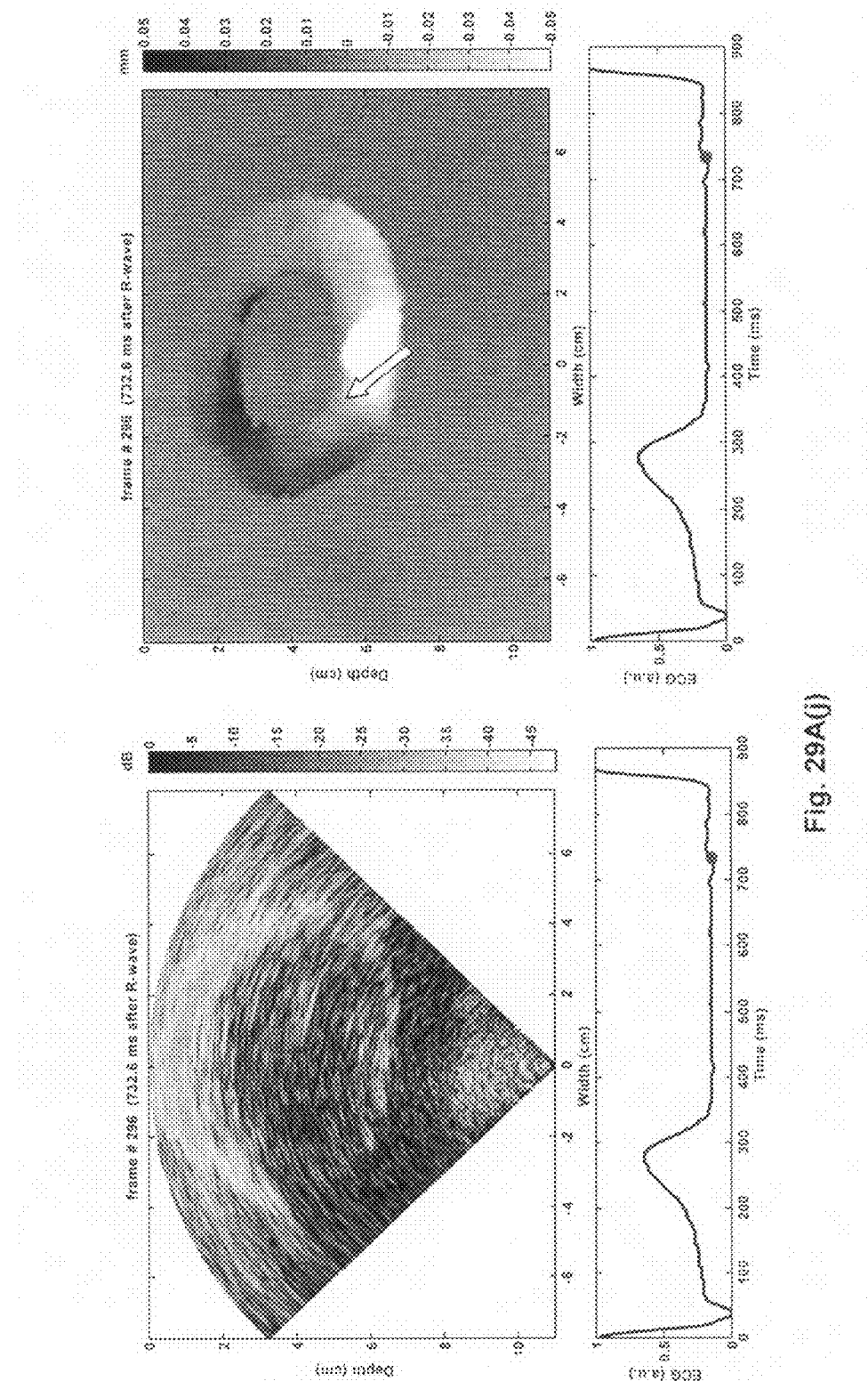
Figure 29A:
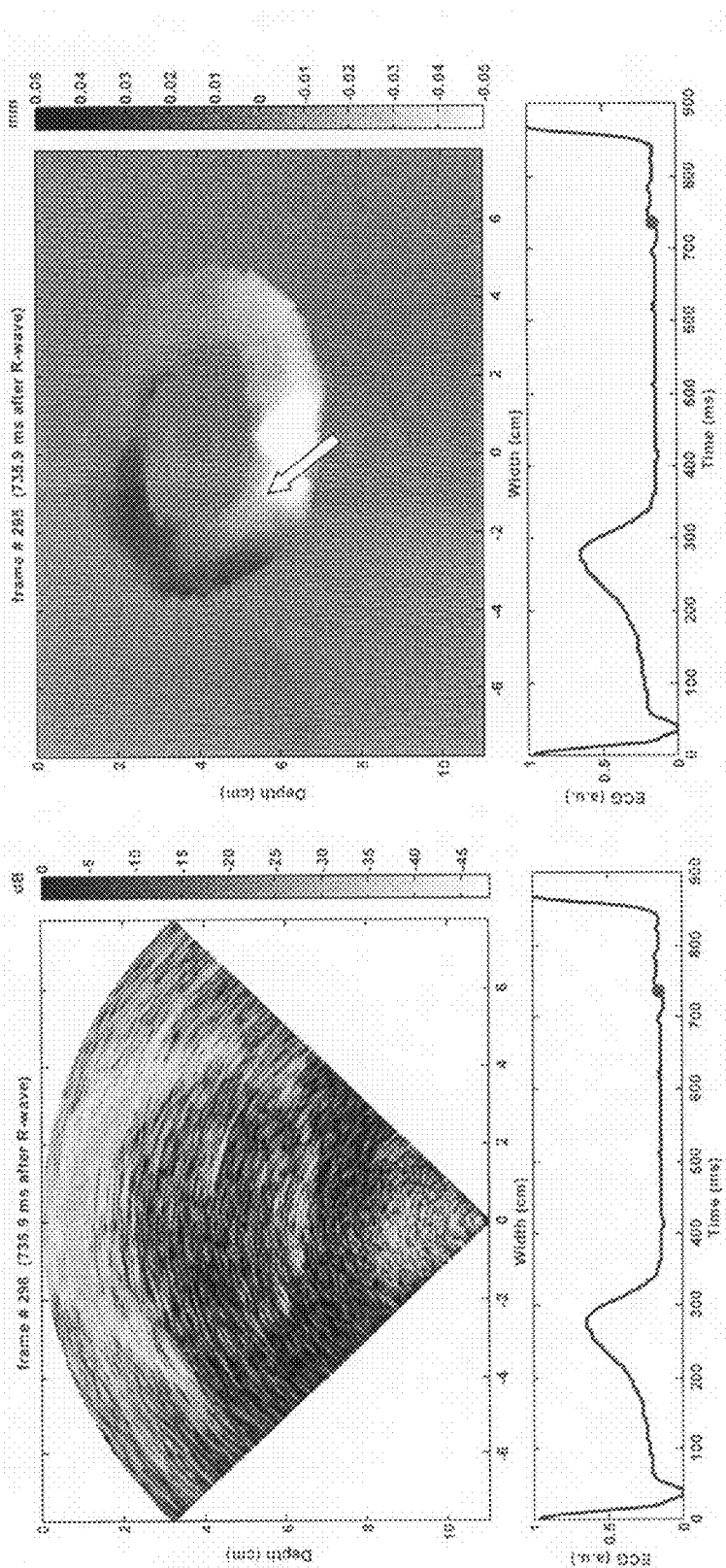
Figure 29A:
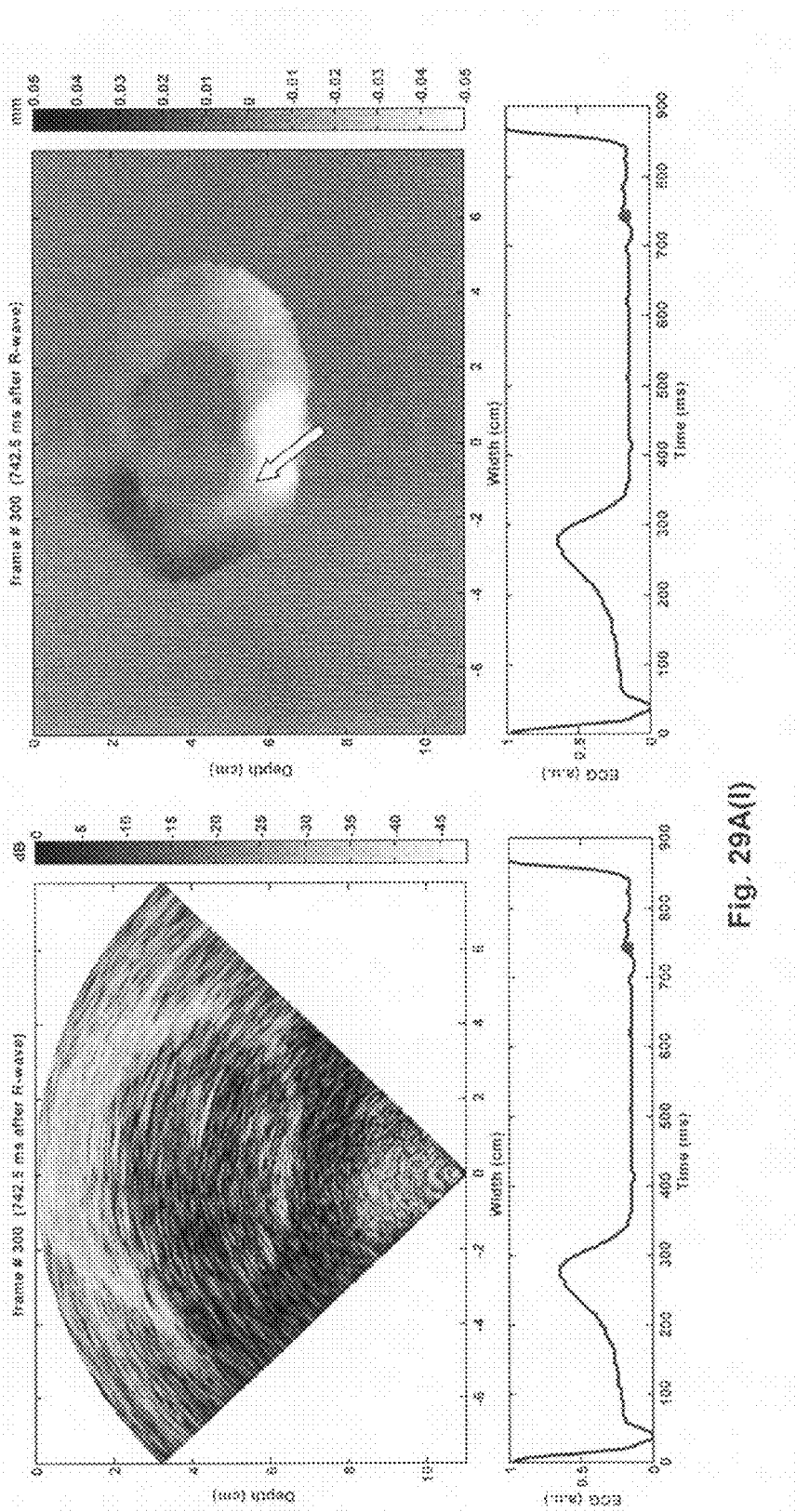
Figure 30A:
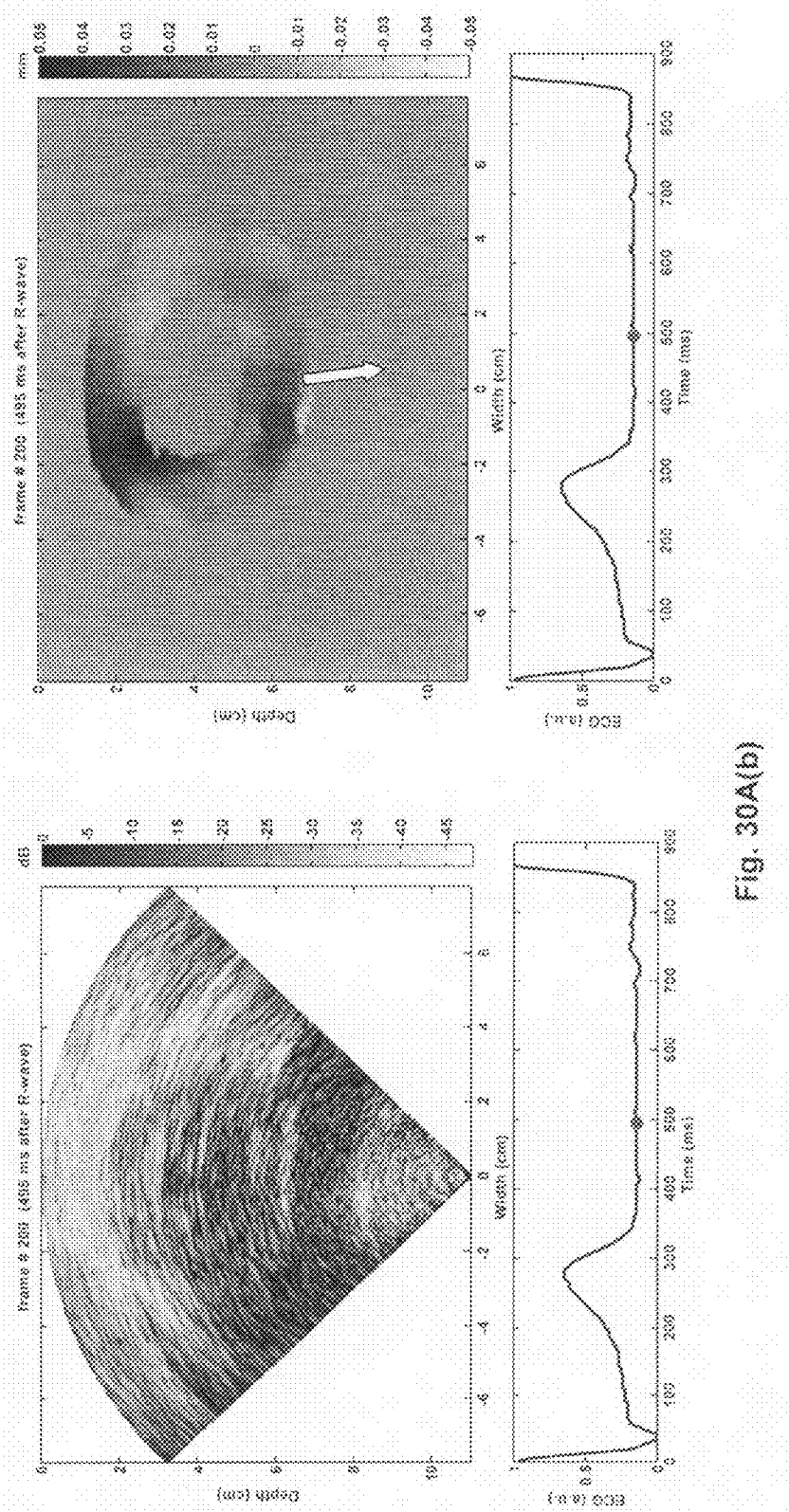
FIGS. 30A(a1),(a2)-(l1),(l2) are grayscale images corresponding to FIGS. 30($a$)-($l$) which show the displacement separately from the B-mode image.
Figure 30A:
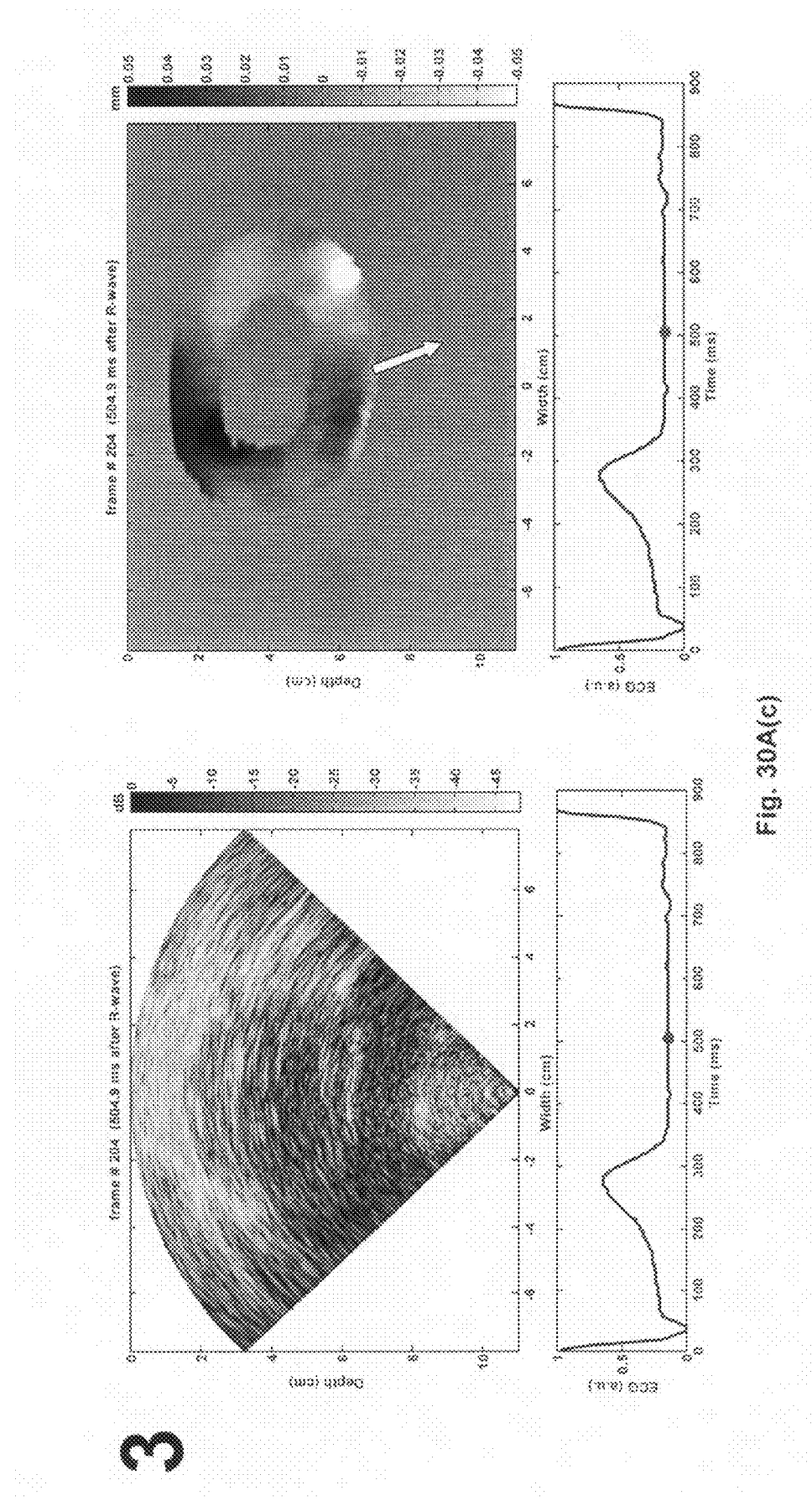
Figure 30A:
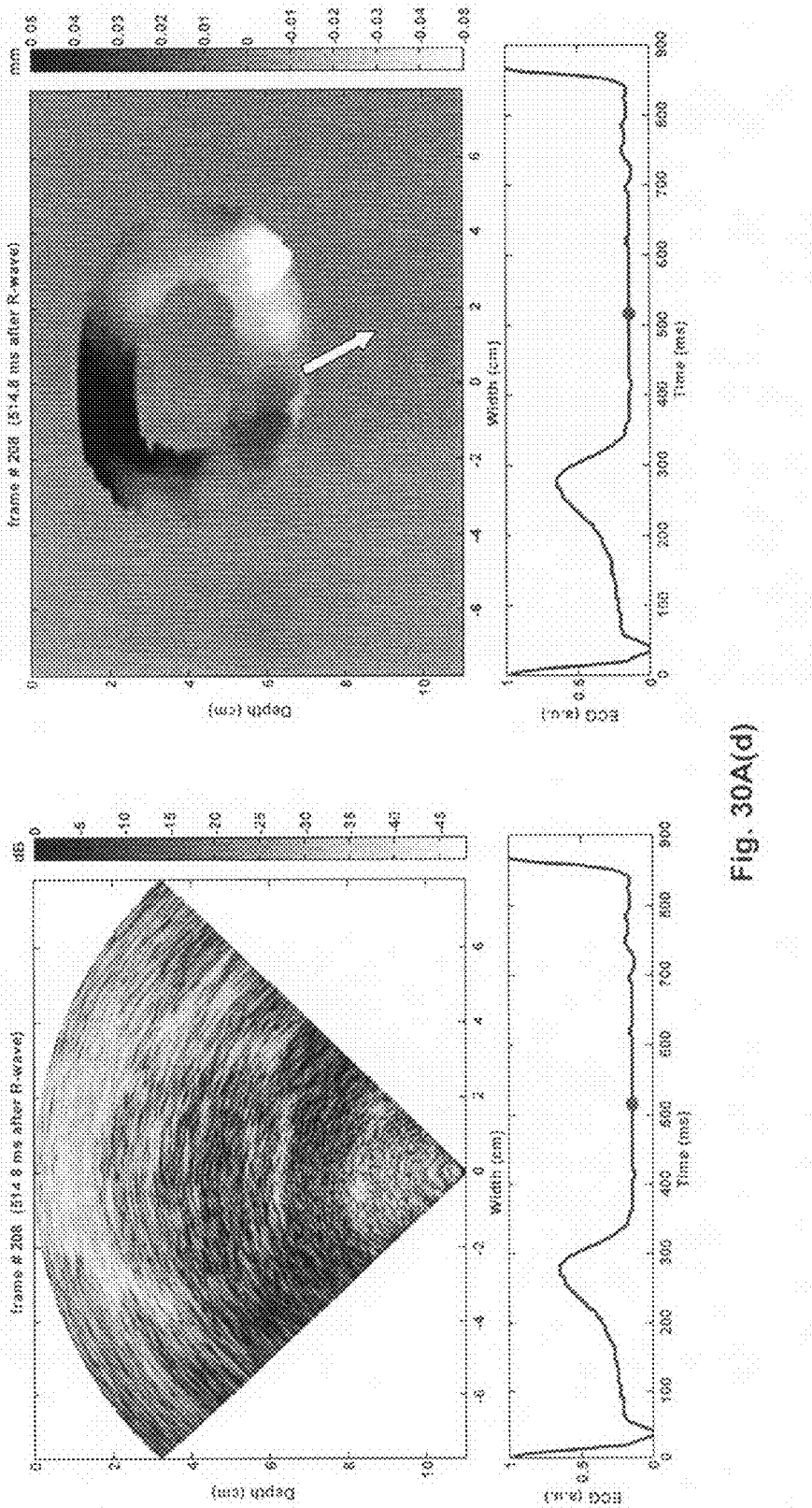
Figure 30A:
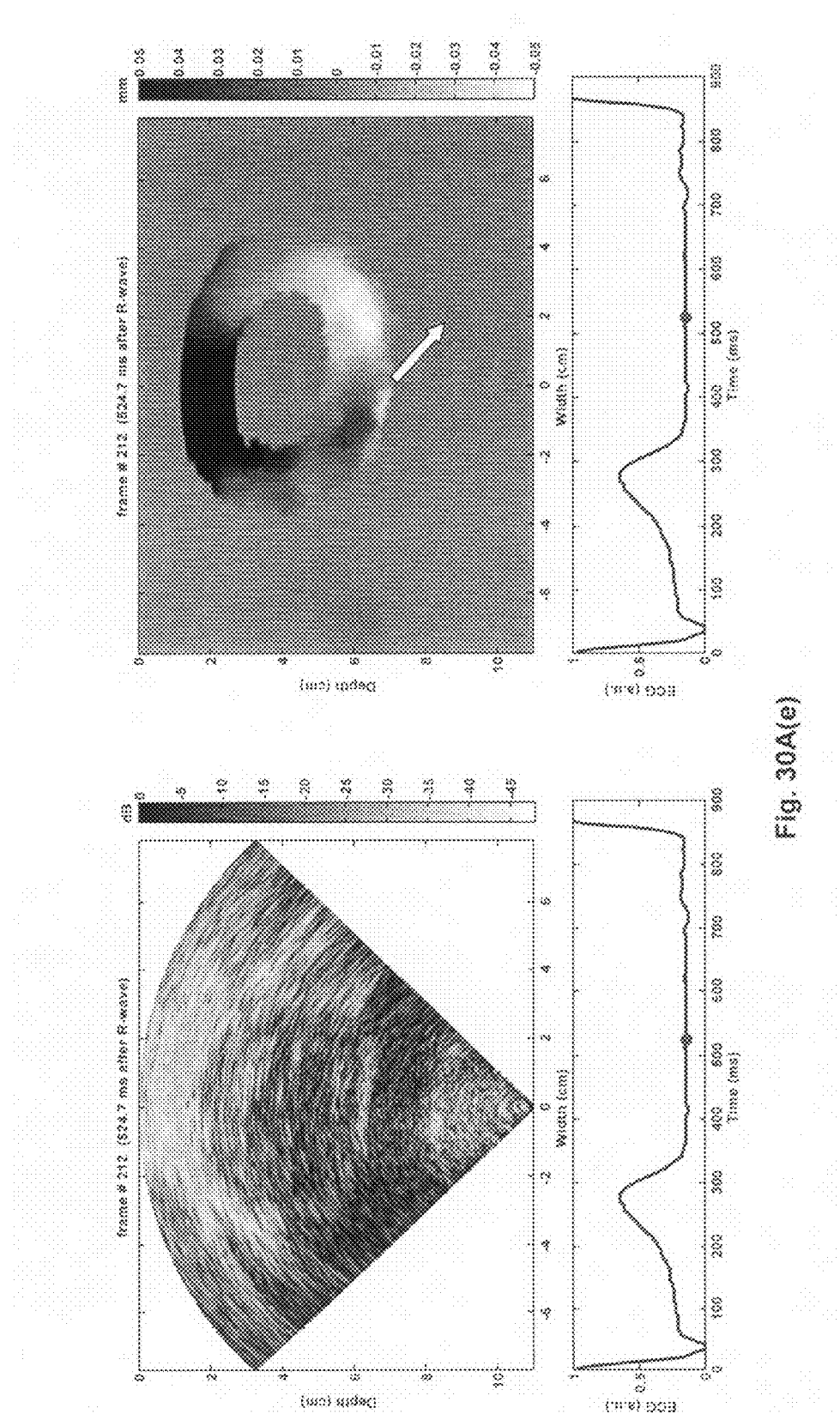
Figure 30A:
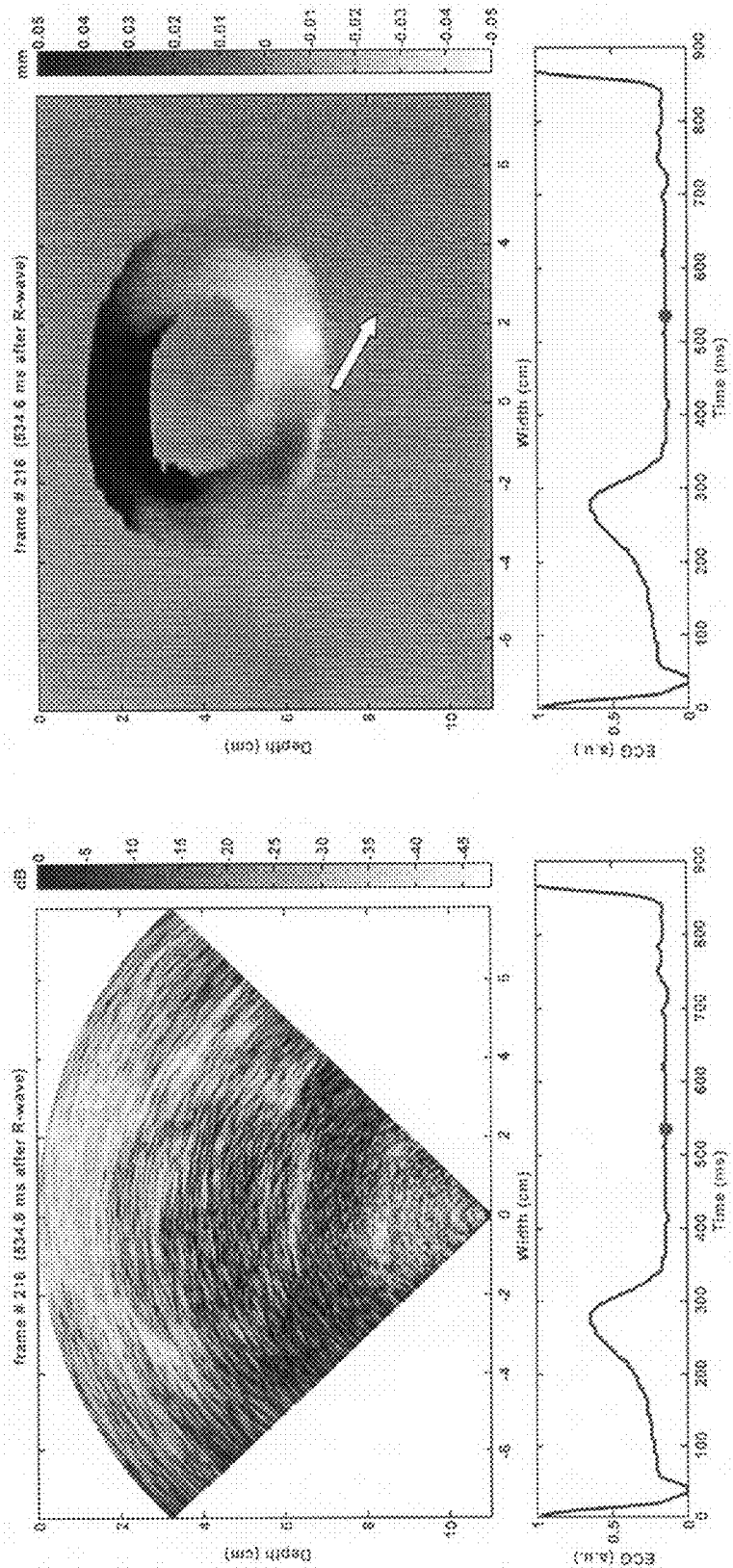
Figure 30A:
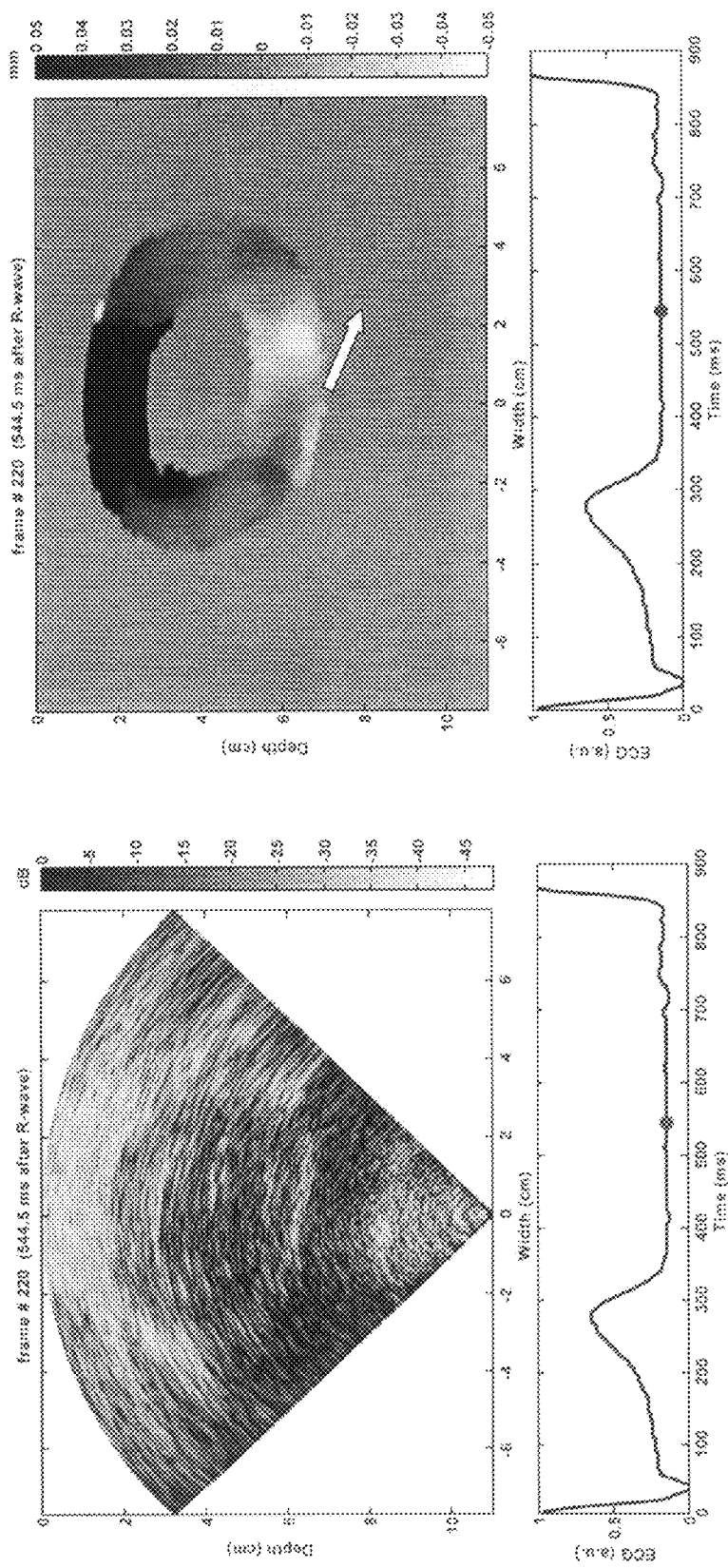
Figure 30A:
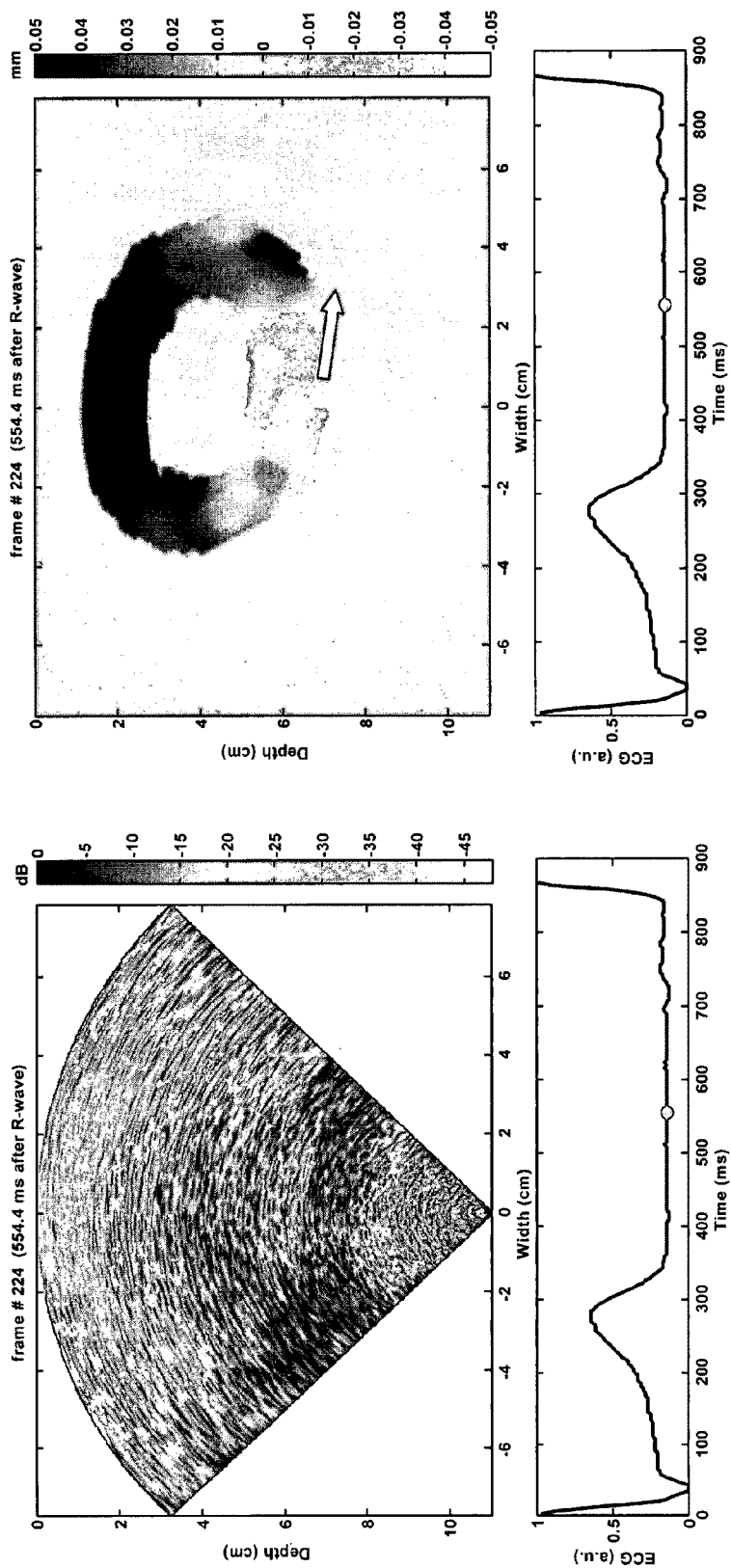
Figure 30A:
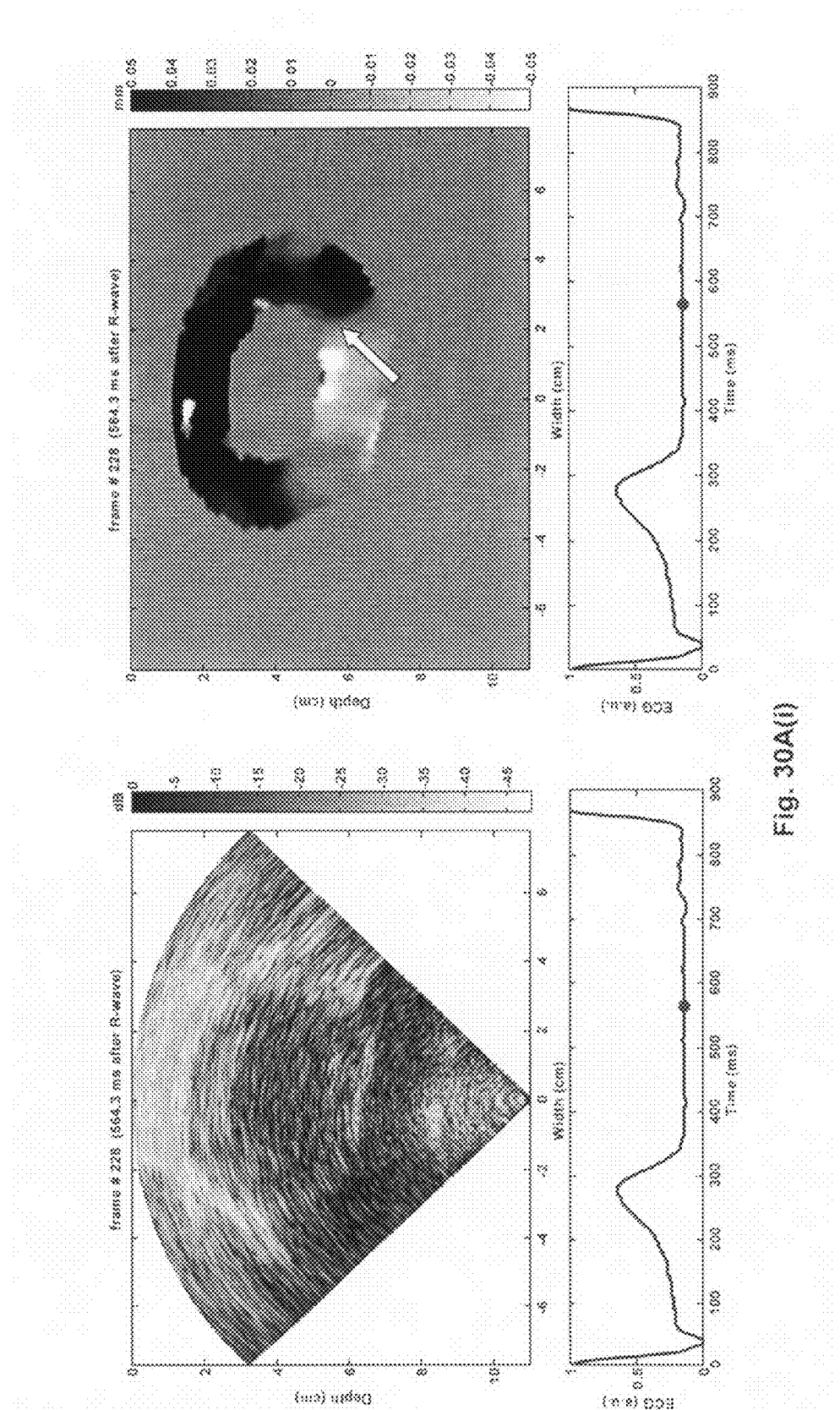
Figure 30A:
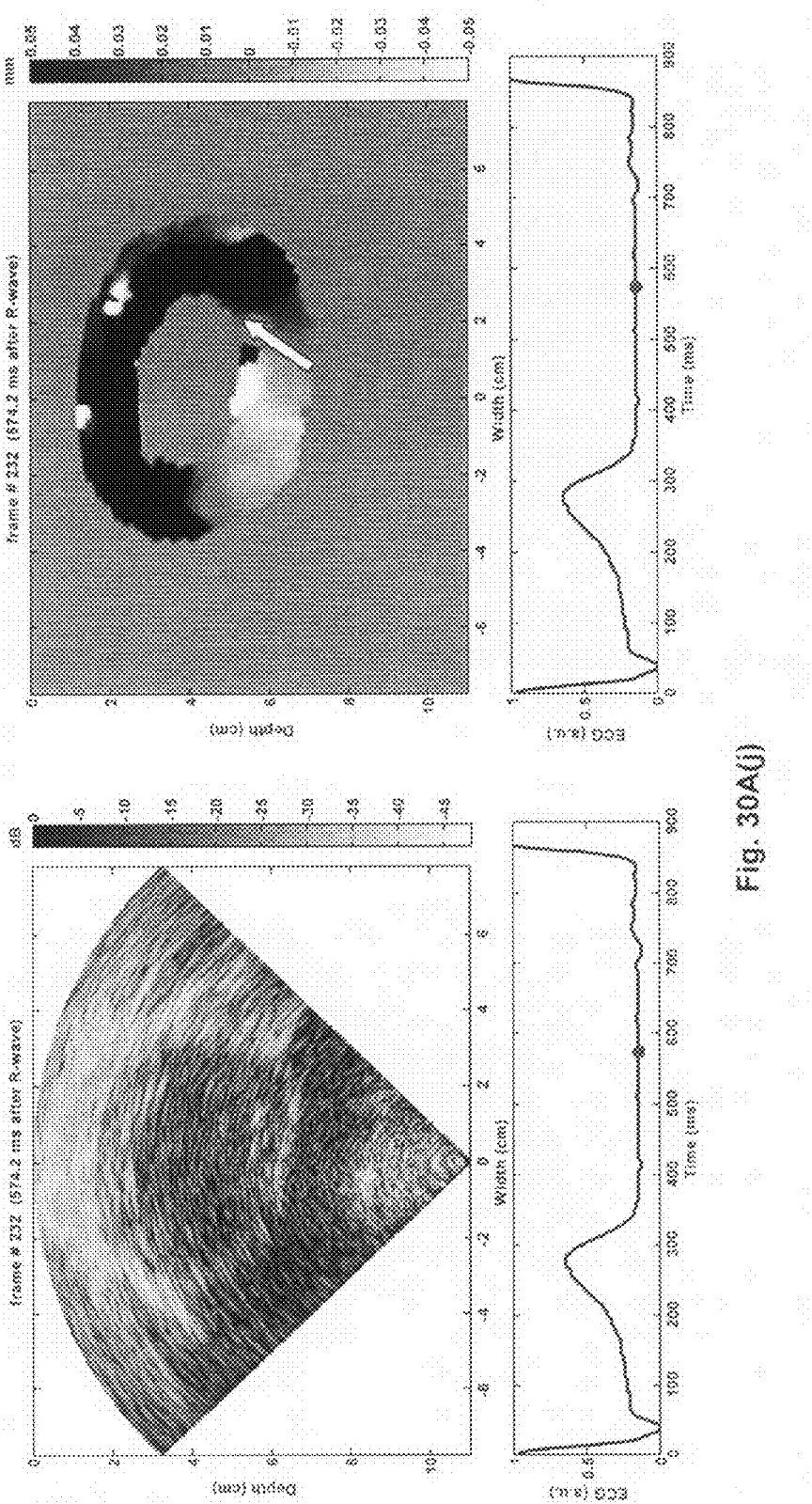
Figure 30A:
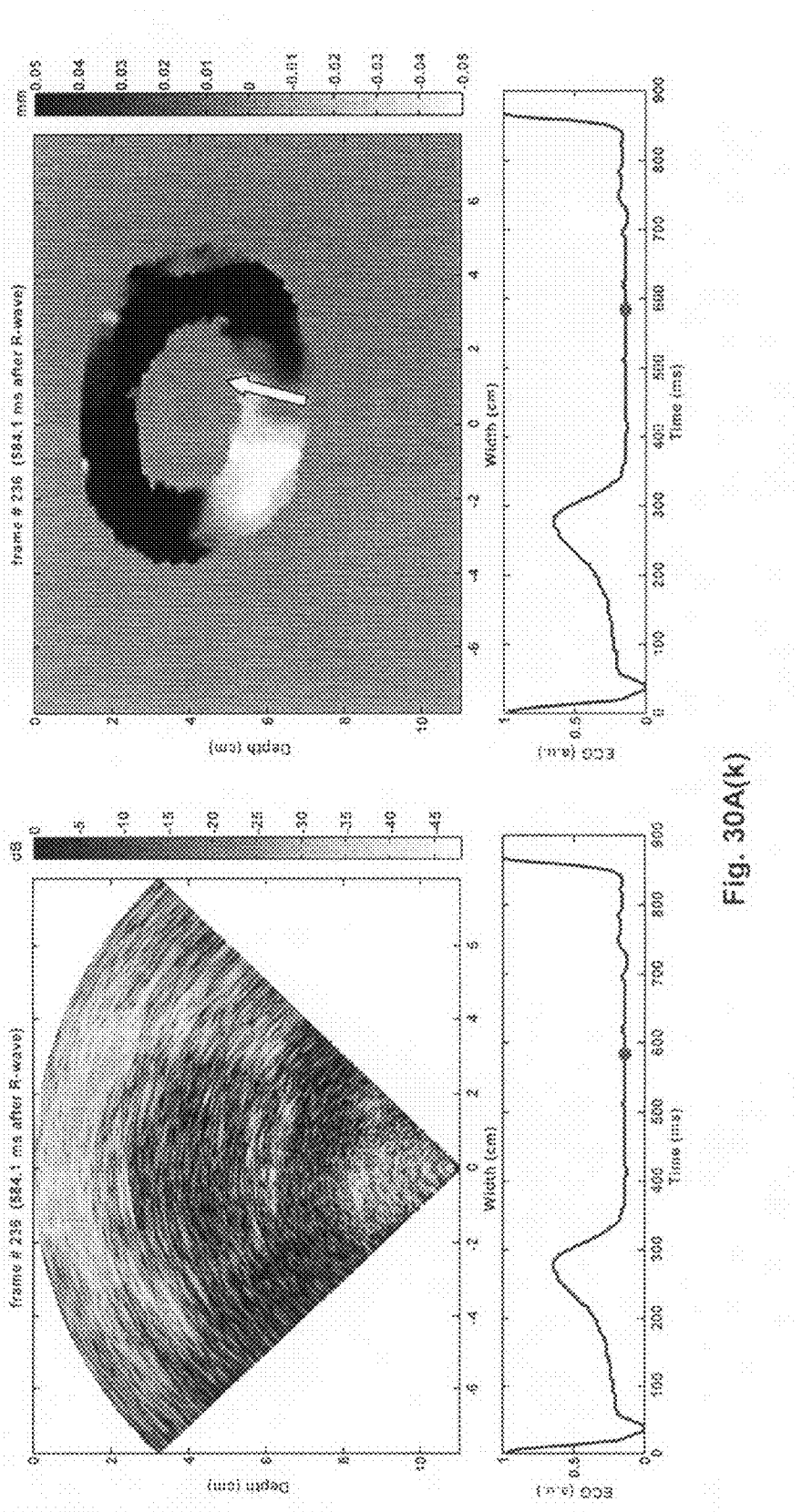
Figure 30A:
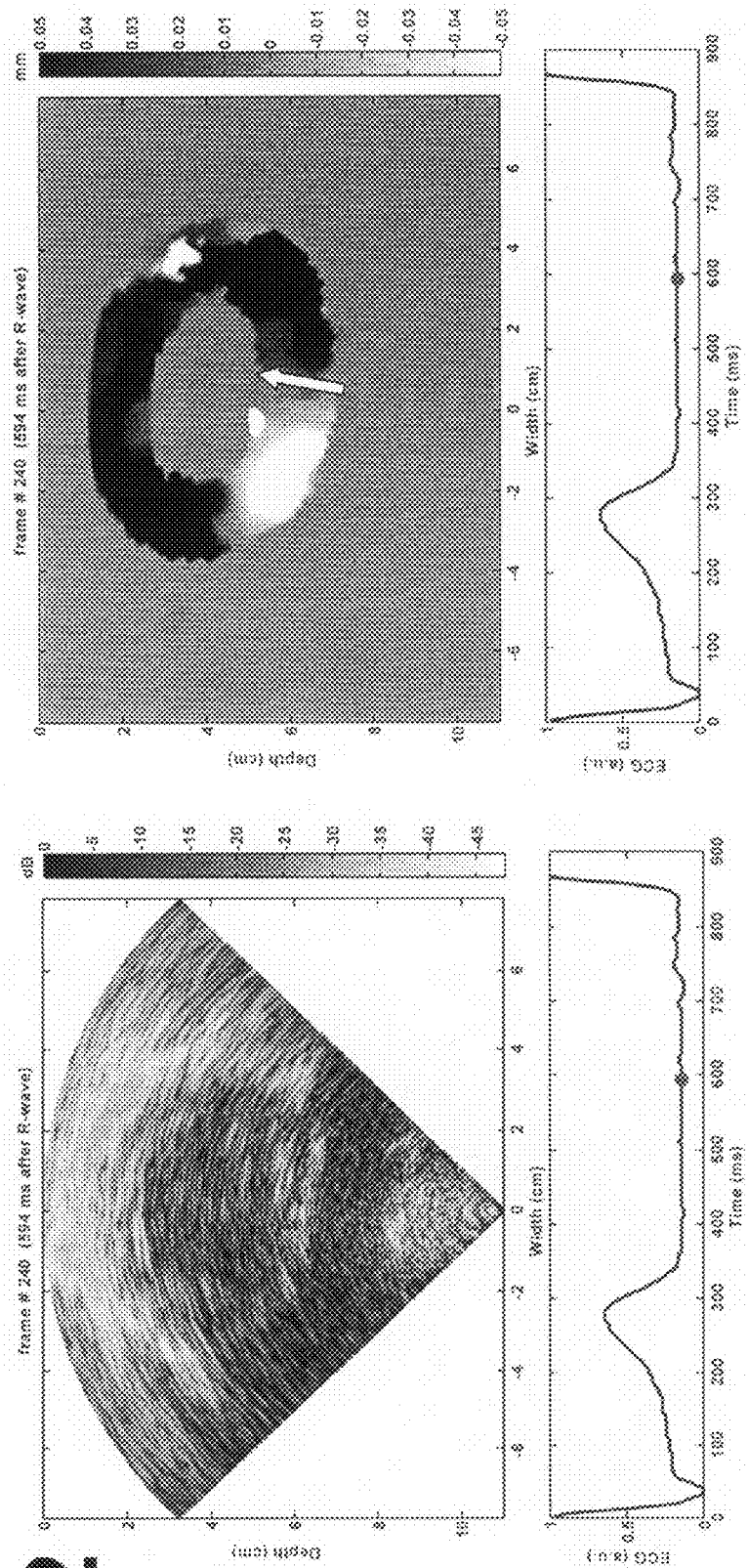

FIG. 28 show a comparison of a seven sector B-mode composite image of heart long axis view (FIG. 28(a)) with a 100% B-mode image without combination. The benefits of FIG. 28(a), created using methods according to the present invention, are clearly seen.

After successful combination of the seven sectors RF data through ECG gating, the motion of the tissue was estimated off-line using an established classical speckle-tracking method. This technique was based on detecting the small local displacement of the tissue that occurs between tow consecutive frames. With the current method, only axial displacements (along the axis of the transducer beam), which coincided with the radial displacement in a long-axis view, were estimated. In our algorithm, the time shifts in the backscattered signals were determined between the two consecutive frames through cross-correlation of small sliding windows over the entire RF-line. This technique allowed the detection of very small displacement on the order of 0.1 um or less (correlation window of 6.9 mm, overlapping 80%). Finally, the cine-loop of the axial displacement was generated at a frame rate 481 Hz for the entire in vivo human cardiac cycle.

Obviously there are complex movements, torsional, sagittal, and horizontal movements, especially during cardiac contraction. However, as shown by the magnetic resonance tagging pattern, there are far fewer torsional, sagittal, and horizontal movements in the IVS compared with those in the right ventricular anterior wall, the left ventricle (LV) posterior wall, and the apex. Thus, our measurements have been applied to the IVS to eliminate complexity of the three-dimensional motions during the cardiac cycle. FIGS. 29(a)-(l) depict a sequence of color-coded axial displacements overlaid onto gray-scale B-mode images at different occurrence times during systole on a human left ventricle. In the displacement images, positive displacements (in red) denoted motion towards transducer whereas negative displacement (in blue) motion away from the transducer. A wave, known as electromechanical wave in red pointed by white arrows, was clearly seen traveling from the lateral, anterior to septal walls in the late diastole.

A "well-organized" heterogeneity in electromechanical coupling is thus a characteristic feature and may be a prerequisite for normal performance of the cardiac muscle.

In short axis view of the subject, another clear wave was also found propagating counter clockwise from posterior to lateral wall during diastole phase as shown in FIGS. 30(a)-(l). The wave front is indicated by white arrows.

Additionally, in a long axis view of the subject, an electromechanical wave was found propagating along the posterior wall in a human left-ventricle during systole. This is depicted in FIGS. 31(a)-(l).

Discussion

The first frame RF data and the first ECG data point are start at the same time as describe in the previous session. which could result in a maximum latency of 3.3 ms between the two data sets. This latency is determined by the maximum time interval of ECG sampling rate and the RF frame rate. In the worst case the latency between ECG and rf frames is min(1/ECG frame rate, 1/rf frame rate) since the first point of ECG data and the first frame of rf data is forced to be aligned.

$$L = \text{Max}(1/r_{ECG}, 1/r_{RF}) \sim 3.3 \text{ ms}$$

Where L—latency of first RF frame and first ECG data
rECG—ECG sampling rate, 300 points/second
rRF—RF frame rate, >360 Hz The ECG R wave peak position is detected by a matlab program where the corresponding RF frame position is calculated by $$P_{rf} = P_r \times \text{round}(N_{rf}/N_{ECG})$$

Where
$P_{rf}$—the position of rf frame corresponding to ECG R wave peak
$P_r$—the ECG R wave peak position
$N_{rf}$—total number of rf frames.
$N_{ECG}$—total number of ECG points.
round—the matlab function to get the closest integer of $N_{rf}/N_{ECG}$ From FIGS. 29, it was seen that at the end of diastole, the contraction activation sequence in the axial direction is from lateral, anterior to septal with a relatively slow speed. This contraction pattern could be beneficial for left ventricle function, because it will first initiate the acceleration of the blood in LV to move toward the aorta exit from the ventricle chamber. High temporal resolution contrast echocardiography, in which bubbles are tracked in time and space for creating trajectories of blood in 2D, had confirmed this blood flow accelerates in the apex-to-base direction, paralleling the apex-to-base direction of electromechanical activation.

A clear understanding of this type of ventricle mechanics and electromechanics is very useful clinically. It is also expected that this type of contraction synchronization would be the first to fail for heart failure diseases. This may be due to the fact that in the heart systolic contraction is an electrically triggered active event whereas diastole is a passive relaxation process.

Thus, in the above-described example, a method with a frame rate five times higher than obtainable using a conventional ultrasound imaging system was obtained. An ECG gating technique was applied for multi-sector recombination of RF signal to generate a 100% full view of the B-mode images.

Exemplary Pseudocode for ECG and RF Data Acquisition from Sonix RP System (Ultrasonix Medical Inc. Canada)

The following is exemplary pseudocode used in the above-described exemplary implementation.

```
//main program
program starts
   parameter initializing;
   declare message map;
      if (!connected_to_Sonix RP host)
         connect_to_host;
      endif
   detect ECG connection;
   create ECG acquisition thread;
   while(!exit) wait for user message;
program ends
// on catch message RUN_SCAN
retrieve scan parameter from panel;
if(!connected_to_host) error;
if(!ECG_running) error;
set scan parameter;
clear memory;
set_data_to_acquire(RF);
if(thread_scan exit)
   terminate(thread_scan);
else
   create_thread(thread_scan);
endif
//pseudo code for thread_scan
calculate total number of sectors;
for(i=starting_angle;i<stoping angle; angle_increment)
   set sector angle;
   post message starting scan
   wait 2 s
   post message stop scan
   save ECG data in memory;
   save RF data in memory;
endif
```

In a preliminary frame rate study conducted by the inventors, three conclusions were drawn: (1) during systole, the minimum frame rate for reliable strain information is approximately 250 fps. This is because the correlation coefficient surpasses 0.9, when the $SNR_e$ is high enough (above 10 dB) for best images. This agrees with what various researchers have reported for cardiac RF speckle tracking, i.e., that the optimal frame rate is within the range of 200-300. (2) during diastole (as the strain rates during fast filling can be up to 2-3 times higher than during systole in humans), the minimum frame rate is approximately 500 fps. The optimal frame rate is directly proportional to the strain and strain rate amplitudes to be estimated. For fast filling, the strain rate is 2-3 times higher, therefore, the optimal frame rate needs to be accordingly adjusted; and (3) the Ultrasonix system can provide sufficiently high correlation coefficients ($\rho > 0.985$), both for systolic and diastolic estimates. This result thus indicates that high correlation in a human heart is possible and that the most reliable strains are obtained at and beyond 250 fps for systole, and 500 fps for diastole, respectively.

While this invention has been described with reference to one or more exemplary embodiments thereof, it is not to be limited thereto and the appended claims are intended to be construed to encompass not only the specific forms and variants of the invention shown, but to further encompass such as may be devised by those skilled in the art without departing from the true scope of the invention.

What is claimed:

1. A method of generating high frame rate composite ultrasound frames, comprising:
   acquiring a series of ultrasound frames for each of N sectors, wherein N is two or more, wherein each of said N sectors corresponds to a different area and wherein each of said series of ultrasound frames is acquired over a different one of one or more cardiac cycles;
   substantially simultaneously acquiring an ECG signal for each cardiac cycle, wherein each of said series of ultrasound frames for each sector is triggered or gated using said ECG signal;
   synchronizing data for each of said N sectors in time using said ECG signals;
   combining said data from said N sectors to generate a series of high frame rate composite ultrasound frames; and
   displaying at least one of said series of high frame rate composite ultrasound frames to a user.

2. The method of claim 1, wherein at least one of said ultrasound frames comprises a 2D ultrasound image.

3. The method of claim 1, wherein at least one of said ultrasound frames comprises a 2D ultrasound signal frame.

4. The method of claim 1, wherein at least one of said ultrasound frames comprises a 3D ultrasound image.

5. The method of claim 1, wherein at least one of said ultrasound frames comprises a 3D ultrasound signal frame.

6. The method of claim 1, further comprising estimating one or more displacements between consecutive time frames for one or more windows of said high frame rate composite ultrasound frames.

7. The method of claim 6, further comprising estimating a propagation of said one or more displacements in a waveform.

8. The method of claim 7, further comprising estimating a direction of said propagation of said one or more displacement waves.

9. The method of claim 8, further comprising estimating a velocity of said propagation of said one or more displacement waves.

10. The method of claim 7, wherein said one or more displacement waves comprise one or more electromechanical waves.

11. The method of claim 10, further comprising estimating a direction of propagation of said one or more electromechanical waves.

12. The method of claim 11, further comprising estimating a velocity of propagation of said one or more electromechanical waves.

13. The method of claim 7, wherein said one or more displacement waves comprise one or more mechanical waves.

14. The method of claim 13, further comprising estimating a direction of propagation of said one or more mechanical waves.

15. The method of claim 13, further comprising estimating a velocity of propagation of said one or more mechanical waves.

16. The method of claim 6, further comprising applying a noise removal algorithm to said estimated one or more displacements.

17. The method of claim 16, further comprising accumulating said estimated one or more displacements with time so as to track motion for an entire cardiac cycle.

18. The method of claim 17, further comprising deriving strains in a cardiac muscle from said accumulated displacements.

19. The method of claim 18, further comprising overlaying data representing at least one of said displacement and said strain onto said high frame rate composite ultrasound images.

20. The method of claim 1, wherein said synchronizing comprises leaving a systolic part of said ECG signal unchanged and interpolating a diastolic part of said ECG signal to a maximum length of all N ECG signals.

21. The method of claim 20, further comprising linearly interpolating the corresponding 2D RF frames to a maximum length of a all sector RF frame sequence.

22. A method of imaging, comprising:
acquiring a series of 2D images for each of N sectors, wherein N is two or more, wherein each of said N sectors corresponds to a different area and wherein each of said series of ultrasound images is acquired over a different one of one or more cycles of a biological periodic signal;
substantially simultaneously acquiring said biological periodic signal for each cycle, wherein each of said series of 2D ultrasound images for each sector is triggered using said biological periodic signal;
synchronizing data for each of said N sectors in time using said biological periodic signal data;
combining said data from said N sectors to generate a series of composite images; and
displaying at least one of said series of composite images to a user.

23. The method of claim 22, wherein all images are obtained acquired within a single breath-hold.

24. The method of claim 22, wherein two or more of said series of ultrasound frames are acquired at separate breath-holds.

25. A computer program product comprising a computer usable medium having computer readable program code means embodied therein, said computer readable program code means in said computer program product comprising means for causing a computer to:
cause an ultrasound machine to acquire a series of 2D ultrasound images for each of N sectors, wherein N is two or more, wherein each of said N sectors corresponds to a different area and wherein each of said series of 2D ultrasound images is acquired over a different one of one or more cardiac cycles;
substantially simultaneously cause an ECG acquisition device acquire an ECG signal for each cardiac cycle, wherein each of said series of 2D ultrasound images for each sector is triggered or gated using said ECG signal;
synchronize data for the each of said N sectors in time using said ECG signals;
combine said data from said N sectors to generate a series of composite ultrasound images; and
display at least one of said series of composite ultrasound images to a user.

26. A computer program product comprising a computer usable medium having computer readable program code means embodied therein, the said computer readable program code means in said computer program product comprising means for causing a computer to:
cause an image acquisition device to acquire a series of 2D images for each of N sectors, wherein N is two or more, wherein each of said N sectors corresponds to a different area and wherein each of said series of 2D images is acquired over a different one of one or more cycles of a biological periodic signal;
substantially simultaneously cause a signal acquisition device to acquire said biological periodic signal for each cycle, wherein each of said series of 2D ultrasound images for each sector is triggered or gated using said biological periodic signal;
synchronize data for each of said N sectors in time using said biological periodic signal;
combine said data from said N sectors to generate a series of composite images; and
display at least one of said series of composite images to a user.

27. An imaging system, comprising:
at least one computer;
at least one ultrasound machine in communication with said at least one computer; and
a periodic signal acquisition device, in communication with said at least one computer and said at least one ultrasound machine, wherein in operation said at least one computer causes said at least one ultrasound machine to acquire a series of 2D ultrasound images for each of N sectors of a field of view of an anatomical object, wherein N is two or more, wherein each of said N sectors corresponds to a different area and wherein each of said series of 2D ultrasound images is acquired over a different one of one or more cycles of motion of said anatomical object; and
wherein said at least one computer causes said periodic signal acquisition device to substantially simultaneously acquire a periodic signal associated with said motion of said anatomical object for each of said one or more cycles of motion, wherein each of said series of 2D ultrasound images for each sector is triggered or gated using said periodic signal; and
wherein in operation the computer:
synchronizes data for each of said N sectors using said periodic signal;
combines said data from said N sectors to generate a series of composite ultrasound images;
processes said series of composite ultrasound images to calculate accumulated displacement as a function of time for a defined region of said anatomical object.

28. The system of claim 27, wherein said anatomical object is a mammalian heart.

29. The system of claim 27, wherein said anatomical object is one of a mammalian aorta, a ventricle, a blood vessel and a liver.

30. The system of claim 27, wherein said periodic signal associated with said motion of said anatomical object is an ECG signal.

31. The system of claim 27, wherein said calculation of accumulated displacement includes estimating one or more displacements between consecutive time frames for one or more windows of said series of composite ultrasound images.

32. The system of claim 31, wherein said calculation of accumulated displacement further comprises applying a noise removal algorithm to said estimated one or more displacements.

33. The system of claim 27, wherein in operation said at least one computer further derives strain or strain rate in a cardiac muscle from said accumulated displacement.

34. The system of claim 33, wherein in operation said at least one computer further overlays data representing at least one of said displacement, said strain and said strain rate onto said series of composite ultrasound images.

* * * * *